United States Patent [19]
Ding et al.

[11] Patent Number: 6,011,029

[45] Date of Patent: Jan. 4, 2000

[54] INHIBITORS OF FARNESYL PROTEIN TRANSFERASE

[75] Inventors: Charles Z. Ding; Soong-Hoon Kim, both of Plainsboro; John T. Hunt, Princeton; Toomas Mitt, Plainsboro, all of N.J.; Rajeev Bhide, Langhorne, Pa.; Katerina Leftheris, Skillman, N.J.

[73] Assignee: Bristol-Myers Squibb Company, Princeton, N.J.

[21] Appl. No.: 08/802,329

[22] Filed: Feb. 20, 1997

Related U.S. Application Data

[60] Provisional application No. 60/012,265, Feb. 26, 1996, and provisional application No. 60/022,805, Jul. 25, 1996.

[51] Int. Cl.[7] .................... A61K 31/55; C07D 243/24; C07D 243/14
[52] U.S. Cl. ................... 514/221; 540/506; 540/510; 540/569
[58] Field of Search .................... 540/569, 510, 540/506; 514/221

[56] References Cited

FOREIGN PATENT DOCUMENTS

94/14776   7/1994   WIPO .

OTHER PUBLICATIONS

Winegrad, B. *Oxford Textbook of Oncology*, vol. 1 (Oxford University Press, Oxford), ed. by Peckham, M. et al., pp. 486–495 (1995).

Cleton, F.J. *Oxford Textbook of Oncology*, vol. 1 (Oxford University Press, Oxford), ed. by Peckham, M. et al., pp. 445–453 (1995).

Bondinell, W.E. et al., *Chemical Abstract*, Abstract No. 123:112082 (1995).

*Primary Examiner*—Mukund J. Shah
*Assistant Examiner*—Bruck Kifle
*Attorney, Agent, or Firm*—Barry J. Marenberg; Frank P. Hoffman

[57] ABSTRACT

The present invention comprises benzodiazepine compounds having farnesyl transferase inhibitory activity.

7 Claims, No Drawings

INHIBITORS OF FARNESYL PROTEIN TRANSFERASE

This application claims benefit of Provisional Application Ser. No. 60/012,265 filed Feb. 26, 1996 and 60/022,805 filed Jul. 25, 1996.

FIELD OF THE INVENTION

This invention relates to compounds that inhibit farnesyl-protein transferase and ras protein farnesylation, thereby making them useful as anti-cancer agents. The compounds are also useful in the treatment of diseases, other than cancer, associated with signal transduction pathways operating through ras and those associated with proteins other than ras that are also post-translationally modified by the enzyme farnesyl protein transferase. The compounds may also act as inhibitors of other prenyl transferases, and thus be effective in the treatment of diseases associated with other prenyl modifications of proteins.

BACKGROUND OF THE INVENTION

The mammalian ras gene family comprises three genes, H-ras, K-ras and N-ras. The ras proteins are a family of GTP-binding and hydrolyzing proteins that regulate cell growth and differentiation. Overproduction of normal ras proteins or mutations that inhibit their GTPase activity can lead to uncontrolled cell division.

The transforming activity of ras is dependent on localization of the protein to plasma membranes. This membrane binding occurs via a series of post-translational modifications of the cytosolic Ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The ras C-terminus contains a sequence motif termed a "Cys-Aaa$_1$-Aaa$_2$-Xaa" box (CAAX box), wherein Cys is cysteine, Aaa is an aliphatic amino acid, and Xaa is a serine or methionine. Farnesylation occurs on the cysteinyl residue of the CAAX box (cys-186), thereby attaching the prenyl group on the protein via a thio-ether linkage.

BRIEF DESCRIPTION OF THE INVENTION

In accordance with the present invention, compounds of the formulas I, II, III and IV

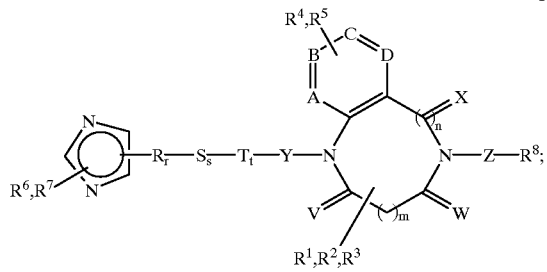

I

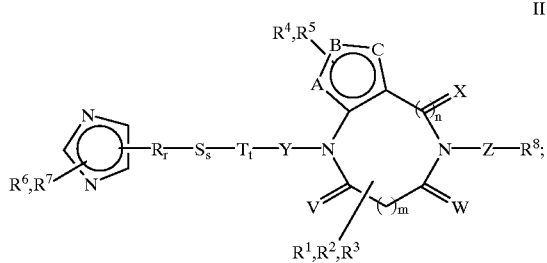

II

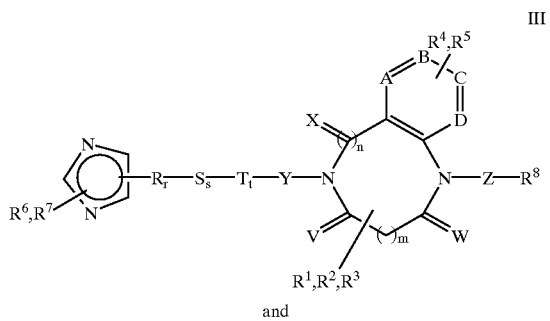

III

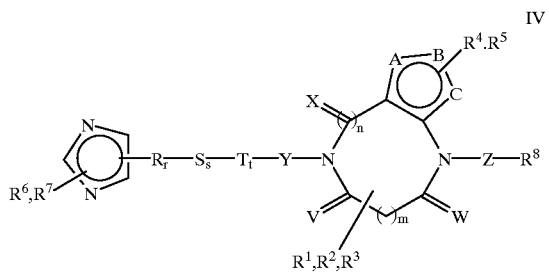

and

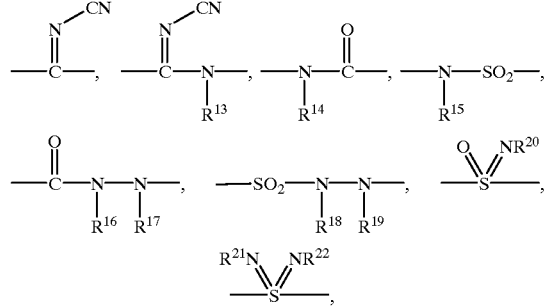

IV their enantiomers, diastereomers, and pharmaceutically acceptable salts, prodrugs and solvates thereof inhibit farnesyl protein transferase which is an enzyme involved in ras oncogene expression. In formulas I–IV and throughout their specification, the above symbols are defined as follows:

m,n,r,s and t are 0 or 1;

p is 0, 1 or 2;

V, W and X are selected from the group consisting of oxygen, hydrogen, $R^1$, $R^2$ or $R^3$;

Z and Y are selected from the group consisting of $CHR^9$, $SO_2$, $SO_3$, $CO$, $CO_2$, $O$, $NR^{10}$, $SO_2NR^{11}$, $CONR^{12}$, or Z may be absent;

$R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ are selected from the group consisting of hydrogen, lower alkyl, substituted alkyl, aryl, or substituted aryl;

$R^4$, $R^5$ are selected from the group consisting of hydrogen, halo, nitro, cyano and $U$-$R^{23}$;

U is selected from the group consisting of sulfur, oxygen, $NR^{24}$, CO, SO, $SO_2$, $CO_2$, $NR^{25}CO_2$, $NR^{26}CONR^{27}$, $NR^{28}SO_2$, $NR^{29}SO_2NR^{30}$, $SO_2NR^{31}$, $NR^{32}CO$, $CONR^{33}$, $PO_2R^{34}$ and $PO_3R^{35}$ or U is absent;

$R^1$, $R^2$, and $R^3$ are selected from the group consisting of hydrogen, alkyl, alkoxycarbonyl, substituted alkyl, alkenyl, substituted alkenyl, alkynyl, substituted alkynyl, aralkyl, cycloalkyl, aryl, substituted aryl, heterocyclo, substituted heterocyclo, cyano, carboxy, carbamyl (e.g. $CONH_2$) or substituted carbamyl further selected from CONH alkyl, CONH aryl, CONH aralkyl or cases where there are two substituents on the nitrogen selected from alkyl, aryl or aralkyl; $R^8$ and $R^{23}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

Any two of $R^1$, $R^2$, and $R^3$ can be joined to form a cycloalkyl group;

R, S and T are selected from the group consisting of $CH_2$, CO and $CH(CH_2)pQ$ wherein Q is $NR^{36}R^{37}$, $OR^{38}$, or CN; and A, B, C and D are carbon, oxygen, sulfur or nitrogen.

with the provisos that

1. When m is zero then V and W are not both oxygen or
2. W and X together can be oxygen only if Z is either absent, O, $NR^{10}$, $CHR^9$,

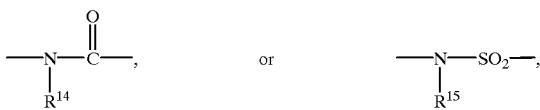

in formulas I and II, and V and X together can be oxygen only if Y is O, $NR^{10}$, $CHR^9$,

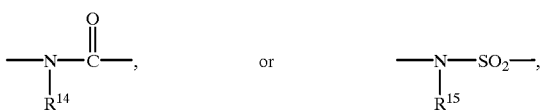

in formulas III and IV or

3. $R^{23}$ may be hydrogen except when U is SO, $SO_2$, $NR^{25}CO_2$ or $NR^{28}SO_2$, or
4. $R^8$ may be hydrogen except when Z is $SO_2$, $CO_2$, or

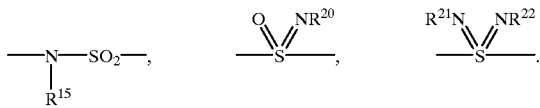

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "heteroatoms" shall include oxygen, sulfur and nitrogen.

The "ABC" ring and the "ABCD" fused ring to the diazepine ring may be monocyclic or bicyclic, e.g. napthyl or quinolyl in nature.

The compounds of formulas I–IV may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formulas I–IV may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compounds I–IV with the desired ion in a medium in which the salt precipitates or in an aqueous medium followed by evaporation. Other salts can be formed as known to those skilled in the art.

The compounds for formulas I–IV may form salts with a variety of organic and inorganic acids. Such salts include those formed with hydrogen chloride, hydroxy methane sulfonic acid, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compounds I–IV in an equivalent amount of the acid in a medium in which the salt precipitates or in an aqueous medium followed by evaporation.

In addition, zwitterions ("inner salts") may be formed.

Compounds of the formulas I–IV may also have prodrug forms. Any compound that will be converted in vivo to provide the bioactive agent (i.e., the compound for formulas I–IV) is a prodrug within the scope and spirit of the invention.

For example compounds of the formulas I–IV may be a carboxylate ester moiety. The carboxylate ester may be conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

d) H. Bundgaard, et al., *Journal of Pharmaceutical Sciences*, 77,285 (1988); and e) N. Kakeya, et al., *Chem Phar Bull*, 32, 692 (1984).

It should further be understood that solvates (e.g., hydrates) of the compounds of formulas I–IV are also with the scope of the present invention. Methods of solvation are generally known in the art.

Preferred Moieties

For compounds of the present invention, the following moieties are preferred:

Compounds of Formulas I, II, III and IV wherein m is zero.

More preferred are compounds of Formula I, II, III and IV wherein m is zero and n is one.

Most preferred are compounds of formula I wherein m, r, s and t are zero, n is one and "ABCD" is a carbocyclic ring, e.g., benzo.

Use and Utility

The compounds of formulas I–IV are inhibitors of S-farnesyl protein transferase. They are thus useful in the treatment of a variety of cancers, including (but not limited to) the following;

carcinoma, including that of the bladder, breast, colon, kidney, liver, lung, including small cell lung cancer, ovary, prostate, testes, pancreas, esophagus, stomach, gall bladder, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma;

hematopoietic tumors of myeloid lineage, including acute and chronic myelogenous leukemias, myelodysplastic syndrome and promyelocytic leukemia;

tumors of the central and peripheral nervous system, including astrocytoma, neuroblastoma, glioma, and schwannomas;

tumors of mesenchymal origin, including fibrosarcoma, rhabdomyoscarcoma, and osteosarcoma;

other tumors, including melanoma, xenoderma pigmentosum, keratoactanthoma, seminoma, thyroid follicular cancer and teratocarcinoma.

The compounds of formulas I–IV are especially useful in treatment of tumors having a high incidence of ras involvement, such as colon, lung, and pancreatic tumors and in tumors in which a prenyl transferase contributes to tumor maintenance, tumor growth or tumor development. By the administration of a composition having one (or a combination) of the compounds of this invention, development of tumors in a mammalian host is reduced, or tumor burden is reduced, or tumor regression is produced.

Compounds of formulas I–IV may also inhibit tumor angiogenesis, thereby affecting the growth of tumors. Such anti-angiogenesis properties of the compounds of formulas I–IV may also be useful in the treatment of certain forms of blindness related to retinal vascularization.

Compounds of formulas I–IV may also be useful in the treatment of diseases other than cancer that may be associated with signal transduction pathways operating through ras, e.g., neurofibromatosis, atherosclerosis, pulmonary fibrosis, arthritis, psoriasis, glomerulonephritis, restenosis following angioplasty or vascular surgery, hypertrophic scar formation, polycystic kidney disease and endotoxic shock. Compounds I–IV may be useful as anti-fungal agents.

Compounds of formula I–IV may induce or inhibit apoptosis, a physiological cell death process critical for normal development and homeostasis. Alterations of apoptotic pathways contribute to the pathogenesis of a variety of human diseases. Compounds of formula I–IV, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowl diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

Compounds of formulas I–IV may also be useful in the treatment of diseases associated with farnesyl transferase substrates other than ras (e.g., nuclear lamins, transducin, rhodopsin kinase, cGMP phosphodiesterase, TC21, phosphorylase kinase, Rap2, RhoB, RhoE, PRL1) that are also post-translationally modified by the enzyme farnesyl protein transferase.

Compounds of formulas I–IV may also act as inhibitors of other prenyl transferases (e.g., geranylgeranyl transferase I and II), and thus be effective in the treatment of diseases associated with other prenyl modifications (e.g., geranylgeranylation) of proteins (e.g. the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glen, et al., *Science*, 256, 1331 (1992)].

The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formulas I–IV may be used sequentially with known anticancer or cytotoxic agents and treatment, including radiation when a combination formulation is inappropriate.

Farnesyl transferase assays were performed as described in V. Manne et al., Drug Development Research, 34, 121–137, (1995). The compounds of Examples 1–431 inhibited farnesyl transferase with IC 50 values between 0.1 nM and 100 μM.

The compounds of this invention may be formulated with a pharmaceutical vehicle or diluent for oral, intravenous, intraperitoneal, subcutaneous, intraabdominal, intramuscular, rectal, vaginal or topical administration. Oral administration may involve the use of slow release formulations, such as biodegradable polymers or prodrugs. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 100 mg/kg/day, in a single dose or in 2 to 4 divided doses.

Process of Preparation

Scheme 1

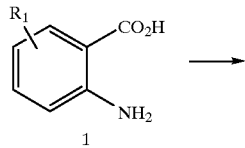

1

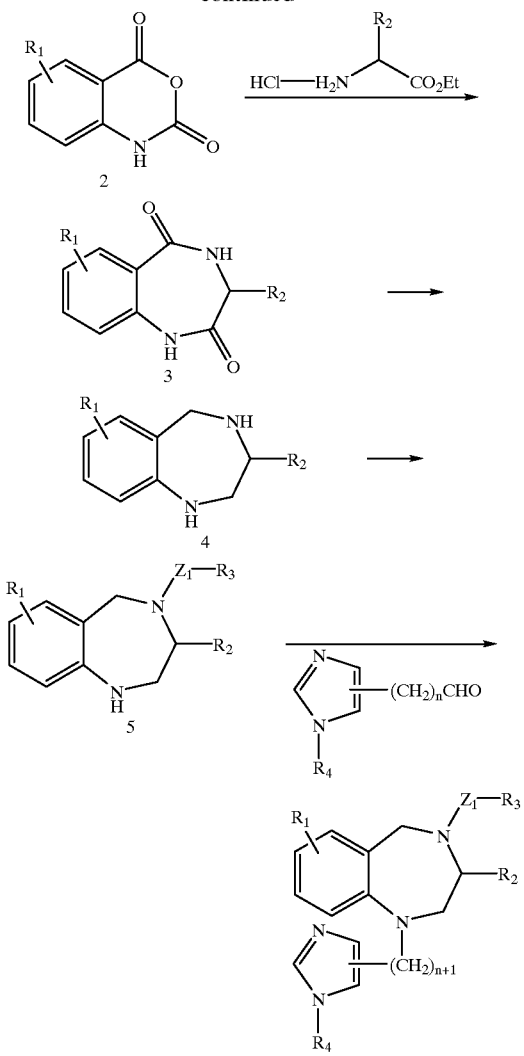

$Z_1$ = CO, $SO_2$, $CO_2$, $CONR_5$, $SO_3$, $SO_2NR_5$, C(NCN)$NR_5$

Step 1

The first step is accomplished by the reaction of the anthranilic acid with a phosgene equivalent, such as, phosgene or triphosgene in a mixed aqueous/organic solvent at room temperature to 50° C. range.

Step 2

The product is reacted with an amino acid hydrochloride salt or an amino acid ester hydrochloride salt in pyridine at an elevated temperature with reflux as preferred. Step 2 of Scheme 1 may be performed in 2 steps, wherein the isatoic anhydride is condensed with an amino acid in an organic solvent solvent such as pyridine at from 0° C. to reflux and the resulting anthraniloylamino acid is cyclized under standard amide bond forming conditions, e.g., using HOBt/carbodiimide in an organic solvent such as DMF at from 0° C. to room temperature. Some compounds 1 of Scheme 1 wherein $R_1$=halogen are not commercially available. Such compounds 3, 4 or 5 of Scheme 1 wherein $R_1$=halogen can be prepared from compounds 3, 4 or 5 of Scheme 1 wherein $R_1$=hydrogen by halogenation, for example by reaction with bromine in an organic solvent such as acetic acid at from 0° C. to room temperature. The compound 3 wherein $R_1$ is aryl or heteroaryl can be prepared from the compound 3 wherein $R_1$ is bromo, iodo or trifluoromethanesulfonyloxy by a palladium coupling of an aryl or heteroaryl metaloid derivative such as phenylboronic acid in a mixed aqueous/organic solvent, e.g. THF/DMF/water, in the presence of a base, e.g. sodium carbonate, at from room temperature to 90° C. (Alternatively, the compound of Scheme 1 where $R_1$=aryl or heteroaryl is also prepared from a compound 2 of Scheme 5 where $R_1$ is bromo, iodo or trifluoromethanesulfonyloxy by reaction with an aryl metaloid derivative such as phenylboronic acid or tributylstannylpyridine in a deoxygenated organic (e.g., THF) or mixed aqueous/organic solvent system such as aqueous $NaHCO_3$/toluene in the presence of a palladium catalyst such as tetrakis(triphenylphosphine) palladium at from room temperature to 100° C. Deprotection then affords the target compound.) Alternatively such Suzuki or Stille couplings can be performed on a compound 1 of Scheme 1, or on a compound 4 of Scheme 1, or on a compound 5 of Scheme 1 where the unacylated benzodiazepine nitrogen may be optionally protected, e.g., with a trifluoroacetyl group, and subsequently deprotected. The compound 3 wherein $R_1$ is alkoxy is prepared by alkylation of the corresponding hydroxy compound under standard conditions. The compound 3 wherein $R_1$ is alkylaminoalkylaryl is prepared from the compound 3 wherein $R_1$ is an aryl aldehyde by reductive amination under standard conditions.

Step 3

Thereafter the compound 3 is reacted with a reducing agent, such as lithium aluminum hydride or borane in an inert organic solvent, such as, tetrahydrofuran at from room temperature to reflux. If $R_1$ or $R_2$ contain functional groups, e.g., $CO_2R$, which are reduced by, e.g. lithium aluminum hydride, to, e.g. $CH_2OH$, these groups will also be reduced by step 3. The compound 4 or 6 wherein $R_1$ is CN can be prepared from the compound 4 or 6 wherein $R_1$=halogen by displacement with CuCN in an inert solvent such as NMP at elevated temperature. The compound 4 wherein $R_1$ is $CO_2H$ can be prepared from the compound 4 wherein $R_1$=CN by hydrolysis, e.g. by heating with aqueous sodium hydroxide in a suitable solvent such as ethanol at 100° C.; thereafter the product wherein R1=$CONR_5R_6$ may be prepared by standard amide bond coupling conditions.

Step 4

Thereafter the product is acylated or sulfonylated under standard conditions at from −78° C. to room temperature (e.g., by reaction with an acid halide $R_3COX$ wherein X is Cl or Br in an inert organic solvent, e.g. acetonitrile, or in a mixed aqueous/organic solvent e.g. NaOH/dichloroethane; by reaction with an O-phenyl ester in an inert organic solvent, e.g. acetonitrile; by reaction with a carboxylic acid in the presence of a coupling agent, e.g. DCC or EDC in an inert organic solvent, such as DMF; by reaction with a haloformate such as ethyl, isopropyl or 4-nitrophenylchloroformate in an inert solvent such as dichloromethane at from 0° C. to room temperature in the presence of an optional base such as diisopropylethylamine to form carbamates, some of which, e.g. 4-nitrophenylcarbamate, are reacted with an amine, e.g. N,N,N'-trimethylethylenediamine, at from room temperature to 110° C. to form ureas; by reaction with a carboxylic or sulfonyl anhydride such as succinic anhydride or trifluoromethanesulfonyl anhydride in an inert solvent such as ethyl acetate, dichloromethane or pyridine at from 0° C. to room temperature in the presence of an optional base such as diisopropylethylamine; by reaction with an isocyanate in an inert solvent such as THF; by reaction with a carbamyl chloride $R_5R_6NCOX$ wherein X is Cl or Br in an inert solvent such as acetonitrile in the presence of a base such as diisopropylethylamine/dimethyl-aminopyridine; by reaction with a sulfonyl halide $R_3SO_2X$ wherein X is Cl or Br in a mixed aqueous/organic solvent e.g. $NaOH/CH_2Cl_2$; by reaction with a halosulfonate $ROSO_2X$ wherein X is Cl or Br in an inert solvent such as $CH_2Cl_2$; by reaction with a sulfamoyl chloride $R_5R_6NSO_2X$ wherein X is Cl or Br in an inert solvent such as acetonitrile in the presence of a base such as diisopropylethylamine/dimethyl-aminopyridine; by reaction with an N-cyano-thiourea $NH(CN)C(S)NR_5R_6$ in the presence of a coupling reagent such as a carbodiimide in an inert solvent such as DMF at about room temperature; by reaction with a cyanocarbonimidate such as diphenylcyanocarbonimidate in a suitable solvent such as DMF in the presence of a base such as diisopropylethylamine at from room temperature to 80° C., followed by reaction with an amine such as methylamine at about room temperature). The compound 5 wherein $R_1$ is halogen, e.g. bromine, may be prepared from the compound 5 wherein $R_1$=H by reaction with a halogenating agent, e.g. tetrabutylammonium perbromide, in an inert solvent such as chloroform at about room temperature. Where $R_1$ or $R_2$ contain $CH_2OH$, the acylation may be performed in such a manner as to obtain the diamide ester; the ester may then be cleaved, e.g., by sodium methoxide in methanol and the resulting alcohol oxidized to an acid, e.g., by Jones reagent; the N1 amide may then be cleaved, e.g., by KOH in aqueous methanol at reflux, and the acid may be coupled with amines under standard peptide coupling conditions to form compounds 5 of Scheme 1 where $R_1$ or $R_2$ is a carboxamide. Where $R_1$ or $R_2$ contain $CH_2O$-Prot, the protecting group may be removed, e.g., Boc by treatment with an acid such as TFA in an inert solvent such as dichloromethane to form a compound 5 or 6 where $R_1$ or $R_2$ is $CH_2OH$. The compound 5 where $R_1$ or $R_2$ is aryloxyalkyl is prepared from a compound 5 where $R_1$ or $R_2$ is $CH_2OH$ by transformation of the alcohol into a leaving group such as a triflate. e.g., by treatment with triflic anhydride in dichloromethane at –40° C., and displacement with an aralkoxide salt, e.g., in dichloromethane at from –40° C. to room temperature. The compound 5 where $R_1$ or $R_2$ is $CH_2NH_2$ is prepared from a compound 5 where $R_1$ or $R_2$ is $CH_2OH$ by transformation of the alcohol into a leaving group such as a triflate. e.g., by treatment with triflic anhydride in dichloromethane at –40° C., and displacement with ammonia, e.g., in dichloromethane at from –40° C. to room temperature. The amine may be subsequently coupled to carboxylic acids by standard amide bond coupling conditions. Where the compound 5 is sulfonylated with a beta-haloalkylsulfonyl halide, the halide may then be eliminated by a base such as diisopropylethylamine and then nucleophiles such as dimethylamine or sodium imidazolate may be added to the resulting unsaturated sulfonamide by treatment in an organic solvent such as THF or dichloromethane at from room temperature to reflux. Where the compound 5 is acylated or sulfonylated with an acylating or sulfonylating agent which contains a leaving group, e.g. chloride or bromide, that leaving group may be displaced by nucleophiles, e.g., by amines such as dimethylamine or N-methylpiperazine in an inert solvent such as THF or DMF in the presence of an optional base such as diisopropylethylamine at from 0° C. to 110° C.

Step 5

Thereafter the various products can undergo reductive alkylation in the presence of an acid e.g. acetic acid, a reducing agent e.g. $NaBH(OAc)_3$ in an inert organic solvent e.g. dichloroethane at about room temperature. Reductive alkylation may also be performed using hydrogen and a catalyst such as Pd on carbon in a solvent such as ethanol in the presence of an acid such as acetic acid at about room temperature.

Thereafter, the compound of Scheme 1 where $R_1$=halogen can be metallated and quenched, e.g., with water to form the compound where $R_1$=H or with carbon dioxide to form the compound where $R_1$=$CO_2H$; this acid may be coupled with amines under standard peptide coupling conditions to form compounds of Scheme 1 where $R_1$ is a carboxamide. The compound of Scheme 1 wherein $R_1$=halogen can be metallated and quenched with a ketone such as cyclohexanone followed by reduction of the alcohol with for example trifluoroacetic acid/sodium borohydride to form the compound where $R_1$=e.g., cyclohexyl. The compound of Scheme 1 in which the imidazole contains a 2-dimethylaminomethyl group can be prepared by standard Mannich conditions. The compound of Scheme 1 in which $R_1$=OH can be prepared from the compound of Scheme 1 in which $R_1$=OMe by dealkylation, e.g., by treatment with $BBr_3$. The compound of Scheme 1 in which $R_1$=arylOalkyl can be prepared from the compound of Scheme 1 in which $R_1$=HOalkyl by Mitsunobu reaction with the aryl alcohol. The compound of Scheme 1 in which $R_3$=aryl-$NH_2$ or heteroaryl-$NH_2$ can be prepared from the compound of Scheme 1 in which $R_3$=aryl-$NO_2$ or heteroaryl-$NO_2$ by reduction (e.g., $SnCl_2$) under standard conditions. The product can be further acylated, sulfonylated or reductively aminated under standard conditions.

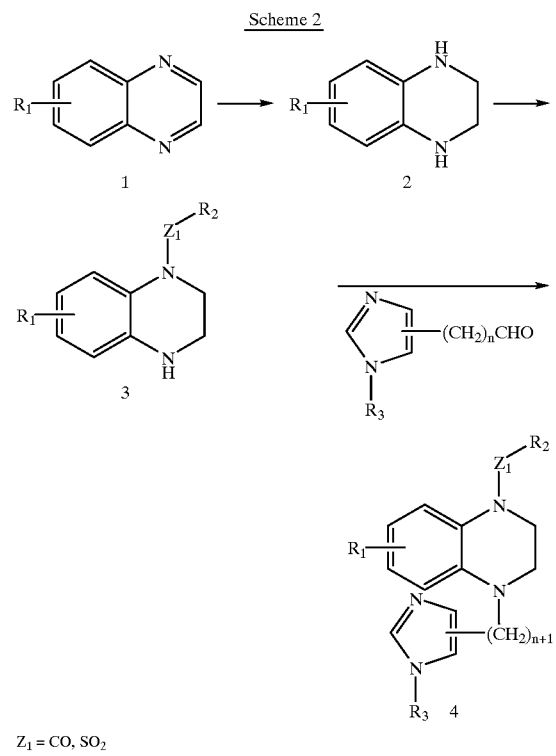

Scheme 2

$Z_1$ = CO, $SO_2$

Step 1

In Scheme 2 the starting material is reduced via hydrogenation in the presence of platinum oxide. The reaction is carried out in the presence of an alcohol e.g. ethanol at about room temperature.

Step 2 and 3

Thereafter the product is monoacylated or monosulfonylated under standard conditions at from –78° C. to room temperature (e.g., by reaction with an acid halide $R_2COX$ wherein X is Cl or Br in an inert organic solvent, e.g. acetonitrile, or in a mixed aqueous/organic solvent e.g.

NaOH/methylene chloride; or by reaction with a sulfonyl halide $R_3SO_2X$ wherein X is Cl or Br in an organic solvent e.g. $CH_2Cl_2$ in the presence of a base such as triethylamine). Thereafter the product undergoes a reductive alkylation as outlined in the last step of Scheme 1.

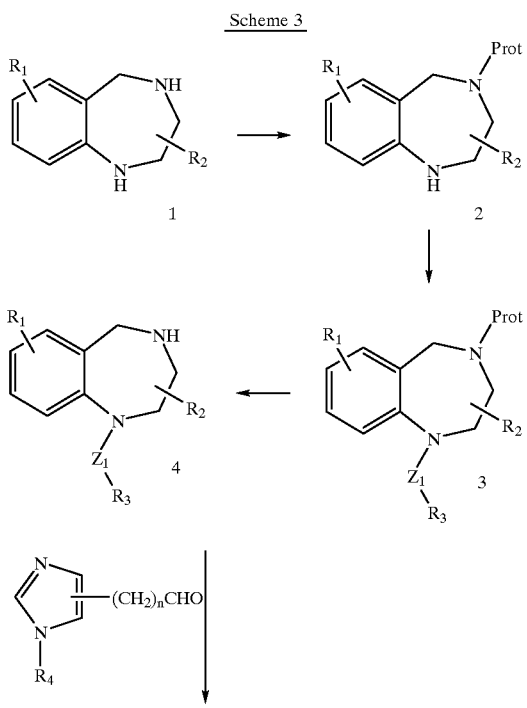

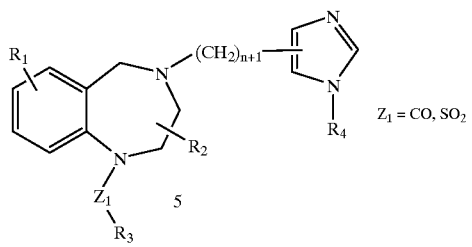

In Scheme 3, compound 1 is suitably protected by, for example, a tertbutoxycarbonyl group. The reaction is carried out in an inert organic solvent e.g. THF at about room temperature. The compound 2 where $R_1$ is an amine may be selectively acylated, e.g., by reaction with isobutylchloroformate in an inert solvent such as methylene chloride in the presence of a base such as diisopropylethylamine at about room temperature. The compound 2 where an $R_1$ is $R_5CONH$ and another $R_1$ is Br is prepared from the compound where an $R_1$ is $R_5CONH$ by bromination, e.g. with tetrabutylammonium tribromide in an inert solvent such as chloroform at about room temperature. Thereafter the compound 2 is reacted with a compound of the formula $R_3COCl$ in the presence of pyridine in an inert organic solvent, such as, dichloroethane at from about 0° C. to room temperature. Thereafter the compound 3 is deprotected by reaction with, for example, trifluoroacetic acid in an inert organic solvent, such as, dichloroethane at about room temperature. Thereafter the compound 4 undergoes reductive alkylation following the steps outlined in Scheme 1.

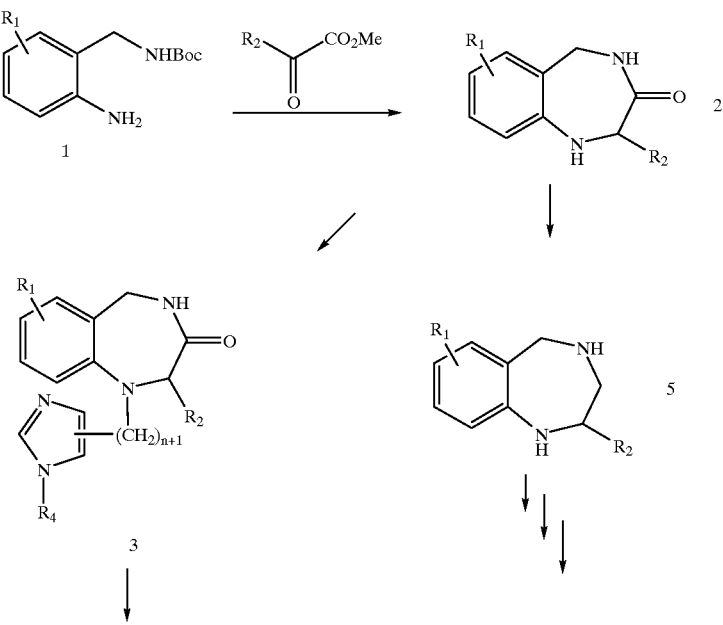

-continued

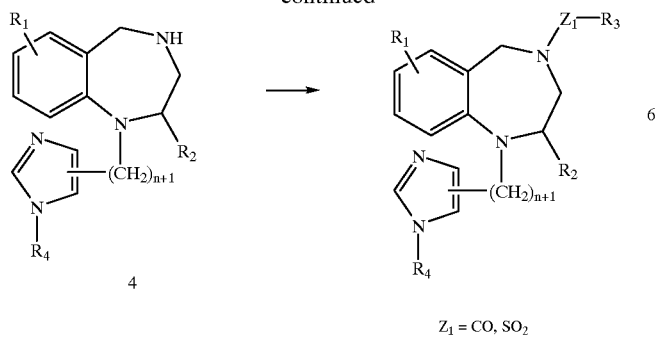

In Scheme 4 the compound 1 is reacted with a compound of the formula $R_2COCO_2Me$ in the presence of an organic acid e.g. acetic acid, a reducing agent, such as, $NaCNBH_3$ or $NaBH(OAc)_3$ in an inert organic solvent, such as, dichloroethane at about room temperature. The intermediate is thereafter deprotected by reaction with, for example, trifluoroacetic acid in an inert organic solvent, e.g. $CH_2Cl_2$ at about room temperature, and cyclized by heating, e.g., at 60° C. to form the compound 2. Thereafter the compound 2 undergoes reductive alkylation as outlined in Scheme 1 to form a compound 3. The compound 3 may be reduced, e.g. with lithium aluminum hydride, to a compound 4, which may be reacted to form a compound 6 as described in Scheme 12. Alternatively, the compound 2 is reduced to the compound 5, as outlined in Scheme 1, and the compound 5 is reacted as outlined in Scheme 1.

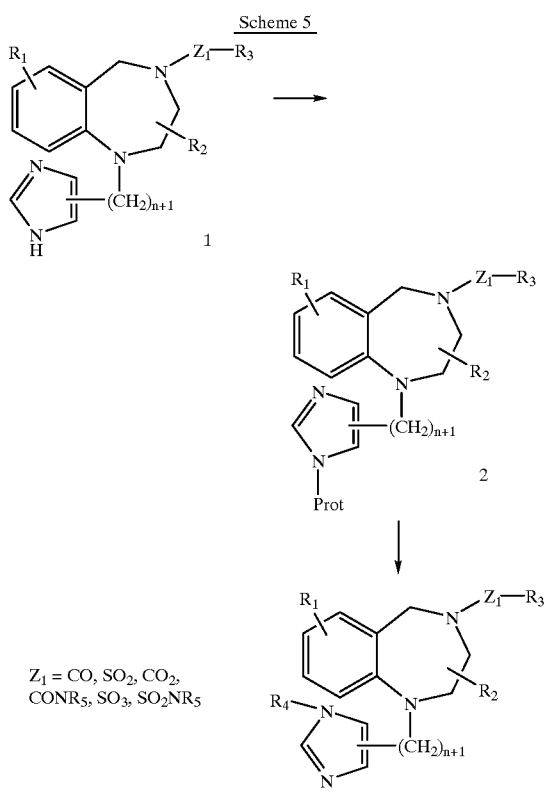

In Scheme 5 the compound 1 is protected by reaction with, for example, triphenylmethyl chloride or Boc anhydride in an inert organic solvent e.g. acetonitrile or tetrahydrofuran, from about room temperature to reflux. Thereafter the compound 2 is reacted with a compound of the formula $R_4$-L wherein L is a leaving group such as triflate, in the presence of a base such as diisopropylethylamine in an inert organic solvent such as tetrahydrofuran at from about −78° C. to room temperature. $R_4$ may contain a protecting group, e.g., phthalimide, removable by e.g. hydrazine. The reaction of Scheme 5 with $R_4$-L may also be performed on a compound 1 to directly produce a compound 3 without protection/deprotection.

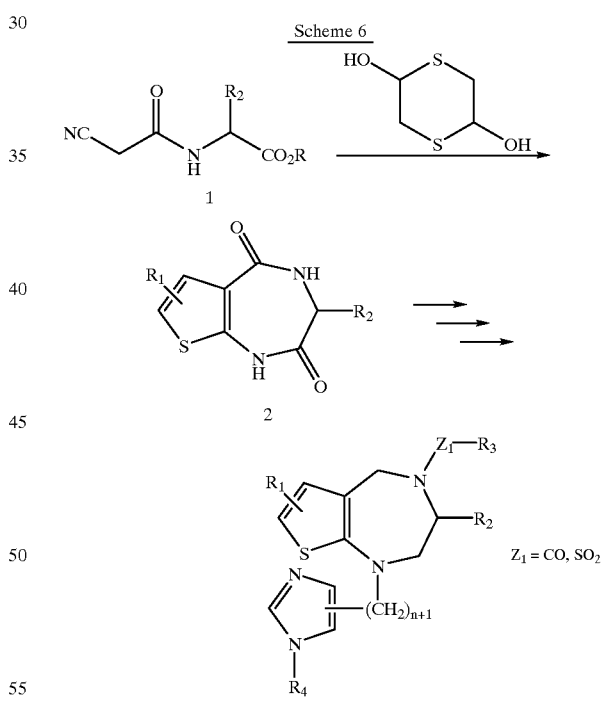

In Scheme 6, a cyanoacetylamino acid is reacted with a dithianediol in a suitable solvent such as ethanol in the presence of bases such as piperidine and triethylamine at from room temperature to 80° C. The intermediate is then cyclized in a suitable solvent such as pyridine in the presence of a catalyst such as pyridinium hydrochloride at an elevated temperature such as 130° C. Thereafter the compound 2 is reacted as described in Scheme 1.

Scheme 7

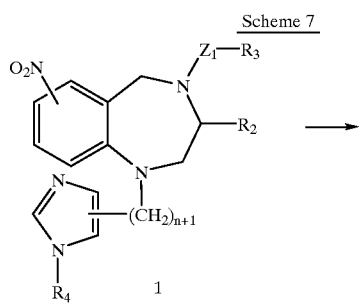

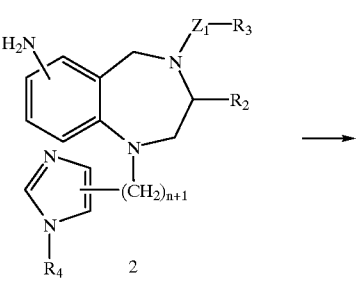

$Z_1$ = CO, $SO_2$, $CO_2$, $CONR_5$, $SO_2NR_5$
$U_1$ = CO, $SO_2$, $CO_2$, $CONR_5$, $SO_2NR_5$ or absent The compound 1 of Scheme 7 undergoes reduction (e.g., Fe, $SnCl_2$, or $TiCl_3$) under standard conditions. The compound 2 is acylated or sulfonylated under standard conditions (e.g., by reaction with an anhydride and an acylation catalyst such as DMAP, by reaction with an acid halide, by reaction with a carboxylic acid under standard peptide coupling conditions, by reaction with an alkoxycarbonylchloride, by reaction with an isocyanate, by reaction with a sulfonyl halide or by reaction with a sulfamyl chloride) or reductively alkylated under standard conditions (e.g., by reaction with an aldehyde and a reducing agent such as $NaCNBH_3$ or $Na(OAc)_3BH$ in an organic solvent such as dichloroethane or DMF in the presence of an acid such as acetic acid at from 0° C. to room temperature).

Scheme 8

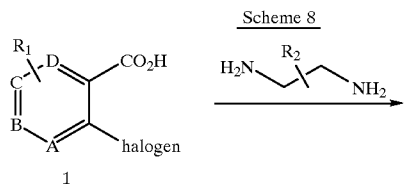

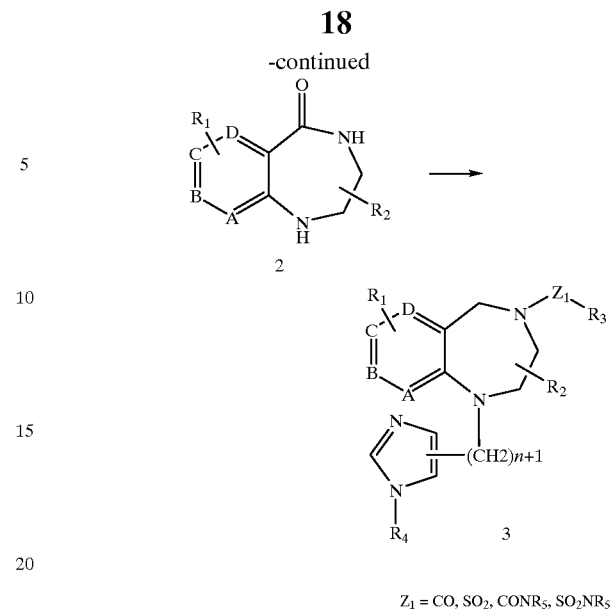

$Z_1$ = CO, $SO_2$, $CONR_5$, $SO_2NR_5$

The compound 1 of Scheme 8 is reacted with an ethylenediamine and the product 2 undergoes reduction, selective acylation or sulfonylation and reductive alkylation to produce a compound 3 as outlined in Scheme 1. Alternatively, Step 1 of Scheme 8 may be performed in 2 steps, wherein the ethylenediamine is condensed with the halogenated heterocycle either neat or in an organic solvent at elevated temperature and the resulting amino acid is cyclized under standard amide bond forming conditions, e.g., using HOBt/carbodiimide in an organic solvent such as DMF or pyridine at from 0° C. to room temperature. Some compounds 1 of Scheme 8 wherein $R_1$=halogen are not commercially available. Such compound 2 of Scheme 8 wherein $R_1$=halogen can be prepared from compound 2 of Scheme 8 wherein $R_1$=hydrogen by halogenation, for example by reaction with bromine in an organic solvent such as acetic acid at from 0° C. to room temperature. The compound 2 wherein $R_1$=aryl or heteroaryl can be prepared from the compound 2 wherein $R_1$ is halogen or trifluoromethanesulfonyloxy by standard Suzuki or Stille couplings as described for Step 2 of Scheme 1. Thereafter the product undergoes reduction, acylation or sulfonylation, and reductive alkylation as outlined in Scheme 1. Compound 2 of Scheme 8 may itself undergo reductive alkylation with an imidazole containing aldehyde as outlined in Scheme 1 to afford a target compound.

Scheme 9
(imidazole aldehydes)

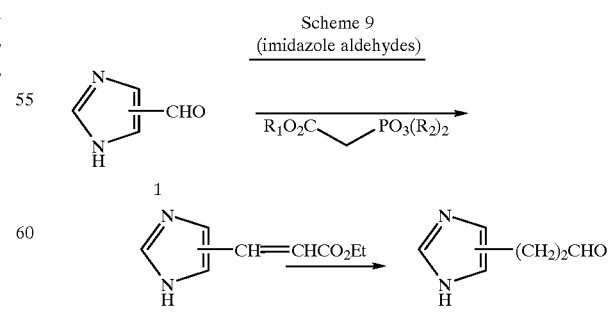

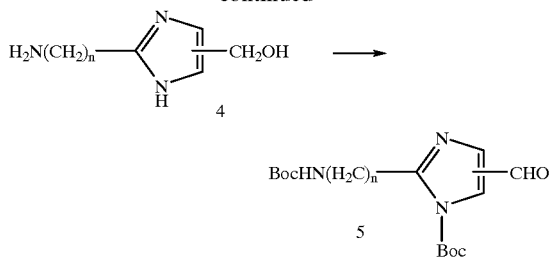

Some imidazole aldehydes are prepared as follows. An imidazole containing aldehyde undergoes a Wittig reaction with a compound of the formula triethylphosphonoacetate in the presence of a base, such as, sodium hydride in an inert organic solvent, such as dimethoxyethane, at from about 0° C. to room temperature. The product is hydrogenated in an alcohol e.g. ethanol at about room temperature and reduced by reaction with DIBAL in for example dichloroethane at about −78° C. Alternatively, some aminoalkyl containing imidazolylalkanols, prepared by known methods (e.g., Buschauer, et. al., Arch. Pharm., 315, 563, (1982)) are protected with a Boc group as in Scheme 3, step 1, and undergo an oxidation, e.g. under Swern conditions.

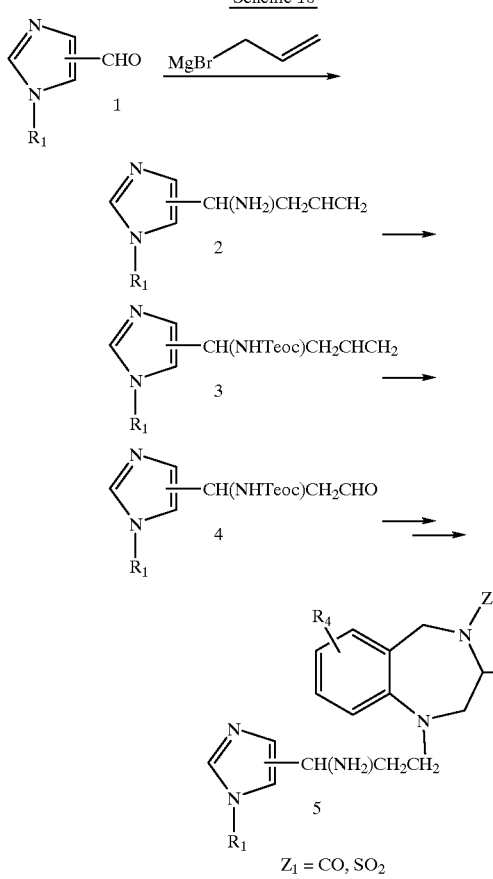

In Scheme 10 the starting material is reacted with allyl magnesium bromide in the presence of lithium hexamethyldisilazide in an inert solvent e.g. THF at from about −78° C. to room temperature. The product is protected, e.g. with a Teoc group, in an aqueous/organic solvent e.g. aqueous dioxane at about room temperature. The product is oxidized by reaction with e.g. $OsO_4/NaIO_4$ in aqueous dioxane at about room temperature. Thereafter the product undergoes reductive alkylation as in Scheme 1 and thereafter the product is deprotected with tetrabutylammonium fluoride at from room temperture to 50° C. in THF.

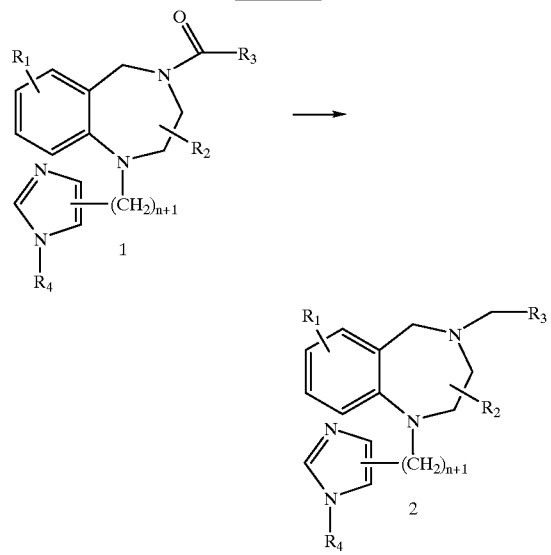

In Scheme 11 the starting material is reduced with e.g. lithium aluminum hydride in an inert organic solvent e.g. ethylene glycol dimethyl ether at from about 0° C. to reflux.

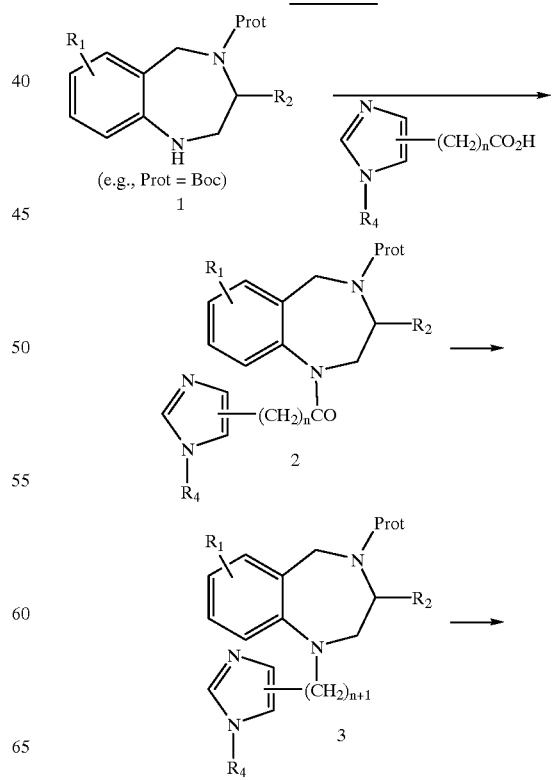

-continued

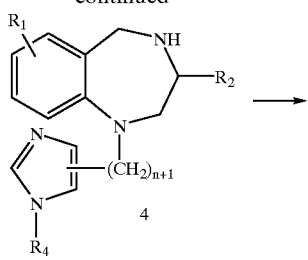
4

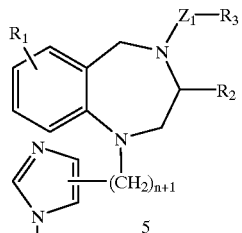
5

$Z_1$ = absent, CO, SO$_2$, CO$_2$, CONR$_5$, SO$_3$, SO$_2$NR$_5$

In step 1 of Scheme 12, a monoprotected benzodiazepine such as that described in Scheme 3 is coupled with an optionally protected imidazole-containing carboxylic acid using standard amide bond formation methods such as isobutylchloroformate in an organic solvent such as THF at from −30° C. to room temperature. In step 2 of Scheme 12, the resulting amide is reduced with for example borane in an organic solvent such as THF at from room temperature to reflux. A compound 3 of Scheme 12 may contain a nitro group which may be reduced, e.g., by TiCl$_3$, to an amine, which may then be acylated or sulfonylated as described in Scheme 7. In step 3 of Scheme 12, the amine protecting group is removed (e.g., Boc by an acid such as TFA in an organic solvent such as methylene chloride). In step 4 of Scheme 12, the resulting compound is reacted under standard conditions with a variety of active acylating or sulfonylating agents to form the claimed compound, such as acids under carbodiimide conditions or acid chlorides to form amides; carbonates or chloroformates to form carbamates; carbamyl chlorides or isocyanates to form ureas; sulfonyl chlorides to form sulfonamides; halosulfonates to form sulfamates; sulfamoyl chlorides to form sulfonylureas. In step 4 of Scheme 12, the resulting compound is alternatively reacted under standard reductive amination conditions with aldehydes as described in Step 5 of Scheme 1 to form the claimed compounds. If the imidazole is optionally protected, it is then deprotected.

Scheme 13

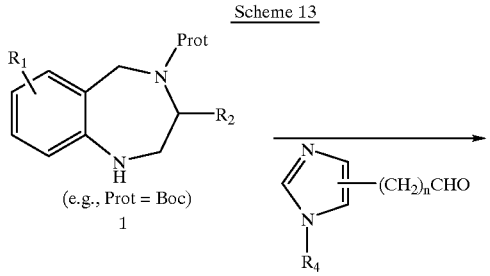

-continued

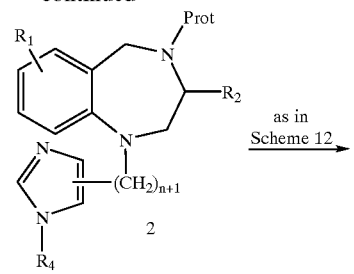
2 as in Scheme 12

In step 1 of Scheme 13, a monoprotected benzodiazepine such as that described in Scheme 3 is reductively alkylated with an imidazole-containing aldehyde and a reducing agent such as NaCNBH$_3$ or Na(OAc)$_3$BH in an organic solvent such as dichloroethane or DMF in the presence of an acid such as acetic acid at from 0° C. to room temperature. Thereafter, the product is reacted as described in Scheme 12. The product 2 may be attached to a solid support, e.g. polystyrene resin, and the reactions of Scheme 1 may be performed on resin-bound material. Removal from the support, e.g. by treatment with an acid such as trifluoroacetic acid in the presence of a scavenger such as triethylsilane at about room temperature, then provides the compound 6 of Scheme 1.

Scheme 14

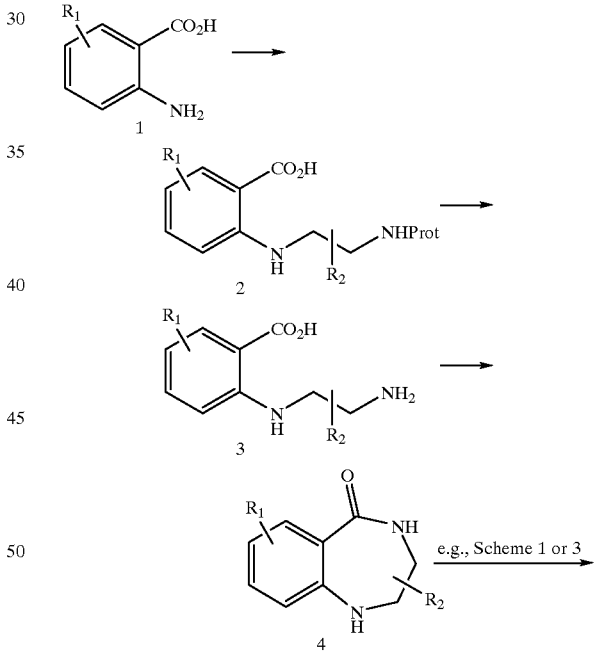

In step 1 of Scheme 14, an aminobenzoic acid is reductively aminated with an N-protected aminoaldehyde under standard conditions, e.g. by reaction with a hydride reagent such as sodium triacetoxyborohydride or sodium cyanoborohydride in a suitable solvent such as methylene chloride or methanol in the presence of an acid such as acetic acid at from 0° C. to about room temperature. The product is deprotected by, e.g., removal of Boc by treatment with an acid such as TFA or HCl in the presence of an optional scavenger such as dimethylsulfide in a suitable solvent such as methylene chloride or dioxane at about room temperature or removal of Fmoc by treatment with a secondary amine in tetrahydrofuran at about room temperature. Thereafter, the product is cyclized under standard amide bond forming conditions, such as by treatment with diphenylphosphoryl azide in an organic solvent such as DMF. Thereafter, the product is reacted as described in Scheme 1.

Scheme 15

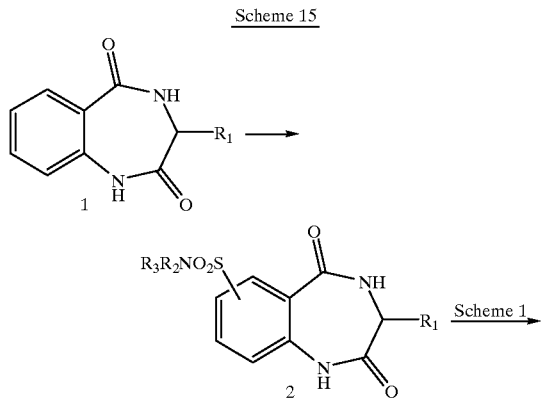

In step 1 of Scheme 15, a benzodiazepinedione is sulfonylated with chlorosulfonic acid and the resulting sulfonyl chloride is condensed with an amine. Thereafter, the product is reacted as described in Scheme 1.

Scheme 16

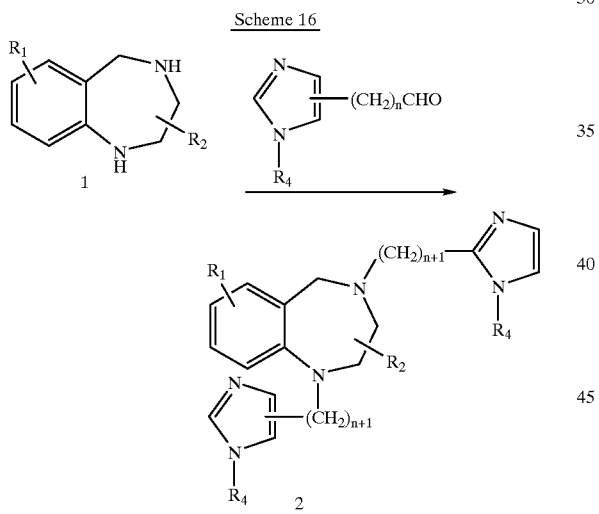

In step 1 of Scheme 16, a benzodiazepine of Scheme 1 can be doubly reductively alkylated with an imidazole containing aldehyde and a reducing agent such as NaCNBH$_3$ or Na(OAc)$_3$BH in an organic solvent such as dichloroethane or DMF in the presence of an acid such as acetic acid at from 0° C. to room temperature.

Scheme 17

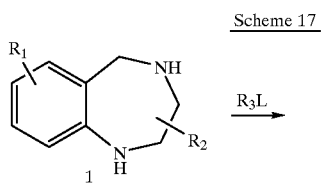

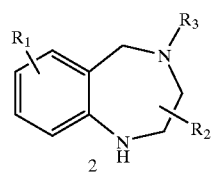

In step 1 of Scheme 17, a benzodiazepine of Scheme 1 can be reacted with R$_3$-L in an inert solvent such as DMF, THF or methylene chloride in the presence of a base such as diisopropylethylamine or potassium carbonate at from 0° C. to 100° C., where L is a leaving group such as chloride, bromide, mesylate, tosylate or triflate and R$_3$ is a substituted alkyl group, a substituted aryl group or a substituted heterocylic group. Thereafter, the product is reacted as described in Scheme 1.

Scheme 18

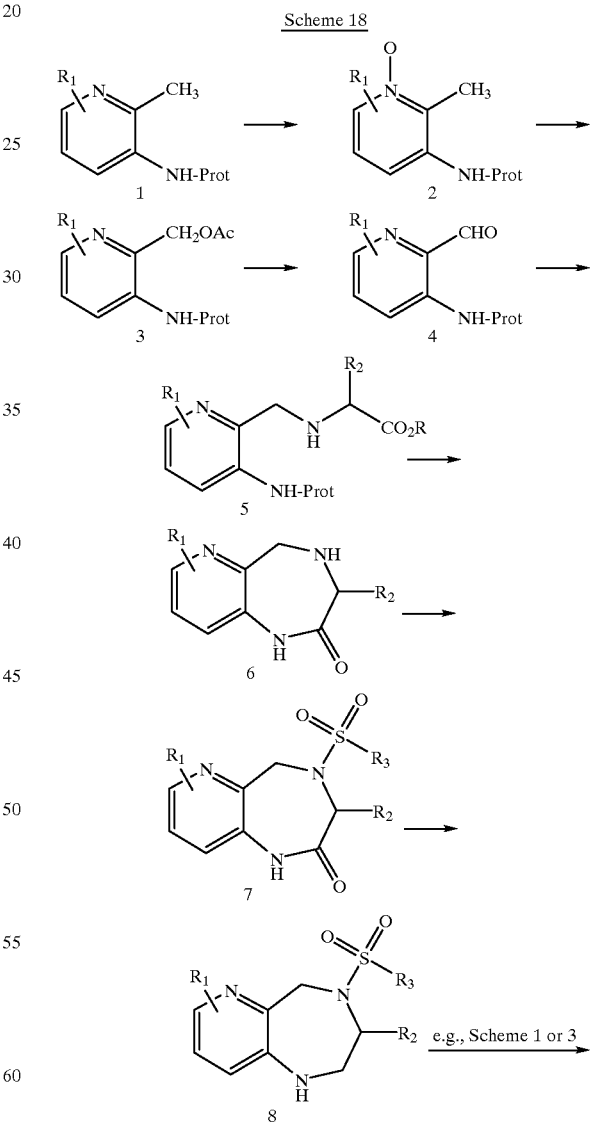

Step 1
The first step is accomplished by the reaction of a pyridine containing a protected amino group and a methyl group with an oxidizing agent, such as hydrogen peroxide in a suitable solvent such as aqueous acetic acid or trifluoroacetic acid at from room temperature to 75° C.

Step 2

The product is acylated with an acylating agent such as acetic anhydride and rearranged by heating from room temperature to 90° C. in a suitable solvent such as acetic acid.

Step 3

The product is deacylated, e.g., with aqueous NaOH at from room temperature to 50° C. and oxidized to the aldehyde with e.g. MnO$_2$ in a suitable solvent such as tetrahydrofuran at about room temperature.

Step 4

The product is reductively aminated with an aminoacid ester under standard conditions, e.g., by hydrogenation in an inert solvent such as methanol or by reaction with a hydride reagent such as sodium triacetoxyborohydride in a suitable solvent such as methylene chloride/acetic acid at about room temperature.

Step 5

The product is deprotected and cyclized with, e.g. treatment with polyphosphoric acid at from room temperature to 100° C.

Step 6

The product is sulfonylated as described for Step 4 of Scheme 1.

Step 7

The product is reduced as described for Step 3 of Scheme 1. Thereafter, the product is reacted as described in Step 5 of Scheme 1.

Scheme 19

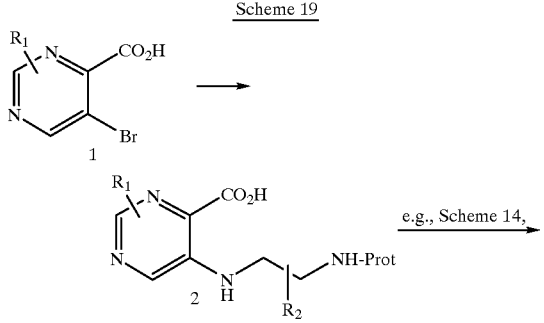

The first step is accomplished by the reaction of a pyrimidine containing a halide and a carboxylic acid group with an optionally monoprotected diamine in a suitable solvent such as water in the presence of a catalyst such as CuSO$_4$ at from room temperature to 100° C. Thereafter, the product is reacted as described in Scheme 14.

Scheme 20

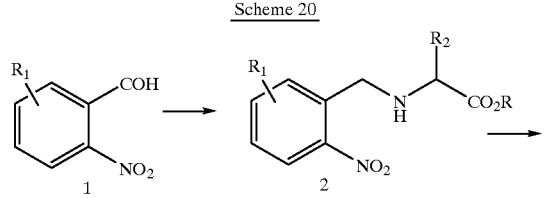

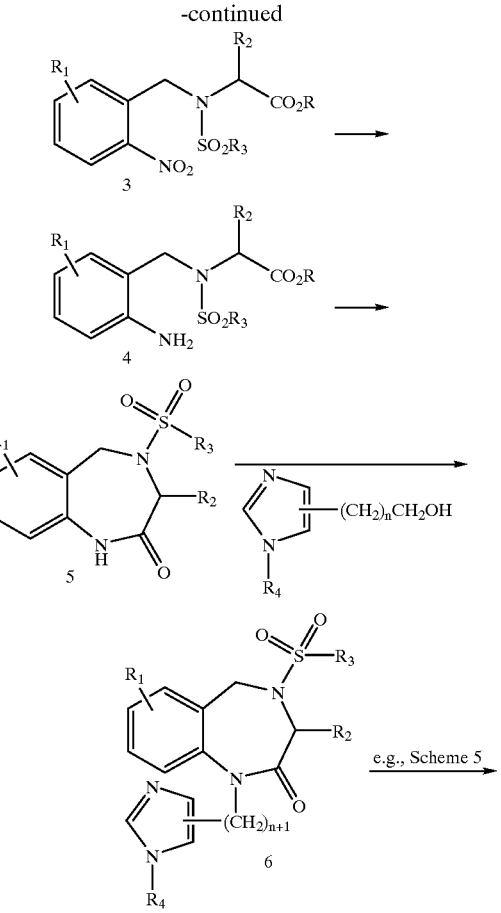

Step 1

The first step is accomplished by reductive amination of a nitrobenzaldehyde With an amino acid ester under standard conditions, e.g., by reaction with a hydride reagent such as sodium triacetoxyborohydride in a suitable solvent such as methylene chloride/acetic acid at about room temperature.

Step 2

The product is sulfonylated as described for Step 4 of Scheme 1.

Step 3

The nitro group of the product is reduced to an amine under standard conditions, such as reaction with SnCl$_2$ or TiCl$_3$. The compound where R$_1$=Br may be prepared from the compound where R$_1$=H by bromination, such as reaction with tetrabutylammonium perbromide in an inert solvent such as chloroform at about room temperature.

Step 4

The product is cyclized by heating with CuCN in an inert solvent such as N-methylpyrrolidinone at from room temperature to 195° C. The compound where R$_1$=CN is prepared from the compound where R$_1$=halogen under the same conditions.

Step 5

The product is alkylated with an optionally protected imidazolylalkanol under Mitsunobu conditions. Thereafter, the product is optionally reacted as described in Scheme 5.

Scheme 21

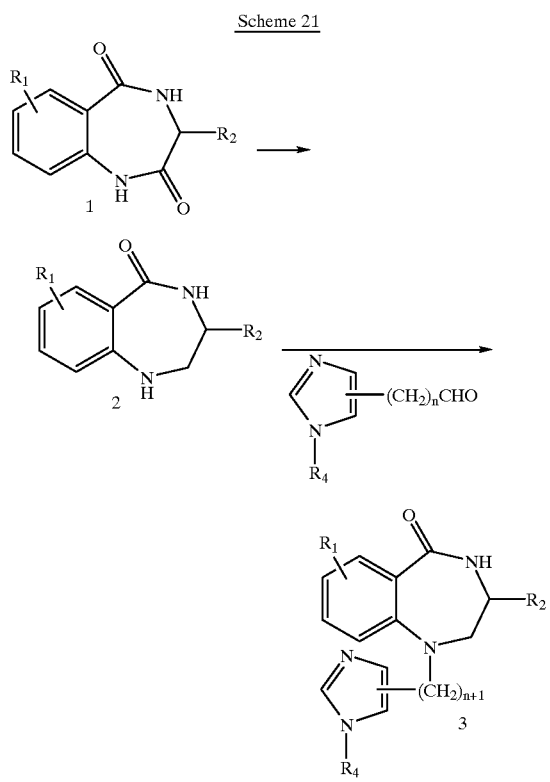

A compound 3 of Scheme 1 may be selectively reduced, e.g. by reaction with a reducing agent, such as borane in an inert organic solvent, such as, tetrahydrofuran at about room temperature. Thereafter, the product (2) is reductively aminated as described in Scheme 1.

Scheme 22

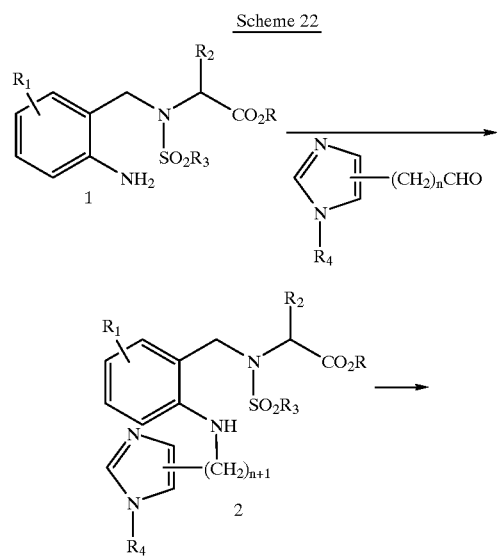

-continued

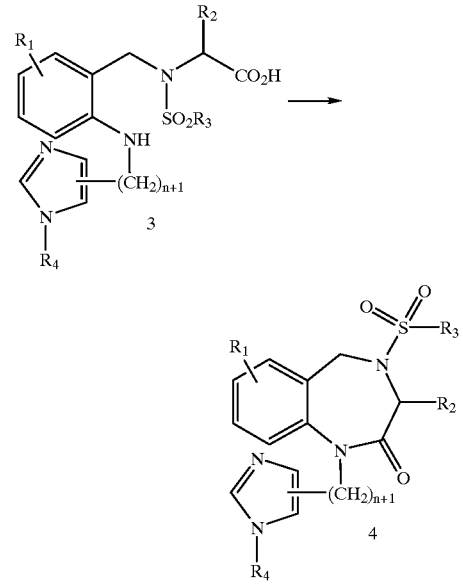

Step 1

A compound 4 of Scheme 20 may be first reductively aminated as described in Step 5 of Scheme 1.

Step 2

The optionally esterified ester of the product is hydrolyzed, e.g. by reaction with an alkali hydroxide in a suitable solvent such as aqueous alcohol at from room temperature to reflux.

Step 3

The product is cyclized by standard amide bond forming conditions, e.g. by reaction with BOP in an inert solvent such as DMF in the presence of an optional base such as diisopropylethylamine at about room temperature.

Scheme 23

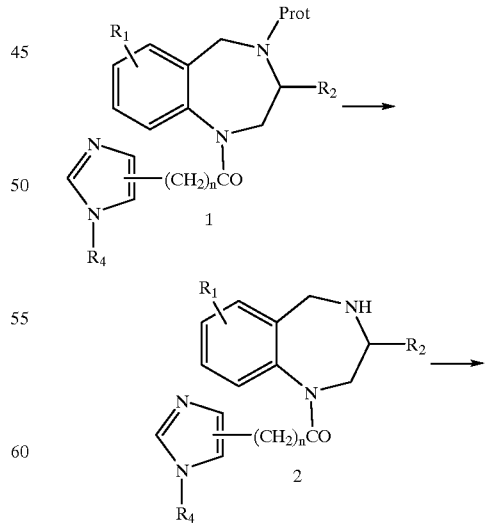

-continued

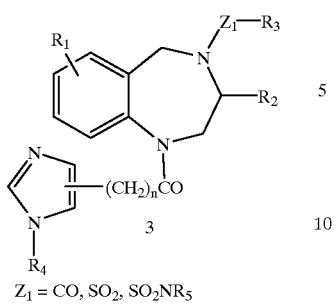

$Z_1 = CO, SO_2, SO_2NR_5$

-continued

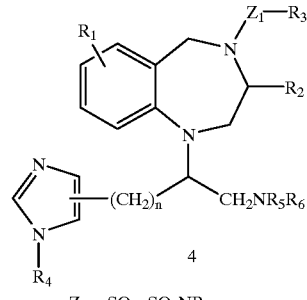

$Z_1 = SO_2, SO_2NR_5$

A compound 2 of Scheme 12 may be directly deprotected as described in Step 3 of Scheme 12 and reacted as described in Step 4 of Scheme 12. Alternatively, a compound 5 of Scheme 12 may be prepared by reduction, e.g. with lithium aluminum hydride or borane, of a compound 3 of Scheme 23, where $Z_1$ does not equal CO.

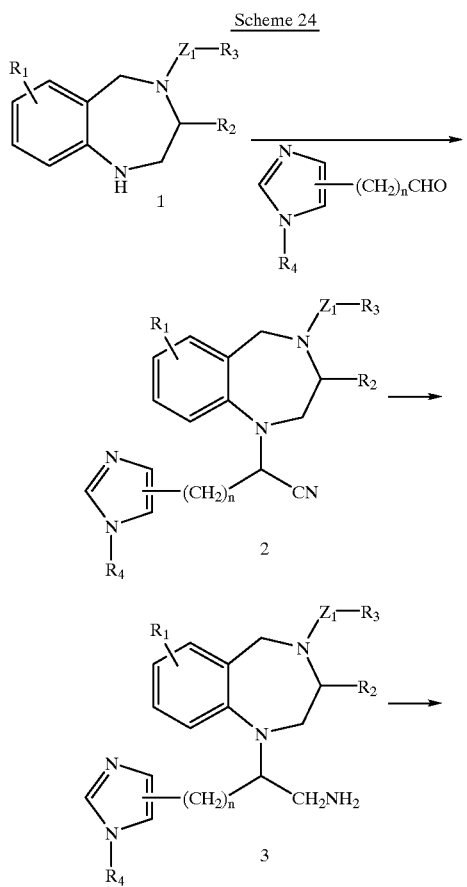

A compound 5 of Scheme 1 may be reacted with an imidazole containing aldehyde and an alkali cyanide such as NaCN in the presence of an acid such as acetic acid in a suitable solvent such as methanol/acetonitrile at about room temperature to form a compound 2. The compound 2 may be reduced, e.g. with lithium aluminum hydride, in a suitable solvent such as ether at about room temperature to form a compound 3. The compound 3 wherein $R_1$ is halogen, e.g. bromine, may be prepared from the compound 3 wherein $R_1$=H by reaction with a halogenating agent, e.g. tetrabutylammonium perbromide, in an inert solvent such as chloroform at about room temperature. The compound 3 may be reductively aminated under standard conditions to form the compound 4.

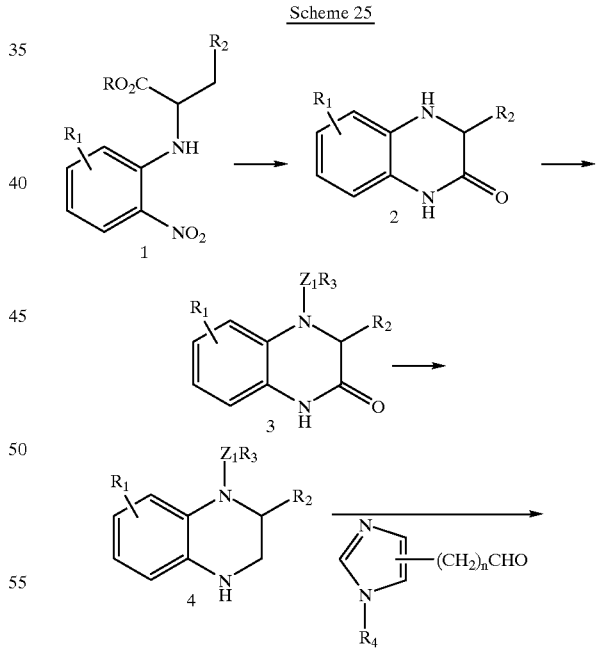

-continued

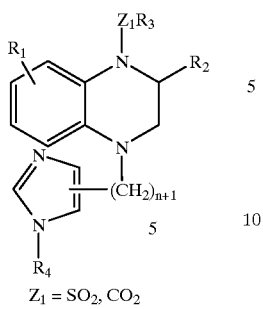

$Z_1 = SO_2, CO_2$

In step 1 of Scheme 25, an N-(2-nitroaryl)-amino acid ester, available by reaction of an amino acid with a 1-fluoro-2-nitrobenzene followed by esterification, is reduced, e.g. with hydrogen and a palladium catalyst in a suitable solvent such as ethyl acetate at about room temperature. The resulting amine is cyclized to a compound 2 under the reduction conditions. The compound 2 is acylated or sulfonylated as described in Step 4 of Scheme 1. The compound 3 is reduced, e.g. with borane in a suitable solvent such as methanol at about room temperature. The compound 3 wherein $R_1$ is halogen, e.g. bromine, may be prepared from the compound 3 wherein $R_1$=H by reaction with a halogenating agent, e.g. tetrabutylammonium perbromide, in an inert solvent such as chloroform at about room temperature. The compound 4 undergoes reductive amination with an imidazole containing aldehyde as described in Step 5 of Scheme 1.

Scheme 26

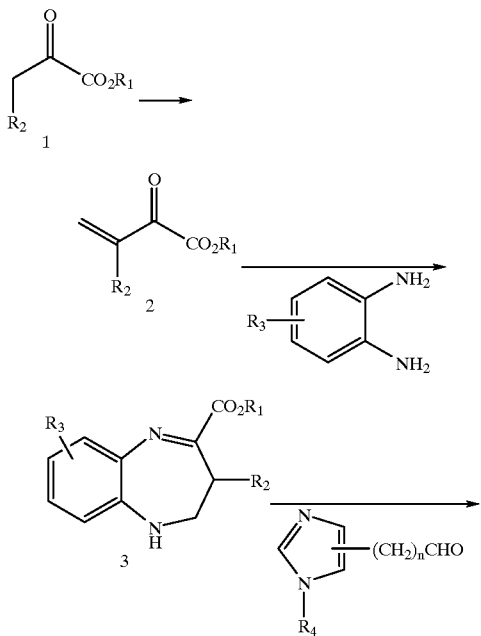

-continued

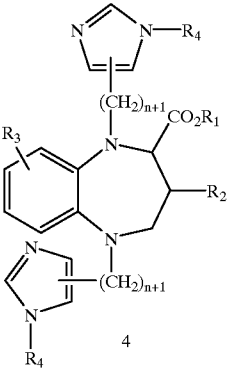

In step 1 of Scheme 26, the compound 1 is reacted with a methylenating agent such as N,N,N'N'-tetramethyldiaminomethane in a suitable solvent such as acetic anhydride and DMF at about room temperature. Thereafter, the compound 2 is reacted with a 1,2-phenylenediamine in a suitable solvent such as toluene at about 115° C. under dehydrating conditions, e.g. with a Dean-Stark trap, in the presence of a hydroquinone. Thereafter, the compound 3 is both reduced and reductively aminated as described in Step 5 of Scheme 1.

The invention will now be further described by the following working examples(s), which are preferred embodiments of the invention. All temperatures are in degrees Celsius (°C.) unless otherwise indicated. These examples are illustrative rather than limiting.

EXAMPLE 1

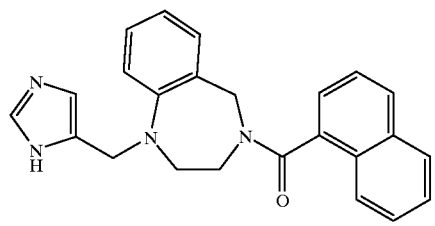

2,3,4,5-Tetrahydro-1-(1H-imidazol-4-ylmethyl)-4-(1-naphthalenylcarbonyl)-1H-1,4-benzodiazepine, hydrochloride.

A. 1,4-Benzodiazepine-2,5-dione.

A stirred solution of isatoic anhydride (16.4 g, 0.1 mol) and glycine ethyl ester hydrochloride in 40 mL of pyridine was heated under reflux for 7 h. The resulting suspension was cooled to 0° C. for 18 h. The precipitate was collected and washed with ethanol and ether to give Compound A as a light yellow solid.

B. 2,3,4,5-Tetrahydro-1H-1,4-benzodiazepine

To a stirred suspension of lithium aluminum hydride (LAH, 3.5 g, 90 mmol) in THF (100 mL) at room temperature under argon was slowly added Compound A (3.5 g, 20 mmol) portionwise as a solid. After the addition, the resultant suspension was heated at reflux under argon for 18 h, cooled to 0° C., and a mixture of $NH_4OH$ (5 mL, conc.) in 30 mL of THF was added via an additional funnel. The resultant suspension was stirred for 1 h and filtered. The filtrate was concentrated in vacuo to give Compound B as an oil.

C. 2,3,4,5-Tetrahydro-4-(1-naphthalenylcarbonyl)-1H-1,4-benzodiazepine

A mixture of Compound B (500 mg, 3.37 mmol) and 1-naphthoic acid, phenyl ester (750 mg, 3.02 mmol) in a small amount of acetonitrile in the presence of a catalytic amount of dimethylaminopyridine (DMAP) was heated at 110° C. for 18 h under argon. The mixture was cooled to room temperature. The product was isolated by flash column chromatography (1:1 ethyl acetate:hexanes) to give Compound C as a white solid (520 mg).

D. 2,3,4,5-Tetrahydro-1-(1H-imidazol-4-ylmethyl)-4-(1-naphthalenylcarbonyl)-1H-1,4-benzodiazepine, hydrochloride To a stirred solution of Compound C (200 mg, 0.66 mmol) and 4-formylimidazole (110 mg, 1.15 mmol) in a mixture of dichloroethane (2 mL) and acetic acid (1.0 mL), NaBH(OAc)$_3$ (190 mg) was added in one portion. The mixture was stirred for 30 min and diluted with ethyl acetate (25 mL) followed by NH$_4$OH (3 mL, conc.). The mixture was stirred at room temperature for 18 h and poured into a mixture of ethyl acetate (50 mL) and sat. NaHCO$_3$ (50 mL). The organic layer was separated and the aqueous layer was extracted with ethyl acetate (50 mL). The combined organic extracts were washed with sat. NH$_4$Cl solution (50 mL), dried over Na$_2$SO$_4$ and concentrated in vacuo. The residue was dissolved in methanol (2 mL), and 1 N HCl solution in ether (2 mL) was added. The solvent was removed in vacuo and the residue was dried under vacuum to give Example 1 as a light yellow solid (240 mg).

MS: (M+H)$^+$ 383$^+$ Analysis calculated for C$_{24}$H$_{22}$N$_4$O.1.75 HCl.2.5 H$_2$O. Calc'd: C, 58.67; H, 5.90; N, 11.41; Cl, 12.63. Found: C, 58.48; H, 6.10; N, 11.32; Cl, 12.46.

EXAMPLE 2

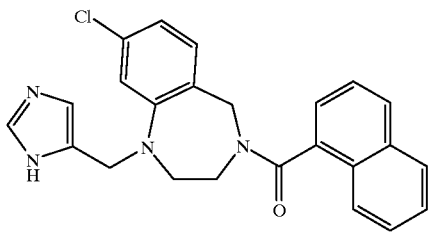

8-Chloro-2,3,4,5-tetrahydro-1-(1H-imidazol-4-ylmethyl)-4-(1-naphthalenylcarbonyl)-1H-1,4-benzodiazepine, hydrochloride A. 8-Chloro-1,4-benzodiazepin-2,5-dione A solution of 7-chloro-isatoic anhydride (34 g, 0.17 mol) and glycine ethyl ester hydrochloride (24 g, 0.17 mol) in anhydrous pyridine (120 ml) was warmed at 80° C. for 1 hour and refluxed overnight. The resulting suspension was stirred at room temperature for 3 hrs. The precipitate was filtered, washed with water and dried to give 4.4 g of Compound A as a white solid. The filtrate was evaporated and the resulting solid was washed with water and dried to provide an additional 27.2 g of Compound A as a white solid (85% total yield). MS (M+H) 211.

B. 8-Chloro-2,3,4,5-tetrahydro-1H-1,4-benzodiazepine

To Compound A (1.4 g, 6.6 mmol) in ethylene glycol dimethyl ether (20 ml) was added borane-THF (1.0 M in THF, 20 ml). The clear solution was refluxed for 6 hrs. The solvent was evaporated and the residue was treated with sat. sodium bicarbonate. The aqueous solution was extracted with methylene chloride. The organic solution was washed with sat. sodium bicarbonate and brine, dried (sodium sulfate) and evaporated to afford an oil (1.0 g). The crude product was purified by chromatography(10% methanol in methylene chloride) to provide Compound B as a slightly yellow solid (0.56 g, 46%). MS (M+H) 183.

C. 8-Chloro-2,3,4,5-tetrahydro-4-(1-naphthalenylcarbonyl)-1H-1,4-benzodiazepine

To a solution of Compound B (0.154 g, 0.84 mmol) in methylene chloride (4 ml) and sodium hydroxide (1N, 4 ml) at 0° C. was added 1-naphthoyl chloride (0.12 ml, 0.84 mmol) in methylene chloride (1 ml) dropwise. The solution was stirred for 1 hour, the organic layer was separated and the aqueous layer was extracted with methylene chloride. The combined organic layers were dried (sodium sulfate) and evaporated. The resulting oil was chromatographed (silica, 5% methanol, 0.5% ammonium hydroxide, 94.5% methylene chloride) to provide Compound C as a yellow solid (0.26 g, 90%). MS (M–H) 335.

D. 8-Chloro-2,3,4,5-tetrahydro-1-(1H-imidazol-4-ylmethyl)-4-(1-naphthalenylcarbonyl)-1H-1,4-benzodiazepine, hydrochloride Compound D was prepared from Compound C as described for Compound D of Example 1. Chromatography (silica, 5% methanol, 0.5% ammonium hydroxide, 94.5% methylene chloride) followed by preparative HPLC and conversion to the hydrochloride salt provided Example 2 as an off white solid, m.p. 160–162° C.

MS: (M+H)$^+$ 383$^+$ Analysis calculated for C$_{24}$H$_{21}$N$_4$OCl.1.85 HCl.2.5 H$_2$O. Calc'd: C, 59.51; H, 4.76; N, 11.57. Found: C, 59.42; H, 4.84; N, 11.48.

EXAMPLE 3

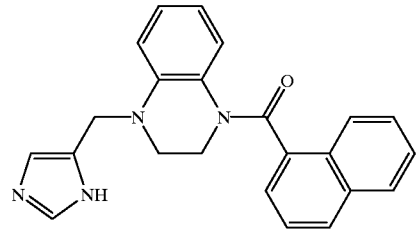

1,2,3,4-Tetrahydro-4-[(3H-imidazol-4-yl)methyl]-1-(naphthalen-1-ylcarbonyl)quinoxaline, dihydrochloride.

A. 1,2,3,4-Tetrahydro-quinoxaline

Pt(IV)O$_2$ (Adams' catalyst, 200 mg) was added to a solution of quinoxaline (2.75 mg, 21 mmol) in absolute EtOH (100 mL) and the mixture was hydrogenated (1 atm) at rt for 6 hrs. The mixture was fitered through Celite and the filtrate was concentrated to give 2.74 g of Compound A as an off-white solid (97%). MS (M+H) 135.

B. 1,2,3,4-Tetrahydro-1-(naphthalen-1-ylcarbonyl)quinoxaline

Naphthoyl chloride (1.12 mL, 7.45 mmol) was added to a solution of Compound A (1.0 g, 7.45 mmol) and triethylamine (TEA, 2.1 mL, 14.9 mmol) in CH$_2$Cl$_2$ (100 mL) at –78° C. After 2 hrs, the cooling bath was removed the mixture was stirred at rt for 1 hr and concentrated. The residue was purified by flash chromatography (silica, 95:5:0.1, CHCl$_3$:MeOH:NH$_4$OH) to afford Compound B as an off-white solid (2.04 g, 95%). MS (M+H) 289.

C. 1,2,3,4-Tetrahydro-4-[(3H-imidazol-4-yl)methyl]-1-(naphthalen-1-ylcarbonyl)quinoxaline, dihydrochloride Compound C was prepared from Compound B as described for Compound D of Example 1. Chromatography (silica, 10% ethanol/ethyl acetate) provided a clear yellow oil which was converted to the hydrochloride with 4N HCl in dioxane (4 mL, rt for 2 hrs) to give Example 3 as an off-white solid.

MS: (M+H)+ 289+ Analysis calculated for $C_{23}H_{20}N_4O \cdot 1.9$ HCl. Calc'd: C, 63.10; H, 5.04; N, 12.47. Found: C, 63.10; H, 5.39; N, 12.47.

EXAMPLE 4

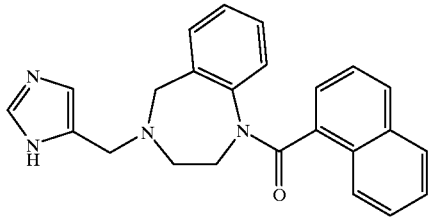

2,3,4,5-Tetrahydro-4-(1H-imidazol-4-yl-methyl)-1-(1-naphthalenylcarbonyl)-1H-1,4-benzodiazepine, dihydrochloride, A. 2,3,4,5-Tetrahydro-4-[(1,1-dimethylethoxy)-carbonyl]-1H-1,4-benzodiazepine To a stirred solution of Compound B of Example 1 (300 mg) was added di-t-butyldicarbonate (400 mg). The mixture was stirred at room temperature for 18 h and quenched by the addition of sat. $NaHCO_3$ solution. The solvent was removed and the residue was chromatographed (flash, silica, 1:2 ethyl acetate:hexanes] to give Compound A as an oil (350 mg).

B. 2,3,4,5-Tetrahydro-1-(1-naphthalenylcarbonyl)-4-[(1,1-dimethylethoxy)-carbonyl]-1H-1,4-benzodiazepine To a stirred solution of Compound A (350 mg, 1.4 mmol) in methylene chloride at 0° C. under argon, was added 1-naphthoyl chloride (0.22 mL, 1.4 mmol), followed by pyridine (0.25 ml). The mixture was stirred for 2 h. Sat. $NaHCO_3$ was added and the mixture was stirred for 18 h at room temperature. The resultant solution was poured into a mixture of methylene chloride and sat. NaHCO3. The organic layer was separated, washed with 10% HCl (2×25 mL), dried (MgSO4) and concentrated in vacuo to give to give Compound B as an oil (450 mg, 80%).

C. 2,3,4,5-Tetrahydro-1-(1-naphthalenylcarbonyl)-1H-1,4-benzodiazepine

Compound B was dissolved in a mixture of methylene chloride and TFA (10 mL, 1:1). The solution was stirred at room temperature for 2 h. The solvent was removed in vauo, the residue was diluted in CHCl3 and made basic with 10 N NaOH solution. The organic layer was separated, dried (MgSO4) and concentrated to give Compound C as an oil (310 mg, 92%).

D 2,3,4,5-Tetrahydro-4-(1H-imidazol-4-yl-methyl)-1-(1-naphthalenylcarbonyl)-1H-1,4-benzodiazepine, dihydrochloride Example 4 was prepared as a light yellow solid from Compound C as described for Compound D of Example 1.

Analysis calculated for $C_{24}H_{22}N_4O \cdot 2.0$ HCl$\cdot 1.3$ $H_2O$ Calc'd: C, 60.20; H, 5.60; N, 11.70; Cl, 14.82. Found: C, 60.21; H, 5.60; N, 11.48; Cl, 14.68.

EXAMPLE 5

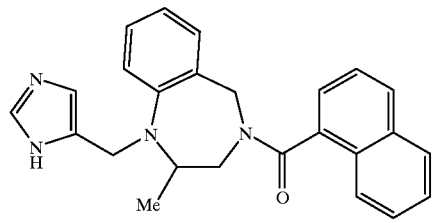

2,3,4,5-Tetrahydro-1-(1H-imidazol-4-yl-methyl)-2-methyl-4-(1-naphthalenylcarbonyl)-1H-1,4-benzodiazepine, hydrochloride.

A. 2-Methyl-1,4-benzodiazepin-3-one

The Boc derivative of Compound A was prepared from 2-amino-N-[(1,1-dimethylethoxy)-carbonyl]-phenylmethylamine and methyl pyruvate as described for Compound D of Example 1. The resulting oil was dissolved in a mixture of methylene chloride and TFA (8 mL, 1:1), the solution was stirred at room temperature for 1 h and concentrated in vacuo. The residue was partitioned between ether and 10% HCl solution and the aqueous solution was made basic with 10N NaOH solution to pH 11 and extracted with ethyl acetate (2×50 mL). The combined organic extracts were dried over $MgSO_4$ and concentrated to give Compound A as a solid (250 mg, 28%), mp: 149–151° C. MS (M+H) 177.

B. 2-Methyl-1,4-benzodiazepine

A solution of Compound A (181 mg, 1.03 mmol) was added to a suspension of LAH (160 mg, 4.21 mmol) in anhydrous THF(5 mL) at room temperature dropwise. The solution was heated at reflux for 5 h, cooled to 0° C. and diluted with THF (20 mL). Brine (0.5 mL) was added dropwise and the mixture was stirred at room temperature for 18 h and filtered through a pad of $MgSO_4$. The pad was washed with ethyl acetate and the combined filtrates were concentrated in vacuo to give Compound B as a semisolid (160 mg, 96%). MS (M+H) 163.

C. 2-Methyl-4-(1-Naphthalenylcarbonyl)-1,4-benzodiazepine

Compound C was prepared from Compound B as described for Compound C of Example 2. Chromatograpy (flash, silica, 1;1 ethyl acetate:hexanes) gave Compound C a solid, mp: 75° C. MS (M+H) 317.

D. 2,3,4,5-Tetrahydro-1-(1H-imidazol-4-yl-methyl)-2-methyl-4-(1-naphthalenylcarbonyl)-1H-1,4-benzodiazepine, hydrochloride Example 5 was prepared as a light yellow solid from Compound C as described for Compound D of Example 1, mp: 165° C. (foams). MS (M+H) 397.

Analysis calculated for $C_{25}H_{24}N_4O \cdot 2.4$ HCl$\cdot 1.0$ $H_2O \cdot 0.5$ $CH_3OH$. Calc'd: C, 59.12; H, 5.92; N, 10.84; Cl, 16.42. Found: C, 59.09; H, 5.58; N, 10.48; Cl, 16.28.

EXAMPLE 6

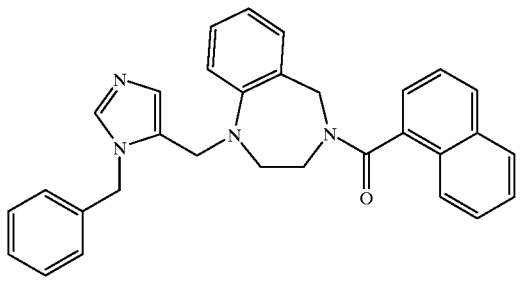

2,3,4,5-Tetrahydro-4-(1-naphthalenylcarbonyl)-1-[[1-(phenylmethyl)-1H-imidazol-5-yl]methyl]-1H-1,4-benzodiazepine, hydrochloride.

A. 2,3,4,5-Tetrahydro-4-(1-naphthalenylcarbonyl)-1-[[1-(triphenylmethyl)-1H-imidazol-4-yl]methyl]-1H-1,4-benzodiazepine To a solution of Example 1 (90 mg, 0.21 mmol) in acetonitrile (1 ml) at rt under argon was added TEA (0.14 μL, 1 mmol) followed by triphenylmethylchloride (56 mg, 0.2 mmol). The mixture was refluxed for 2 hr, cooled to rt and stirred for 14 hr. The precipitate was filtered and the filtrate was concentrated to afford Compound A (110 mg, 92%). MS (M+H)$^+$=625.

B. 2,3,4,5-Tetrahydro-4-(1-naphthalenylcarbonyl)-1-[[1-(phenylmethyl)-1H-imidazol-5-yl]methyl]-1H-1,4-benzodiazepine, hydrochloride To a solution of benzyl alcohol (18 μL, 0.18 mmol) in THF (1 ml) at −78° C. under argon was added triflic anhydride (30 μL, 0.18 mmol) and DIPEA (35 μL, 2 mmol). After 20 min, a THF (1 ml) solution of Compound A (100 mg, 0.15 mmol) was added dropwise. The mixture was allowed to warm to rt over 3 hr and was stirred for 14 hr. Acetic acid (1.5 ml) and water (1 ml) were added and the mixture was refluxed for 30 min, cooled to rt and evaporated. The residue was dissolved in chloroform and the solution was washed with saturated NaHCO$_3$ solution, dried (MgSO4) and concentrated. The residue was chromatographed (flash, silica, 9:1 CHCl$_3$:MeOH). Clean product was dissolved in ethyl acetate and the solution was bubbled with HCl gas for 30 seconds. Evaporation afforded Example 6 (33 mg. 33% overall). MS (M+H)$^+$=473. IR (KBr) 2853, 1630, 1508 cm-1

EXAMPLE 7

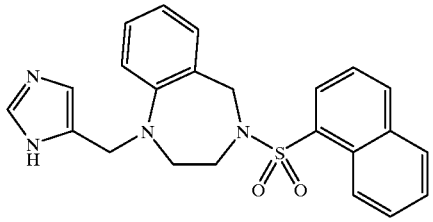

2,3,4,5-Tetrahydro-1-(1H-imidazol-4-yl-methyl)-4-(1-naphthalenylsulfonyl)-1H-1,4-benzodiazepine, hydrochloride, A. 2,3,4,5-Tetrahydro-4-(1-naphthalenylsulfonyl)-1H-1,4-benzodiazepine Compound A was prepared from Compound B of Example 1 and 1-naphthalenesulfonyl chloride as described for Compound C of Example 2. Crystallization from methanol gave Compound A as a solid, mp 165–166° C. MS (M+H) 339.

B. 2,3,4,5-Tetrahydro-1-(1H-imidazol-4-yl-methyl)-4-(1-naphthalenylsulfonyl)-1H-1,4-benzodiazepine, hydrochloride Example 7 was prepared as a white solid from Compound A as described for Compound D of Example 1, mp 140° C. (foams).

MS (M+H) 419. Analysis calculated for C$_{23}$H$_{22}$N$_4$O$_2$S.1.5 HCl.1.0 H$_2$O. Calc'd: C, 56.34; H, 5.22; N, 11.43; Cl, 10.85; S, 6.54. Found: C, 56.70; H, 5.16; N, 11.04; Cl, 10.72; S, 6.54.

EXAMPLE 8

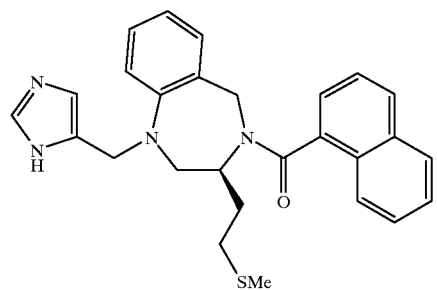

(S)-2,3,4,5-Tetrahydro-1-(1H-imidazol-4-ylmethyl)-3-[2-(methylthio)ethyl]-4-(1-naphthalenylcarbonyl)-1H-1,4-benzodiazepine, hydrochloride.

Example 8 was prepared as a yellow solid from isatoic anhydride and L-methionine methyl ester hydrochloride as described in the following multistep sequence: Compound A of Example 1; Compound B of Example 1, except that ethylene glycol dimethyl ether was used as solvent; Compound C of Example 2; Compound D of Example 1. mp 78–80° C.

MS (M+H) 457 Analysis calculated for C$_{27}$H$_{28}$N$_4$OS.1.6 HCl.2.3 H$_2$O Calc'd: C, 58.28; H, 6.20; N, 10.07; S, 5.76; Cl, 10.19. Found: C, 58.02; H, 5.87; N, 12.23; S, 4.95; Cl, 10.27.

EXAMPLE 9

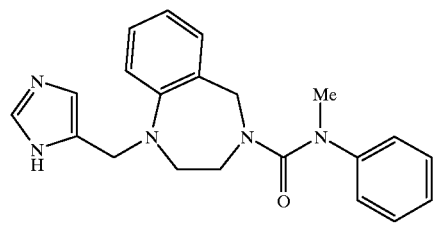

2,3,4,5-Tetrahydro-1-(1H-imidazol-4-yl-methyl)-N-methyl-N-phenyl-4H-1,4-benzodiazepine-4-carboxamide, hydrochloride, A. 2,3,4,5-Tetrahydro-N-methyl-N-phenyl-4H-1,4-benzodiazepine-4-carboxamide To a stirred solution of the Compound B of Example 1 (0.5 g, 3.35 mmol) in THF in the presence of NaHCO$_3$ (1.68, 20 mmol) was added N-methyl-N-phenyl carbamoyl chloride (480 mg, 2.83 mmol). The mixture was stirred at room temperature for 18 h and filtered. The filtrate was concentrated in vacuo and the residue was crystallized from methanol to give Compound A as a white solid (720 mg, 76%), mp: 159–160° C.

B. 2,3,4,5-Tetrahydro-1-(1H-imidazol-4-yl-methyl)-N-methyl-N-phenyl-4H-1,4-benzodiazepine-4-carboxamide, hydrochloride Example 9 was prepared as a white solid from Compound A as described for Compound D of Example 1, mp: 145° C. (shrinks).

MS (M+H) 362 Analysis calculated for $C_{21}H_{23}N_5O.1.8$ HCl.1.0 $H_2O$ Calc'd: C, 56.67; H, 6.07; N, 15.74; Cl, 14.34. Found: C, 57.08; H, 6.03; N, 15.40; Cl, 14.53.

EXAMPLE 10

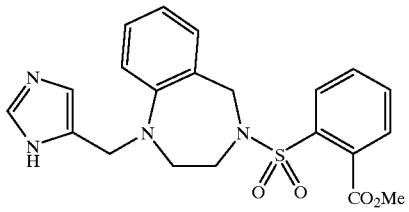

2-[2,3,4,5-Tetrahydro-1-(1H-imidazol-4-yl-methyl)-1H-1,4-benzodiazepin-4-yl]sulfonyl]benzoic acid, methyl ester, hydrochloride, Example 10 was prepared as a white solid from 2-methoxycarbonylbenzenesulfonyl chloride and Compound B of Example 2 as described in the following multistep sequence: Compound C of Example 2; Compound D of Example 1.

MS (M+H) 427 Analysis calculated for $C_{21}H_{22}N_4O4S.1.1$ HCl.1.0 $H_2O$ Calc'd: C, 52.04; H, 5.22; N, 11.56; S, 6.62; Cl, 8.05. Found: C, 52.20; H, 5.11; N, 10.40; S, 7.20; Cl, 8.09.

EXAMPLE 11

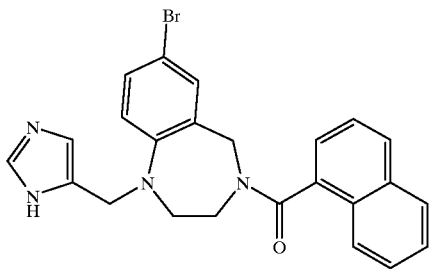

7-Bromo-2,3,4,5-tetrahydro-1-(1H-imidazol-4-ylmethyl)-4-(1-naphthalenylcarbonyl)-1H-1,4-benzodiazepine, hydrochloride.

A. 7-Bromo-1,4-benzodiazepin-2,5-dione

Compound A was prepared from 6-bromoisatoic anhydride as described for Compound A of Example 1.

B. 7-Bromo-2,3,4,5-tetrahydro-1-(1H-imidazol-4-ylmethyl)-4-(1-naphthalenylcarbonyl)-1H-1,4-benzodiazepine, hydrochloride.

Example 8 was prepared as a solid from Compound A as described in the following multistep sequence: Compound B of Example 2; Compound C of Example 2; Compound D of Example 1. Chromatography (5% methanol, 0.5% ammonium hydroxide, 94.5% methylene chloride) followed by preparative HPLC and conversion into the hydrochloride salt provided Example 11, mp 160–162° C.

MS (M+H) 461 Analysis calculated for $C_{24}H_{21}BrN_4O.1.5$ HCl. Calc'd: C, 55.86; H, 4.39; N, 10.86. Found: C, 55.84; H, 4.49; N, 10.71.

EXAMPLE 12

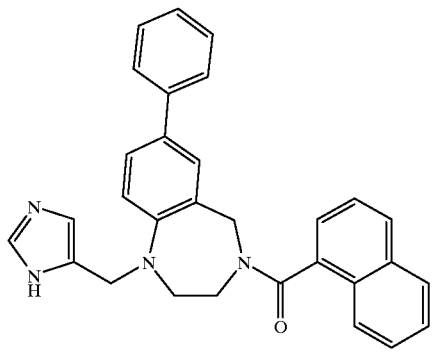

2,3,4,5-Tetrahydro-1-(1H-imidazol-4-ylmethyl)-4-(1-naphthalenylcarbonyl)-7-phenyl-1H-1,4-benzodiazepine, hydrochloride.

A. 7-Phenyl-1,4-benzodiazepin-2,5-dione

A solution of Compound A of Example 11 (0.834 g, 3.1 mmol) in 20 mL of 1:1 DMF:THF was degassed with nitrogen. Tetrakistriphenylphosphine palladium was added. After half an hour, anhydrous sodium carbonate (0.37 g, 3.5 mmol) in water (6 ml) and phenylboronic acid (1.00 g, 8.3 mmol) were added. The suspension was stirred at room temperature overnight, then at 80–90° C. for 2 days. The suspension was filtered. The precipitate was washed with water and ethyl acetate to give a Compound A as slightly grey solid (0.65 g, 84%). LC-MS (M+H)⁺ 253.

B. 7-Phenyl-1,4-benzodiazepine

To a suspension of Compound A (0.62 g, 2.5 mmol) in THF was added LAH in THF (1.0 M in THF, 7 ml). The suspension was stirred for 3 hrs and refluxed for 2 hrs. After cooling to rt, sodium hydroxide (1N, 5 ml) was added followed by 10 mL of saturated sodium potassium tartrate. The aqueous solution was extracted with methylene chloride. The organic phase was dried (sodium sulfate) and evaporated. The resulting oil was purified by chromatography (10% methanol in methylene chloride) to provide Compound B as a slightly yellow solid (0.46 g, 58%). LC-MS (M+H)⁺ 225.

C. 2,3,4,5-Tetrahydro-1-(1H-imidazol-4-ylmethyl)-4-(1-naphthalenylcarbonyl)-7-phenyl-1H-1,4-benzodiazepine, hydrochloride.

Example 12 was prepared as a solid from Compound B as described in the following multistep sequence: Compound C of Example 2; Compound D of Example 1. Chromatography (5% methanol, 0.5% ammonium hydroxide, 94.5% methylene chloride) followed by preparative HPLC and conversion into the hydrochloride salt provided Example 12, mp 158–160° C.

MS (M+H) 459 Analysis calculated for $C_{30}H_{26}N_4O.2.0$ HCl.0.58 $H_2O$ Calc'd: C, 66.50; H, 5.42; N, 10.34. Found: C, 66.56; H, 5.64; N, 10.00.

EXAMPLE 13

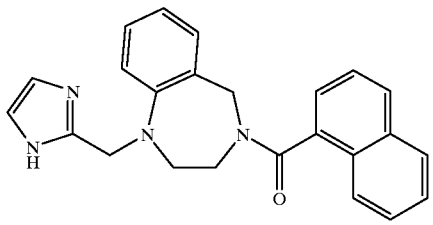

2,3,4,5-Tetrahydro-1-(1H-imidazol-2-ylmethyl)-4-(1-naphthalenylcarbonyl)-1H-1,4-benzodiazepine, dihydrochloride.

To a solution of Compound C of Example 1 (50 mg, 0.085 mmol) in dichloroethane (5 mL) was added 2-imidazole carboxaldehyde (33 mg, 0.34 mmol), NaBH(OAc)$_3$ (72 mg, 0.34 mmol) and glacial acetic acid (0.2 mL). The mixture was stirred for 16 hr. Saturated aqueous sodium bicarbonate solution was added (0.5 mL) and the solution was concentrated to dryness. The residue was dissolved in a 50/50 mixture of 0.1% TFA in methanol and 0.1% TFA in water and applied to a YMC C18 column (S-5, ODS 30×250 mm). HPLC purification was performed under the following conditions; Solvent A; 0.1% TFA in 90% water, 10% methanol, Solvent B; 0.1% TFA in 90% methanol, 10% water; 10–90% B in A over 30 minutes. Fractions containing the major peak were pooled and lyophilized to afford a white solid. 1 M HCl (6 mL) was added and the solution was concentrated to a glass. This step was repeated to give 25 mg (66%) of Example 13 as a glassy white solid.

MS (M+H)$^+$ 383 $^1$H-NMR (CD$_3$OD, 270 MHz) d 8.11 (2H, m), 7.7–7.1 (10H, m), 6.71 (0.5H, t, J=7.05 Hz), 6.07 (0.5H, d, J=7.05 Hz), 5.01(1H, m), 4.7–4.0 (2H, m), 3.6–3.4 (4H, m), 3.1(1H, m).

EXAMPLE 14

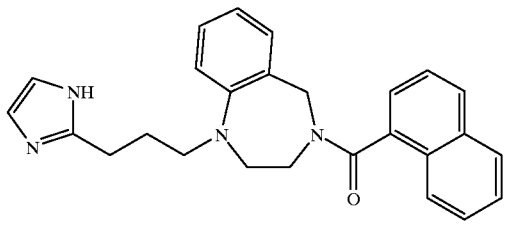

2,3,4,5-Tetrahydro-1-[3-(1H-imidazol-2-yl)propyl]-4-(1-naphthalenylcarbonyl)-1H-1,4-benzodiazepine, dihydrochloride.

A. 3-[Imidazol-2-yl]-propenoic acid, ethyl ester

To a cooled (0° C.) solution of sodium hydride (1.86 g, 45.8 mmol, 60% dispersion in mineral oil, prewashed with THF and dried over N$_2$) in 1,2-dimethoxyethane (DME, 20 mL) was added triethylphosphonoacetate (12 g, 54.1 mmol) dissolved in DME (10 mL) dropwise over 15 minutes. The solution was stirred for 1 hr at ambient temperature followed by the addition of 2-imidazole acetaldehyde (4 g, 41.6 mmol) in 20 mL of DME. The solution was stirred and heated to reflux (85° C.) for 15 minutes followed by cooling to 60° C. for 1 hr. On cooling, the solution was concentrated to ½ volume and filtered. The solid was recrystallized from methanol/ethyl acetate/hexanes to give 5.1 g (74%) of Compound A as a white crystalline solid. MS (M+H)$^+$ 167$^+$.

B. 3-[Imidazol-2-yl]-propanoic acid, ethyl ester

A solution of Compound A (4.01 g, 24.2 mmol) in absolute ethanol (100 mL, heated to dissolve) was hydrogenated using Pd/C (0.5 g) at ambient temperature for 16 hr. Following removal of H$_2$ under vacuum, the catalyst was removed by filtration through a bed of celite. The filtrate was concentrated under vacuum to give 4.0 g (100%) of Compound B as a white crystalline solid. MS (M+H)$^+$ 169$^+$.

C. 3-[N-Triphenylmethyl-imidazol-2-yl]-propanoic acid, ethyl ester

Compound C was prepared from Compound B as described for Compound A of Example 6, using methylene chloride as solvent. After aqueous workup, recrystallization from ethyl acetate/hexanes afforded Compound C as a white crystalline solid. MS (M+H)$^+$ 411$^+$.

D. 3-[N-Triphenylmethyl-imidazol-2-yl]-propanal

A stirred solution of Compound C (300 mg, 0.73 mmol) in dichloromethane (3 mL) was cooled to −78° C. and a precooled (−70° C.) solution of 1M DIBAL in dichloromethane (0.73 mmol, 0.73 mL) was introduced via syringe. After stirring for 1 h, an additional aliquot of precooled (−70° C.) DIBAL solution (0.3 mL, 0.3 mmol) was added. After stirring for an additional 2 h, saturated aqueous NH$_4$Cl was added (10 mL) followed by 0.1N HCl (20 mL). After stirring for 5 min, methylene chloride was added (30 mL). The layers were separated and the aqueous layer was washed with methylene chloride. The pooled organic layers were dried over MgSO$_4$, filtered and concentrated to yield 266 mg (99%) of Compound D as a white solid. $^1$H-NMR(CD$_{30}$D, 270 MHz) d 9.4(1H, s), 7.38 (10H, m), 7.05 (7H, m), 2.7–2.2(4H, m).

E. 2,3,4,5-Tetrahydro-1-[3-(1-triphenylmethyl-imidazol-2-yl)propyl]-4-(1-naphthalenylcarbonyl)-1H-1,4-benzodiazepine Compound E was prepared from Compound D and Compound C of Example 1 as described for Compound D of Example 1, with stirring for 16 hours. Chromatography (flash, silica, 9:1 methylene chloride:methanol) afforded (74%) of Compound E as a glass. MS (M+H)$^+$ 653.3.

F. 2,3,4,5-Tetrahydro-1-[3-(1H-imidazol-2-yl)propyl]-4-(1-naphthalenylcarbonyl)-1H-1,4-benzodiazepine, dihydrochloride A mixture of Compound E (110 mg, 0.18 mmol) in TFA (5 mL), methylene chloride (5 mL) and triethylsilane (0.1 mL) was stirred for 2 h at room temperature and concentrated. Hexanes was added with stirring to the residue and the mixture was decanted. The residue was dissolved in a 50/50 mixture of 0.1% TFA in methanol and 0.1% TFA in water and was applied to a YMC C18 column (S-5, ODS 30×250 mm) and HPLC purification was performed under the following conditions; Solvent A; 0.1% TFA in 90% water, 10% methanol, Solvent B; 0.1% TFA in 90% methanol, 10% water; 0–100% B in A over 30 minutes. Fractions containing the major peak were pooled and lyophilized to an oily residue. 1 M aqueous HCl (6 mL) was added and the solution was concentrated to a glass. This step was repeated to give 50 mg (84%) of Example 14 as a white solid.

MS (M+H)$^+$411. $^1$H-NMR (CD$_3$OD, 300 MHz) d 8.05–7.95 (2H, m), 7.6–7.05 (12H, m), 6.71 (0.5H, m), 6.02(0.5H, m), 4.4 (2H, m), 3.6–3.0 (8H, m), 2.2–2.0(2H, m).

EXAMPLE 15

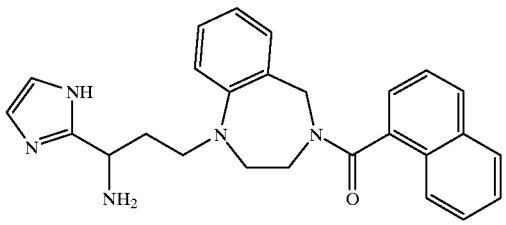

1-[3-Amino-3-(1H-imidazol-2-yl)propyl]-2,3,4,5-tetrahydro-4-(1-naphthalenylcarbonyl)-1H-1,4-benzodiazepine, trihydrochloride.

A. N-[2-(trimethylsilyl)ethoxymethyl]imidazole

To a mixture of NaH (2.1 g, 51 mmol, 60% dispersion in mineral oil, prewashed with hexanes) and DMF (60 mL) was added imidazole (3.0 g, 44 mmol) in small portions. The mixture was stirred under $N_2$ for 1 h followed by the addition of 2-(trimethylsilyl)ethoxymethyl chloride (SEM-Cl) dropwise. The mixture was stirred for 1 h and quenched with water (5 mL). The mixture was poured into water (80 mL) and extracted with ethyl acetate. The organic layer was washed with saturated aqueous $NH_4Cl$, brine, dried ($MgSO_4$), filtered and concentrated to yield 6.3 g (72%) of Compound A as a clear liquid. MS $(M+H)^+$ 199.

B. N-[2-(trimethylsilyl)ethoxymethyl]imidazole-2-carboxaldehyde

To a cooled (–40° C.) mixture of Compound A (3.0 g, 15.1 mmol) in THF (75 mL) was added a solution of nBuLi in hexane (2.5 M, 6.4 mL, 15.1 mmol). After 15 min, DMF (1.4 mL, 18.1 mmol) was added and the mixture was stirred for 3 h followed by addition of saturated aqueous $NH_4Cl$ (30 mL). The mixture was extracted with ethyl acetate and the organic phase was washed with saturated aqueous $NH_4Cl$, brine, dried using $MgSO_4$, filtered and concentrated to yield 3.1 g of Compound B (92%) as a light yellow oil. MS $(2M+H)^+$ 453.2

C. 1-Amino-1-[N-[2-(trimethylsilyl)ethoxymethyl]imidazol-2-yl]-but-3-ene

To a cooled (–78° C.) mixture of Compound B (1.22 g, 5.4 mmol) in THF (10 mL) under Ar was added via syringe a precooled (–78° C.) solution of lithium bistrimethylsilylamide in THF (1M, 5.6 mL, 5.6 mmol). The mixture was warmed to –20° C. for 1 h and recooled to –78° C. To the mixture was added via syringe a precooled (–78° C.) solution of allylmagnesium bromide (1M in ethyl ether, 7.45 mL, 7.45 mmol). The mixture was warmed to room temperature and stirred for 16 h under Ar. The mixture was quenched with 1N aqueous NaOH (20 mL) and extracted with ethyl ether. The organic layer was washed with brine, dried using $MgSO_4$, filtered and concentrated to a yellow residue. The residue was chromatographed on a flash silica gel column (5×20 cm) eluting with methylene chloride:methanol (9:1) followed by ammonium hydroxide:methanol:chloroform (1:5:94) to yield 0.55 g (38%) of Compound C an orange liquid. MS $(M+H)^+$ 267.

D. 1-[(Triethylsilyl)ethoxycarbonylamino]-1-[N-[2-(trimethylsilyl)ethoxymethyl]imidazol-2-yl]-but-3-ene To a stirred suspension of Compound C (450 mg, 1.7 mmol) in water (2 mL) was added a solution of TEA (0.32 mL, 2.3 mmol) in dioxane (2 mL) followed by 2-(triethylsilyl)ethoxycarbonylsuccinimide. The mixture was stirred at room temperature for 16 h. Ethyl ether (30 mL) and 1N aqueous $KHSO_4$ (30 mL) were added. The layers were separated and the aqueous layer was washed with ethyl ether. The pooled organic layers were dried using $MgSO_4$, filtered and concentrated. The residue was chromatographed on a flash silica gel column (5×20 cm) eluting with methylene chloride:methanol (9:1) to yield 531 mg (84%) of Compound D as a glass. MS $(M+H)^+$ 412.

E. 3-[(Triethylsilyl)ethoxycarbonylamino]-3-[N-[2-(trimethylsilyl)ethoxymethyl]imidazol-2-yl]-propanal To a stirred mixture of Compound D in dioxane (5 mL) and water (5 mL) was added sodium periodate (94 mg, 0.37 mmol) and osmium tetroxide (2 mg dissolved in 0.5 mL water, 0.5 mL dioxane). The mixture was stirred for 18 h. Methylene chloride was added, the layers were separated and the aqueous layer was washed with methylene chloride. The combined organic layers were dried using $MgSO_4$, filtered and concentrated. The residue was chromatographed on a flash silica gel column (5×20 cm) eluting with methylene chloride:methanol (9:1) to yield 90 mg (90%) of Compound E as a glass.

F. 1-[[(Triethylsilyl)ethoxycarbonylamino]-3-(1-(trimethylsilyl)ethoxymethyl-imidazol-2-yl)propyl]-2,3,4,5-tetrahydro-4-(1-naphthalenylcarbonyl)-1H-1,4-benzodiazepine Compound F was prepared from Compound E and Compound C of Example 1 as described for Compound D of Example 1, with stirring for 16 hours. Chromatography (flash, silica, 9:1 methylene chloride:methanol) afforded (44%) of Compound F as a glass. MS $(M+H)^+$ 700.

G. 1-[3-Amino-3-(1H-imidazol-2-yl)propyl]-2,3,4,5-tetrahydro-4-(1-naphthalenylcarbonyl)-1H-1,4-benzodiazepine, trihydrochloride To a solution of Compound F (20 mg, 0.029 mmol) in THF (3 mL) was added tetrabutylammonium fluoride (44 mg, 0.17 mmol) and the solution was heated to 50° C. for 16 h. On cooling, the solvent was removed under vacuum and the residue was dissolved in a 50/50 mixture of 0.1% TFA in methanol and 0.1% TFA in water and applied to a YMC C18 column (S-5, ODS 30×250 mm). HPLC purification was performed under the following conditions; Solvent A; 0.1% TFA in 90% water, 10% methanol, Solvent B; 0.1% TFA in 90% methanol, 10% water; 0–100% B in A over 30 minutes. Fractions containing the major peak were pooled and lyophilized to an oily residue. 1 M aqueous HCl (6 mL) was added and the solution was concentrated to a white solid. This step was repeated to give 9 mg (58%) of Example 15 as a white solid.

MS $(M+H)^+$ 425 $^1$H-NMR ($CD_3OD$, 270 MHz) d 8.05–7.95 (2H, m), 7.7–7.05 (10H, m), 6.71 (0.5H, m), 6.02(0.5H, m), 4.4 (2H, m), 4.0 (1H, m), 3.6–3.0 (7H, m), 2.9 (1H, m).

EXAMPLE 16

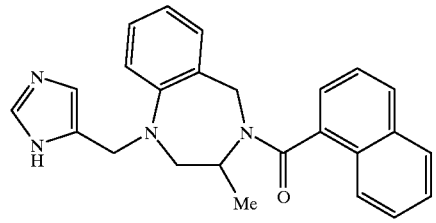

2,3,4,5-Tetrahydro-1-(1H-imidazol-4-ylmethyl)-3-methyl-4-(1-naphthalenylcarbonyl)-1H-1,4-benzodiazepine, hydrochloride.

Example 16 was prepared as a yellow solid from isatoic anhydride and D,L-alanine ethyl ester hydrochloride as described for Example 8, mp 180–185° C.

MS (M+H)+ 397 Analysis calculated for C25H24N4O.1.3 HCl.1.3 H2O Calc'd: C, 64.26; H, 6.02; N, 11.99; Cl, 9.86. Found: C, 64.33; H, 5.82; N, 11.70; Cl, 9.65.

EXAMPLE 17

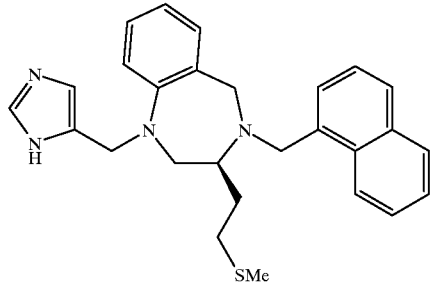

(S)-2,3,4,5-Tetrahydro-1-(1H-imidazol-4-ylmethyl)-3-[2-(methylthio)ethyl]-4-(1-naphthalenylmethyl)-1H-1,4-benzodiazepine, hydrochloride.

To a suspension of ethylene glycol dimethyl ether (anhydrous, 20 mL) and lithium aluminum hydride (17 mg, 0.45 mmol) under argon at 0° C. was slowly added a mixture of Example 8 (75 mg, 0.15 mmol) in ethylene glycol dimethyl ether. The mixture was allowed to warm to room temperature, stirred for 30 min. and heated to reflux (85° C.) for 18 hours. The mixture was cooled to 0° C. and quenched sequentially with a mixture of tetrahydrofuran and water (1 mL each), aqueous sodium hydroxide, (2 mL, 1N) and water (1 mL). The resultant precipitate was removed by filtration and the filtrate was concentrated in vacuo to yield an amber oil. This material was dissolved in methanol (2 mL), treated with a solution of hydrogen chloride (1 mL, anhydrous, 2M in ether), and concentrated in vacuo to yield Example 17 as a yellow solid, mp 115–120° C.

MS (M+H)+ 443 Analysis calculated for C27H30N4S.2.4 HCl.2.6 H2O. Calc'd: C, 56.21; H, 6.57; N, 9.71; Cl, 14.75. Found: C, 56.20; H, 6.55; N, 9.85; Cl, 14.81.

EXAMPLE 18

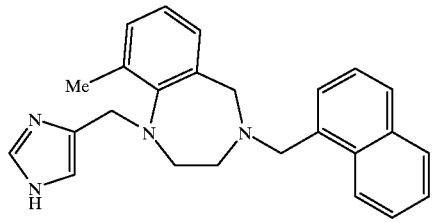

2,3,4,5-Tetrahydro-1-(1H-imidazol-4-ylmethyl)-9-methyl-4-(1-naphthalenylcarbonyl)-1H-1,4-benzodiazepine, dihydrochloride.

Example 18 was prepared as a light yellow solid from 8-methyl isatoic anhydride and glycine ethyl ester hydrochloride as described in the following multistep sequence: Compound A of Example 1, with refluxing for 16 hours; Example 17, except that THF was used as solvent; refluxing with the 4-nitrophenyl ester of 1-naphthoic acid in toluene in the presence of DMAP; Compound D of Example 1.

MS (M+H)+ 397 Analysis calculated for C25H24N4O.2 HCl. Calc'd: C, 63.96; H, 5.58; N, 11.93. Found: C, 62.83; H, 5.77; N, 11.13.

EXAMPLE 19

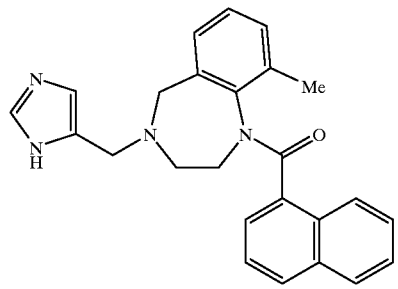

2,3,4,5-Tetrahydro-4-(1H-imidazol-4-ylmethyl)-9-methyl-1-(1-naphthalenylcarbonyl)-1H-1,4-benzodiazepine, dihydrochloride.

Example 19 was prepared from 9-methyl-2,3,4,5-tetrahydro-1,4-benzodiazepine as described in the following multistep sequence: Compound A of Example 4; coupling with 1-naphthoyl chloride using triethylamine in methylene chloride; Boc removal with 4N HCl in dioxane; Compound D of Example 1; chromatography (silica, flash, 9/1 CHCl3/CH3OH) followed by treatment with 1M HCl in ether and trituration with ether afford Example 19 as a light yellow solid.

MS (M+H)+ 397 1H NMR (270 MHz, CD3OD) d 9.12–8.9 (m, 1H), 8.5–8.23 (m, 1H), 8.1–7.9 (m, 3H), 7.9–7.0 (m, 7 H), 57–5.28 (m, 1H), 4.85–4.1 (m, 3H), 4.0–3.05 (m, 4 H), 2.9–2.55 m, 1H), 1.9–1.75 (s, 3H).

EXAMPLE 20

1-[[2-(2-Aminoethyl)-1H-imidazol-4-yl]methyl]-2,3,4,5-tetrahydro-4-(1-naphthalenylcarbonyl)-1H-1,4-benzodiazepine, trihydrochloride.

A. [2-(2-[[(1,1-dimethyl)-ethoxycarbonyl]amino]ethyl)-1-[(1,1-dimethyl)-ethoxycarbonyl]-imidazol-4-yl]methanol

[2-(2-Aminoethyl)-1H-imidazol-4-yl]methanol hydrochloride was prepared as described (Buschauer, et. al., Arch. Pharm., 315, 563, (1982)). To a suspension of 1.0 g of this crude material (assumed 4.7 mmol) in 10 mL of DMF was added 2 mL (14.1 mmol) of triethylamine and the slurry was stirred for 0.5 hr. To the reaction was then added 3.1 g (14.1 mmol) of BOC anhydride and stirring was continued overnight at rt. The reaction was evaporated to dryness and the residue subjected to flash chromatography on a 100 cc column of silica gel. Elution with ethyl acetate afforded 1.27 g (3.7 mmoles, 79%) of Compound A as a viscous yellow oil.

B. [2-(2-[[(1,1-dimethyl)-ethoxycarbonyl]amino]ethyl)-1-[(1,1-dimethyl)-ethoxycarbonyl]-imidazol-4-yl]carboxaldehyde To a solution of 1.2 g (3.5 mmol) of Compound A in 10 mL of chloroform was added 0.9 g (10 mmol) of manganese dioxide. The reaction was heated at 50° C. with vigorous stirring. Additional 0.3 g portions of MnO2 were added after 1, 2 and 4 hrs of heating. After 6 hr at 50° C., the mixture was cooled to room temperature and without workup, was subjected to flash chromatography on a 150 cc column of silica gel. Elution with 50% ethyl acetate-hexane afforded 673 mg (57%) of Compound B as a white crystalline solid.

C. 1-[[2-(2-Aminoethyl)-1H-imidazol-4-yl]methyl]-2,3,4,5-tetrahydro-4-(1-naphthalenylcarbonyl)-1H-1,4-benzodiazepine, trihydrochloride Compound C of Example 1 was reductively aminated with Compound B as described for Compound D of Example 1. The resulting oil was subjected to flash chromatography (silica, 50% ethyl acetate-hexanes) to afford the bis-Boc analog of Compound C as a white foam. A solution of 94 mg (0.15 mmol) of this material in 3 ml of 4 N HCl-dioxane was stirred for 3 hr at rt. Removal of solvent gave a white foam residue which was subjected to preparative HPLC on a YMC S5 ODS (30×250 mm) column. Gradient elution from 0 to 100% solvent B (A: 10% methanol:water+0.1% TFA, B: 10% water:methanol+0.1% TFA) afforded an oil residue which was converted to its HCl salt by the addition of methanolic HCl and removal of solvent. The residue was evaporated from methanol twice more to afford 53 mg (0.10 mmole, 66%) of Example 20 as a white solid, mp 165° C. MS (M+H)+ 426 Analysis calculated for $C_{26}H_{27}N_5O$.3 HCl. Calc'd: C, 58.38; H, 5.65; N, 13.09. Found: C, 59.01; H, 6.15; N, 13.03.

EXAMPLE 21

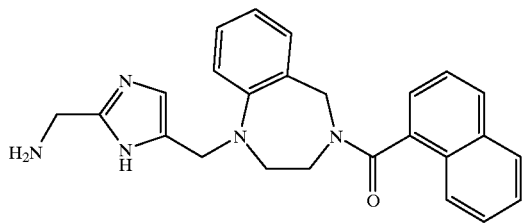

1-[[2-(2-Aminomethyl)-1H-imidazol-4-yl]methyl]-2,3,4,5-tetrahydro-4-(1-naphthalenylcarbonyl)-1H-1,4-benzodiazepine, trihydrochloride.

Example 21 was prepared as a white solid from chloroacetonitrile and Compound C of Example 1 as described for Example 20, mp 155–160° C.

MS (M+H)+ 412 Analysis calculated for $C_{25}H_{25}N_5O$.3 HCl. Calc'd: C, 57.65; H, 5.42; N, 13.45. Found: C, 57.41; H, 5.18; N, 13.17.

EXAMPLE 22

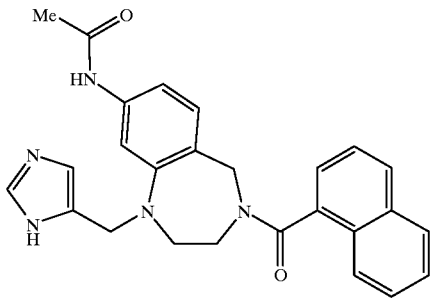

N-[2,3,4,5-Tetrahydro-1-(1H-imidazol-4-ylmethyl)-4-(1-naphthalenylcarbonyl)-1H-1,4-benzodiazepin-8-yl] acetamide, dihydrochloride.

A. 2-[2-[[(1,1-Dimethyl)-ethoxycarbonyl]amino]ethylamino]-4-nitro-benzoic acid

Sodium cyanoborohydride (2.3 g, 38 mmol) was added portionwise to a solution of 2-[[(1,1-dimethyl)-ethoxycarbonyl]amino]acetaldehyde (6.0 g, 38 mmol), 4-nitroanthranilic acid (3.8 g, 19 mmol) and acetic acid (2.0 ml) in methanol (150 ml). The mixture was stirred at room temperature for 16 h, concentrated under vacuum, quenched with 1N HCl (100 ml) and extracted with $CH_2Cl_2$ (3×100 ml). The combined organic extracts were dried ($MgSO_4$), filtered and concentrated under vacuum. The residue was purified by flash chromatogrphy (19/1/0.05 $CHCl_3$/MeOH/AcOH) to afford Compound A (4.4 g, 72%) as a solid. MS: (M+H)+ 326

B. 2-[(2-amino)ethylamino]-4-nitro-benzoic acid

Anhydrous HCl in dioxane (4M, 20 ml, 80 mmol) was added to Compound B (2.8 g, 8.6 mmol) at room temperature and the mixture was stirred for 2 h. The solution was concentrated under vacuum and the residue was triturated with diethyl ether to afford Compound B (2.1 g, 84%) as a solid. MS: (M+H)+ 226

C. 8-Nitro-2,3,-dihydro-1H-1,4-benzodiazepin-5-one

Diphenylphosphoryl azide (1.1 ml, 5.0 mmol) was added to a solution of Compound B (1.0 g, 3.4 mmol) in DMF (12 ml) at room temperature. The mixture was stirred for 10 minutes, N-methyl morpholine (1.3 ml, 12 mmol) was added and the mixture was stirred at room temperature for 5 h. The mixture was quenched with 10% LiCl/10% $NaHCO_3$ (100 ml) and the aqueous solution extracted with ethyl acetate (5×50 ml). The combined organic extracts were washed with 10% LiCl (2×60 ml), dried ($MgSO_4$), filtered and concentrated under vacuum. The residue was triturated with petroleum ether and diethyl ether to afford Compound C (0.42 g, 61%) as a solid. MS: (M+$CH_3CN$+H)+ 249

D. 8-Nitro-2,3,4,5-tetrahydro-1H-1,4-benzodiazepine

Borane dimethyl sulfide (10 M, 1.2 ml, 12 mmol) was added dropwise to solution of Compound C (0.42 g, 2.0 mmol) in THF (5 ml) at 0° C. The mixture was warmed to room temperature and then heated to refluxed for 2 h. The mixture was cooled to 0° C., methanol (10 ml) was carefully added and the solution was saturated with anhydrous HCl. The mixture was heated to reflux for 1 h, concentrated under vacuum and triturated with diethyl ether to afford Compound D (0.34 g, 65%) as a solid. MS: (M+H)+ 194

E. 8-Nitro-2,3,4,5-tetrahydro-4-(1-naphthalenylcarbonyl)-1H-1,4-benzodiazepine

Compound E was prepared from Compound D and 1-naphthoyl chloride as described for Compound C of Example 2, with stirring for 16 hours. MS: (M+CH3CN+H)+ 389

F. 2,3,4,5-Tetrahydro-1-(1H-imidazol-4-ylmethyl)-4-(1-naphthalenylcarbonyl)-8-nitro-1H-1,4-benzodiazepine Compound F was prepared from Compound E as described for Compound D of Example 1, except that methanol was used as solvent and the free base was carried on to the next reaction. MS (M+H)+ 428

G. 2,3,4,5-Tetrahydro-1-(1H-imidazol-4-ylmethyl)-4-(1-naphthalenylcarbonyl)-8-amino-1H-1,4-benzodiazepine Iron powder (0.15 g, 2.6 mmol) was added to a solution of Compound F (0.13 g, 0.29 mmol) in 500/50/1 ethanol/water/concentrated HCl (26 ml) at room temperature. The mixture was heated to reflux for 3 h, cooled to room temperature, filtered and the filtrate was concentrated under vacuum. The residue was dissolved in $CH_2Cl_2$ (100 ml), washed with 1N NaOH (100 ml), and the aqueous layer reextracted with $CH_2Cl_2$ (2×100 ml). The combined organic extracts were dried ($MgSO_4$), filtered and concentrated under vacuum to afford Compound G (0.60 g, 52%) as a solid which was used without further purification.

H. N-[2,3,4,5-Tetrahydro-1-(1H-imidazol-4-ylmethyl)-4-(1-naphthalenylcarbonyl)-1H-1,4-benzodiazepin-8-yl] acetamide, dihydrochloride 4-Dimethylaminopyridine (0.005 g) was added to a solution of Compound G (0.050 g, 0.13 mmol) and acetic anhydride (0.024 ml, 0.25 mmol) in $CH_2Cl_2$ (2 ml) at room temperature. The mixture was stirred for 16 h, quenched with 10% $NaHCO_3$ (1 ml) and MeOH (0.50 ml) and stirred at room temperature for 15 minutes. The mixture was diluted with water (5 ml) and the solution extracted with $CH_2Cl_2$ (3×50 ml). The combined organic extracts were dried ($MgSO_4$), filtered and concentrated under vacuum. The residue was purified by flash chromatography (19/1/0.01 $CHCl_3$/MeOH/$NH_4OH$) and the appropriate fractions were concentrated under vacuum. The residue was dissolved in MeOH (5 ml), treated with 1N HCl (2 ml), millpore filtered and lyophilized to afford Example 22 (0.018 g, 32%) as a solid.

MS (M+H)$^+$ 440 Analysis calculated for $C_{26}H_{25}N_5O_2 \cdot 2.0$ HCl·1.16 $CH_3OH$. Calc'd: C, 59.35; H, 5.80; N, 12.74 Found: C, 59.35; H, 5.81; N, 12.22.

EXAMPLE 23

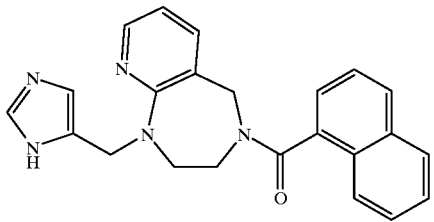

2,3,4,5-Tetrahydro-1-(1H-imidazol-4-ylmethyl)-4-(1-naphthalenylcarbonyl)-1H-pyrido[2,3-e]-1,4-diazepine, trihydrochloride.

A. 2,3,4,5-Tetrahydro-1H-pyrido[2,3-e]-1,4-diazepin-5-one

A solution of 2-chloronicotinamide (4.0 g, 25.5 mmol) in ethylenediamine (25 mL) was heated to reflux for 24 hours. To the solution was added 5 N NaOH (5.1 mL, 25.5 mmol) and the mixture was concentrated in vacuo. The crude material was chromatographed (silica, 5–20% $CH_3OH$/$CHCl_3$) to give Compound A (339 mg, 8%) as a light yellow solid. MS (M+H+$CH_3CN$)$^+$ 205.

B. 2,3,4,5-Tetrahydro-1H-pyrido[2,3-e]-1,4-diazepine

To a solution of Compound A (100 mg, 0.61 mmol) in dry toluene (15 mL) was added diisobutylaluminum hydride (1M in hexanes, 3.1 mL, 3.1 mmol). The mixture was warmed to reflux for 36 hours. At 12 and 24 hours, an additional portion of DiBAH was added (3.1 mL each time). At the end of 36 hours, the reaction was cooled to room temperature and quenched with methanol. A viscous gel was formed which was dissolved in 1N HCl. The mixture was extracted with EtOAc (15 mL) and the organic layer discarded. The aqueous layer was made basic with 5N NaOH and extracted with 10% i-PrOH/$CH_2Cl_2$ (5×15 mL). The organic layers were combined, dried over $Na_2SO_4$, and concentrated in vacuo to afford Compound B (79 mg, 87%) which was carried on directly. MS (M+H+$CH_3CN$)$^+$ 191.

C. 2,3,4,5-Tetrahydro-4-(1-naphthalenylcarbonyl)-1H-pyrido[2,3-e]-1,4-diazepine

To a solution of Compound B (79 mg, 0.53 mmol), 1-naphthoic acid (115.5 mg, 0.67 mmol), EDC (128.4 mg, 0.67 mmol), and HOBt (90.5 mg, 0.67 mmol) in anhydrous DMF (2 mL) was added diisopropylethylamine (0.1 mL, 0.67 mmol). After 3 hours, the reaction was diluted with EtOAc (5 mL) and washed with 10% LiCl. The organic layer was washed with 1N HCl and discarded. The aqueous layer was made basic with 5N NaOH and extracted with EtOAc (5×5 mL). The five organic layers were combined and dried over $Na_2SO_4$ and concentrated. The crude material was chromatographed (silica, 0–5% $CH_3OH$/$CHCl_3$) to give Compound C (96 mg, 60%) as a light brown oil. MS (M+H+$CH_3CN$)$^+$ 345.

D. 2,3,4,5-Tetrahydro-1-(1H-imidazol-4-ylmethyl)-4-(1-naphthalenylcarbonyl)-1H-pyrido[2,3-e]-1,4-diazepine, trihydrochloride To a solution of Compound C (30 mg, 0.10 mmol) and 4-formyl imidazole (14.5 mg, 0.50 mmol) in dichloroethane (0.5 mL) and acetic acid (0.25 mL) was added NaBH(OAc)$_3$ (29.7 mg, 0.14 mmol). The mixture was stirred at room temperature for 12 hours and at 80° C. for 12 hours. Additional portions of 4-formyl imidazole (14.5 mg, 0.50 mmol) and NaBH(OAc)$_3$ (30 mg, 0.14 mmol) were added and the reaction was warmed to 80° C. for an additional 24 hours. The reaction was cooled to room temperature and diluted with EtOAc (2 mL) and $NH_4OH$ (conc., 2 mL) was added. After stirring for 3 hours, $NaHCO_3$ (sat., 3 mL) was added along with more EtOAc (5 mL). The layers were separated and the aqueous layer was extracted with EtOAc (3×5 mL). The organic layers were combined and washed with $NH_4Cl$ (sat., 5 mL), dried over $Na_2SO_4$, and concentrated in vacuo. The crude material was diluted in methanol (2 mL) and purified by HPLC (YMC S5 ODS 30×250 mm column, solvent A: 10% MeOH/$H_2O$ w/0.1% TFA, solvent B: 90% MeOH/$H_2O$ w/0.1% TFA, gradient: 0–100% B in A over 60 min at a rate of 25 mL/min, monitored at 220 nm). The fractions containing the product were combined, concentrated in vacuo, dissolved in 1N HCl and lyophilized, dissolved in water and lyophilized again to give Example 23 as a fluffy white solid (4 mg, 8%). $^1$H-NMR (CD$_3$OD, 400 MHz) d 8.87 (d, $J_1$=1.3, 0.5H), 8.70 (d, $J_1$=1.3, 0.5H), 8.06 (dd, $J_1$=1.7, $J_2$=5.6, 0.5H), 7.96 (d, $J_1$=6.8, 0.5H), 7.83–7.91 (m, 2.5H) 7.60 (d, $J_1$=1.3, 0.5H), 7.52 (dd, $J_1$=1.7, $J_2$=7.3, 0.5H), 7.34–7.49 (m, 4H), 7.26 (dd, $J_1$=1.3, $J_2$=7.6, 0.5H), 7.11 (dd, $J_1$=1.3, $J_2$=7.1, 0.5H), 7.05 (dd, $J_1$=5.6, $J_2$=7.3, 0.5H), 6.57 (d, $J_1$=7.3, 0.5H), 6.52 (dd, $J_1$=5.6, $J_2$=7.7, 0.5H), 5.01 (d, $J_1$=1.3, 1H), 4.95 (d, $J_1$=1.3, 1H), 4.39–4.57 (m, 1.5H), 4.08–4.13 (m, 1H), 3.88–3.94 (m, 1H), 3.53–3.65 (m, 1.5H), 3.42–3.45 (m, 1H); MS (M+H)$^+$ 384.

EXAMPLE 24

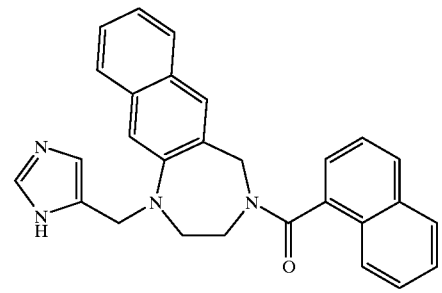

2,3,4,5-Tetrahydro-1-(1H-imidazol-4-ylmethyl)-4-(1-naphthalenylcarbonyl)-1H-naphtho[2,3-e]-1,4-diazepine, dihydrochloride.

A. 2H-3,1-Naphthoxazine-2,4(1H)-dione

To an ice cooled slurry of 25 g (10.7 mmol) of 80% 2-amino-3-naphthoic acid and 2.5 g (8.5 mmol) of triphosgene in 70 mL of acetonitrile, under argon, was added dropwise 0.35 mL (25 mmol) of triethylamine. Stirring was continued while the cooling bath was allowed to warm to room temperature and then overnight at room temperature. To the resulting suspension was then added 2 mL of methanol and stirring was continued for an additional hour. Filtration of the solid afforded 2.5 g (assumed 100%) of crude Compound A as a light brown powder.

B. 2,3,4,5-Tetrahydro-1-(1H-imidazol-4-ylmethyl)-4-(1-naphthalenylcarbonyl)-1H-naphtho[2,3-e]-1,4-diazepine, dihydrochloride Example 24 was prepared as an amorphous off-white solid from Compound A by the following mulitstep sequence: Compound A of Example 1, with refluxing for 10 hours; Compound B of Example 2, except that THf was used as solvent and the product:borane complex was decomposed with refluxing aqueous HCl; Compound C of Example 2, except that chromatography was done with 50% ethyl acetate-hexane afforded; Compound D of Example 1, with the product purified by prep HPLC (YMC S5 ODS (30×250 mm) column, gradient elution from 40 to 100% solvent B (A: 10% methanol:water+0.1% TFA, B: 10% water:methanol+0.1% TFA) and converted to the HCl salt by treatment with HCl-MeOH.

Analysis calculated for $C_{28}H_{24}N_4O.1.5$ $HCl.0.25$ $H_2O$. Calc'd: C, 68.39; H, 5.33; N, 11.39. Found: C, 68.41; H, 5.46; N, 11.31.

EXAMPLE 25

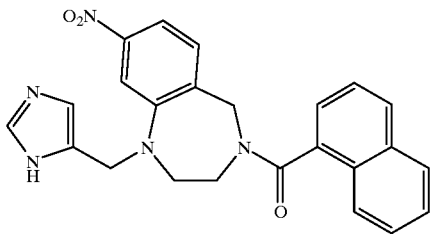

2,3,4,5-Tetrahydro-1-(1H-imidazol-4-ylmethyl)-4-(1-naphthalenylcarbonyl)-8-nitro-1H-1,4-benzodiazepine, dihydrochloride.

Sodium triacetoxyborohydride (0.91 g, 4.3 mmol) was added to a solution of Compound E of Example 22 (0.50 g, 1.43 mmol), 4-formyl imidazole (0.41 g, 4.3 mmol) and AcOH (4 mL) in $CH_2Cl_2$ (4 mL). After stirring for 15 hr, the mixture was diluted with $CH_2Cl_2$ (10 mL), $NH_4OH$ (5 mL) and $NaHCO_3$ (5 mL), and stirred for 30 min. The layers were separated and the aqueous layer was reextracted with $CH_2Cl_2$ (2×50 mL). The combined organic layers were dried over $MgSO_4$, filtered and concentrated. The product was purified over silica gel column eluting with 19/1 $CHCl_3/CH_3OH$ to afford Example 25 (0.52 g, 85%) as a light yellow solid. (Example 25 is also Compound F of Example 22.)

MS $(M+H)^+$ 428.

EXAMPLE 26

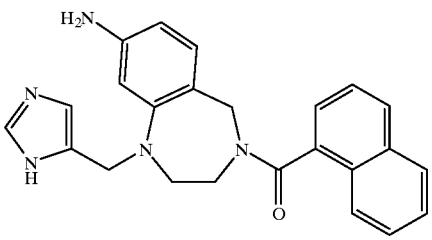

2,3,4,5-Tetrahydro-1-(1H-imidazol-4-ylmethyl)-4-(1-naphthalenylcarbonyl)-8-amino-1H-1,4-benzodiazepine, dihydrochloride.

16% aqueous $TiCl_3$ (2 mL) was added to a solution of Example 25 (0.10 g, 0.23 mmol) in $AcOH/H_2O$ (2 mL, 1:1). After stirring for 15 min, the reaction was made basic with 1N NaOH and $NaHCO_3$ and stirred for 30 min. The layers were separated and the aqueous layer was reextracted with $CHCl_3/CH_3OH$ (9/1). The combined organic layers were dried over $MgSO_4$, filtered and concentrated to afford 0.92 g. (73%) of Example 26. A 20 mg. sample of this material was treated with 1M HCl in ether (2 mL). A light yellow solid was formed which was triturated several times with ether and dried under vacuum to afford Example 26 (23 mg.) as a light yellow solid. (Example 26 is also Compound G of Example 22.)

MS $(M+H)^+$ 398.

EXAMPLE 27

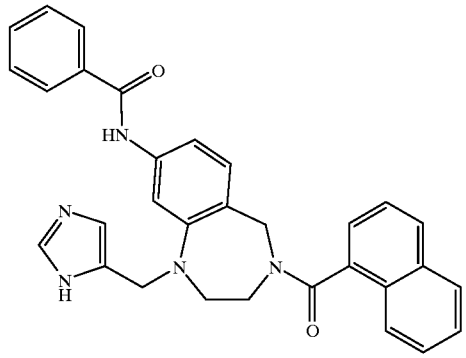

N-[2,3,4,5-Tetrahydro-1-(1H-imidazol-4-ylmethyl)-4-(1-naphthalenylcarbonyl)-1H-1,4-benzodiazepin-8-yl] benzamide, dihydrochloride.

Benzoyl chloride (0.016 g, 0.013 mL) was added to a solution of Example 26 (0.042 g, 0.10 mmol) in $CH_2Cl_2$ (1 mL) and triethyl amine (0.01 g, 0.016 mL) at 0° C. After stirring for 2 hr, the mixture was diluted with $NaHCO_3$ (2 mL) and $CHCl_3$ (10 mL). The layers were separated and the aqueous layer was reextracted with $CHCl_3$ (2×20 mL). The combined organic layers were dried over $MgSO_4$, filtered and concentrated. The residue was purified on a silica flash column eluting with $CH_3Cl/CH_3OH$ (9/1). The product was treated with 1M HCl in ether (2 mL). A light yellow solid was formed which was triturated several times with ether and dried under vacuum to afford Example 27 as a light yellow solid (0.015 g, 28%).

MS $(M+H)^+$ 502. IR: (KBr): 3434, 2930, 1611, 1508, 1424, 1263cm$^{-1}$.

EXAMPLE 28

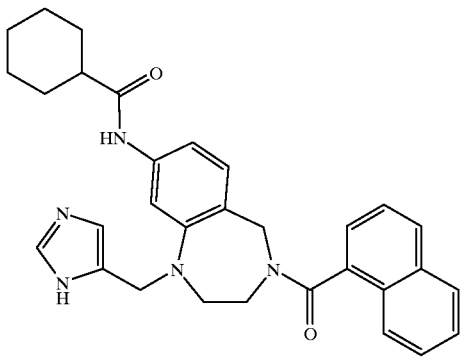

N-[2,3,4,5-Tetrahydro-1-(1H-imidazol-4-ylmethyl)-4-(1-naphthalenylcarbonyl)-1H-1,4-benzodiazepin-8-yl] cyclohexanamide, dihydrochloride.

Example 28 was prepared from Example 26 and cyclohexanecarbonyl chloride as described for Example 27. The crude product was directly treated with HCl/ether. The yellow solid which formed was triturated with ether several times and dried under vacuum to afford Example 28 as a yellow solid in 90% yield.

MS (M+H)$^+$ 508. IR: (KBr): 3434, 2930, 1611, 1508, 1424, 1263 cm$^{-1}$.

EXAMPLE 29

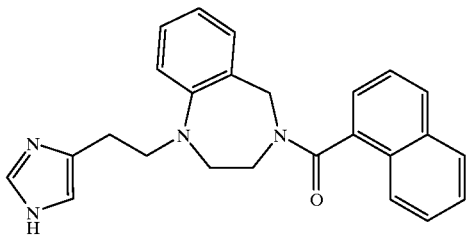

2,3,4,5-Tetrahydro-1-[2-(1H-imidazol-4-yl)ethyl]-4-(1-naphthalenylcarbonyl)-1H-1,4-benzodiazepine, dihydrochloride.

A. 2,3,4,5-Tetrahydro-1-[1-oxo-2-(1-triphenylmethyl-imidazol-4-yl)ethyl]-4-[(1,1-dimethylethoxy)-carbonyl]-1H-1,4-benzodiazepine To a solution of 250 mg (0.68 mmol) of N-triphenylmethyl-4-imidazole acetic acid and 94 μl (0.68 mmol) of triethylamine in 3 mL of THF at −30° C. under argon was added dropwise 97 μl (0.75 mmol) of isobutylchloroformate. Stirring was continued for 10 min and a solution of 253 mg (1.02 mmol) of Compound A of Example 4 in 1 mL of THF was added. The mixture was stirred 7 hours as it warmed to room temperature and diluted with ethyl acetate. The solution was washed with brine, saturated NaHCO$_3$ and brine, dried (MgSO$_4$) and concentrated. The resulting oil was subjected to flash chromatography (silica gel, 75% ethyl acetate:hexanes) to afford 195 mg (0.33 mmol, 48%) of Compound A as a white foamy solid.

B. 2,3,4,5-Tetrahydro-1-[2-(1H-imidazol-4-yl)ethyl]-4-[(1,1-dimethylethoxy)-carbonyl]-1H-1,4-benzodiazepine To a solution of 100 mg (0.17 mmol) of Compound A in 1 mL of THF under argon was added 1 mL (1 mmol) of 1 M borane in THF. After the initial foaming had ceased, the mixture was heated at 60° C. for 1 hour and cooled to room temperature. Conc. HCl (0.5 mL) was added and the solution was heated at 60° C. for 1 hour and evaporated to dryness. The residue was diluted with water and the solution was washed twice with ethyl acetate, rendered alkaline by the dropwise addition of 40% KOH-water, and extracted with methylene chloride (3×). The combined methylene chloride extracts were washed with brine (2×), dried (MgSO$_4$), and the solvent removed to give 39 mg of viscous oil. This material was subjected to flash chromatography (silica gel, CHCl$_3$:MeOH:NH$_4$OH 80:20:2) to afford 16 mg (0.066 mmol, 40%) of Compound B as an oil C. 2,3,4,5-Tetrahydro-1-[2-(1H-imidazol-4-yl)ethyl]-4-(1-naphthalenylcarbonyl)-1H-1,4-benzodiazepine, dihydrochloride.

Compound C was prepared from Compound B (30 mg, 0.12 mmol) as described for Compound C of Example 23 with stirring for 18 hours. The mixture was evaporated to dryness and the residue subjected to flash chromatography (silica gel, 10% methanol:chloroform) to afford 33 mg of material which was subjected to prep HPLC on a YMC S5 ODS (30×250 mm) column. Gradient elution from 30 to 100% solvent B (A: 10% methanol:water+0.1% TFA, B: 10% water:methanol+0.1% TFA) afforded a clear glass residue which was converted to the HCl salt by treatment with HCl-MeOH to give 20 mg (0.04 mmol, 36%) of Example 29 as a solid foam.

MS (M+H)$^+$ 397 Analysis calculated for C$_{25}$H$_{24}$N$_4$O.2 HCl.1.5 H$_2$O Calc'd: C, 60.48 H, 5.89; N, 11.28. Found: C, 60.69 H, 5.63; N, 11.12.

EXAMPLE 30

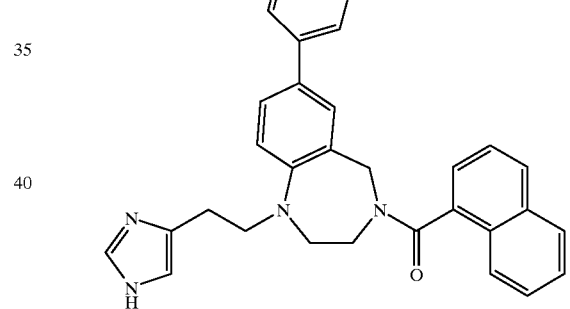

2,3,4,5-Tetrahydro-1-[2-(1H-imidazol-4-yl)ethyl]-4-(1-naphthalenylcarbonyl)-7-phenyl-1H-1,4-benzodiazepine, dihydrochloride.

A. 2,3,4,5-tetrahydro-4-[(1,1-dimethylethoxy)-carbonyl]-7-phenyl-1H-1,4-benzodiazepine Di-tert-butyl dicarbonate (6.1 g, 28 mmol) was added to a solution of Compound B of Example 12 (5.2 g, 23 mmol) in THF (50 mL). The mixture was stirred at room temperature for 2 hours and concentrated under vacuum. The residue was purified by flash chromatography (silica, ethyl acetate) to afford Compound A (5.7 gm, 91%) as an oil. MS: (M+H)$^+$ 325

B. 2,3,4,5-Tetrahydro-1-[2-(1H-imidazol-4-yl)ethyl]-4-(1-naphthalenylcarbonyl)-7-phenyl-1H-1,4-benzodiazepine, dihydrochloride Example 30 was prepared from Compound A by the following 3 step procedure: Compound A of Example 29; Compound B of Example 29, with refluxing for 4 hours and quenching of excess borane by the dropwise addition of methanol; Compound B of Example 3, with stirring at room temperature for 2 hours and flash chromatography on silica with 10% methanol/chloroform followed by preparative HPLC (YMC S5 ODS (30×250 mm) column; gradient elution from 40 to 100% solvent B (A: 10% methanol:water+0.1% TFA, B: 10% water:methanol+0.1% TFA); the clear glassy residue which was converted to the HCl salt by treatment with HCl-MeOH to give Example 30 as a foamy solid.

MS (M+H)$^+$ 473 Analysis calculated for $C_{31}H_{28}N_4O$.2.15 HCl.1 H$_2$O Calc'd: C, 65.44 H, 5.69; N, 9.85 Found: C, 65.56 H, 5.26; N, 9.40.

EXAMPLE 31

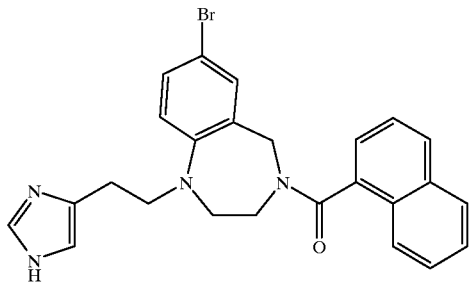

7-Bromo-2,3,4,5-tetrahydro-1-[2-(1H-imidazol-4-yl)ethyl]-4-(1-naphthalenylcarbonyl)-1H-1,4-benzodiazepine, dihydrochloride.

Example 31 was prepared from 7-bromo-1,4-benzodiazepine (prepared as described in Compound B of Example 11) by the following procedure: Compound A of Example 4; Compound A of Example 29 with stirring for 2 hours and chromatography in ethyl acetate; Compound B of Example 29, with the borane reduction refluxed for 3 hours, the HCl treatment at 60° C. for 2 hours, and chromatography with chloroform:methanol:NH$_4$OH (90:10:1); Compound C of Example 23, with silica gel chromatography using 20% methanol:chloroform and preparative HPLC using a 40–100% B gradient.

MS (M+H)$^+$ 475 Analysis calculated for $C_{25}H_{23}N_4OBr$.2 HCl.0.35 H$_2$O Calc'd: C, 55.41 H, 4.67; N, 9.79. Found: C, 55.55 H, 4.53; N, 10.00.

EXAMPLE 32

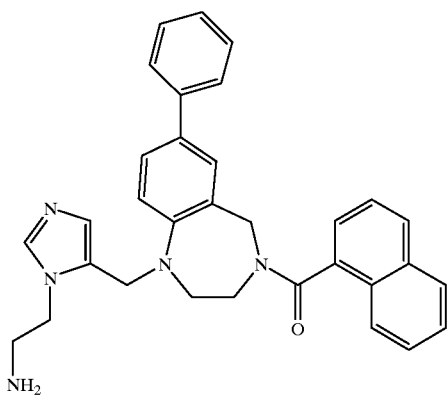

1-[[1-(2-Aminoethyl)-1H-imidazol-5-yl]methyl]-2,3,4,5-tetrahydro-4-(1-naphthalenylcarbonyl)-7-phenyl-1H-1,4-benzodiazepine, trihydrochloride.
A. 1-[[1-[(1,1-dimethylethoxy)-carbonyl]-1H-imidazol-4-yl]methyl]-2,3,4,5-tetrahydro-4-(1-naphthalenylcarbonyl)-7-phenyl-1H-1,4-benzodiazepine A solution of 150 mg (0.33 mmol) of Example 12, 144 mg (0.66 mmol) of di-t-butyldicarbonate, and 5 mg of dimethylaminopyridine in 2 mL of methylene chloride was stirred overnight under argon. The mixture, without workup, was subjected to flash chromatography (silica gel, 50% ethyl acetate-hexanes) afforded 142 mg (0.25 mmol, 77%) of Compound A as a white foamy solid.
B. 1-[[1-(2-(N-phthalimidoethyl)-1H-imidazol-5-yl]methyl]-2,3,4,5-tetrahydro-4-(1-naphthalenylcarbonyl)-7-phenyl-1H-1,4-benzodiazepine To an ice cooled solution, under argon, of 0.5 g (2.6 mmol) of N-hydroxyethylphthalimide and 315 μL (3.9 mmol) of pyridine in 5 mL of methylene chloride was added dropwise a solution of 527 μL (3.1 mmol) of triflic anhydride in 5 mL of methylene chloride. Stirring was continued with cooling for 0.5 hours, and at room temperature for 1 hour. A voluminous precipitate was obtained. The reaction was hydrolyzed by the addition of ice and stirred 10 minutes. The organic layer was washed with 5% NaHSO$_4$ and brine, dried (MgSO$_4$), and the solvent removed to afford 615 mg (1.9 mmol, 73%) of the triflate as a white solid. A solution of 44 mg (0.13 mmol) of this triflate and 75 mg (0.13 mmol) of Compound A in 1.5 mL of methylene chloride was stirred overnight under argon. The mixture, without workup, was subjected to flash chromatography (silica gel, ethyl acetate, followed by 10% methanol-chloroform) to afford 41 mg (0.065 mmol, 50%) of Compound B as a white foamy solid.
C. 1-[[1-(2-Aminoethyl)-1H-imidazol-5-yl]methyl]-2,3,4,5-tetrahydro-4-(1-naphthalenylcarbonyl)-7-phenyl-1H-1,4-benzodiazepine, trihydrochloride.

A solution of 60 mg (0.095 mmol) of Compound C and 100 μL of hydrazine in 0.5 mL of methanol was stirred overnight under argon. The resulting precipitate was removed by filtration and the clear, colorless filtrate subjected to prep HPLC on a YMC S5 ODS (30×250 mm) column. Gradient elution from 25 to 100% solvent B (A: 10% methanol:water+0.1% TFA, B: 10% water:methanol+ 0.1% TFA) afforded a white solid which was converted to the HCl salt by treatment with HCl-MeOH to give 11 mg (0.18 mmol, 19%) of Example 32 as an amorphous pale-yellow solid.

MS (M+H)$^+$ 502 $^1$H NMR (270 MHz, CD$_3$OD, as a mixture of rotamers/conformers): d 3.00 (1H, m), 3.43 (2H, m), 3.57 (2H, m), 4.09 (1H, m), 4.20 (1H, m), 4.50 (1H, m), 4.59 (1H, m), 4.72 (2H, m), 5.02 (1H, m), 6.09 (1H, s), 7.03 (1H, m), 7.22–8.05 (13H, m), 9.12 and 9.18 (1H, m). IR (KBr): 764 cm$^{-1}$, 781, 1144, 1487, 1510, 1609, 2924, 3418.

EXAMPLE 33

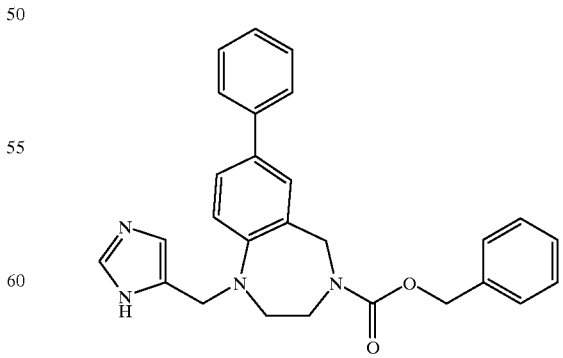

2,3,4,5-Tetrahydro-1-(1H-imidazol-4-ylmethyl)-7-phenyl-1H-1,4-benzodiazepine-4-carboxylic acid, phenylmethyl ester.

A. 2,3,4,5-tetrahydro-1-(1H-imidazol-4-ylmethyl)-4-[(1,1-dimethylethoxy)-carbonyl]-7-phenyl-1H-1,4-benzodiazepine Sodium triacetoxyborohydride (4.5 g, 21 mmol) was added to a solution of Compound A of Example 30 (4.6 g, 14 mmol) and 4-formylimidazole (2.7 g, 28 mmol) in 1:1 methylene chloride/AcOH (40 mL) at room temperature. The mixture was stirred at room temperature for 16 hours and concentrated under vacuum. The residue was dissolved in methylene chloride (100 mL) and 1/1 1N NaOH/NH$_4$OH (100 mL) and the mixture was stirred at room temperature for 16 hours. The organic layer was separated and the aqueous layer was extracted with methylene chloride (3×50 mL). The combined organic extracts were dried (MgSO$_4$), filtered and concentrated under vacuum. The residue was purified by flash chromatography (19/1 CHCl$_3$/MeOH) to afford Compound A (5.7 g, 100%) as a solid. MS: (M+H)$^+$ 405

B. 2,3,4,5-tetrahydro-1-(1H-imidazol-4-ylmethyl)-7-phenyl-1H-1,4-benzodiazepine

Anhydrous HCl (4M, 20 mL, 80 mmol) in dioxane was added to Compound A (2.0 g, 5.0 mmol). The mixture was stirred at room temperature for 4 hours and concentrated under vacuum. The residue was dissolved in water (10 mL) and 1N NaOH (15 mL) was added. The solution was extracted with methylene chloride (4×75 mL) and the combined organic extracts were dried (MgSO$_4$), filtered and concentrated under vacuum to afford Compound B (1.45 g, 97%) as a solid. MS: (M+H)$^+$ 305

C. 2,3,4,5-Tetrahydro-1-(1H-imidazol-4-ylmethyl)-7-phenyl-1H-1,4-benzodiazepine-4-carboxylic acid, phenylmethyl ester p-Nitrophenylbenzylcarbonate (0.04 g, 0.16 mmol) was added to a solution of Compound B (0.2 M, 1.0 ml, 0.16 mmol) in DMF. The mixture was stirred at room temperature for 3 hours, diluted with ethyl acetate (50 mL) and washed with 10% LiCl (50 mL). The aqueous layer was reextracted with ethyl acetate (2×50 mL). The organic fractions were combined, washed with 10% LiCl (2×50 mL), dried (MgSO$_4$), filtered and concentrated under vacuum. The residue was purified by flash chromatography (19/1/0.05 CHCl$_3$/MeOH/AcOH) to afford Example 33 (0.07 g, 93%) as a white solid.

MS (M+H)$^+$ 439. Analysis calculated for C$_{27}$H$_{26}$N$_4$O$_2$.0.05 H$_2$O Calc'd: C, 72.52; H, 6.08; N, 12.53. Found: C, 72.51; H, 5.85; N, 12.47.

EXAMPLE 34

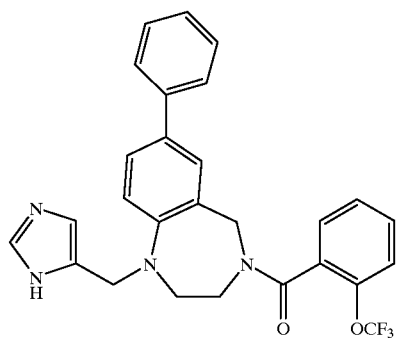

2,3,4,5-Tetrahydro-1-(1H-imidazol-4-ylmethyl)-7-phenyl-4-[2-(trifluoromethoxy)benzoyl]-1H-1,4-benzodiazepine.

A solution of HOAt (0.014 gm, 0.10 mmol) in DMF (0.5 mL) was added to o-trifluoromethoxybenzoic acid (0.021 g, 0.10 mmol) at room temperature. A DMF solution of Compound B of Example 33 (0.2 M, 0.50 ml, 0.16 mmol) and diisopropyl carbodiimide (DIC, 0.013 ml, 0.10 mmol, 1.0 equiv) were added to the mixture, which was stirred at room temperature for 16 hours. The mixture was purified by ion exchange chromatography on a solid phase extraction cartridge using the following protocol:

1) Conditioned a Varian solid phase extraction column (1.5 g, SCX cation exchange) with 10 mL of MeOH/CH$_2$Cl$_2$
2) Loaded mixture onto column using a 10 mL syringe to pressurize the system
3) Wash column with 3×7.5 mL MeOH/CH$_2$Cl$_2$ (1:1)
4) Wash the column with 1×7.5 mL of 0.01 N ammonia in MeOH
5) Eluted column with 7.5 mL of 1.0 N ammonia in MeOH and collect into a tared receiving tube.

The solution containing product was concentrated on a Savant Speed Vac (approx. 2 mm Hg for 20 hours). The residue was dissolved in CH$_3$CN (1 mL) and water (1 mL) and lyophilized to afford Example 34 (0.42 gm, 85%) as a white lyophilate.

MS: (M+H)$^+$ 493 Analysis calculated for C$_{27}$H$_{23}$N$_4$O$_2$F$_3$.0.68 H$_2$O. Calc'd: C, 64.25; H, 4.86; N, 11.29. Found: C, 64.24; H, 4.83; N, 11.40.

EXAMPLE 35

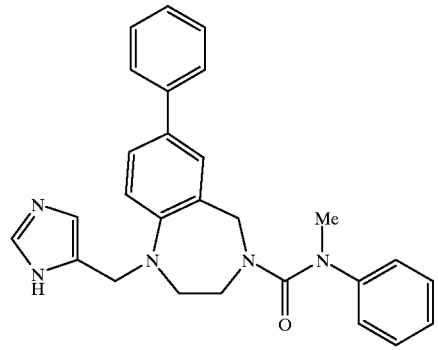

1,2,3,5-Tetrahydro-1-(1H-imidazol-4-ylmethyl)-N-methyl-N,7-diphenyl-4H-1,4-benzodiazepine-4-carboxamide, dihydrochloride.

A. 7-Phenyl-1,2,3,5-tetrahydro-N-methyl-N-phenyl-4H-1,4-benzodiazepine-4-carboxamide A solution of 94 mg (0.55 mmol) of N-methyl-N-phenylcarbamyl chloride in 1.5 mL of CH$_2$Cl$_2$ was added over 3 min. to a stirred mixture of 115 mg (0.5 mmol) of Compound B of Example 12 in 3 mL of CH$_2$Cl$_2$ and 2.5 mL of 1 N NaOH at 0° C. After 1.5 h the reaction was diluted with CH$_2$Cl$_2$ and water and partitioned. The aqueous layer was extracted with CH$_2$Cl$_2$ (2×) and the combined organic layers were dried (Na$_2$SO$_4$) and concentrated to give 177 mg (99%) of Compound A as a glassy residue.

B. 1,2,3,5-Tetrahydro-1-(1H-imidazol-4-ylmethyl)-N-methyl-N,7-diphenyl-4H-1,4-benzodiazepine-4-carboxamide, dihydrochloride Example 35 was prepared from Compound A as described for Compound D of Example 1. Chromatography (silica, 7% methanol, 0.5% ammonium hydroxide, 93% methylene chloride) followed by conversion to the hydrochloride salt provided Example 35 as a powder, m.p. 97–102° C.

MS: (M+H)$^+$ 438$^+$ Analysis calculated for C$_{27}$H$_{27}$N$_5$O.1.2 HCl.0.75 H$_2$O.0.25 C$_4$H$_{10}$O. Calc'd: C,

EXAMPLE 36

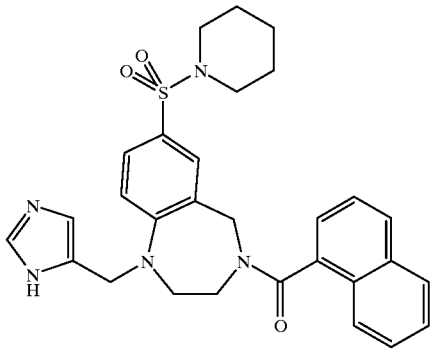

2,3,4,5,-Tetrahydro-1-(1H-imidazol-4-ylmethyl)-4-(1-naphthalenylcarbonyl)-7-(1-piperidinylsulfonyl)-1H-1,4-benzodiazepine, monohydrochloride.

A. 2,3,4,5,-Tetrahydro-7-(1-piperidinylsulfonyl)-1H-1,4-benzodiazepin-2,5-dione

A stirred solution of Compound A of Example 1 (400 mg, 2.3 mmol) in 10 mL of chlorosulfuric acid was heated at 100° C. for 6 h. The solution was poured into ice-water. The aqueous suspension was extracted with ethyl acetate. The combined organic extracts were dried and filtered. The filtrate was mixed with piperidine (0.2 mL) at 0° C. The reaction was allowed to proceed for 30 min. The resultant solution was washed with 10% HCl, sat. NH$_4$Cl solution, dried and concentrated. The residue was triturated with ether to give Compound A as a white solid (250 mg, 34%). (M–H)$^-$ 322.

B. 2,3,4,5,-Tetrahydro-7-(1-piperidinylsulfonyl)-1H-1,4-benzodiazepine

To a stirred suspension of LAH (200 mg, 5 mmol) in glyme was added the Compound A portionwise (185 mg, 0.57 mmol). After completion of the addition, the mixture was heated at 80° C. under argon for 4 h. The mixture was cooled to 0° C. and ethyl acetate (20 mL) and NH$_4$OH (0.3 mL) solution were added successively. The mixture was allowed to stir at room temperature for 18 h. The resultant suspension was filtered. The filtrate was concentrated to give Compound B as an oil (90 mg, 53%). (M–H)$^-$ 295

C. 2,3,4,5,-Tetrahydro-1-(1H-imidazol-4-ylmethyl)-4-(1-naphthalenylcarbonyl)-7-(1-piperidinylsulfonyl)-1H-1,4-benzodiazepine, monohydrochloride Example 36 was prepared from Compound B using the 2 step procedure of Compound C of Example 2 followed by Compound D of Example 1.

MS: (M+H)$^+$ 530$^+$ Analysis calculated for C$_{29}$H$_{31}$N$_5$O$_3$S.1.1 HCl.0.2 toluene.0.5 C$_4$H$_{10}$O. Calc'd: C, 62.22; H, 6.27; N, 11.20; S, 5.13; Cl, 6.23. Found: C, 62.38; H, 6.45; N, 11.18; S, 5.23; Cl, 6.29

EXAMPLE 37

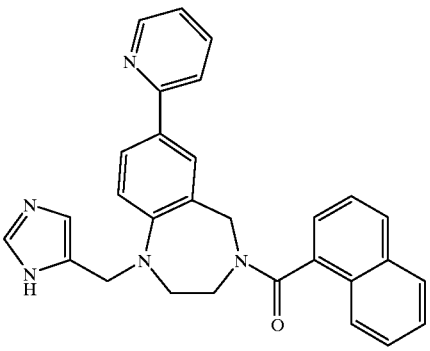

2,3,4,5-Tetrahydro-1-(1H-imidazol-4-ylmethyl)-4-(1-naphthalenylcarbonyl)-7-pyridin-2-yl-1H-1,4-benzodiazepine, trihydrochloride A. 2,3,4,5-Tetrahydro-1-(1-triphenylmethyl-imidazol-4-ylmethyl)-4-(1-naphthalenylcarbonyl)-7-bromo-1H-1,4-benzodiazepine Triphenylmethylchloride (6.83 mmol, 1.9 g) was added to a solution of Example 11 (6.83 mmol, 3.15 g) and triethylamine (34 mmol, 4.7 mL) in acetonitrile (100 mL) and the reaction was stirred for 2 hr. The resulting homogeneous yellow solution was concentrated under reduced pressure and purified by flash chromatography to give 3.9 g (81%) of Compound A as a white solid. MS (M+H)$^+$ 703.

B. 2,3,4,5-Tetrahydro-1-(1H-imidazol-4-ylmethyl)-4-(1-naphthalenylcarbonyl)-7-pyridin-2-yl-1H-1,4-benzodiazepine, trihydrochloride.

A mixture of Compound A (0.28 mmol, 200 mg), 2-(tri-n-butylstannyl) pyridine (1.4 mmol, 520 mg) and Pd(PPh$_3$)$_4$ (40 mg, 0.034 mmol) in degassed THF (3 mL) was heated to 75° C. for 18 hr. The reaction was cooled to room temperature, diluted with 30 mL of MeOH and treated with 2.0 mL of TFA. The mixture was stirred for 12 hr, concentrated, purified by preparative HPLC and converted to the HCl salt to give 46 mg (30% for two steps) of Example 37 as a yellow solid.

MS: (M+H)$^+$ 460$^+$ Analysis calculated for C$_{29}$H$_{25}$N$_5$O.3.09 HCl. Calc'd: C, 60.07; H, 4.95; N, 12.24. Found: C, 60.72; H, 5.09; N, 12.16

EXAMPLE 38

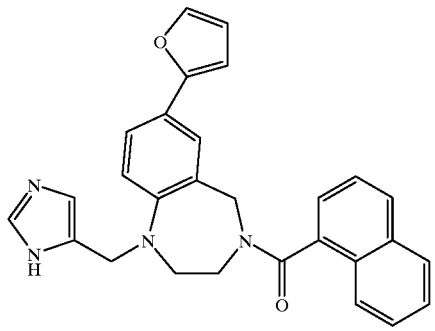

7-(2-Furanyl)-2,3,4,5-tetrahydro-1-(1H-imidazol-4-ylmethyl)-4-(1-naphthalenylcarbonyl)-1H-1,4-benzodiazepine, dihydrochloride.

Example 38 was prepared as a green solid in 11% yield from Compound A of Example 37 and 2-(tributylstannyl) furan as described for Compound B of Example 37.

MS: (M+H)+ 449+

EXAMPLE 39

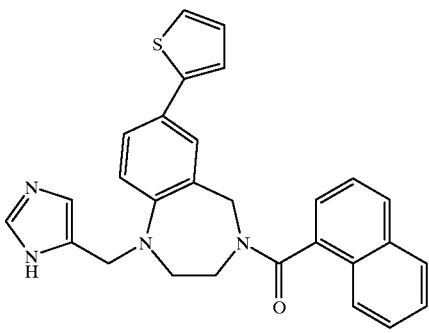

2,3,4,5-Tetrahydro-1-(1H-imidazol-4-ylmethyl)-4-(1-naphthalenylcarbonyl)-7-(2-thienyl)-1H-1,4-benzodiazepine, dihydrochloride.

Example 39 was prepared as a green solid in 10% yield from Compound A of Example 37 and 2-(tributylstannyl) thiophene as described for Compound B of Example 37.

MS: (M+H)+ 465

EXAMPLE 40

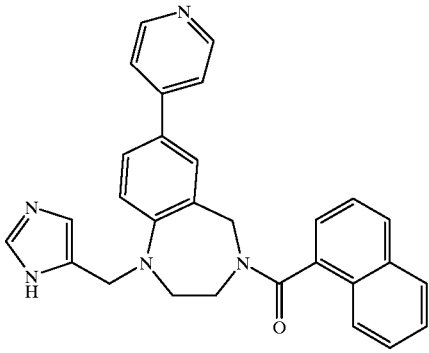

2,3,4,5-Tetrahydro-1-(1H-imidazol-4-ylmethyl)-4-(1-naphthalenylcarbonyl)-7-(4-pyridinyl)-1H-1,4-benzodiazepine, trihydrochloride.

Trifluoroacetic anhydride (0.4 mmol, 60 mL) was added to a solution of 2,3,4,5-tetrahydro-4-(1-naphthalenylcarbonyl)-7-bromo-1H-1,4-benzodiazepine (prepared as described in Example 11, 0.26 mmol, 100 mg) and NEt₃ (1.04 mmol, 150 mL) in CH₂Cl₂ (5 mL) and the homogeneous, colorless solution was maintained at room temperature for 1 hr. The reaction was concentrated, and the residue passed through a short silica gel column (gradient elution: 30% ethyl acetate/hexanes to neat ethyl acetate) to isolate a fluffy white solid which was taken to next step without further purification. This material was dissolved in toluene (2.0 mL) together with 4-(tributylstannyl)pyridine (0.52 mmol, 190 mg) and Pd(PPh₃)₄ (30 mg, 0.026 mmol) and the solution was purged with argon for 15 minutes. The homogeneous brown solution was heated to 115° C. for 20 hrs to give a black heterogeneous solution. The reaction was concentrated and redissolved in MeOH/2N NaOH (aq) (5 mL:5 mL) and stirred at room temperature for 30 minutes. MeOH was removed under reduced pressure and the reaction was partitioned between 10% isopropanol/CH₂Cl₂ and 2N NaOH/saturated NaCl (1:1, 10 mL) and extracted 2× with 10% isopropanol/CH₂Cl₂ (2×5 mL). The pooled organic phase was dried over Na₂SO₄, concentrated and passed through a short silica gel column (eluted with 95:5:1, CHCl₃:MeOH:TEA) to remove polar impurities. The crude material was taken-up in 1,2-dichloroethane:AcOH (1:1, 2 mL total) and treated with 4-formyl imidazole (62 mg, 0.65 mmol) and NaBH(OAc)₃ (0.78 mmol, 165 mg) and the solution was heated to 55° C. for 2 hrs. The reaction was concentrated, partitioned between 10% isopropanol/CH₂Cl₂ and 2N NaOH/saturated NaCl (1:1, 10 mL) and extracted 2× with 10% isopropanol/CH₂Cl₂ (2×5 mL). The pooled organic phase was concentrated, dissolved in MeOH/TFA (5 mL: 0.5 mL) and purified by prep HPLC (YMC S5 ODS 30×250 mm: Rt=19–21 min; gradient elution with 0 to 100% buffer B over 30 min; Buffer A=MeOH:H₂O:TFA (10:90:0.1); Buffer B=MeOH:H₂O:TFA (90:10:0.1); 25 mL/min). The trifluoroacetate salt was converted to the HCl salt by lyophilizing in 1M HCl (2×5 mL) to give 75 mg (50% yield over 4 steps) of Example 40 as a bright yellow solid

MS: (M+H)+ 460

EXAMPLE 41

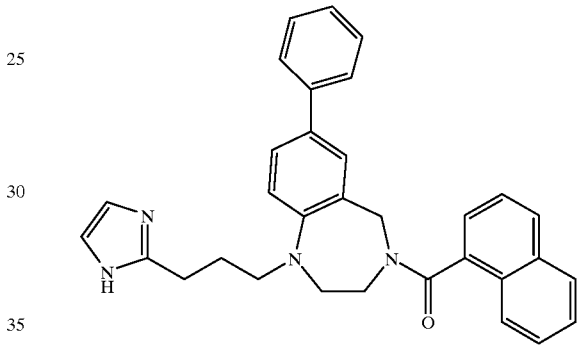

2,3,4,5-Tetrahydro-1-[3-(1H-imidazol-2-yl)propyl]-4-(1-naphthalenylcarbonyl)-7-phenyl-1H-1,4-benzodiazepine, dihydrochloride.

A. 3-[Imidazol-2-yl]-propenoic acid, ethyl ester.

To a cooled (0° C.) solution of sodium hydride (1.86 g, 45.8 mmol, 60% dispersion in mineral oil, prewashed with THF and dried over N₂) in 1,2-dimethoxyethane (DME, 20 mL) was added triethylphosphonoacetate (12 g, 54.1 mmol) dissolved in DME (10 mL) dropwise over 15 minutes. The solution was stirred for 1 hr at ambient temperature followed by the addition of 2-imidazole acetaldehyde (4 g, 41.6 mmol) in 20 mL of DME. The solution was stirred and heated to reflux (85° C.) for 15 minutes followed by cooling to 60° C. for 1 hr. On cooling, the solution was concentrated to ½ volume and filtered. The solid was recrystallized from methanol/ethyl acetate/hexanes to give 5.1 g (74%) of Compound A as a white crystalline solid.

MS (M+H)+ 167+.

B. 3-[Imidazol-2-yl]-propanoic acid, ethyl ester

A solution of Compound A (4.01 g, 24.2 mmol) in absolute ethanol (100 mL, heated to dissolve) was hydrogenated using Pd/C (0.5 g) at ambient temperature for 16 hr. Following removal of H₂ under vacuum, the catalyst was removed by filtration through a bed of celite. The filtrate was concentrated under vacuum to give 4.0 g (100%) of Compound B as a white crystalline solid. MS (M+H)+ 169+.

C. 3-[N-Triphenylmethyl-imidazol-2-yl]-propanoic acid, ethyl ester

Compound B was prepared from Compound A as described for Compound A of Example 6, using methylene chloride as solvent and triethylamine as base. After aqueous workup, recrystallization from ethyl acetate/hexanes afforded Compound B as a white microcrystalline solid. MS (M+H)+ 411+.

D. 3-[N-Triphenylmethyl-imidazol-2-yl]-propan-1-ol

A solution of Compound C (0.80 g, 1.95 mmol) in THF (15 mL) was cooled to 0° C. under argon and a 1M solution of lithium aluminum hydride (2 mL, 2 mmol) was added dropwise with stirring. The reaction was stirred at ambient temperature for 16 hr. Water (2 mL) was added slowly and the solution was concentrated. Water (40 mL) and ethyl ether (60 mL) were added and the layers were separated. The ether layer was dried (MgSO$_4$) and concentrated. The residue was chromatographed (flash silica, 10:1 methylene chloride:methanol). Fractions containing product were pooled and concentrated to give 680 mg (95%) of Compound D as a white crystalline solid. MS (M+H)+.

E. 3-[N-Triphenylmethyl-imidazol-2-yl]-propanal

A solution of oxalyl chloride (0.3 mL, 0.6 mmol) in 2 mL methylene chloride was cooled to −63° C. under argon. DMSO (0.056 mL, 0.8 mmol) in methylene chloride (0.5 mL) was added over 10 min followed by addition of Compound D (147 mg, 0.4 mmol) in methylene chloride (6 mL) over 15 min keeping the reaction temperature below −50° C. The resulting clear solution was stirred for 50 min at −63° C. A solution of triethylamine (0.25 mL, 1.8 mmol) in methylene chloride (1 mL) was added over 15 min keeping the solution below −50° C. The mixture was stirred for 15 min followed by addition of 1M potassium hydrogen sulfate (4.5 mL), water (20 mL) and ethyl ether (60 mL). The layers were separated and the aqueous layer was made basic using half saturated aqueous sodium bicarbonate and washed with ethyl acetate (3×30 mL). The combined organic layers were dried (MgSO$_4$) and concentrated to yield 146 mg (>99%) of Compound E as a yellowish gum.

F. 2,3,4,5-Tetrahydro-4-(1-naphthalenylcarbonyl)-7-phenyl-1H-1,4-benzodiazepine

A solution of Compound B of Example 12 (3.5 g, 15.63 mmol) and N,N-diisopropylethylamine (2.73 mL, 15.63 mmol) in DMF (10 mL) was added at once to a stirred solution of EDC (3.0 g, 15.63 mmol), HOBt (2.1 g, 15.63 mmol) and 1-naphthoic acid (2.42 g, 14.06 mmol) in DMF (20 mL). The mixture was stirred for 4 h, poured into water (200 mL) and the product was extracted with ethyl acetate (2×100 mL). The combined ethyl acetate layers were washed with water (3×200 mL), brine (100 mL), dried (MgSO$_4$), concentrated and chromatographed (silica gel, 50% ethyl acetate/hexane). Fractions containing the desired compound were collected and concentrated to yield Compound A as a clear oil (4.4 g, 93%), (M+H)+ 379+.

G. 2,3,4,5-Tetrahydro-1-[3-(1-triphenylmethyl-imidazol-2-yl)propyl]-4-(1-naphthalenylcarbonyl)-7-phenyl-1H-1,4-benzodiazepine A solution of Compound E (109 mg, 0.29 mmol) and Compound F (100 mg, 0.26 mmol) were dissolved in 1,2-dichloroethane (10 mL). Acetic acid (0.1 mL) was added followed by sodium triacetoxyborohydride (84 mg, 0.40 mmol). The mixture was stirred at 50° C. for 2 h. Saturated NaHCO$_3$ (10 mL) was added and the mixture was concentrated, partitioned between ethyl acetate (50 mL) and water (20 mL). The organic layer was separated, dried (MgSO$_4$), concentrated and chromatographed (silica gel, 40% ethyl acetate/hexane). Fractions containing the desired compound were collected and concentrated to yield Compound G as a clear glass (100 mg, 47%), MS (M+H)+ 729+.

H. 2,3,4,5-Tetrahydro-1-[3-(1H-imidazol-2-yl)propyl]-4-(1-naphthalenylcarbonyl)-7-phenyl-1H-1,4-benzodiazepine, dihydrochloride.

A solution of Compound G (70 mg, 0.096 mmol) in methylene chloride (7 mL), TFA (7 mL), and triethylsilane (0.36 mg, 0.50 mL, 0.31 mmol) was stirred for 30 min at room temperature. The mixture was concentrated and the residue was dissolved in methylene chloride (60 mL) and concentrated. This procedure was repeated five times to yield the crude product as a white sticky solid in quantitative yield. This crude solid was purified by preparative HPLC (YMC S-5 ODS-A column, 30×250 mm; solvent A, 0.1% TFA in 90% water, 10% methanol; solvent B, 0.1% TFA in 10% water, 90% methanol: 20–100% B in 60 min, flow rate 25 mL/min). Fractions containing the desired product were combined, concentrated and lyophilized. This lyophilate was dissolved in methanol (0.5 mL) and 1N HCl (5 mL). This mixture was concentrated and lyophilized. This procedure was repeated to provide Example 41 as a white solid (15 mg, 28%).

MS (M+H)+ 487+ $^1$H-NMR (CD$_3$OD, 400 MHz) d 8.05–7.00 (16H, m), 6.20 (1H, m), 4.47–4.26 (2H, dd, J=15.0), 4.17 (1H, m), 4.08 (1H, m), 3.48 (1H, m), 3.43 (1H, m), 3.33 (1H, m), 3.12 (1H, t), 3.06 (1H, t), 2.98 (1H, m), 2.16 (1H, q), 2.04 (1H, q).

EXAMPLE 42

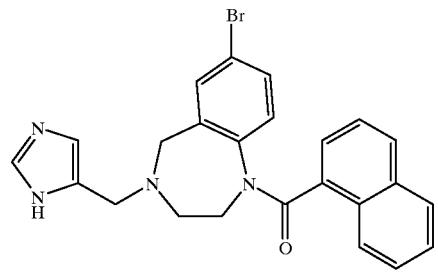

7-Bromo-2,3,4,5-tetrahydro-4-(1H-imidazol-4-ylmethyl)-1-(1-naphthalenylcarbonyl)-1H-1,4-benzodiazepine, dihydrochloride.

Example 42 was prepared as an off white solid from 7-bromo-1,4-benzodiazepine (prepared as described in Compound B of Example 11) using the following procedure: Compound A of Example 4; Compound B of Example 4; Compound C of Example 4; Compound D of Example 1, using methylene chloride as solvent, purification by prep HPLC (YMC S5 ODS 30×250 mm; gradient elution with 0 to 100% buffer B over 45 min; buffer A=MeOH:H$_2$O:TFA (10:90:0.1); buffer B=MeOH:H$_2$O:TFA (90:10:0.1); 25 mL/min) and conversion to the HCl salt by lyophilization from 1M HCl.

MS (M+H+) 462. $^1$H-NMR (CD$_3$OD): 3.5 (br s, 2H), 3.80 (m, 2H), 4.80 (br, 2H), 5.30 (br, 2H), 6.60 (m, 1H), 7.15–8.15 (m, 1 1H), 9.10 (s, 1H).

EXAMPLE 43

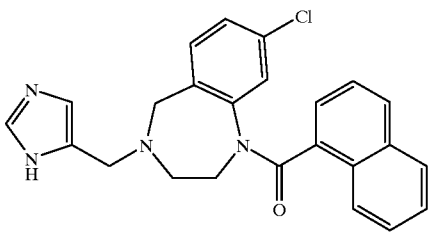

8-Chloro-2,3,4,5-tetrahydro-4-(1H-imidazol-4-ylmethyl)-1-(1-naphthalenylcarbonyl)-1H-1,4-benzodiazepine, dihydrochloride.

Example 43 was prepared as an off white solid from Compound B of Example 2 as described for Example 42.

MS (M+H$^+$) 459. $^1$H-NMR (CD$_3$OD): 3.40–3.80 (br s, 4H), 4.4(br., 2H), 4.7 (br., 2H), 5.20 (br., 2H), 6.65 (d, 1H), 7.00–8.15 (m, 16 H), 9.00(s, 1H).

EXAMPLE 44

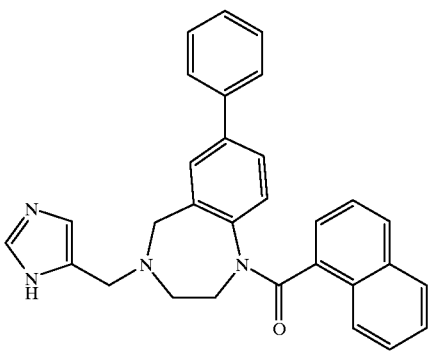

2,3,4,5-Tetrahydro-4-(1H-imidazol-4-ylmethyl)-1-(1-naphthalenylcarbonyl)-7-phenyl-1H-1,4-benzodiazepine, hydrochloride.

Example 44 was prepared as an off white solid from Compound B of Example 12 as described for Example 42.

MS (M+H$^+$) 459. $^1$H-NMR (CD$_3$OD): 3.40–3.80 (br s, 4H), 4.4(br, 2H), 4.7 (br, 2H), 5.20 (br, 2H), 6.65 (d, 1H), 7.00–8.15 (m, 16 H), 9.00 (s, 1H).

EXAMPLE 45

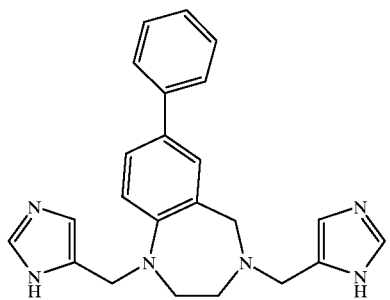

2,3,4,5-Tetrahydro-1,4-bis(1H-imidazol-4-ylmethyl)-7-phenyl-1H-1,4-benzodiazepine, dihydrochloride.

Example 45 was prepared as an off white solid from Compound B of Example 12 as described for Compound D of Example 1, using methylene chloride as solvent, 4.3 equivalents of 4-formylimidazole, 4.3 equivalents of sodium triacetoxyborohydride and with stirring for 4 hours.

MS (M+H$^+$) 385. $^1$H-NMR (CD$_3$OD): 3.5 (br s, 4H), 4.60 (br, 2H), 4.9 (br, 4H), 7.2–8.0 (m, 10 H), 8,90 (s, 1H), 9.05 (s, 1H).

EXAMPLE 46

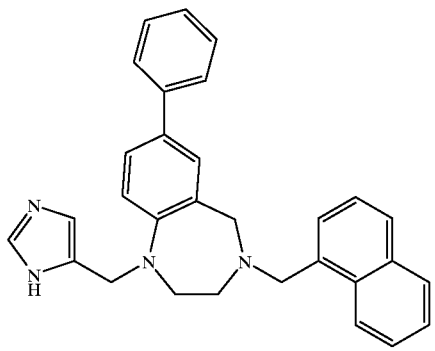

2,3,4,5-Tetrahydro-1-(1H-imidazol-4-ylmethyl)-4-(1-naphthalenylmethyl)-7-phenyl-1H-1,4-benzodiazepine, trifluoroacetate.

Lithium aluminum hydride (1 M in THF, 15 mL, 15 mmol) was added to a suspension of Example 12 (0.25 g, 0.55 mmol) in THF (10 mL). The suspension was refluxed for 5 hr, cooled to 0° C., and 20% aqueous NaOH (10 mL) and H$_2$O (10 mL) were added. The mixture was saturated with NaCl and extracted with CH$_2$Cl$_2$ (2×50 mL). Drying over Na$_2$SO$_4$ and evaporation of the solvent gave a solid (0.21 g) which was dissolved in MeOH/TFA (10:1) and purified by prep HPLC (YMC S5 ODS 30×250 mm; gradient elution with 0 to 100% buffer B over 45 min; Buffer A=MeOH:H$_2$O:TFA (10:90:0.1); Buffer B=MeOH:H$_2$O:TFA (90:10:0.1); 25 mL/min) to provide Example 46 (50 mg) as an off white solid.

MS (M+H$^+$) 445. Analysis calculated for C$_{30}$H$_{28}$N$_4$O.2 HCl.0.3 H$_2$O Calc'd: C, 68.90; H, 5.90; N, 10.71. Found: C, 68.94; H, 5.78; N, 10.43.

EXAMPLE 47

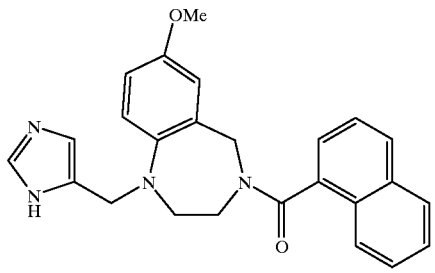

2,3,4,5-Tetrahydro-1-(1H-imidazol-4-ylmethyl)-7-methoxy-4-(1-naphthalenylcarbonyl)-1H-1,4-benzodiazepine, dihydrochloride.

Example 47 was prepared as an off white solid from 6-hydroxy-isatoic anhydride by the following procedure: Compound A of Example 1, with refluxing for 18 hr, and washing of the precipitate with water; formation of the methyl ether by stirring with 1.3 equivalents of methyl iodide in DMF in the presence of K$_2$CO$_3$ at room temperature for 12 hrs; Compound B of Example 1, with quenching with 20% NaOH and water followed by extraction with CH$_2$Cl$_2$; Compound C of Example 2, with the product carried on without chromatography; Compound D of Example 1, using methylene chloride, stirring for 5 hours and purification by flash chromatography (94.5:5:0.5, CH$_2$Cl$_2$:MeOH:NH$_4$OH) before formation of the hydrochloride salt.

Analysis calculated for C$_{24}$H$_{24}$N$_4$O$_2$.2 HCl.0.61 H$_2$O. Calc'd: C, 60.50; H, 5.53; N, 11.29. Found: C, 60.51; H, 5.59; N, 11.14

EXAMPLE 48

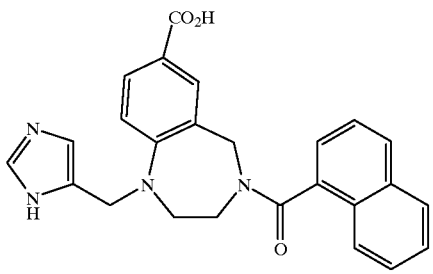

2,3,4,5-Tetrahydro-1-(1H-imidazol-4-ylmethyl)-4-(1-naphthalenylcarbonyl)-1H-1,4-benzodiazepine-7-carboxylic acid, dihydrochloride.

n-BuLi (2.5 M in THF, 0.22 mL, 0.55 mmol) was added to a solution of Example 11 (0.12 g, 0.26 mmol) in THF (10 mL) at −78° C. The resulting brown solution was stirred for 4 min at −78° C., purged with CO$_2$ for 20 min and quenched with acetic acid/water (2:1, 2 mL). The solvent was evaporated, the residue was dissolved in methylene chloride, and the solution was washed with brine, dried (Na$_2$SO$_4$) and evaporated. The residue was purified by prep HPLC (YMC S5 ODS 30×250 mm; gradient elution with 0 to 100% buffer B over 45 min; Buffer A=MeOH:H$_2$O:TFA (10:90:0.1); Buffer B=MeOH:H$_2$O:TFA (90:10:0.1); 25 mL/min) and the product was converted to the HCl salt by lyophilization from 1M HCl (5 mL) to provide Example 48 (50 mg, 45%) as an off white solid.

MS (M+H$^+$) 427. $^1$H-NMR (CD$_3$OD): 3.05 (br m, 1H), 3.20 (m, 1H), 4.00 (br s, 1H), 4.20 (br s, 1H), 4.40 (br d, 1H), 4.50 (br s, 1H), 4.65 (s, 1H), 5.05 (s, 1H), 6.60 (d,1H), 7.19–8.20 (m, 11H), 8.85 (s, 1H), 8.95(s,1H).

EXAMPLE 49

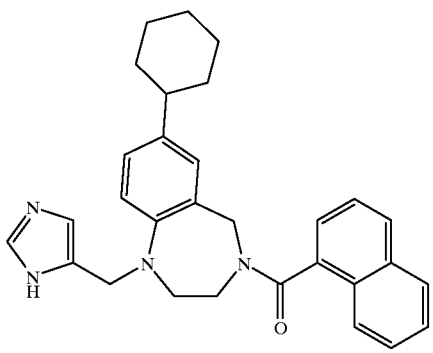

2,3,4,5-Tetrahydro-1-(1H-imidazol-5-ylmethyl)-4-(1-naphthalenylcarbonyl)-7-cyclohexyl-1H-1,4-benzodiazepine, 2.5 hydrochloride.

n-BuLi (2.5M in THF, 1.4 mL, 3.5 mmol) was added to a solution of Example 11 (0.68 g, 1.4 mmol) in THF (15 mL) at −78° C. The resulting brown solution was stirred for 5 min. at −78° C. and cyclohexanone (1.5 ml, 14.4 mmol) was added. After stirring at −78° C. for 10 min., the reaction was quenched with sat. NH$_4$Cl (3 mL) and sat. NaHCO$_3$ (10 mL). The aqueous solution was extracted with CH$_2$Cl$_2$. The organic phase was dried (Na$_2$SO$_4$) and evaporated. The residue was purified by chromatography (silica gel, 10% CH$_3$OH, 0.5% AcOH in CH$_2$Cl$_2$) to give the crude alcohol (80 mg) as well as a 25% yield of Example 50. TFA (3 mL) was added to the crude alcohol (40 mg) in CH$_2$Cl$_2$ (15 mL) at −78° C. The resulting blue solution was treated with solid NaBH$_4$ (0.7 g, 18.5 mmol). The mixture was warmed to room temperature and quenched with NH$_4$OH (10 mL). The solution was diluted with CH$_2$Cl$_2$ (20 mL) and washed with aqueous NaOH (1N, 10 mL) and brine (10 mL). Drying over Na$_2$SO$_4$ and evaporation of solvent gave a solid which was converted to its HCl salt by lyophilization from 1M HCl to provide Example 49 as a yellow solid (30 mg).

MS (M+H$^+$) 465. $^1$H-NMR (CD$_3$OD): 1.50–2.40 (m, 10H), 2.89 (m, 1H), 3.20 (m, 2H), 4.00 (br s, 1H), 4.20 (br s, 1H), 4.40 (br d, 1H), 4.50 (br s, 1H), 4.65 (s, 1H), 4.95 (s, 1H), 6.15 (d, 1H), 7.19–8.10 (m, 11H), 8.85 (s, 1H), 8.95 (s, 1H).

EXAMPLE 50

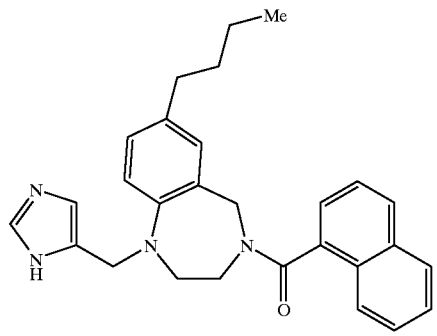

7-Butyl-2,3,4,5-tetrahydro-1-(1H-imidazol-4-ylmethyl)-4-(1-naphthalenylcarbonyl)-1H-1,4-benzodiazepine, dihydrochloride.

See Example 49 for the preparation of Example 50.

MS (M+H$^+$) 439 $^1$H-NMR (CD$_3$OD): 0.5–2.40 (m, 9H), 2.9 (m, 2H), 3.20 (m, 2H), 4.00 (br s, 1H), 4.20 (br s, 1H), 4.40 (br d, 1H), 4.50 (br s, 1H), 4.65 (s, 1H), 4.95 (s, 1H), 6.00 (br s, 1H), 7.19–8.10 (m, 11H), 8.85 (s, 1H), 8.95(s, 1H).

EXAMPLE 51

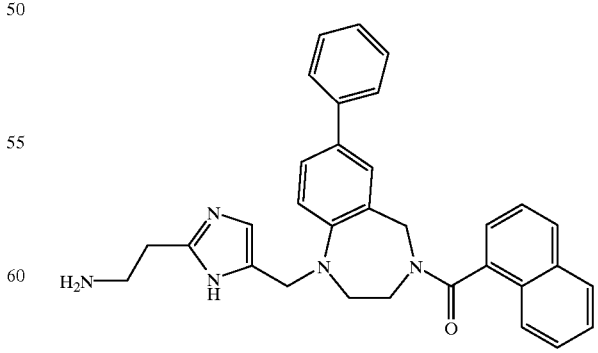

1-[[2-(2-Aminoethyl)-1H-imidazol-4-yl]methyl]-2,3,4,5-tetrahydro-4-(1-naphthalenylcarbonyl)-7-phenyl-1H-1,4-benzodiazepine, trihydrochloride.

Example 51 was prepared by the following 2 step procedure. Tetrahydro-4-(1-naphthalenylcarbonyl)-7-phenyl-1H-1,4-benzodiazepine (prepared as described in Example 12) was reductively alkylated with Compound B of Example 20 as described for Compound D of Example 1, with stirring for 18 hours. Without workup, the mixture was subjected to flash chromatography (silica, 60% ethyl acetate-hexanes) to afford the bis-Boc analog. Deprotection and purification as described in Compound C of Example 20 afforded Example 51 as an off-white powder.

MS (M+H)+ 502 Analysis calculated for $C_{32}H_{31}N_5O.3$ HCl.0.5 $H_2O$ Calc'd: C, 61.99; H, 5.69; N, 11.29. Found: C, 61.68; H, 6.07; N, 11.22.

EXAMPLE 52

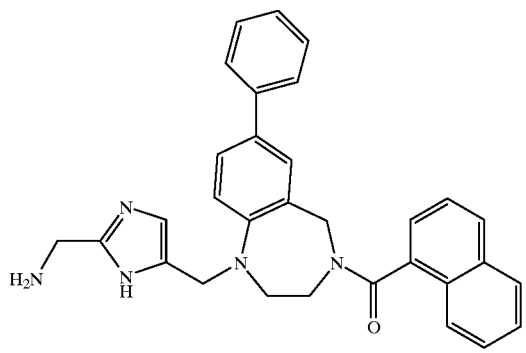

1-[[2-(Aminomethyl)-1H-imidazol-4-yl]methyl]-2,3,4,5-tetrahydro-4-(1-naphthalenylcarbonyl)-7-phenyl-1H-1,4-benzodiazepine, trihydrochloride.

Example 52 was prepared from tetrahydro-4-(1-naphthalenylcarbonyl)-7-phenyl-1H-1,4-benzodiazepine and [2-(2-[[(1,1-dimethyl)-ethoxycarbonyl]amino]methyl)-1-[(1,1-dimethyl)-ethoxycarbonyl]-imidazol-4-yl] carboxaldehyde (see Example 21) as described for Example 51.

MS (M+H)+ 488 Analysis calculated for $C_{31}H_{29}N_5O.3$ HCl. Calc'd: C, 62.37; H, 5.40; N, 11.73. Found: C, 62.13 H, 5.67; N, 11.73.

EXAMPLE 53

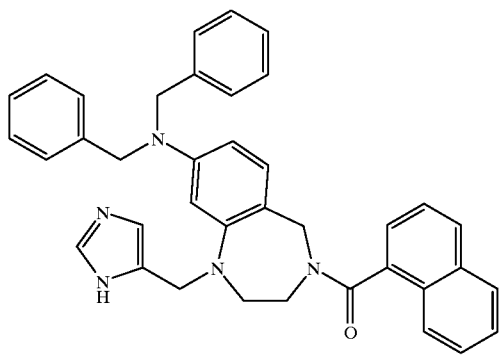

2,3,4,5-Tetrahydro-1-(1H-imidazol-4-ylmethyl)-4-(1-naphthalenylcarbonyl)-8-[N,N-bis(phenyl-methyl)amino]-1H-1,4-benzodiazepine, trihydrochloride.

Sodium triacetoxyborohydride (0.079 g, 0.37 mmol) was added to a solution of Example 26 (0.50 g, 0.12 mmol), benzaldehyde (0.04 g, 0.37 mmol) and AcOH (1 mL) in $CH_2Cl_2$ (1 mL). After stirring for 16 hr, the reaction was diluted with $CH_2Cl_2$ (10 mL), $NH_4OH$ (3 mL) and $NaHCO_3$ (3 mL), and stirred for 30 min. The layers were separated and the aqueous layer was reextracted with $CH_2Cl_2$ (2×50 mL). The combined organic layers were dried over $MgSO_4$, filtered and concentrated. The residue was treated with HCl/ether, a yellow solid was formed which was triturated with ether several times and dried under vacuum to afford Example 53 (0.43 g, 60%).

MS (M+H)+ 579 $^1$H NMR (270 MHz, $CD_3OD$): d 8.8 (d, 1H, J=20 Hz), 8.04–7.9 (m, 2H), 7.6–7.2 (m, 18 H), 7.0 (s, 0.5H), 5.87 (s, 0.5H), 4.95–4.8 (m, 5H), 4.5–4.1 (m, 3H), 3.85 (m, 1H), 3.4–3.2 (m, 2H), 3.0 (m, 1H).

EXAMPLE 54

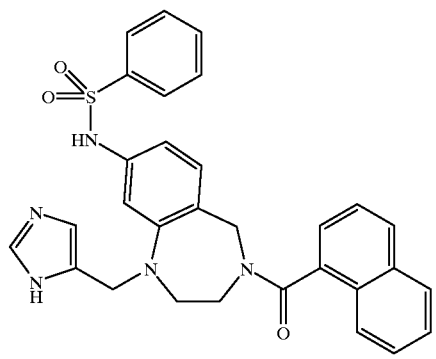

N-[2,3,4,5-Tetrahydro-1-(1H-imidazol-4-yl-methyl)-4-(1-naphthalenylcarbonyl)-1H-1,4-benzodiazepin-8-yl] phenylsulfonamide, dihydrochloride.

Benzenesulphonamide (0.024 g, 0.13 mmol) was added to a solution of Example 26 (0.50 g, 0.12 mmol) and triethylamine (0.019 mL, 0.13 mmol) in $CH_2Cl_2$ (1 mL). After stirring for 16 hr, the reaction was diluted with $CHCl_3$ (10 mL) and $NaHCO_3$ (3 mL) and stirred for 30 min. The layers were separated and the aqueous layer was reextracted with $CHCl_3$ (2×20 mL). The combined organic layers were dried over $MgSO_4$, filtered and concentrated. The residue was treated with HCl/ether, a yellow solid was formed which was triturated with ether several times and dried under vacuum to afford Example 54 (0.64.2 g, 83%) as a light brown solid.

MS (M+H)+ 538 $^1$H NMR (270 MHz, $CD_3OD$): d 8.8 (d, 1H, J=20 Hz), 8.1–7.23 (m, 13H), 7.1 (d,0.5H, J=8 Hz), 7.0 (d, 0.5H, J=8 Hz ), 6.9 (d, 0.5H, J=8 Hz), 6.62 (d, 0.5H, J=8 Hz), 6.12 (d, 0.5H, J=8 Hz), 5.71 (d, 0.5H, J=8 Hz) 4.55 (m, 1H), 4.55–3.9 (m, 3H), 3.45–3.25 (m, 2H), 3.0–2.8 (m, 2H).

EXAMPLE 55

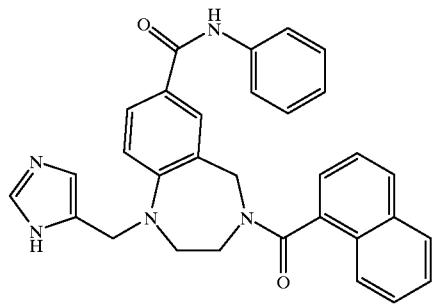

N-Phenyl-2,3,4,5-tetrahydro-1-(1H-imidazol-4-yl-methyl)-4-(1-naphthalenylcarbonyl)-1H-1,4-benzodiazepine-7-carboxamide, dihydrochloride.

A mixture of Example 48 (50 mg, 0.11 mmol), PyBROP (0.28 g, 0.6 mmol), DMAP (0.04 g, 0.3 mmol) and DIEA (0.3 g, 2.3 mmol) in DMF (5 mL) was stirred for 5 min, aniline (1 mL, 11 mmol) was added and the resulting homogeneous solution was stirred for two days. After removing DMF, the residue was purified by prep HPLC (YMC S5 ODS 30×250 mm: Rt=22–23 min; gradient elution with 0 to 100% buffer B over 45 min; Buffer A=MeOH:H$_2$O:TFA (10:90:0.1); Buffer B=MeOH:H$_2$O:TFA (90:10:0.1); 25 mL/min) and conversion to the HCl salt was accomplished by lyophilizing from 1M HCl (5 mL) to provide Example 55 (40 mg, 34%) as a yellow solid.

MS (M+H)$^+$ 502 $^1$H-NMR (CD$_3$OD): 3.10 (br m, 1H), 3.25 (m, 1H), 4.10 (br s, 1H), 4.25 (br s, 1H), 4.45 (br d, 1H), 4.55 (br s, 1H), 4.60 (s, 1H), 5.10 (s, 1H), 6.64 (d, 1H), 7.19–8.20 (m, 16H), 8.85 (s, 1H), 8.95(s, 1H).

EXAMPLE 56

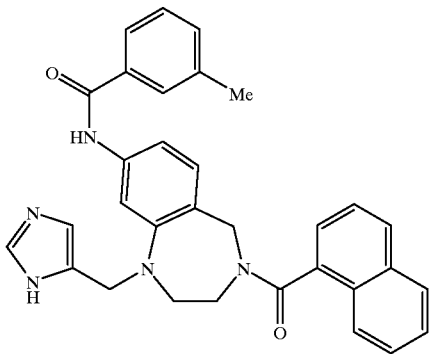

N-[2,3,4,5-Tetrahydro-1-(1H-imidazol-4-ylmethyl)-4-(1-naphthalenylcarbonyl)-1H-1,4-benzodiazepin-8-yl]-3-methylbenzamide, dihydrochloride.

Example 56 was prepared from m-toluoyl chloride and Example 26 as described for Example 27, with stirring for 16 hr. The HCl salt was formed directly from the crude product to provide a 94% yield of Example 56 as a brown solid.

MS (M+H)$^+$ 516 $^1$H NMR (270 MHz, CD$_3$OD): d 8.8 (d, 1H, J=20 Hz), 8.15–7.2 (m, 14H), 6.8 (d, 0.5 H, J=7 Hz), 5.95 (d, 0.5 H, J=7 Hz), 4.98 (s, 1H), 4.7–4.19 (m, 3H), 4.19–3.9 (m, 1H), 3.52–3.2 (m, 1.5H), 3.25–3.15 (m, 0.5H), 3.1–2.8 (m, 1H), 2.46–2.33 (m, 3H).

EXAMPLE 57

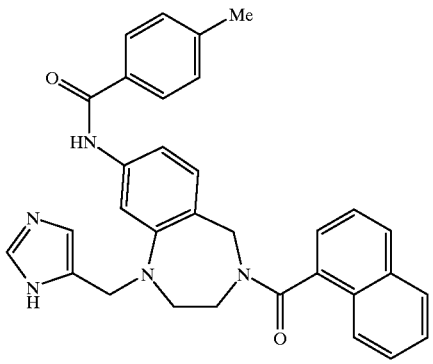

N-[2,3,4,5-Tetrahydro-1-(1H-imidazol-4-ylmethyl)-4-(1-naphthalenylcarbonyl)-1H-1,4-benzodiazepin-8-yl]-4-methylbenzamide, dihydrochloride.

Example 57 was prepared from p-toluoyl chloride and Example 26 as described for Example 56.

MS (M+H)$^+$ 516 $^1$H NMR (270 MHz, CD$_3$OD): d 8.8 (d, 1H, J=20 Hz), 8.15–7.72 (m, 5H), 7.7–7.2 (m, 9H), 6.77 (d, 0.5H, J=7 Hz), 5.92 (d, 0.5H, J=7 Hz), 4.98 (s, 1H), 4.7–4.19 (m, 3H), 4.12–3.9 (m, 1H), 3.52–3.2 (m, 1.5H), 3.25–3.15 (m, 0.5H), 3.1–2.8 (m, 1H), 2.46–2.33 (m, 3H).

EXAMPLE 58

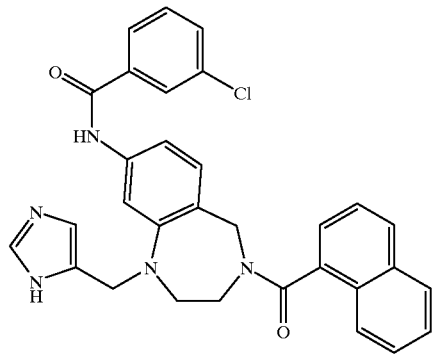

3-Chloro-N-[2,3,4,5-tetrahydro-1-(1H-imidazol-4-ylmethyl)-4-(1-naphthalenylcarbonyl)-1H-1,4-benzodiazepin-8-yl]benzamide, dihydrochloride.

Example 58 was prepared from 3-chlorobenzoyl chloride and Example 26 as described for Example 56.

MS (M+H)$^+$ 536 $^1$H NMR (270 MHz, CD$_3$OD): d 8.87 (d,1H, J=20 Hz), 8.05–7.82 (m, 4H), 7.75–7.2 (m, 10H), 6.8 (d, 0.5 H, J=8 Hz), 5.9 (d, 0.5 H, J=8 Hz), 4.96 (s, 1H), 4.65–3.9 (m, 4H), 3.4–3.3 (m, 2H), 3.05–2.9 (m, 1H).

EXAMPLE 59

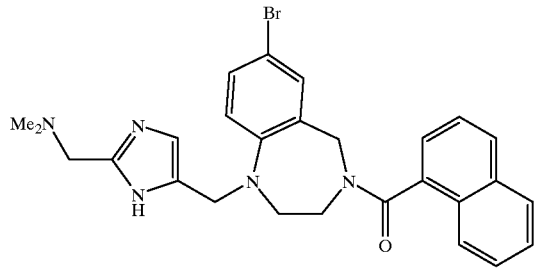

7-Bromo-2,3,4,5,-tetrahydro-1-[[2-[(dimethylamino)-methyl]-1H-imidazol-4-yl]methyl]-4-(1-naphthalenylcarbonyl)-1H-1,4-benzodiazepine, dihydrochloride.

A stirred suspension of Example 11 (100 mg, 0.22 mmol), paraformaldehyde (10 mg, 0.33 mmol) and dimethylamine (40% in water, 0.041 mL) in acetic acid was heated at 90° C. for 18 h. The mixture was partitioned between ethyl acetate and sat. NaHCO$_3$ solution. The organic layer was separated, dried and concentrated in vacuo. The residue was purified by flash chromatography (30% MeOH, 69% ethyl acetate and 1% NH$_4$OH) to give a solid which was dissolved in methanol. 1N HCl in ether was added, and the solvent removed to give Example 59 as a yellow solid (30 mg, 23%).

MS (M+H)$^+$ 518

EXAMPLE 60

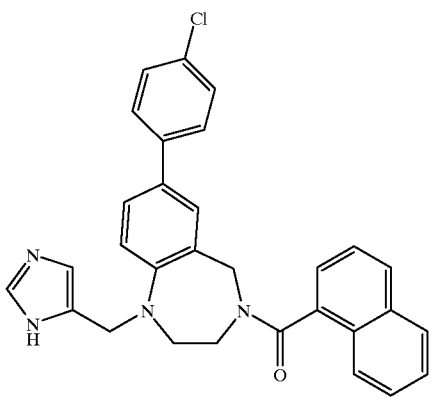

7-(4-Chlorophenyl)-2,3,4,5-tetrahydro-1-(1H-imidazol-4-ylmethyl)-4-(1-naphthalenylcarbonyl)-1H-1,4-benzodiazepine, dihydrochloride.

A solution of Compound A of Example 37 (0.142 g, 0.2 mmol) in DMF (5 mL) and THF (10 mL) was degassed for 5 min with argon. Tetrakis(triphenylphosphine)palladium (0.10 g, 0.08 mmol) was added and the solution was degassed for 20 min with argon. Sodium carbonate (0.11 g, 0.8 mmol) in degassed $H_2O$ (2 mL) was added, followed by 4-chlorobenzeneboronic acid (0.17 g, 1.1 mmol). The resulting solution was heated to 110° C. for 14 hrs. The solvent was evaporated, the residue was dissolved in $CH_2Cl_2$ (15 mL), and the solution was treated with $HSiMe_3$ (3 eq) and TFA (10 eq). The solvent was evaporated and the residue was purified by prep HPLC and converted to HCl salt as described for Example 48 to provide Example 60 (40 mg, 40%) as a gray solid.

MS (M+H)$^+$ 493 $^1$H-NMR (CD$_3$OD, 300 MHz) d 2.95 (br m, 1H), 3.30 (m, 1H), 4.00 (br s, 1H), 4.20 (br s, 1H), 4.40 (br d, 1H), 4.60 (m, 1H), 4.65 (m, 1H), 5.05 (s, 1H), 6.05 (d, 1H), 7.00 (d, 1H), 7.15–8.10 (m, 13H), 8.85 (s, 1H), 8.95 (s, 1H).

EXAMPLE 61

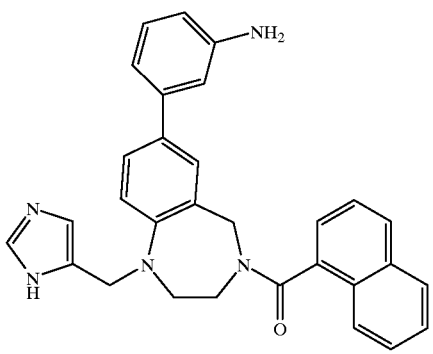

7-(3-Aminophenyl)-2,3,4,5-tetrahydro-1-(1H-imidazol-4-ylmethyl)-4-(1-naphthalenylcarbonyl)-1H-1,4-benzodiazepine, trihydrochloride Compound 61 was prepared as a gray solid in 45% yield from Compound A of Example 37 and 3-aminobenzeneboronic acid (0.17 g, 1.1 mmol) as described for Example 60.

MS (M+H)$^+$474

$^1$ H-NMR (CD$_3$OD, 300 MHz) d 2.95 (br m, 1H), 3.30 (m,1H), 4.00 (br s,1H), 4.20 (br s, 1H), 4.40 (br d,1H), 4.60 (m,1H), 4.65 (m,1H), 5.05 (s,1H), 6.05 (d,1H), 7.00 (d, 1H), 7.15–8.10 (m, 13H), 8.85 (s, 1H), 8.95(s, 1H).

EXAMPLE 62

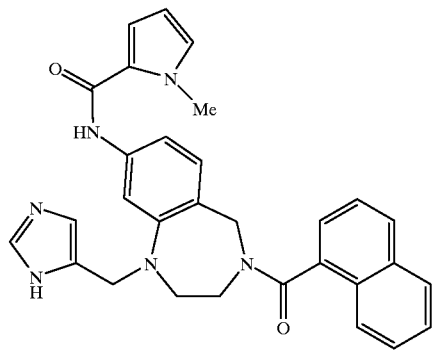

1-Methyl-N-[2,3,4,5-tetrahydro-1-(1H-imidazol-4-ylmethyl)-4-(1-naphthalenylcarbonyl)-1H-1,4-benzodiazepin-8-yl]-1H-pyrrole-2-carboxamide, trihydrochloride Example 26 (0.050 g, 0.12 mmol) was added to a solution of EDC (0.071, 0.37 mmol), HOAt (0.051 g, 0.37 mmol) and 1-methyl-2-pyrrolecarboxylic acid (0.046 g, 0.37 mmol) in DMF (1 mL). After stirring for 16 hr, the mixture was diluted with CHCl$_3$ (10 mL) and NaHCO$_3$ (3 mL) and stirred for 30 min. The layers were separated and the aqueous layer was reextracted with CHCl$_3$ (2×20 mL). The combined organic layers were dried over MgSO$_4$, filtered and concentrated. The residue was purified on a silica gel column eluting with CHCl$_3$ followed by CHCl$_3$/MeOH (19/1). The product was treated with HCl/ether to afford a yellow solid which was triturated with ether few times and dried under vacuum to afford Example 62 (0.007 g, 11%) as a light brown solid.

MS (M+H)$^+$505

$^1$H$^-$NMR (270 MHz, CD$_3$OD): d 8.88 (d, 1H, J=21 Hz), 8.07–7.9 (m, 2.5H), 7.72–7.4 (m, 5H), 7.3 (d, 0.5H, J=8 Hz), 7.23 (d, 0.5H, J=8 Hz), 7.16 (d, 0.5H, J=8 Hz), 7.0 (m, 0.5H), 6.95–6.85 (m, 1H), 6.7 (d, 0.5H, J=8 Hz), 6.15–6.1 (m, 1H), 5.92 (d, 0.5H, J=8 Hz), 5–4.9 (m, 2H), 4.65–4.15 (m, 4H), 3.98–3.9 (d, 3H, J=10), 3.43–3.3 (m, 2.5H), 3.05–2.87 (m, 1H).

EXAMPLE 63

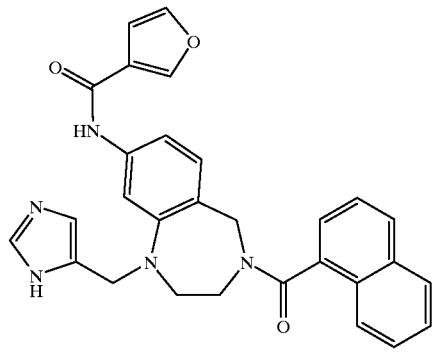

N-[2,3,4,5-Tetrahydro-1-(1H-imidazol-4-ylmethyl)-4-(1-naphthalenylcarbonyl)-1H-1,4-benzodiazepin-8-yl]-3-furancarboxamide, dihydrochloride Example 63 was prepared as a yellow solid from Example 26 and 3-furoic acid as described for Example 62.

MS (M+H)+492

¹H NMR (270 MHz, CD₃OD): d 8.88 (d, 1H, J=20 Hz), 8.25 (d, 1H, J=16 Hz), 8.13–7.38 (m, 9H) 7.38 (d, 0.5H, J=6 Hz), 7.25 (0.5 H, J=6 Hz) 7.19 (d, 0.5H, J=8 Hz), 6.95 (d, 0.5H, J=17 Hz), 6.72–6.68 (m, 1H), 5.93 (d, 0.5H, J=8 Hz), 5.0–4.9 (m, 2H), 4.66–3.91 (m, 3.5H), 3.4–3.3 (m, 2H), 3.05–2.89 (m, 1H).

EXAMPLE 64

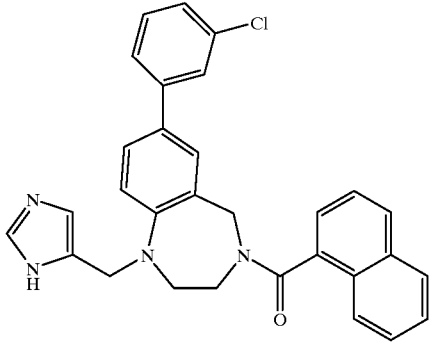

7-(3-Chlorophenyl)-2,3,4,5-tetrahydro-1-(1H-imidazol-4-ylmethyl)-4-(1-naphthalenylcarbonyl)-1H-1,4-benzodiazepine, dihydrochloride Compound 64 was prepared as a gray solid in 55% yield from Compound A of Example 37 and 3-chlorobenzeneboronic acid (0.17 g, 1.1 mmol) as described for Example 60.

MS (M+H)+493

¹H-NMR (CD₃OD, 300 MHz) d 2.95 (br m, 1H), 3.30 (m, 1H), 4.00 (br s, 1H), 4.20 (br s, 1H), 4.40 (br d, 1H), 4.60 (m, 1H), 4.65 (m, 1H), 5.05 (s, 1H), 6.05 (d, 1H), 7.00 (d, 1H), 7.15–8.10 (m, 13H), 8.85 (s, 1H), 8.95 (s, 1H).

EXAMPLE 65

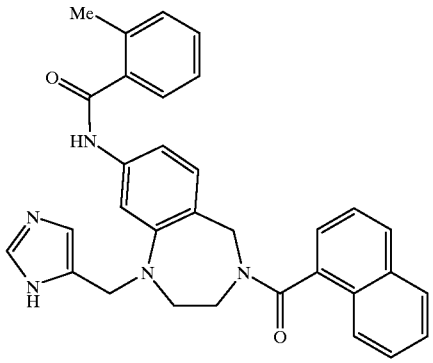

2-Methyl-N-[2,3,4,5-tetrahydro-1-(1H-imidazol-4-ylmethyl)-4-(1-naphthalenylcarbonyl)-1H-1,4-benzodiazepin-8-yl]benzamide, dihydrochloride Example 65 was prepared as a light yellow solid in 23% yield from o-toluoyl chloride and Example 26 as described for Example 56.

MS (M+H)+516

¹H NMR (270 MHz, CD₃OD): d 8.8 (d, 1 H, J=20 Hz), 8.05–7.2 (m, 13.5H), 7.1 (d, 0.5H, J=6 Hz), 6.7 (d, 0.5H, J=8 Hz), 5.95 (d, 0.5H, J=8 Hz), 5.1–4.9 (m, 2H), 4.7–3.9 (m, 3H), 3.45–3.3 (m, 2H), 3.8–2.9 (m, 1H), 2.5–2.4 (d, 3H, J=15 Hz).

EXAMPLE 66

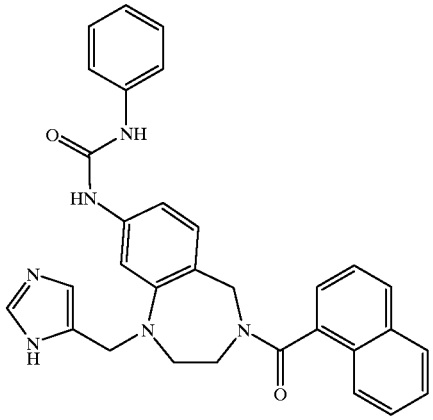

N-Phenyl-N'-[2,3,4,5-tetrahydro-1-(1H-imidazol-4-ylmethyl)-4-(1-naphthalenylcarbonyl)-1H-1,4-benzodiazepin-8-yl]urea, dihydrochloride Phenyl isocyanate (0.016 mL, 0.15 mmol) was added to a solution of Example 26 (0.050 g, 0.12 mmol) and triethyl amine (0.020 mL, 0.15 mmol) in CH₂Cl₂ (1 mL). After stirring for 16 hr, the reaction was diluted with CHCl₃ (10 mL) and NaHCO₃ (3 mL) and stirred for 30 min. The layers were separated and the aqueous layer was reextracted with CHCl₃ (2×20 mL). The combined organic layers were dried over MgSO₄, filtered and concentrated. The residue purified on a silica gel eluting with (19/1) CHCl₃/CH₃OH. The appropriate fractions were concentrated and the residue was treated with HCl/ether. The solid was triturated with ether several times and dried under vacuum to afford Example 66 (0.018 g, 25%) as a light yellow solid.

MS (M+H)+517

¹H NMR (400 MHz, CD₃OD): d 8.83 (d, 1H, J=19 Hz), 8.07–7.89 (m, 2H), 7.68–7.2 (m, 11.5H), 7.07–6.98 (m, 1H) 6.85 (d, 0.5H, J=6 Hz), 6.4 (d, 0.5H, J=8 Hz), 5.89 (d, 0.5H, J=8 Hz), 5.1–4.9 (m, 1H), 4.69–3.9 (m, 4H), 3.45–3.3 (m, 2H), 3.05–2.88 (m,1H).

EXAMPLE 67

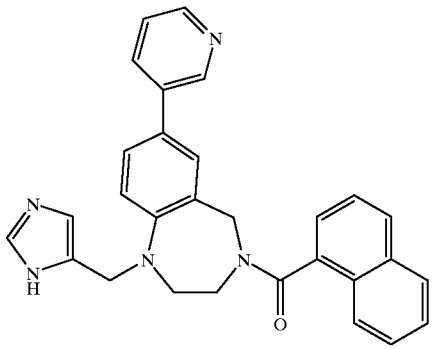

2,3,4,5-Tetrahydro-1-(1H-imidazol-4-ylmethyl)-4-(1-naphthalenylcarbonyl)-7-(3-pyridinyl)-1H-1,4-benzodiazepine, trihydrochloride Example 67 was prepared as a yellow solid in 8% yield from Compound A of Example 37 and 3-(tributylstannyl) pyridine as described for Compound B of Example 37.

MS: (M+H)+460

EXAMPLE 68

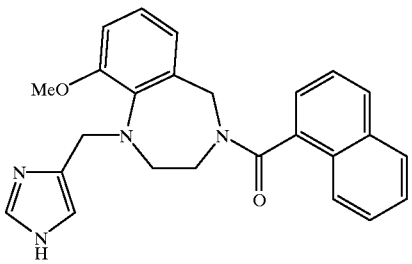

2,3,4,5-Tetrahydro-1-(1H-imidazol-4-ylmethyl)-9-methoxy-4-(1-naphthalenylcarbonyl)-1H-1,4-diazepine, dihydrochloride Example 68 was prepared as a light yellow solid from 8-methoxyisatoic anhydride and glycine ethyl ester hydrochloride as described in the following multistep sequence: Compound A of Example 1; Reduction was accomplished by refluxing a solution of the dione with 5 eq of borane-THF in THF for 20 hr; cooling to 0° C., acidifying with 3N HCl, heating at 100° C. for 30 min, neutralizing with 5N NaOH followed by extraction with methylene chloride; Compound C of Example 2;

Compound D of Example 1.
MS (M+H)$^+$413
IR: (KBr):–2926, 2837, 1732, 1630, 1580, 1474, 1252, 1078, 804, 781 cm$^{-1}$.

EXAMPLE 69

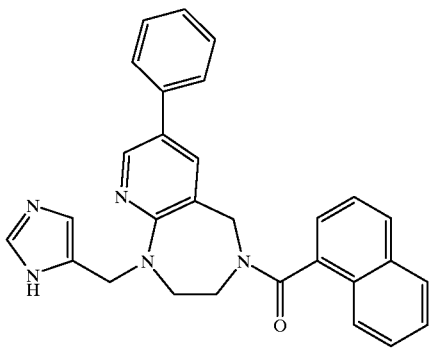

2,3,4,5-Tetrahydro-1-(1H-imidazol-4-ylmethyl)-4-(1-naphthalenylcarbonyl)-7-phenyl-1H-pyrido[2,3-e]-1,4-diazepine, trihydrochloride A. 2,3,4,5-Tetrahydro-7-bromo-1H-pyrido[2,3-e]-1,4-diazepin-5-one To a solution of Compound A of Example 23 (100 mg, 0.61 mmol) in acetic acid (10 mL) was added bromine (32 µL, 0.61 mmol). The mixture stirred for 30 minutes after which another equivalent of bromine (32 µL) was added to drive the reaction to completion. After an additional 30 minutes, the reaction was diluted with 30 mL H$_2$O and neutralized to pH 7 with 5N NaOH. The mixture was extracted with Et$_2$O (50 mL) then with CH$_2$Cl$_2$ (2×100 mL). The organic layers were combined, washed with brine and dried over Na$_2$SO$_4$. Concentration gave Compound A as a solid (116 mg, 79%). MS (M+CH$_3$CN)$^+$283

B. 2,3,4,5-Tetrahydro-7-phenyl-1H-pyrido[2,3-e]-1,4-diazepin-5-one

A solution of Compound A (27 mg, 0.11 mmol), PhB(OH)$_2$ (34 mg, 0.28 mmol), and K$_3$PO$_4$ (59 mg, 0.28 mmol) in anhydrous DMF (0.6 mL) and anhydrous THF (0.6 mL) was degassed by bubbling with a stream of N$_2$ for 1 hour. To this solution was added recrystallized Pd(PPh$_3$)$_4$ and the solution was warmed to 65° C. for 30 hours. The mixture was cooled to room temperature and diluted with CH$_2$Cl$_2$ (6 mL). This was extracted with 10% LiCl and the aqueous layer back-extracted once with CH$_2$Cl$_2$ (6 mL). The organic layers were combined and washed with 1N HCl. The organic layer was discarded, and the aqueous layer was basified with 5N NaOH and extracted with CH$_2$Cl$_2$ (3×10 mL). These organic layers were washed once more with 10% LiCl, dried over Na$_2$SO$_4$ and concentrated to give Compound B as a white solid (18 mg, 70%). MS (M+H+CH$_3$CN)$^+$281.

C. 2,3,4,5-Tetrahydro-7-phenyl-1H-pyrido[2,3-e]-1,4-diazepine

Compound C was prepared as described for Compound B of Example 23, with refluxing for 60 hours. The crude material was chromatographed (flash silica, 230–400 mesh, 5–10% MeOH/CHCl$_3$) to give Compound C as a white solid (34%). MS
(M+H+CH$_3$CN)$^+$267.

D. 2,3,4,5-Tetrahydro-1-(1H-imidazol-4-ylmethyl)-4-(1-naphthalenylcarbonyl)-7-phenyl-1H-pyrido[2,3-e]-1,4-diazepine, trihydrochloride Example 69 was prepared as a fluffy white solid in 36% overall yield from Compound C as described for Compound C of Example 23 and Compound D of Example 23, with a total of 6 aliquots of aldehyde and hydride necessary to drive the reaction to completion.

MS (M+H)$^+$460
Analysis calculated for C$_{29}$H$_{25}$N$_5$O•3 HCl. Calc'd: C, 61.22; H, 4.96; N, 12.31. Found: C, 61.50 H, 5.21; N, 12.29.

EXAMPLE 70

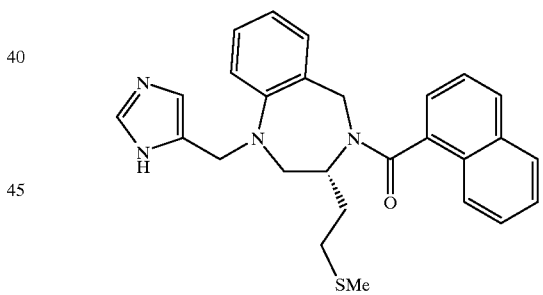

(R)-2,3,4,5-Tetrahydro-1-(1H-imidazol-4-ylmethyl)-3-[2-(methylthio)ethyl]-4-(1-naphthalenylcarbonyl)-1H-1,4-benzodiazepine, hydrochloride Example 70 was prepared as a yellow solid from isatoic anhydride and L-methionine-O methyl ester hydrochloride as described in the following sequence: Compound A of Example 1, with refluxing for 18 hours, evaporation of solvent and partitioning between 1N hydrochloric acid and dichloromethane; Example 17, except that the free base was carried on; Compound C of Example 2, with flash chromatography on silica eluting with ethyl acetate:hexane (1:2); Compound D of Example 1. mp 145–150° C.

MS (M+H)$^+$456
Analysis calculated for C$_{27}$H$_{28}$N$_4$OS•1.6 H$_2$O•1.3 HCl. Calc'd: C, 60.86; H, 6.15; N, 10.51; S, 8.65; Cl, 6.02. Found: C, 60.96; H, 5.67; N, 10.14; S, 8.39; Cl, 5.68.

EXAMPLE 71

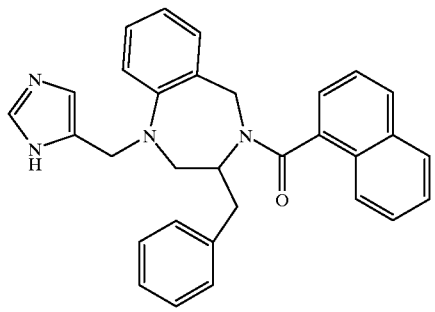

2,3,4,5-Tetrahydro-1-(1H-imidazol-4-ylmethyl)-4-(1-naphthalenylcarbonyl)-3-(phenylmethyl)-1H-1,4-benzodiazepine, hydrochloride Example 71 was prepared as a yellow solid from isatoic anhydride and D,L-phenylalanine-O methyl ester hydrochloride as described for Example 70. mp 78–80° C.

MS (M+H)$^+$473

Analysis calculated for $C_{31}H_{28}N_4O \cdot 1.6\ H_2O \cdot 1.8$ HCl. Calc'd: C, 65.66; H, 5.87; N, 9.88; Cl, 11.25. Found: C, 65.85; H, 5.68; N, 9.64; Cl, 11.55.

EXAMPLE 72

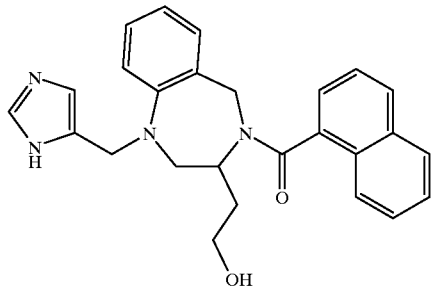

2,3,4,5-Tetrahydro-3-(2-hydroxyethyl)-1-(1H-imidazol-4-ylmethyl)-4-(1-naphthalenylcarbonyl)-1H-1,4-benzodiazepine, trifluoroacetate Example 72 was prepared as a white solid from isatoic anhydride and D,L-aspartate-O-dimethyl ester hydrochloride as described for Example 70, except that 5 equivalents of lithium aluminum hydride were used in the reduction step, and the final product was purified by preparative HPLC (gradient of aqueous methanol with 0.1% TFA). mp 155–160° C.

MS (M+H)$^+$427

Analysis calculated for $C_{26}H_{26}N_2O_2 \cdot 1.0\ H_2O \cdot 1.3$ TFA. Calc'd: C, 57.95; H, 4.98; N, 9.45; Cl, 11.25. Found: C, 58.09; H, 4.71; N, 9.32; Cl, 11.55.

EXAMPLE 73

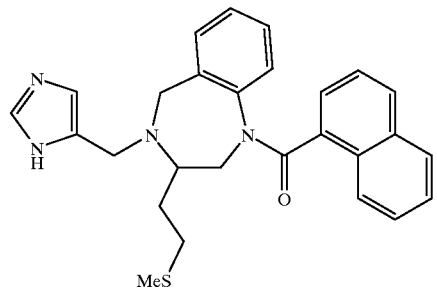

2,3,4,5-Tetrahydro-4-(1H-imidazol-4-ylmethyl)-3-[2-(methylthio)ethyl]-4-(1-naphthalenylcarbonyl)-1H-1,4-benzodiazepine, trifluoroacetate Example 73 was prepared from 2,3,4,5-tetrahydro-3-[2-(methylthio)ethyl]-1H-1,4-benzodiazepine (prepared from D,L-methionine-O methyl ester hydrochloride as described in Example 70) by the following procedure: Compound A of Example 4; Compound C of Example 2, carried on without purification; Compound C of Example 4; Compound D of Example 1, with purification by preparative HPLC (gradient of aqueous methanol with 0.1% TFA). mp 130–135° C.

MS (M+H)$^+$456

Analysis calculated for $C_{27}H_{28}N_4OS \cdot 1.5\ H_2O \cdot 1.3$ TFA. Calc'd: C, 56.27; H, 5.15; N, 8.87; S, 5.07; F, 11.73. Found: C, 56.24; H, 4.84; N, 8.74; S, 5.10; F, 12.05.

EXAMPLE 74

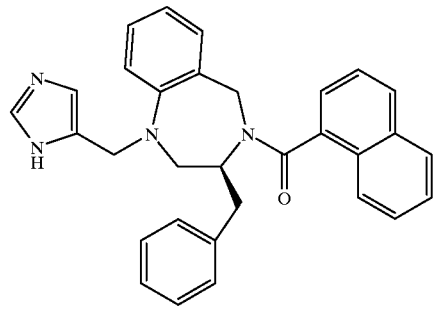

(S)-2,3,4,5-Tetrahydro-1-(1H-imidazol-4-ylmethyl)-4-(1-naphthalenylcarbonyl)-3-(phenylmethyl)-1H-1,4-benzodiazepine, trifluoroacetate Example 74 was prepared as a white solid from isatoic anhydride and L-phenylalanine-O methyl ester hydrochloride as described for Example 70, with final purification by preparative HPLC (gradient of aqueous methanol with 0.1% TFA). mp 152–154° C.

MS (M+H)$^+$473

Analysis calculated for $C_{31}H_{28}N_4O \cdot 1.0\ H_2O \cdot 1.2$ TFA. Calc'd: C, 63.94; H, 5.01 N, 8.93; Cl, 10.90. Found: C, 64.12; H, 4.87; N, 8.73; Cl, 11.01.

EXAMPLE 75

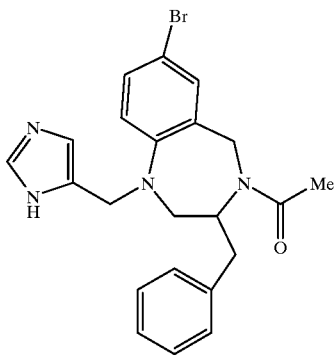

4-Acetyl-7-bromo-2,3,4,5-tetrahydro-1-(1H-imidazol-4-ylmethyl)-3-(phenylmethyl)-1H-1,4-benzodiazepine, hydrochloride A. 7-Bromo-2,3,4,5-Tetrahydro-3-(phenylmethyl)-1H-1,4-benzodiazepin-2,5-dione A mixture of bromoisatoic anhydride (2.93 g, 12.1 mmol), D,L-phenylalanine-O methyl ester hydrochloride salt (2.62 g, 12.1 mmol), dimethylaminopyridine (100 mg, catalytic) and pyridine (50 ml) was refluxed (bath temperature ~140° C.) under argon for 48 hours. The solution was concentrated in vacuo to a semi-solid and the residue was suspended in 1 NHCl (200 mL) and dichloromethane (200 mL). The resultant precipitate was filtered and washed with dichloromethane (50 mL) and dried in vacuo at 50° C. for 18 hrs to provide Compound A (1.1 g, 26%) as a gray solid.

B. 7-Bromo-2,3,4,5-Tetrahydro-3-(phenylmethyl)-1H-1,4-benzodiazepine

To a solution of Compound A (500 mg, 1.45 mmol) in ethylene glycol dimethyl ether (anhydrous, 50 mL) under argon at 0° C. was slowly added a solution of BH$_3$:THF (20 mL, 1M solution in THF). The solution was allowed to warm to room temperature, heated to reflux for 18 hours, cooled to 0° C., quenched with methanol (5 mL), and concentrated in vacuo to an oil. The oil was treated with 6M HCl (100 mL), on a steam bath for 2 hours, during which time partial dissolution occurred. The mixture was cooled to 0° C. and adjusted to pH 10 with solid NaOH. The resultant mixture was partitioned in ethyl acetate (200 mL) and extracted with ethyl acetate (2×100 mL), dried (Na$_2$SO$_4$) and concentrated in vacuo to provide Compound B as a brown solid (300 mg, 0.94 mm, 65%)

C. 4-Acetyl-7-bromo-2,3,4,5-tetrahydro-3-(phenylmethyl)-1H-1,4-benzodiazepine

A mixture of Compound B (200 mg, 0.63 mmol), dichloromethane (5 mL), and aqueous sodium hydroxide (1 ml, 1N) was combined and cooled to 0° C. Acetyl chloride (66 mL, 0.94 mmol) was added to the mixture, and after stirring for 2 hour at 0° C. aqueous sodium hydroxide (20 ml, 1N) and dichloromethane (50 mL) were added, followed by extraction with dichloromethane (50 mL). The organic portions were combined, dried (Na$_2$SO$_4$), and concentrated to a crude oil (230 mg, 100%).

D. 4-Acetyl-7-bromo-2,3,4,5-tetrahydro-1-(1H-imidazol-4-ylmethyl)-3-(phenylmethyl)-1H-1,4-benzodiazepine Example 75 was prepared as a white solid from Compound C as described for Compound D of Example 1, with purification of the final product by preparative HPLC (gradient of aqueous methanol with 0.1% TFA). mp 112° C.

MS (M+H)$^+$440

Analysis calculated for C$_{22}$H$_{23}$N$_4$OBr•0.5 H$_2$O•1.3 TFA. Calc'd: C, 49.53; H, 4.27 N, 9.39; F, 12.42. Found: C, 49.44; H, 4.07; N, 9.34; F, 12.32.

EXAMPLE 76

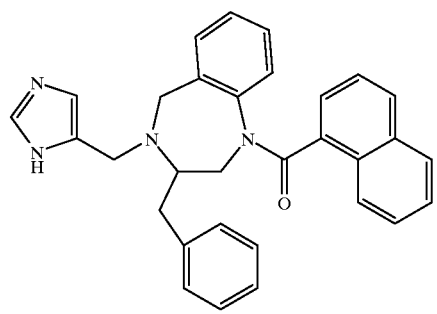

2,3,4,5-Tetrahydro-4-(1H-imidazol-4-ylmethyl)-1-(1-naphthalenyl-carbonyl)-3-(phenylmethyl)-1H-1,4-benzodiazepine, 1.5 hydrochloride Example 76 was prepared as a white solid from 2,3,4,5-tetrahydro-3-(phenylmethyl)-1H-1,4-benzodiazepine (prepared as described in Example 71) by the following procedure: Compound A of Example 4; Compound C of Example 2, with catalytic pyridine and purification on silica eluting with hexane: ethyl acetate (4:1); Compound C of Example 4; Compound D of Example 1, with purification by preparative HPLC (gradient of aqueous methanol with 0.1% TFA). mp 117–120° C.

MS (M+H)$^+$473

Analysis calculated for C$_{31}$H$_{28}$N$_4$OBr•0.8 H$_2$O•1.52 TFA. Calc'd: C, 61.92; H, 4.75 N, 8.48; F, 13.12. Found: C, 62.31; H, 4.40; N, 8.09; F, 12.76.

EXAMPLE 77

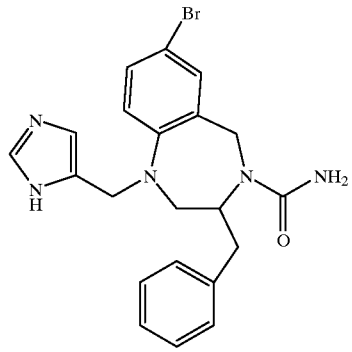

7-Bromo-1,2,3,5-tetrahydro-1-(1H-imidazol-4-ylmethyl)-3-(phenylmethyl)-4H-1,4-benzodiazepine-4-carboxamide, trifluoroacetate A. 7-Bromo-1,2,3,5-tetrahydro-3-(phenylmethyl)-4H-1,4-benzodiazepine-4-carboxamide A mixture of Compound B of Example 75 (200 mg, 0.63 mmol, ), THF (20 mL), and trimethylsilylisocyanate (0.13 mL, 0.95 mmol) was stirred under argon at room temperature for 18 hours. Water was added to the solution (5 mL), followed by aqueous hydrochloric acid (20 ml, 1N). The mixture was extracted with ethyl acetate (2×100 mL), the organic extracts were combined, dried (MgSO$_4$), and concentrated in vacuo to provide Compound A as a yellow solid (200 mg, 88%)

B. 7-Bromo-1,2,3,5-tetrahydro-1-(1H-imidazol-4-ylmethyl)-3-(phenylmethyl)-4H-1,4-benzodiazepine-4-carboxamide, trifluoroacetate Example 77 was prepared as a white solid from Compound A as described for Compound D of Example 1, with purification by preparative HPLC (gradient of aqueous methanol with 0.1% TFA). mp 162–165° C.

MS (M+H)$^+$440

Analysis calculated for $C_{21}$ $H_{22}N_5OBr \cdot 0.3$ $H_2O \cdot 1.2$ TFA. Calc'd: C, 48.24; H, 4.12 N, 12.02; Br, 13.72; F, 11.74. Found: C, 48.23; H, 3.91; N, 11.95; Br, 13.63; F, 11.39.

EXAMPLE 78

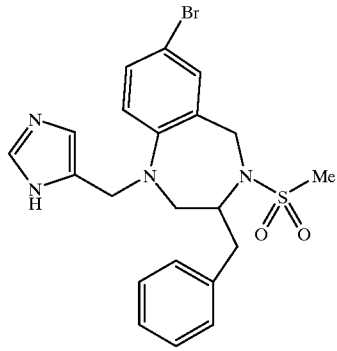

7-Bromo-2,3,4,5-tetrahydro-1-(1H-imidazol-4-ylmethyl)-4-(methylsulfonyl)-3-(phenylmethyl)-1H-1,4-benzodiazepine, hydrochloride A. 7-Bromo-2,3,4,5-tetrahydro-4-(methylsulfonyl)-3-(phenylmethyl)-1H-1,4-benzodiazepine A mixture of Compound B of Example 75 (1.0 g, 3.15 mmol,), THF (20 mL), DIEA (0.6 mL, 6.3 mmol) and methanesulfonyl chloride (0.5 mL, 6.3 mmol) was stirred under argon at room temperature for 2 hours. The mixture was partitioned in aqueous hydrochloric acid (100 ml, 1N), and ethyl acetate (100 mL). The aqueous phase was extracted with ethyl acetate (2×100 mL) and the combined organic layers were combined, dried (MgSO$_4$) and concentrated under vacuum to provide an oil. The oil was flash chromatographed (50 g silica eluted with hexane:ethyl acetate (3:1) to provide Compound A as a clear oil (330 mg, 27%).

B. 7-Bromo-2,3,4,5-tetrahydro-1-(1H-imidazol-4-ylmethyl)-4-(methylsulfonyl)-3-(phenylmethyl)-1H-1,4-benzodiazepine, hydrochloride To a stirred solution of Compound A (330 mg, 0.84 mmol), formyl imidazole (120 mg, 1.26 mmol), dichloroethane (10 mL) and acetic acid (2 mL) at room temperature was added sodium triacetoxyborohydride (267 mg, 1.26 mmole). The solution was stirred for 1 hour, diluted with ethyl acetate (20 mL) and ammonium hydroxide (2 ml, conc), and stirred for an additional 18 hours. The mixture was extracted with ethyl acetate (2×25 mL), and the combined organic extracts were washed with aqueous sodium bicarbonate (25 ml, saturated solution) and ammonium chloride (25 mL, sat aqueous solution), dried (Na$_2$SO$_4$), and concentrated in vacuo to a semi-solid. The crude was purified by preparative HPLC (gradient of aqueous methanol with 0.1% TFA) and lyophilized to provide the TFA salt of Example 78 as a white solid (330 mg, 83%), mp 118–120° C. This material was dissolved in methanol (3 mL) and 1M HCl (3 mL) was added. The solution was evaporated and the residue triturated with methylene chloride to provide Example 78 as a white solid, mp 178–180° C.

MS (M+H)$^+$476

Analysis calculated for $C_{21}$ $H_{23}N_4O_2SBr \cdot 0.25$ $H_2O \cdot 1.2$ HCl. Calc'd: C, 48.17; H, 4.75 N, 10.70; S. 6.12; Cl, 8.12; Br, 15.26. Found: C, 48.53; H, 4.60; N, 10.25; S, 6.95; Cl, 8.27; Br, 14.93.

EXAMPLE 79

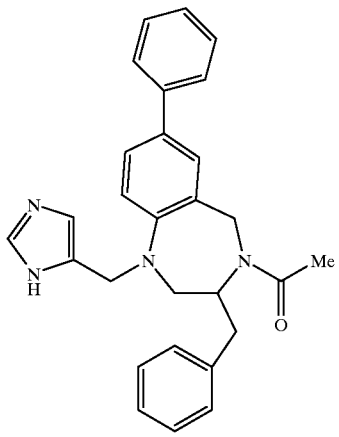

4-Acetyl-2,3,4,5-tetrahydro-1-(1H-imidazol-4-ylmethyl)-7-phenyl-3-(phenylmethyl)-1H-1,4-benzodiazepine, trifluoroacetate A. 4-Acetyl-2,3,4,5-tetrahydro-7-phenyl-3-(phenylmethyl)-1H-1,4-benzodiazepine To a solution of Compound C of Example 75 (500 mg, 1.39 mmol) in toluene (20 mL,), and NaHCO$_3$ (5 mL, sat solution) under argon was added a solution of phenylboronic acid (340 mg, 2.8 mmol, in 2 mL ethanol). Tetrakistriphenylphosphine palladium(0) (42 mg, 0.07 mmol) was added to the mixture and it was brought to reflux under argon for three hours. The mixture was poured into brine, extracted with ethyl acetate (2×100 mL), the organics combined and dried (MgSO$_4$), and concentrated in vacuo to provide a crude red oil, which was purified by flash chromatography (50 g silica eluted with hexane:ethyl acetate 1:1 to provide Compound A as a white solid (290 mg, 59%).

B. 4-Acetyl-2,3,4,5-tetrahydro-1-(1H-imidazol-4-ylmethyl)-7-phenyl-3-(phenylmethyl)-1H-1,4-benzodiazopine, trifluoroacetate Example 79 was prepared as a white solid in 79% yield from Compound A as described for Compound D of Example 1, with purification by preparative HPLC (gradient of aqueous methanol with 0.1% TFA). mp 120–123° C.

MS (M+H)$^+$437

Analysis calculated for $C_{28}H_{28}N_4O \cdot 1.3$ $H_2O \cdot 1.05$ TFA. Calc'd: C, 62.36; H, 5.50 N, 9.66; F, 10.32. Found: C, 62.42; H, 5.17; N, 9.61; F, 10.24.

EXAMPLE 80

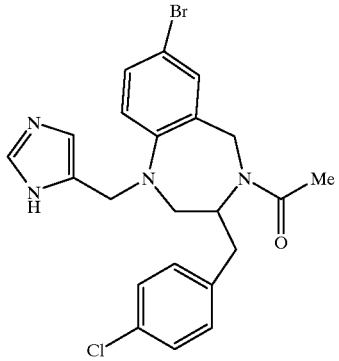

4-Acetyl-7-bromo-3-[(4-chlorophenyl)methyl]-2,3,4,5-tetrahydro-1-(1H-imidazol-4-ylmethyl)-1H-1,4-benzodiazepine, dihydrochloride A. D,L-N-(2-Amino-5-bromobenzoyl)-4-chlorophenylalanine D,L-4-chlorophenylalanine (prepared from N-Boc-D,L-4-chlorophenylalanine and 4N HCl in dioxane with dimethyl sulfide) and 6-bromoisoatoic anhydride (1.0 g, 4.15 mmol) were combined in pyridine (50 mL) and the mixture was refluxed for 4 h. The mixture was cooled, concentrated and the residue was partitioned between water (200 mL) and ethyl acetate (200 mL). The organic layer was washed with water (3×100 mL), brine (50 mL), dried (MgSO$_4$) and concentrated to yield Compound A as a yellowish glass (450 mg, 27%), MS (M+H)$^+$398.

B. 7-bromo-3-[(4-chlorophenyl)methyl]-2,3,4,5-tetrahydro-1H-1,4-benzodiazepin-2,5-dione Compound A (450 mg, 1.13 mmol), EDC (737 mg, 3.85 mmol), and HOBt (519 mg, 3.85 mmol) were dissolved in DMF (10 mL) and DIEA (0.52 mL, 2.96 mmol) was added at once. The mixture was stirred for 16 h, poured into water (100 mL) and the product was extracted with ethyl acetate (2×50 mL). The combined ethyl acetate layers were washed with water (3×100 mL), brine (100 mL), dried (MgSO$_4$) and concentrated to yield compound B as a brown glass (200 mg, 46%), (M+H)$^+$380.

C. 7-bromo-3-[(4-chlorophenyl)methyl]-2,3,4,5-tetrahydro-1H-1,4-benzodiazepine

Compound B (200 mg, 0.53 mmol) was dissolved in THF (10 mL) and borane (1M in THF, 4 mL, 4 mmol) was added. The solution was refluxed for 3 h and cooled to room temperature. Methanol (5 mL) was added and the solution was concentrated. 5N HCl (10 mL) was added to the concentrate and the mixture was refluxed for 4 h. The mixture was cooled to room temperature, neutralized to pH 6 with 50% NaOH and extracted with methylene chloride (3×50 mL). The organic layers were combined, washed with brine (30 mL), dried (MgSO$_4$) and concentrated to yield compound C as a slightly yellow glass (60 mg, 32%), MS (M+H)$^+$352.

D. 4-Acetyl-7-bromo-3-[(4-chlorophenyl)methyl]-2,3,4,5-tetrahydro-1H-1,4-benzodiazepine Compound D (60 mg, 0.17 mmol) was dissolved in THF (5 mL) and DIEA (30 µL, 0.17 mmol) was added followed by acetyl chloride (12 µL, 0.17 mmol). The solution was stirred for 30 min, concentrated, redissolved in ethyl acetate (50 mL) and washed with water (3×20 mL). The organic layer was dried (MgSO$_4$) and concentrated to yield Compound D as a light brown glass.

E. 4-Acetyl-7-bromo-3-[(4-chlorophenyl)methyl]-2,3,4,5-tetrahydro-1-(1H-imidazol-4-ylmethyl)-1H-1,4-benzodiazepine, dihydrochloride Example E was prepared from Compound D as a white solid in 13% yield as described for Compound D of Example 1, with purification by preparative HPLC (YMC S-5 ODS-A column, 30×250 mm; solvent A, 0.1% TFA in 90% water, 10% methanol; solvent B, 0.1% TFA in 10% water, 90% methanol: 20–100% B in 60 min, flow rate 25 mL/min) and conversion to the HCl salt by adding 1N HCl to methanol solution of the TFA salt and lyophilizing.

MS (M+H)$^+$475

$^1$H-NMR (CD$_3$OD, 400 MHz) d 8.85 (1H, s), 7.49–7.15 (7H, m), 6.81 (1H, m), 4.60 (2H, m), 4.49–4.35 (2H, m), 3.63 (1H, m), 2.84–2.63 (2H, m), 2.07 (2H, m), 1.94 (3H, s).

EXAMPLE 81

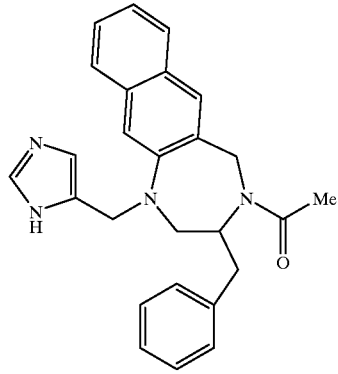

4-Acetyl-2,3,4,5-tetrahydro-1-(1H-imidazol-4-ylmethyl)-3-(phenylmethyl)-1H-naphtho[2,3-e]-1,4-diazepine, monohydrochloride A. 2,3,4,5-Tetrahydro-3-(phenylmethyl)-1H-naphtho[2,3-e]-1,4-diazepin-2,5-dione A solution of the 2,3-naphthyl analog of isatoic anhydride (prepared from 3-amino-2-naphthoic acid, 2.3 eq of triphosgene and triethyl amine in acetonitrile), D,L-phenylalanine (0.77g, 4.7 mmol) and pyridine hydrochloride (540 mg, 4.7 mmol) in pyridine (60 mL) was refluxed for 20 h under nitrogen followed by concentration to an oil. Water (100 mL) was added and the solution was triturated to give a brown solid. This material was filtered and dried under high vacuum to give 1.3g (87%) of Compound A as a brown solid. MS (M+H)$^+$317.

B. 4-Acetyl-2,3,4,5-tetrahydro-1-(1H-imidazol-4-ylmethyl)-3-(phenylmethyl)-1H-naphtho[2,3-e]-1,4-diazepine, monohydrochloride Example 81 was prepared as an offwhite solid from Compound A by the following procedure: Compound C of Example 80; Compound D of Example 80, with stirring for 1 hour and with purification by flash chromatography on silica with ethyl acetate:hexanes (1:5–1:1); Compound E of Example 80.

MS (M+H)$^+$411

Analysis calculated for C$_{26}$H$_{26}$N$_4$O•1.19 H$_2$O •1.5 HCl. Calc'd: C, 64.44; H, 6.17 N, 11.02; Cl, 10.71. Found: C, 64.04; H, 6.38; N, 11.40; Cl, 10.90.

EXAMPLE 82

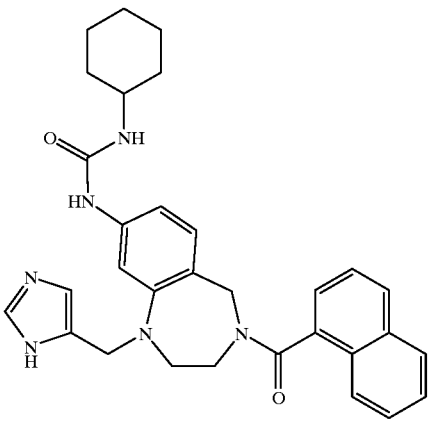

N-Cyclohexyl-N'-[2,3,4,5-tetrahydro-1-(1H-imidazol-4-ylmethyl)-4-(1-naphthalenylcarbonyl)-1H-1,4-benzodiazepin-8-yl]urea, dihydrochloride Example 82 was prepared from cyclohexylisocyanate as described for Example 66, with column chromatography performed with CHCl$_3$/CH$_3$OH (19/1 then 9/1).

MS (M+H)$^+$523

$^1$H NMR (270 MHz, CD$_3$OD): d 8.83 (d, 1H, J=19 Hz), 8.0–7.89 (m, 2.5H) 7.63–7.3 (m, 6.5H), 7.23 (d, 0.5H, J=7 Hz), 6.8 (d, 0.5H, J=8 Hz), 6.31 (d, 0.5H, J=7 Hz), 5.83 (d, 0.5H, J=8 Hz), 4.8 (s, 1H), 4.6–3.8 (m, 4H), 3.6–3.5 (m, 1H), 3.45–3.3 (m, 2H), 3.0–2.8 (m, 1H), 1.9–1.58 (m, 5H), 1.48–1.13 (m, 5H).

EXAMPLE 83

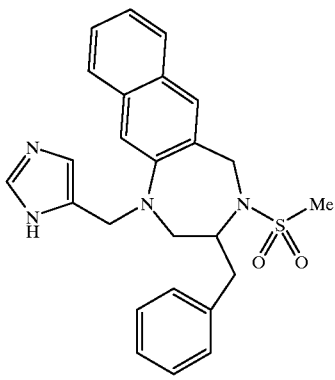

2,3,4,5-Tetrahydro-1-(1H-imidazol-4-ylmethyl)-4-(methylsulfonyl)-3-(phenylmethyl)-1H-naphtho[2,3-e]-1,4-diazepine, monohydrochloride Example 83 was prepared as an offwhite solid from 2,3,4,5-tetrahydro-3-(phenylmethyl)-1H-naphtho[2,3-e]-1,4-diazepine (prepared as described in Example 81) as described in Example 78.

MS (M+H)$^+$447

$^1$H-NMR (CDCl$_3$, 400 MHz) d 8.72 (1H,m), 7.7–7.1 (12H, m), 5.01 (1H, m), 4.43 (1H, s), 4.41 (1H, s) 3.62 (1H, m), 3.15 (1H, m), 2.95 (1H, m), 2.72 (1H, m), 2.3 (3H, s).

EXAMPLE 84

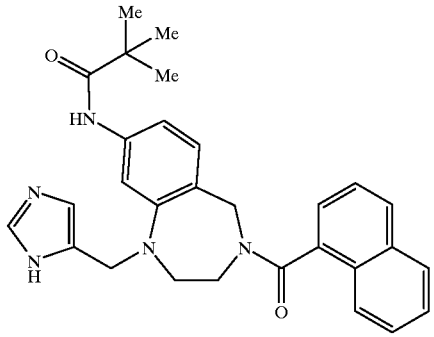

2,2-Dimethyl-N-[2,3,4,5-tetrahydro-1-(1H-imidazol-4-ylmethyl)-4-(1-naphthalenylcarbonyl)-1H-1,4-benzodiazepin-8-yl]propanamide, dihydrochloride Example 84 was prepared Example 26 and pivaloyl chloride as described for Example 27.

MS (M+H)$^+$482

$^1$H NMR (270 MHz, CD$_3$OD): d 8.88 (d,1H, J=20 Hz), 8.05–7.89 (m, 2H), 7.8–7.4 (m, 6.5H), 7.35 (d, 0.5H, J=7 Hz), 7.22 (d, 0.5H, J=7 Hz), 7.1 (d, 0.5H, J=8 Hz), 6.6 (d, 0.5H, J=8 Hz), 5.9 (d, 0.5H, J=8 Hz), 4.6 (s, 1H), 4.5 (m, 2H), 4.22–3.9 (m, 2H), 3.4–3.3 (m, 2H), 3.05–2.85 (q, 1H), 1.3 (d, 9H, J=16 Hz).

EXAMPLE 85

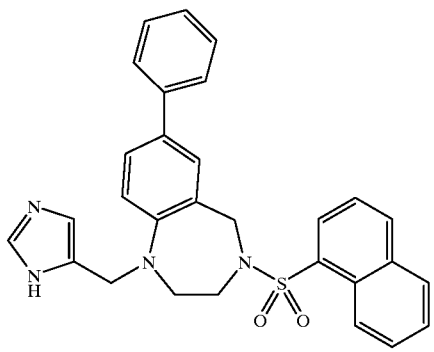

2,3,4,5-Tetrahydro-1-(1H-imidazol-4-ylmethyl)-4-(1-naphthalenylsulfonyl)-7-phenyl-1H-1,4-benzodiazepine, monohydrochloride A. 2,3,4,5-Tetrahydro-4-(1-naphthalenylsulfonyl)-7-phenyl-1H-1,4-benzodiazepine To a solution of Compound B of Example 12 (500 mg, 2.2 mmol) in dichloromethane (20 mL) was added 1-naphthylsulfonyl chloride (500 mg, 2.2 mmol) and triethylamrine (0.31 mL, 2.2 mmol). The solution was stirred for 1 h and concentrated. The residue was partitioned between saturated aqueous sodium bicarbonate (30 mL) and ethyl acetate (40 mL). The organic layer was washed with saturated aqueous sodium bicarbonate (2×30 mL), water (1×30 mL), 1M aqueous potassium hydrogen sulfate (3×30 mL), dried (Na$_2$SO$_4$) and concentrated to give 800 mg (88%) of Compound A as a white solid. MS (M+H)$^+$415.2

B. 2,3,4,5-Tetrahydro-1-(1H-imidazol-4-ylmethyl)-4-(1-naphthalenylsulfonyl)-7-phenyl-1H-1,4-benzodiazepine, monohydrochloride Example 85 was prepared as an offwhite solid in 83% yield from Compound A as described for Compound D of Example 1.

MS (M+H)⁺415

¹H-NMR (CD₃OD, 270 MHz) d 8.83 (1H, s), 8.5 (1H, m), 8.24 (1H, d, J=8 Hz), 8.11 (1H, J=8 Hz), 7.94 (1H, m), 7.61–7.25 (9H, m), 7.02 (1H, d, J=8 Hz). 4.61 (2H, s), 4.41 (2H, s) 3.52 (2H, m), 3.09 (2H, m).

EXAMPLE 86

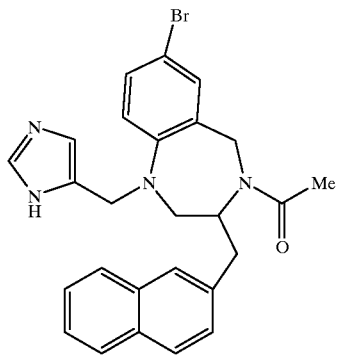

4-Acetyl-7-bromo-2,3,4,5-tetrahydro-1-(1H-imidazol-4-ylmethyl)-3-(2-naphthalenylmethyl)-1H-1,4-benzodiazepine, dihydrochloride Example 86 was prepared as a white solid from D,L-2-naphthylalanine as described for Example 80.

MS (M+H)⁺475

¹H-NMR (CD₃OD, 400 MHz) d 8.81 (1H, s), 7.84 (4H, m), 7.70 (1H, m), 7.50–7.25 (5H, m), 6.87 (1H, m), 4.73–4.54 (3H, m), 4.43 (1H, m), 3.73 (1H, m), 3.23 (1H, m), 3.05 (1H, m), 2.93 (1H, m), 2.13 (1H, m), 2.05 (3H, s).

EXAMPLE 87

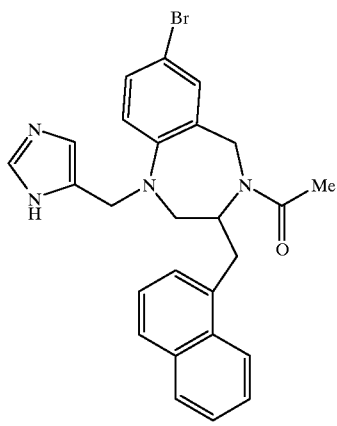

4-Acetyl-7-bromo-2,3,4,5-tetrahydro-1-(1H-imidazol-4-ylmethyl)-3-(1-naphthalenylmethyl)-1H-1,4-benzodiazepine, dihydrochloride Example 87 was prepared as a white solid from D,L-1-naphthylalanine as described for Example 80.

MS (M+H)⁺475

¹H-NMR (CD₃OD, 400 MHz) d 8.53 (1H, s), 7.87 (1H, m), 7.74 (1H, m), 7.55–7.23 (8H, m), 6.74 (1H, m), 4.57–4.43 (2H, m), 4.15 (1H, m), 3.90 (1H, m), 3.83 (1H, m), 3.48 (2H, m), 3.12 (1H, m), 3.00 (1H, m), 2.06 (2H, m), 2.01 (3H, s).

EXAMPLE 88

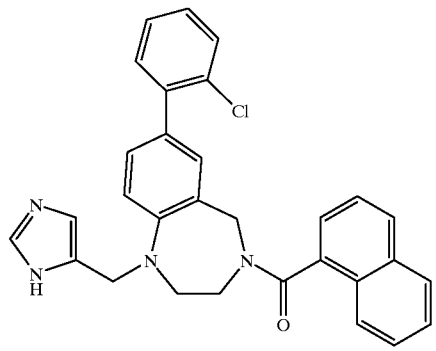

7-(2-Chlorophenyl)-2,3,4,5-tetrahydro-1-(1H-imidazol-4-ylmethyl)-4-(1-naphthalenylcarbonyl)-1H-1,4-benzodiazepine, dihydrochloride A. 2-Chlorobenzeneboronic acid Borane-THF (100 mL, 100 mmol) was slowly added to a mixture of 2-bromochlorobenzene (5.4 mL, 46 mmol) and magnesium (ribbon, 1.12 g, 46 mmol). The flask was placed in a water bath and sonicated overnight. Water (30 mL) was slowly added to destroy excess borane. The aqueous solution was refluxed for 2 hrs. The solvent was evaporated and the residue was neutralized with aq HCl. The aqueous solution was extracted with ether (2×50 mL), dried (Na₂SO₄) and evaporated to afford Compound A (6.24 g, 86%).

B. 7-(2-Chlorophenyl)-2,3,4,5-tetrahydro-1-(1H-imidazol-4-ylmethyl)-4-(1-naphthalenylcarbonyl)-1H-1,4-benzodiazepine, dihydrochloride Example 88 was prepared as a gray solid in 55% yield from Compound A and Compound A of Example 37 as described for Example 60.

MS (M+H)⁺493

¹H-NMR (CD₃OD, 300 MHz) d 2.95 (br m, 1H), 3.30 (m, 1H), 4.00 (br s, 1H), 4.20 (br s, 1H), 4.40 (br d, 1H), 4.60 (m, 1H), 4.65(m, 1H), 5.05 (s, 1H), 6.05 (d, 1H), 7.00 (d, 1H), 7.15–8.10(m, 13H), 8.85 (s, 1H), 8.95(s, 1H).

EXAMPLE 89

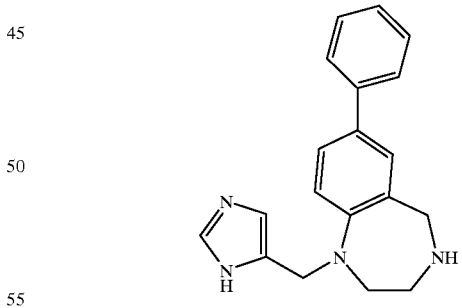

2,3,4,5-Tetrahydro-1-(1H-imidazol-4-ylmethyl)-7-phenyl-1H-1,4-benzodiazepine, monohydrochloride A solution of 2,3,4,5-tetrahydro-4-[(1,1-dimethylethoxy)-carbonyl]-7-phenyl-1H-1,4-benzodiazepine (prepared from Compound B of Example 12 as described for Compound A of Example 4, 0.20 g) and 4-formyl imidazole (0.52 g, 5.6 mmol) in CH₂Cl₂ (10 mL) and acetic acid (2 mL) was stirred for 40 min. Sodium triacetoxyborohydride (0.9 g, 6 mmol) was added and stirring was continued for 4 hrs. Sodium bicarbonate (sat., 5 mL) and ammonium hydroxide (conc, 5 mL) were added and the mixture was stirred for another 3 hrs. The aqueous layer was extracted with CH₂Cl₂ (3×50 mL). The combined organic layers were washed with 1N NaOH (2×10 mL) and conc. NH₄OH (10 mL), dried (Na₂SO₄) and evaporated. The residual solid was stirred in MeOH (5 mL) and aqueous HCl in dioxane (4M, 10 mL) overnight. The solvent was evaporated and the residue was triturated with CHCl₃ to give a solid (0.35 g) which was purified by preparative HPLC (methanolwater gradient with 0.1% TFA) and converted to the HCl salt by lyophilization from 1M HCl (5 mL) to provide Example 89 (0.12 g, 57%) as an off white solid.

MS (M+H)⁺305

¹H-NMR (CD₃OD): 3.26 (m, 4H), 4.45 (s, 2H), 4.62 (s, 2H), 7.2–7.8 (m, 1OH), 8.95 (s, 1H).

EXAMPLE 90

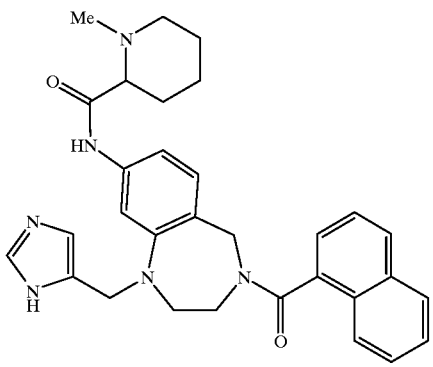

1-Methyl-N-[2,3,4,5-tetrahydro-1-(1H-imidazol-4-ylmethyl)-4-(1-naphthalenylcarbonyl)-1H-1,4-benzodiazepin-8-yl]-2-piperidinecarboxamide, trihydrochloride Example 90 was prepared as a light yellow solid from Example 26 and N-methyl-pipecolic acid as described for Example 62.

MS (M+H)⁺523

¹H NMR (270 MHz, CD₃OD): d 8.9 (d, 1H, J=22 Hz), 8.08–7.88 (m, 2.5H), 7.7–7.2 (m, 6H), 6.8 (d, 0.5H), 5.9 (m, 0.5H), 5.0 (m, 1.5H), 4.6 (s, 1H), 4.5 (m, 2H), 4.3–4.1 (m, 1H), 4.05–3.9 (m, 1H), 3.6–2.7 (m, 8H), 2.3 (t, 1H), 2.05–1.56 (m, 3H), 1.5–0.8 (m, 3H).

EXAMPLE 91

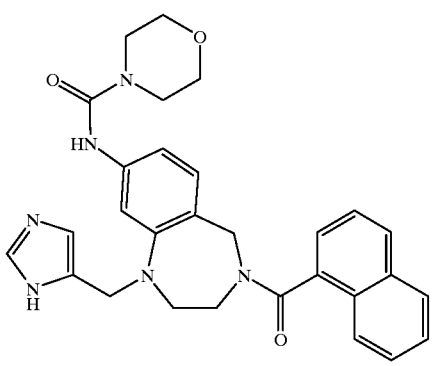

N-[2,3,4,5-tetrahydro-1-(1H-imidazol-4-ylmethyl)-4-(1-naphthalenyl-carbonyl)-1H-1,4-benzodiazepin-8-yl]-4-morpholinecarboxamide, dihydrochloride Example 91 was prepared as a light yellow solid from Example 26 and morpholine N-carbonyl chloride as described for Example 27.

MS (M+H)⁺511

¹H NMR (270 MHz, CD₃OD): d 8.88 (q, 1H), 8.1–7.88 (m, 2.5H), 7.7–7.3 (m, 6.5H), 7.2 (t, 0.5H), 6.9 (d, 0.5H), 6.5 (d, 0.5H), 5.85 (d, 0.5H), 5.08–4.9 (m, 2H) 4.6–4.15 (m, 4H), 3.7–3.65 (m, 3H), 3.6–3.4 (m, 4H), 3.4–3.28 (m, 2H), 3.15–2.8 (m, 1H).

EXAMPLE 92

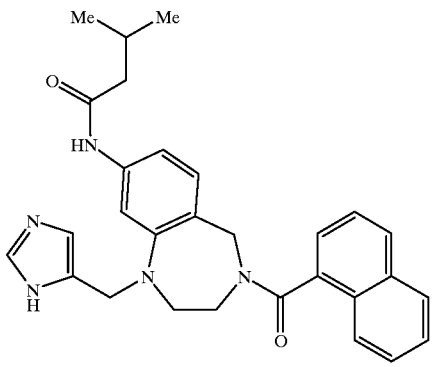

N-[2,3,4,5-Tetrahydro-1-(1H-imidazol-4-ylmethyl)-4-(1-naphthalenyl-carbonyl)-1H-1,4-benzodiazepin-8-yl]-3-methylbutanamide, dihydrochloride Example 92 was prepared as a light yellow solid in 67% yield from Example 26 and isobutyryl chloride as described for Example 27, except that the reaction mixture was concentrated after no starting material was observed, the residue was treated with MeOH and 1N NaOH for 30 min, and after workup, the product was treated with HCl/ether.

MS (M+H)⁺482

¹H NMR (270 MHz, CD₃OD): d 8.88 (d, 1H, J=21 Hz), 8.08–7.9 (m, 2.5H), 7.7–7.19 (m, 6.5H), 6.81 (d, 0.5H), 5.9 (d, 0.5H) 4.9 (m, 1H), 4.6–3.9 (m, 4H), 3.6–3.08 (m, 2H), 3.0–2.76 (m, 4H), 2.3 (m, 1H), 2.05–1.5 (m, 3H) 1.45–0.8 (m, 3H).

EXAMPLE 93

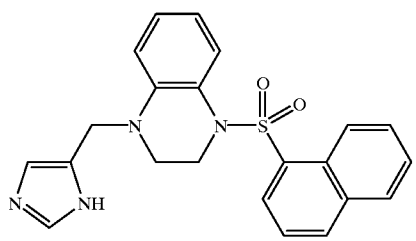

1,2,3,4-Tetrahydro-4-[(1H-imidazol-4-yl)methyl]-1-(naphthalen-1-ylsulfonyl)quinoxaline, dihydrochloride A. 1,2,3,4-Tetrahydro-1-(naphthalen-1-ylsulfonyl)quinoxaline To a solution of Compound A of Example 3 (270 mg, 2 mmol) in dichloromethane (8 mL) at rt under argon was added triethylamine (0.42 mL, 3 mmol) and naphthalene-sulfonyl chloride (500 mg, 2.2 mmol). After 18 hr, the mixture was washed successively with saturated NaHCO₃ and brine (10 mL each), dried (MgSO₄) and concentrated. Dichloromethane (1 mL) was added to the residual yellow solid and Compound A crystallized. The solution was purified by silica gel column chromatography eluting with 30% ethyl acetate in hexanes to afford additional Compound A, total yield 560 mg, 87%.

MS: (M+H)⁺=325⁺

B. 1,2,3,4-Tetrahydro-4-[(1H-imidazol-4-yl)methyl]-1-(naphthalen-1-ylsulfonyl)quinoxaline, dihydrochloride Example 93 was prepared as a pale yellow solid from Compound A as described for Compound D of Example 1. Purification by flash silica gel column chromatography eluting with 9:1 CHCl₃: MeOH afforded a solid which was converted to its HCl salt by treatment 1M HCl in ether (95 mg, 80%).

MS (M+H)⁺405

¹H NMR (free base) (CDCl₃) d 8.22 (1H, d, J=7.3 Hz), 8.15 (1H, d, J=8 Hz), 8.02 (1H, d, J=8 Hz), 7.87 (1H, d, J=7.3 Hz), 7.49 (2H, t, J=8 Hz), 7.39 (1H, s), 7.37 (1H, s), 7.31 (1H, t, J=7.3 Hz), 7.26 (1H, s), 7.02 (1H, t, J=7.3 Hz), 6.65 (1H, t, J=7.3 Hz), 6.54 (1H, d, J=8.0 Hz), 6.0 (1H, s), 4.0 (2H, s), 3.83 (2H, t, J=5.3 Hz), 2.85 3.83 (2H, t, J=5.3 Hz)

EXAMPLE 94

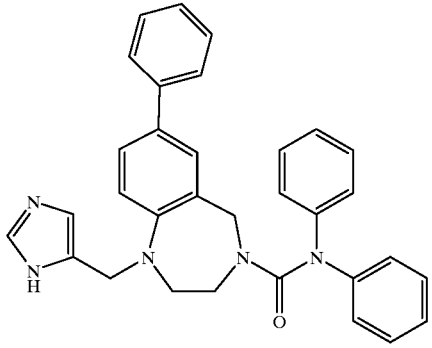

1,2,3,5-Tetrahydro-1-(1H-imidazol-4-ylmethyl)-N,N,7-triphenyl-4H-1,4-benzodiazepine-4-carboxamide, dihydrochloride Example 94 was prepared as a slightly pink powder from N,N-diphenylcarbamyl chloride as described for Example 35, mp>200° C.

MS (M+H)⁺500

Analysis calculated for $C_{32}H_{29}N_5O \cdot 0.4 H_2O \cdot 1.0$ HCl. Calc'd: C, 70.75; H, 5.71 N, 12.89; Cl, 6.53 Found: C,70.89; H, 5.53; N, 12.77; Cl, 6.65.

EXAMPLE 95

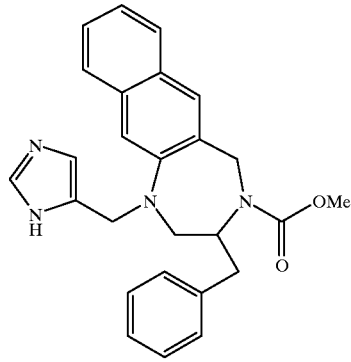

1,2,3,5-Tetrahydro-1-(1H-imidazol-4-ylmethyl)-3-(phenylmethyl)-4H-naphtho[2,3-e]-1,4-diazepine-4-carboxylic acid, methyl ester, monohydrochloride Example 95 was prepared as an off white solid from methyl chloroformate as described for Example 83.

MS (M+H)⁺427

¹H-NMR(CD₃OD, 400 MHz) d 8.72 (1H,m), 7.7–7.1 (12H, m), 5.01 (1H, m), 4.43 (1H, s), 4.41 (1H, s) 3.62 (1H, m), 3.15 (1H, m), 2.95 (1H, m), 2.72 (1H, m), 2.6 (3H, s).

EXAMPLE 96

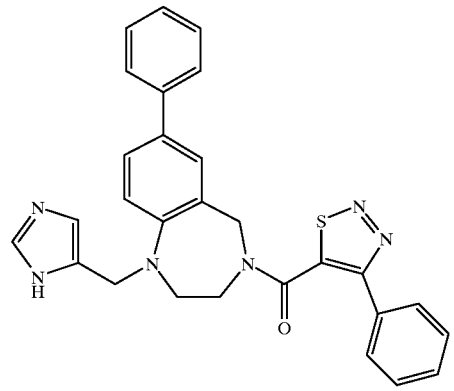

2,3,4,5-Tetrahydro-1-(1H-imidazol-4-ylmethyl)-7-phenyl-4-[(4-phenyl-1,2,3-thiadiazol-5-yl)carbonyl]-1H-1,4-benzodiazepine, trifluoroacetate Example 96 was prepared as a white lyophilate in 50% yield from 4-pheny-5-carboxy-1,2,3-thiadiazole as described for Example 34, with purification by preparative HPLC (gradient of aqueous methanol with 0.1% TFA).

MS (M+H)⁺493

Analysis calculated for $C_{28}H_{24}N_6OS \cdot 0.11 H_2O \cdot 1.6$ TFA. Calc'd: C, 55.35; H, 3.84 N, 12.41 Found: C, 55.28; H, 3.71; N, 12.37.

EXAMPLE 97

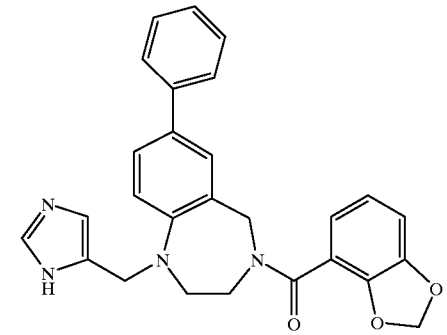

2,3,4,5-Tetrahydro-1-(1H-imidazol-4-ylmethyl)-7-phenyl-4-[(4-phenyl-1,2,3-thiadiazol-5-yl)carbonyl]-1H-1,4-benzodiazepine, trifluoroacetate Example 97 was prepared as a white lyophilate in 6% yield from 2,3-methylenedioxy-benzoic acid as described for Example 34, with purification by preparative HPLC (gradient of aqueous methanol with 0.1% TFA).

MS (M+H)⁺453

¹HNMR(CD₃OD): 3.11 (m, 1H), 3.61 (m, 1H), 3.87 (br m, 2H), 4.61–4.64 (m, 2H), 5.81, 6.06 (s, 2H), 5.96 (s, 2H), 6.68–7.69 (m, 12H), 8.42 (m, 1H), 8.89 (m, 1H).

EXAMPLE 98

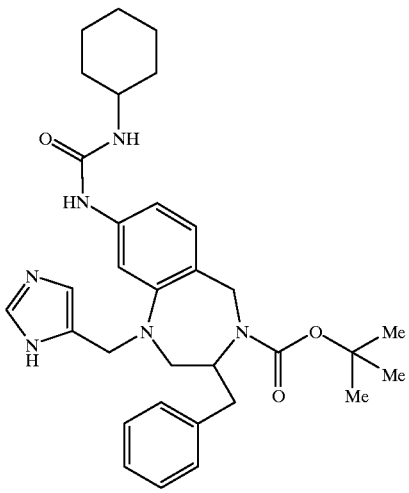

8-[[(Cyclohexylamino)carbonyl]amino]-2,3,4,5-tetrahydro-1-(1H-imidazol-4-ylmethyl)-3-(phenylmethyl)-1H-1,4-benzodiazepine-4-carboxylic acid,1,1-dimethylethyl ester A. 2,3,4,5-Tetrahydro-3-(phenylmethyl)-8-nitro-1H-1,4-benzodiazepin-2,5-dione Compound A was prepared from 7-nitroisatoic anhydride and phenylalanine as described for Compound A of Example 1, except that after refluxing for 1 day, the mixture was concentrated. Dimethyl acetamide was added and the mixture was heated at 150° C. for 4 hr, concentrated and water was added. The olive green solid obtained was filtered and air dried to obtain Compound A in 80% yield). MS (M+H)$^+$ 312

B. 2,3,4,5-Tetrahydro-3-(phenylmethyl)-8-nitro-1H-1,4-benzodiazepine

Borane in THF (1M, 86 mL) was added to Compound A (7.5 g, 24.01 mmol) and the mixture was refluxed for 2 days, cooled to rt, acidified with 3N HCl, and steam heated for 30 min. The solid was filtered and dried to afford Compound B (3.75 g, 95% ) as an olive green solid. MS (M+H)$^+$254. The filtrate was made basic with 5N NaOH (pH 8–9) and extracted with CHCl$_3$, dried over MgSO$_4$, filtered and concentrated to afford 2,3,4,5-tetrahydro-3-(phenylmethyl)-8-amino-1H-1,4-benzodiazepine (1.1 g, 21%).

C. 8-Nitro-2,3,4,5-tetrahydro-3-(phenylmethyl)-1H-1,4-benzodiazepine-4-carboxylic acid,1,1-dimethylethyl ester Boc anhydride (1.5 g, 7 mmol) was added to a solution of Compound B (2.0 g, 7 mmol) and triethylamine (0.71 g, 7 mmol) in THF (30 mL) under argon. After stirring for 6 hr, the mixture was extracted with CHCl$_3$ (3×70 mL). The combined extracts were washed with water (2×50 mL), and brine (1×50 mL), dried over MgSO$_4$, filtered and concentrated. The residue was triturated with hexane/CHCl$_3$ to afford Compound C as an olive green solid (0.89 g, 34%). MS (M−H)$^-$382

D. 8-Nitro-2,3,4,5-tetrahydro-1-(1H-imidazol-4-ylmethyl)-3-(phenylmethyl)-1H-1,4-benzodiazepine-4-carboxylic acid,1,1-dimethylethyl ester Compound D was prepared from Compound C as described for Compound D of Example 1, with stirring for 15 hours. MS (M+H)$^+$464

E. 8-Amino-2,3,4,5-tetrahydro-1-(1H-imidazol-4-ylmethyl)-3-(phenylmethyl)-1H-1,4-benzodiazepine-4-carboxylic acid,1,1-dimethylethyl ester 16% aqueous TiCl$_3$ (2.66 g, in 15 mL H$_2$O, 17.2 mmol) was added to a solution of Compound D (1.0 g, 2.15 mmol) in AcOH/H$_2$O (16 mL, 1:1). After stirring for 15 min, the mixture was made basic with 5N NaOH, stirred for 30 min and extracted with 10% isopropanol/CH$_2$Cl$_2$. The layers were separated, the aqueous layer was extracted with 10% isopropanol/CH$_2$Cl$_2$ and the combined organic layers were dried over MgSO$_4$, filtered and concentrated to afford Compound E (0.70 g, 75%).

MS (M+H)$^+$434.

F. 8-[[(Cyclohexylamino)carbonyl]amino]-2,3,4,5-tetrahydro-1-(1H-imidazol-4-ylmethyl)-3-(phenylmethyl)-1H-1,4-benzodiazepine-4-carboxylic acid,1,1-dimethylethyl ester Compound F was prepared from Compound E using the procedure described by Example 27, using cyclohexylisocyanate. The reaction mixture was concentrated and the residue was treated with 1N NaOH and MeOH. After stirring for 30 min, the mixture was diluted with CHCl$_3$ and NaHCO$_3$. The layers were separated and the aqueous layer was reextracted twice with CHCl$_3$. The combined organic layers were washed with water, brine, dried over MgSO$_4$, filtered and concentrated to afford Example 98 as a light yellow solid. MS: [M+H]$^+$=559$^+$.

MS (M+H)$^+$559

EXAMPLE 99

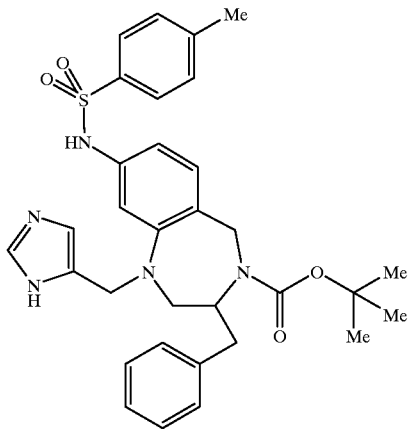

2,3,4,5-Tetrahydro-1-(1H-imidazol-4-ylmethyl)-8-[[(4-methylphenyl)sulfonyl]amino]-3-(phenylmethyl)-1H-1,4-benzodiazepine-4-carboxylic acid, 1,1-dimethylethylester p-Toluenesulfonyl chloride (0.054 g, 0.34 mmol) was added to a solution of 8-amino-2,3,4,5-tetrahydro-1-(1H-imidazol-4-ylmethyl)-3-(phenylmethyl)-1H-1,4-benzodiazepine-4-carboxylic acid, 1,1-dimethylethyl ester (prepared as described in Compound E of Example 98, 0.125 g, 0.28 mmol) and triethylamine (0.048 mL, 0.34 mmol) in CH$_2$Cl$_2$ (1 mL) at 0° C. under argon. After stirring for 16 hr, the mixture was concentrated and the residue was treated with 1N NaOH (0.6 mL) and MeOH (1 mL). After stirring for 30 min, the reaction mixture was diluted with CHCl$_3$ (5 mL) and NaHCO$_3$ (3 mL). The layers were separated and the aqueous layer was reextracted with CHCl$_3$ (2×20 mL). The combined organic layers were washed with water (1×5 mL), brine (1×5 mL), dried over MgSO$_4$, filtered and concentrated to afford Example 99 (0.15 g, 89%) as a light yellow solid.

MS (M+H)$^+$588

EXAMPLE 100

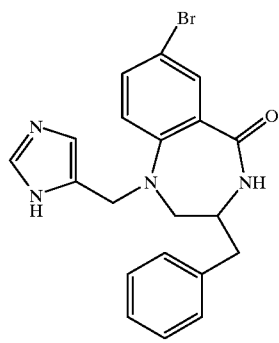

7-Bromo-1,2,3,4-tetrahydro-1-(1H-imidazol-4-ylmethyl)-3-(phenylmethyl)-5H-1,4-benzodiazepin-5-one, dihydrochloride A. 7-Bromo-2,3,4,5-Tetrahydro-3-(phenylmethyl)-1H-1,4-benzodiazepin-5-one To a suspension of 0.5 g (1.45 mmoles) of Compound A of Example 75 in 5 mL of THF at rt and under argon, was added 3 mL (3 mmol) of 1M borane in THF. A clear, bright yellow solution was obtained on addition. Stirring was continued overnight, after which an additional 2 mL (2 mmol) of 1M borane in THF was added and stirring was continued an additional 8 hr. After hydrolysis of excess borane by the dropwise addition of methanol, the reaction was evaporated to dryness and the residue dissolved in 0.5 mL each of methanol and conc HCl. The resulting solution was heated at reflux for 2 hr, cooled to rt and evaporated to dryness. The residue was evaporated from methanol an additional three times, dissolved in ethyl acetate and the solution washed with brine, dried, and the solvent removed to afford a viscous yellow oil. Flash chromatography on silica gel. with 50% ethyl acetate—hexane gave 205 mg (0.62 mmole, 43%) of Compound A as a white solid.

B. 7-Bromo-1,2,3,4-tetrahydro-1-(1H-imidazol-4-ylmethyl)-3-(phenylmethyl)-5H-1,4-benzodiazepin-5-one, dihydrochloride Example 100 was prepared as a nearly white solid in 60% yield from Compound A as described for Compound D of Example 1, with purification by preparative HPLC (gradient of aqueous methanol with 0.1% TFA) and conversion to the HCl salt by treatment with HCl—MeOH.

MS (M+H)$^+$411

Analysis calculated for $C_{20}H_{19}N_4OBr \cdot 0.5\ C_2H_{10}O \cdot 1.5$ HCl. Calc'd: C,52.53; H, 5.11 N, 11.14. Found: C, 52.82; H, 4.71; N, 11.52.

EXAMPLES 101–201

The coupling of each carboxylic acid to Compound B of Example 33 was carried out using standard HOAt/DIC mediated coupling. The process was automated by using a Hamilton 2200 Liquid Handler. A Zymark Benchmate® robotic workstation was used to carry out the weighings of the test tubes and for purification of the resulting amide products. An IBM PC was used to run the Zymark Benchmate® workstation operating program and to write the Benchmate® procedures. The standard protocol for preparation of amides is illustrated by the following examples: A 16×100 mm tube was charged with the appropriate carboxylic acid (0.10 mmol, 1.0 eq) and the Liquid Handler then carried out the following steps on the tube:

1) Added 0.5 mL of a 0.2M 1-hydroxy-7-aza-benzotriazole (HOAt) solution in DMF
2) Added 0.5 mL of Compound B of Example 33 (0.2M, 0.10 mmol, 1.0 eq) in DMF
3) Added 1.0 mL of a methylene chloride solution of diisopropylcarbodiimide (0.016 mL, 0.10 mmol, 1.0 eq)
4) Mixed tube contents by vortexing at speed 3 for 30 sec.

After 24 hr, the mixture was concentrated on a Savant Speed Vac (approx. 2 mm Hg for 72 hr). The residue was purified by ion exchange chromatography on a solid phase extraction cartridge mediated by the Benchmate® robotic workstation using the following protocol:

1) Added 5.0 mL of methanol/methylene chloride(1:1) to the reaction
2) Mixed tube contents by vortexing at speed 3 for 60 sec
3) Conditioned a Varian solid phase extraction column (1.5 g, SCX cation exchange) with 10 mL of methanol/methylene chloride at 0.15 mL/sec
4) Loaded reaction contents onto column at 0.02 mL/sec
5) Washed column with 2×7.5 mL of methanol/methylene chloride(1:1) at 0.1 mL/sec
6) Washed column with 1×7.5 mL of methanol at 0.1 mL/sec
7) Washed column with 0.01M ammonia in methanol
8) Eluted column with 7.5 mL of 1M ammonia in methanol and collect into a tared receiving tube at 0.05 mL/sec.

All solution/solvent deliveries were followed by 1.0 mL of air and a 5 sec push delay was used after loading reaction contents onto the ion exchange column. The product solution was concentrated on a Savant Speed Vac (approx. 2 mm Hg for 20 hr) to afford the target compound.

Syntheses requiring further purification were subjected to preparative HPLC (YMC S3 ODS 50×100 mm, 30 mL/min, 10 minute gradient of 10–90% aqueous methanol with 0.1% TFA, monitored at 220 nm). The appropriate fractions were combined and concentrated under vacuum. The residues were dissolved in methanol (5 mL) and 1N HCl (1 mL) and concentrated on a Savant Speed Vac (approx. 2 mm Hg for 20 hr) to afford the target compound. Target compounds were characterized by analytical HPLC and mass spectrometry.

| Example | Structure | | Mass Spectrum |
|---|---|---|---|
| 101 | 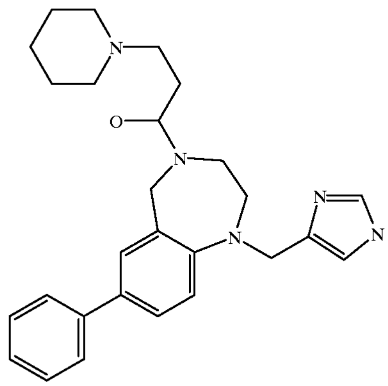 | 2,3,4,5-Tetrahydro-1-(1H-imidazol-4-ylmethyl)-4-[1-oxo-3-(1-piperidinyl)propyl]-7-phenyl-1H-1,4-benzodiazepine, trihydrochloride. | m/z 444 (M + H) |
| 102 | 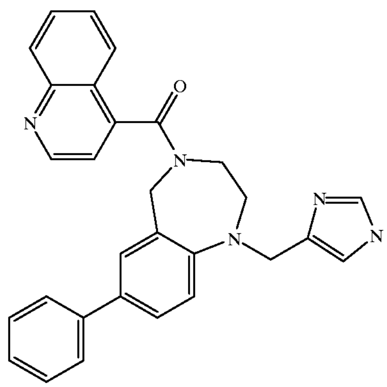 | 2,3,4,5-Tetrahydro-1-(1H-imidazol-4-ylmethyl)-7-phenyl-4-(4-quinolinylcarbonyl)-1H-1,4-benzodiazepine, trihydrochloride. | m/z 460 (M + H) |
| 103 | 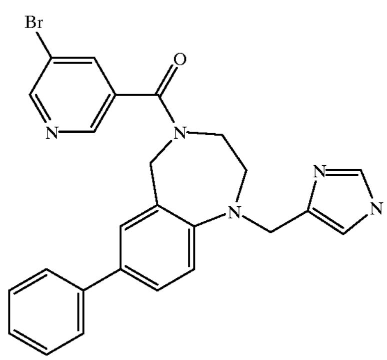 | 4-[(5-Bromo-3-pyridinyl)carbonyl]-2,3,4,5-tetrahydro-1-(1H-imidazol-4-ylmethyl)-7-phenyl-1H-1,4-benzodiazepine, trihydrochloride. | m/z 489 (M + H) |
| 104 | 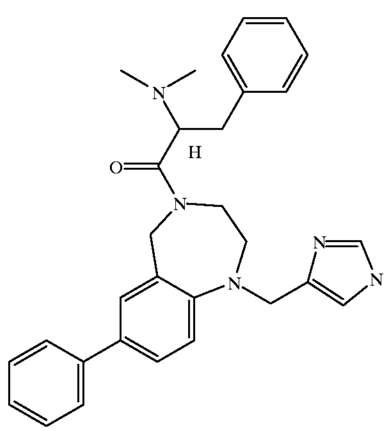 | (S)-4-[2-(Dimethylamino)-1-oxo-3-phenylpropyl]-2,3,4,5-tetrahydro-1-(1H-imidazol-4-ylmethyl)-7-phenyl-1H-1,4-benzodiazepine, trihydrochloride. | m/z 480 (M + H) |

| Example | Structure | | Mass Spectrum |
|---|---|---|---|
| 105 | 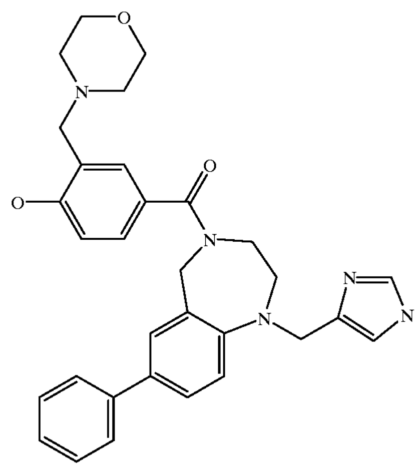 | 2,3,4,5-Tetrahydro-4-[4-hydroxy-3-(4-morpholinyl-methyl)benzoyl]-1-(1H-imidazol-4-ylmethyl)-7-phenyl-1H-1,4-benzodiazepine, trihydrochloride. | m/z 524 (M + H) |
| 106 | 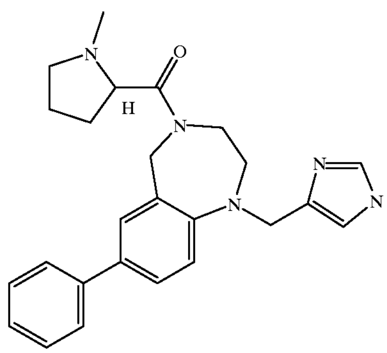 | (S)-2,3,4,5-Tetrahydro-1-(1H-imidazol-4-ylmethyl)-4-[(1-methyl-2-pyrrolidinyl)carbonyl]-7-phenyl-1H-1,4-benzodiazepine, trihydrochloride. | m/z 416 (M + H) |
| 107 | 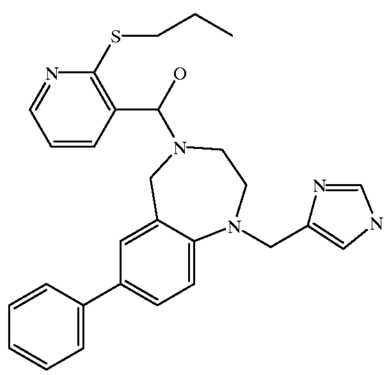 | 2,3,4,5-Tetrahydro-1-(1H-imidazol-4-ylmethyl)-7-phenyl-4-[[2-(propylthio)-3-pyridinyl]carbonyl]-1H-1,4-benzodiazepine, trihydrochloride. | m/z 484 (M + H) |

-continued

| Example | Structure | | Mass Spectrum |
|---|---|---|---|
| 108 | 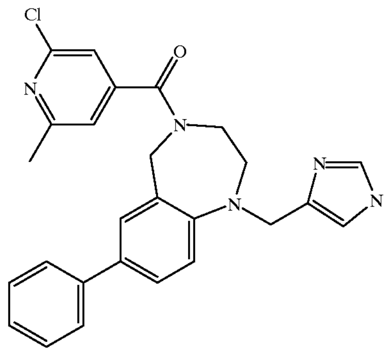 | 4-[(2-Chloro-6-methyl-4-pyridinyl)carbonyl]-2,3,4,5-tetrahydro-1-(1H-imidazol-4-ylmethyl)-7-phenyl-1H-1,4-benzodiazepine, trihydrochloride. | m/z 458 (M + H) |
| 109 | 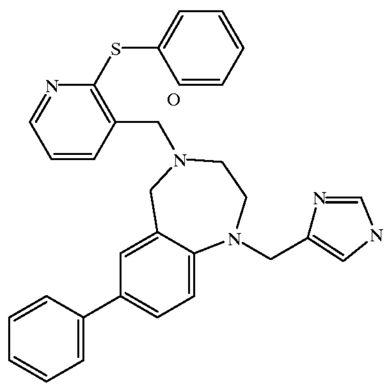 | 2,3,4,5-Tetrahydro-1-(1H-imidazol-4-ylmethyl)-7-phenyl-4-[[2-(phenylthio)-3-pyridinyl]carbonyl]-1H-1,4-benzodiazepine, trihydrochloride. | m/z 518 (M + H) |
| 110 | 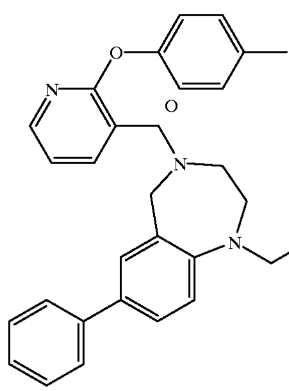 | 2,3,4,5-Tetrahydro-1-(1H-imidazol-4-ylmethyl)-4-[[2-(4-methylphenoxy)-3-pyridinyl]carbonyl]-7-phenyl-1H-1,4-benzodiazepine, trihydrochloride. | m/z 516 (M + H) |
| 111 | 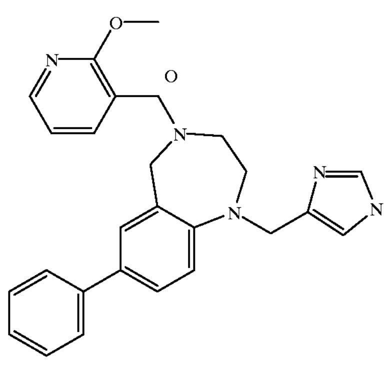 | 2,3,4,5-Tetrahydro-1-(1H-imidazol-4-ylmethyl)-4-[(2-methoxy-3-pyridinyl)carbonyl]-7-phenyl-1H-1,4-benzodiazepine, trihydrochloride. | m/z 440 (M + H) |

-continued

| Example | Structure | | Mass Spectrum |
|---|---|---|---|
| 112 | 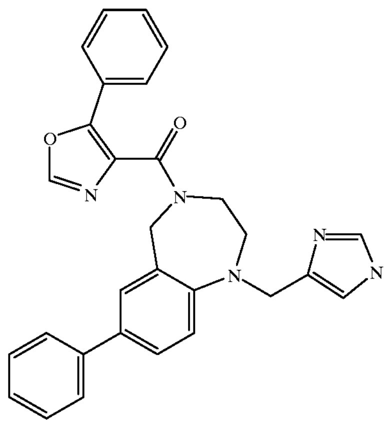 | 2,3,4,5-Tetrahydro-1-(1H-imidazol-4-ylmethyl)-7-phenyl-4-[(5-phenyl-4-oxazolyl)carbonyl]-1H-1,4-benzodiazepine, dihydrochloride. | m/z 476 (M + H) |
| 113 | 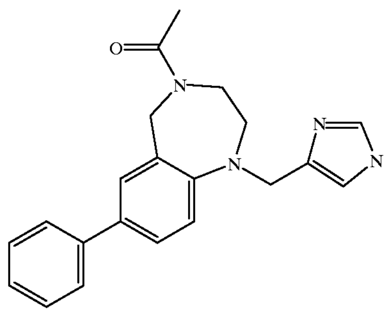 | 4-Acetyl-2,3,4,5-tetrahydro-1-(1H-imidazol-4-ylmethyl)-7-phenyl-1H-1,4-benzodiazepine, dihydrochloride. | m/z 347 (M + H) |
| 114 | 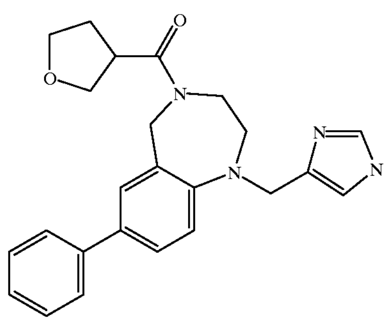 | 2,3,4,5-Tetrahydro-1-(1H-imidazol-4-ylmethyl)-7-phenyl-4-[(tetrahydro-3-furanyl)carbonyl]-1H-1,4-benzodiazepine, dihydrochloride. | m/z 403 (M + H) |
| 115 | 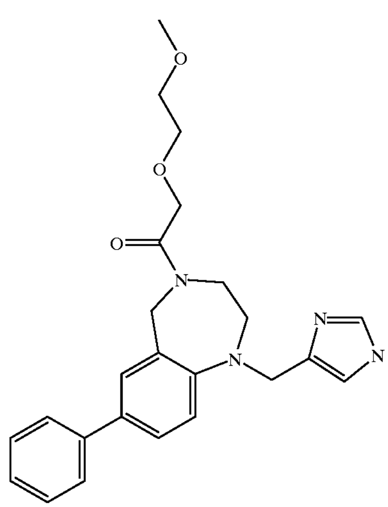 | 2,3,4,5-Tetrahydro-1-(1H-imidazol-4-ylmethyl)-4-[(2-methoxyethoxy)acetyl]-7-phenyl-1H-1,4-benzodiazepine, dihydrochloride. | m/z 421 (M + H) |

-continued

| Example | Structure | | Mass Spectrum |
|---|---|---|---|
| 116 | 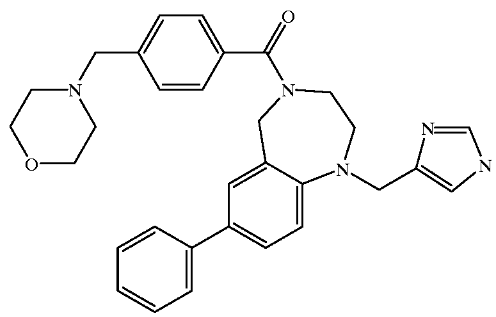 | 2,3,4,5-Tetrahydro-1-(1H-imidazol-4-ylmethyl)-4-[4-(4-morpholinylmethyl)benzoyl]-7-phenyl-1H-1,4-benzodiazepine, trihydrochloride. | m/z 508 (M + H) |
| 117 | 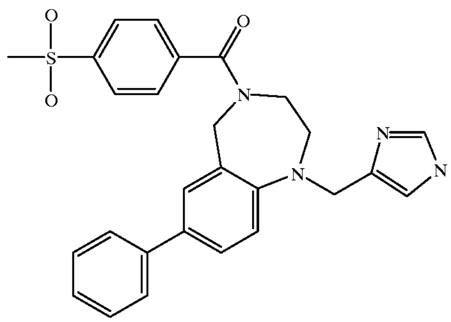 | 2,3,4,5-Tetrahydro-1-(1H-imidazol-4-ylmethyl)-4-[4-(methylsulfonyl)benzoyl]-7-phenyl-1H-1,4-benzodiazepine, dihydrochloride. | m/z 487 (M + H) |
| 118 | 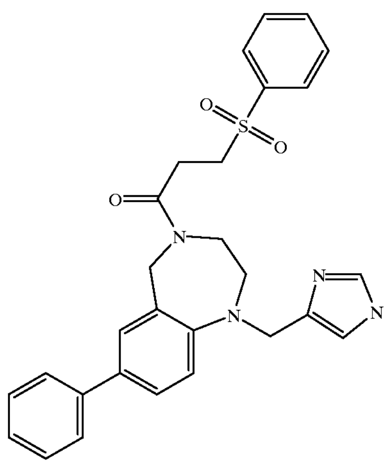 | 2,3,4,5-Tetrahydro-1-(1H-imidazol-4-ylmethyl)-4-[1-oxo-3-(phenylsulfonyl)propyl]-7-phenyl-1H-1,4-benzodiazepine, dihydrochloride. | m/z 501 (M + H) |
| 119 | 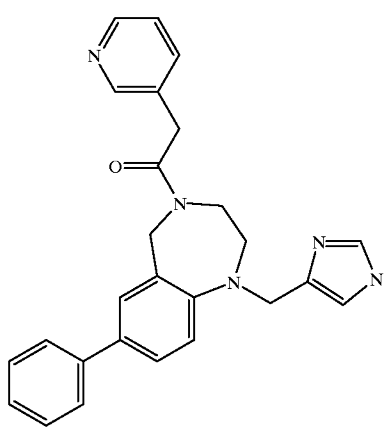 | 2,3,4,5-Tetrahydro-1-(1H-imidazol-4-ylmethyl)-7-phenyl-4-(3-pyridinylacetyl)-1H-1,4-benzodiazepine, trihydrochloride. | m/z 424 (M + H) |

| Example | Structure | | Mass Spectrum |
|---|---|---|---|
| 120 | 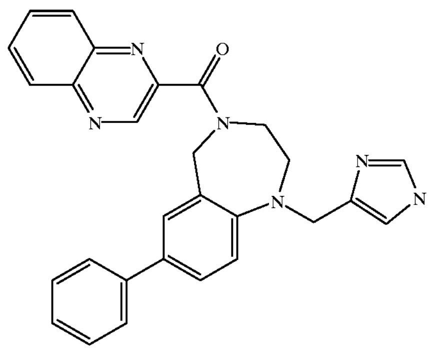 | 2,3,4,5-Tetrahydro-1-(1H-imidazol-4-ylmethyl)-7-phenyl-4-(2-quinoxalinylcarbonyl)-1H-1,4-benzodiazepine, tetrahydrochloride. | m/z 461 (M + H) |
| 121 | 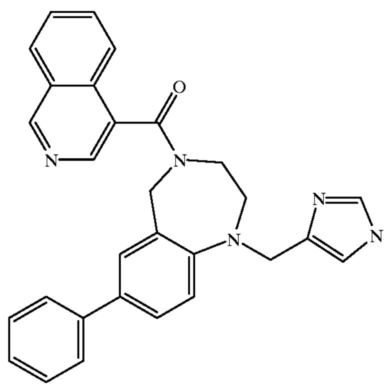 | 2,3,4,5-Tetrahydro-1-(1H-imidazol-4-ylmethyl)-4-(4-isoquinolinylcarbonyl)-7-phenyl-1H-1,4-benzodiazepine, trihydrochloride. | m/z 460 (M + H) |
| 122 | 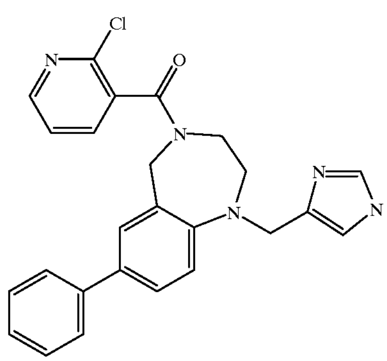 | 4-[(2-Chloro-3-pyridinyl)carbonyl]-2,3,4,5-tetrahydro-1-(1H-imidazol-4-ylmethyl)-7-phenyl-1H-1,4-benzodiazepine, trihydrochloride. | m/z 444 (M + H) |
| 123 | 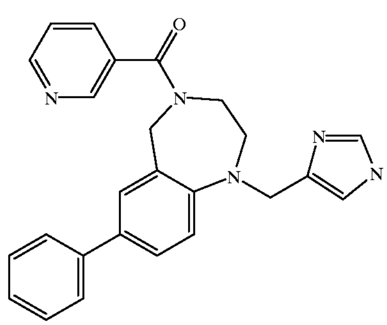 | 2,3,4,5-Tetrahydro-1-(1H-imidazol-4-ylmethyl)-7-phenyl-4-(3-pyridinylcarbonyl)-1H-1,4-benzodiazepine, trihydrochloride. | m/z 410 (M + H) |

-continued

| Example | Structure | | Mass Spectrum |
|---|---|---|---|
| 124 | 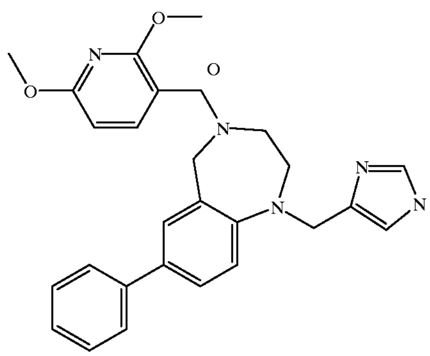 | 4-[(2,6-Dimethoxy-3-pyridinyl)carbonyl]-2,3,4,5-tetrahydro-1-(1H-imidazol-4-ylmethyl)-7-phenyl-1H-1,4-benzodiazepine, trihydrochloride. | m/z 470 (M + H) |
| 125 | 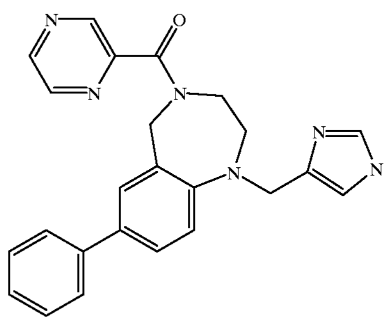 | 2,3,4,5-Tetrahydro-1-(1H-imidazol-4-ylmethyl)-7-phenyl-4-(2-pyrazinylcarbonyl)-1H-1,4-benzodiazepine, tetrahydrochloride. | m/z 411 (M + H) |
| 126 | 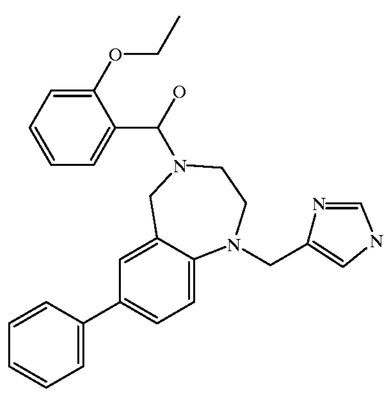 | 4-(2-Ethoxybenzoyl)-2,3,4,5-tetrahydro-1-(1H-imidazol-4-ylmethyl)-7-phenyl-1H-1,4-benzodiazepine, dihydrochloride. | m/z 453 (M + H) |
| 127 | 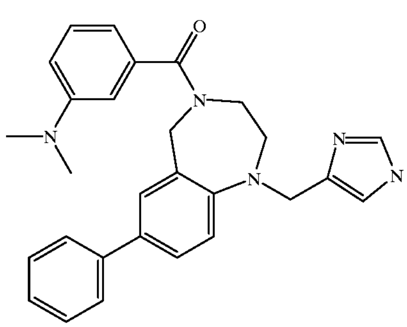 | 4-[3-(Dimethylamino)benzoyl]-2,3,4,5-tetrahydro-1-(1H-imidazol-4-ylmethyl)-7-phenyl-1H-1,4-benzodiazepine, trihydrochloride. | m/z 452 (M + H) |

-continued

| Example | Structure | | Mass Spectrum |
|---|---|---|---|
| 128 | 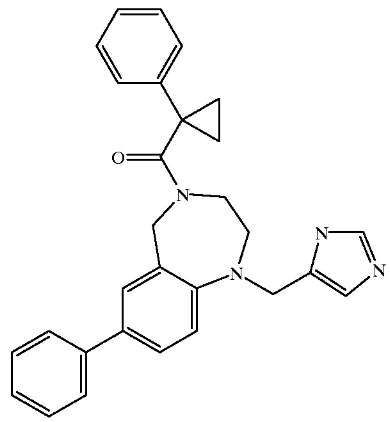 | 2,3,4,5-Tetrahydro-1-(1H-imidazol-4-ylmethyl)-7-phenyl-4-[(1-phenylcyclopropyl)carbonyl]-1H-1,4-benzodiazepine, dihydrochloride. | m/z 449 (M + H) |
| 129 | 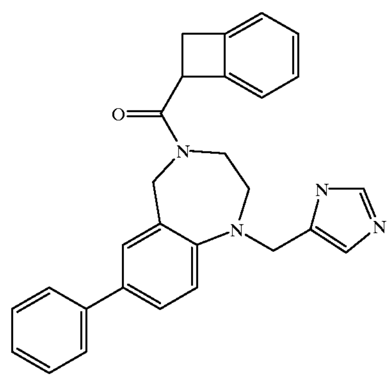 | 4-[(Bicyclo[4.2.0]octa-1,3,5-trien-7-yl)carbonyl]-2,3,4,5-tetrahydro-1-(1H-imidazol-4-ylmethyl)-7-phenyl-1H-1,4-benzodiazepine, dihydrochloride. | m/z 435 (M + H) |
| 130 | 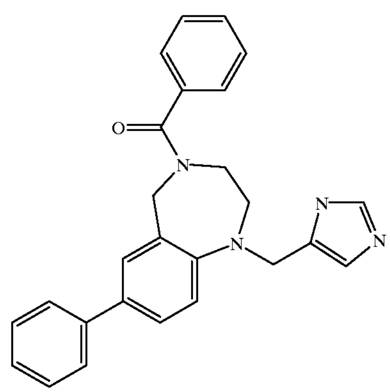 | 4-Benzoyl-2,3,4,5-tetrahydro-1-(1H-imidazol-4-ylmethyl)-7-phenyl-1H-1,4-benzodiazepine, dihydrochloride. | m/z 409 (M + H) |
| 131 | 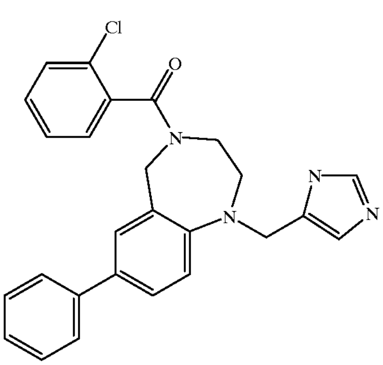 | 4-(2-Chlorobenzoyl)-2,3,4,5-tetrahydro-1-(1H-imidazol-4-ylmethyl)-7-phenyl-1H-1,4-benzodiazepine, dihydrochloride. | m/z 443 (M + H) |

-continued
| Example | Structure | | Mass Spectrum |
|---|---|---|---|
| 132 | 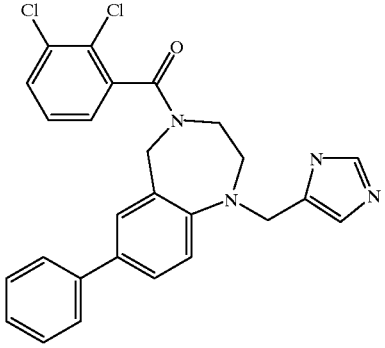 | 4-(2,3-Dichlorobenzoyl)-2,3,4,5-tetrahydro-1-(1H-imidazol-4-ylmethyl)-7-phenyl-1H-1,4-benzodiazepine, dihydrochloride. | m/z 478 (M + H) |
| 133 | 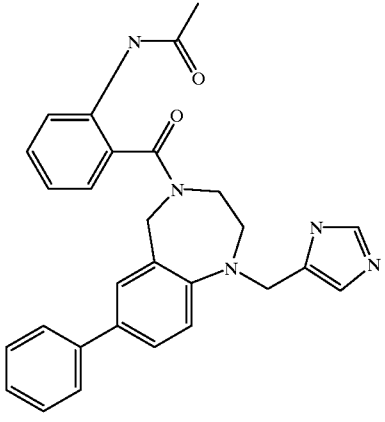 | N-[2-[[2,3,4,5-Tetrahydro-1-(1H-imidazol-4-ylmethyl)-7-phenyl-1H-1,4-benzodiazepin-4-yl]carbonyl]phenyl]-acetamide, dihydrochloride. | m/z 466 (M + H) |
| 134 | 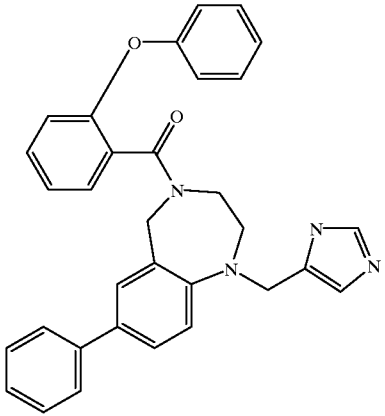 | 2,3,4,5-Tetrahydro-1-(1H-imidazol-4-ylmethyl)-4-(2-phenoxybenzoyl)-7-phenyl-1H-1,4-benzodiazepine, dihydrochloride. | m/z 501 (M + H) |

-continued

| Example | Structure | | Mass Spectrum |
|---|---|---|---|
| 135 | 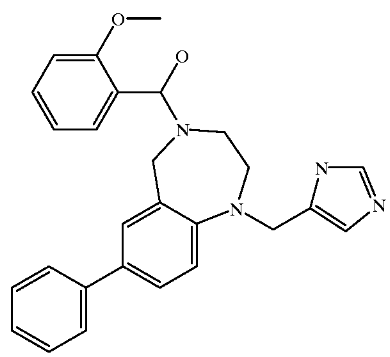 | 2,3,4,5-Tetrahydro-1-(1H-imidazol-4-ylmethyl)-4-(2-methoxybenzoyl)-7-phenyl-1H-1,4-benzodiazepine, dihydrochloride. | m/z 439 (M + H) |
| 136 | 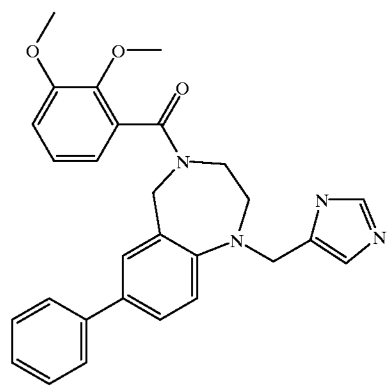 | 4-(2,3-Dimethoxybenzoyl)-2,3,4,5-tetrahydro-1-(1H-imidazol-4-ylmethyl)-7-phenyl-1H-1,4-benzodiazepine, dihydrochloride. | m/z 469 (M + H) |
| 137 | 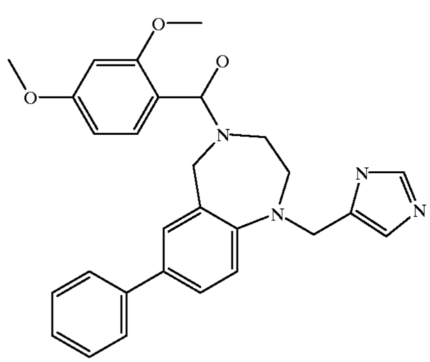 | 4-(2,4-Dimethoxybenzoyl)-2,3,4,5-tetrahydro-1-(1H-imidazol-4-ylmethyl)-7-phenyl-1H-1,4-benzodiazepine, dihydrochloride. | m/z 469 (M + H) |
| 138 | 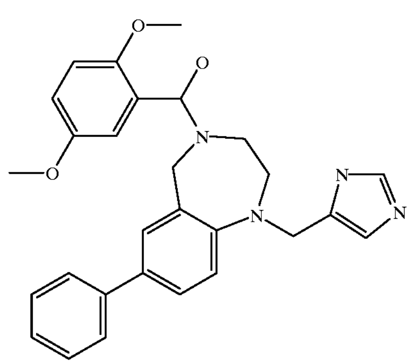 | 4-(2,5-Dimethoxybenzoyl)-2,3,4,5-tetrahydro-1-(1H-imidazol-4-ylmethyl)-7-phenyl-1H-1,4-benzodiazepine, dihydrochloride. | m/z 469 (M + H) |

-continued

| Example | Structure | | Mass Spectrum |
|---|---|---|---|
| 139 | 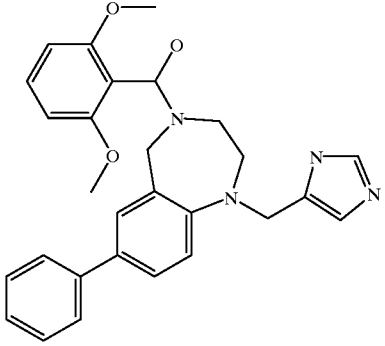 | 4-(2,6-Dimethoxybenzoyl)-2,3,4,5-tetrahydro-1-(1H-imidazol-4-ylmethyl)-7-phenyl-1H-1,4-benzodiazepine, dihydrochloride. | m/z 469 (M + H) |
| 140 | 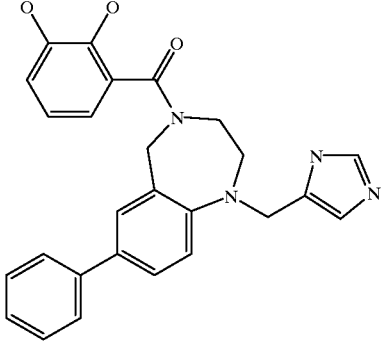 | 4-(2,3-Dihydroxybenzoyl)-2,3,4,5-tetrahydro-1-(1H-imidazol-4-ylmethyl)-H)7-phenyl-1H-1,4-benzodiazepine, dihydrochloride. | m/z 439 (M-H) |
| 141 | 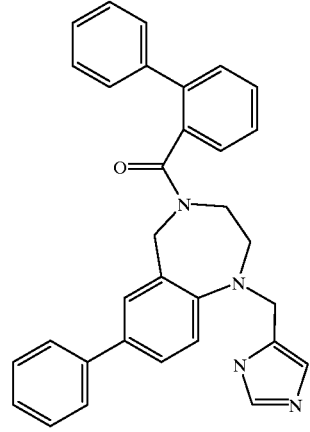 | 4-([1,1'-Biphenyl]-2-ylcarbonyl)-2,3,4,5-tetrahydro-1-(1H-imidazol-4-ylmethyl)-7-phenyl-1H-1,4-benzodiazepine, dihydrochloride. | m/z 485 (M + H) |
| 142 | 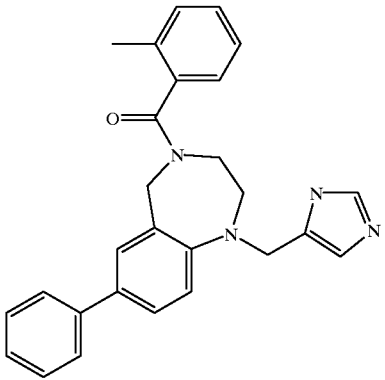 | 2,3,4,5-Tetrahydro-1-(1H-imidazol-4-ylmethyl)-4-(2-methylbenzoyl)-7-phenyl-1H-1,4-benzodiazepine, dihydrochloride. | m/z 423 (M + H) |

-continued

| Example | Structure | | Mass Spectrum |
|---|---|---|---|
| 143 | 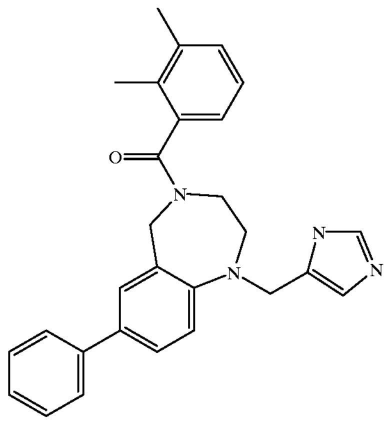 | 4-(2,3-Dimethylbenzoyl)-2,3,4,5-tetrahydro-1-(1H-imidazol-4-ylmethyl)-7-phenyl-1H-1,4-benzodiazepine, dihydrochloride. | m/z 437 (M + H) |
| 144 | 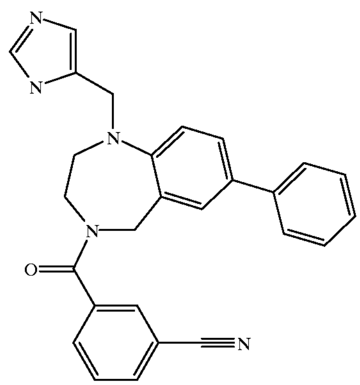 | 4-(3-Cyanobenzoyl)-2,3,4,5-tetrahydro-1-(1H-imidazol-4-ylmethyl)-7-phenyl-1H-1,4-benzodiazepine, dihydrochloride. | m/z 434 (M + H) |
| 145 | 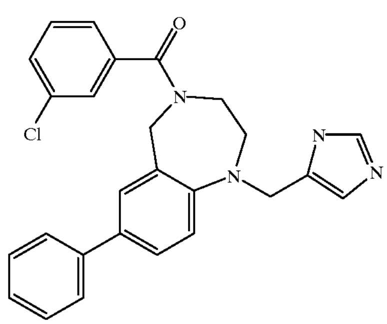 | 4-(3-Chlorobenzoyl)-2,3,4,5-tetrahydro-1-(1H-imidazol-4-ylmethyl)-7-phenyl-1H-1,4-benzodiazepine, dihydrochloride. | m/z 443 (M + H) |
| 146 | 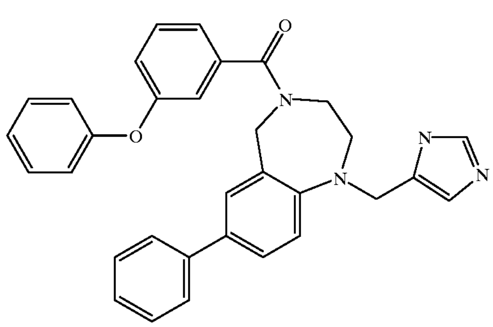 | 2,3,4,5-Tetrahydro-1-(1H-imidazol-4-ylmethyl)-4-(3-phenoxybenzoyl)-7-phenyl-1H-1,4-benzodiazepine, dihydrochloride. | m/z 501 (M + H) |

-continued

| Example | Structure | | Mass Spectrum |
|---|---|---|---|
| 147 | 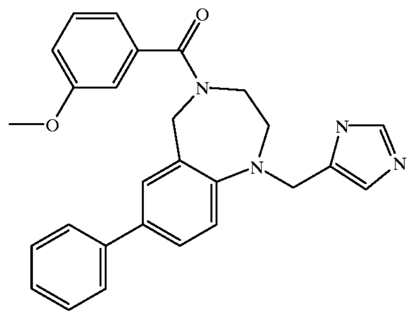 | 2,3,4,5-Tetrahydro-1-(1H-imidazol-4-ylmethyl)-4-(3-methoxybenzoyl)-7-phenyl-1H-1,4-benzodiazepine, dihydrochloride. | m/z 439 (M + H) |
| 148 | 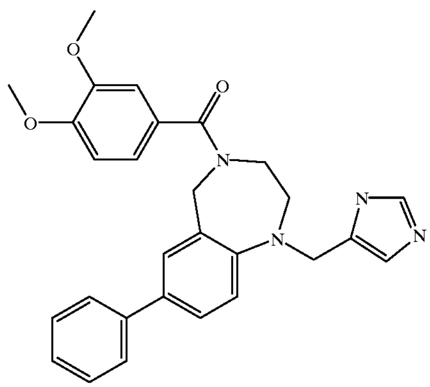 | 4-(3,4-Dimethoxybenzoyl)-2,3,4,5-tetrahydro-1-(1H-imidazol-4-ylmethyl)-7-phenyl-1H-1,4-benzodiazepine, dihydrochloride. | m/z 469 (M + H) |
| 149 | 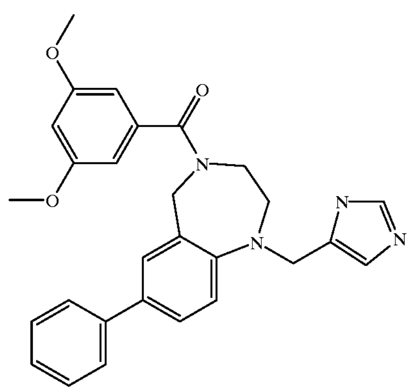 | 4-(3,5-Dimethoxybenzoyl)-2,3,4,5-tetrahydro-1-(1H-imidazol-4-ylmethyl)-7-phenyl-1H-1,4-benzodiazepine, dihydrochloride. | m/z 469 (M + H) |
| 150 | 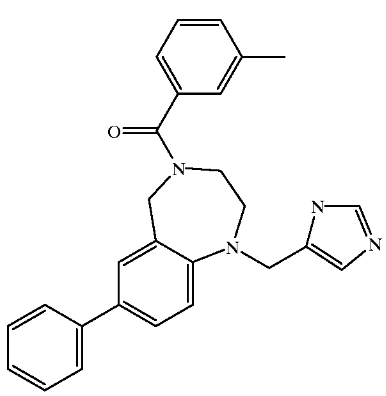 | 2,3,4,5-Tetrahydro-1-(1H-imidazol-4-ylmethyl)-4-(3-methylbenzoyl)-7-phenyl-1H-1,4-benzodiazepine, dihydrochloride. | m/z 423 (M + H) |

-continued

| Example | Structure | | Mass Spectrum |
|---|---|---|---|
| 151 | 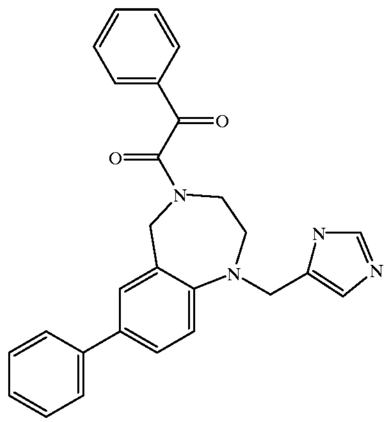 | 4-(1,2-Dioxo-2-phenylethyl)-2,3,4,5-tetrahydro-1-(1H-imidazol-4-ylmethyl)-7-phenyl-1H-1,4-benzodiazepine, dihydrochloride. | m/z 437 (M + H) |
| 152 | 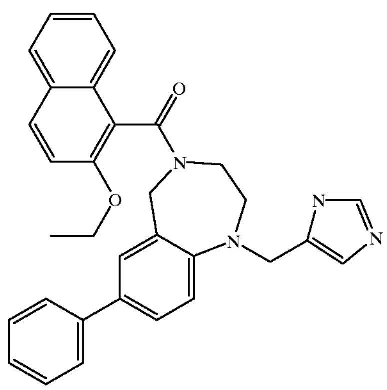 | 4-[(2-Ethoxy-1-naphthalenyl)carbonyl]-2,3,4,5-tetrahydro-1-(1H-imidazol-4-ylmethyl)-7-phenyl-1H-1,4-benzodiazepine, dihydrochloride. | m/z 503 (M + H) |
| 153 | 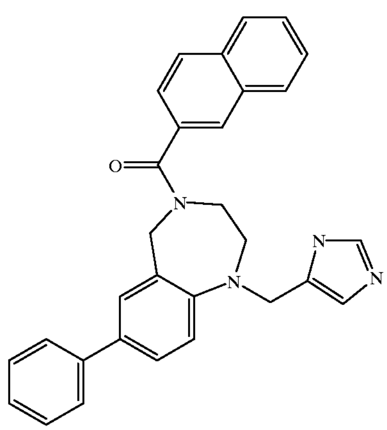 | 2,3,4,5-Tetrahydro-1-(1H-imidazol-4-ylmethyl)-4-(2-naphthalenylcarbonyl)-7-phenyl-1H-1,4-benzodiazepine, dihydrochloride. | m/z 459 (M+ H) |

-continued
| Example | Structure | | Mass Spectrum |
|---|---|---|---|
| 154 | 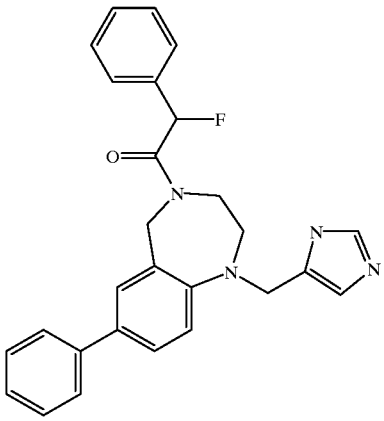 | 4-(Fluorophenylacetyl)-2,3,4,5-tetrahydro-1-(1H-imidazol-4-ylmethyl)-7-phenyl-1H-1,4-benzodiazepine, dihydrochloride. | m/z 441 (M + H) |
| 155 | 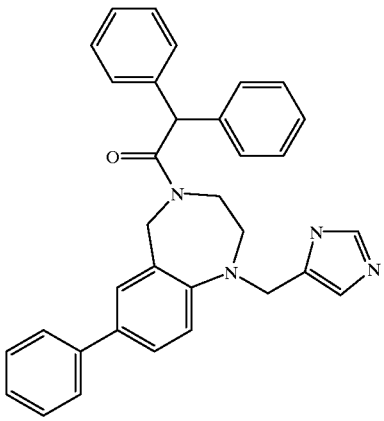 | 4-(Diphenylacetyl)-2,3,4,5-tetrahydro-1-(1H-imidazol-4-ylmethyl)-7-phenyl-1H-1,4-benzodiazepine, dihydrochloride. | m/z 499 (M + H) |
| 156 | 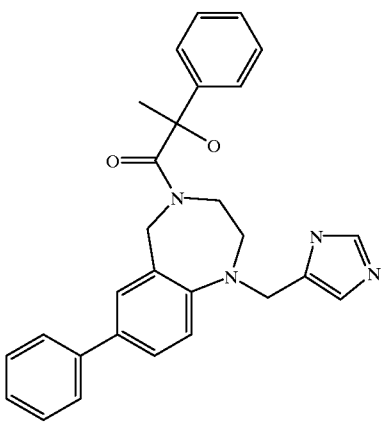 | 2,3,4,5-Tetrahydro-4-(2-hydroxy-1-oxo-2-phenylpropyl)-1-(1H-imidazol-4-ylmethyl)-7-phenyl-1H-1,4-benzodiazepine, dihydrochloride. | m/z 453 (M + H) |

-continued

| Example | Structure | | Mass Spectrum |
|---|---|---|---|
| 157 | 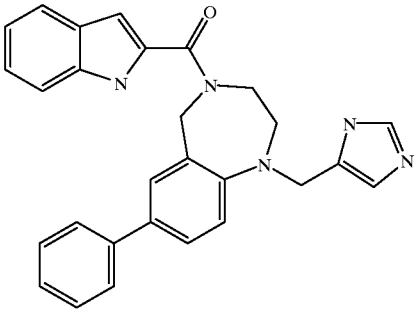 | 2,3,4,5-Tetrahydro-1-(1H-imidazol-4-ylmethyl)-4-(1H-indol-2-ylcarbonyl)-7-phenyl-1H-1,4-benzodiazepine, dihydrochloride. | m/z 448 (M + H) |
| 158 | 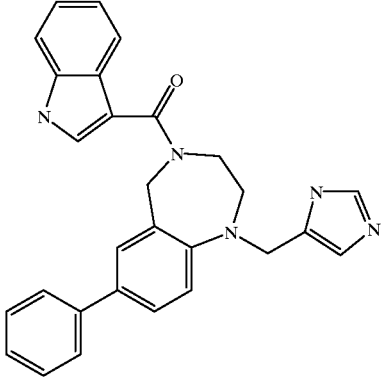 | 2,3,4,5-Tetrahydro-1-(1H-imidazol-4-ylmethyl)-4-(1H-indol-3-ylcarbonyl)-7-phenyl-1H-1,4-benzodiazepine, dihydrochloride. | m/z 448 (M + H) |
| 159 | 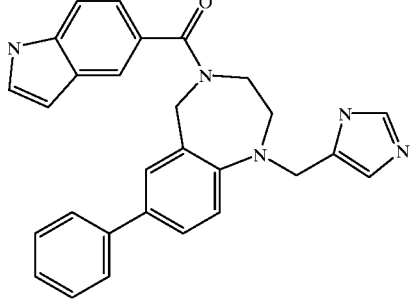 | 2,3,4,5-Tetrahydro-1-(1H-imidazol-4-ylmethyl)-4-(1H-indol-5-ylcarbonyl)-7-phenyl-1H-1,4-benzodiazepine, dihydrochloride. | m/z 448 (M + H) |
| 160 | 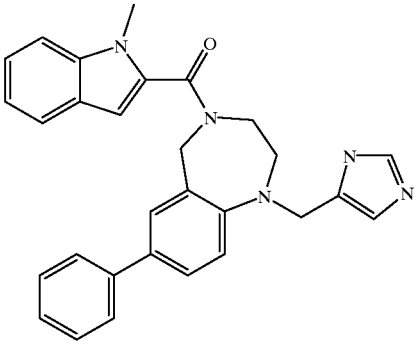 | 2,3,4,5-Tetrahydro-1-(1H-imidazol-4-ylmethyl)-4-[(1-methyl-1H-indol-2-yl)carbonyl]-7-phenyl-1H-1,4-benzodiazepine, dihydrochloride. | m/z 462 (M + H) |

| Example | Structure | | Mass Spectrum |
|---|---|---|---|
| 161 | 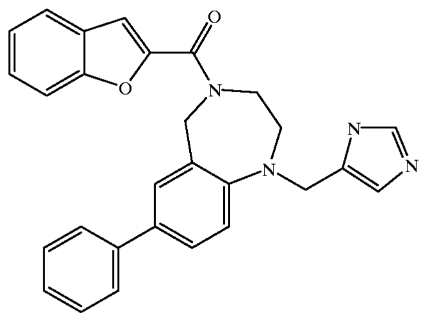 | 4-(2-Benzofuranylcarbonyl)-2,3,4,5-tetrahydro-1-(1H-imidazol-4-ylmethyl)-7-phenyl-1H-1,4-benzodiazepine, dihydrochloride. | m/z 449 (M + H) |
| 162 | 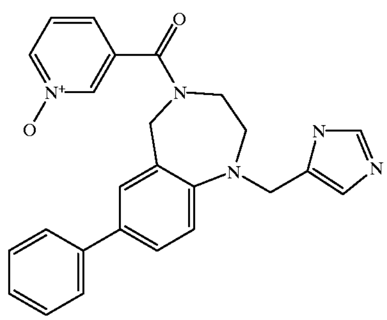 | 2,3,4,5-Tetrahydro-1-(1H-imidazol-4-ylmethyl)-7-phenyl-4-(3-pyridinylcarbonyl)-1H-1,4-benzodiazepine, N-oxide, dihydrochloride. | m/z 426 (M + H) |
| 163 | 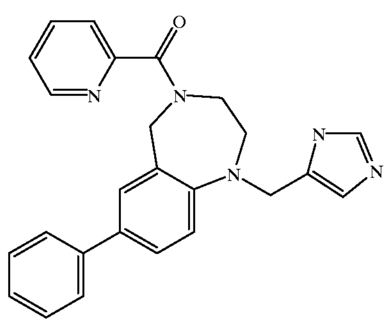 | 2,3,4,5-Tetrahydro-1-(1H-imidazol-4-ylmethyl)-7-phenyl-4-(2-pyridinylcarbonyl)-1H-1,4-benzodiazepine, trihydrochloride. | m/z 410 (M + H) |
| 164 | 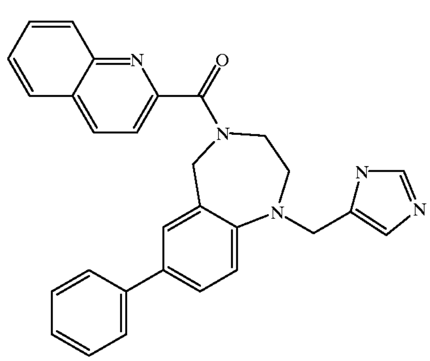 | 2,3,4,5-Tetrahydro-1-(1H-imidazol-4-ylmethyl)-7-phenyl-4-(2-quinolinylcarbonyl)-1H-1,4-benzodiazepine, trihydrochloride. | m/z 460 (M + H) |

-continued

| Example | Structure | | Mass Spectrum |
|---|---|---|---|
| 165 | 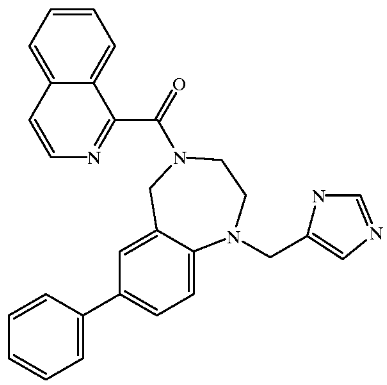 | 2,3,4,5-Tetrahydro-1-(1H-imidazol-4-ylmethyl)-7-phenyl-4-(1-isoquinolinylcarbonyl)-1H-1,4-benzodiazepine, trihydrochloride. | m/z 460 (M + H) |
| 166 | 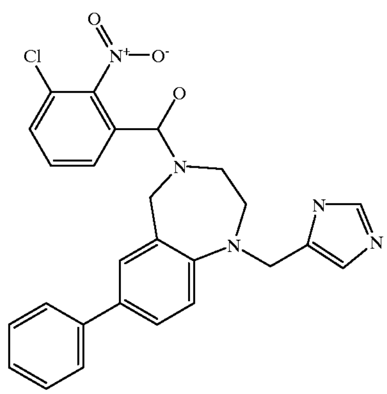 | 4-(3-Chloro-2-nitrobenzoyl)-2,3,4,5-tetrahydro-1-(1H-imidazol-4-ylmethyl)-7-phenyl-1H-1,4-benzodiazepine, dihydrochloride. | m/z 488 (M + H) |
| 167 | 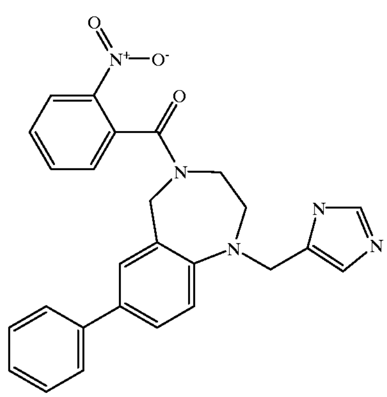 | 2,3,4,5-Tetrahydro-1-(1H-imidazol-4-ylmethyl)-4-(2-nitrobenzoyl)-7-phenyl-1H-1,4-benzodiazepine, dihydrochloride. | m/z 454 (M + H) |
| 168 | 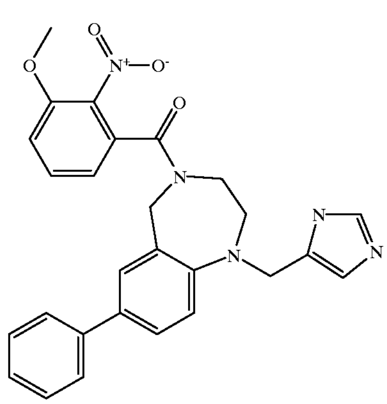 | 2,3,4,5-Tetrahydro-1-(1H-imidazol-4-ylmethyl)-4-(3-methoxy-2-nitrobenzoyl)-7-phenyl-1H-1,4-benzodiazepine, dihydrochloride. | m/z 484 (M + H) |

-continued

| Example | Structure | | Mass Spectrum |
|---|---|---|---|
| 169 | 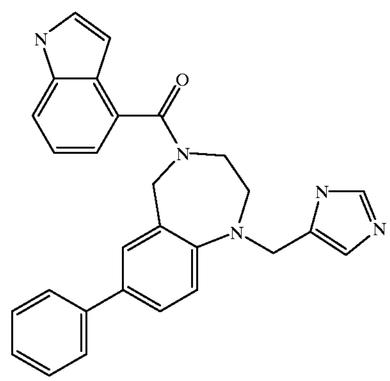 | 2,3,4,5-Tetrahydro-1-(1H-imidazol-4-ylmethyl)-4-(1H-indol-4-ylcarbonyl)-7-phenyl-1H-1,4-benzodiazepine, dihydrochloride. | m/z 448 (M + H) |
| 170 | 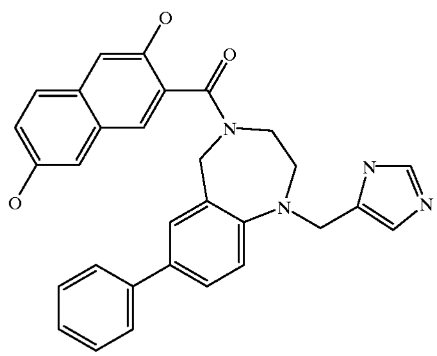 | 4-[(2,6-Dihydroxy-3-naphthalenyl)carbonyl]-2,3,4,5-tetrahydro-1-(1H-imidazol-4-ylmethyl)-7-phenyl-1H-1,4-benzodiazepine, dihydrochloride. | m/z 491 (M + H) |
| 171 | 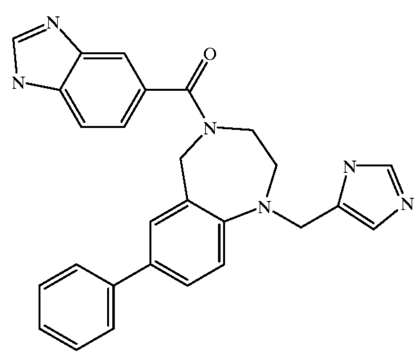 | 4-(1H-Benzimidazol-5-ylcarbonyl)-2,3,4,5-tetrahydro-1-(1H-imidazol-4-ylmethyl)-7-phenyl-1H-1,4-benzodiazepine, trihydrochloride. | m/z 449 (M + H) |
| 172 | 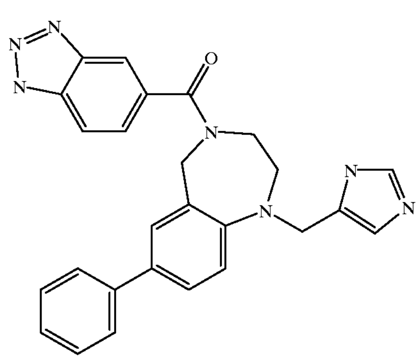 | 4-(1H-Benzotriazol-5-ylcarbonyl)-2,3,4,5-tetrahydro-1-(1H-imidazol-4-ylmethyl)-7-phenyl-1H-1,4-benzodiazepine, dihydrochloride. | m/z 450 (M + H) |

| Example | Structure | | Mass Spectrum |
|---|---|---|---|
| 173 | 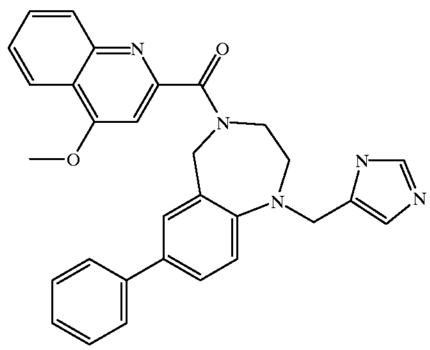 | 2,3,4,5-Tetrahydro-1-(1H-imidazol-4-ylmethyl)-4-[(4-methoxy-2-quinolinyl)carbonyl]-7-phenyl-1H-1,4-benzodiazepine, trihydrochloride. | m/z 490 (M + H) |
| 174 | 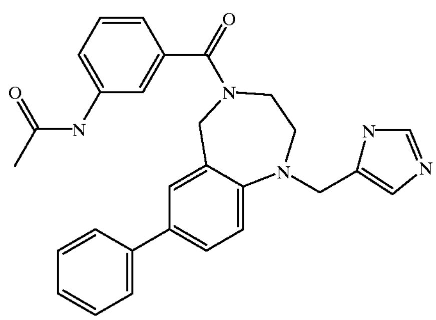 | N-[3-[[2,3,4,5-Tetrahydro-1-(1H-imidazol-4-ylmethyl)-7-phenyl-1H-1,4-benzodiazepin-4-yl]carbonyl]phenyl]-acetamide, dihydrochloride. | m/z 466 (M + H) |
| 175 | 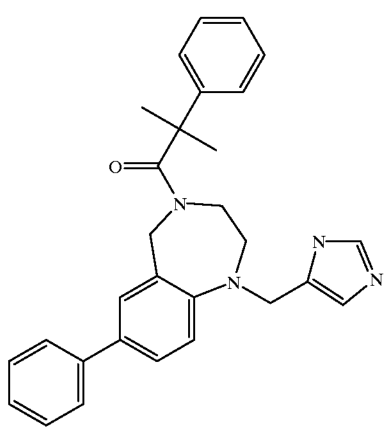 | 2,3,4,5-Tetrahydro-1-(1H-imidazol-4-ylmethyl)-4-(2-methyl-1-oxo-2-phenylpropyl)-7-phenyl-1H-1,4-benzodiazepine, dihydrochloride. | m/z 451 (M + H) |
| 176 | 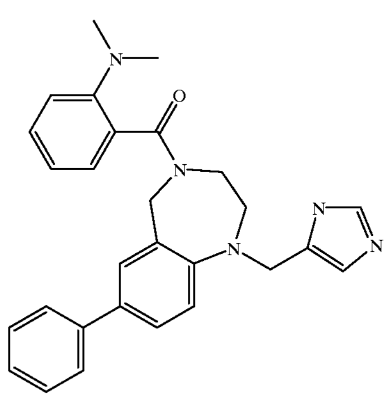 | 4-[2-(Dimethylamino)benzoyl]-2,3,4,5-tetrahydro-1-(1H-imidazol-4-ylmethyl)-7-phenyl-1H-1,4-benzodiazepine, trihydrochloride. | m/z 452 (M + H) |

-continued

| Example | Structure | | Mass Spectrum |
|---|---|---|---|
| 177 | 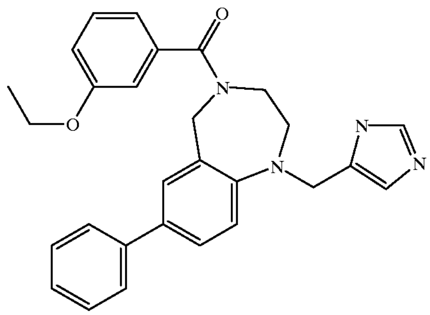 | 4-(3-Ethoxybenzoyl)-2,3,4,5-tetrahydro-1-(1H-imidazol-4-ylmethyl)-7-phenyl-1H-1,4-benzodiazepine, dihydrochloride. | m/z 453 (M + H) |
| 178 | 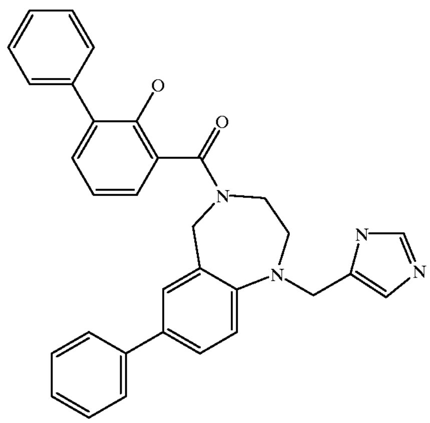 | 2,3,4,5-Tetrahydro-4-(2-hydroxy[1,1'-biphenyl]-3-ylcarbonyl)-1-(1H-imidazol-4-ylmethyl)-7-phenyl-1H-1,4-benzodiazepine, dihydrochloride. | m/z 501 (M + H) |
| 179 | 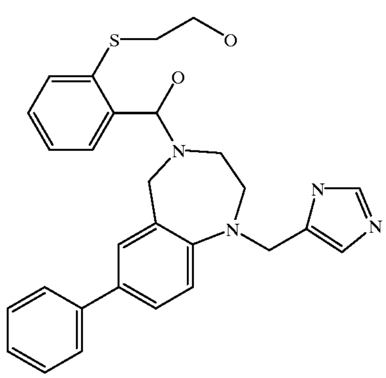 | 2,3,4,5-Tetrahydro-4-[2-[(2-hydroxyethyl)thio]benzoyl]-1-(1H-imidazol-4-ylmethyl)-7-phenyl-1H-1,4-benzodiazepine, dihydrochloride. | m/z 485 (M + H) |
| 180 | 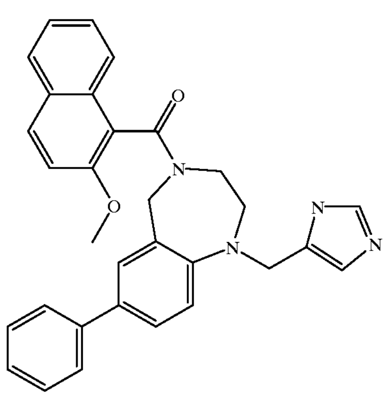 | 2,3,4,5-Tetrahydro-1-(1H-imidazol-4-ylmethyl)-4-[(2-methoxy-1-naphthalenyl)carbonyl]-7-phenyl-1H-1,4-benzodiazepine, dihydrochloride. | m/z 489 (M + H) |

-continued

| Example | Structure | | Mass Spectrum |
|---|---|---|---|
| 181 | 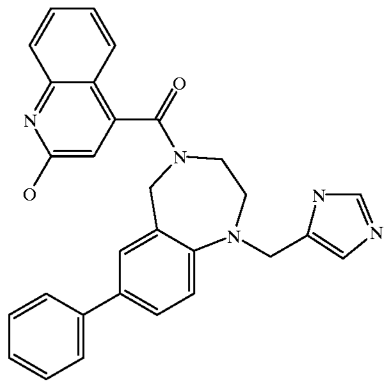 | 2,3,4,5-Tetrahydro-4-[(2-hydroxy-4-quinolinyl)-carbonyl]-1-(1H-imidazol-4-ylmethyl)-7-phenyl-1H-1,4-benzodiazepine, dihydrochloride. | m/z 476 (M + H) |
| 182 | 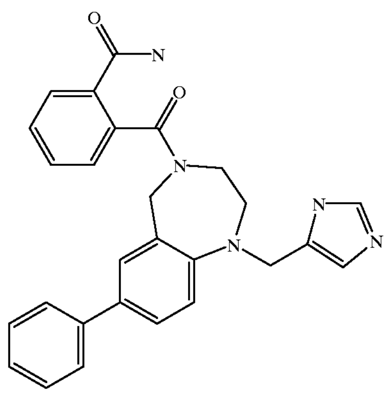 | 2-[[2,3,4,5-Tetrahydro-1-(1H-imidazol-4-ylmethyl)-7-phenyl-1H-1,4-benzodiazepin-4-yl]carbonyl]benzamide, dihydrochloride. | m/z 452 (M + H) |
| 183 | 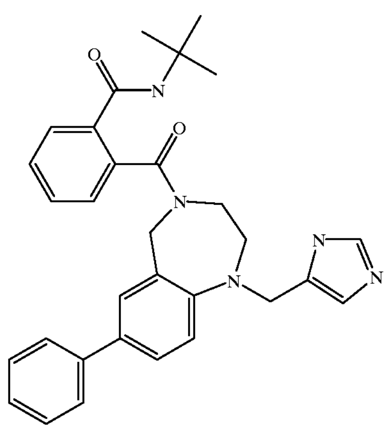 | N-(1,1-Dimethylethyl)-2-[[2,3,4,5-tetrahydro-1-(1H-imidazol-4-ylmethyl)-7-phenyl-1H-1,4-benzodiazepin-4-yl]carbonyl]benzamide, dihydrochloride. | m/z 508 (M + H) |
| 184 | 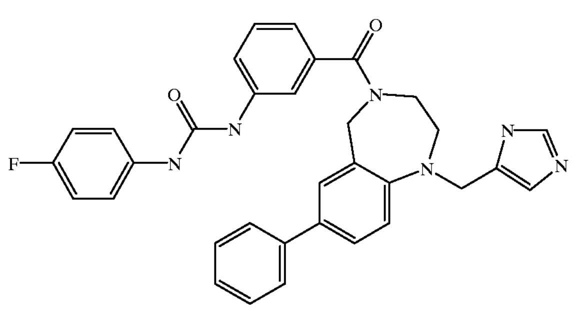 | N-(4-Fluorophenyl)-N'-[3-[[2,3,4,5-tetrahydro-1-(1H-imidazol-4-ylmethyl)-7-phenyl-1H-1,4-benzodiazepin-4-yl]carbonyl]phenyl]urea, dihydrochloride. | m/z 561 (M + H) |

| Example | Structure | | Mass Spectrum |
|---|---|---|---|
| 185 | 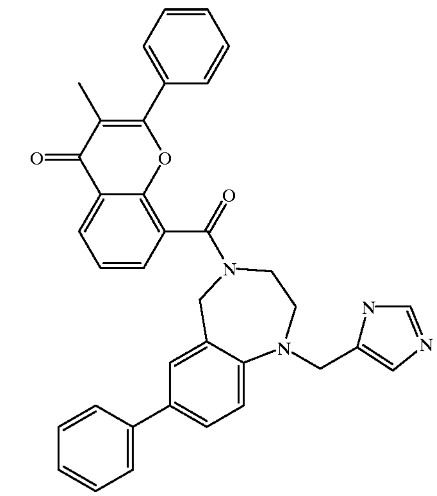 | 2,3,4,5-Tetrahydro-1-(1H-imidazol-4-ylmethyl)-4-[(3-methyl-4-oxo-2-phenyl-4H-benzopyran-8-yl)carbonyl]-7-phenyl-1H-1,4-benzodiazepine, dihydrochloride. | m/z 567 (M + H) |
| 186 | 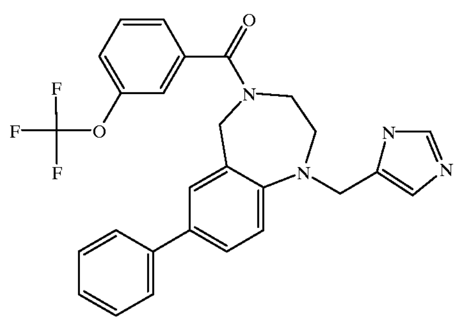 | 2,3,4,5-Tetrahydro-1-(1H-imidazol-4-ylmethyl)-7-phenyl-4-[3-(trifluoromethoxy)benzoyl]-1H-1,4-benzodiazepine, dihydrochloride. | m/z 493 (M + H) |
| 187 | 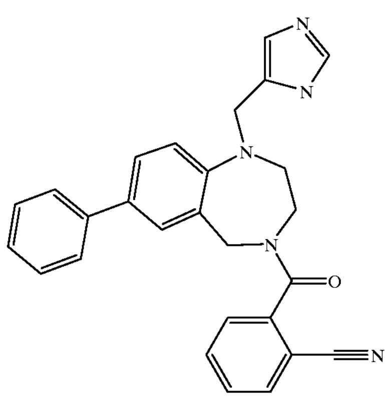 | 4-(2-Cyanobenzoyl)-2,3,4,5-tetrahydro-1-(1H-imidazol-4-ylmethyl)-7-phenyl-1H-1,4-benzodiazepine, dihydrochloride. | m/z 434 (M + H) |

-continued

| Example | Structure | | Mass Spectrum |
|---|---|---|---|
| 188 | 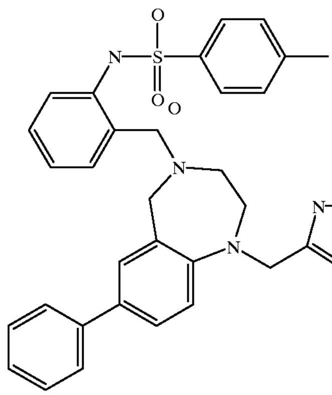 | 2,3,4,5-Tetrahydro-1-(1H-imidazol-4-ylmethyl)-4-[2-[[(4-methylphenyl)sulfonyl]amino]benzoyl]-7-phenyl-1H-1,4-benzodiazepine, dihydrochloride. | m/z 578 (M + H) |
| 189 | 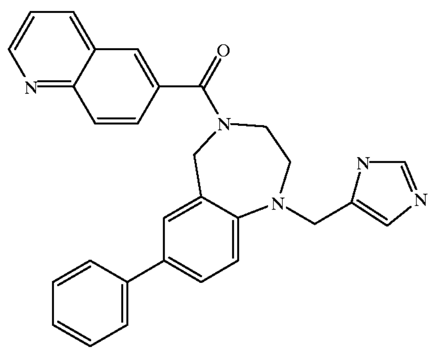 | 2,3,4,5-Tetrahydro-1-(1H-imidazol-4-ylmethyl)-7-phenyl-4-(6-quinolinylcarbonyl)-1H-1,4-benzodiazepine, trihydrochloride. | m/z 460 (M + H) |
| 190 | 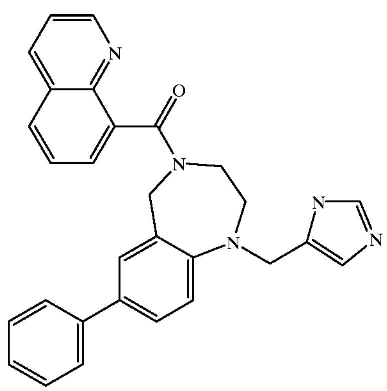 | 2,3,4,5-Tetrahydro-1-(1H-imidazol-4-ylmethyl)-7-phenyl-4-(8-quinolinylcarbonyl)-1H-1,4-benzodiazepine, trihydrochloride. | m/z 460 (M + H) |
| 191 | 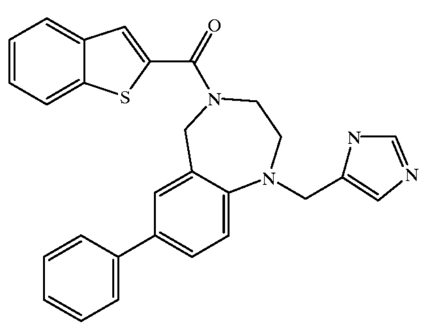 | 4-(Benzo[b]thiophen-2-ylcarbonyl)-2,3,4,5-tetrahydro-1-(1H-imidazol-4-ylmethyl)-7-phenyl-1H-1,4-benzodiazepine, dihydrochloride. | m/z 465 (M + H) |

-continued

| Example | Structure | | Mass Spectrum |
|---|---|---|---|
| 192 | 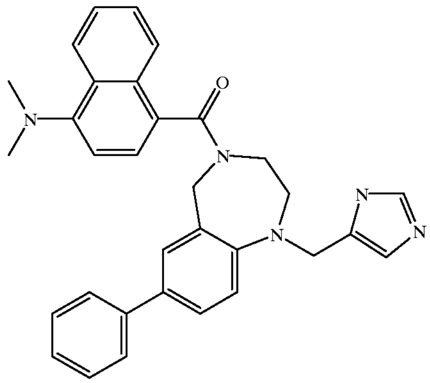 | 4-[[4-(Dimethylamino)-1-naphthalenyl]carbonyl]-2,3,4,5-tetrahydro-1-(1H-imidazol-4-ylmethyl)-7-phenyl-1H-1,4-benzodiazepine, trihydrochloride. | m/z 502 (M + H) |
| 193 | 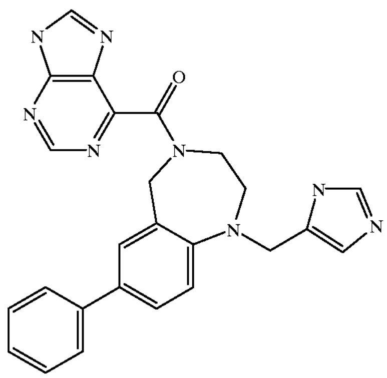 | 2,3,4,5-Tetrahydro-1-(1H-imidazol-4-ylmethyl)-7-phenyl-4-(1H-purin-6-ylcarbonyl)-1H-1,4-benzodiazepine, trihydrochloride. | m/z 449 (M − H) |
| 194 | 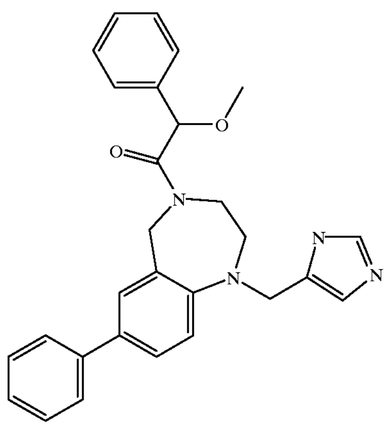 | 2,3,4,5-Tetrahydro-1-(1H-imidazol-4-ylmethyl)-4-(methoxyphenylacetyl)-7-phenyl-1H-1,4-benzodiazepine, dihydrochloride. | m/z 453 (M + H) |

-continued

| Example | Structure | | Mass Spectrum |
|---|---|---|---|
| 195 | 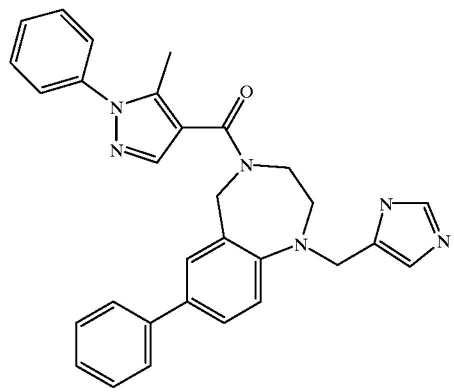 | 2,3,4,5-Tetrahydro-1-(1H-imidazol-4-ylmethyl)-4-[(5-methyl-1-phenyl-1H-pyrazol-4-yl)carbonyl]-7-phenyl-1H-1,4-benzodiazepine, trihydrochloride. | m/z 489 (M + H) |
| 196 | 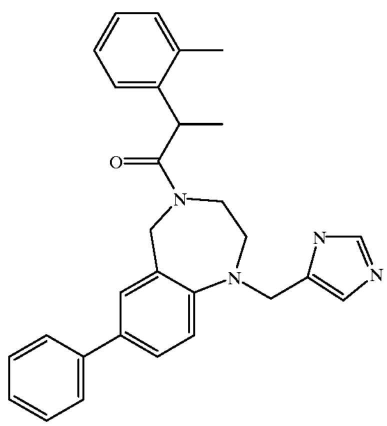 | 2,3,4,5-Tetrahydro-1-(1H-imidazol-4-ylmethyl)-4-[2-(2-methylphenyl)-1-oxopropyl]-7-phenyl-1H-1,4-benzodiazepine, dihydrochloride. | m/z 451 (M + H) |
| 197 | 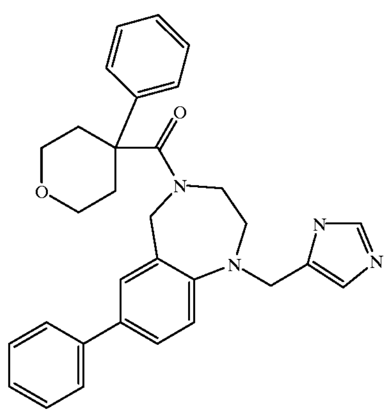 | 2,3,4,5-Tetrahydro-1-(1H-imidazol-4-ylmethyl)-7-phenyl-4-[(tetrahydro-4-phenyl-2H-pyran-4-yl)carbonyl]-1H-1,4-benzodiazepine, dihydrochloride. | m/z 493 (M + H) |

-continued

| Example | Structure | | Mass Spectrum |
|---|---|---|---|
| 198 | 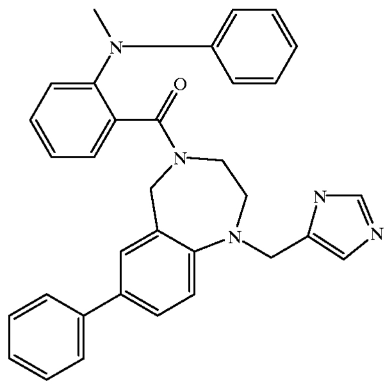 | 2,3,4,5-Tetrahydro-1-(1H-imidazol-4-ylmethyl)-4-[2-(methylphenylamino)benzoyl]-7-phenyl-1H-1,4-benzodiazepine, trihydrochloride. | m/z 531 (M + 18) |
| 199 | 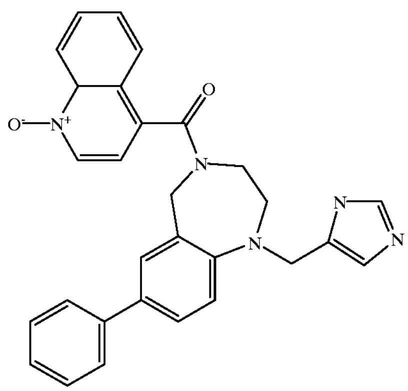 | 2,3,4,5-Tetrahydro-1-(1H-imidazol-4-ylmethyl)-7-phenyl-4-(4-quinolinylcarbonyl)-1H-1,4-benzodiazepine, N-oxide, dihydrochloride. | m/z 476 (M + H) |
| 200 | 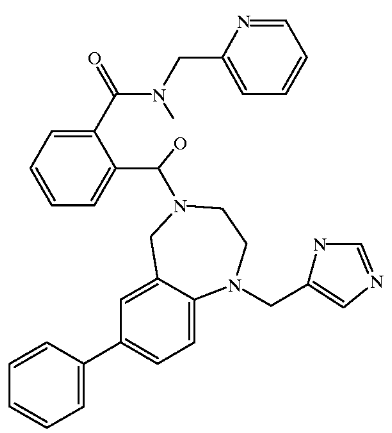 | N-Methyl-N-(2-pyridinylmethyl)-2-[[2,3,4,5-tetrahydro-1-(1H-imidazol-4-ylmethyl)-7-phenyl-1H-1,4-benzodi-azepin-4-yl]carbonyl]benzamide, trihydrochloride. | m/z 557 (M + H) |

-continued

| Example | Structure | | Mass Spectrum |
|---|---|---|---|
| 201 | 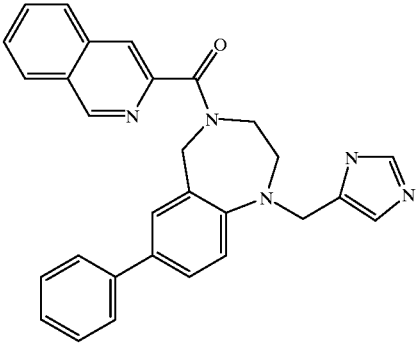 | 2,3,4,5-Tetrahydro-1-(1H-imidazol-4-ylmethyl)-4-(3-isoquinolinylcarbonyl)-7-phenyl-1H-1,4-benzodiazepine, trihydrochloride. | m/z 460 (M + H) |

EXAMPLES 202–219

To a mixture of compound Compound A of Example 4 (3.83 g, 15.4 mmol) and 4-imidazolecarboxaldehyde (2.22g, 23.1 mmol) in 120 mL of $CH_2Cl_2$ and 3 mL of AcOH at room temperature was added $NaBH(OAc)_3$ (4.89 g, 23.1 mmol). The mixture was stirred for 1.5 hours, diluted with 200 mL of $CH_2Cl_2$, and washed with 5% $NaHCO_3$. The organic phase was dried over $Na_2SO_4$, filtered and concentrated in vacuo. Flash chromatography of the residue on silica (eluting with 5% $MeOH/CH_2Cl_2$ and trace $NH_4OH$) afforded 2.01 g (40%) of 2,3,4,5-tetrahydro-4-[(1,1-dimethylethoxy)-carbonyl]-1-(1H-imidazol-4-yl-methyl)-1H-1,4-benzodiazepine. An additional 0.42 g (8%) of product was obtained by stirring 1.5 g of a high Rf material in 1:1:1 $THF/MeOH/NH_4OH$, followed by extraction with EtOAc, and flash chromatography.

Hydroxymethyl resin (3.5 g, 6.58 mmol, 1.88 mmol/g) was swelled with 50 mL of 1,2-dichloroethane for 45 min at room temperature in a 125 mL shake flask. To this was added paraformaldehyde (0.15 g, 5.0 mmol). HCl (g) was bubbled through the mixture for 15 min. Then, an additional amount of paraformaldehyde (0.15 g, 5.0 mmol) was added to the reaction mixture. HCl (g) was bubbled through the mixture with shaking for 4 h. The 1,2-dichloroethane was removed and the resin was rinsed with 1,2-dichloroethane (4×20 mL).

The resin was suspended in 20 mL of 1,2-dichloroethane and then treated with a solution of 2,3,4,5-tetrahydro-4-[(1,1-dimethylethoxy)-carbonyl]-1-(1H-imidazol-4-yl-methyl)-1H-1,4-benzodiazepine (2.23 g, 6.78 mmol) in 25 mL of 1,2,dichloroethane and 6 mL of DIEA. The mixture was shaken at room temperature for 12 h. MeOH (2 mL) was added and the mixture was shaken for an additional 1.5 h.

The solvent was removed and the resin was rinsed sequentially with 1,2-dichloroethane (2×20 mL), DMF (2×20 mL), and MeOH (2×20 mL). The material was dried in vacuo to afford 4.58 g (67%) of resin containing imidazole-bound 2,3,4,5-tetrahydro-4-[(1,1-dimethylethoxy)-carbonyl]-1-(1H-imidazol-4-yl-methyl)-1H-1,4-benzodiazepine (%N= 4.39).

To 150 mg (0.135 mmol, 0.90 mmol/g) of this resin in a 5 mL polypropylene syringe barrel was added 1.5 mL of 3% $Et_3SiH$ in $CH_2Cl_2$ and 0.5 mL of TFA. The tube was placed in a vac-elute chamber (capacity for 24 syringe barrels) and the entire apparatus was shaken on an orbital shaker for 3 h. The solvent was removed and the resin was rinsed sequentially with 2 mL each of $CH_2Cl_2$, 25% $Et_3N/CH_2Cl_2$, MeOH, DMF, and $CH_2Cl_2$. The resin was swelled with 0.5 mL of a DMF solution containing 1M DIEA and 0.5M HOBT. To this was added 50 mg of carboxylic acid, followed by 1.5 mL of a $CH_2Cl_2$ solution containing 0.2M EDC. The mixture was shaken for 18 h. The solvent was removed and the resin was rinsed sequentially with 2 mL each of $CH_2Cl_2$, 25% $Et_3N/CH_2Cl_2$, MeOH, DMF, and $CH_2Cl_2$. The coupling procedure was repeated. The products were cleaved from the resin by shaking for 18 h in the presence of a HBr/TFA/thioanisole solution (prepared by mixing 45 mL of TFA, 1.25 mL of thioanisole, and 5 mL of 30% HBr/HOAc). The solvent was removed and the resin was rinsed with MeOH (3×3 mL). The solvent was removed in vacuo, and the residue was purified by HPLC (C18, 50×100 mm, 10%–90% MeOH with 0.1% TFA, 10 min gradient, 20 mL/min). Target compounds were characterized by analytical HPLC and mass spectrometry.

| Example | Structure | | Mass Spectrum |
|---|---|---|---|
| 202 | 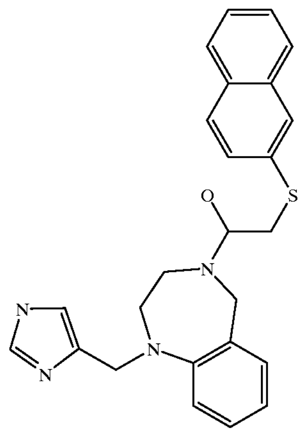 | 2,3,4,5-Tetrahydro-1-(1H-imidazol-4-ylmethyl)-4-[(2-naphthalenylthio)acetyl]-1H-1,4-benzodiazepine, trifluoroacetate (1:2) | m/z 429 (M + H) |
| 203 | 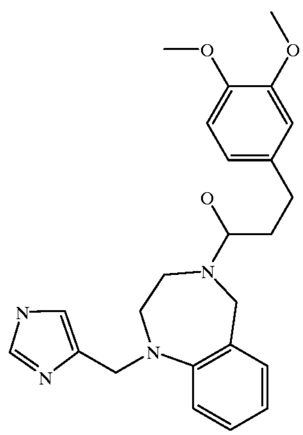 | 4-[3-(3,4-Dimethoxyphenyl)-1-oxopropyl]-2,3,4,5-tetrahydro-1-(1H-imidazol-4-ylmethyl)-1H-1,4-benzodiazepine, trifluoroacetate (1:2). | m/z 421 (M + H) |
| 204 | 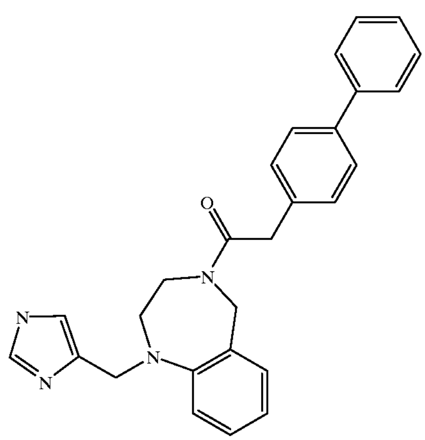 | 4-([1,1'-Biphenyl]-4-ylacetyl)-2,3,4,5-tetrahydro-1-(1H-imidazol-4-ylmethyl)-1H-1,4-benzodiazepine, trifluoroacetate (1:2). | m/z 423 (M + H) |

-continued

| Example | Structure | | Mass Spectrum |
|---|---|---|---|
| 205 | 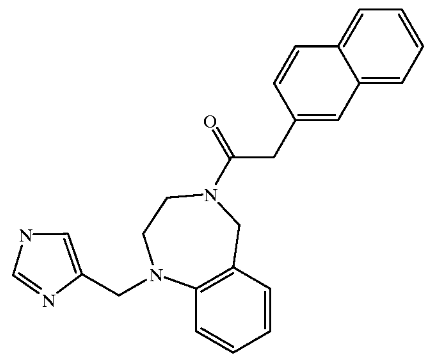 | 2,3,4,5-Tetrahydro-1-(1H-imidazol-4-ylmethyl)-4-(2-naphthalenylacetyl)-1H-1,4-benzodiazepine, trifluoroacetate (1:2). | m/z 397 (M + H) |
| 206 | 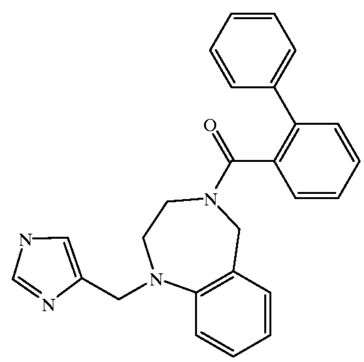 | 4-([1,1'-Biphenyl]-2-ylcarbonyl)-2,3,4,5-tetrahydro-1-(1H-imidazol-4-ylmethyl)-1H-1,4-benzodiazepine, trifluoroacetate (1:2). | m/z 409 (M + H) |
| 207 | 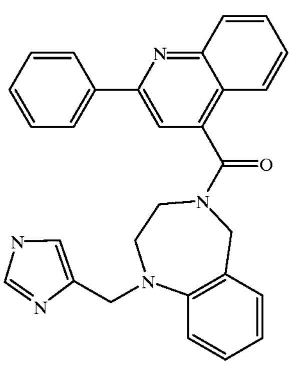 | 2,3,4,5-Tetrahydro-1-(1H-imidazol-4-ylmethyl)-4-[(2-phenyl-4-quinolinyl)carbonyl]-1H-1,4-benzodiazepine, trifluoroacetate (1:3). | m/z 460 (M + H) |
| 208 | 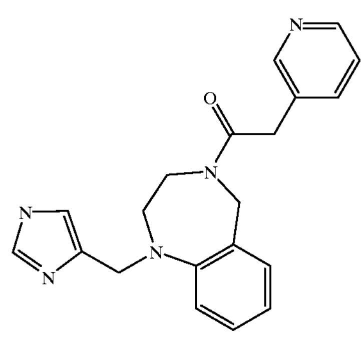 | 2,3,4,5-Tetrahydro-1-(1H-imidazol-4-ylmethyl)-4-(3-pyridinylacetyl)-1H-1,4-benzodiazepine, trifluoroacetate (1:3). | m/z 348 (M + H) |

| Example | Structure | | Mass Spectrum |
|---|---|---|---|
| 209 | 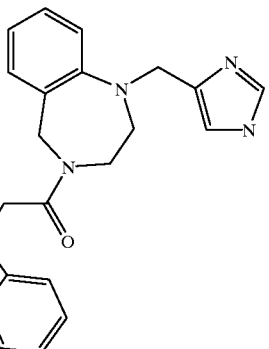 | 4-(9H-Fluoren-9-ylacetyl)-2,3,4,5-tetrahydro-1-(1H-imidazol-4-ylmethyl)-1H-1,4-benzodiazepine, trifluoroacetate (1:2). | m/z 435 (M + H) |
| 210 | 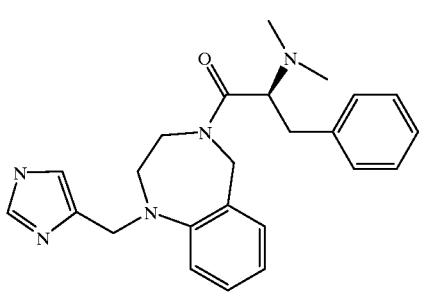 | (S)-4-[2-(Dimethylamino)-1-oxo-3-phenylpropyl]-2,3,4,5-tetrahydro-1-(1H-imidazol-4-ylmethyl)-1H-1,4-benzodiazepine, trifluoroacetate (1:3). | m/z 404 (M + H) |
| 211 | 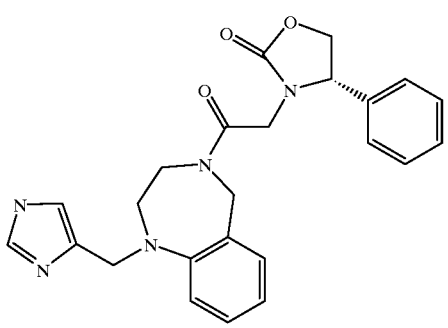 | (S)-2,3,4,5-Tetrahydro-1-(1H-imidazol-4-ylmethyl)-4-[(2-oxo-4-phenyl-3-oxazolidinyl)acetyl]-1H-1,4-benzodiazepine, trifluoroacetate (1:2). | m/z 432 (M + H) |
| 212 | 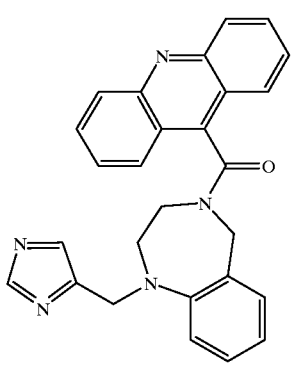 | 4-(9-Acridinylcarbonyl)-2,3,4,5-tetrahydro-1-(1H-imidazol-4-ylmethyl)-1H-1,4-benzodiazepine, trifluoroacetate (1:3). | m/z 434 (M + H) |

-continued

| Example | Structure | | Mass Spectrum |
|---|---|---|---|
| 213 | 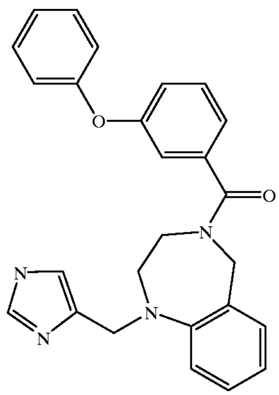 | 2,3,4,5-Tetrahydro-1-(1H-imidazol-4-ylmethyl)-4-(3-phenoxybenzoyl)-1H-1,4-benzodiazepine, trifluoroacetate (1:2). | m/z 425 (M + H) |
| 214 | 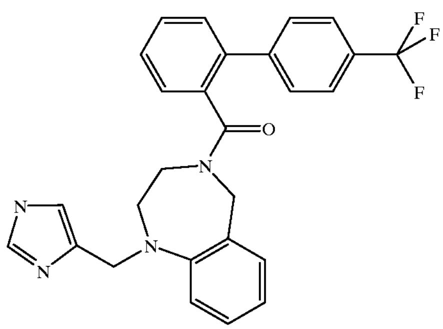 | 2,3,4,5-Tetrahydro-1-(1H-imidazol-4-ylmethyl)-4-[[4'-(trifluoromethyl)[1,1'-biphenyl]-2-yl]carbonyl]-1H-1,4-benzodiazepine, trifluoroacetate (1:2). | m/z 477 (M + H) |
| 215 | 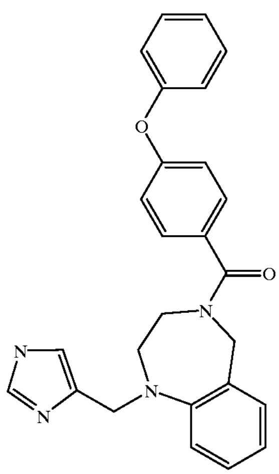 | 2,3,4,5-Tetrahydro-1-(1H-imidazol-4-ylmethyl)-4-(4-phenoxybenzoyl)-1H-1,4-benzodiazepine, trifluoroacetate (1:2). | m/z 425 (M + H) |
| 216 | 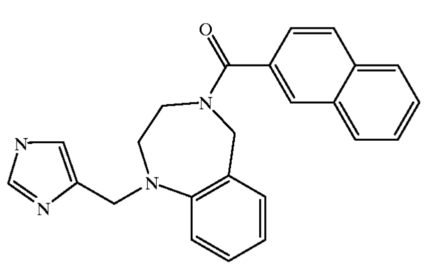 | 2,3,4,5-Tetrahydro-1-(1H-imidazol-4-ylmethyl)-4-(2-naphthalenylcarbonyl)-1H-1,4-benzodiazepine, trifluoroacetate (1:2). | m/z 383 (M + H) |

| Example | Structure | | Mass Spectrum |
|---|---|---|---|
| 217 | 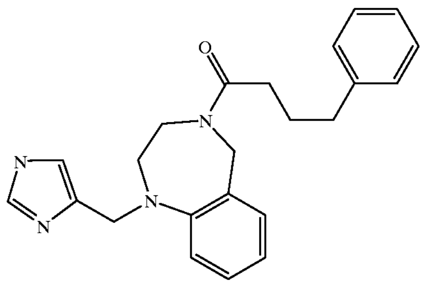 | 2,3,4,5-Tetrahydro-1-(1H-imidazol-4-ylmethyl)-4-(1-oxo-4-phenylbutyl)-1H-1,4-benzodiazepine, trifluoroacetate (1:2). | m/z 375 (M + H) |
| 218 | 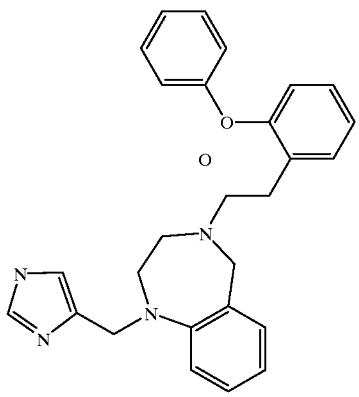 | 2,3,4,5-Tetrahydro-1-(1H-imidazol-4-ylmethyl)-4-[(2-phenoxyphenyl)acetyl]-1H-1,4-benzodiazepine, trifluoroacetate (1:2). | m/z 439 (M + H) |
| 219 | 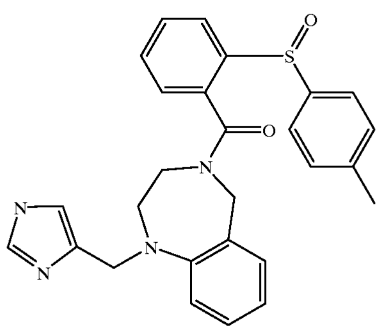 | 2,3,4,5-Tetrahydro-1-(1H-imidazol-4-ylmethyl)-4-[2-[(4-methylphenyl)sulfinyl]benzoyl]-1H-1,4-benzodiazepine, trifluoroacetate (1:2) | m/z 471 (M + H) |
| 220 | 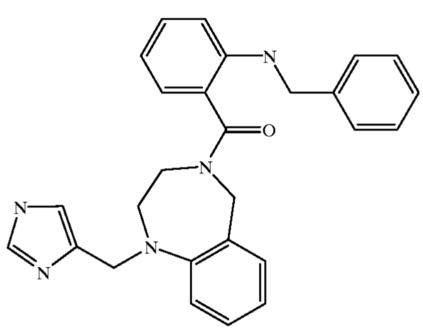 | 2,3,4,5-Tetrahydro-1-(1H-imidazol-4-ylmethyl)-4-[2-[(phenylmethyl)amino]benzoyl]-1H-1,4-benzodiazepine, trifluoroacetate (1:3) | m/z 438 (M + H) |

EXAMPLE 221

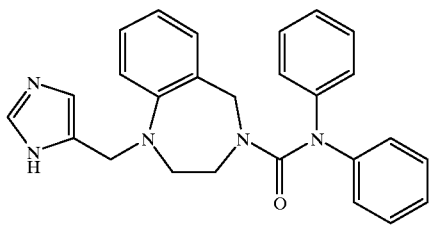

1,2,3,5-Tetrahydro-1-(1H-imidazol-4-yl-methyl)-N,N-diphenyl-4H-1,4-benzodiazepine-4-carboxamide, hydrochloride Example 221 was prepared as a light yellow solid from N,N-diphenylcarbamyl chloride as described for Example 9.

MS (M+H)$^+$424

Analysis calculated for $C_{26}H_{25}N_5O \cdot 2.2\ H_2O \cdot 2.2\ HCl$. Calc'd: C, 57.47; H, 5.87 N, 12.89; Cl, 14.35 Found: C, 57.25; H, 5.78; N, 13.25; Cl, 14.73.

EXAMPLE 222

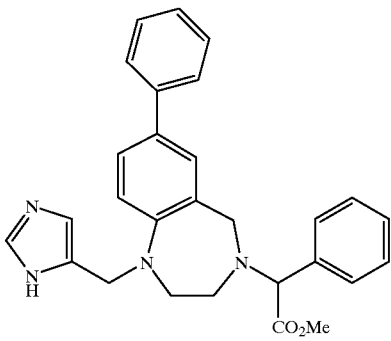

1,2,3,5-Tetrahydro-1-(1H-imidazol-4-yl-methyl)-a,7-diphenyl-4H-1,4-benzodiazepine-4-acetic acid, methyl ester, hydrochloride To a stirred suspension of Compound B of Example 12 (220 mg, 1.0 mmol) in MeOH in the presence of solid $K_2CO_3$ at room temperature under argon was added methyl bromophenylacetate (0.18 mL, 1.1 mmol). The mixture was stirred for 18 h, the solvent was removed, and the residue was purified by flash column chromatography (3:2, hexanes and ethyl acetate) to give 1,2,3,5-tetrahydro-a,7-diphenyl-4H-1,4-benzodiazepine-4-acetic acid, methyl ester as an oil (220 mg, 63%). This material was reacted as described for Compound D of Example 1 to afford Example 222 as a yellow solid.

MS (M+H)$^+$453

Analysis calculated for $C_{28}H_{28}N_4O_2 \cdot 0.2\ H_2O \cdot 2.5\ HCl$. Calc'd: C, 61.44; H, 5.69 N, 10.24; Cl, 16.19. Found: C, 61.33; H, 5.88; N, 9.94; Cl, 16.00.

EXAMPLE 223

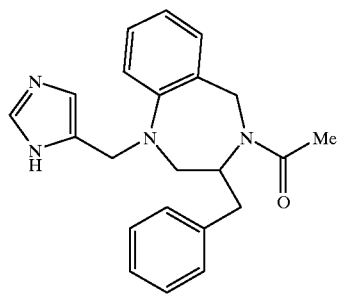

4-Acetyl-2,3,4,5-tetrahydro-1-(1H-imidazol-4-ylmethyl)-3-(phenylmethyl)-1H-1,4-benzodiazepine, hydrochloride Example 223 was prepared as a tan solid from isatoic anhydride and D,L-phenylalanine-O methyl ester hydrochloride as described for Example 71, except that acetyl chloride (0.25 eq) was used in place of napthoyl chloride.

MS (M+H)$^+$453

Analysis calculated for $C_{22}H_{24}N_4O \cdot 1.5\ H_2O \cdot 1.2\ HCl$. Calc'd: C, 61.74; H, 6.26; N, 13.26; Cl, 9.49. Found: C, 61.80; H, 6.62; N, 13.10; Cl, 9.12.

EXAMPLE 224

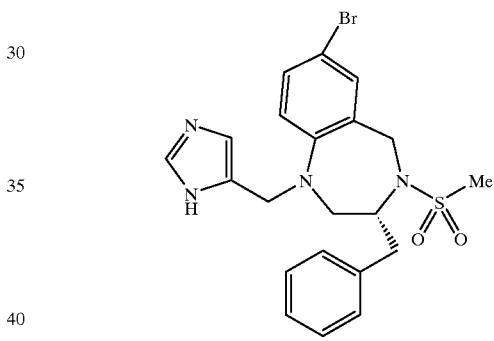

(R)-7-Bromo-2,3,4,5-tetrahydro-1-(1H-imidazol-4-ylmethyl)-4-(methylsulfonyl)-3-(phenylmethyl)-1H-1,4-benzodiazepine, hydrochloride A. (R)-7-Bromo-2,3,4,5-tetrahydro-3-(phenylmethyl)-1H-1,4-benzodiazepin-2,5-dione A stirred solution of bromoisatoic anhydride (150 g, 0.62 mol) and D-phenylalanine methyl ester hydrochloride (127.3 g, 0.59 mol) in the presence of 4-dimethylaminopyridine (2 g) in pyridine (1500 mL) was heated at reflux under argon for 3 days. The pyridine was removed in vacuo and the residue was dissolved in methylene chloride (3L). This solution was washed with 10% HCl solution and brine. The organic solution was dried and concentrated in vacuo to a small volume. The solid thus formed was collected and dried to give 152 g (71%) of Compound A, mp 242–243° C.

B. (R)-7-Bromo-2,3,4,5-tetrahydro-3-(phenylmethyl)-1H-1,4-benzodiazepine

A stirred solution Compound A (30 g, 87 mmol) in anhydrous THF (870 mL) under argon was treated with a solution of borane-tetrahydrofuran complex (440 mL of a 1M solution, 440 mmol) at room temperature. The solution was slowly heated to reflux and heated at reflux for 18 h. The mixture was cooled to 0° C., and methanol (150 mL) was added to destroy excess of BH3. The resultant solution was concentrated in vacuo, the residue was dissolved in methanol (250 mL), and 7N HCl solution (50 mL) was added. This mixture was heated on a steam-bath for 2 h. The solid thus formed was collected, resuspended in water (400 mL) and the aqueous suspension was made basic to pH 11 with 5N NaOH solution and extracted with ethyl acetate (2×300 mL). The organic extracts were combined, dried, concentrated in vacuo and the residue was crystallized from methanol and water (9:1) to give 25 grams of Compound B as a white solid (91%), mp 135–138° C.

C. (R)-7-Bromo-2,3,4,5-tetrahydro-4-(methylsulfonyl)-3-(phenylmethyl)-1H-1,4-benzodiazepine To a stirred solution of Compound B (1.5 g, 4.73 mmol), pyridine (3 mL), and DIEA (1.6 mL, 9.46 mmol) was added methanesulfonyl chloride (0.55 mL, 7.11 mmol) at 0° C. under argon. The resultant mixture was stirred at 0° C. for 2 h and 1N NaOH solution (30 mL) was added. The mixture was stirred for 2 hours and the organic layer was separated, washed with 1N HCl solution (2×100 mL), dried, and concentrated in vacuo to give 1.7 g of Compound C as a yellow solid (91%).

D. (R)-7-Bromo-2,3,4,5-tetrahydro-1-(1H-imidazol-4-ylmethyl)-4-(methylsulfonyl)-3-(phenylmethyl)-1H-1,4-benzodiazepine, hydrochloride To a stirred solution of Compound C (18 g, 45.6 mmol) in acetic acid (50 mL) and dichloroethane (200 mL) at room temperature, was added 4-formylimidazole (6.6 g, 68.5 mmol). The mixture was stirred at room temperature for 30 min. To the resultant solution was added sodium triacetoxyborohydride (14.5 g, 68.5 mmol). The mixture was stirred at room temperature for 18 hours, diluted with ethyl acetate (500 mL), cooled to 0° C. and made basic to pH 9 with concentrated NH4OH solution. The mixture was stirred for 2 h and partitioned between ethyl acetate and saturated NaHCO3 solution. The organic layer was separated and washed with saturated NH4Cl solution, dried over Na2SO4 and concentrated in vacuo. The residue was crystallized from methanol to give a white solid (14 g, 65%). The solid was dissolved in ethyl acetate and 1N HCl solution in ether (60 mL) was added. The solvent was removed in vacuo and the solid was dried in a heated oven under vacuum to give Example 224 as a white solid, mp 180–185° C.

MS (M+H)$^+$476

[a]D20: +58° (c=0.4, MeOH).

EXAMPLE 225

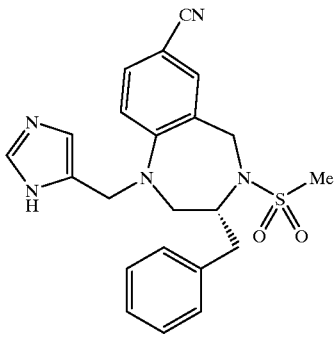

(R)-2,3,4,5-Tetrahydro-1-(1H-imidazol-4-ylmethyl)-4-(methylsulfonyl)-3-(phenylmethyl)-1H-1,4-benzodiazepine-7-carbonitrile, monohydrochloride A. (R)-2,3,4,5-Tetrahydro-4-(methylsulfonyl)-3-(phenylmethyl)-1H-1,4-benzodiazepine-7-carbonitrile A stirred solution of Compound C of Example 224 (6.9 g, 17.5 mmol) and copper cyanide (4.0 g, 44 mmol) in N-methylpyrrolidinone (90 mL) was heated at 200° C. for 5 h. The mixture was cooled to room temperature and poured into a 10% aqueous solution of ethylene diamine (800 mL). The resultant suspension was stirred at room temperature for 2 h and extracted with ethyl acetate (3×150 mL). The combined organic extracts were washed with 5% NH4OH solution (2×100 mL), brine, dried over MgSO4, and concentrated. The residue was purified by flash chromatography (ethyl acetate, hexanes; 1:1) to give Compound A as a foam (4.5 g, 75%).

B. (R)-2,3,4,5-Tetrahydro-1-(1H-imidazol-4-ylmethyl)-4-(methylsulfonyl)-3-(phenylmethyl)-1H-1,4-benzodiazepine-7-carbonitrile, monohydrochloride To a stirred solution of Compound A (4.7 g, 13.8 mmol) in acetic acid (30 mL) and dichloroethane (120 mL) at room temperature was added 4-formylimidazole (2.1 g, 22 mmol). The mixture was stirred at room temperature for 30 min. To the resultant solution was added sodium triacetoxyborohydride (4.4 g, 22 mmol). The mixture was stirred at room temperature for 2 h, 4-formylimidazole (1.3 g, 13.5 mmol) was added, the mixture was stirred for 30 min, and sodium triacetoxyborohydride (3.0 g, 14 mmol) was added. This cycle was repeated two times until all starting material was consumed. Workup and product isolation were performed as described for Compound D of Example 224 to provide Example 225 as a white solid (4.1 g, 65%). mp 165° C.

MS (M+H)$^+$422

[a]D20:+218° (c=0.23, MeOH).

Analysis calculated for $C_{22}H_{23}N_5O_2S$•1.7 $H_2O$•1HCl. Calc'd: C, 54.08; H, 5.65; N, 14.33; Cl, 7.26. Found: C, 54.04; H, 5.38; N, 14.33; Cl, 7.27.

EXAMPLE 226

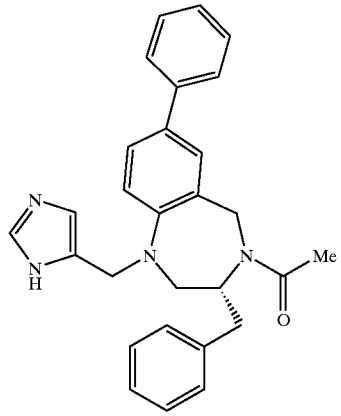

(R)-4-Acetyl-2,3,4,5-tetrahydro-1-(1H-imidazol-4-ylmethyl)-7-phenyl-3-(phenylmethyl)-1H-1,4-benzodiazepine, monohydrochloride A. 2-Amino-5-phenyl-benzoic acid 2-Amino-5-bromo-benzoic acid (30.0 g, 139 mmol), benzeneboronic acid (18.6 g, 153 mmol) and K$_2$CO$_3$ (48.0 g, 348 mmol) were combined in a mixture of water (300 mL) and THF (300 mL). The mixture was bubbled with Ar vigorously for an hour to degas and a solution of Palladium (ll) acetate (2.52 g, 11.2 mmol) in degassed THF (50 mL) was added dropwise over 1 h. The mixture was stirred for 16 h at room temperature with Ar bubbling. The mixture was concentrated, filtered through a pad of celite and lyophilized to remove water. The lyophilate was triturated with 90% dichloromethane, 10% methanol (500 mL). The filtrate was concentrated and recrystallized from ethyl acetate/hexane to yield Compound A as a brown solid (25g, 84%), MS (M+H)$^+$214.

B. 6-Phenyl-3,1-oxazine-2,4(1H)-dione

To a solution of Compound A (25.0 g, 0.117 mol) and triphosgene (25.0 g, 0.084 mol) in acetonitrile (250 mL) at 0° C. under N$_2$ was added a solution of triethylamine (3.0 g, 4.1 mL, 0.029 mol) in acetonitrile(50 mL) dropwise over 1 hour. The mixture was stirred at room temperature for 16h and the solid was filtered. The filter cake was washed with dichloromethane and dried under vacuum to yield Compound B as a light brown solid (17.8 g, 63%), MS (M+H)$^+$ 241.

C. (R)-2,3,4,5-tetrahydro-7-phenyl-3-(phenylmethyl)-1H-1,4-benzodiazepin-2,5-dione Compound B (9.40 g, 0.0392 mol), D-Phe (6.5 g, 0.0392 mol) and pyridine-HCl (22.6 g, 0.196 mol) were dissolved in pyridine (100 mL). The solution was refluxed for 4 h, cooled and concentrated. The residue was partitioned between water (200 mL) and ethyl acetate (200 mL). The organic layer was washed with water (3×100 mL), brine (50 mL), dried (MgSO$_4$) and concentrated to yield compound C as a yellowish glass (6.0 g, 45%), MS (M+H)$^+$343.

D. (R)-2,3,4,5-tetrahydro-7-phenyl-3-(phenylmethyl)-1H-1,4-benzodiazepine

Compound C (6.0 g, 0.017 mol) was dissolved in THF (100 mL) and borane (1M in THF, 50 mL, 50 mmol) was added. The solution was refluxed for 4 h and cooled to room temperature. Methanol (50 mL) was added to quench the residual borane and the solution was concentrated. 1N HCl (100 mL) was added to the residue and the mixture was refluxed for 4h. The mixture was cooled to room temperature, acidified to pH 2 with 1N NaOH (110 mL) and extracted with dichloromethane (3×200 mL). The organic layers were combined, washed with brine (300 mL), dried (Na$_2$SO$_4$) and concentrated to yield compound D as a slightly yellow glass (5.5 g, 99%), MS (M+H)$^+$315.

E. (R)-4-Acetyl-2,3,4,5-tetrahydro-7-phenyl-3-(phenylmethyl)-1H-1,4-benzodiazepine Compound D (5.0 g, 0.016 mol) was dissolved in dichloromethane (300 mL) and DIEA (2.06 g, 2.8 mL, 0.016 mol) was added at once. A solution of acetic anhydride (1.46 g, 1.35 mL, 0.0143 mol) in dichloromethane (20 mL) was added dropwise over 30 min. The solution was stirred for 30 min, washed with saturated sodium bicarbonate (3×100 mL), water (3×100 mL), brine (100 mL), dried (Na$_2$SO$_4$) and concentrated to yield Compound E as a light brown glass (5.0 g, 88%).

F. (R)-4-Acetyl-2,3,4,5-tetrahydro-1-(1H-imidazol-4-ylmethyl)-7-phenyl-3-(phenylmethyl)-1H-1,4-benzodiazepine, monohydrochloride Compound E (5.0 g, 14.0 mmol) and 4-formylimidazole (4.45 g, 46.3 mmol) were dissolved in 1,2-DCE (100 mL) and acetic acid (50 mL). Sodium triacetoxyborohydride (4.45 g, 21.0 mmol) was added all at once and the mixture was stirred at room temperature for 1 h. Saturated NaHCO$_3$ (50 mL) was added followed by ammonium hydroxide (50 mL). The mixture was stirred for 2 h, concentrated and the residue was partitioned between water (100 mL) and ethyl acetate (200 mL). The organic layer was washed with water (100 mL), brine (100 mL), dried (Na$_2$SO$_4$), concentrated and chromatographed (silica gel, 5.1×15 cm, 95% dichloromethane, 5% methanol) to yield the free base of Example 225 as a brown solid (4.9 g). This brown solid was further purified by preparative HPLC (YMC S-15 ODS column, 50×500 mm; solvent A, 0.1% TFA in 90% water, 10% methanol; solvent B, 0.1% TFA in 10% water, 90% methanol: 20–100% B in 60 min, flow rate 25 mL/min). Fractions containing the desired product were combined, concentrated and lyophilized. This lyophilate was dissolved in acetonitrile (50 mL) and 1N HCl (50 mL). This mixture was concentrated and lyophilized. This procedure is repeated to provide Example 226 as a yellow solid (2.3 g, 35%)

MS (M+H)$^+$437

$^1$H-NMR (CD$_3$OD, 400 MHz) d (ppm) 8.95 (1H, m), 7.68–7.30 (13H, m), 7.04 (1H, m), 5.21–5.10 (1H, m), 4.78–4.63 (2H, m), 4.63–4.48 (1H, m), 4.38 (1H, m), 3.81–3.76 (1H, m), 3.28–3.15 (1H, m), 2.98–2.93 (1H, m), 2.88–2.80 (1H, m), 2.09 (2H, s), 1.62 (1H, s).

EXAMPLE 227

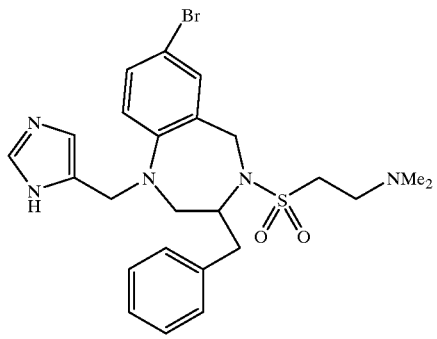

7-Bromo-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, trifluoroacetate (1:2)

A. 7-Bromo-4-[ethenylsulfonyl]-2,3,4,5-tetrahydro-3-(phenylmethyl)-4H-1,4-benzodiazepine To a mixture of Compound B of Example 224 (250 mg, 0.79 mmol) in THF (20 mL) was added sequentially 2-chloroethane sulfonyl chloride (0.1 mL, 0.95 mmol) and DIEA (0.18 mL, 1.98 mmol). The solution was stirred under argon at room temperature for 18 hours, partitioned between aqueous hydrochloric acid (100 ml, 1N), and ethyl acetate (100 mL), and extracted with ethyl acetate (2×100 mL). The organic layers were combined, dried (MgSO$_4$) and concentrated in vacuo to provide a crude oil which was purified by flash chromatography (silica, hexane: ethyl acetate 3:1) to provide Compound A as a clear oil (85 mg, 26%).

B. 7-Bromo-4-[[2-(dimethylamino)ethyl]sulfonyl]-2,3,4,5-tetrahydro-3-(phenylmethyl)-4H-1,4-benzodiazepine To a solution of Compound A (85 mg, 0.21 mmol) in THF (5 mL) was added a solution of dimethylamine (2 mL, 2M in THF). The solution was heated in a sealed pressure bottle at 60° C. for 48 hrs, cooled to room temperature and concentrated under vacuum to afford crude Compound B as an oil.

C. 7-Bromo-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, trifluoroacetate (1:2)

To a stirred solution of Compound B (90 mg, crude, assume 0.21 mmol), 4-formyl imidazole (30 mg, 0.32 mmol), dichloroethane (4 mL) and acetic acid (2 mL) at room temperature was added sodium triacetoxyborohydride (67 mg, 0.32 mmole). The solution was stirred for 48 hour, diluted with ethyl acetate (20 mL) and ammonium hydroxide (5 ml, conc), and stirred for an additional 18 hours. The mixture was extracted with ethyl acetate (2×25 mL), and the combined organic extracts were washed with aqueous sodium bicarbonate (25 mL, saturated solution), and then ammonium chloride (25 mL, sat aqueous solution), dried (Na$_2$SO$_4$), and concentrated in vacuo to a semi-solid. The

EXAMPLE 228

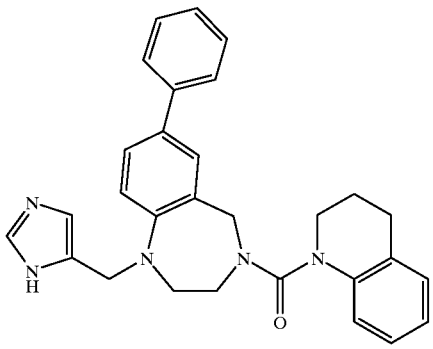

2,3,4,5-Tetrahydro-1-(1H-imidazol-4-ylmethyl)-7-phenyl-4-[(1,2,3,4-tetrahydro-1-quinolinyl)carbonyl]-1H-1,4-benzodiazepine, monohydrochloride Example 228 was prepared from N-chlorocarbonyl-1,2,3,4-tetrahydroquinoline as described for Example 35, except that the acylation product was chromatographed (silica, 8:2 chloroform:ethyl acetate).

MS (M+H)$^+$464

Analysis calculated for $C_{29}H_{29}N_5O \cdot 1.0\ H_2O \cdot 1.1$ HCl$\cdot$0.25 ether. Calc'd: C, 66.70; H, 6.46; N, 12.96; Cl, 7.22. Found: C, 66.88; H, 6.36; N, 12.62; Cl, 7.30.

EXAMPLE 229

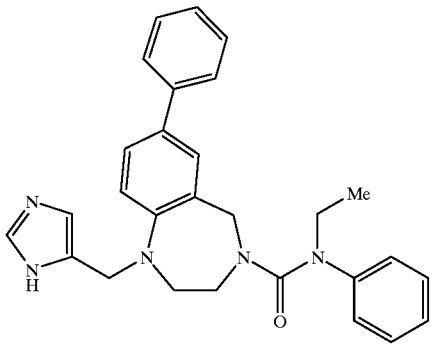

N-Ethyl-1,2,3,5-tetrahydro-1-(1H-imidazol-4-ylmethyl)-N,7-diphenyl-4H-1,4-benzodiazepine-4-carboxamide, monohydrochloride Example 229 was prepared from N-chlorocarbonyl-N-ethyl-aniline as described for Example 35. The HCl salt was prepared by dissolving the product in methanol, adding 4N HCl in dioxane, evaporation, redissolving in methanol and precipitating with ether.

MS (M+H)$^+$452

Analysis calculated for $C_{28}H_{29}N_5O \cdot 0.4\ H_2O \cdot 1.2$ HCl$\cdot$0.25 ether. Calc'd: C, 66.85; H, 6.48; N, 13.44; Cl, 8.16. Found: C, 66.78; H, 6.38; N, 13.49; Cl, 8.05.

EXAMPLE 230

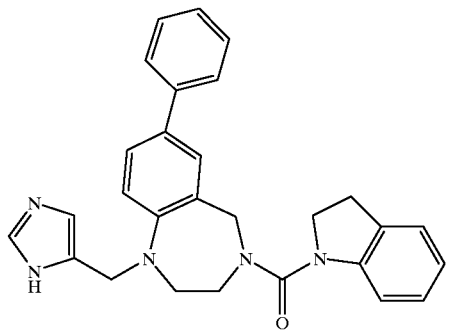

4-[(2,3-Dihydro-1H-indol-1-yl)carbonyl]-2,3,4,5-tetrahydro-1-(1H-imidazol-4-ylmethyl)-7-phenyl-1H-1,4-benzodiazepine, monohydrochloride Example 230 was prepared from N-chlorocarbonyl-indoline as described for Example 229, mp 156–166° C.

MS (M+H)$^+$450

Analysis calculated for $C_{28}H_{27}N_5O \cdot 0.5\ H_2O \cdot 0.5$ HCl. Calc'd: C, 65.52; H, 5.79; N, 13.65; Cl, 10.36. Found: C, 65.40; H, 5.74; N, 13.47; Cl, 10.49.

EXAMPLE 231

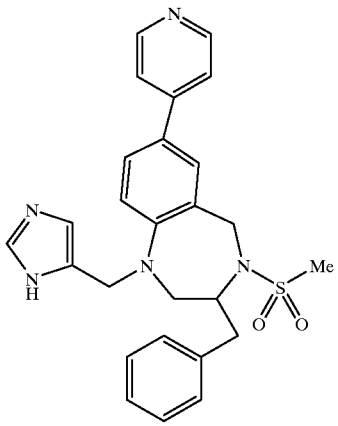

2,3,4,5-Tetrahydro-1-(1H-imidazol-4-ylmethyl)-4-(methylsulfonyl)-3-(phenylmethyl)-7-(4-pyridinyl)-1H-1,4-benzodiazepine, trihydrochloride A. 2,3,4,5-Tetrahydro-1-(trifluoroacetyl)-4-(methylsulfonyl)-3-(phenylmethyl)-7-bromo-1H-1,4-benzodiazepine Trifluoroacetic anhydride (1.2 mmol, 165 mL) was added to a solution of Compound A of Example 78 (0.3 mmol) and triethylamine (2.75 mmol, 384 mL) in CH$_2$Cl$_2$ (4 mL) and the homogeneous solution was maintained at rt for 5 hrs. The reaction was concentrated and purified by flash chromatography (40%EtOAc/Hex) to isolate Compound A as a fluffy white solid (100 mg, 68%). MS (M+NH4) 508.

B. 2,3,4,5-Tetrahydro-1-(trifluoroacetyl)-4-(methylsulfonyl)-3-(phenylmethyl)-7-(4-pyridinyl)-1H-1,4-benzodiazepine Compound A (0.15 mmol), 4-stannylpyridine (0.3 mmol, 110 mg) and 15 mol % Pd(PPh3)$_4$ (26 mg) in 3 mL THF was degassed and heated to reflux under argon. Over the period of 48 hrs, an additional 20 mol % catalyst was added until starting material was fully consumed. The reaction was concentrated and purified by flash chromatography (EtOAc) to isolate Compound B as a yellow oil (46 mg, 63%). MS (M+H) 490.

C. 2,3,4,5-Tetrahydro-1-(1H-imidazol-4-ylmethyl)-4-(methylsulfonyl)-3-(phenylmethyl)-7-(4-pyridinyl)-1H-1,4-benzodiazepine, trihydrochloride NaOH (5 drops of 2N NaOH aqueous solution) was added to a solution of Compound B (40 mg, 0.082 mmol) in 3 mL MeOH and the mixture was maintained at RT for 20 min and concentrated. The residue was partitioned between 2N NaOH (5 mL) and 10% isopropanol-CH2Cl2 (5 mL) and extracted with 10% isopropanol-CH2Cl2 (3×5 mL), dried over Na2SO4 and concentrated. This material was dissolved in 1 mL of 1:1 AcOH:dichloroethane and treated with 4-formylimidazole (0.66 mmol, 63 mg) and NaBH(OAc)3 (0.66 mmol, 140 mg) and the mixture was heated at 50° C. for 2 hrs and concentrated. The residue was partitioned between 2N NaOH-brine-sat. NH4OH (10:10:0.3, 23 ml total) and 10% isopropanol-CH2Cl2 (5 mL) and the aqueous phase was extracted with 10% isopropanol-CH2Cl2 (2×5 mL). The combined organic phases were concentrated and purified with prep. HPLC (YMC S5 ODS 20×100 mm, gradient elution with 15 to 75% buffer B over 60 min. Buffer A=MeOH: H$_2$O:TFA (10:90:0.1); Buffer B=MeOH:H$_2$O:TFA (90:10:0.1); flow rate 25 ml/min). The TFA salt was converted to HCl salt with 1N HCl to produce Example 231 as a yellow solid (6.0 mg, 13%).

MS (M+H)+474

1H NMR (CD3OD) d 8.9 (s, 1H), 8.7 (m, 2H), 8.3 (m, 2H), 7.8 (m, 2H), 7.5 (s, 1H), 7.3 (m, 4H), 7.0 (d, J=9 Hz, 1H), 4.8 (d, J=8 Hz, 2H), 4.65 (t, J=14 Hz, 2H), 4.45 (br s, 1H), 3.7 (dd, J=7,14 Hz, 1H), 3.4 (dd, J=7,5 Hz, 1H), 2.96(dd, J=14,7 Hz, 1H), 2.8 (dd, J=14,7 Hz, 1H), 2.3 (s, 3H).

EXAMPLE 232

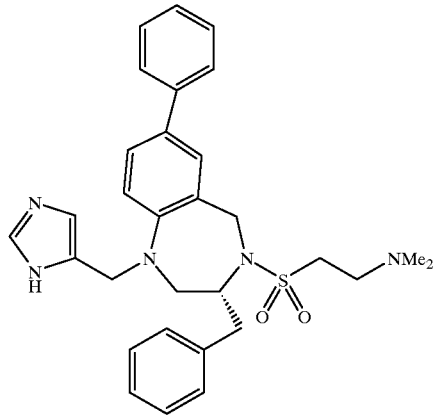

(R)-4-[[2-(Dimethylamino)ethyl]sulfonyl]-2,3,4,5-tetrahydro-1-(1H-imidazol-4-ylmethyl)-7-phenyl-3-(phenylmethyl)-1H-1,4-benzodiazepine, trifluoroacetate (1:1)

A. (R)-7-Bromo-2,3,4,5-tetrahydro-3-(phenylmethyl)-1H-1,4-benzodiazepine

Compound A was prepared from Compound A of Example 224 as described for Compound B of Example 75.

B. (R)-7-Phenyl-2,3,4,5-tetrahydro-3-(phenylmethyl)-1H-1,4-benzodiazepine

To a mixture of Compound A (500 mg, 1.58 mmol) in toluene (20 mL) and aqueous sodium bicarbonate (10 mL, saturated solution) under argon was added a solution of phenyboronic acid (385 mg in 5 ml absolute ethanol). Tetrakis(triphenylphosphine) palladium(O) (91 mg) was added, and the solution heated to reflux (~80° C.). After 18 hours, the mixture was cooled to room temperature and partitioned between aqueous sodium hydroxide (100 mL, 3N) and ethyl acetate (100 mL). The mixture was extracted with ethyl acetate (2×200 mL), and the organic layers were combined, dried (MgSO$_4$) and concentrated in vacuum to an oil, which was purified using flash chromatography (60 g silica, 10:0.5:0.05 ethyl acetate:methanol: ammonium hydroxide) to provide Compound B (350 mg, 70%) as a waxy solid C. (R)-4-Ethenylsulfonyl-2,3,4,5-tetrahydro-7-phenyl-3-(phenylmethyl)-1H-1,4-benzodiazepine To a mixture of Compound B (45 mg, 0.14 mmol) in methylene chloride (5 mL) and aqueous sodium hydroxide (1 mL, 1M solution) was added 2-chloroethane sulfonyl chloride (0.8 mL, 0.07 mmol). Additional portions of 2-chloroethane sulfonyl chloride (0.1 mL, 0.2 mL, 0.2 mL) were added over a period of 6 hours and the mixture was stirred for 18 hours, poured into brine and extracted with ethyl acetate (3×100 mL). The organic layers were combined, dried (MgSO4) and concentrated in vacuum to an oil, which was purified using preparative HPLC (ODS column, aqueous methanol gradient containing trifluoroacetic acid). Appropriate product containing samples were pooled and concentrated under vacuum to provide Compound C (10 mg, 17%) as a clear oil.

D. (R)-4-[[2-(Dimethylamino)ethyl]sulfonyl]-2,3,4,5-tetrahydro-7-phenyl-3-(phenylmethyl)-1H-1,4-benzodiazepine To a solution of Compound C (20 mg, 0.025 mmol) in tetrahydrofuran (2 mL) was added a solution of dimethyl amine (1 mL, 2M in THF). The solution was heated in a sealed pressure bottle at 60° C. for 18 hrs, cooled to room temperature and concentrated in vacuum to an oil.

E. (R)-4-[[2-(Dimethylamino)ethyl]sulfonyl]-2,3,4,5-tetrahydro-1-(1H-imidazol-4-ylmethyl)-7-phenyl-3-(phenylmethyl)-1H-1,4-benzodiazepine, trifluoroacetate (1:1)

A solution of Compound D (20 mg, crude, assume 0.05 mmol) and 4-formyl imidazole (10 mg, 0.1 mmol) in dichloroethane (4 mL) and acetic acid (2 mL) was stirred at room temperature for 30 min. Sodium triacetoxy borohydride (22 mg, 0.1 mmole) was added and the solution was stirred for 48 hour, diluted with ethyl acetate (20 mL) and ammonium hydroxide (5 ml, conc), and stirred for an additional 30 min. The mixture was extracted with ethyl acetate (2×25 mL), and the combined organic extracts were washed with aqueous sodium bicarbonate (25 ml, saturated solution), and then ammonium chloride (25 mL, sat aqueous solution), dried (Na$_2$SO$_4$), and concentrated in vacuo to a semi-solid. The crude product was purified by preparative HPLC (aqueous methanol gradient containing 0.1% trifluoroacetic acid, C-18 column) and lyophilized to provide Example 232 as a white solid (10 mg, 37% yield from Compound C). mp 115–120° C.

MS (M+H)+530

$^1$H NMR (200 MHz, CD$_3$OD) d 8.8 (d, 1H), 7.7–7.4 (m, 12H), 7.1 (d, 1H), 4.9 (s, 6H), 3.4–3.1 (m, 8H), 3.8–3.2 (m,8H), 2.7 (s, 6H).

EXAMPLE 233

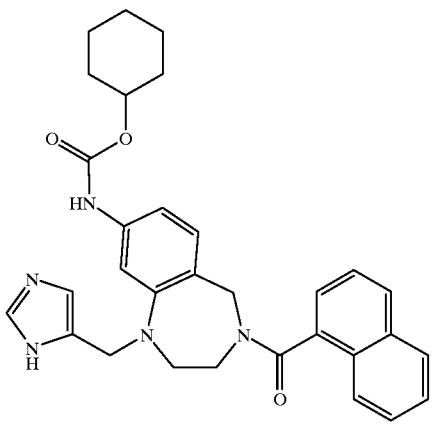

[2,3,4,5-Tetrahydro-1-(1H-imidazol-4-ylmethyl)-4-(1-naphthalenylcarbonyl)-1H-1,4-benzodiazepin-8-yl] carbamic acid, cyclohexyl ester, dihydrochloride A solution of cyclohexanol (0.14 mL, 0.137 g, 1.38 mmol) and phosgene (0.14 mL, 2 M solution in THF) was stirred at 4° C. for 2 hrs. To this cold solution were added triethylamine (0.19 mL, 0.14 g, 1.38 mmol) and Example 26 (0.050 g, 0.12 mmol). After stirring for 16 hrs at 4° C. the mixture was diluted with chloroform and $NaHCO_3$ solution and the layers were separated. The aqueous layer was extracted with CHCl3 (2×30 mL) and the combined organic layers were washed with brine (1×30 mL), dried over MgSO4, filtered and concentrated. The residue was treated with MeOH and 1N NaOH for 30 min. The crude product was purified by preparative HPLC (aqueous methanol gradient containing 0.1% trifluoroacetic acid, C-18 column) and lyophilized. The residue was treated with HCl/ether to afford Example 233 (0.030 g, 46%) as a light yellow solid.

MS $(M+H)^+$524

$^1$H NMR (270 MHz, $CD_3OD$): d 8.0–6.9 (m, 1H), 6.81 (d, 0.5H, J=8 Hz), 5.85 (d, 0.5H, J=9 Hz) 5.85 (m, 1H), 4.4–4.0 (m, 3H), 3.9–3.7 (m, 0.5H), 3.4–3.1 (m, 1.5H), 2.88 (m, 1H), 2.0–1.2 (m, 12H).

EXAMPLE 234

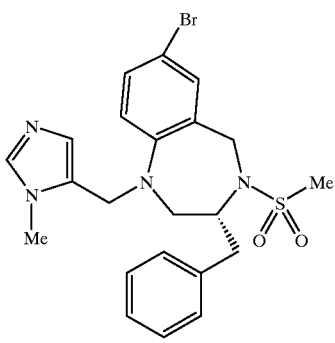

(R)-7-Bromo-2,3,4,5-tetrahydro-1-(1-methyl-1H-imidazol-5-yl)methyl)-4-(methylsulfonyl)-3-(phenylmethyl)-1H-1,4-benzodiazepine, hydrochloride A. (R)-7-Bromo-2,3,4,5-tetrahydro-1-[(((1,1-dimethylethoxy)-carbonyl)-1H-imidazol-4-yl)methyl]-4-(methylsulfonyl)-3-(phenylmethyl)-1H-1,4-benzodiazepine To a solution of 260 mg (0.55 mmol) of Example 224 in 10 ml of methylene chloride was added 131 mg (0.60 mmol) of BOC anhydride and 3 mg (0.025 mmol) of DMAP. The clear colorless solution was stirred at rt under argon for 3 hr. An additional 40 mg of BOC anhydride was added and stirring was continued overnight. The mixture, without workup, was placed a 30 cc column of silica gel and eluted with 25% ethyl acetate:hexane to afford 290 mg (0.55 mmol, 100%) of Compound A as a solid white foam.

B. (R)-7-Bromo-2,3,4,5-tetrahydro-1-(1-methyl-1H-imidazol-5-yl)methyl)-4-(methylsulfonyl)-3-(phenylmethyl)-1H-1,4-benzodiazepine, hydrochloride To a solution of 275 mg (0.48 mmol) of Compound A and 0.091 ml (0.52 mmol) of DIEA in 5 ml of methylene chloride, at –78° C. and under argon, was added dropwise 0.059 ml (0.52 mmol) of methyl triflate. The mixture was allowed to warm to rt over 3 hr. An additional 0.091 ml (0.52 mmol) of DIEA and 0.059 ml (0.52 mmol) of methyl triflate were added. Stirring was continued at rt overnight. Three more additions of 0.091 ml (0.52 mmol) of diisopropylethylamine and 0.059 ml (0.52 mmol) of methyl triflate were made at 1 hr intervals. The reaction, without workup, was placed a 50 cc column of silica gel. Elution with CHCl3:MeOH (98:2) afforded 134 mg of the free base of Example 234 as a white foam. To this material, as a solution in 2 ml of ethyl acetate, was added dropwise 0.26 ml of 1N HCV ether. The resulting solid was filtered to give Example 234 (102 mg, 38%) as a white solid.

MS $(M+H)^+$489, 491

Analysis calculated for $C_{22}H_{24}N_4O_2Cl\cdot0.25$ EtOAc•1.25 HCl. Calc'd: C, 49.59; H, 5.11; N, 10.06. Found: C, 49.97; H, 5.15; N, 9.90.

EXAMPLE 235

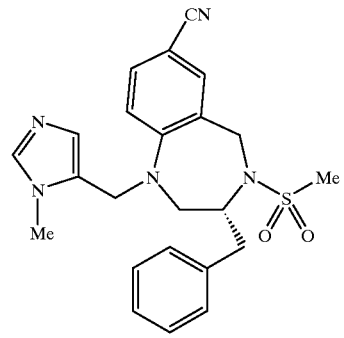

(R)-7-Cyano-2,3,4,5-tetrahydro-1-[(1-methyl-1H-imidazol-5-yl)methyl]-4-(methylsulfonyl)-3-(phenylmethyl)-1H-1,4-benzodiazepine, monohydrochloride To a solution of 200 mg (0.38 mmol) of (R)-7-cyano-2,3,4,5-tetrahydro-1-[(((1,1-dimethylethoxy)-carbonyl)-1H-imidazol-4-yl)methyl]-4-(methylsulfonyl)-3-(phenylmethyl)-1H-1,4-benzodiazepine (prepared from Example 224 as described for Compound A of Example 225) in 2 mL of methylene chloride, at –78° C. and under argon, was added dropwise 59 µL (0.48 mmol) of methyl triflate. The reaction was allowed to warm to rt, during which time a white precipitate was obtained. Stirring was continued at rt for 3 hr, after which time 140 µL (0.8 mmol) of DIEA was added and stirring continued overnight at rt. The mixture, without workup, was subjected to flash chromatography on a 30 cc column of silica gel. Elution with 2% MeOH—CHCl3 afforded 122 mg (0.28 mmol, 74%) of a clear colorless oil which crystallized on standing. This material was converted to its hydrochloride by the addition of 0.28 mL of 1M HCl in ether to a methylene chloride solution (2 mL) of the free base. A white precipitate was obtained which on filtration afforded 90 mg of Example 235 as a white powder.

MS (M+H)+436

EXAMPLE 236

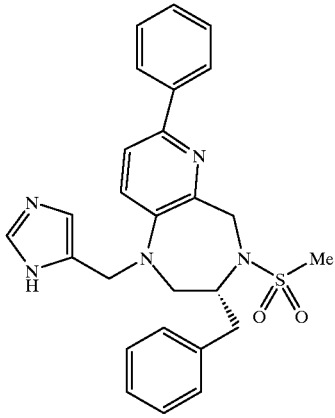

(R)-2,3,4,5-Tetrahydro-1-(1H-imidazol-4-ylmethyl)-4-(methylsulfonyl)-7-phenyl-3-(phenylmethyl)-1H-pyrido[3,2-e]-1,4-diazepine, monohydrochloride A. 2-Hydroxy-5-nitro-6-methylpyridine To a suspension of a 2:1 mixture of 2-amino-5-nitro-6-methylpyridine and 2-amino-3-nitro-6-methylpyridine (2.5 g, 16.3 mmol) in 15 mL of water at 0° C. was added concentrated sulfuric acid (5 mL), followed by a solution of NaNO2 (2.25 g, 32.6 mmol) in 5 mL of water dropwise over 90 minutes. The solution was stirred 5 hours as it warmed to room temperature, cooled to 0° C. and filtered. The solid was washed with water (2x) and dried under vacuum to afford 1.84 g of a >4:1 mixture (by HPLC) of Compound A and 2-hydroxy-3-nitro-6-methylpyridine (73%) as a tan solid.

B. 2-Chloro-5-nitro-6-methylpyridine

A mixture of Compound A, 2-hydroxy-3-nitro-6-methylpyridine (0.93 g, 6.05 mmol) and phosphorus pentachloride (48.9 g, 235 mmol) in toluene (10 mL) was heated at 92° C. for 16 hours and cooled to 0° C. Ice was added and the mixture was stirred and partitioned. The aqueous layer was washed with toluene and the combined organic phases were dried (magnesium sulfate), filtered and evaporated to afford 1.03 g of a 6:1 mixture of Compound B and 2-chloro-3-nitro-6-methylpyridine (100%) as a reddish brown crystalline semi-solid.

C. 2-Phenyl-5-nitro-6-methylpyridine

A mixture of Compound B and 2-chloro-3-nitro-6-methylpyridine (0.42 g, 2.40 mmol) in THF (10 mL) was degassed with nitrogen. Tetrakistriphenylphosphine palladium (28 mg, 0.024 mmol) was added and the mixture was stirred 30 minutes. 25 Phenylboronic acid (0.44 g, 3.6 mmol) and 2M Na$_2$CO$_3$ (1.8 mL) were added and the mixture was heated at 75° C. for 17 hours and stirred at room temperature for 48 hours. Methylene chloride was added and the mixture was filtered through celite and partitioned. The mixture was washed with saturated aqueous NaHCO$_3$, dried (magnesium sulfate), filtered and evaporated to afford 0.77 g of brown solid. Flash chromatography (silica, 10% ethyl acetate/hexanes) afforded 0.37 g of Compound C (72%) as an off white solid and 0.05 g of 2-phenyl-3-nitro-6-methylpyridine (10%) as an oil.

D. 2-Phenyl-5-amino-6-methylpyridine

To a suspension of Compound C (3.0 g, 14 mmol) in concentrated HCl (30 mL) was added tin chloride dihydrate (9.91 g, 44 mmol) in portions over 45 minutes. The solution was allowed to warm to room temperature over 2 hours, heated at 78° C. for 15 minutes, cooled to 0° C., neutralized with 4M NaOH and extracted with methylene chloride (3x). The combined organic phases were dried (magnesium sulfate), filtered and evaporated to afford 2.62 g of Compound D (100%) as a yellow oil which crystallized on standing.

E. 2-Phenyl-5-(phenylsulfonylamino)-6-methylpyridine

A mixture of 2-phenyl-5-amino-6-methylpyridine (2.29 g, 12.4 mmol) and benzenesulfonyl chloride (1.65 mL, 12.9 mmol) was heated at 88° C. for 15 hours. The mixture was cooled and the resulting glass was dissolved in methylene chloride/10% NaOH. The mixture was partitioned, the organic phase was washed with 10% NaOH and the combined aqueous phases were acidified with concentrated HCl and extracted with methylene chloride (2x). The combined organic phases were dried (magnesium sulfate), filtered and evaporated to afford 3.40 g of Compound D (85%) as a light yellow crystalline solid.

F. 2-Phenyl-5-(phenylsulfonylamino)-6-methylpyridine-N-oxide

To a suspension of Compound E (3.0 g, 9.24 mmol) in acetic acid (28 mL) was added 30% aqueous hydrogen peroxide (9.25 mL). The mixture was heated at 72° C. for 4 hours and at 62° C. for 22 hours. An additional 3 mL of H2O2 was added and the mixture was heated at 54° C. for 20 hours and poured onto ice. The mixture was allowed to stand overnight, 200 mL of water was added and the resulting solid was filtered, washed with water and ether and dried under vacuum to afford 1.43 g (46%) of Compound F as a yellow solid contaminated with Compound E. The combined water and ether washes were extracted with methylene chloride to afford 1.0 g of an approximate 4:1 mixture of Compound E and Compound F. MS (M+H)+ 341.1.

G. 2-Phenyl-5-(phenylsulfonylamino)-6-acetoxymethyl-pyridine

A solution of crude Compound F (0.50 g,<1.47 mmol) and acetic anhydride (2.5 mL) in acetic acid (5 mL) was heated at 90° C. for 4 hours, cooled, and poured onto ice. After standing overnight, the mixture was extracted twice with methylene chloride and the combined organic extracts were dried (MgSO4), filtered and evaporated to afford Compound G (0.60 g,>100%) as a yellow foamy gum.

H. 2-Phenyl-5-(phenylsulfonylamino)-6-hydroxymethyl-pyridine

A mixture of Compound G (0.60 g,<1.47 mmol) in 2M NaOH (2 mL) was heated at 50° C. for 2.25 hours and cooled to 0° C. Methylene chloride was added, followed by concentrated aqueous HCl until the solid dissolved. Solid Na2HPO4 was added until the aqueous phase was pH 7, and the mixture was partitioned. The aqueous phase was extracted with methylene chloride and the combined organic extracts were dried (MgSO4), filtered and evaporated. The residue was flash chromatographed on silica with 50% ethyl acetate/hexanes to afford 0.09 g of Compound F and 0.24 g of Compound H (48% from crude compound F) as a gum.

I. 2-Phenyl-5-(phenylsulfonylamino)-pyridine-6-carboxaldehyde

To a solution of crude Compound H (0.70 g, 2.06 mmol) in THF (10 mL) was added MnO2 (0.36 g, 4.11 mmol). The mixture was stirred at room temperature and additional MnO2 was added at the following times: 1 hour, 0.36 g; 2 hour, 0.36 g; 3 hour, 0.36 g; 7.5 hour, 0.72 g; 22.5 hour, 0.72 g; 32 hour, 0.72 g. After stirring for 32.5 hours, the mixture was filtered through celite, the pad was washed three times with celite and the filtrate was evaporated to afford 0.55 g of Compound 1 (79%) as an orange solid. MS (M+H)+339.0.

J. D-[N-(2-phenyl-5-(phenylsulfonylamino)-6-pyridinylmethyl)-phenylalanine], methyl ester A suspension of Compound 1(0.55 g, 1.62 mmol), D-phenylalanine methyl ester hydrocloride (1.05 g, 4.88 mmol), NaOAc (0.40 g, 4.88 mmol) and 10% Pd/C (50 mg) in 4 mL methanol/2 mL acetic acid was hydrogenated with a balloon for 18 hours and filtered through celite. The pad was rinsed twice with methanol and the filtrate was evaporated. The residue was partitioned between pH 7 phosphate buffer and methylene chloride. The aqueous phase was extracted with methylene chloride and the combined organic extracts were dried (MgSO4), filtered and evaporated to afford Compound J (1.21 g,>100%).

K. (R)-2,3,4,5-Tetrahydro-7-phenyl-3-(phenylmethyl)-1H-pyrido[3,2-e]-1,4-diazepin-2-one A mixture of Compound J (1.21 g,<1.62 mmol) and polyphosphoric acid (16 g) was heated at 100° C. for 5 hours. Ice and methylene chloride were added and the mixture was chilled, made basic with 4N NaOH and partitioned. The aqueous phase was washed twice with methylene chloride and the combined organic extracts were dried (MgSO4), filtered and evaporated. The residue was flash chromatographed on silica with 75% ethyl acetate/hexanes to afford 0.31 g (58% from Compound I) of Compound K as an off white solid. MS (M+H)+330.0.

L. (R)-2,3,4,5-Tetrahydro-4-(methylsulfonyl)-7-phenyl-3-(phenylmethyl)-1H-pyrido[3,2-e]-1,4-diazepin-2-one To a solution of Compound K (117 mg, 0.36 mmol) and TEA (0.06 mL, 0.43 mmol) in methylene chloride (3 mL) at 0° C. was added mesyl chloride (0.033 mL, 0.43 mmol). The solution was stirred at 0° C. for 30 minutes and at room temperature for 90 minutes. Additional TEA (0.06 mL) and mesyl chloride (0.032 mL) were added and the solution was stirred for 1 hour and partitioned between aqueous NaHCO$_3$ and methylene chloride containing a little isopropanol (<10%). The aqueous layer was washed with methylene chloride and the combined organic extracts were dried (MgSO4), filtered and evaporated to afford 145 mg of Compound L as a solid (100%). MS (M+H)+408.1.

M. (R)-2,3,4,5-Tetrahydro-4-(methylsulfonyl)-7-phenyl-3-(phenylmethyl)-1H-pyrido[3,2-e]-1,4-diazepine To a solution of Compound L (53 mg, 0.13 mmol) in THF (2 mL) at 0° C. was added 1M borane in THF (0.39 mL). The solution was allowed to warm to room temperature overnight, methanol was added and the mixture was evaporated. The residue was dissolved in a small amount of 10% HCl and methanol, warmed until a clear solution was obtained, and the methanol was evaporated. Methylene chloride was added followed by solid K2CO3 until the aqueous layer was pH 11. The mixture was partitioned and the aqueous layer was washed with methylene chloride and the combined organic extracts were dried (MgSO4), filtered and evaporated. The residue was subjected to preparative TLC on silica with 50% ethyl acetate/hexanes. The main mid Rf band was cut and extracted with methylene chloride containing a few drops of methanol to afford 25 mg of Compound M as a light yellow foam (49%).

N. (R)-2,3,4,5-Tetrahydro-1-(1H-imidazol-4-ylmethyl)-4-(methylsulfonyl)-7-phenyl-3-(phenylmethyl)-1H-pyrido[3,2-e]-1,4-diazepine, monohydrochloride To a solution of Compound M (24 mg, 0.06 mmol) and imidazole-4-carboxaldehyde (17 mg, 0.18 mmol) in dichloroethane (1 mL)/ acetic acid (0.5 mL) was added sodium triacetoxyborohydride (32 mg, 0.15 mmol). The solution was stirred 1 hour and additional aldehyde (16 mg) and hydride (16 mg) were added The solution was stirred 45 minutes and additional hydride (16 mg) was added. NH4OH (0.5 mL) was added, followed by ethyl acetate and aqueous NaHCO3. The mixture was partitioned and the aqueous layer was washed with ethyl acetate and the combined organic extracts were washed with saturated NaHCO3 and brine, dried (MgSO4), filtered and evaporated to afford the free base of Compound N (25 mg, 89%) as a white foamy gum. This material was dissolved in methylene chloride and the solution filtered through glass wool and evaporated. The residue was dissolved in methanol, 0.5 mL of 1M HCl in ether was added and the mixture was evaporated.

The residue was evaporated from methanol, dissolved in 2 mL of methanol and the solution filtered through glass wool. The filtrate was evaporated and the residue dissolved in 0.5 mL of methanol. Ether (10 mL) was added and the resulting precipitate was filtered, rinsed with ether and dried to afford Example 236 (24 mg) as a yellow solid.

MS (M+H)+474.3.

$^1$H (CD$_3$OD) d 2.18, 3H, s; 2.76–2.92, 2H, m; 3.65, 1H, dd (J=4.7, 15.2 Hz); 3.98, 1H, dd (J=10.6,15.2 Hz); 4.75, 1H, m; 5.18, 1H, d (J=18.8 Hz); 7.26–7.40, 5H, m; 7.58–7.61, 4H, m; 7.76–7.90 4H, m.

EXAMPLE 237

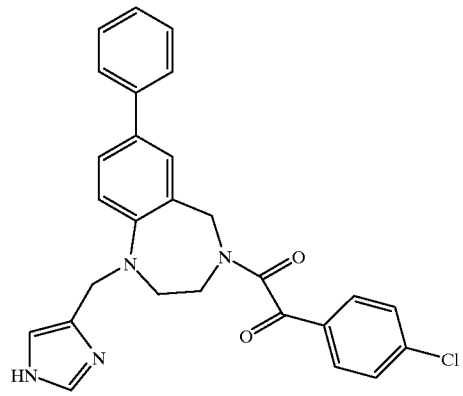

4-[2-(4-Chlorophenyl)-1,2-dioxoethyl]-2,3,4,5-tetrahydro-1-(1H-imidazol-4-ylmethyl)-7-phenyl-1H-1,4-benzodiazepine, hydrochloride A solution of HOAt (0.013 gm, 0.092 mmol) in DMF (0.5 mL) was added to 2-(4-chlorophenyl)-2-oxo-acetic acid (0.01 7 g, 0.092 mmol). Solutions in DMF of Compound B of Example 33 (0.2M, 0.46 mL, 0.092 mmol) and DIC (0.2M, 0.014 mL, 0.092 mmol) were added to the mixture, which was stirred at room temperature for 16 h. The mixture was purified by ion exchange chromatography on a solid phase extraction cartridge using the following protocol:
1) Conditioned a Varian solid phase extraction column (1.5 g, SCX cation exchange) with 10 mL of MeOH/CH$_2$Cl$_2$
2) Loaded mixture onto column using a 10 mL syringe to pressurize the system
3) Wash column with 3×7.5 mL MeOH/CH$_2$Cl$_2$ (1:1)
4) Wash the column with 1×7.5 mL of 0.01N ammonia in MeOH
5) Eluted column with 7.5 mL of 1.0N ammonia in MeOH and collect into a tared receiving tube.

The product was concentrated on a Savant Speed Vac (approx. 2mm Hg for 20 hr).

The residue was dissolved in CH$_3$CN (2 mL), 1N HCl (0.10 mL) and water (1 mL) and lyophilized to afford Example 237 (0.042 gm, 86%) as a white lyophilate.

MS: (M+H)⁺471

Analysis calculated for $C_{27}H_{23}N_4O_2Cl \cdot 0.15\ CH_3CN \cdot 1.0\ HCl \cdot 0.84\ H_2O$. Calc'd: C, 61.40; H, 4.93; N, 10.88. Found: C, 61.41; H, 5.02; N, 11.28.

EXAMPLE 238

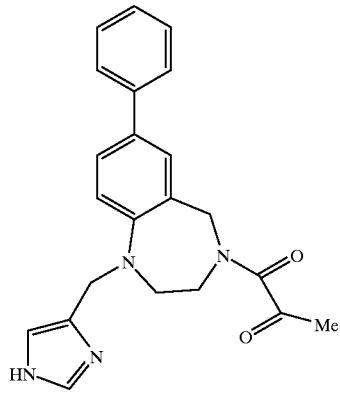

4-(1,2-Dioxopropyl)-2,3,4,5-tetrahydro-1-(1H-imidazol-4-ylmethyl)-7-phenyl-1H-1,4-benzodiazepine, hydrochloride Example 238 was prepared from pyruvic acid as described for Example 237.

MS: (M+H)⁺375

Analysis calculated for $C_{22}H_{22}N_2O_2 \cdot 1.0\ HCl \cdot 0.67\ H_2O$. Calc'd: C, 62.47; H, 5.80; N, 13.25. Found: C, 62.46; H, 5.59; N, 13.28.

EXAMPLE 239

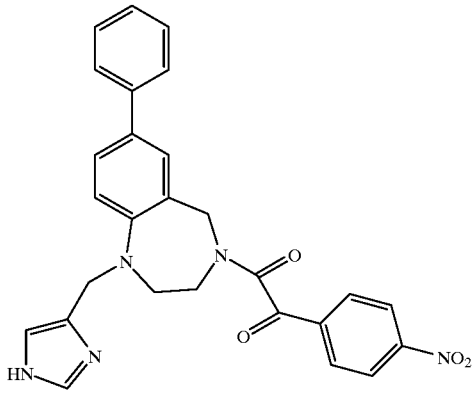

2,3,4,5-Tetrahydro-1-(1H-imidazol-4-yl methyl)-4-[2-(4-nitrophenyl)-1,2-dioxoethyl]-7-phenyl-1H-1,4-benzodiazepine, hydrochloride Example 239 was prepared from 4-nitrophenylpyruvic acid as described for Example 237.

MS: (M+H)⁺482

Analysis calculated for $C_{27}H_{23}N_5O_4 \cdot 1.0\ HCl \cdot 0.38\ H_2O$. Calc'd: C, 61.79; H, 4.76; N, 13.34. Found: C, 61.80; H, 4.72; N, 13.54.

EXAMPLE 240

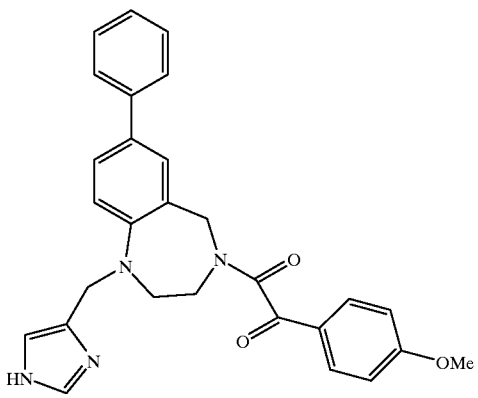

2,3,4,5-Tetrahydro-1-(1H-imidazol-4-ylmethyl)-4-[2-(4-methoxyphenyl)-1,2-dioxoethyl]-1-phenyl-1H-1,4-benzodiazepine, hydrochloride Example 240 was prepared from 4-methoxyphenylpyruvic acid as described for Example 237.

MS: (M+H)⁺467

Analysis calculated for $C_{28}H_{26}N_4O_3 \cdot 1.0\ HCl \cdot 0.79\ H_2O$. Calc'd: C, 65.02; H, 5.57; N, 10.83. Found: C, 65.01; H, 5.66; N, 10.75.

EXAMPLE 241

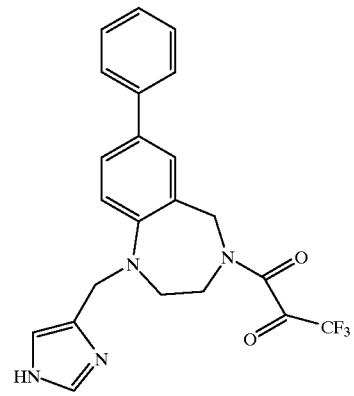

2,3,4,5-Tetrahydro-1-(1H-imidazol-4-ylmethyl)-7-phenyl-4-(3,3,3-trifluoro-1,2-dioxopropyl)-1H-1,4-benzodiazepine, trifluoroacetate Example 241 was prepared from trifluoropyruvic acid as described for Example 237, with methylene chloride as cosolvent. Purification was by reverse phase preparative HPLC (aqueous methanol, 0.1% TFA).

MS: (M+H)⁺429

Analysis calculated for $C_{22}H_{19}N_4O_2F_3 \cdot 1.5\ TFA \cdot 0.81\ H_2O$. Calc'd: C, 48.90; H, 3.63; N, 9.12. Found: C, 48.90; H, 3.58; N, 9.13.

EXAMPLE 242

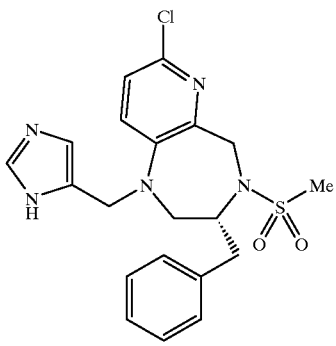

(R)-7-Chloro-2,3,4,5-tetrahydro-1-[(1H-imidazol-4-yl)-methyl]-4-(methylsulfonyl)-3-(phenylmethyl)-1H-pyrido[3,2-e]-1,4-diazepine, hydrochloride A. 2-Chloro-5-(phenylsulfonylamino)-6-methylpyridine Compound A was prepared from Compound B of Example 236 as described for Compound D of Example 236 and Compound E of Example 236.

B. 2-Chloro-5-(phenylsulfonylamino)-6-methylpyridine-N-oxide

To a suspension of Compound A (3.0 g, 10.6 mmol) in TFA (12.5 mL) was added 30% aqueous hydrogen peroxide (2.2 mL). The mixture was heated at reflux for 80 minutes. An additional 2.5 mL of H2O2 was added and the mixture was heated at reflux for 95 minutes. An additional 2.5 mL of H2O2 was added and the mixture was heated at reflux for 1 hour and poured onto ice. The mixture was allowed to stand overnight and was filtered. The solid was washed with water and dissolved in 10% isopropanol/methylene chloride and the solution dried to afford 2.44 g of Compound B contaminated with Compound A. An additional 0.33 g of impure compound B later precipitated from the aqueous filtrate for a combined yield of 2.77 g (88%). (M+H)+298.9.

C. 2-Chloro-5-(phenylsulfonylamino)-6-hydroxymethyl-pyridine

Compound C was prepared as a gum from Compound B as described for Compounds G and H of Example 236. (M+H)+299.0.

D. 2-Chloro-5-(phenylsulfonylamino)-pyridine-6-carboxaldehyde

To a solution of crude Compound C (2.45 g, 8.20 mmol) in THF (20 mL) was added MnO2 (1.43 g, 16.4 mmol). The mixture was stirred at room temperature and additional MnO2 was added at the following times: 1 hour, 2.86 g; 28 hour, 2.86 g. After stirring for 21 hours, the mixture was directly flash chromatographed (25% ethyl acetate/hexanes) to afford 0.82 g of crude compound D.

E. D-[N-(2-chloro-5-(phenylsulfonylamino)-6-pyridinylmethyl)-phenylalanine], methyl ester To a solution of crude Compound D (0.81 g, 2.73 mmol), D-phenylalanine methyl ester hydrochloride (0.88 g, 4.10 mmol) and NaOAc (0.67 g, 8.20 mmol) in 15 mL methylene chloride/3 mL acetic acid was added sodium triacetoxyborohydride (0.87 g, 4.10 mmol) in aliquots over 90 minutes. The mixture was stirred for 90 minutes and partitioned between pH 7 phosphate buffer and methylene chloride. The aqueous phase was extracted with methylene chloride and the combined organic extracts were dried (MgSO4), filtered and evaporated to afford Compound E (1.62 g,>100%) as an orange gum.

F. (R)-2,3,4,5-Tetrahydro-1-(1H-imidazol-4-ylmethyl)-4-(methylsulfonyl)-7-chloro-3-(phenylmethyl)-1H-pyrido[3,2-e]-1,4-diazepine, monohydrochloride Example 242 was prepared from Compound E as described in the following sequence: Compound K of Example 236, Compound L of Example 236, Compound M of Example 236, Compound N of Example 236. The HCl salt was precipitated from isopropanol with ether to afford Example 242 as a very hygroscopic foam. MS (M+H)+ 432.1.

$^{13}$C (CDCl3, free base) d 37.96, 39.60, 47.97, 48.34, 55.73, 59.27, 118.66, 122.59, 124.89, 126.91, 128.64, 129.16, 135.59, 137.15, 138.88, 139.63, 144.10, 144.54, 182.64 ppm.

EXAMPLE 243

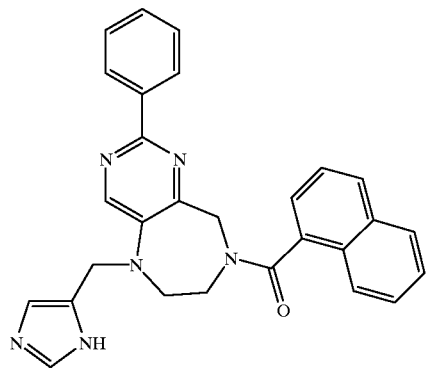

6,7,8,9-Tetrahydro-5-(1H-imidazol-4-ylmethyl)-8-(1-naphthalenylcarbonyl)-2-phenyl-5H-pyrimido-[5,4-e][1,4]diazepine, monohydrochloride A. 2-Phenyl-5-bromo-4-pyrimidine carboxylic acid To a solution of mucobromic acid (16 g, 62 mmol) in 800 ml of water was added benzamidine hydrochloride hydrate (26 g, 166 mmol) and Triton B (100 ml, 40% in water). The solution was stirred 23 hours, filtered of a small amount of dark solid, and acidified with concentrated HCl. The gummy precipitate was filtered and recrystallized from 4:1 ethanol-:water to afford 5.87 g (34%) of Compound A as a brown crystalline solid. Concentration of the mother liquor afforded an additional 1.72 g (44% total yield).

B. 2-Phenyl-5-(2-aminoethylamino)-4-pyrimidine carboxylic acid

A mixture of 3.0 g (10.8 mmol) of Compound A and 300 mg of copper sulfate in 15 20 ml each of water and ethylenediamine was heated at 100° C. for 3 hr. The dark solution was evaporated to dryness and the semi-solid residue diluted with water to yield a voluminous white precipitate which was filtered, washed well with water, and air dried overnight to afford 2.45 g of Compound B as a light tan solid. The filtrate was evaporated to dryness and the residue diluted with water. Standing at rt afforded an additional 0.6 g of Compound B. The materials were combined and dried overnight at 60° C. under vacuum to give 2.85 g (approx 100%) of Compound B as a pale yellow solid.

C. 6,7,8,9-Tetrahydro-2-phenyl-5H-pyrimido-[5,4-e][1,4]-diazepin-9-one

To a suspension of 2.8 g (10.8 mmol) of Compound B in 100 ml of pyridine was added 3.1 g (16.3 mmol) of EDC and 2.2 g (16.3 mmol) of HOBT and the slurry was stirred at rt, under argon, for 36 hr. The resulting hazy solution was evaporated to dryness and the semi-solid residue diluted with 10% i-propanol:water and washed with brine (2×). A bright yellow precipitate formed in the aqueous layer during the washing. Filtration of this material afforded 1.9 g of crude Compound C. This material was suspended into methanol and heated on the steam bath. The remaining insolubles were removed by filtration and the filter cake again extracted with hot methanol. The combined filtrates were evaporated to dryness to afford 1.53 g (59%) of Compound C as a pale yellow powder.

D. 6,7,8,9-Tetrahydro-2-phenyl-5H-pyrimido-[5,4-e][1,4]-diazepine

To a stirred solution of 100 mg (0.42 mmol) of Compound C in 2 ml of glyme was added 85 mg (2.1 mmol) of lithium aluminum hydride and the reaction heated at reflux for 18 hr. To the reaction was added 0.5 ml of pyridine and an additional 80 mg of LAH and heating continued at 85° C. for an additional 18 hr. The mixture was quenched by the addition of 5 ml of ethyl acetate, followed by 0.5 ml of conc $NH_4OH$. The resulting suspension was filtered and the filter cake washed well with ethyl acetate. The filtrate was evaporated to dryness and the resulting crude product used in the subsequent reaction without further purification. This material may also be flash chromatographed on silica with 10% methanol:ethyl acetate to afford pure Compound D as an orange crystalline solid.

E. 6,7,8,9-Tetrahydro-8-(1-naphthalenylcarbonyl)-2-phenyl-5H-pyrimido-[5,4-e][1,4]diazepine To a solution of 80 mg (assumed 0.35 mmol) of crude Compound D in 3 ml of methylene chloride and 3 ml of 1N sodium hydroxide was added 60 μl (0.4 mmol) of 1-naphthoyl chloride. The reaction was stirred at 0° C. for 1 hr. The organic layer was separated, washed with sat. ammonium chloride, dried (MgSO4) and evaporated. The residue was subjected to flash chromatography on silica gel. Elution with ethyl acetate-hexane (3:1) afforded 40 mg (25% from Compound C) of Compound E as a foam.

F. 6,7,8,9-Tetrahydro-5-(1H-imidazol-4-ylmethyl)-8-(1-naphthalenylcarbonyl)-2-phenyl-5H-pyrimido-[5,4-e][1,4]diazepine, monohydrochloride To a solution of 23 mg (0.062 mmol) of Compound E in 1 ml of methylene chloride and 0.2 ml of acetic acid was added 10 mg (1 mmol) of 4-formyl imidazole. The reaction was allowed to stir for 15 min and 21 mg (1 mmol) of sodium triacetoxyborohydride was added. Additional 10 mg portions of the imidazole and 21 mg portions of the hydride were added as above after 1,2,3 and 4 hr of stirring. Stirring was continued overnight. The reaction was diluted with methanol and, without further workup, subjected to preparative HPLC on a YMC ODS-A S10 column with gradient elution from 0–100% solvent B (A: 10% MeOH—H2O+ 0.1% TFA, B: 10% H2O—MeOH+0.1% TFA). The appropriate fractions were combined and evaporated. The residue was converted to the hydrochloride salt by dilution with methanolic HCl and removal of solvent to give 31 mg of yellow solid. This material was dissolved into minimal methanol and precipitated by the dropwise addition of ether to afford 12 mg (39%) of pure Example 243 as a yellow powder.

MS (M+H)$^+$461.

$^1$H NMR (CD$_3$OD): d 3.69 (2H, bs), 3.90 (2H, m), 4.20 (1H, m), 4.45 (1H, m), 4.70 (1H, m), 4.82 (1H, m), 5.49 (1H, m), 7.32–8.30 (11 H, m), 8.43 (1H, s), 8.60 (1H, s), 8.95 (1H, m), 9.11 (1H, s).

EXAMPLE 244

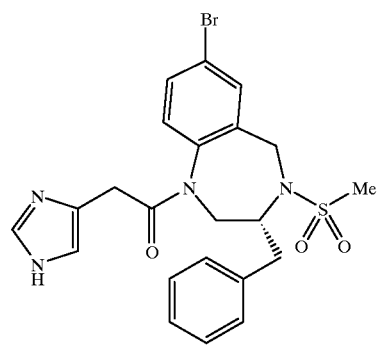

(R)-7-Bromo-2,3,4,5-tetrahydro-i-(1H-imidazol-4-ylacetyl)-4-(methylsulfonyl)-3-(phenylmethyl)-1H-1,4-benzodiazepine, monohydrochloride A. (R)-7-Bromo-2,3,4,5-tetrahydro-4-(1,1-dimethylethoxycarbonyl)-3-(phenylmethyl)-1H-1,4-benzodiazepine To a solution of 250 mg (0.79 mmol) of Compound B of Example 224 in 5 ml of methylene chloride, at rt and under argon, was added 192 mg (0.88 mmol) of BOC anhydride as a solution in 1 ml of methylene chloride. After 1 hr, an additional 100 mg of BOC anhydride was added and stirring continued an additional 0.5 hr. The reaction, without workup, was subjected to flash chromatography on a 50 cc column of silica gel. Elution with 20% EtOAc-hexane afforded 319 mg (96%) of Compound A as a white solid.

B. (R)-7-Bromo-2,3,4,5-tetrahydro-1-(1-triphenylmethyl-imidazol-4-ylacetyl)-4-(1,1-dimethylethoxycarbonyl)-3-(phenylmethyl)-1H-1,4-benzodiazepine To a suspension of 2.2 g (6 mmol) of 1-triphenylmethyl-4-imidazolyl-acetic acid in 50 ml of THF, at rt and under argon, was added 836 μl (6 mmol) of triethylamine. The resulting cloudy solution was cooled to −30° C. and 839 μl (6.6 mmoles) of i-butylchloroformate was added dropwise. After stirring an additional 0.5 hr at −30° C., a solution of 500 mg (1.2 mmoles) of Compound A in 10 ml of THF was added dropwise. The reaction was allowed to warm to rt over three hours and stirring was continued overnight. The resulting black reaction was diluted with ethyl acetate and washed with brine (2×), dried (MgSO$_4$) and the solvent removed to yield a black foam residue which was subjected to flash chromatography on silica gel. Elution with 25% ethyl acetate-hexane afforded 376 mg (40%) of Compound B as a gray solid foam, as well as 294 mg of Compound A.

C. (R)-7-Bromo-2,3,4,5-tetrahydro-1-(1-triphenylmethyl-imidazol-4-ylacetyl)-3-(phenylmethyl)-1H-1,4-benzodiazepine, hydrochloride A solution of 370 mg (0.48 mmol) of Compound B in 2 ml of 1M HCl in acetic acid was stirred at rt for 0.5 hr. The reaction was evaporated to dryness at low temperature and the residue diluted with ethyl acetate. Filtration of the resulting solid afforded 280 mg (83%) of Compound C.

D. (R)-7-Bromo-2,3,4,5-tetrahydro-1-(1-triphenylmethyl-imidazol-4-ylacetyl)-4-(methylsulfonyl)-3-(phenylmethyl)-1H-1,4-benzodiazepine To a solution of 280 mg (0.4 mmol) of Compound C in 3 ml of methylene chloride, at rt and under argon, was added 167 μl (1.2 mmoles) of triethylamine, followed by 46 μl (0.6 mmole) of methanesulfonyl chloride. After stirring 0.5 hr, an additional 167 μl of triethylamine and 46 μl methanesulfonyl chloride was added and stirring continued for an additional 0.5 hr. The solution, without workup, was subjected to flash chromatography on a 50 cc column of silica gel. Elution with 50% ethyl acetate-hexane afforded 165 mg (55%) of Compound D as a solid white foam.

E. (R)-7-Bromo-2,3,4,5-tetrahydro-1-(1H-imidazol-4-ylacetyl)-4-(methylsulfonyl)-3-(phenylmethyl)-1H-1,4-benzodiazepine, monohydrochloride To a solution of 80 mg (0.11 mmol) of Compound D in 2 ml of methylene chloride was added 0.5 ml of triethylsilane and 1 ml of TFA and the solution stirred at rt, under argon, for 3 hr. The reaction was evaporated to dryness to yield a white solid residue which was diluted with ether and stirred 0.5 hr. The solvent was decanted and the remaining insolubles washed twice more with ether. The remaining solid was taken into ethyl acetate and washed with sat NaHCO$_3$, brine, dried (MgSO$_4$) and the solvent removed at give 45 mg of solid white foam. This material was dissolved in minimal methylene chloride and 90 μl of 1M HCl in ether was added dropwise. The reaction was diluted with additional ether and the resulting slurry allowed to stand overnight under refrigeration. The solid was filtered under an atmosphere of nitrogen to afford 36 mg (62%) of Example 244 as a white powder.

MS (M+H)+503.

Analysis calculated for C$_{22}$H$_{23}$N$_4$O$_3$S•1.5 HCl. Calc'd: C, 47.35; H, 4.42; N, 10.04. Found: C, 47.55; H, 4.41; N, 9.92.

EXAMPLE 245

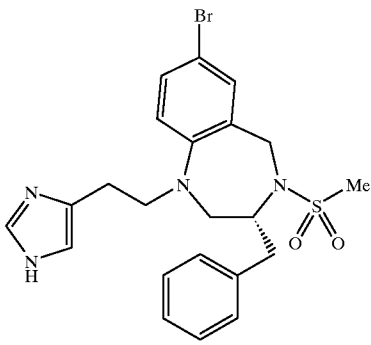

(R)-7-Bromo-2,3,4,5-tetrahydro-1-(2-1H-imidazol-4-ylethyl)-4-(methylsulfonyl)-3-(phenylmethyl)-1H-1,4-benzodiazepine, monohydrochloride To a solution of 80 mg (0.107 mmole) of the free base of Example 244 in 0.5 ml of THF, at rt and under argon, was added 1 ml of 1M borane in THF. The clear colorless solution was heated at reflux for 2 hr, 0.5 ml of conc. HCl was added and heating continued for an additional 2 hr at 65° C. The reaction was diluted with water and washed twice with ethyl acetate. The combined organic layers were backwashed once with brine, dried and the solvent removed to afford a clear oil residue which was subjected to flash chromatography on a 30 cc column of silica gel. Elution with CHCl$_3$:MeOH:NH$_4$OH (95:5:0.5) afforded 112 mg of an oil. This material was diluted with 0.5 ml conc. HCl and again heated at 80° C. for 2 hr. After cooling to rt, the reaction was diluted with water and extracted twice with ethyl acetate. The combined organic layers were dried (MgSO$_4$), and the solvent removed to give 30 mg of residue. Trituration of this material with ether afforded a white solid which was dissolved in 0.2 ml of methanol and precipitated by the dropwise addition of ether. Filtration of the resulting solid afforded 12 mg (21%) of Example 245 as a white powder.

MS (M+H)+(high res): calc, 489.0957. Obs, 489.096.

$^{13}$C NMR (67.8 MHz, CD$_3$OD): 24.7, 39.2, 40.3, 47.3, 53.3, 58.1, 60.8, 113.3, 118.1, 118.8, 128.3, 130.1, 130.8, 131.0, 132.4, 134.0, 135.3, 139.8, 149.9 ppm.

EXAMPLE 246

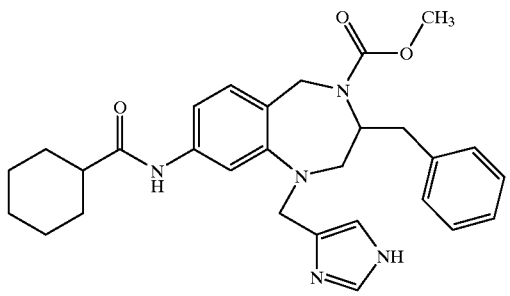

8-[(Cyclohexylcarbonyl)amino]-1,2,3,5-tetrahydro-1l-(1H-imidazol-4-ylmethyl)-3-(phenylmethyl)-4H-1,4-benzodiazepine-4-carboxylic acid, methyl ester, dihydrochloride A. 8-Amino-2,3,4,5-tetrahydro-1-(1H-imidazol-4-ylmethyl)-3-(phenylmethyl)-1H-1,4-benzodiazepine-4-carboxylic acid,1,1-dimethylethyl ester Compound A was prepared as a white solid from Compound D of Example 98 as described for Example 26. The crude free base was carried on. MS (M+H)$^+$=434.

B. 8-(Cyclohexylcarbonylamino)-2,3,4,5-tetrahydro-1-(1H-imidazol-4-ylmethyl)-3-(phenylmethyl)-1H-1,4-benzodiazepine-4-carboxylic acid,1,1-dimethylethyl ester Compound B was prepared as a white foamy solid from Compound A as described for Example 27. The crude free base was carried on. MS (M+H)$^+$=544.

C. N-[2,3,4,5-Tetrahydro-1-(1H-imidazol-4-ylmethyl)-3-(phenylmethyl)-1H-1,4-benzodiazepin-8-yl] cyclohexanamide Compound C was prepared as a light brown solid from Compound B by treatment with HCl/dioxane in methanol at rt. MS (M+H)$^+$=444.

D. 8-[(Cyclohexylcarbonyl)amino]-1,2,3,5-tetrahydro-1-(1H-imidazol-4-ylmethyl)-3-(phenylmethyl)-4H-1,4-benzodiazepine-4-carboxylic acid, methyl ester, dihydrochloride Methyl chloroformate (0.05 g, 0.09 mmol) was added to a stirred solution of Compound C (0.05 g, 0.09 mmol) in CH$_2$Cl$_2$ at rt, under argon. After stirring for 3 days the mixture was partitioned with CHCl$_3$ (5 mL) and NaHCO$_3$ (2 mL). The aqueous layer was extracted with CHCl$_3$ (2×10 mL). The combined organic layers were washed with NaHCO$_3$ and brine, dried over MgSO$_4$, filtered and concentrated. The residue was purified by preparative HPLC, with a gradient of 50–100% aqueous methanol containing 0.1% TFA and the HCl salt was formed by treatment with 1M HCl/ether.

MS (M+H)$^+$=502.

$^1$H NMR (CD$_3$OD): δ8.8 (s, 1H), 7.45–7.1 (m, 7.5H), 7.05 (m, 1H), 6.8 (m, 0.5H), 4.67–4.35 (m, 4H), 4.58 (s, 3H), 3.4–3.0 (m, 3H), 2.9 (m, 1H), 2.7 (m, 1H), 2.3 (m, 1H), 1.9–1.2 (m, 10H).

EXAMPLE 247

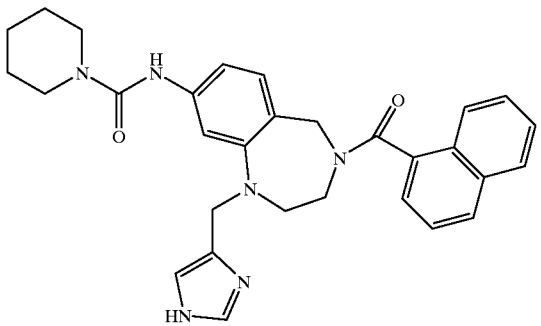

N-[2,3,4,5-Tetrahydro-1-(1H-imidazol-4-ylmethyl)-4-(1-naphthalenylcarbonyl)-1H-1,4-benzodiazepin-8-yl]-1-piperidinecarboxamide, dihydrochloride Carbonyidiimidazole (0.045 g, 0.137 mmol), was added to a solution of Example 26 (0.050 g, 0.125 mmol), and triethylamine (0.038 mL, 0.275 mmol) in dry methylene chloride (1 mL) at rt under argon. After stirring for 2 hr, piperidine (0.013 mL, 0.13 mmol) was added. After stirring for 15 hr, the reaction was diluted with NaHCO3 and CHCl3. The organic layer was washed with NaHCO$_3$, water, and brine (1×3 mL each), dried over MgSO4, filtered and concentrated. The product was purified by reverse phase HPLC with a gradient of 40–90% aquous methanol with 0.1% TFA and the HCl salt was formed by treatment with 1M HCl/ether to afford Example 247 (0.006 g, 10%).

MS (M+H)+509.

$^1$H NMR (CD$_3$OD): δ8.5 (d, 1H, J=19 Hz), 8.06–7.9 (m, 2H), 7.69–7.3 (m, 7H), 7.2 (d, 0.5H, J=7 Hz), 6.9 (d, 0.5H, J=7 Hz), 6.5 (d, 0.5 H, J=7 Hz), 5.89 (t, 0.5H), 4.6–3.88 (m, 4.5H), 3.6–3.3 (m, 6H), 3.18–2.85 (m, 1.5H), 1.65 –1.55 (m, 6H).

EXAMPLE 248

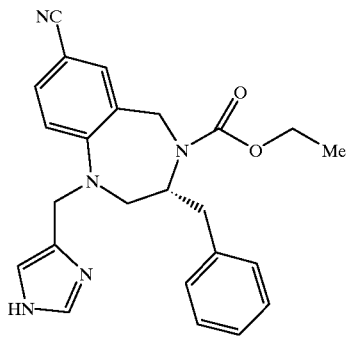

(R)-7-Cyano-1,2,3,5-tetrahydro-1-(1H-imidazol-4-ylmethyl)-3-(phenylmethyl)-4H-1,4-benzodiazepine-4-carboxylic acid, ethyl ester, hydrochloride A. (R)-7-Bromo-2,3,4,5-tetrahydro-3-(phenylmethyl)-1H-1,4-benzodiazepin-2,5-dione To a stirred solution of 5-bromoisatoic anhydride (150 g, 563 mmol) in anhydrous pyridine (1.5L) under argon was added D-phenylalanine methyl ester hydrochloride (127 g, 590 mmol) and 4-dimethylaminopyridine (2 g). The resulting solution was refluxed for 3 days and cooled to room temperature. The solvent was evaporated. The residue was dissolved in CH$_2$Cl$_2$ (3 liter) and the solution was washed with 10% HCl and brine, dried over anhydrous Na$_2$SO$_4$ and evaporated to give a foam which was suspended in Et$_2$O (1.0L). The mixture was stirred and CH$_2$Cl$_2$ (100 ml) was added to help break up the emulsion. After cooling 3 hr in an ice bath, the solid was filtered, washed with Et$_2$O and a small amount of CH$_2$Cl$_2$ and dried in high vacuum to give 152 g (78.4%) of Compound A.

$^3$C-NMR (DMSO-d$_6$) 33.31, 53.69, 115.94, 123.31, 126.43, 128.22, 129.39, 132.63, 134.97, 136.19, 137.76, 166.45, 171.11 ppm B. (R)-7-Bromo-2,3,4,5-tetrahydro-3-(phenylmethyl)-1H-1,4-benzodiazepine To a stirred and chilled (0°, ice bath) solution of Compound A (100 g, 290 mmol) in anhydrous THF (1.5L) under argon was added borane tetrahydrofuran complex (1.0M solution, 1450 ml, 1450 mmol). The resulting solution was gently refluxed overnight. The solution was cooled to 0° and MeOH was slowly added until foaming ceased. The solvent was evaporated to dryness. The residue was diluted with MeOH (900 ml), an aqueous solution of 25% HCl (180 ml) added and the mixture was gently refluxed under argon for 2 hr. The resulting solution was cooled to 0° in an ice bath, Et$_2$O (300ml) was slowly added and the mixture was stirred for 1 hr. The solid was filtered. The filtrate was evaporated and the residue and the solid were combined, rinsed with Et$_2$O (500 ml) and acetone (500 ml) and suspended in CH$_2$Cl$_2$ (2L) and water (1L). The pH of the slurry was adjusted to 11 with 3N NaOH. The CH$_2$Cl$_2$ layer was separated. The aqueous layer was saturated with NaCl and extracted with CH$_2$Cl$_2$. The combined CH$_2$Cl$_2$ extracts were washed with brine, dried over anhydrous Na$_2$SO$_4$ and evaporated to give 89 g (97% yield) of Compound B as light tan solid.

$^{13}$C-NMR (CDCl$_3$) 40.55, 52.19, 54.22, 61.74, 112.52, 120.25, 126.50, 128.60, 129.30, 130.13, 132.09, 133.96, 138.52, 148.13 ppm C. (R)-2,3,4,5-Tetrahydro-3-(phenylmethyl)-1H-1,4-benzodiazepine-7-carbonitrile To a stirred suspension of Compound B (60 g, 190 mmol) in anhydrous 1-methyl-2-pyrrolidinone (600 ml) under nitrogen was added copper(I) cyanide (51 g, 569 mmol). The mixture was heated to 200° for 3.5 hr. The mixture was slowly added to 15% ethylenediamine solution in water (1.5L) with vigorous stirring. After 1.0 hr stirring, the slurry was extracted with EtOAc (3×750ml). The EtOAC extracts were combined, washed with 10% NH$_4$OH (2×750ml) and brine, dried over anhydrous Na$_2$SO$_4$ and evaporated to give a black gum. This was passed through a pad of silica gel (E. Merck 230–400 mash, 1.2 kg) eluting with EtOAC to give 40 g (80%) of Compound C as a tan solid.

$^{13}$C-NMR (CD$_3$OD) 40,84, 49.23, 51.62, 51.71, 62.56, 101.42, 119.14, 120.99, 127.56, 129.66, 130.38, 132.71, 134.86, 139.82, 156.29 ppm D. (R)-7-Cyano-1,2,3,5-tetrahydro-1-(1H-imidazol-4-ylmethyl)-3-(phenylmethyl)-4H-1,4-benzodiazepine Compound D was prepared from Compound C by the following sequence: Compound C of Example 98, run in the absence of triethylamine and with purification by flash chromatography on silica with 4:1 hexanes:ethyl acetate; Compound D of Example 1; treatment with 4M HCl in 1:1 dioxane:ethyl acetate. MS (M+H)+344.

E. (R)-7-Cyano-1,2,3,5-tetrahydro-1-(1H-imidazol-4-ylmethyl)-3-(phenylmethyl)-4H-1,4-benzodiazepine-4-carboxylic acid, ethyl ester, hydrochloride Ethylchloroformate (0.023 mL, 0.24 mmol) was added to a solution of Compound D (0.10 g, 0.22 mmol) and DIPEA (0.16 mL, 0.9 mmol) in dry methylene chloride (1 mL) at 0° C. under argon. After stirring for 2.5 days the reaction was partitioned with NaHCO₃ (5 mL) and CHCl₃ (20 mL). The aqueous layer was extracted with CHCl₃ (2×10 mL). The combined organic layers were washed with NaHCO₃, water and brine, dried over MgSO₄, filtered and concentrated. The product was purified on a flash column eluting with EtOAc (200 mL) and 19/1 CHCl₃/CH₃OH (200 mL), treated with 1N NaOH to remove acylation on imidazole, and treated with HCl/ether to afford Example 248 (0.047 g, 52%).

MS (M+H)⁺=416.

¹H NMR (CD₃OD): d 8.9 (d, 1H, J=16 Hz), 7.48–7.12 (m, 8H), 6.9 (m, 1H), 5.0–4.4 (m, 5H), 4.8–3.7 (m, 3H), 3.4–3.2 (m, 2H), 2.89–2.7 (m, 2H), 1.03 (m, 3H).

EXAMPLE 249

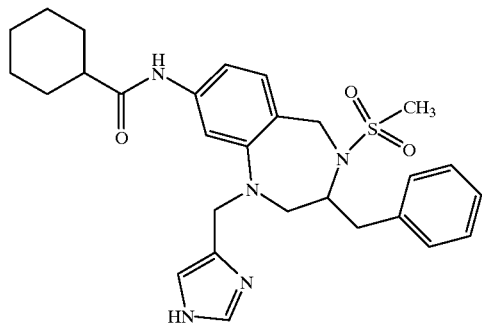

N-[2,3,4,5-Tetrahydro-1-(1H-imidazol-4-ylmethyl)-4-(methylsulfonyl)-3-(phenylmethyl)-1H-1,4-benzodiazepin-8-yl]cyclohexanecarboxamide, dihydrochloride Methanesulphonyl chloride (0.024 mL, 0.38 mmol) was added to a heterogeneous mixture of Compound C of Example 246 (0.030 g, 0.054 mmol), DMF (0.2 mL), and triethylamine (0.2 mL) in dry methylene chloride (0.3 mL) at rt under argon. After stirring for 2.5 days another eq of mesylchloride was added. After stirring for 3 hr the mixture was diluted with NaHCO3 and CHCl3, the layers were separated and the aqueous layer was extracted with chloroform (2×20 mL). The combined organic layers were washed with water (5 mL) and brine (5 mL), dried over MgSO4, filtered and concentrated. The residue was purified on a silica flash column eluting with CHCl3, and 9/1 CHCl3/CH3OH (200 mL each), to afford Example 249 (5 mg, 17%).

MS (M+H)⁺=522.

¹H NMR (CD₃OD): δ8.88 (s, 1H), 7.5 (m, 2H), 7.3 (m, 5H), 7.05 (d, 1H, J=8 Hz), 6.8 (d, 1H, J=8 Hz), 4.8–4.2 (m, 5H), 3.6 (m, 1H), 3.2 (m, 1H), 3.0 (m, 1H), 2.7 (m, 1H), 2.3 (m, 3H), 1.6–1.9 (m, 5H), 1.1–1.5 (m, 4H), 0.9 (m, 2H).

EXAMPLE 250

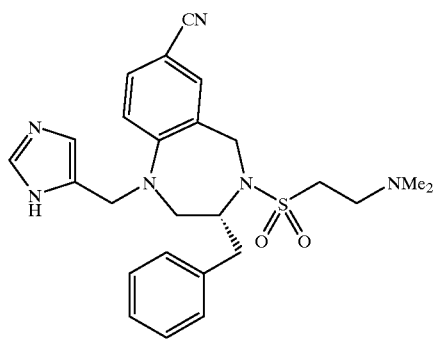

(R)-7-Cyano-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, dihydrochloride A. (R)-7-Cyano-4-(ethenylsulfonyl)-2,3,4,5-tetrahydro-1-(1H-imidazol-4-ylmethyl)-3-(phenylmethyl)-4H-1,4-benzodiazepine 2-Chloroethanesulfonyl chloride (1.85 g, 11.4 mmol) was added to a solution of Compound D of Example 248 (1.0 g, 3.79 mmol) and DIPEA (2.6 mL, 15.2 mmol) in dichloromethane (16 mL) at 0° C. under argon. After stirring for 16 hr, the reaction was diluted with chloroform and aq NaHCO₃. The layers were separated, the aqueous layer was reextracted twice with chloroform. The combined organic extract was washed twice with NaHCO₃ and brine, dried over MgSO₄, filtered and concentrated. The product was purified on a silica flash column eluting with 75% followed by 50%hexanes/ethyl acetate to afford Compound A (0.31 g, 23%). MS: (M+H)+=434.

B. (R)-7-Cyano-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, dihydrochloride Compound A (0.59 g, 1.36 mmol) in a 2M solution of dimethylamine in THF (15 mL, 30 mmol) was warmed in a sealed tube to 60° C. for 16 hours. The reaction was concentrated and the residue was purified by preparative HPLC (gradient of 30–90% aqueous methanol with 0.1% TFA). The purified TFA salt was converted to its HCl salt with HCl/ether and lyophilized to afford Example 250 (11 mg, 1.7%).

MS: (M+H)+=479.

1H NMR (CD₃OD): d 8.9 (s, 1H), 7.5–7.2 (m, 8H), 6.9 (m, 1H), 4.8–4.4 (m, 5H), 3.95 (m, 1H), 3.4–3.1 (m, 5H), 3.0–2.7 (m, 8H).

EXAMPLE 251

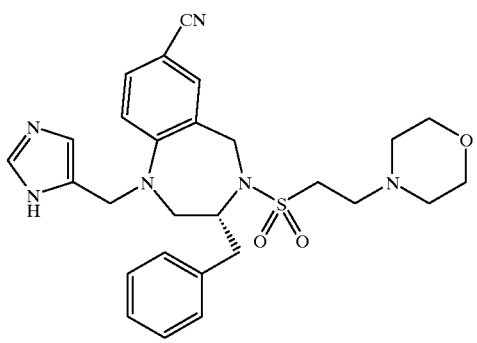

(R)-7-Cyano-2,3,4,5-tetrahydro-1-(1H-imidazol-4-ylmethyl)-4-[[2-(4-morpholinyl)ethyl]sulfonyl]-3-(phenylmethyl)-4H-1,4-benzodiazepine, dihydrochloride Example 251 was prepared from Compound A of Example 250 and morpholine as described for Example 250 (61%).

MS: (M+H)+=521.

1H NMR (CD$_3$OD): d 8.9 (s, 1H), 7.75–7.2 (m, 8H), 6.95 (m, 1H), 5.0–4.4 (m, 3H), 4.1–3.7 (m, 7H), 3.5–3.1 (m, 6H), 3.0 (m, 3H), 2.85 (m, 1H), 2.55 (m, 1H).

EXAMPLE 252

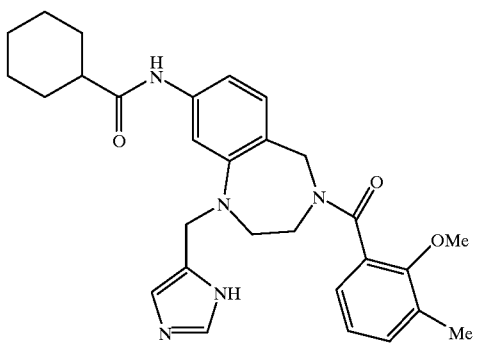

N-[2,3,4,5-Tetrahydro-1-(1H-imidazol-4-ylmethyl)-4-(2-methoxy-3-methylbenzoyl)-1H-1,4-benzodiazepin-8-yl] cyclohexanecarboxamide, dihydrochloride.

To a solution of Compound C of Example 246 (46 mg, 0.1 mmol) in DMF (1 mL) at rt under argon were added sequentially, 2-methoxy-3-methylbenzoic acid (20 mg, 0.12 mmol), DIPEA (0.09 mL, 0.5 mmol), HOAt (16 mg, 0.12 mmol) and EDC (23 mg, 0.12 mmol). After 18 hr, NaOH (1N, 1 mL) and MeOH (2 mL) were added. After 25 min, the volatiles were removed in vacuo and the residue was partitioned between chloroform (15 mL) and NaHCO$_3$ (10 mL). The organic layer was separated, dried and concentrated in vacuo. The residue was purified by silica gel chromatography eluting with 5% MeOH in chloroform to afford a white solid (42 mg, 83%) which was dissolved in MeOH (1 mL) and HCl in ether (1N, 2 mL) was added. The mixture was concentrated in vacuo to afford Example 252 as a yellow solid (50 mg). MS (M+H)+=502.3.

EXAMPLE 253

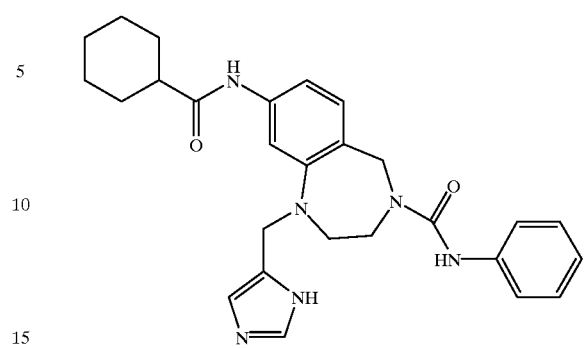

8-[(Cyclohexylcarbonyl)amino]-2,3,4,5-tetrahydro-1-(1H-imidazol-4-ylmethyl)-N-phenyl-1H-1,4-benzodiazepine-4-carboxamide, dihydrochloride.

To a solution of Compound C of Example 246 (46 mg, 0.1 mmol) in DMF (1 mL) at rt under argon were added sequentially, phenylisocyanate (13 µL, 0.12 mmol) and DIPEA (0.09 mL, 0.5 mmol). After 18 hr, NaOH (1N, 1 mL) and MeOH (2 mL) were added. After 25 min, the volatiles were removed in vacuo and the residue was partitioned between chloroform (15 mL) and water (10 mL). Some of the desired product that precipitated was filtered. The organic layer was separated and concentrated in vacuo. The residue was mixed with the solid obtained by filtration, dissolved in MeOH/TFA mixture and purified by reverse phase preparative HPLC eluting with 50%–90% aqueous MeOH containing 0.1% TFA. Appropriate fractions were collected and concentrated. The residue was treated with 1N HCl followed by concentration. After three treatments, the residue was dissolved in water and lyophilized to afford Example 253 as a yellow solid (30 mg, 55%). MS (M+H)+= 473.3.

EXAMPLE 254

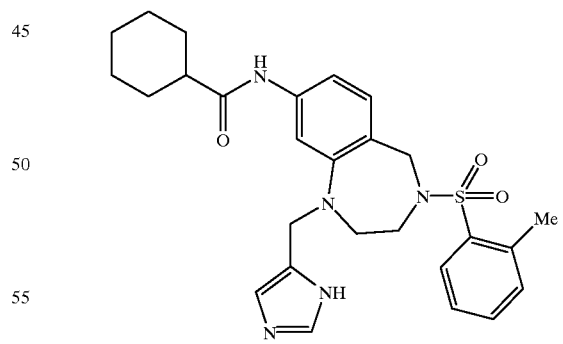

N-[2,3,4,5-Tetrahydro-1-(1H-imidazol-4-ylmethyl)-4-[(2-methylphenyl)sulfonyl]-1H-1,4-benzodiazepin-8-yl] cyclohexanamide, dihydrochloride.

Example 254 was prepared as a yellow solid from Compound C of Example 246 and 2-methylbenzenesulfonyl chloride as described for Example 253, except that the quenched, evaporated reaction mixture was directly purified by preparative HPLC (29%). MS (M+H)+=508.2.

EXAMPLE 255

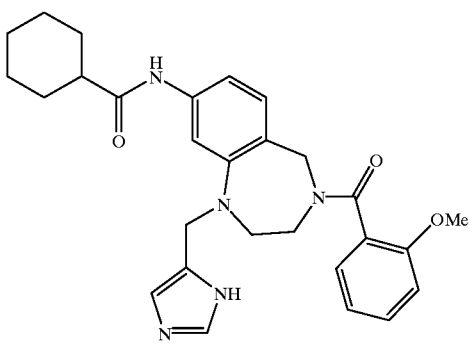

N-[2,3,4,5-Tetrahydro-1-(1H-imidazol-4-ylmethyl)-4-[(2-methoxyphenyl)carbonyl]-1H-1,4-benzodiazepin-8-yl]cyclohexanamide, dihydrochloride.

Example 255 was prepared as a pale yellow solid from Compound C of Example 246 and 2-methoxylbenzoic acid as described for Example 252. MS (M+H)$^+$=488.3.

EXAMPLE 256

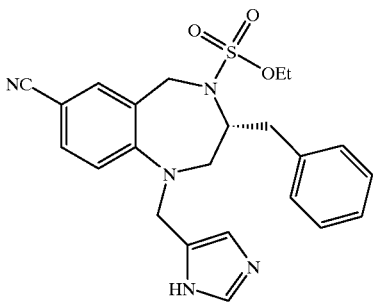

(R)-7-Cyano-1,2,3,5-tetrahydro-1-(1H-imidazol-4-ylmethyl)-3-(phenylmethyl)-4H-1,4-benzodiazepine-4-sulfonic acid, ethyl ester, hydrochloride.

A. (R)-7-Cyano-1,2,3,5-tetrahydro-3-(phenylmethyl)-4H-1,4-benzodiazepine-4-sulfonic acid, ethyl ester Ethyl chlorosulfonate (0.49 g, 3.41 mmol) was added to a solution of Compound C of Example 248 (0.3 g, 1.13 mmol) and DIPEA (0.78 mL, 4.55 mmol) in dichloromethane (8 mL) at 0° C. under argon. After stirring for 16 hr as it warmed to rt, the mixture was diluted with chloroform and NaHCO$_3$. The layers were separated and the aqueous layer was extracted with chloroform. The combined organic extracts were washed with NaHCO$_3$, water, 1N HCl and twice with brine, dried over MgSO$_4$, filtered and concentrated, to afford Compound A (0.54 g, 13 %). MS (M-H)-=370.

B. (R)-7-Cyano-1,2,3,5-tetrahydro-1-(1H-imidazol-4-ylmethyl)-3-(phenylmethyl)-4H-1,4-benzodiazepine-4-sulfonic acid, ethyl ester, hydrochloride.

Example 256 was prepared from Compound A as described for Compound D of Example 1, using dichloroethane and 3A sieves. Purification by preparative HPLC followed by conversion to the HCl salt and lyophilization afforded Example 256. MS (M+H)+=535.

$^1$HNMR (400 MHz, CD$_3$OD): d 8.9 (s, 1H), 7.5–7.2 (m, 8H), 6.9 (d, 1H, J=8 Hz), 5–4.4 (m, 4H), 4.3 (m, 1H), 4–3.2 (m, 4H), 3.0 (m, 1H), 2.8 (m, 1H), 1.05 (t, 3H).

EXAMPLE 257

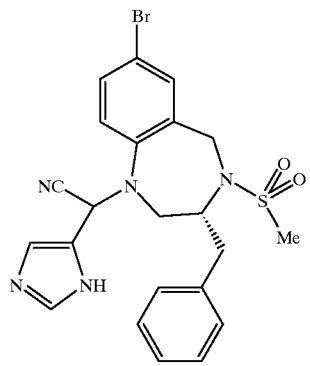

(3R)-7-Bromo-1-[cyano(1H-imidazol-4-yl)methyl]-2,3,4,5-tetrahydro-4-(methylsulfonyl)-3-(phenylmethyl)-1H-1,4-benzodiazepine, monohydrochloride.

To a stirred solution of Compound C of Example 224 (390 mg, 1.0 mmol) in a mixture of acetonitrile, methanol and acetic acid (3 mL, 1:1:1) was added 4-formylimidazole (100 mg, 1.04 mmol) followed by sodium cyanide (55 mg, 1.12 mmol). The mixture was stirred at room temperature for 2 days, quenched with saturated potassium carbonate (2 mL) and partitioned between ethyl acetate and 1N NH4OH solution. The organic layer was separated and washed with brine, dried, and concentrated to give a solid (400 mg, 80%). A portion was converted to its HCl salt by dissoving in methanol, addition of 1N HCl in ether, and removal of the solvent to afford Example 257. TLC Rf=0.50 (ethyl acetate, two spots) MS (M+H)$^+$500

EXAMPLE 258

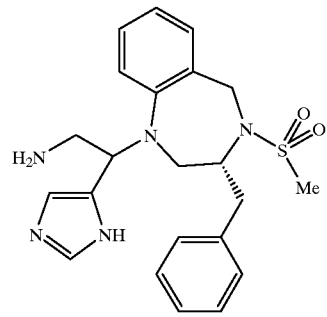

(3R)-1-[2-Amino-1-(1H-imidazol-4-yl)ethyl]-2,3,4,5-tetrahydro-4-(methylsulfonyl)-3-(phenylmethyl)-1H-1,4-benzodiazepine, dihydrochloride.

To a stirred suspension of lithium aluminium hydride (95 mg, 2.5 mmol) in ether under argon at room temperature, was added a solution of the free base of Example 257 (250 mg, 0.5 mmol) in anhydrous THF. The mixture was stirred at room temperature for 8 h and was diluted with THF, followed by ethyl acetate and ammonium hydroxide. The suspension was stirred at room temperature for 18 h and filtered. The filtrate was concentrated in vacuo and the residue was purified by chromatography (ethyl acetate/methanol/NH4OH, 10:1:0.1) on silica to give a semisolid (80 mg, 38%). A portion of it was converted to its HCl as described in Example 257. MS (M+H)$^+$426

EXAMPLE 259

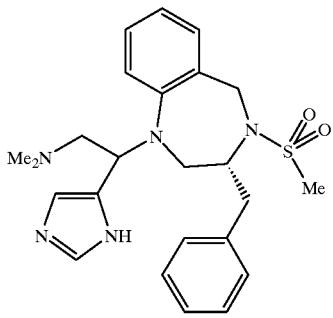

(3R)-1-[2-(Dimethylamino)-1-(1H-imidazol-4-yl)ethyl]-2,3,4,5-tetrahydro-4-(methylsulfonyl)-3-(phenylmethyl)-1H-1,4-benzodiazepine, dihydrochloride.

To a stirred solution of the free base of Example 258 (20 mg) in methanol (1 mL) and acetic acid (0.5 mL) with sodium acetate (100 mg), was added 30 μL of formaldehyde (37% aq. solution), followed by NaCNBH3 (15 mg). The mixture was stirred for 15 min, additional formaldehyde (30 μL) and NaCNBH3 were added and the mixture was stirred for 30 min and diluted with ethyl acetate and quenched with 3 mL of NH4OH solution. The organic layer was separated, washed with 1 N NH4OH solution and brine, dried, and concentrated. The residue was converted to its HCl salt as described in Example 257 (23 mg). MS (M+H)+454.

EXAMPLE 260

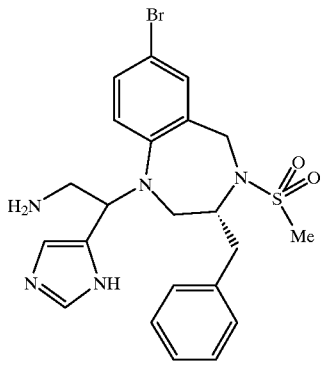

(3R)-1-[2-Amino-1-(1H-imidazol-4-yl)ethyl]-7-bromo-2,3,4,5-tetrahydro-4-(methylsulfonyl)-3-(phenylmethyl)-1H-1,4-benzodiazepine, dihydrochloride.

To a stirred solution of the free base of Example 258 (20 mg) in chloroform (1.5 mL) was added tetrabutylammonium perbromide. The mixture was stirred at room temperature for 10 min and quenched with an aqueous solution of NaS2O3. The organic layer was separated and washed with chloroform. The combined organic layers were dried over MgSO4 and concentrated in vacuo. The residue was purified by column chromatography (ethyl acetate/methanol/NH4OH; 10:1:0.1) to give a white solid (17 mg), which was converted to its hydrochloride salt as described in Example 257. MS (M+H)+504.

EXAMPLE 261

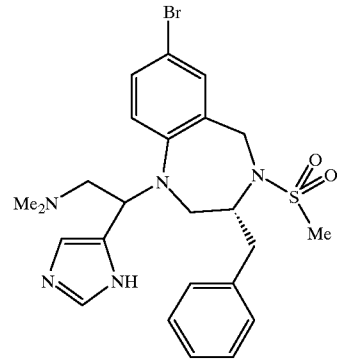

(3R)-1-[2-(Dimethylamino)-1-(1H-imidazol-4-yl)ethyl]-7-bromo-2,3,4,5-tetrahydro-4-(methylsulfonyl)-3-(phenylmethyl)-1H-1,4-benzodiazepine, dihydrochloride.

Example 261 was prepared from Example 260 as described for Example 259. MS (M+H)+532.

EXAMPLE 262

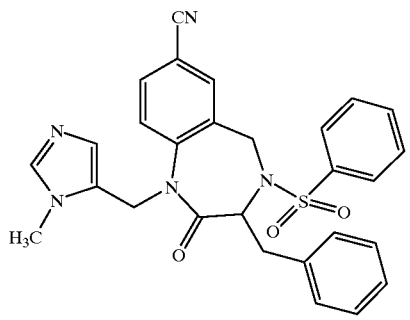

7-Cyano-1,3,4,5-tetrahydro-1-(1-methyl-1H-imidazol-5-ylmethyl)-3-(phenylmethyl)-4-(phenylsulfonyl)-2H-1,4-benzodiazepin-2-one, monohydrochloride.

A. (R)-N-(2-amino-5-bromo-phenylmethyl)-N-(methanesulfonyl)-phenylalanine methyl ester To a stirred solution of (R)-N-(2-aminophenylmethyl)-N-(methanesulfonyl)-phenylalanine methyl ester (prepared from D-phenylalanine methyl ester hydrochloride by reductive amination with 2-nitrobenzaldehyde followed by reaction with methanesulfonyl chloride in pyridine and reduction with stannnous chloride in ethyl acetate; 7.0 g, 16.5 mmol) in chloroform (75 mL) at room temperature was added tetrbutylammonium perbromide (7.1 g, 14.8 mmol) portionwise. The mixture was allowed to stir at room temperature for 30 min. Saturated NaHCO3 solution was added, followed by solid Na2S2O3. The mixture was stirred for 1 hour, concentrated in vacuo, and the residue was partitioned between water and 50% ethyl acetate/hexanes. The organic layer was separated, washed with water, brine, dried, concentrated in vacuo. The residue was purified by flash column chromatography to give Compound A as an oil (4.5 g, 54%). MS (M+H)+503. [a]D20:+29.60 (CHCl3, c=0.25)

B. 7-Cyano-1,3,4,5-tetrahydro-3-(phenylmethyl)-4-(phenylsulfonyl)-2H-1,4-benzodiazepin-2-one A solution of Compound A (2.05 g, 4.07 mmol) in N-methylpyrrolidinone (10 mL) in the presence of CuCN (1.1 g, 12.3 mmol) was heated at 195° C. for 4 h. The mixture was cooled to room temperature and partitioned between NH4OH solution and methylene chloride. The organic layer was separated and the aqueous layer was extracted with methylene chloride. The combined organic layers were washed with brine, dried, and concentrated. The residue was crystalized from methanol to give Compound B as a brown solid (1.1 g, 65%). MS(M+H)+416. mp 222–223° C.

C. 7-Cyano-1,3,4,5-tetrahydro-1-(1-triphenylmethyl-1H-imidazol-4-ylmethyl)-3-(phenylmethyl)-4-(phenylsulfonyl)-2H-1,4-benzodiazepin-2-one To a stirred solution of Compound B (310 mg, 0.74 mmol), N-tritylimidazole-4-methanol (510 mg, 1.5 mmol) and triphenylphosphine (450 mg, 1.72 mmol) in toluene and dichloroethane (20 mL/3 mL) at 60° C. under argon, was added diethylazodicarboxylate (300 uL, 1.9 mmol). The mixture was stirred at 60° C. for 1 h and partitioned between ethyl acetate and water. The organic layer was washed with water and brine, dried, concentrated in vacuo, and purified by flash column chromatography (ethyl acetate/hexanes 2:3) to give Compound C as an oil (450 mg, 82%). MS(M+H)+ 740.

D. 7-Cyano-1,3,4,5-tetrahydro-1-(1-methyl-1H-imidazol-5-ylmethyl)-3-(phenylmethyl)-4-(phenylsulfonyl)-2H-1,4-benzodiazepin-2-one, monohydrochloride To a stirred solution of Compound C (210 mg, 0.28 mmol) in THF at room temperature under argon, was added methyl trifluoromethylsulfonate (35 µL, 0.31 mmol). The mixture was stirred at room temperature for 10 min. Acetic acid (0.5 mL) and triethylsilane (0.25 mL) were added. The mixture was heated at 60° C. for 30 min and partitioned between 1 N NaOH and ethyl acetate. The organic layer was separated and washed with brine, dried and concentrated in vacuo. The residue was purified by flash column chromatography to give the free base of Compound D an oil (100 mg, 71%). This was dissolved in methanol, and 1N HCl solution in ether was added. The solvent was removed to give Example 262 as a solid. MS (M+H)+512. mp: 160° C.

EXAMPLE 263

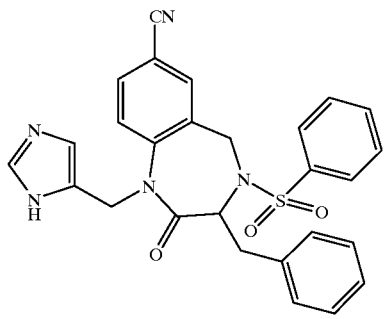

7-Cyano-1,3,4,5-tetrahydro-1-(1H-imidazol-4-ylmethyl)-3-(phenylmethyl)-4-(phenylsulfonyl)-2H-1,4-benzodiazepin-2-one, monohydrochloride.

To a stirred solution of Compound C of Example 262 (200 mg, 0.27 mmol) in CHCl3 10 at room temperature under argon, was added trifluoroacetic acid (1 mL), followed by triethylsilane (0.5 mL). The mixture was stirred at room temperature for 2 h and partitioned between 1 N NH4OH and ethyl acetate. The organic layer was separated and washed with brine, dried and concentrated in vacuo. The residue was purified by flash column chromagraphy (ethyl acetate, methanol; 95:5) to give the free base of Example 263 as an oil (110 mg, 82%). This was dissolved in methanol, and 1N HCl solution in ether was added. The solvent was removed to give Example 263 as a solid. MS (M+H)+498. mp: 195° C.

EXAMPLE 264

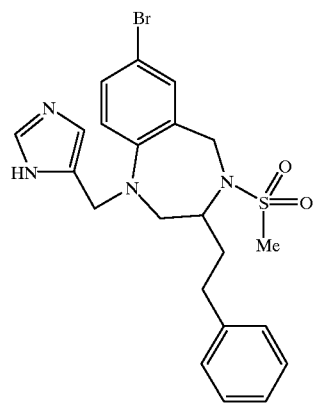

7-Bromo-2,3,4,5-tetrahydro-1-(1H-imidazol-4-ylmethyl)-4-(methylsulfonyl)-3-(2-phenylethyl)-1H-1,4-benzodiazepine, dihydrochloride.

A. 7-Bromo-2,3,4,5-tetrahydro-3-(2-phenylethyl)-1H-1,4-benzodiazepine

Compound A was prepared from D,L-homoPhe and 6-bromoisatoic anhydride as described in the following sequence: Compound A of Example 80, except that DMF was used instead of pyridine, and heating was at 50° C. for 24 hours; Compound B of Example 80; Compound C of Example 80.

B. 7-Bromo-2,3,4,5-tetrahydro-4-(methylsulfonyl)-3-(2-phenylethyl)-1H-1,4-benzodiazepine Compound A (100 mg, 0.30 mmol) was dissolved in THF (5 mL) and DIEA (211 µL, 1.21 mmol) was added followed by methanesulfonyl chloride (94 µL, 1.21 mmol). The solution was stirred for 30 min, concentrated, redissolved in ethyl acetate (50 mL) and washed with water (3×20 mL). The organic layer was dried (Na$_2$SO$_4$) and concentrated to yield Compound B as a light brown glass.

C. 7-Bromo-2,3,4,5-tetrahydro-1-(1H-imidazol-4-ylmethyl)-4-(methylsulfonyl)-3-(2-phenylethyl)-1 H-1,4-benzodiazepine, dihydrochloride Compound C and 4-formylimidazole were dissolved in 1,2-DCE (5 mL) and acetic acid (0.5 mL) and sodium triacetoxyborohydride was added. The mixture was stirred at 50° C. for 2h and saturated NaHCO$_3$ (5 mL) was added. The mixture was concentrated and the residue was partitioned between water (20 mL) and ethyl acetate (20 mL). The organic layer was washed with water (10 mL), brine (10 mL), dried (MgSO$_4$), concentrated and purified by preparative HPLC (gradient of aq methanol, 0.1% TFA). Appropriate fractions were combined, concentrated and lyophilized. The lyophilate was dissolved in methanol (0.5 mL) and 1N HCl (5 mL). The mixture was concentrated and lyophilized. This procedure was repeated to provide Example 264 as a white solid (15 mg, 19%). MS (M+H)$^+$490.

EXAMPLE 265

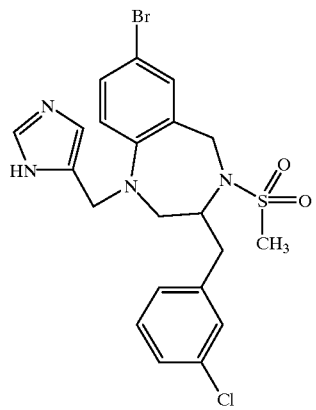

7-Bromo-3-[(3-chlorophenyl)methyl]-2,3,4,5-tetrahydro-1-(1H-imidazol-4-ylmethyl)-4-(methylsulfonyl)-1H-1,4-benzodiazepine, dihydrochloride.

A. 2-[2-(1,1-dimethyl-ethoxycarbonylamino)-3-(3-chloro-phenyl)-propylamino])-5-bromobenzoic acid N-Boc-3-chloro-phenylalaninal (800 mg, 2.8 mmol) and 2-amino-5-bromobenzoic acid (660 mg, 3.06 mmol) were dissolved in MeOH (10 mL). Molecular sieves (3 A, 7.0 g) and glacial acetic acid (0.2 mL) were added and the mixture was stirred for 30 min. Sodium cyanoborohydride (200 mg, 2.99 mmol) was added portionwise over 30 min. The mixture was stirred for 16 h, cooled to 0° C. and saturated NaHCO$_3$ (30 mL) was slowly added. The mixture was stirred for 30 min, concentrated and extracted with ethyl acetate (100 mL). The ethyl acetate layer was washed with water (100 mL), brine (100 mL), dried (MgSO$_4$), and concentrated. Preparative HPLC (gradient of aq methanol, 0.1% TFA) afforded Compound A as a clear oil (100 mg, 7%). MS (M+H)$^+$481.

B. 2-[2-amino-3-(3-chloro-phenyl)-propylamino])-5-bromobenzoic acid

Compound A (100 mg, 0.21 mmol) was stirred in dimethyl sulfide (0.1 mL) and 4N HCl in dioxane (10 mL) for 40 min. The mixture was concentrated, redissolved in methylene chloride (20 mL) and concentrated. This latter procedure was repeated three times to yield Compound B as a clear glass.

C. 7-Bromo-3-[(3-chlorophenyl)methyl]-2,3,4,5-tetrahydro-1-(1H-imidazol-4-ylmethyl)-4-(methylsulfonyl)-1H-1,4-benzodiazepine, dihydrochloride.

Compound C was prepared as a white solid from Compound B by the following sequence: Compound B of Example 80; Compound C of Example 80; Compound B of Example 264; Compound C of Example 264. MS (M+H)$^+$ 510.

EXAMPLE 266

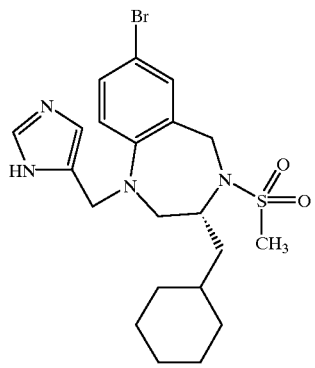

(R)-7-Bromo-3-(cyclohexylmethyl)-2,3,4,5-tetrahydro-1-(1H-imidazol-4-ylmethyl)-4-(methylsulfonyl)-1H-1,4-benzodiazepine, dihydrochloride.

Example 266 was prepared as a white solid from D-N-Boc-cyclohexylalaninal as described in Example 265. MS (M+H)$^+$510.

EXAMPLE 267

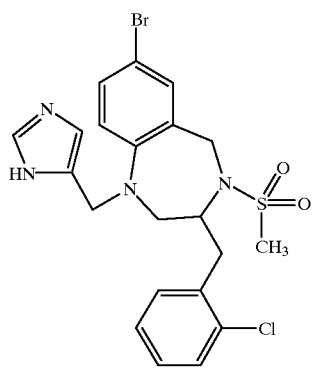

7-Bromo-3-[(2-chlorophenyl)methyl]-2,3,4,5-tetrahydro-1-(1H-imidazol-4-ylmethyl)-4-(methylsulfonyl)-1H-1,4-benzodiazepine, dihydrochloride.

Example 267 was prepared as a white solid from D,L-N-Boc-2-chlorophenylalaninal as described in Example 265. MS (M+H)$^+$510.

EXAMPLE 268

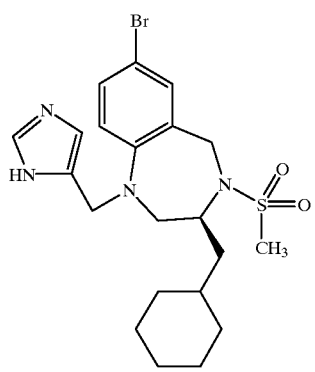

(S)-7-Bromo-3-(cyclohexylmethyl)-2,3,4,5-tetrahydro-1-(1H-imidazol-4-ylmethyl)-4-(methylsulfonyl)-1H-1,4-benzodiazepine, dihydrochloride.

Example 268 was prepared as a white solid from L-N-Boc-cyclohexylalaninal as described in Example 265. MS (M+H)⁺482.

EXAMPLE 269

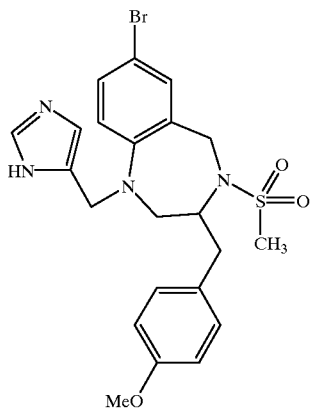

7-Bromo-2,3,4,5-tetrahydro-1-(1H-imidazol-4-ylmethyl)-3-[(4-methoxyphenyl)methyl]-4-(methylsulfonyl)-1H-1,4-benzodiazepine, dihydrochloride.

Example 269 was prepared as a white solid from D,L-N-Boc-4-methoxyphenylalaninal as described in Example 265. MS (M+H)⁺506.

EXAMPLE 270

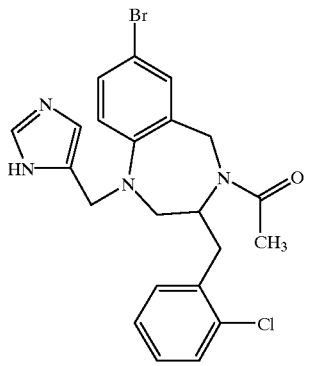

4-Acetyl-7-bromo-3-[(2-chlorophenyl)methyl]-2,3,4,5-tetrahydro-1-(1H-imidazol-4-ylmethyl)-1H-1,4-benzodiazepine, dihydrochloride.

Example 270 was prepared as a white solid from 7-bromo-3-[(2-chlorophenyl)methyl]-2,3,4,5-tetrahydro-1H-1,4-benzodiazepine as described in Compounds D and E of Example 80. MS (M+H)⁺475.

EXAMPLE 271

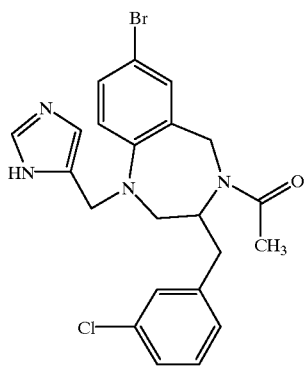

4-Acetyl-7-bromo-3-[(3-chlorophenyl)methyl]-2,3,4,5-tetrahydro-1-(1H-imidazol-4-ylmethyl)-1H-1,4-benzodiazepine, dihydrochloride.

Example 271 was prepared as a white solid from 7-bromo-3-[(3-chlorophenyl)methyl]-2,3,4,5-tetrahydro-1H-1,4-benzodiazepine as described in Example 270. MS (M+H)⁺475.

EXAMPLE 272

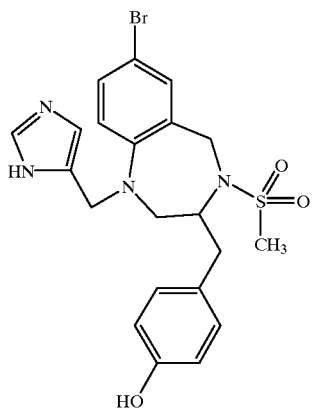

7-Bromo-2,3,4,5-tetrahydro-1-(1H-imidazol-4-ylmethyl)-3-[(4-hydroxyphenyl)methyl]-4-(methylsulfonyl)-1H-1,4-benzodiazepine, dihydrochloride.

To a solution of Example 269 (30 mg, 0.059 mmol) in a mixture of dichloromethane (5 mL) and 1,2-dichloroethane (5 mL) was added a solution of $BBr_3$ (1M in dichloromethane, 0.5 mL). The mixture was stirred for 16h and 5% ammonium hydroxide (10 mL) was added. The mixture was stirred for additional 1 h, concentrated and the residue purified by preparative HPLC (gradient of aqueous methanol with 0.1% TFA). Appropriate fractions were combined, concentrated and lyophilized. This lyophilate was dissolved in methanol (0.5 mL) and 1N HCl (5mL). This mixture was concentrated and lyophilized. This procedure was repeated to provide Example 272 as a white solid (20 mg, 60%). MS (M+H)⁺490.

EXAMPLE 273

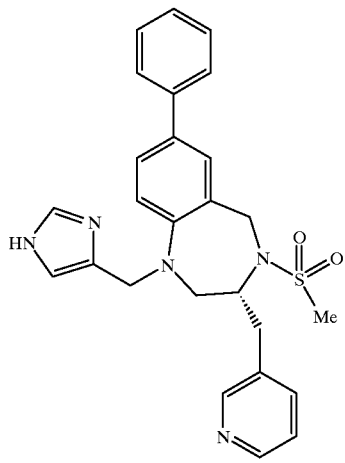

(R)-2,3,4,5-Tetrahydro-1-(1H-imidazol-4-ylmethyl)-4-(methylsulfonyl)-7-phenyl-3-(3-pyridinylmethyl)-1H-1,4-benzodiazepine, dihydrochloride.

Example 273 was prepared as a light yellow solid from D-pyridylalanine and Compound B of Example 226 using the following sequence: Compound C of Example 226; Compound D of Example 226; Compound B of Example 264; Compound C of Example 264. MS (M+H)$^+$474.

EXAMPLE 274

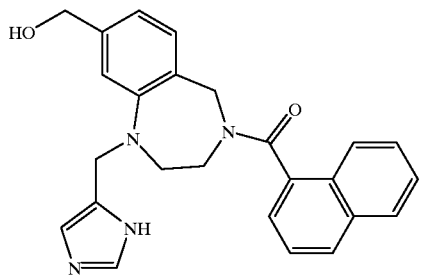

2,3,4,5-Tetrahydro-8-(hydroxymethyl)-1-(1H-imidazol-4-ylmethyl)-4-(1-naphthalenylcarbonyl)-1H-1,4-benzodiazepine, dihydrochloride.

A. 8-[2,3,4,5-Tetrahydro-1H-1,4-benzodiazepin-2,5-dionyl]-carboxylic acid

A mixture of 7-carboxyisatoic anhydride (prepared from triphosgene and 4-carboxylic-2-amino-benzoic acid, 20 g, 0.09 mol) and ethyl glycine hydrochloride (13.5 g, 0.097 mol) in anhydrous pyridine (200 mL) was refluxed 30 hrs and cooled to rt. The pyridine was evaporated and the residue was washed with water followed by EtOAc. The solid was dried under reduced pressure to give Compound A (17.5 g, 88%) as a white solid.

B. 2,3,4,5-Tetrahydro-8-(hydroxymethyl)-1H-1,4-benzodiazepine

Borane (1.0 M in THF, 1L) was added to a suspension of Compound A (10 g, 45 mmol) in ethylene glycol dimethyl ether (10 mL). The suspension was stirred at r.t. for 1 hr, refluxed for 8 hrs, cooled to 0° C. and quenched with 6N HCl (20 mL). The solvent was evaporated, the residue dissolved in water (30 mL) and the mixture neutralized with sat. Na$_2$CO$_3$ and evaporated. The residue was evaporated from methanol and purified by flash column chromatography (10% MeOH, 1% NH$_4$OH in CH$_2$Cl$_2$) to provide Compound B as a white solid. MS (M+H)$^+$179.

C. 2,3,4,5-Tetrahydro-8-(hydroxymethyl)-1-(1H-imidazol-4-ylmethyl)-4-(1-naphthalenylcarbonyl)-1H-1,4-benzodiazepine, dihydrochloride Example 274 was prepared as an off white solid from Compound B as described for Compound F of Example 41, with chromatography using 5% MeOH/0.5% NH$_4$OH/methylene chloride, and Compound D of Example 1, with purification by prep HPLC before formation of the HCl salt. MS (M+H) 413.

EXAMPLE 275

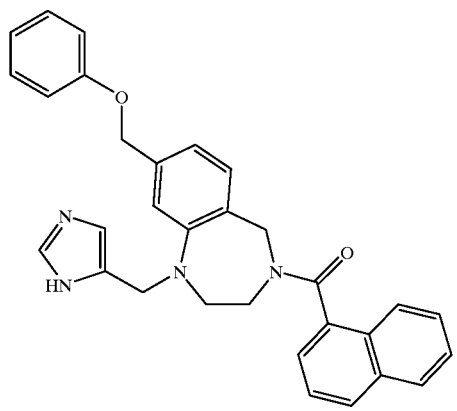

2,3,4,5-Tetrahydro-1-(1H-imidazol-4-ylmethyl)-4-(1-naphthalenylcarbonyl)-8-(phenoxymethyl)-1H-1,4-benzodiazepine, dihydrochloride.

A solution of Example 274 (0.38 g, 0.9 mmol) and Boc$_2$O (1.2 g, 5.4 mmol) in CH$_2$Cl$_2$ (10 mL) was stirred for 48 hrs and evaporated. The residue was purified by flash chromatography (4% MeOH in CH$_2$Cl$_2$) to give the protected imidazole analog as a white solid (0.190 g, 40%). A mixture of a portion of this material (42 mg, 0.08 mmol), Ph$_3$P (28 mg, 0.1 mmol), phenol (30 mg, 0.3 mmol) and diethylazodicarboxylate (0.05 mL, 0.3 mmol) in THF (7 mL) was stirred for 48 hrs. under N$_2$. 1N HCl (5 mL) was added. The mixture was stirred for 1 hr and evaporated. The residue was treated with 6M HCl, extracted with CH$_2$Cl$_2$ (2×10 mL) and the aqueous layer evaporated to give a solid which was purifed by prep HPLC (gradient of aqueous methanol with 0.1% TFA) and converted into its HCl salt by lyophilization from 1M HCl (5 mL) to give Example 275 as a white solid (10 mg, 24%) MS (M+H)$^+$489.

EXAMPLE 276

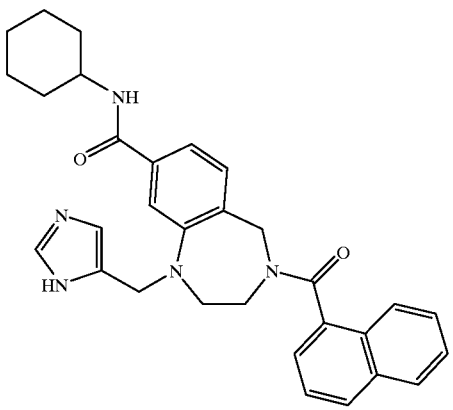

N-Cyclohexyl-2,3,4,5-tetrahydro-1-(1H-imidazol-4-ylmethyl)-4-(1-naphthalenylcarbonyl)-1H-1,4-benzodiazepine-8-carboxamide, dihydrochloride.

A. 2,3,4,5-Tetrahydro-8-(hydroxymethyl)-1H-1,4-bis-(1-naphthalenylcarbonyl)-benzodiazepine Naphthoyl chloride (18 mL g, 110 mmol) was added to a solution of compound B of Example 274 (24 g, 29 mmol) in pyridine (150 mL) and the resulting solution was stirred for 10 hrs and poured into ice-water. The resulting precipitate was filtered and the solid was washed with water and subjected to flash chromatography (3% MeOH in $CH_2Cl_2$) to provide the trinaphthoate as a yellow solid (8.4 g, 45%). A portion of this material (5.63 g, 87 mmol) in MeOH (60 mL) was stirred with 1M NaOMe in MeOH (40 mL) for 10 hrs and evaporated. The residue was dissolved in $CH_2Cl_2$ (150 mL) and the solution was washed with $H_2O$ (50 mL) and 1N HCl (50 mL), dried over $Na_2SO_4$ and evaporated. Purification by flash chromatography (5% MeOH in $CH_2Cl_2$) provided Compound A as a white solid (3.8 g, 89%). MS $(M+H)^+486$.

B. 2,3,4,5-Tetrahydro-1-(1-naphthalenylcarbonyl)-4-(1-naphthalenylcarbonyl)-1H-1,4-benzodiazepine-8-carboxylic acid Jones reagent (5% $CrO_3$ in 10% $H_2SO_4$ in $H_2O$, 15 mL) was slowly added to a solution of Compound A (2.7 g, 5.6 mmol) in acetone (50 mL) at 0° C. The solution was stirred for 1 hr. at r.t. The excess $CrO_3$ was destroyed by adding iPrOH. The aqueous solution was extracted with $CH_2Cl_2$ (3×100 mL). The combined organic phases were dried over $Na_2SO_3$ and evaporated to give a solid which was purified by flash chromatography (5% MeOH in $CH_2Cl_2$) to provide Compound B as a solid (2.30 g, 82.7%). MS $(M+H)^+499$.

C. 2,3,4,5-Tetrahydro-4-(1-naphthalenylcarbonyl)-1H-1,4-benzodiazepine-8-carboxylic acid A mixture of Compound B (1.02 g, 2 mmol) in MeOH (40 mL) was refluxed with KOH (7.75 g, 138 mmol) in $H_2O$ (10 mL) for 40 hrs. The MeOH was evaporated and aqueous solution was neutralized with conc. HCl. The resulting precipitate was filtered and washed with $H_2O$. The solid was dried to provide Compound C as a white solid (0.635 g, 90%). MS(M+H)+347.

D. N-Cyclohexyl-2,3,4,5-tetrahydro-4-(1-naphthalenylcarbonyl)-1H-1,4-benzodiazepine-8-carboxamide A solution of cyclohexylamine (0.32 g, 3.2 mmol) and diisopropylethylamine (1 mL, 5.7 mL) in DMF (1 mL) was added to a solution of EDC (0.12 9, 0.62 mmol), HOBT (0.13 g, 0.9 mmol) and Compound C (20 mg, 0.06 mmol) in DMF (5 mL). The solution was stirred for 24 hrs and evaporated. The residue was dissolved in EtOAc (20 mL) and the solution was washed with sat. $NaHCO_3$, 1N HCl (5 mL), dried over $Na_2SO_4$ and evaporated to give Compound D as a pale yellow solid (40 mg).

E. N-Cyclohexyl-2,3,4,5-tetrahydro-i-(1H-imidazol-4-ylmethyl)-4-(1-naphthalenylcarbonyl)-1 H-1,4-benzodiazepine-8-carboxamide, dihydrochloride Compound E was prepared from Compound D as described for Compound D of Example 1, with purification by prep HPLC before formation of the HCl salt. MS $(M+H)^+508$.

EXAMPLE 277

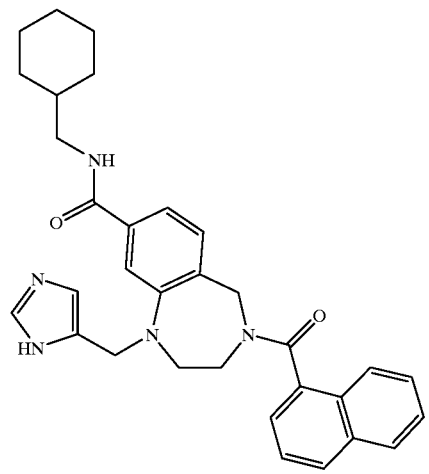

N-(Cyclohexylmethyl)-2,3,4,5-tetrahydro-1-(1H-imidazol-4-ylmethyl)-4-(1-naphthalenylcarbonyl)-1H-1,4-benzodiazepine-8-carboxamide, dihydrochloride.

Example 277 was prepared as an off white solid from Compound C of Example 276 and cyclohexylamine as described in Compounds D and E of Example 276. MS $(M+H)^+522$.

EXAMPLE 278

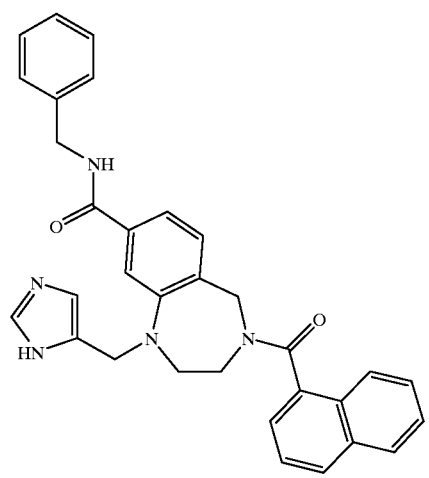

2,3,4,5-Tetrahydro-1-(1H-imidazol-4-ylmethyl)-4-(1-naphthalenyl-carbonyl)-N-(phenylmethyl)-1H-1,4-benzodiazepine-8-carboxamide, dihydrochloride.

Example 278 was prepared as an off white solid from Compound C of Example 276 and benzylamine as described in Compounds D and E of Example 276. MS $(M+H)^+517$.

EXAMPLE 279

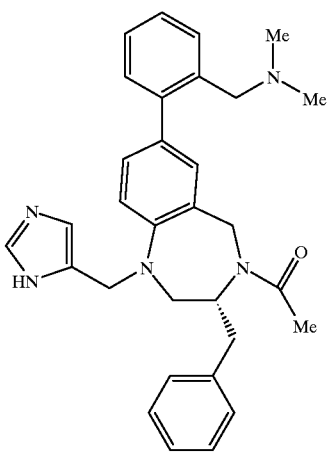

(R)-4-Acetyl-7-[2-[(dimethylamino)methyl]phenyl]-2,3,4,5-tetrahydro-1-(1H-imidazol-4-ylmethyl)-3-(phenylmethyl)-1H-1,4-benzodiazepine, dihydrochloride.

A. 2-[(R)-2,3,4,5-tetrahydro-3-(phenylmethyl)-1H-1,4-benzodiazepin-2,5-dion-7-yl]-benzaldehyde Compound A was prepared as a yellow solid from Compound A of Example 224 and 4-formylbenzeneboronic acid as described for Compound A of Example 12, with THF as solvent, refluxing for 10 hours, and extractive workup. MS (M+H)$^+$371.

B. (R)-7-(2-(Dimethylaminomethyl)-phenyl)-2,3,4,5-tetrahydro-3-(phenylmethyl)-1H-1,4-benzodiazepin-2,5-dione A solution of Compound A and dimethylamine (1.0 M in THF, 10 mL) in 1:10/AcOH:CH$_2$Cl$_2$ (20 mL) was stirred for 1 hr. NaBH(OAc)$_3$ (2.0 g) was added. Stirring was continued for 14 hrs. The solvent was evaporated and residue was treated with 1N NaOH (10 mL). The aqueous layer was extracted with 10% iPrOH in CH$_2$Cl$_2$. The organic phase was dried and evaporated to give a pale yellow solid which was purified by flash chromatography (10% MeOH, 1% Et$_3$N in CH$_2$Cl$_2$) to provide Compound B as a white solid (1.13 g, 98%). MS(M+H)$^+$400.

C. (R)-7-(2-(Dimethylaminomethyl)-phenyl)-2,3,4,5-tetrahydro-3-(phenylmethyl)-1 H-1,4-benzodiazepine A solution of Compound B (1.13 g) in dry THF was treated with LAH (1.0 M in THF, 15 mL) at 0° C. The solution was refluxed for 10 hrs, cooled to 0° C. and H$_2$O (5 mL) was added followed by THF (10 mL) and 20% NaOH (5 mL). The THF solution was decanted and the solid was washed with THF. The combined THF solutions were evaporated and the residue dissolved in CH$_2$Cl$_2$ (20 mL). The solution was evaporated to give Compound C as a pale yellow solid (0.7 g, 67%). MS (M+H)$^+$372.

D. (R)-4-Acetyl-7-[2-[(dimethylamino)methyl]phenyl]-2,3,4,5-tetrahydro-3-(phenylmethyl)-1H-1,4-benzodiazepine Acetyl chloride (0.03 mL, 1.1 eq.) in CH$_2$Cl$_2$ (0.3 mL) was added to a solution of Compound C (0.155 g, 0.41 mmol) and DIEA (0.4 mL, 2.7 mmol) in CH$_2$Cl$_2$ (10 mL). The mixture was stirred 20 minutes and evaporated. The residue was dissolved in EtOAc and the solution was washed with sat. NaHCO$_3$, dried over Na$_2$SO$_4$ and evaporated to give Compound D as an oil (0.14 g, 84%).

E. (R)-4-Acetyl-7-[2-[(dimethylamino)methyl]phenyl]-2,3,4,5-tetrahydro-1-(1H-imidazol-4-ylmethyl)-3-(phenylmethyl)-1H-1,4-benzodiazepine, dihydrochloride.

Compound E was prepared from Compound D as described for Compound E of Example 276. MS (M+H)$^+$ 492.

EXAMPLE 280

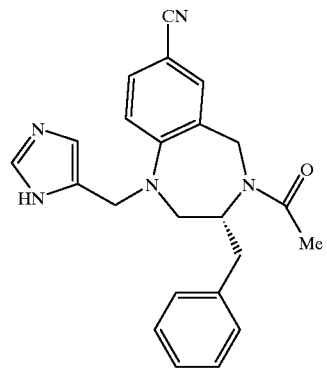

(R)-4-Acetyl-7-cyano-2,3,4,5-tetrahydro-1-(1H-imidazol-4-ylmethyl)-3-(phenylmethyl)-1H-1,4-benzodiazepine, monohydrochloride.

A. (R)-7-Cyano-2,3,4,5-tetrahydro-3-(phenylmethyl)-4-[(1,1-dimethylethoxy)-carbonyl]-1H-1,4-benzodiazepine Compound A was prepared as a white solid from Compound C of Example 248 as described for Compound A of Example 4, with stirring in THF for 10 hours.

B. (R)-7-Cyano-2,3,4,5-tetrahydro-1-(1H-imidazol-4-ylmethyl)-3-(phenylmethyl)-4-[(1,1-dimethylethoxy)-carbonyl]-1H-1,4-benzodiazepine Compound B was prepared from Compound A as described for Compound D of Example 1.

C. (R)-7-Cyano-2,3,4,5-tetrahydro-1-(1H-imidazol-4-ylmethyl)-3-(phenylmethyl)-1H-1,4-benzodiazepine Compound C was prepared from Compound B by treatment with 4M HCl in 4:1 ethyl acetate:dioxane. MS(M+H)$^+$ 244.

D. (R)-4-Acetyl-7-cyano-2,3,4,5-tetrahydro-1-(1H-imidazol-4-ylmethyl)-3-(phenylmethyl)-1H-1,4-benzodiazepine, monohydrochloride Compound D was prepared from Compound C by treatment with DIEA, EDC, HOBT and acetic acid in DMF for 14 hours. Purification by prep HPLC (gradient of aqueous methanol with 0.1% TFA) and conversion into its HCl salt by lyophilization from 1M HCl afforded Example 280 as a solid. MS (M-H)$^+$386.

EXAMPLE 281

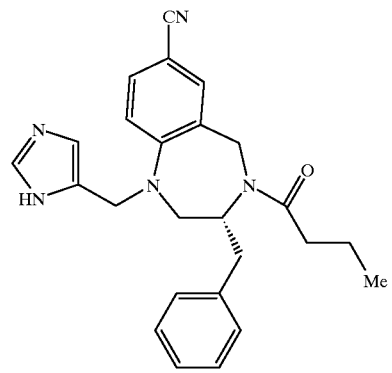

(R)-7-Cyano-2,3,4,5-tetrahydro-1-(1H-imidazol-4-ylmethyl)-4-(1-oxobutyl)-3-(phenylmethyl)-1H-1,4-benzodiazepine, monohydrochloride.

Example 281 was prepared as a solid from Compound C of Example 280 and butyric acid as described for Compound D of Example 280. MS (M-H)$^+$414.

EXAMPLE 282

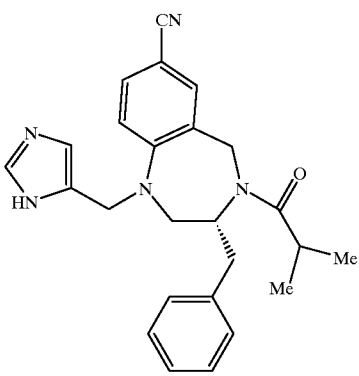

(R)-7-Cyano-2,3,4,5-tetrahydro-1-(1H-imidazol-4-ylmethyl)-4-(2-methyl-1-oxopropyl)-3-(phenylmethyl)-1H-1,4-benzodiazepine, monohydrochloride.

Example 282 was prepared as a solid from Compound C of Example 280 and isobutyric acid as described for Compound D of Example 280. MS (M−H)$^+$414.

EXAMPLE 283

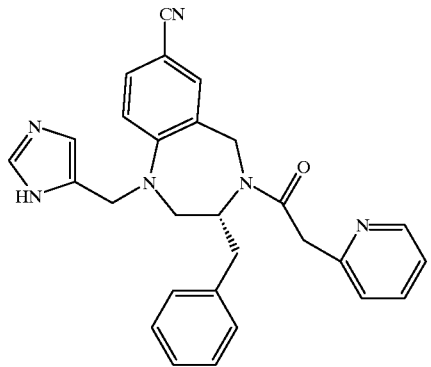

(R)-7-Cyano-2,3,4,5-tetrahydro-1-(1H-imidazol-4-ylmethyl)-3-(phenylmethyl)-4-(2-pyridinylacetyl)-1H-1,4-benzodiazepine, dihydrochloride. Example 283 was prepared as an off white solid from Compound C of Example 280 and 2-pyridylacetic acid as described for Compound D of Example 280. MS (M−H)$^+$464.

EXAMPLE 284

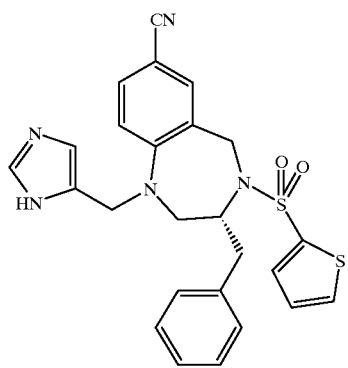

(R)-7-Cyano-2,3,4,5-tetrahydro-1-(1H-imidazol-4-ylmethyl)-3-(phenylmethyl)-4-(2-thienylsulfonyl)-1H-1,4-benzodiazepine, monohydrochloride.

A. (R)-7-Cyano-2,3,4,5-tetrahydro-3-(phenylmethyl)-4-(2-thienylsulfonyl)-1H-1,4-benzodiazepine 2-Thiophenesulfonyl chloride (34.56 g, 0.19 mol) in CH$_2$Cl$_2$ (200 mL) was added to a solution of Compound C of Example 248 (37.4 g, 0.142 mol) and DIEA (38 mL, 0.23 mol) in CH$_2$Cl$_2$ (500 mL) at rt. The solution was stirred for 48 hrs and evaporated. The residue was partitioned between CH$_2$Cl$_2$ (500 mL) and saturated NaHCO$_3$ (2×500 mL). The organic layer was dried (Na$_2$SO$_4$) and evaporated. The residual yellow oil was purified by flash chromatography (20% followed by 50% ethyl acetate/hexanes) to provide Compound A as a yellow solid (55 g, 95%).

B. (R)-7-Cyano-2,3,4,5-tetrahydro-1-(1H-imidazol-4-ylmethyl)-3-(phenylmethyl)-4-(2-thienylsulfonyl)-1 H-1,4-benzodiazepine, monohydrochloride.

A mixture of Compound A (55 g, ~0.134 mol) and 4-formylimidazole (51 g, 0.53 mol) in AcOH/CH$_2$ClCH$_2$Cl (140 ml/600 mL) was stirred for 50 min at 55° C. under N$_2$. NaBH(OAc)$_3$ (total: 72 g, 0.34 mol) was added over 15 hrs (every 1.5 to 2 hrs, average about 6 g was added) until HPLC analysis showed the absence of Compound A. MeOH (250 mL) was added and the solvent was evaporated. The residue was stirred with H$_2$O (100 mL), then 4% NaOH (800 mL) for 30 min. The aqueous solution was extracted with ethyl acetate (2×800 mL). The combined organic layers were washed with 5% NaOH (800 mL) and dried over Na$_2$SO$_4$. Evaporation of solvent gave an oil (85 g) which was purified by flash chromatography (silica, 5% MeOH in EtOAc) to provide 70 g of a wet solid. HCl (1.0 M in ether, 400 mL, 0.4 mol) was added to a solution of the solid in EtOAc (600 mL). The resulting suspension was stirred for 20 min and evaporated. The residue was washed with EtOAc (2×500 mL) and ether (2×100 mL) and dried under high vacum to provide Compound B (63 g, 83%) as an off white solid. MS (M+H)$^+$490.

$^1$H-NMR (CD$_3$OD, 300 MHz) δ 2.90 (m, 2H), 3.15 (m, 2H), 3.90 (m, 1H), 4.3 to 5.1 (m, 4H), 6.40 (d, 7Hz, 1H), 7.0 to 7.6 (m, 11 H), 8.90 (s, 1H).

EXAMPLES 285–295

Examples 285–295 were prepared from Compound C of Example 248 (Exs 285, 286, 291, 292, 293, 294, 295), Compound B of Example 224 (Exs 287, 288) or Compound B of Example 232 (Exs 289, 290) and the appropriate sulfonyl chloride as described for Example 284.

| Example | | | Mass Spectrum |
|---|---|---|---|
| 285 | (R)-7-Cyano-2,3,4,5-tetrahydro-1-(1H-imidazol-4-ylmethyl)-4-[(1-methylethyl)sulfonyl]-3-(phenylmethyl)-1H-1,4-benzodiazepine, monohydrochloride. BMS-214665 | | m/z 450 (M + H) |
| 286 | (R)-7-Cyano-2,3,4,5-tetrahydro-1-(1H-imidazol-4-ylmethyl)-3-(phenylmethyl)-4-[(trifluoromethyl)sulfonyl]-1H-1,4-benzodiazepine, monohydrochloride. BMS-214666 | | m/z 476 (M + H) |
| 287 | (R)-7-Bromo-2,3,4,5-tetrahydro-1-(1H-imidazol-4-ylmethyl)-3-(phenylmethyl)-4-(propylsulfonyl)-1H-1,4-benzodiazepine, monohydrochloride. BMS-215354 | | m/z 501 (M + H) |
| 288 | (R)-7-Bromo-2,3,4,5-tetrahydro-1-(1H-imidazol-4-ylmethyl)-3-(phenylmethyl)-4-(phenylsulfonyl)-1H-1,4-benzodiazepine, monohydrochloride. BMS-215355 | | m/z 539 (M + H) |

-continued

| Example | | | Mass Spectrum |
|---|---|---|---|
| 289 | (R)-2,3,4,5-Tetrahydro-1-(1H-imidazol-4-ylmethyl)-7-phenyl-3-(phenylmethyl)-4-(phenylsulfonyl)-1H-1,4-benzodiazepine, monohydrochloride. BMS-215356 | 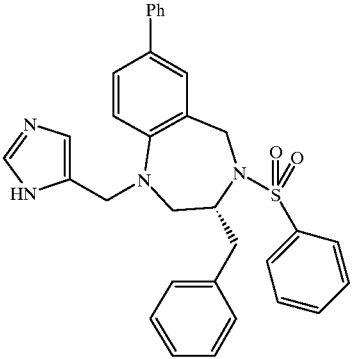 | m/z 535 (M + H) |
| 290 | (R)-2,3,4,5-Tetrahydro-1-(1H-imidazol-4-ylmethyl)-7-phenyl-3-(phenylmethyl)-4-(propylsulfonyl)-1H-1,4-benzodiazepine, monohydrochloride. BMS-215357 | 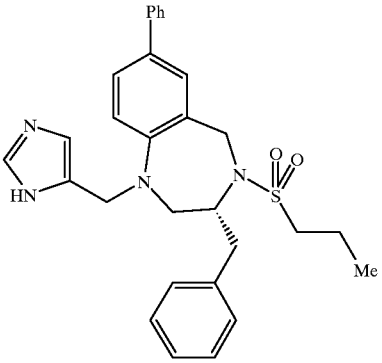 | m/z 501 (M + H) |
| 291 | (R)-7-Cyano-4-[(4-fluorophenyl)sulfonyl]-2,3,4,5-tetrahydro-1-(1H-imidazol-4-ylmethyl)-3-(phenylmethyl)-1H-1,4-benzodiazepine, monohydrochloride. BMS-218319 | 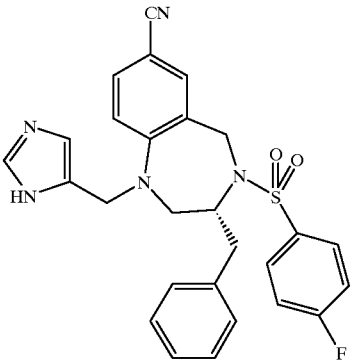 | m/z 502 (M + H) |

-continued

| Example | | | Mass Spectrum |
|---|---|---|---|
| 292 | (R)-7-Cyano-4-[(3-cyanophenyl)sulfonyl]-2,3,4,5-tetrahydro-1-(1H-imidazol-4-ylmethyl)-3-(phenylmethyl)-1H-1,4-benzodiazepine, monohydrochloride. BMS-218320 | 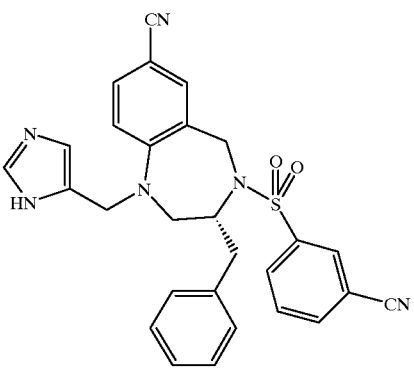 | m/z 509 (M + H) |
| 293 | (R)-7-Cyano-2,3,4,5-tetrahydro-1-(1H-imidazol-4-ylmethyl)-4-[(1-methyl-1H-imidazol-4-yl)sulfonyl]-3-(phenylmethyl)-1H-1,4-benzodiazepine, dihydrochloride. BMS-218322 | 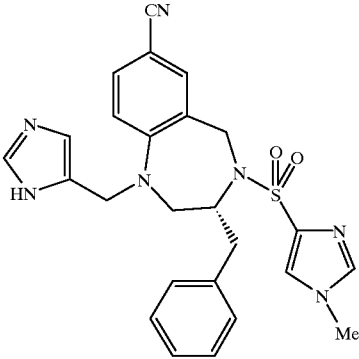 | m/z 488 (M + H) |
| 294 | (R)-4-[(3-Bromophenyl)sulfonyl]-7-cyano-2,3,4,5-tetrahydro-1-(1H-imidazol-4-ylmethyl)-3-(phenylmethyl)-1H-1,4-benzodiazepine, monohydrochloride. BMS-218735 | 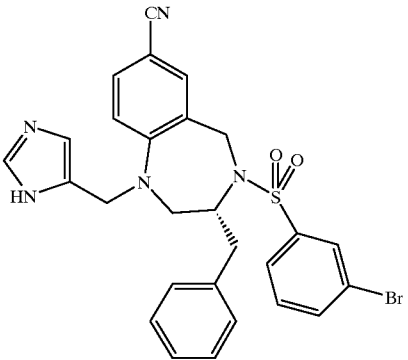 | m/z 563 (M + H) |

-continued

| Example | | Mass Spectrum |
|---|---|---|
| 295 | (R)-N-[5-[[7-cyano-2,3,4,5-tetrahydro-1-(1H-imidazol-4-ylmethyl)-3-(phenylmethyl)-1H-1,4-benzodiazepin-4-yl]sulfonyl]-4-methyl-2-thiazolyl]acetamide, dihydrochloride. BMS-218736 | m/z 562 (M + H) |

EXAMPLE 296

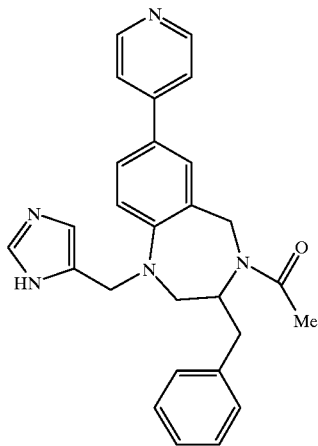

4-Acetyl-2,3,4,5-tetrahydro-1-(1H-imidazol-4-ylmethyl)-3-(phenylmethyl)-7-(4-pyridinyl)-1 H-1,4-benzodiazepine, trihydrochloride.

A. 4-Acetyl-2,3,4,5-tetrahydro-1-trifluoroacetyl-3-(phenylmethyl)-7-bromo-1H-1,4-benzodiazepine Acetyl chloride (35mL, 0.47 mmol) was added to a solution of Compound B of Example 75 (0.32 mmol, 100 mg) and NEt₃ (220 mL, 1.58 mmol) in 5 mL of CH₂Cl₂ at 0° C. After 5 minutes, trifluoroacetic anhydride (0.63 mmol, 90 mL) was added, and the reaction was stirred for an additional 10 minutes, concentrated and the residue purified by flash chromatography (50%EtOAc/Hexanes) to afford Compound A as a white solid (140 mg, 98% for two steps). MS (M+H) 455.

B. 4-Acetyl-2,3,4,5-tetrahydro-1-trifluoroacetyl-3-(phenylmethyl)-7-(4-pyridinyl)-1H-1,4-benzodiazepine A mixture of Compound A (0.27 mmol, 124 mg), 4-tributylstannylpyridine (0.54 mmol, 200 mg) and 15 mol% Pd(PPh₃)₄ (47 mg) in 3 mL of toluene was degassed and heated to reflux under argon. After 16 hours, the reaction was concentrated and purified by flash chromatography (10%EtOAc/Hexanes) to isolate Compound B as a yellow oil (60 mg, 49%). MS (M+H) 454.

C. 4-Acetyl-2,3,4,5-tetrahydro-3-(phenylmethyl)-7-(4-pyridinyl)-1H-1,4-benzodiazepine NaOH (5 drops of 2N NaOH aqueous solution) was added to a solution of Compound B (60 mg, 0.13 mmol) in 3 mL MeOH and the mixture was maintained at rt for 30 minutes, concentrated and partitioned between 2N NaOH (5 mL) and 10% isopropanol-CH₂Cl₂ (5 mL). The aqueous layer was extracted 3 times with 10% isopropanol-CH₂Cl₂ and the combined organic layers were dried over Na₂SO₄ and concentrated to afford Compound C.

D. 4-Acetyl-2,3,4,5-tetrahydro-1-(1H-imidazol-4-ylmethyl)-3-(phenylmethyl)-7-(4-pyridinyl)-1H-1,4-benzodiazepine, trihydrochloride To a mixture of Compound D in 2 mL of 1:1 AcOH:ClCH₂CH₂Cl was added 4-formylimidazole (0.39 mmol, 38 mg) and NaBH(OAc)₃ (0.39 mmol, 83 mg). The mixture was heated at 50° C. for 4 hours, concentrated and partitioned between 2N NaOH and 10% isopropanol/CH₂Cl₂ (5 mL). The aqueous layer was extracted 3 times with 10% isopropanol-CH₂Cl₂ and the combined organic layers were dried over Na₂SO₄, concentrated and purified by prep HPLC (gradient of aqueous methanol with 0.1% TFA). The TFA salt was converted to the HCl salt with 1N HCl to afford Example 296 as a yellow solid (32 mg, 49% from Compound B). MS (M+H) 438.

EXAMPLE 297

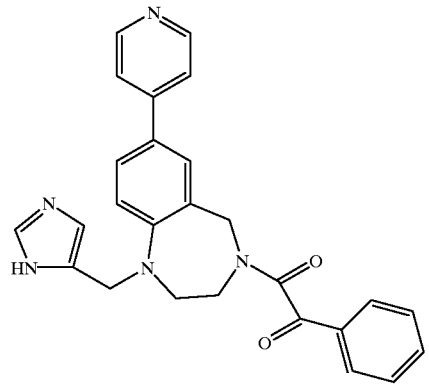

2,3,4,5-Tetrahydro-1-(1H-imidazol-4-ylmethyl)-4-(2-phenyl-1,2-dioxoethyl)-7-(4-pyridinyl)-1H-1,4-benzodiazepine, trihydrochloride.

Example 297 was prepared as a yellow solid from 7-bromo-1,4-benzodiazepine (see Example 11) and benzoylformic acid by the following sequence: Example 252, in 10:1 methylene chloride:DMF and with chromatography with 50% EtOAc/hexanes; treatment with trifluoracetic anhydride and workup as described in Compound A of Example 296; Compounds B, C and D of Example 296. M+H (438).

EXAMPLE 298

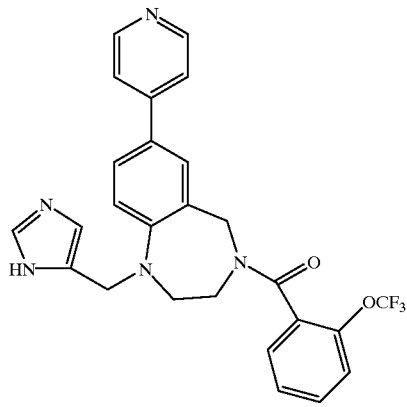

2,3,4,5-Tetrahydro-1-(1H-imidazol-4-ylmethyl)-7-(4-pyridinyl)-4-[2-(trifluoromethoxy)benzoyl]-1H-1,4-benzodiazepine, trihydrochloride.

Example 298 was prepared as a yellow solid from 2-(trifluoromethoxy)-benzoic acid as described for Example 297. MS (M+H) 494.

EXAMPLE 299

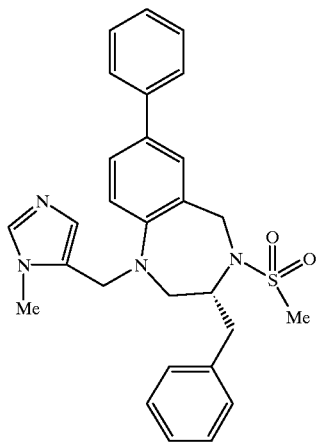

(R)-2,3,4,5-Tetrahydro-1-[(1-methyl-1H-imidazol-5-yl)methyl]-4-(methylsulfonyl)-7-phenyl-3-(phenylmethyl)-1H-1,4-benzodiazepine A. (R)-2,3,4,5-Tetrahydro-4-(methylsulfonyl)-7-phenyl-3-(phenylmethyl)-1H-1,4-benzodiazepine Mesyl chloride (0.12 ml, 1.6 mmol) was added dropwise to a solution of Compound D of Example 226 (0.50 g, 1.3 mmol) and DIEA (0.78 ml, 4.5 mmol) in methylene chloride (20 ml) at −78° C. The mixture was allowed to warm to room temperature and stirred for 16 h, quenched with 10% NaHCO$_3$ (100 ml) and extracted with ethyl acetate (3×150 ml). The combined organic layers were dried (Na$_2$SO$_4$), filtered and concentrated under vacuum. The residue was purified by flash chromatography (5/2 hexane/ethyl acetate) to afford Compound A (0.52 g, 100%) as a yellow solid.

B. 1-[1,1-Dimethylethoxycarbonyl]-4-imidazolecarboxaldehyde

Di-tert-butyl dicarbonate (55.4 g, 254 mmol) was added to a suspension of 4-formyl imidazole (20.0 g, 208 mmol) and DIEA (36.2 ml, 208 mmol) in 400 ml of methylene chloride at room temperature. The mixture was heated to 40° C. upon which it became a clear solution and was stirred 16 h, cooled to room temperature, quenched with saturated NaHCO$_3$ (200 ml) and extracted with CH$_2$Cl$_2$ (3×400 ml). The combined organic extracts were dried (Na2SO$_4$), filtered and concentrated under vacuum. The residue was purified by flash chromatography (5–50% ethyl acetate/hexane) to afford Compound B (35.2 g, 87%) as a white solid. MS: (M+NH$_4$+CH$_3$CN)$^+$256

C. 1-Methyl-5-imidazolecarboxaldehyde

Methyl triflate (22.3 ml, 197 mmol) was added slowly to a solution of Compound B (35.1 g, 179 mmol) in CH$_2$Cl$_2$ (740 ml) at −78° C. The mixture was allowed to warm to room temperature slowly and stirred 16h. The resultant white precipitate was quenched portionwise with a saturated solution of potassium carbonate (112 g/100 ml H$_2$O) at room temperature. The biphasic solution was stirred at room temperature for 30 minutes. The phases were separated and the aqueous layer was extracted with 9/1 CH$_2$Cl$_2$/iPrOH (4×300 ml). The combined organic extracts were dried (Na$_2$SO$_4$), filtered and concentrated under vacuum. The residue was purified by flash chromatography (19/1 CHCl$_3$/MeOH) to afford Compound C (17.4 g, 88%) as a white solid. MS (M+H)$^+$111

D. (R)-2,3,4,5-Tetrahydro-1-[(1-methyl-1H-imidazol-5-yl)methyl]-4-(methylsulfonyl)-7-phenyl-3-(phenylmethyl)-1 H-1,4-benzodiazepine Compound C (0.065 g, 0.59 mmol) was added to a solution of Compound A (0.23 g, 0.59 mmol) and 3A molecular sieves in 1/1 DCE: acetic acid (4 ml) and the mixture was stirred at 70° C. for 1h. Sodium triacetoxyborohydride (0.13 g, 0.59 mmol) was added and the mixture was stirred at 70° C. for 30 minutes. The latter procedure was repeated two more times. The mixture was cooled to room temperature, diluted with methylene chloride (10 ml), filtered and the filtrate was concentrated under vacuum. The residue was diluted with 25% NH$_4$OH (100 ml) and stirred at room temperature for 10 minutes. The solution was extracted with CH$_2$Cl$_2$ (3×100 ml), the combined organic extracts were dried (Na$_2$SO$_4$), filtered and concentrated under vacuum. The residue was purified by preparative HPLC (10–90% aq MeOH with 0.1% TFA) and the appropriate fractions were pooled and concentrated under vacuum. The residue was evaporated from CH$_3$OH (5 ml) and 1N HCl (3 ml) four times. The residue was dissolved in CH$_3$CN (3 ml) and water (3 ml) and lyophilized to afford Example 299 (0.26 g, 80 %) as a white solid. mp: 106–114° C. MS (M+H)$^+$487

[a]D=+910 (c=0.35, CH$_3$OH)

Elemental analysis for C$_{28}$H$_{30}$N$_4$O$_2$S-HCl-0.9 H$_2$O

Calc: C, 57.88; H, 5.17; N, 9.06; Cl, 4.59; S, 5.18

Found: C, 57.88; H, 5.49; N, 9.14; Cl, 4.64; S, 5.31

EXAMPLE 300

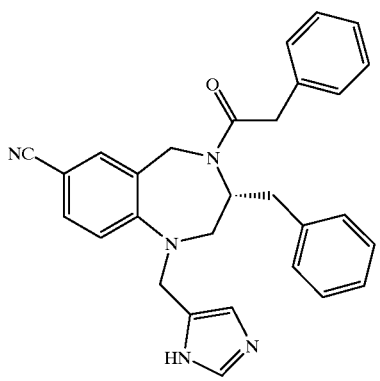

(R)-7-Cyano-2,3,4,5-tetrahydro-1-(1H-imidazol-4-ylmethyl)-4-(phenylacetyl)-3-(phenylmethyl)-1H-1,4-benzodiazepine, monohydrochloride.

To a refluxing solution of (R)-7-cyano-2,3,4,5-tetrahydro-4-(phenylacetyl)-3-(phenylmethyl)-1H-1,4-benzodiazepine (prepared from Compound C of Example 248 by EDC/HOAt coupling with phenylacetic acid, 0.100 g, 0.26 mmol) and 4-formylimidazole (0.025 g, 0.26 mmol) in AcOH (0.3 mL) and dichloroethane (0.5 mL) with 3 A sieves was added sodium triacetoxyborohydride (0.055 g, 0.26 mmol). The mixture was stirred 16 hr, and then for 3 days, with additional aldehyde and sodium triacetoxyborohydride (3×1 eq each) added each day. The mixture was diluted with CHCl$_3$ (10 mL), NH$_4$OH (5 mL) and NaHCO$_3$ (5 mL), and stirred for 30 min. The layers were separated and the aqueous layer was extracted with CHCl$_3$ (2×20 mL). The combined organic extracts were washed with NaHCO$_3$, water and brine, dried over MgSO$_4$, filtered and concentrated. The product was purified by preparative HPLC (gradient of 20–90% aqueous methanol with 1% TFA) and the HCl salt formed to afford Example 300 as a light yellow solid (4 mg, 3%). MS (M+H)$^+$=462$^+$

EXAMPLE 301

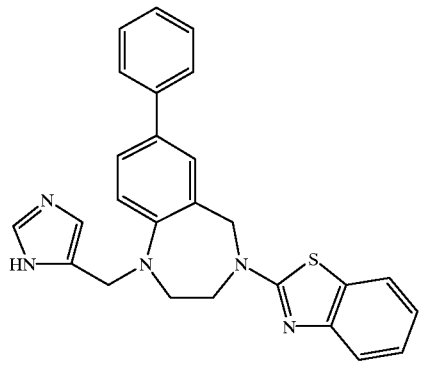

4-(2-Benzothiazolyl)-2,3,4,5-tetrahydro-1-(1H-imidazol-4-ylmethyl)-7-phenyl-1H-1,4-benzodiazepine, trihydrochloride.

A. 4-(2-Benzothiazolyl)-2,3,4,5-tetrahydro-7-phenyl-1H-1,4-benzodiazepine

Chlorobenzothiazole (0.41 mmol, 53 mL) was added to a solution of Compound B of Example 12 (0.34 mmol, 100 mg) and triethylamine (1.36 mmol, 190 mL) in DMF (1.0 mL) and the reaction was maintained at 60° C. After 1 hr, additional 2-chlorobenzothiazole (60 mL) was added. After 2 hrs, the reaction was quenched with 2N NaOH (10 mL), extracted (2×10 mL) with CH$_2$Cl$_2$, dried over Na$_2$SO$_4$ and concentrated to afford Compound A.

B. 4-(2-Benzothiazolyl)-2,3,4,5-tetrahydro-1-(1H-imidazol-4-ylmethyl)-7-phenyl-1H-1,4-benzodiazepine, trihydrochloride 4-Formylimidazole (0.68 mmol, 65 mg) and NaBH(OAc)$_3$ (0.51 mmol, 108 mg) was added to a solution of Compound A in 1:1 AcOH/(CH$_2$Cl)$_2$ (2 mL). The mixture was stirred for 1 hr, quenched with 5 mL sat'd NaHCO$_3$, diluted with 2N NaOH (50 mL) and extracted (2×25 mL) with 10% IPA/CH$_2$Cl$_2$. The combined organic extracts were dried over Na$_2$SO$_4$, evaporated and the residue purified by flash chromatography (94 mg, 50% yield in two steps). Lyophilization from 1N HCl afforded Example 301 as a gray solid. MS (M+H)+438

EXAMPLE 302

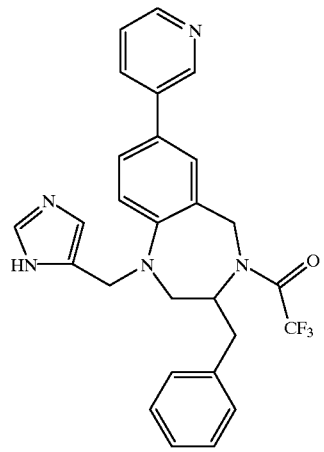

2,3,4,5-Tetrahydro-1-(1H-imidazol-4-ylmethyl)-3-(phenylmethyl)-7-(3-pyridinyl)-4-(trifluoroacetyl)-1H-1,4-benzodiazepine, trihydrochloride.

A. 2,3,4,5-Tetrahydro-3-(phenylmethyl)-7-bromo-1,4-bis(trifluoroacetyl)-1H-1,4-benzodiazepine (CF$_3$CO)$_2$O (7.25 mmol, 1.0 mL) was added to Compound B of Example 75 (1.61 mmol, 510 mg) and triethylamine (9.66 mmol, 1.35 mL) in CH$_2$Cl$_2$ (10 mL) at RT. After 30 minutes, the reaction was concentrated and purifed by flash chromatography to provide Compound A as a white solid (770 mg, 94%). MS (M−H)+507.

B. 2,3,4,5-Tetrahydro-1-(1H-imidazol-4-ylmethyl)-3-(phenylmethyl)-7-(3-pyridinyl)-4-(trifluoroacetyl)-1H-1,4-benzodiazepine, trihydrochloride Example 302 was prepared as a yellow solid from Compound A by the following sequence: Compound B of Example 296, using 3-tributylstannylpyridine; Compound C of Example 296; Compound D of Example 296. MS (M+H)+492.

EXAMPLE 303

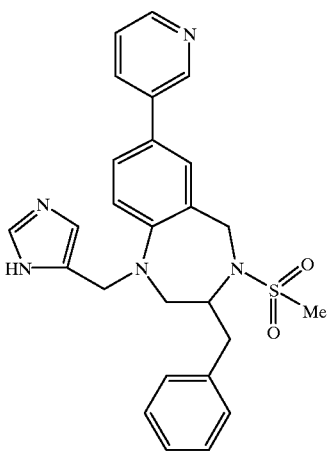

2,3,4,5-Tetrahydro-1-(1H-imidazol-4-ylmethyl)-4-(methylsulfonyl)-3-(phenylmethyl)-7-(3-pyridinyl)-1H-1,4-benzodiazepine, trihydrochloride.

A. 2,3,4,5-Tetrahydro-3-(phenylmethyl)-7-(3-pyridinyl)-1H-1,4-benzodiazepine

Solid KOH (150 mg) was added to a solution of 2,3,4,5-tetrahydro-3-(phenylmethyl)-7-(3-pyridinyl)-1,4-bis(trifluoroacetyl)-1 H-1,4-benzodiazepine (prepared as described in Compound B of Example 302; 100 mg, 0.2 mmol) in MeOH (4 mL). The solution was stirred at 50° C. for 3 hrs, concentrated, diluted in 2N NaOH (15 mL), and extracted (3×5 mL) with 10% IPA/CH$_2$Cl$_2$ to afford 60 mg of Compound A.

B. 2,3,4,5-Tetrahydro-1-(1H-imidazol-4-ylmethyl)-4-(methylsulfonyl)-3-(phenylmethyl)-7-(3-pyridinyl)-1H-1,4-benzodiazepine, trihydrochloride Methanesulfonyl chloride (0.39 mmol, 30 mL) was added to a mixture of Compound A (0.086 mmol, 27 mg) and DIEA (0.86 mmol, 150 mL) in CH$_2$Cl$_2$ (1.0 mL). The mixture was stirred for 1 hour, concentrated, diluted in 2N NaOH (10 mL) and extracted (2×5 mL) with 10% IPA/CH$_2$Cl$_2$. The solution was dried over Na$_2$SO$_4$ and concentrated. The residue was dissolved in 1:1 AcOH:(CH$_2$Cl)$_2$ (2 mL). 4-Formylimidazole (0.69 mmol, 66.3 mg) and NaBH(OAc)$_3$ (0.69 mmol, 146 mg) were added and the mixture was heated at 50° C. for 16 hrs, concentrated, diluted in 2N NaOH (20 mL)/sat'd NH$_4$OH (5mL) and extracted (2×5 mL) with 10% IPA/CH$_2$Cl$_2$. The combined organic extracts were concentrated and purified by prep HPLC (gradient of aqueous methanol with 0.1%TFA). Appropriate fractions were pooled, evaporated and the TFA salt was converted to the HCl salt with 1N HCl to afford Example 303 as a yellow solid (5 mg, yield in 3 steps: 9%). MS (M+H)+474

EXAMPLE 304

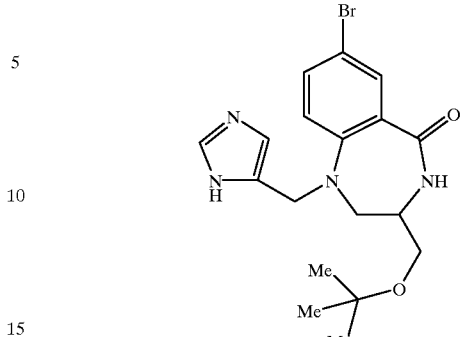

7-Bromo-3-[(1,1-dimethylethoxy)methyl]-1,2,3,4-tetrahydro-1-(1H-imidazol-4-ylmethyl)-5H-1,4-benzodiazepin-5-one.

A. 2-[(2-(fluorenylmethoxycarbonylamino)-3-(1,1-dimethylethoxy)propyl)amino]-5-bromo-benzoic acid A solution of D,L-Fmoc-(O-tBu)-serinal (prepared by LAH reduction of D,L-Fmoc-Ser(tBu)-N(Me)OMe; 18 g, 49 mmol), bromoanthranilic acid (19 g, 88 mmol) and glacial acetic acid (2 mL) in dry methanol (5 mL) and THF (40 mL) was stirred for 10 minutes followed by the addition of NaBH3CN (5.5 g,88 mmol) over 1 hour. Stirring was continued for 1 h. The precipitated product was filtered, washed with water and dried under high vacuum to give 25 g (89.4%) of Compound A as a white solid. (M+H)$^+$569.

B. 7-Bromo-3-[(1,1-dimethylethoxy)methyl]-1,2,3,4-tetrahydro-5H-1,4-benzodiazepin-5-one To a solution of Compound A (17g, 29 mmol) in THF (150 mL) was added diethylamine (30 mL, 290 mmol). The solution stirred for 2 h and concentrated. The resulting residue was dissolved in ethyl ether (100 mL) and 1 N aqueous hydrogen chloride (400 mL). A heavy white precipitate formed and was filtered, washed with hexanes/ethyl ether and dried under high vacuum. A portion of the resulting white solid (8.2 g, 24 mmol) with EDC (4.5 g, 24 mmol), HOBt (3.2 g, 24 mmol) and DIEA (12.4 mL, 71 mmol) in DMF (80 mL) was stirred for 16 h and poured into a solution of 10% aq LiCl (200 mL) and ethyl acetate (90 ml). The layers were separated. The organic layer was washed with 4×40 mL 10%aq LiCl, 4×1 N aq hydrogen chloride, 2×50 mL brine and 1×50 mL water. The solution was dried (Na2SO4), filtered and concentrated to give 7.2g (83% overall for the two steps) of Compound B as a white solid. (M+H)$^+$329.

C. 7-Bromo-3-[(1,1-dimethylethoxy)methyl]-1,2,3,4-tetrahydro-1-(1H-imidazol-4-ylmethyl)-5H-1,4-benzodiazepin-5-one Example 304 was prepared as a white solid in 40% yield from Compound B as described for Compound D of Example 224 (M+H)$^+$409.

EXAMPLE 305

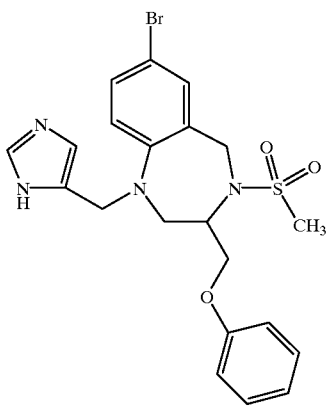

7-Bromo-2,3,4,5-tetrahydro-1-(1H-imidazol-4-ylmethyl)-4-(methylsulfonyl)-3-(phenoxymethyl)-1H-1,4-benzodiazepine, dihydrochloride.

A. 7-Bromo-3-[(1,1-dimethylethoxy)methyl]-1,2,3,4-tetrahydro-5H-1,4-benzodiazepine Compound B of Example 304 (0.5g, 1.5 mmol) was combined with 10 mL THF and 1M LAH in THF (4 mL, 4 mmol). The solution was refluxed for 16 h. Diethyl ether (40 mL) and 1 N NaOH (40 mL) were added followed by brine and the layers were separated. The organic layer was washed with 1 N aq NaOH, dried (Na2SO4), filtered and concentrated to give 413 mg (88%) of Compound A as a glassy solid. MS (M+H)$^+$314.

B. 7-Bromo-3-[(1,1-dimethylethoxy)methyl]-4-methanesulfonyl-1,2,3,4-tetrahydro-5H-1,4-benzodiazepine Compound B was prepared as a white solid in 71% yield from Compound A as described for Compound C of Example 224. MS (M+H-tBu)$^+$337.

C. 7-Bromo-3-(hydroxymethyl)-4-methanesulfonyl-1,2,3,4-tetrahydro-5H-1,4-benzodiazepine A solution of Compound B ( 1.1g, 2.8 mmol) in TFA (8 mL) and methylene chloride (8 mL) was stirred for 3 h and concentrated. Trituration with ethyl ether and drying under vacuum afforded 700 mg (74%) of Compound C as a white solid. MS (M+H)$^+$337.

D. 7-Bromo-2,3,4,5-tetrahydro-4-(methylsulfonyl)-3-(phenoxymethyl)-1H-1,4-benzodiazepine To a solution of Compound C (50 mg, 0.15 mmol) in methylene chloride (10 mL) was added 2,6-di-tert-butyl-4-methylpyridine (62 mg, 0.30 mmol). The solution was cooled to –40° C. under N2. Triflic anhydride (0.85 mL, 0.30 mmol) was added and the solution was stirred under N2 for 1 h at –40° C. In a separate flask, phenol (100 mg, 1.1 mmol) was added to a solution of sodium hydride (44 mg, 1.1 mmol, 60% dispersion in mineral oil, prewashed with hexanes) in THF (2.5 mL). The solution was stirred for 20 min at ambient temperature under N2 and was added quickly to the triflate solution. After stirring for 20 minutes, the solution was diluted with methylene chloride (40 mL) and washed with saturated aq sodium bicarbonate solution. The organic layer was dried (Na2SO4), filtered and concentrated to give a solid. This material was chromatographed on flash silica eluting with 1:1 ethyl acetate:hexanes to afford 30 mg (49%) of Compound D as an off-white solid. MS (M+H)$^+$411.

E. 7-Bromo-2,3,4,5-tetrahydro-1-(1H-imidazol-4-ylmethyl)-4-(methylsulfonyl)-3-(phenoxymethyl)-1H-1,4-benzodiazepine, dihydrochloride Example 305 was prepared from Compound D as a white solid in 27% yield as described for Compound D of Example 224. MS (M+H)$^+$491.

EXAMPLE 306

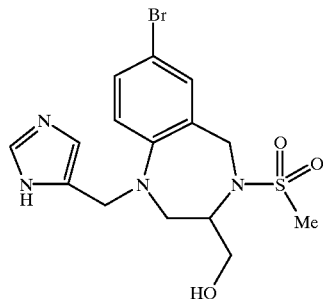

7-Bromo-2,3,4,5-tetrahydro-3-(hydroxymethyl)-1-(1H-imidazol-4-ylmethyl)-4-(methylsulfonyl)-1 H-1,4-benzodiazepine, monohydrochloride.

Example 306 was prepared as an offwhite solid in 12% yield from Compound C of Example 305 as described for Compound D of Example 224.

MS (M+H)$^+$417.

EXAMPLE 307

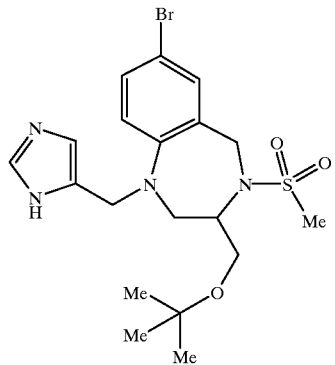

7-Bromo-3-[(1,1-dimethylethoxy)methyl]-2,3,4,5-tetrahydro-1-(1H-imidazol-4-ylmethyl)-4-(methylsulfonyl)-1H-1,4-benzodiazepine.

Example 307 was prepared as an offwhite solid in 23% yield from Compound B of Example 305 as described for Compound D of Example 224. MS (M+H)$^+$472.

EXAMPLE 308

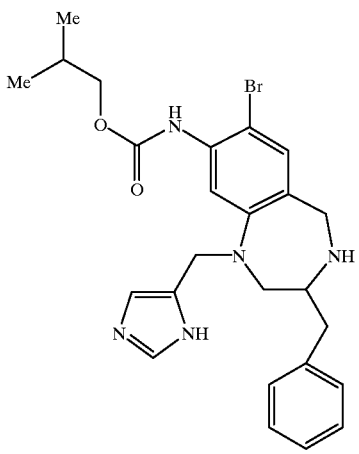

[7-Bromo-2,3,4,5-tetrahydro-1-(1H-imidazol-4-ylmethyl)-3-(phenylmethyl)-1 H-1,4-benzodiazepin-8-yl]carbamic acid, 2-methylpropyl ester, trihydrochloride.

A. 2,3,4,5-Tetrahydro-3-(phenylmethyl)-4-[(1,1-dimethylethoxy)-carbonyl]-8-amino-1H-1,4-benzodiazepine A solution of 2,3,4,5-tetrahydro-3-(phenylmethyl)-8-amino-1H-1,4-benzodiazepine (described in Compound B of Example 98, 1.0 g, 3.5 mmol) and Boc anhydride (0.77 g, 3.5 mmol) were stirred in THF (15 mL) under argon at RT. After 16 hrs, the mixture was concentrated. The residue was triturated with hexane and CHCl₃ to afford an olive grey solid. The filtrate was concentrated and triturated with hexane and CHCl₃, to afford additional olive green solid. The solids were combined and purified by flash silica gel chromatography (20% then 30% EtOAc in hexane) to afford Compound A (0.542 g, 40%). MS (M+H) 354⁺.

B. [2,3,4,5-Tetrahydro-3-(phenylmethyl)-4-[(1,1-dimethyl-ethoxy)-carbonyl]-1H-1,4-benzodiazepin-8-yl] carbamic acid, 2-methylpropyl ester To a solution of Compound A (115 mg, 0.3 mol) in dichloromethane (2 mL) under argon was added DIPEA (0.1 mL, 0.6 mmol) and isobutyl chloroformate dropwise. After 20 min, water (2 mL) and saturated NaHCO₃ were added and the mixture was extracted with chloroform (15 mL). The organic layer was dried (MgSO₄) and concentrated in vacuo to afford a solid which was purified by flash silica gel eluting with 20% EtOAc in hexanes to afford Compound B (125 mg, 92%) as a solid. MS (M+H)⁺=454⁺

C. [7-Bromo-2,3,4,5-tetrahydro-3-(phenylmethyl)-4-[(1,1-dimethylethoxy)-carbonyl]-1H-1,4-benzodiazepin-8-yl] carbamic acid, 2-methylpropyl ester To a solution of Compound B (100 mg, 0.22 mmol) in chloroform (2 mL) was added dropwise a solution of tetrabutylammonium tribromide (106 mg, 0.22 mmol) in chloroform (1 mL) over 5 min. After 10 min, the mixture was washed with sodium bisulfate solution (5 mL), dried (MgSO₄) and concentrated. Purification by silica gel column chromatography eluting with 20% EtOAc in hexanes afforded Compound C (110 mg, 94%) as a solid. MS (M+H)⁺=532⁺

D. [7-Bromo-2,3,4,5-tetrahydro-1-(1H-imidazol-4-ylmethyl)-3-(phenylmethyl)-4-[(1,1-dimethylethoxy)-carbonyl]-1H-1,4-benzo-diazepin-8-yl]carbamic acid, 2-methylpropyl ester To a solution of Compound C (100 mg, 0.19 mmol) and 4-formylimidazole (36 mg, 0.3 mmol) in a mixture of dichloromethane (2 mL) and acetic acid (0.6 mL) was added 3 A molecular sieves and the mixture was stirred for 15 min. Sodium triacetoxyborohydride (105 mg, 0.5 mmol) was added and the mixture was stirred overnight (18 hr). Another portion of the aldehyde and borohydride reagent (36 mg and 105 mg respectively) were added. After 4 hr., the mixture was filtered through celite and washed with chloroform. The filtrate was concentrated and treated with chloroform and NH₄OH (10 mL each). After stirring vigorously for 30 min, the organic layer was separated, dried (MgSO₄), and concentrated in vacuo to afford Compound D (110 mg, 86%). MS (M+H)⁺=612⁺

E. [7-Bromo-2,3,4,5-tetrahydro-1-(1H-imidazol-4-ylmethyl)-3-(phenylmethyl)-1H-1,4-benzodiazepin-8-yl] carbamic acid, 2-methyl-propyl ester, trihydrochloride To a solution of Compound D (105 mg, 0.17 mmol) in chloroform (1 mL) was added HCl in dioxane (3 mL, 4M solution). After 4 hr the mixture was concentrated. Chloroform (5 mL) was added and the mixture concentrated in vacuo to afford Example 308 as an off-white powder (110 mg, 100%). MS (M+H)⁺=512

EXAMPLE 309

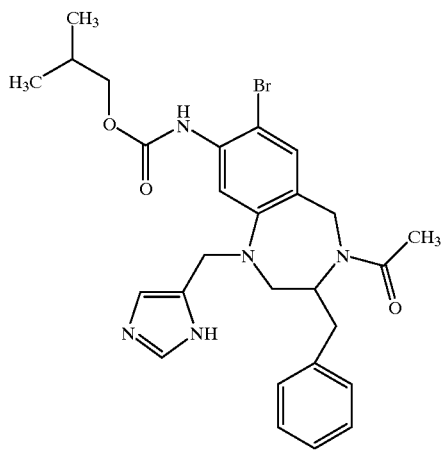

[4-Acetyl-7-bromo-2,3,4,5-tetrahydro-1-(1H-imidazol-4-ylmethyl)-3-(phenylmethyl)-1H-1,4-benzodiazepin-8-yl] carbamic acid, 2-methyl-propyl ester.

To a solution of Example 308 (18 mg, 0.03 mmol) in DMF (0.2 mL) were added pyridine (0.3 mL), acetic anhydride (0.2 mL), and DMAP (10 mg) and the mixture was stirred for 20 hr. Acetic anhydride (0.1 mL) was added and the mixture was stirred for 4 hr. The mixture was partitioned between chloroform and water (10 mL each). The organic layer was separated and washed with saturated CuSO₄ (2×10 mL), dried (K₂CO₃) and concentrated. Purification by RP HPLC eluting with 40–90% aqueous methanol containing 0.1% TFA on a C-18 column afforded a solid which was treated with 1N aqueous HCl (2×10 mL) followed by concentration. The solid was dissolved in water and lyophilized to afford Example 309 as a pale yellow solid (13 mg, 70%). MS (M+H)⁺=554

EXAMPLE 310

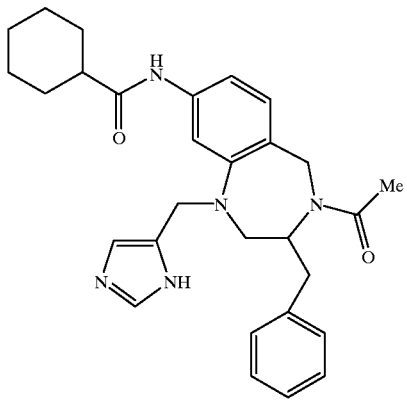

N-[4-Acetyl-2,3,4,5-tetrahydro-1-(1H-imidazol-4-ylmethyl)-3-(phenylmethyl)-1H-1,4-benzodiazepin-8-yl]cyclohexanecarboxamide, dihydrochloride.

Example 310 was prepared in 50% yield as a pale yellow solid from Compound C of Example 246 as described for Example 309. MS (M+H)$^+$=486

EXAMPLE 311

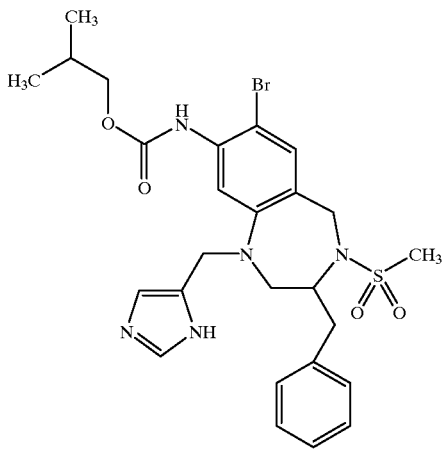

[7-Bromo-2,3,4,5-tetrahydro-1-(1H-imidazol-4-ylmethyl)-4-(methylsulfonyl)-3-(phenylmethyl)-1H-1,4-benzodiazepin-8-yl]carbamic acid, 2-methylpropyl ester.

To a solution of Example 308 (31 mg, 0.05 mmol) in DMF (0.2 mL) at RT were added TEA (0.2 mL), dichloromethane (0.2 mL), and methanesulfonyl chloride (0.024 mL, 0.3 mmol) and the mixture was stirred for 18 hr and partitioned between chloroform and saturated NaHCO$_3$ (10 mL each). The organic layer was separated, dried (K$_2$CO$_3$) and concentrated. Purification by RP HPLC eluting with 40–90% aqueous methanol containing 0.1% TFA on a C-18 column afforded a solid which was treated with 1N aqueous HCl (2×10 mL) followed by concentration. The solid was dissolved in water and lyophilized to afford Example 311 as a pale yellow solid (13 mg, 70%). MS (M+H)$^+$=590

EXAMPLE 312

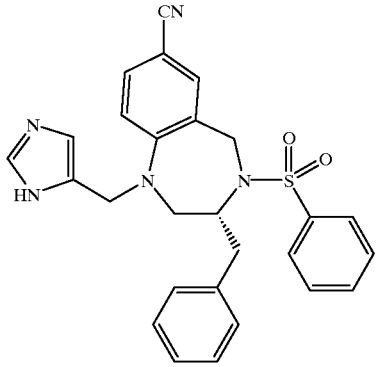

(R)-2,3,4,5-Tetrahydro-1-(1H-imidazol-4-ylmethyl)-4-(phenylsulfonyl)-3-(phenylmethyl)-1H-1,4-benzodiazepine-7-carbonitrile, monohydrochloride.

A. (R)-2,3,4,5-Tetrahydro-4-(phenylsulfonyl)-3-(phenylmethyl)-1H-1,4-benzodiazepine-7-carbonitrile To a stirred and chilled (0°, ice bath) solution of Compound C of Example 248 (45 g, 171.54 mmole) containing DIEA (50 ml, 287 mmol) in anhydrous CH$_2$Cl$_2$ (1 L) under argon was added dropwise a solution of benzenesulfonyl chloride (30 ml, 235 mmol) in anhydrous CH$_2$Cl$_2$ (50ml). After the addition was complete, the mixture was warmed to room temperature and stirred for 4 hr. The solution was diluted with CH$_2$Cl$_2$ (500ml), washed with water (2×250ml), 10% KHSO$_4$ (750ml), saturated NaHCO$_3$ and brine, which was crystallized from EtOAc-hexane to give 65g (94%) of Compound A as solid. MS (M–H)–402.

$^{13}$C-NMR (CDCl$_3$) 40.22, 46.00, 47.23, 61.36, 116.34, 119.55, 120.99, 126.99, 127.11, 128.10, 129.76, 129.40, 131.97, 132.09, 134.03, 136.77, 139.53, 150.77 ppm B. (R)-2,3,4,5-Tetrahydro-1-(1H-imidazol-4-ylmethyl)-4-(phenylsulfonyl)-3-(phenylmethyl)-1H-1,4-benzodiazepine-7-carbonitrile, monohydrochloride To a stirred solution of Compound A (64.3 g, 159 mmol) and 4-formylimidazole (15.3 g, 159 mmol) in a mixture of HOAc (glacial, 150 ml) and 1,2-dichloroethane (720 ml) under argon was added sodium triacetoxyborohydride (33.8 g, 159 mmol). The mixture was heated to 60° C. for 6 hr. Additional 4-formylimidazole (15.3 g) and sodium triacetyborohydride (33.8 g) were added. The addition was repeated three times until HPLC showed 7% unreacted Compound A. The resulting solution was cooled to room temperature. MeOH (250 ml) was slowly added and the mixture was stirred for 30 minutes and evaporated. The residue was azeotroped with toluene (2×500ml). The gummy residue was diluted with saturated NaHCO$_3$ solution and stirred. Solid NaHCO$_3$ was added until the foaming ceased. The slurry was extracted with EtOAc (3×1 L). The combined EtOAc extracts were washed with saturated NaHCO$_3$ solution and brine, dried over anhydrous MgSO$_4$ and evaporated to give a foam. This was flash-chromatographed on a column of silica gel (E. Merck 230–400 mesh, 1.6 kg) eluting with EtOAc-MeOH (95:5) to give the free base of Example 312. This was dissolved in EtOAc (1.0 L), treated with a solution of 1.0N HCl in Et$_2$O (250 ml), and the mixture stirred for 30 minutes and filtered. The solid was washed with EtOAc (500 ml) and Et$_2$O (500 ml) and dried in high vacuum at 50° overnight to give 58 g (70%) of Example 312 as a solid. MS (M+H)$^+$=484

Analysis calculated for C$_{27}$H$_{25}$N$_5$O$_2$S·0.7 H$_2$O·1 HCl ·0.05 EtOAc·0.03 ether.

Calc'd: C, 60.85; H, 5.25; N, 12.99; Cl, 6.57; S, 5.94.
Found: C, 60.85; H, 5.19; N, 13.05; Cl, 6.60; S, 5.95.

EXAMPLE 313

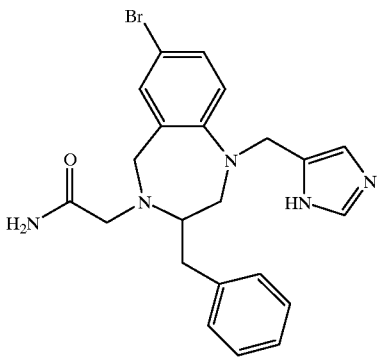

7-Bromo-1,2,3,5-tetrahydro-1-(1H-imidazol-4-ylmethyl)-3-(phenylmethyl)-4H-1,4-benzodiazepine-4-acetamide.

A. 7-Bromo-1,2,3,5-tetrahydro-3-(phenylmethyl)-4H-1,4-benzodiazepine-4-acetamide A mixture of Compound B of Example 75 (250 mg, 0.74 mmol,), DIEA (0.067 mL, 0.74 mmol) and 2-chloroacetamide (69 mg, 0.74 mmol) in THF (10 mL) was stirred under argon at room temperature for 8 hours. The mixture was partitioned in brine (50 ml) and ethyl acetate (50 mL), the aqueous layer was extracted with ethyl acetate (2×50 mL), and the combined organic layers were dried (MgSO$_4$) and concentrated to provide Compound A as a clear oil (260 mg, 94 %).

B. 7-Bromo-1,2,3,5-tetrahydro-1-(1H-imidazol-4-ylmethyl)-3-(phenylmethyl)-4H-1,4-benzodiazepine-4-acetamide Example 313 was prepared as a white solid in 38% yield from Compound A as described in Compound D of Example 1, with stirring for 18 hours and purification by preparative HPLC. MS (M+H)$^+$=454

Analysis calculated for C$_{22}$H$_{24}$N$_5$OBr·0.3 H$_2$O·1.5 TFA.
Calc'd: C, 45.81; H, 3.95; N, 10.35; Br, 11.81; F, 16.01.
Found: C, 45.43; H, 3.80; N, 9.96; Br, 11.50; F, 15.74.

EXAMPLE 314

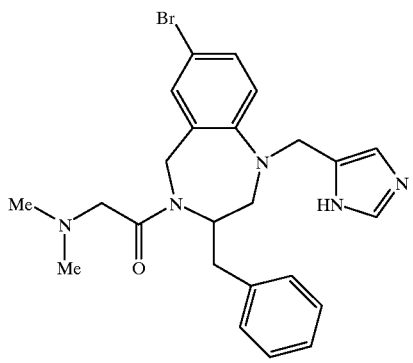

7-Bromo-4-[(dimethylamino)acetyl]-2,3,4,5-tetrahydro-1-(1H-imidazol-4-ylmethyl)-3-(phenylmethyl)-1H-1,4-benzodiazepine.

A. 7-Bromo-4-(bromoacetyl)-2,3,4,5-tetrahydro-3-(phenylmethyl)-1H-1,4-benzodiazepine Compound A was prepared as a clear oil from Compound B of Example 75 and bromoacetyl bromide as described for Compound A of Example 313, with purification by using flash chromatography (silica, 3:1 hexanes: ethyl acetate)

B. 7-Bromo-4-[(dimethylamino)acetyl]-2,3,4,5-tetrahydro-3-(phenylmethyl)-1H-1,4-benzodiazepine To a solution of Compound A (126 mg, 0.29 mmol) in THF (2 mL) was added dimethyl amine (2 mL, 1 M in THF). The solution was stirred at room temperature in a sealed pressure tube for 7 hours, poured into water and extracted with ethyl acetate. The solution was dried (MgSO$_4$) and concentrated to afford Compound B as an oil(110mg,94%).

C. 7-Bromo-4-[(dimethylamino)acetyl]-2,3,4,5-tetrahydro-1-(1H-imidazol-4-ylmethyl)-3-(phenylmethyl)-1H-1,4-benzodiazepine Compound C was prepared as a white solid in 65% yield from Compound B as described for Compound B of Example 313. MS (M+H)$^+$=483

Analysis calculated for C$_{24}$H$_{28}$N$_5$OBr·1.2 H$_2$O·2.1 TFA.

Calc'd: C, 45.56; H, 4.41; N, 9.42; Br, 10.75; F, 16.10.

Found: C, 45.75; H, 4.02; N, 9.19; Br, 11.14; F, 16.08.

EXAMPLE 315

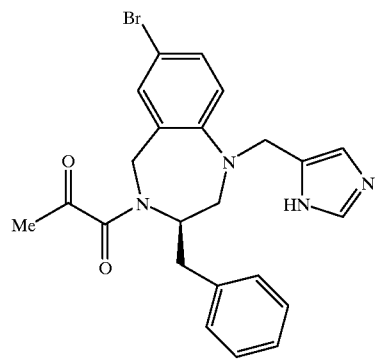

(R)-7-Bromo-4-(1,2-dioxopropyl)-2,3,4,5-tetrahydro-1-(1H-imidazol-4-ylmethyl)-3-(phenylmethyl)-1H-1,4-benzodiazepine, trifluoroacetate.

Example 315 was prepared as a white solid in 25% overall yield from Compound B of Example 224 by an EDC/HOBt mediated coupling of pyruvic acid in DMF, with purification by flash chromatography (silica, 4:1 hexanes: ethyl acetate), followed by the method of Compound B of Example 313. MS (M+H)$^+$=468

Analysis calculated for C$_{23}$H$_{23}$N$_4$O$_2$Br·0.8 H$_2$O·0.95 TFA.

Calc'd: C, 50.68; H, 4.36; N, 9.49; Br, 13.54; F, 9.18.

Found: C, 50.37; H, 4.04; N, 9.23; Br, 14.07; F, 9.55.

EXAMPLE 316

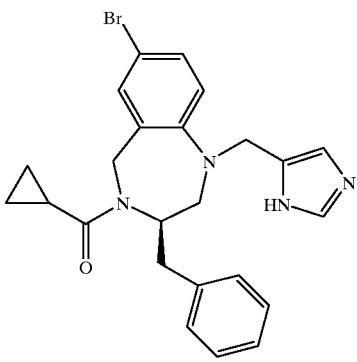

(R)-7-Bromo-4-(cyclopropylcarbonyl)-2,3,4,5-tetrahydro-1-(1H-imidazol-4-ylmethyl)-3-(phenylmethyl)-1H-1,4-benzodiazepine, trifluoroacetate.

Example 316 was prepared as a white solid in 6% overall yield from Compound B of Example 224 and cyclopropanecarboxylic acid by the two step procedure described in Example 315, with no purification of the intermediate. MS (M+H)$^+$=466

Analysis calculated for $C_{24}H_{25}N_4OBr \cdot 1.0\ H_2O \cdot 0.8$ TFA.
Calc'd: C, 52.59; H, 4.68; N, 9.43; Br, 13.46; F, 9.60.
Found: C, 52.62; H, 4.37; N, 9.46; Br, 12.23; F, 9.46.

EXAMPLE 317

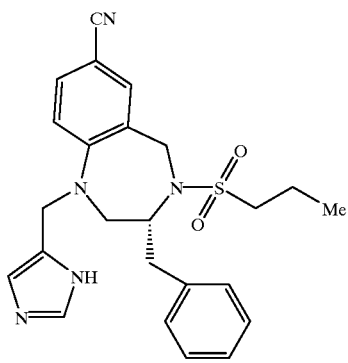

(R)-7-Cyano-2,3,4,5-tetrahydro-1-(1H-imidazol-4-ylmethyl)-3-(phenylmethyl)-4-(propylsulfonyl)-1H-1,4-benzodiazepine, monohydrochloride.

A. (R)-7-Cyano-2,3,4,5-tetrahydro-3-(phenylmethyl)-4-(propylsulfonyl)-1H-1,4-benzodiazepine n-Propylsulfonylchloride (3.4 ml, 34 mmol) was added dropwise to a solution of Compound C of Example 248 (6.0 g, 23 mmol) and DIEA (12 ml, 68 mmol) in methylene chloride (120 ml) at −78° C. The mixture was allowed to warm to room temperature and stirred for 16h, quenched with 10% NaHCO$_3$ (50 ml) and extracted with methylene chloride (3×75 ml). The combined organic layers were dried (Na$_2$SO$_4$), filtered and concentrated under vacuum. The residue was purified by flash chromatography (2/1 hexane/ethyl acetate) to afford Compound A (7.1 g, 85%) as a yellow solid. MS (M+H)$^{+370}$ Analysis calculated for $C_{20}H_{23}N_3O_2S \cdot 0.19\ H_2O$.
Calc'd: C, 64.42; H, 6.32; N, 11.27.
Found: C, 64.43; H, 6.25; N, 11.09.

B. (R)-7-Cyano-2,3,4,5-tetrahydro-1-(1H-imidazol-4-ylmethyl)-3-(phenylmethyl)-4-(propylsulfonyl)-1 H-1,4-benzodiazepine, monohydrochloride 4-Formylimidazole (3.1 g, 33 mmol) was added to a solution of Compound A (6.0 g, 16 mmol) and 3A molecular sieves in 1/1 CH$_2$Cl$_2$:acetic acid (80 ml) and the mixture was stirred at 70° C. for 1 h. Sodium triacetoxyborohydride (6.9 g, 33 mmol) was added and the mixture was stirred at 70° C. for 30 minutes. 4-Formylimidazole (3.1 g, 33 mmol, 2.0 eqiuv) was again added to the mixture and stirring was continued at 70° C. for 1 h. Sodium triacetoxyborohydride (6.9 g, 33 mmol, 2.0 equiv) was added and the mixture was stirred at 70° C. for 30 minutes. Addition of more formylimidazole and hydride was repeated eight times. The mixture was cooled to room temperature, diluted with methylene chloride (200 ml), filtered and the filtrate concentrated under vacuum. The residue was diluted with 25% NH$_4$OH (200 ml). The solution was stirred at room temperature for 10 minutes, extracted with CH$_2$Cl$_2$ (2×200 ml) and the combined organic extracts were dried (MgSO$_4$), filtered and concentrated. The residue was purified by preparative HPLC (gradient of aq MeOH with 0.1% TFA) and the appropriate fractions were isolated and concentrated under vacuum. The residue was dissolved in CH$_3$OH (20 ml) and 1N HCl (40 ml) and concentrated under vacuum and this procedure was repeated 3×. The residue was dissolved in CH$_3$CN (20 ml) and 1N HCl (20 ml) and lyophilized to afford Example 317 (6.8 g, 74 %) as a white solid., mp: 140–151° C. MS (M+H)$^+$450

Analysis calculated for $C_{24}H_{27}N_5O_2S \cdot 1.1\ HCl \cdot 0.59\ H_2O$.

Calc'd: C, 57.62; H, 5.90; N, 14.00; Cl, 7.79; S, 6.41.

Found: C, 57.61; H, 5.70; N, 13.97; Cl, 7.62; S, 6.44.

[a]D=+201° (c=1.41, CH$_3$OH)

EXAMPLE 318

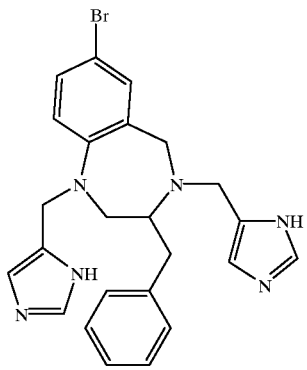

7-Bromo-2,3,4,5-tetrahydro-1,4-bis(1H-imidazol-4-ylmethyl)-3-(phenylmethyl)-1H-1,4-benzodiazepine, dihydrochloride.

Example 318 was prepared in 55% yield as a white solid from Compound B of Example 75 as described for Compound D of Example 1, using 3 equivalents of formylimidazole and stirring for 2 hours. MS (M+H)$^+$=477

EXAMPLE 319

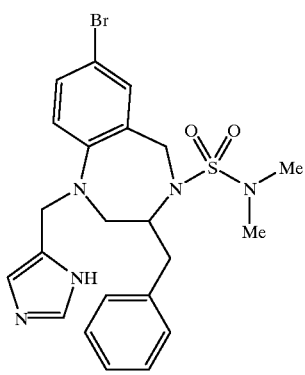

7-Bromo-1,2,3,5-tetrahydro-1-(1 H-imidazol-4-ylmethyl)-N,N-dimethyl-3-(phenylmethyl)-4H-1,4-benzodiazepine-4-sulfonamide, monohydrochloride.

A. 7-Bromo-1,2,3,5-tetrahydro-N,N-dimethyl-3-(phenylmethyl)-4H-1,4-benzodiazepine-4-sulfonamide A stirred solution of Compound B of Example 75 (100 mg, 0.32 mmol), N,N-dimethylsulfamoyl chloride (50 mg, 0.35 mmol) and DIPEA (61 uL, 0.35 mmol) in acetonitrile in the presence of a catalytic amount of DMAP was heated at reflux for 18 h. The mixture was partitioned between ethyl acetate and 1 N HCl solution. The organic layer was separated, dried (MgSO$_4$) and concentrated. The residue was purified by flash chromatography (1:2, hexanes:ethyl acetate) to give Compound A as an oil.

B. 7-Bromo-1,2,3,5-tetrahydro-1-(1H-imidazol-4-ylmethyl)-N,N-dimethyl-3-(phenylmethyl)-4H-1,4-benzodiazepine-4-sulfonamide, monohydrochloride Example 319 was prepared in 92% yield as a solid from Compound A as described for Compound D of Example 224. MS (M+H)$^+$504

Analysis calculated for C$_{22}$H$_{26}$N$_5$O$_2$SBr·1.0 HCl·0.5 ether.
Calc'd: C, 49.88; H, 5.58; N, 12.12; Br, 13.82; S, 5.55.
Found: C, 49.90; H, 5.42; N, 12.13; Br, 13.22; S, 6.44.

EXAMPLE 320

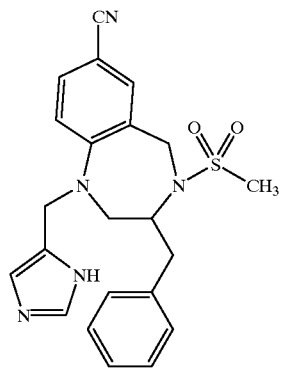

2,3,4,5-Tetrahydro-1-(1H-imidazol-4-ylmethyl)-4-(methylsulfonyl)-3-(phenylmethyl)-1H-1,4-benzodiazepine-7-carbonitrile, monohydrochloride.

Example 320 was prepared as a yellow solid from Compound B of Example 75 as described in the following sequence: Compound C of Example 224, Compound A of Example 225, and Compound B of Example 225.
MS (M+H)$^+$422

Analysis calculated for C$_{22}$H$_{23}$N$_5$O$_2$S·1.0 HCl·0.2 CH$_3$OH.
Calc'd: C, 57.42; H, 5.38; N, 15.08; Cl, 7.63; S, 6.90.
Found: C, 57.12; H, 5.58; N, 11.94; Cl, 7.77; S, 4.95.

EXAMPLE 321

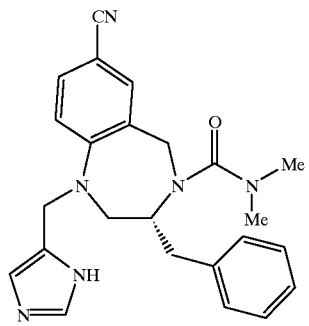

(R)-7-Cyano-1,2,3,5-tetrahydro-1-(1H-imidazol-4-ylmethyl)-N,N-dimethyl-3-(phenylmethyl)-4H-1,4-benzodiazepine-4-carboxamide, monohydrochloride.

Example 321 was prepared as a yellow solid from Compound C of Example 248 by the following sequence: Compound A of Example 319, using dimethylcarbamoyl chloride and stirring at 60° C. for 2 h and chromatography with 1:1 hexanes:ethyl acetate; Compound B of Example 225. mp: 147–150° C. MS (M+H)$^+$=415

Analysis calculated for C$_{24}$H$_{26}$N$_6$O·0.74 H$_2$O·1.0 HCl.
Calc'd: C, 62.09; H, 6.18; N, 18.10; Cl, 7.61.
Found: C, 62.09; H, 6.04; N, 17.86; Cl, 7.91.
[a]D20: +244° (c =0.24, MeOH).

EXAMPLE 322

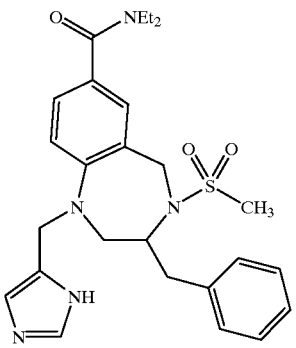

N,N-Diethyl-2,3,4,5-tetrahydro-1-(1H-imidazol-4-ylmethyl)-4-(methylsulfonyl)-3-(phenylmethyl)-1H-1,4-benzodiazepine-7-carboxamide, monohydrochloride.

A. 2,3,4,5-tetrahydro-4-(methylsulfonyl)-3-(phenylmethyl)-1H-1,4-benzodiazepine-7-carboxylic acid A solution of Compound A of Example 225 (200 mg, 0.59 mmol) in ethanol in the presence of 1ON NaOH solution (4 mL, 40 mmol) was heated at reflux for 5 h. The mixture was cooled to room temperature, concentrated and aqueous HCl was added to adjust the pH to 3. The mixture was concentrated. The residue was partitioned between 1N HCl and ethyl acetate. The organic layer was separated, dried over MgSO4 and concentrated. The residue was triturated with methanol to give Compound A as a solid (156 mg, 73%).

B. N,N-Diethyl-2,3,4,5-tetrahydro-4-(methylsulfonyl)-3-(phenylmethyl)-1H-1,4-benzodiazepine-7-carboxamide To a solution of Compound A (50 mg, 0.14 mmol) in DMF was added diethylamine (50 uL), followed by catalytic amounts of HOBT and DMAP and then EDC (30 mg). The mixture was stirred at room temperature for 2 days and partitioned between ethyl acetate and 1N HCl solution. The organic layer was separated, washed with sat. NaHCO3 solution, dried MgSO4, concentrated to give Compound B as an oil.

C. N,N-Diethyl-2,3,4,5-tetrahydro-1-(1H-imidazol-4-ylmethyl)-4-(methylsulfonyl)-3-(phenylmethyl)-1H-1,4-benzodiazepine-7-carboxamide, monohydrochloride Compound C was prepared from Compound B as described for Compound B of Example 225. MS (M+H)$^+$=496.

EXAMPLE 323

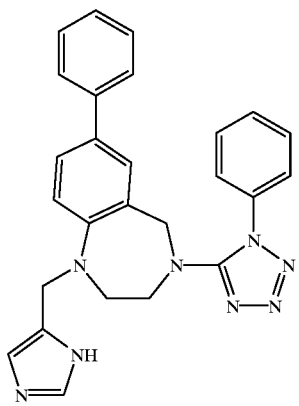

2,3,4,5-Tetrahydro-1-(1H-imidazol-4-ylmethyl)-7-phenyl-4-(1-phenyl-1H-tetrazol-5-yl)-1H-1,4-benzodiazepine, monohydrochloride.

A. 2,3,4,5-Tetrahydro-7-phenyl-4-(1-phenyl-1H-tetrazol-5-yl)-1H-1,4-benzodiazepine A solution of Compound B of Example 12 (100 mg, 0.45 mmol) in DMF (2 mL) was treated with 5-chloro-1-phenyltetrazole (100 mg, 0.55 mmol) in the presence of potassium carbonate (60 mg). The mixture was stirred at 60° C. for 18 h and partitioned between ethyl acetate and sat. NH4Cl solution. The organic layer was washed with sat. NaHCO3 solution, dried (MgSO4), and concentrated. The residue was purified by column chromatography to give Compound A as a white solid (75 mg, 45%), mp: 150–151° C.

B. 2,3,4,5-Tetrahydro-1-(1H-imidazol-4-ylmethyl)-7-phenyl-4-(1-phenyl-1H-tetrazol-5-yl)-1H-1,4-benzodiazepine, monohydrochloride Compound B was prepared as a yellow solid from Compound A as described for Compound D of Example 1, mp 158° C.

Analysis calculated for C$_{26}$H$_{24}$N$_8$·0.5 CH$_3$OH·2.5 HCl.

Calc'd: C, 57.28; H, 5.17; N, 20.16.

Found: C, 57.62; H, 5.12; N, 19.93.

EXAMPLE 324

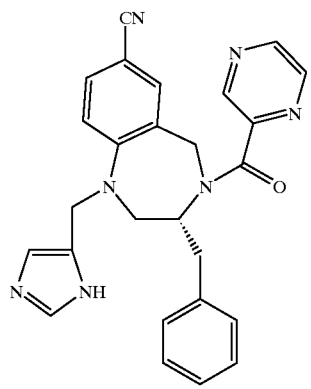

(R)-7-Cyano-2,3,4,5-tetrahydro-1-(1H-imidazol-4-ylmethyl)-3-(phenylmethyl)-4-(2-pyrazinylcarbonyl)-4H-1,4-benzodiazepine, monohydrochloride.

Example 324 was prepared as a yellow solid from Compound C of Example 248 and pyrazinecarboxylic acid by the following sequence: Compound B of Example 322, with stirring for 18 hours and purification by flash chromatography (3:2, ethyl acetate: hexanes); Compound B of Example 225. MS (M+H)$^+$=450.

Analysis calculated for C$_{26}$H$_{23}$N$_7$O·1.2 H$_2$O·1.0 HCl·1.2 toluene.

Calc'd: C, 66.09; H, 5.78; N, 16.35; Cl, 5.91.
Found: C, 65.83; H, 5.45; N, 16.11; Cl, 5.96.

EXAMPLE 325

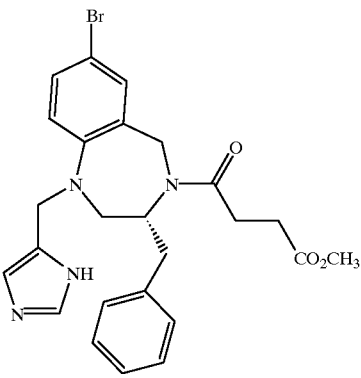

(R)-4-[7-Bromo-2,3,4,5-tetrahydro-1-(1H-imidazol-4-ylmethyl)-3-(phenylmethyl)-4H-1,4-benzodiazepin-4-yl]-4-oxobutanoic acid, methyl ester, monohydrochloride.

A. (R)-4-[7-Bromo-2,3,4,5-tetrahydro-3-(phenylmethyl)-4H-1,4-benzodiazepin-4-yl]-4-oxobutanoic acid, methyl ester A stirred solution of Compound B of Example 224 (100 mg, 0.31 mmol) was treated with succinic anhydride (40 mg, 0.40 mmol) in ethyl acetate. The mixture was stirred at room temperature for 18 h and partitioned with 1N HCl solution. The organic layer was dried (MgSO4), and concentrated to afford Compound A.

B. (R)-4-[7-Bromo-2,3,4,5-tetrahydro-1-(1H-imidazol-4-ylmethyl)-3-(phenylmethyl)-4H-1,4-benzodiazepin-4-yl]-4-oxobutanoic acid, methyl ester, monohydrochloride Compound B was prepared as a yellow solid from Compound A as described for Compound B of Example 225. MS (M+H)$^+$=511.

EXAMPLE 326

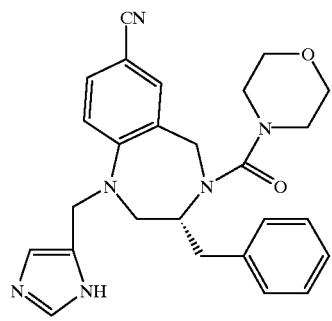

(R)-7-Cyano-2,3,4,5-tetrahydro-1-(1H-imidazol-4-ylmethyl)-4-(4-morpholinylcarbonyl)-3-(phenylmethyl)-1H-1,4-benzodiazepine, monohydrochloride.

Example 326 was prepared as a yellow solid from Compound C of Example 248 and morpholinocarbamoyl chloride as described for Example 321. MS (M+H)$^+$=457.

Analysis calculated for $C_{26}H_{28}N_6O_2 \cdot 0.8\ H_2O \cdot 1.2\ HCl \cdot 0.2$ ether.

Calc'd: C, 60.79; H, 6.24; N, 15.87, Cl, 8.03.

Found: C, 60.85; H, 6.02; N, 15.56; Cl, 8.06.

EXAMPLE 327

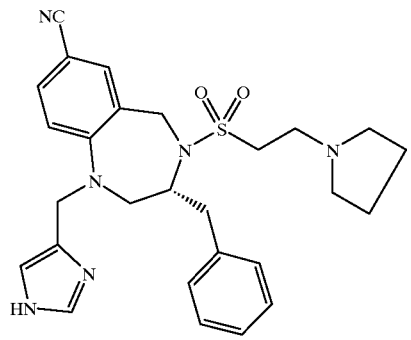

(R)-7-Cyano-2,3,4,5-tetrahydro-1-(1H-imidazol-4-ylmethyl)-3-(phenylmethyl)-4-[[2-(1 pyrrolidinyl)ethyl]sulfonyl]-1H-1,4-benzodiazepine, dihydrochloride.

Example 327 was prepared in 46% yield as a light yellow solid from Compound A of Example 250 and pyrrolidine as described for Compound B of Example 250. MS (M+H)$^+$=505.

EXAMPLE 328

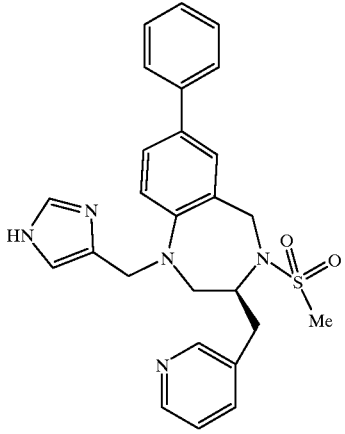

(S)-2,3,4,5-Tetrahydro-1-(1H-imidazol-4-ylmethyl)-4-(methylsulfonyl)-7-phenyl-3-(3-pyridinylmethyl)-1 H-1,4-benzodiazepine, dihydrochloride.

Example 328 was prepared as an off white solid from L-(3-pyridyl)alanine and Compound B of Example 226 by the following sequence: Compound C of Example 226; Compound D of Example 226; Compound B of Example 264; Compound C of Example 264. MS (M+H)$^+$474.

EXAMPLE 329

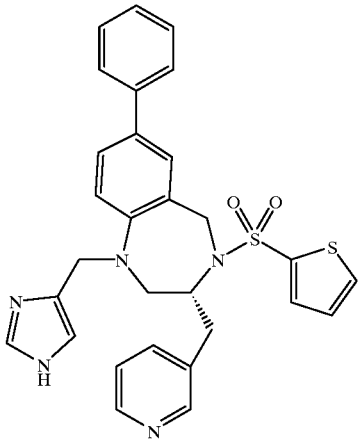

(R)-2,3,4,5-Tetrahydro-1-(1H-imidazol-4-ylmethyl)-7-phenyl-3-(3-pyridinylmethyl)-4-(2-thienylsulfonyl)-1 H-1,4-benzodiazepine, dihydrochloride.

Example 329 was prepared as an off white solid from (R)-2,3,4,5-tetrahydro-7-phenyl-3-(3-pyridinylmethyl)-1H-1,4-benzodiazepine (prepared as described in Example 273) and 2-thiophenesulfonyl chloride by the following sequence: Compound C of Example 224; Compound D of Example 224. MS (M+H)$^+$542.

EXAMPLE 330

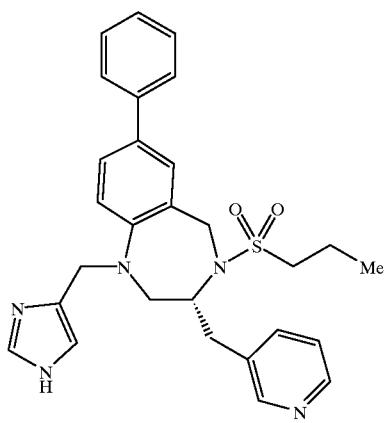

(R)-2,3,4,5-Tetrahydro-1-(1H-imidazol-4-ylmethyl)-7-phenyl-4-(propylsulfonyl)-3-(3-pyridinylmethyl)-1 H-1,4-benzodiazepine, monohydrochloride.

A. (R)-2,3,4,5-Tetrahydro-7-phenyl-4-(propylsulfonyl)-3-(3-pyridinylmethyl)-1 H-1,4-benzodiazepine To a stirred solution of (R)-2,3,4,5-tetrahydro-7-phenyl-3-(3-pyridinylmethyl)-1H-1,4-benzodiazepine (prepared as described in Example 273; 200 mg, 0.63 mmol) and DIEA (0.33 mL, 1.9 mmol) was added propanesulfonyl chloride (0.11 mL, 0.94 mmol) at −60° C. under argon. The mixture was kept at 4° C. for two days, quenched with aqueous saturated NaHCO3 solution (10 mL) and extracted with CH2Cl2 (3×10 mL). The combined extracts were dried (Na2SO4) and evaporated under reduced pressure to afford Compound A as a yellow solid. MS (M+H)+422.

B. (R)-2,3,4,5-Tetrahydro-1-(1H-imidazol-4-ylmethyl)-7-phenyl-4-(propylsulfonyl)-3-(3-pyridinylmethyl)-1H-1,4-benzodiazepine, monohydrochloride Compound B was prepared as a yellow solid from Compound A in 45% yield as described for Compound D of Example 224, with purification by preparative HPLC (gradient of aqueous methonaol with 0.1% TFA). The HCl salt was prepared by adding 1N HCl in ether to a solution of the TFA salt in ethyl acetate and evaporation. MS: (M+H)+ 502

EXAMPLE 331

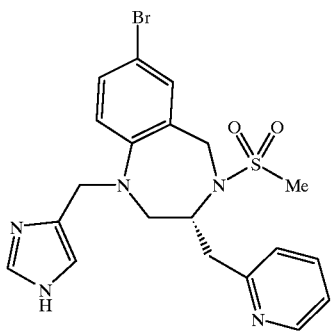

(R)-7-Bromo-2,3,4,5-tetrahydro-1-(1H-imidazol-4-ylmethyl)-4-(methylsulfonyl)-3-(2-pyridinylmethyl)-1H-1,4-benzodiazepine, monohydrochloride.

Example 331 was prepared as a yellow solid from D-(2-pyridyl)alanine and Compound B of Example 226 using the following sequence: Compound C of Example 226; Compound D of Example 226, with refluxing for 48 hr; Compound B of Example 264, with purification by preparative HPLC using a gradient of aqueous methanol with 0.1% TFA; Compound C of Example 264. MS (M+H)+478.

EXAMPLE 332

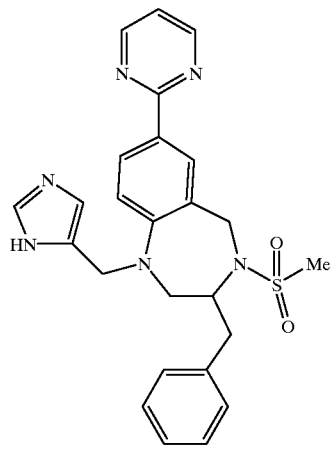

2,3,4,5-Tetrahydro-1-(1H-imidazol-4-ylmethyl)-4-(methylsulfonyl)-3-(phenylmethyl)-7-(2-pyrimidinyl)-1H-1,4-benzodiazepine,dihydrochloride.

Example 332 was prepared as a yellow solid from Compound A of Example 231 and 2-stannylpyrimidine as described for Compound B of Example 231 and Compound C of Example 231. MS (M+H)+475.

EXAMPLE 333

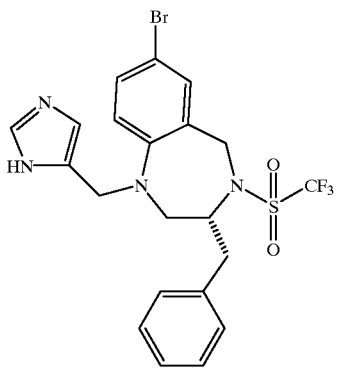

(R)-7-Bromo-2,3,4,5-tetrahydro-1-(1H-imidazol-4-ylmethyl)-3-(phenylmethyl)-4-[(trifluoromethyl)sulfonyl]-1 H-1,4-benzodiazepine, monohydrochloride.

Example 333 was prepared in 44% yield as an off-white solid from Compound B of Example 224 as described for Compound C of Example 224 (using trifluoromethanesulfonyl anhydride instead of methanesulfonyl chloride) and Compound D of Example 224. MS (M+H)+528.

EXAMPLE 334

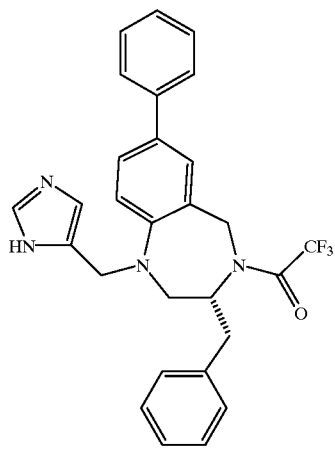

(R)-2,3,4,5-Tetrahydro-1-(1H-imidazol-4-ylmethyl)-7-phenyl-3-(phenylmethyl)-4-(trifluoroacetyl)-1H-1,4-benzodiazepine, monohydrochloride.

Example 334 was prepared in 26% yield as a white solid from Compound D of Example 226 by reaction with trifluoroacetic anhydride and DIEA in methylene chloride, followed by the method of Compound C of Example 264, with purification by preparative HPLC (gradient of aqueous methonaol with 0.1% TFA). The HCl salt was prepared by lyophilization twice from 1N HCl. MS (M+H)$^+$491.

EXAMPLE 335

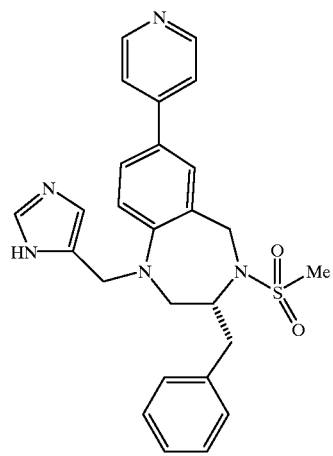

(R)-2,3,4,5-Tetrahydro-1-(1H-imidazol-4-ylmethyl)-4-(methylsulfonyl)-3-(phenylmethyl)-7-(4-pyridinyl)-1 H-1, 4-benzodiazepine, dihydrochloride.

A. (R)-2,3,4,5-Tetrahydro-3-(phenylmethyl)-7-(4-pyridinyl)-1H-1,4-benzodiazepin-2,5-dione A mixture of Compound A of Example 224 (55.6 mmol, 19.2 g), 4-stannylpyridine (111 mmol, 40.9 g) and Pd(PPh$_3$)$_4$ (8.24 mmol, 9.6 g) in toluene (2000 mL) was degassed and heated to 110° C. for 16 hrs. The reaction was concentrated, diluted with 1:1 ether/hexanes and filtered. The solid was washed with 500 mL of 1:1 ether/hexanes to afford 16.7 g of Compound A. The combined filtrate was concentrated and filtered to yield 5.8 g of Compound A (total yield 80%). MS (M+H)+344.

B. (R)-2,3,4,5-Tetrahydro-3-(phenylmethyl)-7-(4-pyridinyl)-1H-1,4-benzodiazepine A suspension of Compound A (16.7, 32 mmol) in THF (250 mL) was treated with BH$_3$·THF (1.0 M in THF). The mixture was heated to reflux for 12 hrs and quenched by the slow addition of 6N HCl (500 mL). THF was removed under reduced pressure, and the remaining solution was made alkaline with the slow addition of concentrated NaOH. The aqueous phase was extracted with 10%IPA-CH$_2$Cl$_2$ (3×300 mL), dried over Na$_2$SO$_4$ and concentrated to isolate 9.0 g (90% yield) of Compound B. MS (M+H)+316.

C. (R)-2,3,4,5-Tetrahydro-4-(methylsulfonyl)-3-(phenylmethyl)-7-(4-pyridinyl)-1H-1,4-benzodiazepine To a solution of Compound B (28.5 mmol, 9.0 g) in CH$_2$Cl$_2$ (200 mL) was added TEA (142.5 mmol, 20 mL) and methanesulfonyl chloride (37.5 mmol, 2.9 mL). The mixture was stirred at rt for 1 hr, poured over 2N NaOH (500 mL) and extracted with 10%IPA-CH$_2$Cl$_2$ (3×250 mL). The combined organic layers were dried over Na$_2$SO$_4$, concentrated, and azeotroped with toluene to afford Compound C.

D. (R)-2,3,4,5-Tetrahydro-1-(1H-imidazol-4-ylmethyl)-4-(methylsulfonyl)-3-(phenylmethyl)-7-(4-pyridinyl)-1 H-1,4-benzodiazepine, dihydrochloride Crude Compound C was dissolved in 300 mL of 1:1 AcOH:CH$_2$Cl$_2$ together with NaBH(OAc)$_3$ (123 mmol, 26 g) and 4-formylimidazole (123 mmol, 11.8 g) and the mixture heated to 55° C. for 3 hrs. The reaction was concentrated, diluted with 2N NaOH (500 mL) and extracted with 10%IPA-CH$_2$Cl$_2$ (3×250 mL). The combined organic layers were evaporated and the residue purifed by preparative HPLC (gradient of aq methanol with 0.1% TFA). The TFA salt was converted to the HCl salt with 1N HCl (2×150 mL) to afford Compound D as a yellow solid (2.9 g, 18% from Compound B). MS (M+H)+491.

EXAMPLE 336–343

Examples 336–343 were prepared from the appropriate sulfonyl chloride and Compound B of Example 335 as described for Compounds C and D of Example 335 (Exs 336–338) or from Compound C of Example 248 as described for Compound A of Example 317 (from 0° C. to rt) and Compound D of Example 335 (Exs 339–343).

| Example | | | Mass Spectrum |
|---|---|---|---|
| 336 | (R)-2,3,4,5-Tetrahydro-1-(1H-imidazol-4-ylmethyl)-3-(phenylmethyl)-7-(4-pyridinyl)-4-(2-thienylsulfonyl)-1H-1,4-benzodiazepine, dihydrochloride. BMS-218962 | | m/z 542 (M + H) |
| 337 | (R)-2,3,4,5-Tetrahydro-1-(1H-imidazol-4-ylmethyl)-3-(phenylmethyl)-4-(phenylsulfonyl)-7-(4-pyridinyl)-1H-1,4-benzodiazepine, dihydrochloride. BMS-218963 | | m/z 536 (M + H) |
| 338 | (R)-2,3,4,5-Tetrahydro-1-(1H-imidazol-4-ylmethyl)-3-(phenylmethyl)-4-(propylsulfonyl)-7-(4-pyridinyl)-1H-1,4-benzodiazepine, dihydrochloride. BMS-219395 | | m/z 502 (M + H) |

| Example | | | Mass Spectrum |
|---|---|---|---|
| 339 | (R)-7-Cyano-2,3,4,5-tetrahydro-1-(1H-imidazol-4-ylmethyl)-3-(phenylmethyl)-4-[(3,5-dimethyl-isoxazol-4-yl)sulfonyl]-1H-1,4-benzodiazepine, dihydrochloride. BMS220904 | 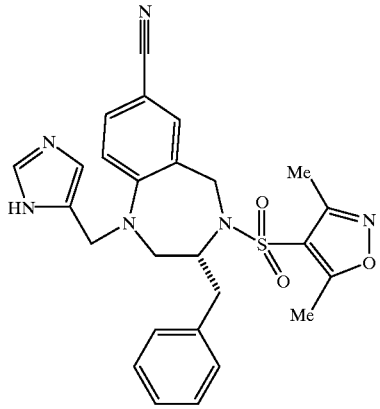 | m/z 539 (M + H) |
| 340 | (R)-7-Cyano-4-[(4-cyanophenyl)sulfonyl]-2,3,4,5-tetrahydro-1-(1H-imidazol-4-ylmethyl)-3-(phenylmethyl)-1H-1,4-benzodiazepine, dihydrochloride. BMS-221604 | 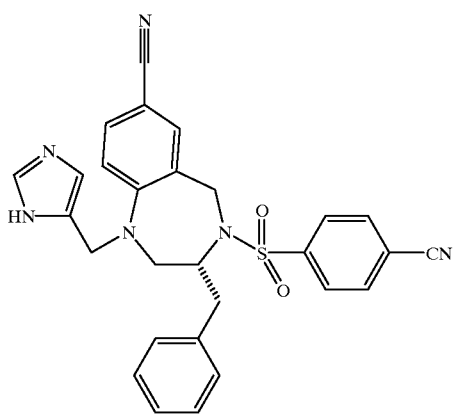 | m/z 509 (M + H) |
| 341 | (R)-7-Cyano-2,3,4,5-tetrahydro-1-(1H-imidazol-4-ylmethyl)-3-(phenylmethyl)-4-[(2,2,2-trifluoroethyl)sulfonyl]-1H-1,4-benzodiazepine, dihydrochloride. BMS-221764 | 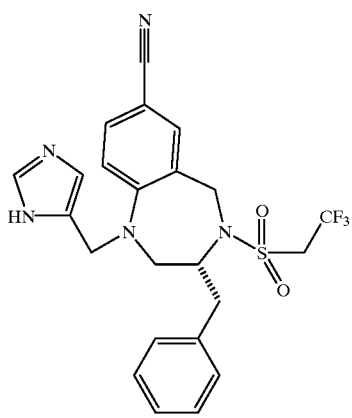 | m/z 490 (M + H) |

| Example | | | Mass Spectrum |
|---|---|---|---|
| 342 | (R)-[(5-Bromo-2-thienyl)sulfonyl]-7-cyano-2,3,4,5-tetrahydro-1-(1H-imidazol-4-ylmethyl)-3-(phenylmethyl)-1H-1,4-benzodiazepine, dihydrochloride. BMS-221766 | | m/z 569 (M + H) |
| 343 | (R)-7-Cyano-2,3,4,5-tetrahydro-1-(1H-imidazol-4-ylmethyl)-4-[(4-methoxyphenyl)sulfonyl]-3-(phenylmethyl)-1H-1,4-benzodiazepine, dihydrochloride. BMS-221970 | | m/z 514 (M + H) |

EXAMPLE 344

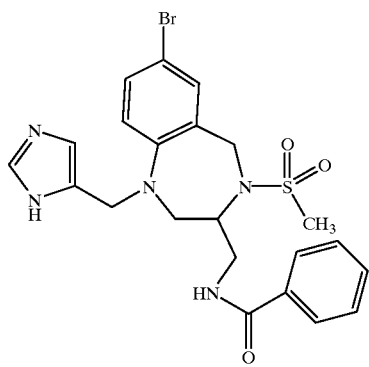

N-[[7-Bromo-2,3,4,5-tetrahydro-1-(1H-imidazol-4-ylmethyl)-4-(methylsulfonyl)-1H-1,4-benzodiazepin-3-yl]methyl]benzamide, dihydrochloride.

A. N-[[7-Bromo-2,3,4,5-tetrahydro-4-(methylsulfonyl)-1H-1,4-benzodiazepin-3-yl]methyl]benzamide To a solution of Compound C of Example 305 (50 mg, 0.15 mmol) in methylene chloride (10 mL) was added 2,6-di-tert-butyl-4-methylpyridine (62 mg, 0.30 mmol). The solution was cooled to −40° C. under N2. Triflic anhydride (0.85 mL, 0.30 mmol) was added and the solution was stirred under N2 for 1 h at −40° C. NH3 gas was added via cannula and bubbling continued for 10 min at −40° C. The solution was slowly warmed to rt with continuous bubbling. Ethyl ether (30 mL) and saturated aqueous sodium bicarbonate solution (30 mL) were added and the layers were separated. The organic layer was washed with 1N aqueous HCl. The aqueous layer was made basic with 5N aq. NaOH and the product was extracted with methylene chloride (30 mL). The organic layer was dried (Na2SO4) and concentrated to 5 mL. Benzoic acid (26 mg, 0.21 mmol) and EDC (40 mg, 0.21 mmol) were added and the solution stirred for 16 h and concentrated. The residue was chromatographed (flash silica gel, 1:5–1:1; ethyl acetate:hexane) to give 15 mg (16% for the two steps) of Compound A as a white solid. MS (M+H)⁺439.

B. N-[[7-Bromo-2,3,4,5-tetrahydro-1-(1H-imidazol-4-ylmethyl)-4-(methylsulfonyl)-1H-1,4-benzodiazepin-3-yl]methyl]benzamide, dihydrochloride Compound B was prepared as a white solid in 16% yield as described for Compound D of Example 224. MS (M+H)⁺ 518.

EXAMPLE 345

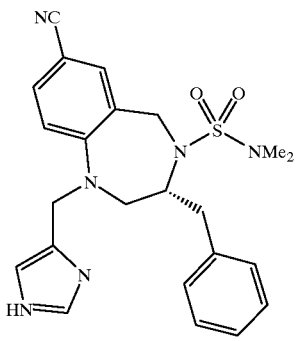

(R)-7-Cyano-1,2,3,5-tetrahydro-1-(1H-imidazol-4-ylmethyl)-N,N-dimethyl-3-(phenylmethyl)-4H-1,4-benzodiazepine-4-sulfonamide, hydrochloride.

A. (R)-7-Cyano-1,2,3,5-tetrahydro-N,N-dimethyl-3-(phenylmethyl)-4H-1,4-benzodiazepine-4-sulfonamide Dimethylsulfamoyl chloride (0.12 mL, 0.16 g, 1.13 mmol) was added to a solution of Compound C of Example 248 (0.2 g, 0.75 mmol) and DIEA (0.19 mL, 1.13 mmol) in acetonitrile (3 mL) at 0° C. under argon. After stirring for 16 hr at rt, the reaction was diluted with chloroform (20 mL) and NaHCO₃ (5 mL). The layers were separated and the aqueous layer was extracted with chloroform (2×20 mL). The combined organic extracts were washed with NaHCO₃ (2×5 mL), water (1×10 mL), and brine (2×10 mL), dried over MgSO₄, filtered and concentrated. The residue was purified on a flash silica column eluting with 30% EtOAc in hexane to afford Compound A as a yellow oil (0.14 g, 51%). MS [M+H]⁺=371⁺.

B. (R)-7-Cyano-1,2,3,5-tetrahydro-1-(1H-imidazol-4-ylmethyl)-N,N-dimethyl-3-(phenylmethyl)-4H-1,4-benzodiazepine-4-sulfonamide, hydrochloride A solution of Compound A (0.068 g, 0.18 mmol), 4-formylimidazole (0.017 g, 0.18 mmol) and AcOH (0.5 mL) in dichloroethane (0.5 mL) and 3 A mol. sieves was refluxed for 1 hr. Sodium triacetoxyborohydride (0.0389, 0.18 mmol) was added. Every day for 6 days additional aldehyde and sodium triacetoxyborohydride were added (1 eq each). After stirring for 6 days, the mixture was diluted with CHCl₃ (10 mL), NH₄OH (5 mL) and NaHCO₃ (5 mL), and stirred for 30 min. The layers were separated and the aqueous layer was extracted with CHCl₃ (3×30 mL). The combined organic extracts were dried over MgSO₄, filtered and concentrated. The product was purified by preparative HPLC (gradient of aqueous methanol with 0.1 % TFA) to afford Compound B as a light yellow solid (40 mg, 50%). MS (M+H)⁺=451

EXAMPLE 346

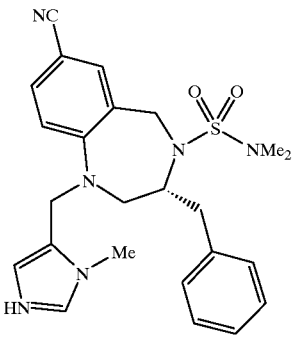

(R)-7-Cyano-1,2,3,5-tetrahydro-N,N-dimethyl-1-[(1-methyl-1H-imidazol-5-yl)methyl]-3-(phenylmethyl)-4H-1,4-benzodiazepine-4-sulfonamide, hydrochloride.

A solution of Compound A of Example 345 (0.068 g, 0.18 mmol), 1-methyl-5-formylimidazole (0.041 g, 0.36 mmol), AcOH (0.2 mL) and 3A mol. sieves in dichloroethane (0.5 mL) was warmed for 2 hr. Sodium triacetoxyborohydride (0.076 g, 0.36 mmol) was added. Additional aldehyde and sodium triacetoxyborohydride (2 eq each) were added at 1.5, 3 and 4.5 hours. After stirring for 2 days, the mixture was diluted with CHCl₃ (10 mL), NH₄OH (5 mL) and NaHCO₃ (5 mL), and stirred for 30 min. The layers were separated and the aqueous layer was extracted with CHCl₃ (3×30 mL). The combined organic extracts were washed with NaHCO₃ and brine (each 2×5 mL), dried over MgSO₄, filtered and concentrated. The product was purified by reverse phase preparative HPLC (gradient of aq methanol with 0.1% TFA) and converted to its HCl salt to afford Example 246 as a light yellow solid (32 mg, 38%). MS (M+H)⁺465

EXAMPLE 347

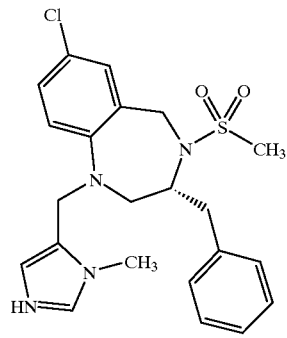

(R)-7-Chloro-2,3,4,5-tetrahydro-1-[(1-methyl-1H-imidazol-5-yl)methyl]-4-(methylsulfonyl)-3-(phenylmethyl)-1H-1,4-benzodiazepine, monohydrochloride.

A. (R)-7-Chloro-2,3,4,5-tetrahydro-3-(phenylmethyl)-1H-1,4-benzodiazepin-2,5-dione A mixture of chloroisatoic anhydride (25 g, 0.126 mol), D-Phe methyl ester (27.2 g, 0.126 mol) and DMAP (0.4 g) in pyridine (275 mL) was refluxed for 5 days. The mixture was concentrated and dissolved in CH₂Cl₂. The solution was washed with 10% HCl (3×100 mL), dried over MgSO₄, filtered and concentrated to afford a pink solid (39 g) which was recrystallized 3 times from ether/CH₂Cl₂ to afford Compound A (15.0 g, 40%). MS [M+H]⁺=301⁺.

B. (R)-7-Chloro-2,3,4,5-tetrahydro-3-(phenylmethyl)-1H-1,4-benzodiazepine

Borane in THF (1 M, 300 mL) was added to Compound A (20 g, 66.5 mmol) in THF (200 mL). The mixture was refluxed for 1 day, cooled in an ice bath, MeOH (115 mL) added slowly, and the mixture concentrated. The residue was diluted with MeOH (200 mL), 40 mL of 25% HCl was added and the mixture was refluxed for 2 hrs and concentrated to dryness to afford an off white solid which was triturated with ether several times and suspended in water. NaOH (1N, to pH 11) was added to the suspension and the solid which formed was filtered, washed with ether, and dried in vacuo to afford 7.9 g of Compound B as a light yellow solid. The filtrate was concentrated to afford an additional 10.5 g of Compound B as a light yellow solid (100 %). MS [M+H]$^+$= 273

C. (R)-7-Chloro-2,3,4,5-tetrahydro-4-(methylsulfonyl)-3-(phenylmethyl)-1H-1,4-benzodiazepine Methanesulfonyl chloride (3.68 mL, 47.6 mmol) was added dropwise as a solution in $CH_2Cl_2$ (20 mL) to a solution of Compound B (10 g, 36.6 mmol) in $CH_2Cl_2$ (130 mL) at 0° C. under argon. After stirring at rt for 16 hr the reaction was diluted with water (20 mL). The layers were separated and the aqueous layer was extracted with $CH_2Cl_2$ (2×40 mL). The combined organic layers were washed with water (1×30 mL), $KHSO_4$ (2×30 mL), water (1×30 mL), $NaHCO_3$ (2×30 mL), brine (1×30 mL), dried over $MgSO_4$, filtered and concentrated to afford a golden brown oil. The oil was crystalized from EtOAc/hexanes and the yellow solid triturated with hexane and dried to afford Compound C (10.6 g, 82 %). MS: [M+H]$^+$=351

D. (R)-7-Chloro-2,3,4,5-tetrahydro-1-[(1-methyl-1H-imidazol-5-yl)methyl]-4-(methylsulfonyl)-3-(phenylmethyl)-1H-1,4-benzo-diazepine, monohydrochloride Sodium triacetoxyborohydride (4.83 g, 22.8 mmol) was added to a solution of Compound C (4.0 g, 11.4 mmol), 1-methyl-5-formylimidazole (2.6 g, 22.8 mmol) and AcOH (22 mL) in $CH_2Cl_2$ (22 mL). After stirring for 2 days, the mixture was diluted with $CH_2Cl_2$ (30 mL), $NH_4OH$ (30 mL) and $NaHCO_3$ (30 mL), and stirred for 30 min. The layers were separated, the aqueous layer was extracted with $CH_2Cl_2$ (3×50 mL). The combined organic layers were washed with $NaHCO_3$, water, brine (3×30 mL), dried over $MgSO_4$, filtered and concentrated to afford 6.0 g of a foamy solid. The product was purified on a flash column eluting with 7/3 EtOAc/hexane (1 L) and 19/1 CHCl/MeOH (2L) to afford a white foamy solid, which was treated with 1N HCl in ether (2×25 ml). The solid was triturated with ether and dried to afford Compound D as a light yellow solid (3.44 g, 63 %). MS (M+H)$^+$445

EXAMPLE 348

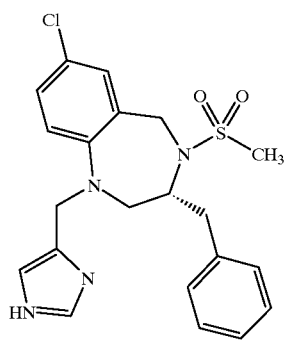

(R)-7-Chloro-2,3,4,5-tetrahydro-1-(1H-imidazol-4-ylmethyl)-4-(methylsulfonyl)-3-(phenylmethyl)-1H-1,4-benzodiazepine, monohydrochloride.

Example 348 was prepared as a light yellow solid in 70% yield from Compound C of Example 247 as described for Compound D of Example 247, using 4-formylimidazole and with refluxing for 1 hour and stirring at rt for 16 hours. MS (M+H)$^+$=431

EXAMPLE 349

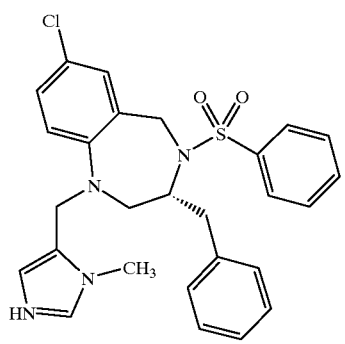

(R)-7-Chloro-2,3,4,5-tetrahydro- -[(1-methyl-1H-imidazol-5-yl)methyl]-4-(phenylsulfonyl)-3-(phenylmethyl)-1H-1,4-benzodiazepine, monohydrochloride.

Example 249 was prepared as a light yellow solid from Compound B of Example 247 by the following sequence: Compound C of Example 247, with benzenesulfonyl chloride, with stirring at rt for 3 hours and chromatography on silica with 7/3 hexanes/EtOAc (57 %); Compound D of Example 247, with stirring at rt for 12 hours and with stirring for 2 days following addition of another equivalent of hydride and aldehyde, and with purification by reverse phase HPLC (gradient of aqueous methanol with 0.1% TFA; 52%). MS (M+H)$^+$=507.

EXAMPLE 350

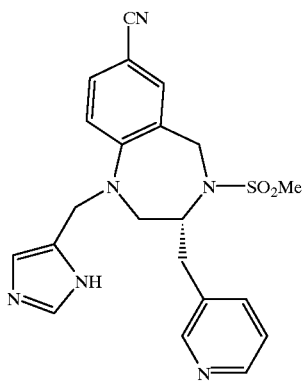

(R)-7-Cyano-2,3,4,5-tetrahydro-1-(1H-imidazol-4-ylmethyl)-3-(pyridin-3-ylmethyl)-4-(methylsulfonyl)-1H-1,4-benzodiazepine, tetrahydrochloride.

A. (R)-7-Bromo-2,3,4,5-tetrahydro-3-(pyridin-3-ylmethyl)-1H-1,4-benzodiazepine

Borane-THF (1 M, 168 ml, 0.168 mmol) was added dropwise to a solution of (R)-7-bromo-2,3,4,5-tetrahydro-3-(pyridin-3-ylmethyl)-1H-1,4-benzodiazepin-2,5-dione (prepared from 5-bromoisotoic anhydride and D-3-pyridylalanine methyl ester hydrochloride as described for Compound C of Example 226; 11.2 gm, 32.4 mmol) in THF (50 ml) at 0° C. When effervescence ceased, the mixture was heated to reflux for 4 h, cooled to 0° C. and an additional equivalent of 1 M borane-THF (32.4 ml, 32.4 mmol) was added. The mixture was refluxed for 2h, cooled to 0° C. and quenched by dropwise addition of 6N HCl (125 ml) followed by refluxing the mixture for 1 h. The reaction was cooled to rt and concentrated under vacuum. The solid was dissolved in water (100 ml) and the solution was extracted with Et$_2$O (3×100 ml). The aqueous layer was cooled to 0° C. and sodium hydroxide (50%) was added until the solution became basic. The basic solution was extracted with 9/1 CH$_2$Cl/iPrOH (3×200 ml). The combined organic extracts were dried (MgSO$_4$), filtered and concentrated under vacuum to afford Compound A (8.0 gm, 80%). MS (M+H)$^+$ 318, 320.

B. (R)-7-Cyano-2,3,4,5-tetrahydro-3-(pyridin-3-ylmethyl)-1H-1,4-benzodiazepine

Copper cyanide (2.6 gm, 29 mmol) was added to a nitrogen purged solution of Compound A (8.3 gm, 26 mmol) in NMP (41.5 ml) at room temperature. The mixture was heated to 195° C. for 3 h, cooled to room temperature and quenched with conc NH$_4$OH (100 ml). Water was added and the mixture was extracted with 9/1 CH$_2$Cl$_2$/iPrOH (3×200 ml). The combined organic extracts were concentrated under vacuum. The residue was dissolved in 6N HCl (200 ml) and extracted with ethyl acetate (4×200 ml). The aqueous solution was cooled to 0° C., made basic with concentrated ammonium hydroxide and extracted with 9/1 CH$_2$Cl$_2$/iPrOH (3×200 ml). The combined organic extracts were dried (Na$_2$SO$_4$), filtered and concentrated under vacuum. The residue was flash chromatographed (step gradient, ethyl acetate, 19/1 CH$_2$Cl$_2$/iPrOH, 4/1/0.2 CH$_2$Cl$_2$/MeOH/triethylamine). The appropriate fractions were concentrated under vacuum to afford Compound B (4.1 g, 60%) as a brown solid. MS (M+H)$^+$265

C. (R)-7-Cyano-2,3,4,5-tetrahydro-3-(pyridin-3-ylmethyl)-4-(methylsulfonyl)-1H-1,4-benzodiazepine Methylsulfonylchloride (0.031 ml, 0.39 mmol) was added dropwise to a solution of Compound B (0.070 g, 0.27 mmol) and DIEA (0.14 ml, 0.80 mmol) in methylene chloride (2 ml) at −78° C. The mixture was allowed to warm slowly to room temperature and was stirred at rt for 16h. The mixture was quenched with 10% NaHCO$_3$ (10 ml) and the solution was extracted with methylene chloride (3×10 ml). The combined organic layers were dried (Na$_2$SO$_4$), filtered and concentrated under vacuum. The residue was purified by flash chromatography (19/1 methylene chloride/iPrOH) to afford Compound C (0.064 g, 85%) as a solid. MS (M+H)$^+$ 343

D. (R)-7-Cyano-2,3,4,5-tetrahydro-1-(1H-imidazol-4-ylmethyl)-3-(pyridin-3-ylmethyl)-4-(methylsulfonyl)-1 H-1,4-benzodiazepine, tetrahydrochloride 4-Formylimidazole (0.062 g, 0.64 mmol) was added to a solution of Compound C (0.55 g, 0.16 mmol) and 3A molecular sieves in 1/1 DCE: acetic acid (2 ml) and the mixture was stirred at 70° C. for 1 h. Sodium triacetoxyborohydride (0.034 g, 0.32 mmol) was added and the mixture was stirred at 70° C. for 30 minutes. 4-Formylimidazole (0.032 g, 0.32 mmol) was added and the mixture was stirred at 70° C. for 1 h. Sodium triacetoxyborohydride (0.34 g, 0.32 mmol) was added and the mixture was stirred at 70° C. for 30 minutes. The latter two steps were repeated six times. The mixture was cooled to rt, diluted with methylene chloride (30 ml), filtered and the filtrate concentrated under vacuum. The residue was diluted with 25% NH$_4$OH (50 ml) and the solution was extracted with CH$_2$Cl$_2$ (2×200 ml). The combined organic extracts were dried (Na$_2$SO$_4$), filtered and concentrated under vacuum. The residue was purified by preparative HPLC (gradient of aq MeOH with 0.1% TFA) and the appropriate fractions were concentrated under vacuum. The residue was evaporated from CH$_3$OH (1 ml) and 1N HCl (1 ml) 4x. The residue was dissolved in CH$_3$CN (1 ml) and 1N HCl (1 ml) and lyophilized to afford Compound D (0.040 g, 50 %) as a solid. mp: decomp above 180° C. MS: (M+H)$^+$423

[a]D=+89° (c=0.39, CH$_3$OH)

Analysis calculated for C$_{21}$H$_{22}$N$_6$ O$_2$S·1.4 H$_2$O·4 HCl.

Calc'd: C, 42.44; H, 4.90; N, 14.14.

Found: C, 42.44; H, 4.66; N, 14.01.

EXAMPLE 351

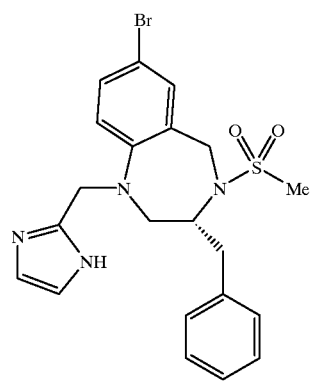

(R)-7-Bromo-2,3,4,5-tetrahydro-1-(1H-imidazol-2-ylmethyl)-4-(methylsulfonyl)-3-(phenylmethyl)-1H-1,4-benzodiazepine, dihydrochloride.

The product was prepared as an offwhite solid in 54% yield from Compound C of Example 224 and 2-formyl imidazole as described for Compound D of Example 1. MS (M+H)$^+$=476.

EXAMPLE 352

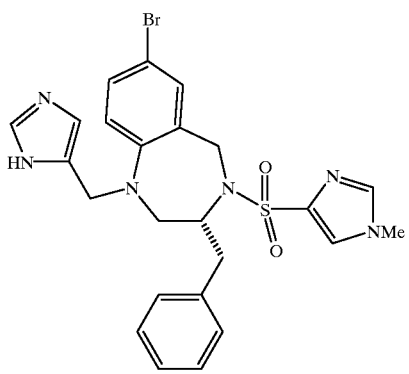

(R)-7-Bromo-2,3,4,5-tetrahydro-1-(1H-imidazol-4-ylmethyl)-4-[(1-methyl-1H-imidazol-4-yl)sulfonyl]-3-(phenylmethyl)-1H-1,4-benzodiazepine, trihydrochloride.

Example 352 was prepared as an offwhite solid in 54% yield from Compound B of Example 224 and 1-methylimidazole-4-sulfonyl chloride as described for Compounds C and D of Example 224. MS (M+H)$^+$=542.

EXAMPLE 353

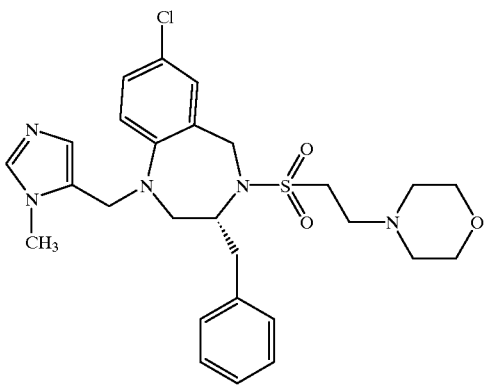

(R)-7-Chloro-2,3,4,5-tetrahydro-1-(1-methyl-imidazol-5-ylmethyl)-4-[(2-morpholin-4-yl-ethyl)sulfonyl]-3-(phenylmethyl)-1H-1,4-benzodiazepine, dihydrochloride.

A. (R)-7-Chloro-2,3,4,5-tetrahydro-4-(ethenylsulfonyl)-3-(phenylmethyl)-1H-1,4-benzodiazepine To a solution of 4.4g (16.1 mmol) of Compound B of Example 347 in 75 ml of methylene chloride, at −78° C. and under argon, was added dropwise approximately one-half of a solution of 2.5 ml (24.2 mmol) of 2-chlorosulfonyl chloride in 15 ml of methylene chloride. Then was added rapidly dropwise 5 ml of DIPEA, followed by the remaining sulfonyl chloride solution and an additional 2.4 ml of DIPEA (total 7.4 ml, 40.3 mmol). The resulting pale yellow solution was stirred at −78° C. for 0.5 hr, allowed to warm to rt and reduced to one-half volume. The solution of crude Compound A was used directly.

B. (R)-7-Chloro-2,3,4,5-tetrahydro-4-[(2-morpholin-4-yl-ethyl)sulfonyl]-3-(phenylmethyl)-1H-1,4-benzodiazepine Morpholine (15 ml) was added rapidly dropwise to the solution of Compound A and stirring was continued overnight at rt. The reaction was washed with water and brine, dried (MgSO$_4$) and the solvent removed to give an orange oil residue, which was subjected to flash chromatography on a silica gel (5% ethyl acetate-hexane) to afford 3.9 g (54%) of Compound B as a solid white foam.

C. (R)-7-Chloro-2,3,4,5-tetrahydro-1-(1-methyl-imidazol-5-ylmethyl)-4-[(2-morpholin-4-yl-ethyl)sulfonyl]-3-(phenylmethyl)-1H-1,4-benzodiazepine, dihydrochloride.

To a solution of 3.9 g (8.7 mmol) of Compound B in 40 ml of methylene chloride and 4 ml of acetic acid, at rt and under argon, was added 3.8 g (34 mmol) of 1-methyl-5-imidazolecarboxaldehyde. After stirring 0.5 hr, 1.9 g (9 mmol) of sodium triacetoxyborohydride was added and the solution heated at 40° C. Additional 1.9 g portions of hydride were added at 1 and 2.5 hours. At 4 hr an additional 1.0 g of aldehyde and 1.9 g of hydride were added and stirring was continued overnight at rt. The reaction was evaporated to dryness and the residue diluted with ethyl acetate and sat NaHCO$_3$. Additional solid NaHCO$_3$ was added in portions until the aqueous layer remained alkaline. The organic layer was separated and the aqueous layer extracted twice more with ethyl acetate. The combined organic fractions were washed with brine, dried (MgSO$_4$) and the solvent removed to give a viscous oil residue, which was purified by flash chromatography on silica (10% methanol-chloroform) followed by preparative HPLC (gradient of aqueous methanol with 0.1% TFA) to afford 3.2 g of the free base as a solid white foam. To a solution of the free amine in ethyl acetate was added excess 1 M HCl-ether and the resulting white precipitate collected by filtration to afford 3.2 g (63%) of Compound C as a white powder. MS: (M+H)$^+$544

Analysis calculated for $C_{27}H_{34}N_5O_3SCl\cdot 2HCl\cdot H_2O$.
Calc'd: C, 51.07; H, 6.03: N, 11.03.
Found: C, 50.76: H, 5.94: N, 11.13.

EXAMPLE 354

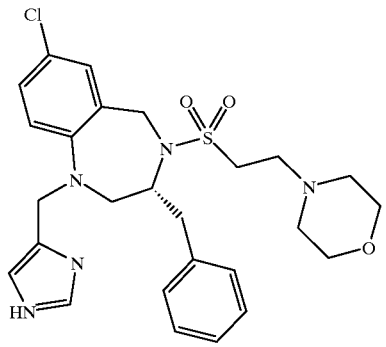

(R)-7-Chloro-2,3,4,5-tetrahydro-1-(1H-imidazol-4-ylmethyl)-4-[(2-morpholin-4-yl-ethyl)sulfonyl]-3-(phenylmethyl)-1H-1,4-benzodiazepine, dihydrochloride.

A mixture of Compound B of Example 353 (0.10 g, 0.22 mmol), 4-formylimidazole (0.042 g, 0.32 mmol), 3 A sieves and AcOH (0.3 mL) was refluxed in dichloroethane (0.3 mL) under argon for 2 hours. Sodium triacetoxyborohydride (0.07 g, 0.32 mmol) was added and the mixture was refluxed for 1 hour, stirred at rt for 16 hr, and diluted with CHCl$_3$, NH$_4$OH, and NaHCO$_3$ (each 5 mL). The layers were separated and the aqueous layer was extracted with CHCl$_3$ (2×20 mL). The combined organic extracts were washed with water and brine (each 2×5 mL), dried over MgSO$_4$, filtered and concentrated. The residue was purified by preparative HPLC (gradient of aqueous MeOH with 0.1% TFA). The appropriate fractions were concentrated and the residue evaporated from MeOH (1 mL) and 1 N HCl (1 mL) 3 times. The residue was dissolved in water and lyophilized to afford Example 354 (0.034 g, 29%) as a solid. MS (M−H)$^-$=529.

EXAMPLE 355

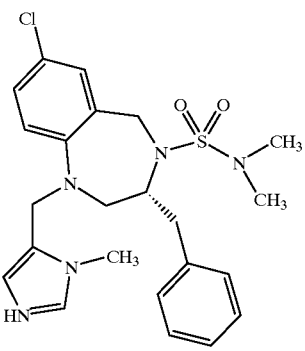

(R)-7-Chloro-4-[(dimethylamino)sulfonyl]-1-[(1-methyl-1H-imidazol-5-yl)methyl]-3-(phenylmethyl)-1H-1,4-benzodiazepine, monohydrochloride.

A. (R)-7-Chloro-4-[(dimethylamino)sulfonyl]-3-(phenylmethyl)-1H-1,4-benzodiazepine Dimethylsulfamoyl chloride (0.058 mL, 0.54 mmol) was added dropwise to a solution of Compound B of Example 347 (0.1 g, 0.36 mmol) and DIEA (0.095 mL, 0.54 mmol) in CH$_3$CN (2 mL) at 0° C. under argon. The mixture was slowly warmed to rt over 16 hr and diluted with NaHCO$_3$ (3 mL) and CHCl$_3$ (10 mL). The layers were separated and the aqueous layer was extracted with CHCl$_3$ (2×30 mL). The combined organic layer was washed with NaHCO$_3$ (1×10 mL), water (1×10 mL) and brine (1×10 mL), dried over MgSO$_4$, filtered and concentrated to afford an orange oil, which was purified on a silica gel flash column (30 % EtOAc/hexane) to afford Compound A as a clear oil 2 (0.44 g, 32 %). MS (M+H)+380.

B. (R)-7-Chloro-4-[(dimethylamino)sulfonyl]-1-[(1-methyl-1H-imidazol-5-yl)methyl]-3-(phenylmethyl)-1 H-1, 4-benzodiazepine, monohydrochloride Compound B was prepared as a white solid in 52% yield from Compound A as described for Compound C of Example 353, with refluxing for 4 hours and with purification only by preparative HPLC. MS (M+H)$^+$474.

EXAMPLE 356

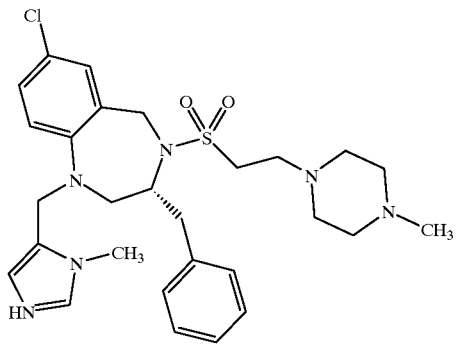

(R)-7-Chloro-2,3,4,5-tetrahydro-1-(1-methyl -imidazol-5-ylmethyl)-4. [(4-methyl-piperidin-4-yl -ethyl)sulfonyl]-3-(phenylmethyl)- 1H- 1,4-benzodiazepine, dihydrochloride.

Example 356 was prepared as a light yellow solid in 28% yield from Compound A of Example 353 and 1-methylpiperazine as described for Compound B of Example 353, with chromatography using 20% acetone in hexane followed by 10% methanol in CHCl$_3$ and Compound C of Example 353, with purification by preparative HPLC only. MS: [M+H]$^+$=557.

EXAMPLE 357

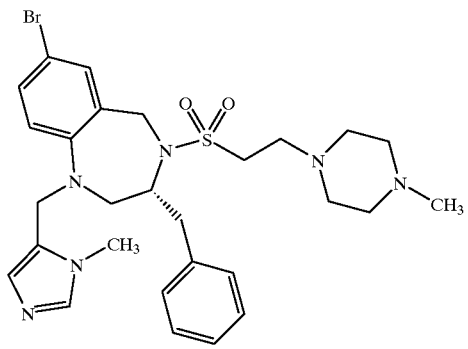

(R)-7-Bromo-2,3,4,5-tetrahydro-1 -(1-methyl-imidazol-5-ylmethyl)-4-[(4-methyl-piperidin-4-yl-ethyl)sulfonyl]-3-(phenylmethyl)-1H-1,4-benzodiazepine, dihydrochloride.

Example 357 was prepared as a white solid in 23% yield from Compound B of Example 224 and 1-methylpiperazine as described by the following sequence: Compound A of Example 353; Compound B of Example 353, with chromatography using 9/1 CHCl$_3$/MeOH; Compound C of Example 353, with purification by preparative HPLC only. MS: [M+H]$^+$=601.

EXAMPLE 358

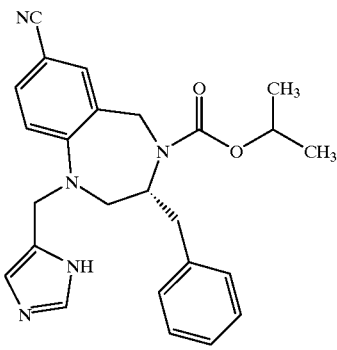

(R)-7-Cyano-1 ,2,3,5-tetrahydro-1-(1H-imidazol-4-ylmethyl)-3-(phenylmethyl)-4H-1,4-benzodiazepine-4-carboxylic acid, isopropyl ester, hydrochloride.

Example 358 was prepared as a light yellow solid in 42% yield from Compound C of Example 248 by the following sequence: Compound E of Example 248, using a toluene solution of isopropyl chloroformate with chromatography using 40% hexane in EtOAc and with the free base carried on; Example 354. MS: [M+H]$^+$=430.

EXAMPLE 359

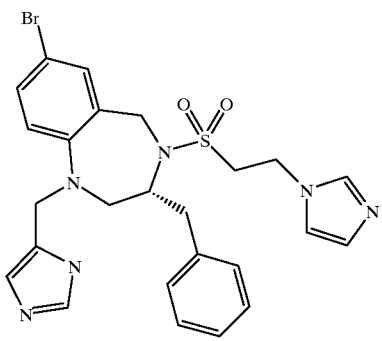

(R)-7-Bromo-2,3,4,5-tetrahydro-4-[[2-(1H-imidazol-1-yl)ethyl]sulfonyl]-1-(1H-imidazol-4-ylmethyl)-3-(phenylmethyl)-1H-1,4-benzodiazepine, dihydrochloride.

Example 359 was prepared as a light yellow solid in 21% yield from Compound B of Example 224 as described in the following sequence: Compound A of Example 353; Compound B of Example 353, using sodium imidazolate, 2:1 THF:IPA as solvent, and chromatography using 10% EtOAc in CHCl3 followed by EtOAc; Compound C of Example 353, with addition of aldehyde and hydride every day for 8 days, and no purification. MS: [M+H]$^+$=557.

EXAMPLE 360

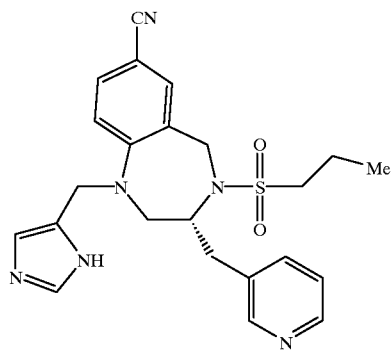

(R)-7-Cyano-2,3,4,5-tetrahydro-1-(1H-imidazol-4-ylmethyl)-4-(propylsulfonyl)-3-(3-pyridinylmethyl)-1H-1,4-benzodiazepine, hydrochloride.

Example 360 was prepared as a white solid in 15% yield from n-propanesulfonylchloride and Compound B of Example 350 as described for Compounds C and D of Example 350. MS: (M+H)$^+$451

Analysis calculated for $C_{23}H_{26}N_6O_2S \cdot 2.6\ HCl \cdot 2.02\ H_2O$.

Calc'd: C, 47.50; H, 5.65; N, 14.45.

Found: C, 47.50; H, 5.51; N, 14.10.

EXAMPLE 361

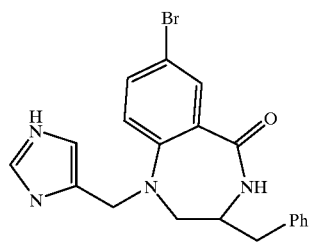

7-Bromo-2,3,4,5-tetrahydro-1-(1H-imidazol-4-ylmethyl)-3-(phenylmethyl)-1H-1,4-benzodiazepin-5-one, hydrochloride.

A. 7-Bromo-2,3,4,5-tetrahydro-3-(phenylmethyl)-1H-1,4-benzodiazepin-5-one

To a suspension of 0.5 g (1.45 mmol) of Compound A of Example 75 in 5 ml of THF, at rt and under argon, was added 3 ml (3 mmol) of 1 M borane in THF. Stirring was continued overnight, after which an additional 2 ml (2 mmol) of 1 M borane in THF was added and stirring continued an additional 8 hr. After hydrolysis of excess borane by the dropwise addition of methanol, the reaction was evaporated to dryness and the residue dissolved in 0.5 ml each of methanol and conc HCl. The resulting solution was heated at reflux for 2 hr, cooled to rt and evaporated to dryness. The residue was evaporated from methanol an additional three times. The crude product was dissolved in ethyl acetate and the solution washed with brine, dried, and the solvent removed to afford a viscous yellow oil, which was subjected to flash chromatography on silica gel (50% ethyl acetate/hexane) to give 205 mg (43%) of Compound A as a white solid.

B. 7-Bromo-2,3,4,5-tetrahydro-1-(1H-imidazol-4-ylmethyl)-3-(phenylmethyl)-1 H-1,4-benzodiazepin-5-one, hydrochloride To a suspension of 205 mg (0.62 mmole) of Compound A in 10 ml of methylene chloride and 1 ml of acetic acid was added 120 mg (1.25 mmol) of 4-formylimidazole. The solution was stirred 1 hr, 197 mg (0.93 mmol) of sodium triacetoxyborohydride was added and stirring continued overnight. An additional 60 mg of 4-formylimidazole and 100 mg of sodium triacetoxy- borohydride were added and stirring continued an additional 4 hr. The reaction was evaporated to dryness. The residue was diluted with methylene chloride and the solution washed with sat.

NaHCO$_3$ and brine, dried (MgSO$_4$), and the solvent removed to afford a pale yellow solid foam residue, which was subjected to preparative HPLC (gradient of aqueous methanol with 0.1% TFA). Concentration of the appopriate fractions afforded a clear oil residue which was converted to the HCl salt by treatment with HCl-MeOH to give 187 mg (60%) of Compound B as a near white solid. MS: (M+H)$^+$ 411.

Analysis calculated for $C_{20}H_{19}N_4OBr \cdot 1.5\ HCl \cdot 0.5\ C_2H_{10}O$.

Calc'd: C; 52.53, H; 5.11, N; 11.14.

Found: C; 52.82, H; 4.71, N; 11.52.

EXAMPLE 362

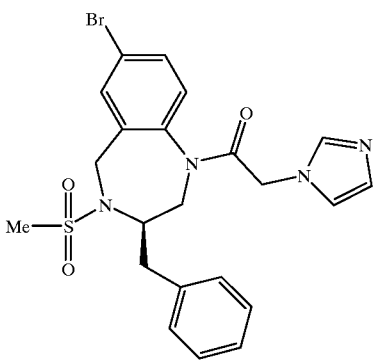

(R)-7-Bromo-2,3,4,5-tetrahydro-1-(1H-imidazol-1-ylacetyl)-4-(methylsulfonyl)-3-(phenylmethyl)-1H-1,4-benzodiazepine, trifluoroacetate.

A. (R)-7-Bromo-2,3,4,5-tetrahydro-1-(chloroacetyl)-4-(methylsulfonyl)-3-(phenylmethyl)-1H-1,4-benzodiazepine To a mixture of Compound C of Example 224 (2.0 g, 5.06 mmol) and DIEA (4.4 mL, 25 mmol) in dichloromethane (100 mL) in an ice bath under argon, was added chloroacetyl chloride (2.0 mL, 25.3 mmol). The mixture was stirred for 30 min, poured into aqueous sodium hydroxide (200 mL, 1 N) and extracted with dichloromethane (2×100 mL). The organic layers were combined, washed with brine (200 mL), and water (200 mL), dried (MgSO$_4$) and concentrated to an oil, which was purified by flash chromatography (60 g silica, 3:1 hexane:ethylacetate) to provide Compound A (760 mg, 1.62 mmol, 33 %) as a colorless oil.

B. (R)-7-Bromo-2,3,4,5-tetrahydro-1-(1H-imidazol-1-ylacetyl)-4-(methylsulfonyl)-3-(phenylmethyl)-1H-1,4-benzodiazepine, trifluoroacetate A mixture of Compound A (300 mg, 0.64 mm), potassium carbonate (177 mg, 1.28 mmol) and imidazole (87 mg, 1.28) was stirred for 48 hours. The mixture was poured into aqueous hydrochloric acid (200 mL, 1 N) and ethyl acetate (200 mL), separated, and the aqueous adjusted to pH 11 with solid sodium hydroxide. The basic aqueous solution was extracted with ethyl acetate (200 mL) and the organic extracts were combined and dried (Na$_2$SO$_4$), and concentrated in vacuo to a semi-solid which was purified by preparative HPLC (aqueous methanol gradient containing 0.1% trifluoroacetic acid, C-18 column) and lyophilized to provide Compound B as a white solid (100 mg, 32%). MS: (M+H)$^+$504

EXAMPLE 363

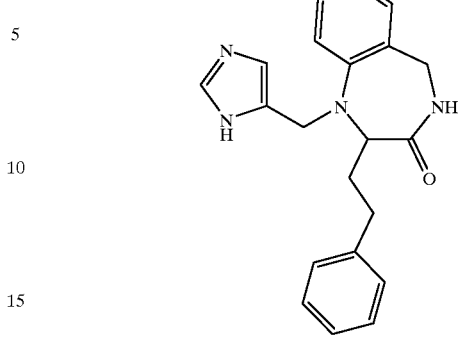

1,2,4,5-Tetrahydro-1-(1H-imidazol-4-ylmethyl)-2-(2-phenylethyl)-3H-1,4-benzodiazepin-3-one.

A. 1,2,4,5-Tetrahydro-2-(2-phenylethyl)-3H-1,4-benzodiazepin-3-one

To a stirred solution of N-Boc-(2-amino)-benzylamine (1.0 g, 4.5 mmol) and ethyl 2-oxo-4-phenylbutyrate (1.0 mL, 5.3 mmol) in dichloroethane (20 mL) and acetic acid (1.0 mL) was added NaBH(OAc)3 in one portion at room temperature under argon. The mixture was allowed to stir for 18 h, TFA (4 mL) was added, and the mixture was heated at 60° C. under argon for 2 h. The solvent was removed and the residue was dissolved in methanol (15 mL). The solution was cooled to 0° C., and 10 N NaOH solution was added to pH 11. The solution was allowed to stir at rt for 18 h. The solvent was removed and the residue was partitioned between ethyl acetate and saturated NaHCO3 solution. The organic layer was separated, dried over MgSO4, and concentrated in vacuo. The residue was crystallized from MeOH to give Compound A (480 mg, 40%) as a white solid, mp: 147–148° C.

B. 1,2,4,5-Tetrahydro-1-(1H-imidazol-4-ylmethyl)-2-(2-phenylethyl)-3H-1,4-benzodiazepin-3-one Compound B was prepared as a white solid from Compound A as described for Compound D of Example 1. MS: (M+H)+347.

EXAMPLE 364

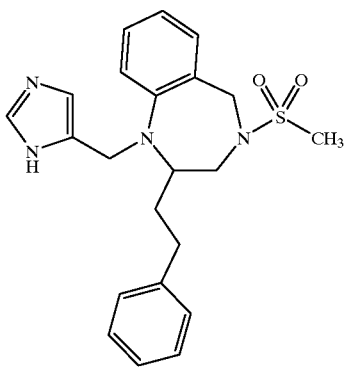

2,3,4,5-Tetrahydro-1-(1H-imidazol-4-ylmethyl)-4-(methylsulfonyl)-2-(2-phenylethyl)-1H-1,4-benzodiazepine, monohydrochloride.

A. 2,3,4,5-Tetrahydro-1-(1H-imidazol-4-ylmethyl)-2-(2-phenylethyl)-1H-1,4-benzodiazepine To a stirred suspension of lithium aluminium hydride (160 mg) in glyme was added a solution of the free base of Example 363 (150 mg) in glyme at room temperature under argon. The mixture was allowed to stir at room temperature for 18 h, quenched by addition of ethyl acetate (20 mL) followed by ammonium hydroxide (0.5 mL), stirred for 2 h and filtered. The filtrate was concentrated in vacuo to give Compound A as an oil.

B. 2,3,4,5-Tetrahydro-1-(1H-imidazol-4-ylmethyl)-4-(methylsulfonyl)-2-(2-phenylethyl)-1H-1,4-benzodiazepine, monohydrochloride To a stirred solution of Compound A (50 mg) in methylene chloride (5 mL) in the presence of solid K2CO3 was added 100 uL of methanesulfonyl chloride at room temperature. The solution was stirred for 30 min, diluted with 10 mL of methanol followed by 1 mL of 10 N NaOH solution, stirred for 2 h and concentrated. The residue was partitioned between ethyl acetate and saturated NH4Cl solution. The organic layer was separated, dried over MgSO4, and concentrated in vacuo. The residue was purified by column chromatography (ethyl acetate/methanol/NH4OH; 10:1:0.1) to give an oil, which was converted to its HCl salt as described for Compound D of Example 1. MS: (M+H)411.

EXAMPLE 365

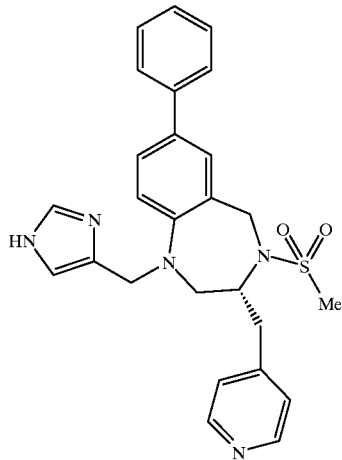

(R)-2,3,4,5-Tetrahydro-1-(1H-imidazol-4-ylmethyl)-4-(methylsulfonyl)-7-phenyl-3-(4-pyridinylmethyl)-1 H-1,4-benzodiazepine, dihydrochloride.

Example 365 was prepared as a light yellow solid in 99% yield from Compound B of Example 226 and D-(4-pyridyl) alanine by the following sequence: Compound C of Example 226; Compound D of Example 226; Compound B of Example 264; Compound D of Example 264. MS (M+H)+ 474.

EXAMPLE 366

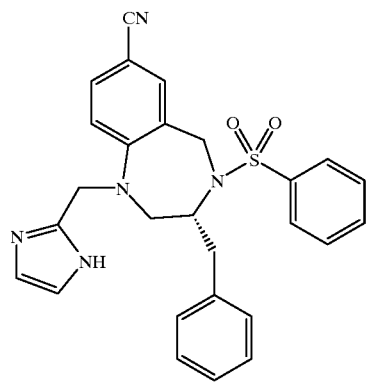

(R)-2,3,4,5-Tetrahydro-1-(1H-imidazol-2-ylmethyl)-4-(phenyl-sulfonyl)-3-(phenylmethyl)-1H-1,4-benzodiazepine-7-carbonitrile, hydrochloride.

Example 366 was prepared as a yellow solid in 95% yield from Compound A of Example 312 and 2-formyl imidazole as described for Compound D of Example 1. MS (M+H)+= 484.1.

Analysis calculated for $C_{27}H_{25}N_5O_2S \cdot 0.6\ H_2O \cdot 1.1$ HCl.

Calc'd: C, 60.67; H, 5.15; N, 13.10; S, 5.99; Cl, 7.29.

Found: C, 60.34; H, 5.16; N, 12.81; S, 5.74; Cl, 7.46.

EXAMPLE 367

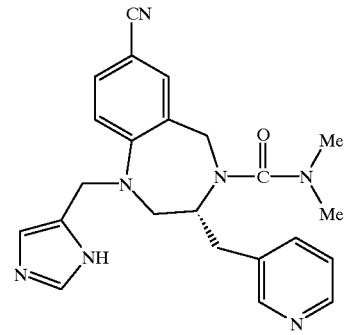

(R)-7-Cyano-1,2,3,5-tetrahydro-1-(1H-imidazol-4-ylmethyl)-N,N-dimethyl-3-(3-pyridinylmethyl)-4H-1,4-benzodiazepine-4-carboxamide, dihydrochloride.

Example 367 was prepared as a solid in 2% yield from N,N-dimethylcarbamoyl chloride and Compound B of Example 350 as described in the following sequence: Compound C of Example 350, with extraction using 10% isopropanol/methylene chloride; Compound D of Example 350, with extraction using 10% isopropanol/methylene chloride and lyophilization from 1 N HCl/methanol. HRMS: (M+H)+Calc: 416.2198; Found: 416.2211.

EXAMPLE 368

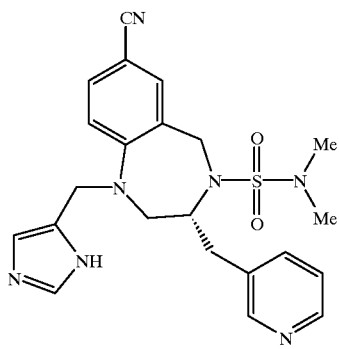

(R)-7-Cyano-1,2,3,5-tetrahydro-1-(1H-imidazol-4-ylmethyl)-N,N-dimethyl-3-(3-pyridinylmethyl)-4H-1,4-benzodiazepine-4-sulfonamide, dihydrochloride.

Example 368 was prepared as a solid in 1% yield from N,N-dimethylsulfamoyl chloride and Compound B of Example 350 as described in Example 367. HRMS: (M+H)⁺ Calc: 452.1868; Found: 452.1860.

EXAMPLE 369

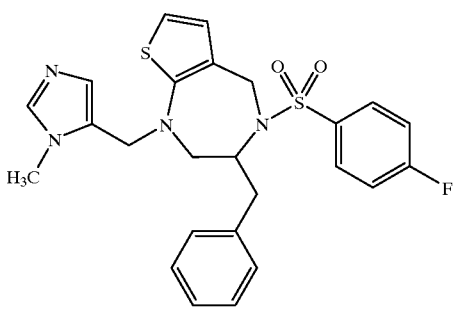

4-[(4-Fluorophenyl)sulfonyl]-2,3,4,5-tetrahydro-1-[(1-methyl-1H-imidazol-5-yl)-3-(phenylmethyl)-1H-thieno[2,3-e]-1,4-diazepine, monohydrochloride.

A. 2,3,4,5-tetrahydro-3-(phenylmethyl)-1H-thieno[2,3-e]-1,4-diazepin-2,5-dione

A stirred solution of D,L-N-(2-cyano-1-oxoethyl)-phenylalanine, methyl ester (5.0 g, 20 mmol), dithianediol (1.6 g, 10.5 mmol), piperidine (2.0 mL, 20.2 mmol) and TEA (2.8 mL, 20.2 mmol) in ethanol (30 mL) was heated at reflux for 3 h and evaporated. The residue was evaporated from toluene three times. The dry residue was dissolved in pyridine, and pyridinium chloride (2.0 g) was added. The solution was heated under argon at 130° C. for 3 days and evaporated. The residue was dissolved in methylene chloride and the solution was washed with 1 N HCl solution (2×100 mL). The organic layer was dried and concentrated in vacuo. The residue was triturated with ether to give Compound A as a brown solid (2.0 g, 40%), mp 268–270° C.

B. 2,3,4,5-tetrahydro-3-(phenylmethyl)-1H-thieno[2,3-e]-1,4-diazepine

To a stirred suspension of lithium aluminum hydride (400 mg) in glyme was added Compound A (500 mg, 2.05 mmol) in small portions at room temperature under argon. The resultant suspension was heated at reflux for 3 days, cooled to 0° C., and the excess LAH was destroyed by slow addition of ethyl acetate. NH4OH solution (1 mL) was added and the resultant suspension was filtered and the filter cake was washed with ethyl acetate. The filtrate was concentrated in vacuo. The residue was triturated in ether to give Compound B as a brown solid (220 mg), mp 139–141° C. MS: (M+H)+ 245.

C. 4-[(4-Fluorophenyl)sulfonyl]-2,3,4,5-tetrahydro-3-(phenylmethyl)-1H-thieno[2,3-e]-1,4-diazepine To a stirred solution of Compound B (150 mg, 0.6 mmol) in methylene chloride with saturated NaHCO3 solution was added 4-fluorobenzenesulfonyl chloride (300 mg, 1.55 mmol). The mixture was stirred at room temperature for 18 h and diluted with methanol. 10 N NaOH was added and the mixture was stirred for 2 h. Concentrated NH4OH was added and the mixture was stirred for 18 h and concentrated in vacuo. The residue was partitioned between ethyl acetate and saturated NaHCO3. The organic layer was separated, dried over MgSO4, and concentrated in vacuo. The residue was purified by chromatography (1:4, ethyl acetate and hexanes) to give Compound C as an oil (120 mg, 50%).

D. 4-[(4-Fluorophenyl)sulfonyl]-2,3,4,5-tetrahydro-1-[(1-methyl-1H-imidazol-5-yl)-3-(phenylmethyl)-1H-thieno[2,3-e]-1,4-diazepine, monohydrochloride Compound D was prepared as a solid in 48% yield from Compound C and 1-methyl-5-formylimidazole as described for Compound D of Example 224. MS (M+H)⁺ 497.

EXAMPLE 370

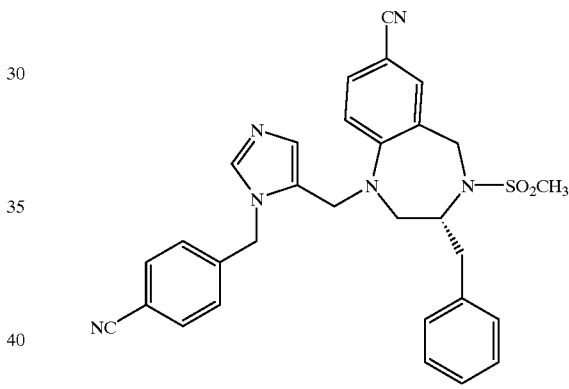

(R)-2,3,4,5-Tetrahydro-1-(1-(4-cyanophenylmethyl)-imidazol-5-ylmethyl)-4-(methylsulfonyl)-3-(phenylmethyl)-1H-1,4-benzodiazepine-7-carbonitrile, hydrochloride A. (R)-2,3,4,5-Tetrahydro-1-(1-(triphenylmethyl)-imidazol-4-ylmethyl)-4-(methylsulfonyl)-3-(phenylmethyl)-1H-1,4-benzodiazepine-7-carbonitrile To a solution of 1.2 g (2.85 mmol) of the free base of Example 225 in 20 ml of acetonitrile, at rt and under argon, was added 1.2 ml (8.55 mmol) of TEA, followed by 1.2 g (4.3 mmol) of triphenylmethyl chloride. Stirring was continued overnight. The resulting cloudy solution was evaporated to dryness and the residue subjected to flash chromatography on a 100 cc column of silica gel (50% ethyl acetate-hexane) to afford 1.2 g (64%) of Cmpd A as a viscous white foam.

B. (R)-2,3,4,5-Tetrahydro-1-(1-(4-cyanophenylmethyl)-imidazol-5-ylmethyl)-4-(methylsulfonyl)-3-(phenylmethyl)-1H-1,4-benzodiazepine-7-carbonitrile, hydrochloride A solution of 200 mg (0.3 mmol) of Compound A and 59 mg (0.3 mmol) of 4-cyanobenzyl bromide in 0.5 ml of DMF was heated at 100° C., under argon, for 10 hr. The reaction was diluted with methylene chloride and 0.1 ml of triethylsilane was added, followed by 0.5 ml of TFA. The mixture was stirred 1 hour and evaporated to give a yellow viscous oil residue which was combined with material obtained form a similar reaction and subjected to silica flash chromatography (2% methanol-chloroform) to afford 76 mg of viscous tan foam. A second silica flash chromatography (1% methanol-chloroform, then 3% methanol-chloroform) afforded 53 mg of the free base of Compound B as a solid white foam. To a solution of 50 mg of free base in ethyl acetate was added 90 µl 1 M HCl in ether. The resulting white precipitate was collected by filtration and dried to afford 43 mg (0.07 mmole) of Compound B as a white solid.

Analysis calculated for $C_{20}H_{28}N_6N_2S \cdot HCl \cdot H_2O$. Calc'd: C, 60.96; H, 5.29: N, 14.22. Found: C, 61.11; H, 5.10; N, 14.07. MS (M+H)$^+$ =537.

EXAMPLE 371

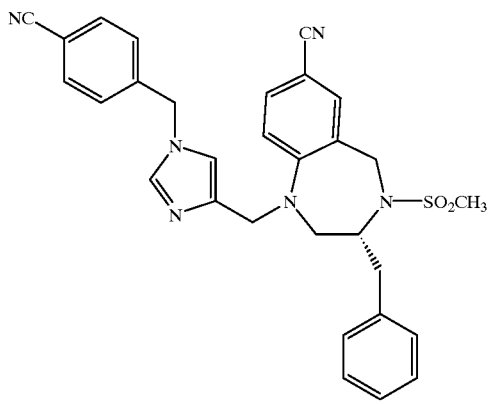

(R)-2,3,4,5-Tetrahydro-1-(1-(4-cyanophenylmethyl)-imidazol-4-ylmethyl)-4-(methylsulfonyl)-3-(phenylmethyl)-1H-1,4-benzodiazepine-7-carbonitrile, hydrochloride A. (R)-2,3,4,5-Tetrahydro-1-(1-((1,1-dimethyl)-ethoxycarbonyl)-imidazol-4-ylmethyl)-4-(methylsulfonyl)-3-(phenylmethyl)-1H-1,4-benzodiazepine-7-carbonitrile To a solution of 250 mg (0.53 mmol) of the free base of Example 225 and 0.6 mg (0.005 mmol) of DMAP in 2 ml of methylene chloride, at rt and under argon, was added a solution of 144 mg (0.66 mmol) of BOC anhydride in 2 ml of methylene chloride. Stirring was continued for 1 hr. The reaction, without workup, was subjected to flash chromatography on a 50 cc column of silica gel (45% ethyl acetate-hexane) to afford 307 mg (approx 100%) of Compound A as a solid white foam.

B. (R)-2,3,4,5-Tetrahydro-1-(1-(4-cyanophenylmethyl)-imidazol-4-ylmethyl)-4-(methylsulfonyl)-3-(phenylmethyl)-1H-1,4-benzodiazepine-7-carbonitrile, hydrochloride A solution of 60 mg (0.115 mmol) of Compound A and 23 mg (0.115 mmol) of 4-cyanobenzyl bromide in 1 ml of DMF was heated at 100° C., under argon, for 10 hr and evaporated. The residue was diluted with methylene chloride and sat NaHCO$_3$ and stirred for 0.5 hr. The organic layer was separated, dried (MgSO$_4$) and the solvent removed to yield a clear colorless glass residue. The crude product was subjected to flash chromatography on a 25 cc column of silca gel (1% methanol-chloroform, then 3% methanol chloroform) to afford 6 mg of the free base of Compound B as a solid white foam. To this material in minimal ethyl acetate was added 100 µl 1 M HCl in ether. The resulting white precipitate was collected by filtration and dried to afford 4.5 mg (7%) of Compound B as a white solid. MS: (M+H)$^+$ 537

EXAMPLE 372

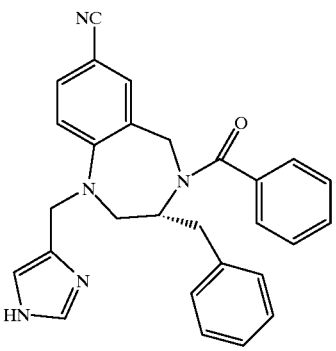

(R)-4-Benzoyl-7-cyano-2,3,4,5-tetrahydro-1-(1H-imidazol-4-ylmethyl)-3-(phenylmethyl)-1H-1,4-benzodiazepine, monohydrochloride A. (R)-4-Benzoyl-7-cyano-2,3,4,5-tetrahydro-3-(phenylmethyl)-1H-1,4-benzodiazepine Benzoyl chloride (2.2 mL, 1.9 mmol) was added to a solution of Compound C of Example 248 and DIEA (0.32 mL, 1.99 mmol) in dichloromethane (3 mL) at 0° C. under argon. The solution was slowly warmed to rt. At 15 and 30 hr, 0.5 equivalents of benzoyl chloride and DIEA were added. After stirring for 2 days, the mixture was diluted with chloroform (20 mL) and NaHCO$_3$ (5 mL). The layers were separated, the aqueous layer was extracted with chloroform (2×15 mL). The combined organic extracts were washed with NaHCO$_3$ (2×5 mL), water (1×10 mL) and brine (2×10 mL), dried over MgSO$_4$, filtered and concentrated. The residue was purified on a flash column eluting with 20% and 30% EtOAc in hexane to afford Compound A as a yellow oil 2 (0.21 g, 77 %). MS (M+H)$^+$ 368.

B. (R)-4-Benzoyl-7-cyano-2,3,4,5-tetrahydro-1-(1H-imidazol-4-ylmethyl)-3-(phenylmethyl)-1H-1,4-benzodiazepine, monohydrochloride A mixture of Compound A (0.1 g, 0.27 mmol), 4-formylimidazole (0.039 g, 0.40 mmol), AcOH (0.3 mL) in toluene (1 mL) and 3A sieves was refluxed for 15 hrs. Sodium triacetoxyborohydride (0.086 g, 0.4 mmol) was added and the mixture was refluxed for 8 hr, cooled to rt and stirred 15 hours. An additional equivalent of aldehyde was added, the solution was stirred 30 minutes, and an additional equivalent of hydride was added and the solution was stirred 16 hours. An additional equivalent of aldehyde and hydride was added as above, and the mixture was stirred 4 hours, diluted with CHCl$_3$ (10 mL), NH$_4$OH (5 mL) and NaHCO$_3$ (5 mL), and stirred for 10 min. The layers were separated and the aqueous layer was extracted with CHCl$_3$ (3×30 mL). The combined organic extracts were washed with NaHCO$_3$, water, and brine ( each 2×10 mL) dried over MgSO$_4$, filtered and concentrated. The product was purified by preparative HPLC, (gradient of aqueous MeOH with 0.1% TFA). The appropriate fractions were concentrated under vacuum. The residue was evaporated from MeOH (1 mL) and 1 N HCl (1 mL) three times. The residue was dissolved in water and lyophilized to afford Compound B as a light yellow solid (36 mg, 30%). MS (M+H)$^+$=448.

EXAMPLE 373

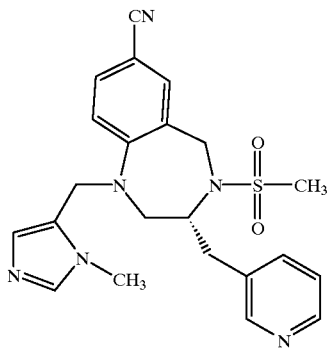

(R)-7-Cyano-2,3,4,5-tetrahydro-1-[(1-methyl-1H-imidazol-5-yl)methyl]-3-(pyridin-3-ylmethyl)-4-(methylsulfonyl)-1H-1,4-benzodiazepine, dihydrochloride Example 373 was prepared as a solid in 13% yield from Compound B of Example 350 as described for Compound C of Example 350 and Compound D of Example 350, using 1-methyl-5-formylimidazole.

MS: (M+H)$^+$ 437

Analysis calculated for $C_{22}H_{24}N_6O_2S \cdot 2HCl \cdot 2.1\ H_2O$. Calc'd: C, 48.28; H, 5.56; N, 15.36. Found: C, 48.28; H, 5.42; N, 15.45.

EXAMPLE 374

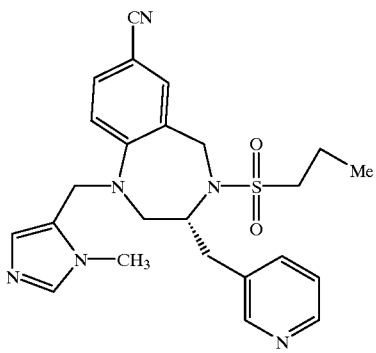

(R)-7-Cyano-2,3,4,5-tetrahydro-1-[(1-methyl-1H-imidazol-5-yl)methyl]-3-(pyridin-3-ylmethyl)-4-(propylsulfonyl)-1H-1,4-benzodiazepine, trihydrochloride Example 374 was prepared as a solid in 11% yield from propanesulfonyl chloride as described for Example 373. MS: (M+H)$^+$ 465

Analysis calculated for $C_{24}H_{28}N_6O_2S \cdot 3HCl \cdot 0.26\ H_2O$. Calc'd: C, 49.82; H, 5.49; N, 14.52. Found: C, 49.81; H, 5.37; N, 14.58.

EXAMPLE 375

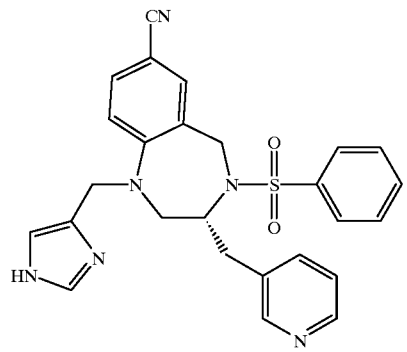

(R)-7-Cyano-2,3,4,5-tetrahydro-1-[(1H-imidazol-4-yl)methyl]-3-(pyridin-3-ylmethyl)-4-(phenylsulfonyl)-1H-1,4-benzodiazepine, dihydrochloride Example 375 was prepared as a solid in 2% yield from Compound B of Example 350 as described for Compound C of Example 350 using benzenesulfonyl chloride, and Compound D of Example 350. MS: (M+H)$^+$ 485

EXAMPLE 376

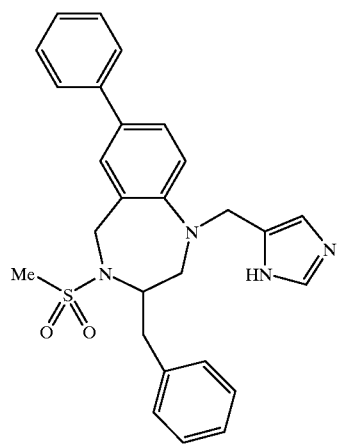

2,3,4,5-Tetrahydro-1-(1H-imidazol-4-ylmethyl)-4-(methylsulfonyl)-7-phenyl-3-(phenylmethyl)-1H-1,4-benzodiazepine A. 2,3,4,5-Tetrahydro-7-phenyl-3-(phenylmethyl)-1H-1,4-benzodiazepine To a mixture of Compound B of Example 75 (200 mg, 0.63 mmol) in toluene (20 mL) and aq sodium bicarbonate (10 mL, saturated solution) under argon was added a solution of phenyboronic acid (153 mg in 5 ml abs ethanol). Tetrakis(triphenylphosphine) palladium(0) (36 mg) was added, and the solution was heated to reflux (~80° C.) for 18 hours, cooled to room temperature and partitioned between aqueous sodium hydroxide (100 mL, 3 N) and ethyl acetate (100 mL). The mixture was extracted with ethyl acetate (2×200 mL) and the organic layers were combined, dried (MgSO4) and concentrated in vacuum to a crude oil which was purified using flash chromatography (silica, 10:0.5:0.05 ethyl acetate:methanol:ammonium hydroxide) to provide Compound A (90 mg, 45%) as a waxy solid.

B. 2,3,4,5-Tetrahydro-1-(1H-imidazol-4-ylmethyl)-4-(methylsulfonyl)-7-phenyl-3-(phenylmethyl)-1H-1,4-benzodiazepine Compound B was prepared as a white solid in 40% yield from Compound A was described in the following sequence: Compound A of Example 78, with stirring for 18 hours and no chromatography; Compound B of Example 78. MS: (M+H)+ 473

Analysis calculated for C$_{27}$H$_{28}$N$_4$O$_2$.0.5 H$_2$O. 0.8 TFA. Calc'd: C, 59.97; H, 5.24; N, 9.78; S, 5.60; F, 7.96. Found: C, 59.94; H, 4.87; N, 8.21; S, 4.48; F, 7.86.

EXAMPLE 377

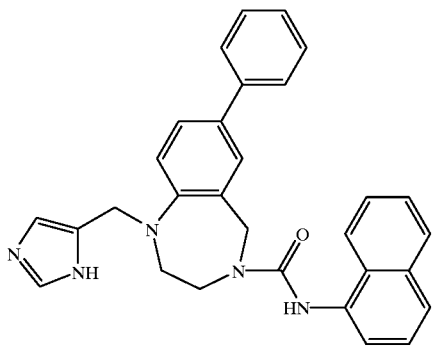

1,2,3,5-Tetrahydro-1-(1H-imidazol-4-ylmethyl)-N-(1-naphthalenyl)-7-phenyl-4H-1,4-benzodiazepine-4-carboxamide, monohydrochloride.

A. 1,2,3,5-Tetrahydro-N-(1-naphthalenyl)-7-phenyl-4H-1,4-benzodiazepine-4-carboxamide Compound B of Example 12 (148 mg, 0.66 mmol) was added to 1-naphthylisocyanate (116 mg, 0.66 mmol) in 3 mL of dry CH$_2$Cl$_2$ under argon and the mixture was stirred for 16 hours and concentrated to give crude compound A (267 mg).

B. 1,2,3,5-Tetrahydro-1-(1H-imidazol-4-ylmethyl)-N-(1-naphthalenyl)-7-phenyl-4H-1,4-benzodiazepine-4-carboxamide, monohydrochloride Compound B was prepared as a light pink solid in 46% yield from Compound A as described for Compound D of Example 1. mp 170–177° C. dec. MS: (M+H)+ 474

Analysis calculated for C$_{30}$H$_{27}$N$_5$O.1.2 HCl.0.6 H$_2$O.0.25 Et$_2$O. Calc'd: C, 68.11; H, 5.88; N, 12.81; Cl, 7.78. Found: C, 68.02; H, 5.92; N, 12.61; Cl, 7.75.

EXAMPLE 378

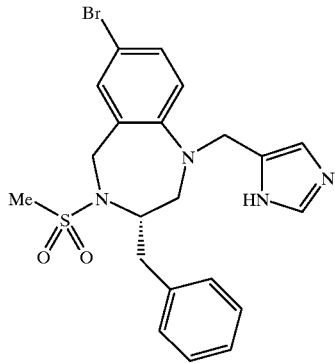

(S)-7-Bromo-2,3,4,5-tetrahydro-1-(1H-imidazol-4-ylmethyl)-4-(methylsulfonyl)-3-(phenylmethyl)-1H-1,4-benzodiazepine, hydrochloride A solution of the free base of Example 78 (100 mg, 0.31 mmol) in isopropanol (5 mL) was purified using chiral-phase prepative HPLC (chiralpak AD column produced by Chiral Technologies Inc. (50 mm×500 mm), 25:75:0.1 isopropanol:hexane:triethylamine, flow rate 55 ml/min) to provide isomer A at 36 min (18 mg, 13%, free base of Example 378) and isomer B at 54 min retention times. The hydrochloride was prepared as described for Compound D of Example 224. MS: (M+H)+ 476

Analysis calculated for C$_{21}$H$_{23}$N$_4$O$_2$ SBr 1.2H$_2$O.0.7 HCl. Calc'd: C, 47.43; H, 4.85; N, 10.54; S, 6.03; Br, 15.03; Cl, 8.00. Found: C, 47.71; H, 4.66; N, 9.71; S, 5.59; Br, 12.54, Cl, 8.14.

EXAMPLE 379

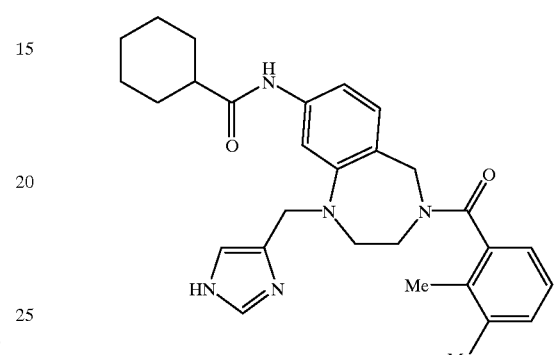

N-[2,3,4,5-Tetrahydro-1-(1H-imidazol-4-ylmethyl)-4-(2,3-dimethylbenzoyl)-1H-1,4-benzodiazepin-8-yl]cyclohexanecarboxamide, dihydrochloride A. 8-Nitro-2,3,4,5-tetrahydro-4-Fmoc-1H-1,4-benzodiazepine FmocOSu (19.0 g, 56.4 mmol) was added to a –10° C. solution of the dihydrochloride of Compound D of Example 22 (15.0 g, 56.4 mmol) and DIEA (19.6 ml, 113 mmol) in dichloromethane (100 ml). The mixture was stirred at 0° C. for 2 h, quenched with 10% NaHCO$_3$ (100 ml) and extracted with CH$_2$Cl$_2$ (2×100 ml). The combined organic extracts were washed with 1 N HCl (2×100 ml). The organic fraction was washed with 10% NaHCO$_3$ (2×100 ml), dried (MgSO$_4$), filtered and concentrated under vacuum. The residue was triturated with ether and dried under vacuum to afford Compound A as a white solid (15.6 g, 67%). MS: (M+H)+ 416

B. 8-Nitro-2,3,4,5-tetrahydro-1-(1H-imidazol-4-ylmethyl)-4-Fmoc-1H-1,4-benzodiazepine 4-Formylimidazole (7.16 g, 74.6 mmol) was added to a solution of Compound A (15.5 g, 37.3 mmol) with 4A molecular sieves (6 gm) in 1/1 CH$_2$Cl$_2$/AcOH (200 ml). The mixture was stirred at rt for 2 h. Sodium triacetoxyborohydride (11.9 g, 56 mmol) was added portionwise over 15 minutes and the resulting solution was stirred for 3 h. 4-Formylimidazole (1.10 g, 11.5 mmol) was added and the mixture was stirred for 1 h. Sodium triacetoxyborohydride (2.39 g, 11.3 mmol) was added portionwise over 15 minutes and the resulting solution was stirred for 16 h. The mixture was filtered and the filtrate was concentrated under vacuum. The residue was dissolved in CH$_2$Cl$_2$ (100 ml) and quenched with 10% NaHCO$_3$ (200 ml). The organic fraction was separated and the aqueous layer extracted with CH$_2$Cl$_2$ (2×100 ml). The combined organic fractions were dried (MgSO$_4$), filtered and concentrated under vacuum. The residue was purified by silica gel chromatography (eluting with CH$_2$Cl$_2$, discarding all fractions and removing the product with 9/1 CHCl$_3$/MeOH) to afford Compound B (17.6 g, 95%) as a glassy solid. (M+H)+ 496

C. N-[2,3,4,5-Tetrahydro-1-(1H-imidazol-4-ylmethyl)-4-(2,3-dimethylbenzoyl)-1H-1,4-benzodiazepin-8-yl]cyclohexane-carboxamide, dihydrochloride A solution of Compound B (12.0 g, 24.2 mmol) in DCE (70 ml) was added to 2-chlorotritylchloride polystyrene resin (13.9 g, 24.2 mmol, 1.74 mmol/g load, Advanced ChemTech) in a glass shaker flask, previously swollen with DCE (50 ml) at room temperature. DIEA (4.19 ml, 24.2 mmol) was added and the mixture was shaken at room temperature for 72 h. The resin was filtered and washed with DCE (4×50 ml). The resin was washed with MeOH (4×50 ml), filtered and dried under vacuum to afford Compound B attached to resin via the imidazole group (23.1 g, 89%; loading 0.90 mmol/g based on nitrogen analysis) as orange beads. The resin (23.1 g, 23.1 mmol) was swelled with DMF (50 ml) for 15 minutes. Piperidine (50 ml) was added and the mixture was shaken for 5 h, filtered, washed with DMF (50 ml) and filtered. DMF (50 ml) was added and the mixture was shaken for 15 minutes. Piperidine (50 ml) was added and the mixture was shaken for 5 h. The resin was filtered, washed and filtered with successive treatments of DMF (3×50 ml), CH$_2$Cl$_2$ (3×50 ml), and MeOH (3×80 ml) allowing 15 minutes to equilibrate resin after addition of each solvent. The resin was dried under vacuum to afford deprotected resin bound material (18.2 g 80%, loading 1.17 mmol/g based on nitrogen analysis) as orange beads. Resin (0.275 g, 0.322 mmol) was placed in a 25 ml Varian Bond Elut Reservoir tube fitted with a 20 mM Varian frit and polypropylene leuer tip stopcock. The tube was attached to Vac Elut SPS 24 on a Innova 2000 Platform Shaker. The resin was swelled with CH$_2$Cl$_2$ (2 ml) for 15 minutes. A 0.77 M DMF solution of 2,3 dimethylbenzoic acid (1.25 ml) was added to the resin. A 0.92 M DMF solution of HOAT (1.04 ml) and a 0.46 M CH2Cl2 solution of DIC (2.08 ml) were added to the resin mixture. The platform shaker mixed the solid phase reaction @ 285 RPM for 16 h. The tube was filtered and the resin was washed and filtered with successive treatments of DMF (3×5 ml), CH$_2$Cl$_2$ (3×5 ml), and MeOH (3×5 ml) allowing 15 minutes to equilibrate resin after addition of each solvent. The resin was again swelled with CH$_2$Cl$_2$ (2 ml) for 15 minutes. A 0.77 M DMF solution of 2,3 dimethylbenzoic acid (1.25 ml) was added to the resin. A 0.92 M DMF solution of HOAT (1.04 ml) and a 0.46 M CH2Cl2 solution of DIC (2.08 ml) were added to the resin mixture. The platform shaker mixed the solid phase reaction @ 285 RPM for 16 h. The tube was filtered and the resin was washed and filtered with successive treatments of DMF (3×5 ml), CH$_2$Cl$_2$ (3×5 ml), and MeOH (3×5 ml) allowing 15 minutes to equilibrate resin after addition of each solvent. This sequence of events afforded N4-acylated resin-bound material that was carried on to the next step. The resin was swelled with 1/1 DMF/CH$_2$Cl$_2$ (2 ml) for 15 minutes. A 0.23 M solution of SnCl$_2$.2H$_2$O (0.222 g, 0.97 mmol), and TEA (0.672 ml, 4.83 mmol) in CH$_2$Cl$_2$ (4 ml) was added to the resin mixture. The resin mixture was shaken for 16 h. The tube was filtered and the resin was washed and filtered with successive treatments of DMF (3×5 ml), CH$_2$Cl$_2$ (3×5 ml), and MeOH (3×5 ml) allowing 15 minutes to equilibrate resin after addition of each solvent. The resin was swelled with 1/1 DMF/CH2Cl2 (2 ml) for 15 minutes and the entire procedure for this step was repeated two times. This sequence of events afforded 8-amino resin-bound material that was carried on to the next step. The resin was swelled with CH$_2$Cl$_2$ (2 ml) for 15 minutes. A 0.77 M DMF solution of cyclohexylcarboxylic acid (1.25 ml) was added to the resin. A 0.92 M DMF solution of HOAT (1.04 ml) and a 0.46 M CH$_2$Cl$_2$ solution of DIC (2.08 ml) were added. The platform shaker mixed the solid phase reaction @ 285 RPM for 16 h. The tube was filtered and the resin was washed and filtered with successive treatments of DMF (3×5 ml), CH$_2$Cl$_2$ (3×5 ml), and MeOH (3×5 ml) allowing 15 minutes to equilibrate resin after addition of each solvent. The resin was again swelled with CH$_2$Cl$_2$ (2 ml) for 15 minutese. A 0.77 M DMF solution of cyclohexylcarboxylic acid (1.25 ml) was added to the resin. A 0.92 M DMF solution of HOAT (1.04 ml) and a 0.46 M CH$_2$Cl$_2$ solution of DIC (2.08 ml) were added to the resin mixture. The platform shaker mixed the solid phase reaction @ 285 RPM for 16 h. The tube was filtered and the resin was washed and filtered with successive treatments of DMF (3×5 ml), CH$_2$Cl$_2$ (3×5 ml), and MeOH (4×5 ml) allowing 15 minutes to equilibrate resin after addition of each solvent. This sequence of events afforded 8-acylated resin-bound material that was carried on to the next step. Resin was swelled with CH$_2$Cl$_2$ (4 ml) for 15 minutes. Triethylsilane (0.51 ml, 3.2 mmol, 10 equiv) was added. The resin mixture was treated with TFA (4 ml) and the reaction was shaken for 1 h. The filtrate was collected by vacuum filtration. The resin was again swelled with CH$_2$Cl$_2$ (4 ml) for 15 minutes. Triethylsilane (0.51 ml, 3.2 mmol, 10 equiv) was added. The resin mixture was treated with TFA (4 ml) and the reaction was shaken for 1 h. The filtrate was collected by vacuum filtration. The combined filtrates were concentrated under vacuum. The residue was purified by preparative HPLC (gradient of aqueous methanol with 0.1% TFA) and appropriate fractions were collected and concentrated under vacuum. The residue was dissolved in CH$_3$CN (2 ml), treated with 1 N HCl (1 ml) and concentrated under vacuum four times. The residue was dissolved in CH$_3$CN (2 ml), treated with 1 N HCl (1 ml) and the solution was lyophilized to afford Example 379 (0.0075 g, 4% overall yield) as a glassy solid. MS (M+H)$^+$ 486

EXAMPLE 380

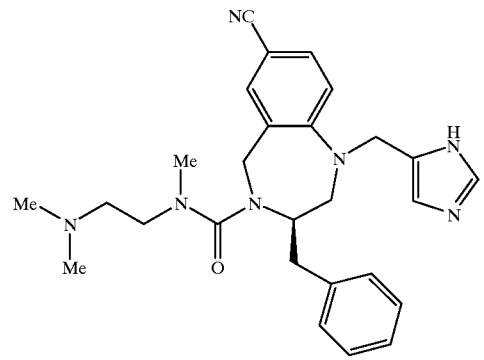

(R)-7-Cyano-N-[2-(dimethylamino)ethyl]-2,3,4,5-tetrahydro-1-(1H-imidazol-4-ylmethyl)-N-methyl-3-(phenylmethyl)-1H-1,4-benzodiazepine-4-carboxamide, trifluoroacetate (1:2)

A. (R)-7-Cyano-2,3,4,5-tetrahydro-4-(4-nitrophenyloxycarbonyl)-3-(phenylmethyl)-1H-1,4-benzodiazepine To a solution of Compound C of Example 248 (200 mg, 0.76 mmol) in THF (20 mL) under argon was added 4-nitrophenylchloroformate (0.88 mL, 0.76 mmol). The solution was stirred for 8 hours, poured into aqueous hydrochloric acid (150 mL, 1 N), extracted with ethyl acetate (2×150 mL), dried (MgSO4), and concentrated to an oil which was purified using flash chromatography (50 g silica, 2:1 hexane:ethyl acetate) to provide Compound A (230 mg, 70%) as a clear oil.

B. (R)-7-Cyano-N-[2-(dimethylamino)ethyl]-2,3,4,5-tetrahydro-N-methyl-3-(phenylmethyl)-1H-1,4-benzodiazepine-4-carboxamide A solution of Compound A (110 mg, 0.26 mmol), in N,N,N'-trimethyethylene diamine (2 mL) was heated in a sealed pressure tube at 110° C. for 18 hours. After cooling to room temperature, the solution was poured into aqueous sodium hydroxide (100 mL, 1 N), extracted with ethyl acetate (2×150 mL), dried (MgSO4) and concentrated under vacuum to afford crude Compound B as a brown paste (yield >100%).

C. (R)-7-Cyano-N-[2-(dimethylamino)ethyl]-2,3,4,5-tetrahydro-1-(1H-imidazol-4-ylmethyl)-N-methyl-3-(phenylmethyl)-1H-1,4-benzodiazepine-4-carboxamide, trifluoroacetate (1:2)

A solution of Compound B (140 mg, 0.35 mmol), 4-formyl imidazole (68 mg, 0.7 mmol), dichloroethane (2 mL) and acetic acid (2 mL) was stirred at room temperature for 30 min and sodium triacetoxyborohydride (150 mg, 0.7 mmol) was added. The solution was heated to 60° C., stirred for 18 hour, and additional portions of 4-formyl imidazole and sodium triacetoxyborohydride were added (0.2 mmol each, 4 portions over 8 hours); the mixture was diluted with ethyl acetate (20 mL) and ammonium hydroxide (5 ml, conc), and stirred for an additional 30 min. The mixture was extracted with ethyl acetate (2×25 mL) and the combined organic extracts were washed with aqueous sodium bicarbonate (25 ml, saturated solution), and then ammonium chloride (25 mL, sat aqueous solution), dried ($Na_2SO_4$), and concentrated in vacuo to a semi-solid. The crude was purified by preparative HPLC (aqueous methanol gradient containing 0.1% TFA, C-18 column) and lyophilized to provide Compound C as a white solid (80 mg, 48%). MS: $(M+H)^+$ 471

Analysis calculated for $C_{27}H_{33}N_7O$ 1.1$H_2O$.2.1 TFA. Calc'd: C, 51.27; H, 5.14; N, 13.42; F, 16.38. Found: C, 51.60; H, 4.93; N, 13.47; F, 16.28.

EXAMPLE 381

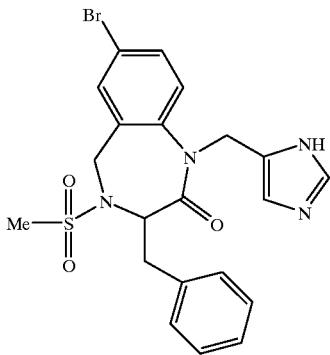

7-Bromo-2,3,4,5-tetrahydro-1-(1H-imidazol-4-ylmethyl)-4-(methylsulfonyl)-2-oxo-3-(phenylmethyl)-1H-1,4-benzodiazepine, trifluoroacetate A. N-((2-Nitrophenyl)-methyl)-phenylalanine methyl ester To a solution of 2-nitrobenzaldehyde (5 g, 33 mmol) in acetic acid (150 mL) was added D,L phenylalanine-O-methyl ester (8.54 g, 40 mmol) and then sodium acetate (3.5 g, 43 mmol). Sodium triacetoxyborohydride (9.09 g, 43 mmol) was slowly added and the mixture was heated to 80° C. for four hours, cooled to room temperature, concentrated under vacuum to a paste (~20 mL) and dissolved in ethyl acetate (100 mL). The solution was neutralized with saturated sodium carbonate and extracted with ethyl acetate (3×200 mL). The combined organic layers were dried (MgSO4), and concentrated to provide Compound A as a brown oil (11.25 g, >100%).

B. N-((2-Nitrophenyl)-methyl)-N-(methanesulfonyl)-phenylalanine methyl ester

To a solution of Compound A (1.12 g, 3.5 mmol) in pyridine (10 mL) under argon in an ice bath was slowly added methanesulfonyl chloride (1.08 mL, 14.0 mmol). The solution was warmed to room temperature, poured into aqueous hydrochloric acid (250 mL, 1 N), extracted with ethyl acetate (2×200 mL) and the combined organic layers dried (MgSO4) and concentrated. The oil was purified by flash chromatography (4:1 hexane:ethyl acetate) to provide Compound B (660 mg, 48%) as a clear oil.

C. N-((2-Aminophenyl)-methyl)-N-(methanesulfonyl)-phenylalanine methyl ester

A mixture of Compound B (660 mg, 1.68 mmol), tin (II) chloride (1.52 g, 6.7 mmol) and ethyl acetate (75 mL) was stirred at room temperature for 18 hours and quenched with aqueous and then solid potassium carbonate (5 mL, then 5 gms). The mixture was filtered, the filtrate partitioned and the organic phase dried (MgSO4), concentrated in vacuum, and purified using flash chromatography (3:1 hexane:ethyl acetate) to provide Compound C (315 mg, 52%) as a clear oil.

D. N-((2-Amino-5-bromophenyl)-methyl)-N-(methanesulfonyl)-phenylalanine methyl ester Compound D was prepared as a white solid in 60% yield from Compound C as described for Compound A of Example 262 except that the product was purified by crystallization from methanol.

E. N-[[2-(((Imidazol-4-yl)-methyl)-amino)-phenyl]-methyl]-N-(methanesulfonyl)-phenylalanine methyl ester Compound E was prepared as a semi-solid in 100% yield from Compound D as described for Compound D of Example 1, with stirring for 4 hours and with the crude free base carried on directly.

F. N-[[2-(((Imidazol-4-yl)-methyl)-amino)-phenyl]-methyl]-N-(methanesulfonyl)-phenylalanine A solution of Compound E (200 mg, 0.38 mmol) and LiOH (80 mg, 2 mmol) in THF (6 mL), methanol (1 mL) and water (1 mL) was stirred at room temperature for 1 hour, concentrated under vacuum to 2 mL and poured into aqueous hydrochloric acid (20 mL, aqueous). The mixture was extracted with ethyl acetate (2×50 mL) and the combined organic layers were dried (MgSO4), and concentrated to provide Compound F (150 mg, 78%) as a clear oil.

G. 7-Bromo-2,3,4,5-tetrahydro-1-(1H-imidazol-4-ylmethyl)-4-(methylsulfonyl)-2-oxo-3-(phenylmethyl)-1H-1,4-benzodiazepine, trifluoroacetate A mixture of Compound F (150 mg, 0.29 mmol), DMF (3 mL), DIEA (0.66 mL, 0.725 mmol), and BOP (193 mg, 0.43 mmol) was stirred at room temperature for 3 hours. The mixture was partitioned between sodium carbonate (100 ml, sat soln) and ethyl acetate (100 mL), the aqueous phase was extracted with ethyl acetate (2×50 mL) and the combined organic layers were dried ($MgSO_4$) and concentrated. The residue was purified by preparative HPLC (aqueous methanol gradient containing 0.1% trifluoroacetic acid, C-18 column) and lyophilized to provide Compound G as a white solid (65 mg, 46%). MS: $(M+H)^+$ 490

Analysis calculated for $C_{21}H_{21}N_4O_3$.1.1$H_2O$.1.0 TFA. Calc'd: C, 44.33; H, 3.91; N, 8.99; S, 5.14; Br, 12.82. Found: C, 44.29; H, 3.59; N, 8.74; S, 5.05; Br, 12.78.

EXAMPLE 382

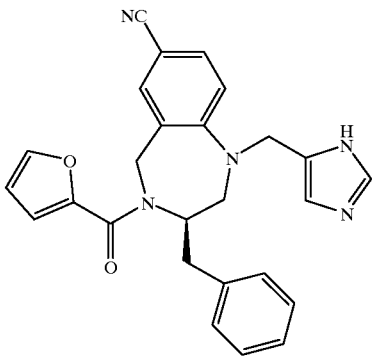

(R)-7-Cyano-4-(2-furanylcarbonyl)-2,3,4,5-tetrahydro-1-(1H-imidazol-4-ylmethyl)-3-(phenylmethyl)-1H-1,4-benzodiazepine, trifluoroacetate (1:1)

A. (R)-7-Cyano-4-(2-furanylcarbonyl)-2,3,4,5-tetrahydro-3-(phenylmethyl)-1H-1,4-benzodiazepine Compound A was prepared as a oil in 100% yield from Compound C of Example 248 and furan-2-carboxylic acid as described for Compound G of Example 381, with stirring for 18 hours, workup with citric acid, and no purification.

B. (R)-7-Cyano-4-(2-furanylcarbonyl)-2,3,4,5-tetrahydro-1-(1H-imidazol-4-ylmethyl)-3-(phenylmethyl)-1H-1,4-benzodiazepine, trifluoroacetate (1:1)

Compound B was prepared as a white solid in 7% yield from Compound A as described for Compound C of Example 380. MS: (M+H)+ 438

Analysis calculated for $C_{26}H_{23}N_5O_2 \cdot 2.0H_2O \cdot 1.0$ TFA. Calc'd: C, 57.24; H, 4.80; N, 11.92. Found: C, 57.22; H, 4.26; N, 11.74.

EXAMPLE 383

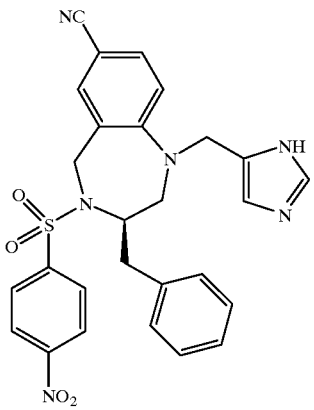

(R)-7-Cyano-2,3,4,5-tetrahydro-1-(1H-imidazol-4-ylmethyl)-4-[(4-nitrophenyl)sulfonyl]-3-(phenylmethyl)-1H-1,4-benzodiazepine, trifluroracetate Example 383 was prepared as a white solid in 3% yield from 4-nitrobenzene sulfonylchloride and Compound C of Example 248 by the following sequence: Compound C of Example 350, except that the reaction was run at room temperature and no purification was performed; Compound C of Example 380. MS: (M+H)+ 529

EXAMPLE 384

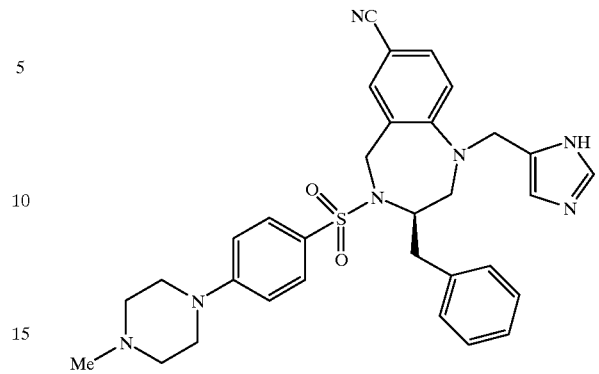

(R)-7-Cyano-2,3,4,5-tetrahydro-1-(1H-imidazol-4-ylmethyl)-4-[[4-(4-methyl-1-piperazinyl)phenyl]sulfonyl]-3-(phenylmethyl)-1H-1,4-benzodiazepine, trifluoroacetate A. (R)-7-Cyano-2,3,4,5-tetrahydro-4-[[4-(4-methyl-1-piperazinyl)phenyl]sulfonyl]-3-(phenylmethyl)-1H-1,4-benzodiazepine To a mixture of (R)-7-cyano-2,3,4,5-tetrahydro-4-[(4-fluorophenyl)sulfonyl]-3-(phenylmethyl)-1H-1,4-benzodiazepine (200 mg, 0.48 mmol, prepared as described in Example 291) in DMF (2 mL) was added N-methylpiperazine (2 mL). The solution was heated to 110° C. and stirred for six hours, poured into aqueous hydrochloric acid (150 mL, 1 M) and extracted with ethyl acetate (2×100 mL). The organic layers were combined, dried (MgSO4), concentrated and the residue crystallized from dichloromethane to provide Compound A (50 mg, 21%) as a grey solid.

B. (R)-7-Cyano-2,3,4,5-tetrahydro-i-(1H-imidazol-4-ylmethyl)-4-[[4-(4-methyl-1-piperazinyl)phenyl]sulfonyl]-3-(phenylmethyl)-1H-1,4-benzodiazepine, trifluoroacetate Compound B was prepared as a white solid in 65% yield from Compound A as described for Compound C of Example 380, with stirring at room termperature. MS: (M+H)+ 581

Analysis calculated for $C_{32}H_{35}N_7O_3S \cdot 2.0H_2O \cdot 2.0$ TFA. Calc'd: C, 51.12; H, 4.89; N, 11.59; S, 3.79. Found: C, 50.83; H, 4.68; N, 11.43; S, 4.47.

EXAMPLE 385

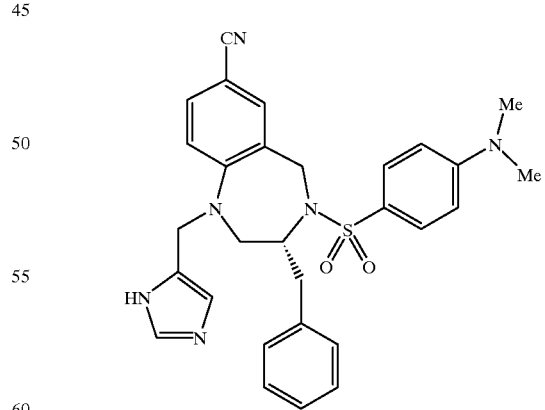

(R)-7-Cyano-2,3,4,5-tetrahydro-1-(1H-imidazol-4-ylmethyl)-4-[[(4-dimethylamino)phenyl]sulfonyl]-3-(phenylmethyl)-1H-1,4-benzodiazepine, trifluoroacetate A. (R)-7-Cyano-2,3,4,5-tetrahydro-4-[[(4-dimethylamino)phenyl]sulfonyl]-3-(phenylmethyl)-1H-1,4-benzodiazepine A solution of (R)-7-cyano-2,3,4,5-tetrahydro-4-[(4-fluorophenyl)sulfonyl]-3-(phenylmethyl)-1H-1,4-benzodiazepine (200 mg, 0.48 mmol, prepared as described in Example 291) in dimethylamine (2 mL, 2 M in THF) was stirred at 60° C. in a sealed pressure tube for 24 hours. Additional dimethylamine (4 mL, 2 M in THF) was added and the solution was stirred for an additional 6 hours. The reaction was concentrated to a paste under vacuum and the residue crystallized from methanol to provide Compound A (50 mg, 25%) as a grey solid.

B. (R)-7-Cyano-2,3,4,5-tetrahydro-1-(1H-imidazol-4-ylmethyl)-4-[[(4-dimethylamino)phenyl]sulfonyl]-3-(phenylmethyl)-1H-1,4-benzodiazepine, trifluoroacetate Compound B was prepared as a white solid in 43% yield from Compound A as described for Compound C of Example 380.

Analysis calculated for Calcd for $C_{29}H_{30}N_6O_2S.1.3$ $H_2O.0.9$ TFA Calc'd: C, 56.68; H, 5.17; N, 12.88; S, 4.91; F, 7.80. Found: C, 56.36; H, 5.07; N, 12.51; S, 5.39; F, 7.78.

EXAMPLE 386

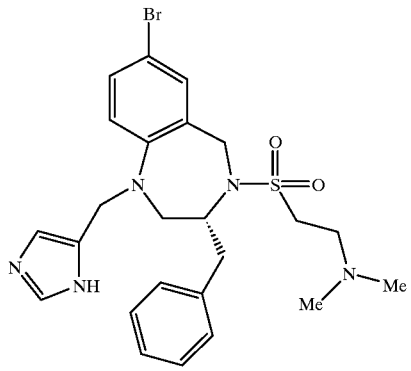

(R)-7-Bromo-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, dihydrochloride A. (R)-7-Bromo-4-[ethenylsulfonyl]-2,3,4,5-tetrahydro-3-(phenylmethyl)-4H-1,4-benzodiazepine To a solution of Compound B of Example 224 (10 g, 31.5 mmol) in dichloromethane (120 mL) at 0° C. was added dropwise a solution of 2-chloroethanesulfonyl chloride (3.2 mL, 30 mmol) in dichloromethane (10 mL). DIEA (5.2 mL, 30 mmol) was added dropwise. After 15 min, 2-chloroethanesulfonyl chloride (1.5 mL, 15 mmol) followed by DIEA (10.4 mL, 60 mmol) were added. The mixture was allowed to warm to rt and poured into water (80 mL). The organic layer was separated, washed with 1 N HCl and saturated aqueous $NaHCO_3$ (80 mL each), dried ($MgSO_4$) and concentrated in vacuo to afford Compound A as a yellowish foamy solid (15.2 g). MS: $(M+H)^+=406^+$ B. (R)-7-Bromo-4-[[2-(dimethylamino)ethyl]sulfonyl]-2,3,4,5-tetrahydro-3-(phenylmethyl)-4H-1,4-benzodiazepine A flask was charged with Compound A (7 g) and a THF solution of dimethylamine (2 M, 20 mL). The flask was stoppered and the mixture was stirred 18 hr, concentrated and purified by silica gel column chromatography eluting with 20% acetone in chloroform to afford Compound B (48% from Compound B of Example 224).

C. (R)-7-Bromo-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, dihydrochloride To a solution of Compound B (5.3 g, 11.7 mmol) in dichloromethane (100 mL) were added acetic acid (15 mL) and 4-formylimidazole (1.15 g, 12 mmol). After 10 min, sodium triacetoxyborohydride (2.54 g, 12 mmol) was added. After 3 hr, 4-formylimidazole (0.5 g, 5.8 mmol) and borohydride (1.2 g, 5.5 mmol) were added. After 18 hr, aldehyde (0.5 g) and borohydride (1.2 g) were added. After 5 hr, the mixture was concentrated. Aqueous ammonia (100 mL) and chloroform (100 mL) were added to the residue and the mixture was stirred vigorously for 0.5 hr. The two layers were separated and the organic layer was washed again with aqueous ammonia (100 mL). The combined aqueous layer was extracted with chloroform (100 mL), the two organic extracts were combined, dried ($K_2CO_3$), and concentrated. The residue was purified by flash silica gel column chromatography (step gradient of 5% and 10% MeOH in chloroform) to afford a solid which was dissolved in dichloromethane (50 mL) and HCl gas was bubbled through the solution. The mixture was concentrated in vacuo to afford a solid which was dissolved in water and lyophilized to afford Compound C (5.2 g, 73%). MS: $(M+H)^+$ 532

Analysis calculated for $C_{24}H_{30}BrN_5O_2S.$ 2HCl. Calc'd: C, 47.61; H, 5.33; N, 11.57. Found: C, 47.36; H, 5.45; N, 11.34.

EXAMPLE 387

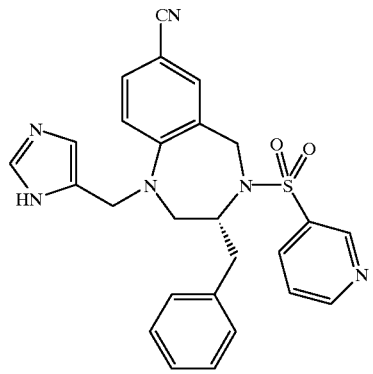

(R)-7-Cyano-2,3,4,5-tetrahydro-1-(1H-imidazol-4-ylmethyl)-3-(phenylmethyl)-4-(3-pyridinylsulfonyl)-1H-1,4-benzodiazepine, trihydrochloride Example 387 was prepared as a yellow solid in 15% yield from Compound C of Example 248 and 3-pyridinesulfonyl chloride as described for Example 284. MS: $(M+H)^+$ 485

EXAMPLE 388

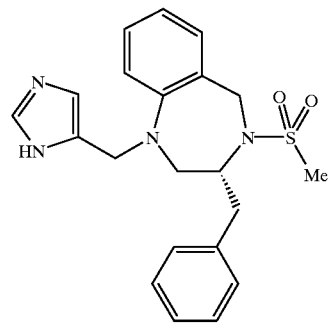

2,3,4,5-Tetrahydro-1-(1H-imidazol-4-ylmethyl)-4-(methylsulfonyl)-3-(phenylmethyl)-1H-1,4-benzodiazepine, dihydrochloride BuLi (1.0 M in THF, 5 mmol) was added to a solution at −78° C. of the free base of Example 224 (0.104 g, 0.19 mmol) in THF (10 mL). After 5 min., H2O/THF (1:1, 10 mL) was added. The solution was saturated with NaCl. The aqueous layer was extracted with $CH_2Cl_2$. The combined organic phases were dried over $Na_2SO_4$. Evaporation of solvent gave a solid which was purified by reverse phase preparative HPLC (gradient of aqueous methanol with 0.1% TFA) and converted into its HCl salt to afford 25 mg (30%) of Example 388 as a yellow solid. MS: $(M+H)^+$ 397

EXAMPLE 389

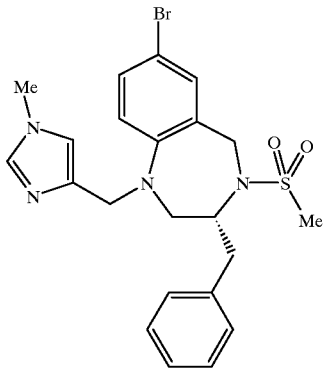

(R)-7-Bromo-2,3,4,5-tetrahydro-1-[(1-methyl-1H-imidazol-4-yl)methyl]-4-(methylsulfonyl)-3-(phenylmethyl)-1H-1,4-benzodiazepine, dihydrochloride NaH (60% in mineral oil, 1 g) was added to a solution at −10° C. of the free base of Example 224 (0.23 g, 0.19 mmol) in DMF/THF (1:1, 10 mL). After 20 min., MeI (0.7 mL) was added. The mixture was stirred at −5° C. for 1 hr, quenched with MeOH (5 mL) and diluted with $CH_2Cl_2$ (20 mL). The organic phase was washed with 2.5% NaOH. The organic phase was dried over $Na_2SO_4$. Evaporation of solvent gave a solid which was purified by reverse phase preparative HPLC (gradient of aqueous methanol with 0.1% TFA) followed by preparative TLC (8% MeOH, 2% $iPr_2NH$ in $CH_2Cl_2$) to provide 10 mg of Example 389 (10%) as a white solid. MS: $(M+H)^+$ 491

EXAMPLE 390

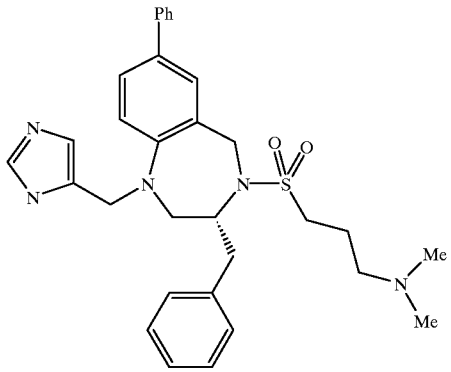

(R)-$^4$-[[$^3$-(Dimethylamino)propyl]sulfonyl]-2,3,4,5-tetrahydro-1-(1H-imidazol-4-ylmethyl)-7-phenyl-3-(phenylmethyl)-1H-1,4-benzodiazepine, dihydrochloride A. (R)-$^4$-[[$^3$-Chloropropyl]sulfonyl]-2,3,4,5-tetrahydro-7-phenyl-3-(phenylmethyl)-1H-1,4-benzodiazepine To a solution of Compound D of Example 226 (4.7 g, 15 mmol) and DIEA (7 mL, 40 mmol) in $CH_2Cl_2$ (40 mL) at 0° C. was added slowly 3-chloropropanesulfonyl chloride (2 mL, 16 mmol) in $CH_2Cl_2$ (5 mL). After 2 hrs, the solvent was evaporated. The residue was dissolved in $CH_2Cl_2$ (20 mL) and the solution was washed with 1 N NaOH (2×50 mL), dried and evaporated to provide Compound A as an oil (5.5 g).

B. (R)-4-[[3-Chloropropyl]sulfonyl]-2,3,4,5-tetrahydro-1-(1H-imidazol-4-ylmethyl)-7-phenyl-3-(phenylmethyl)-1H-1,4-benzodiazepine A solution of Compound A (5.5 g) and 4-formylimidozle (3 g, 30 mmol) in $AcOH/CH_2Cl_2$ (1:5, 300 mL) was stirred for 1 hr. $NaBH(OAc)_3$ (total 9 g, 42 mmol) was added (3 g every 4 hrs) and the solution was stirred for 12 hr. The solvent was evaporated and the residue was treated with 3% NaOH (50 mL). The solid was filtered and washed with water (5×100 mL) and dried to give Compound B (7.5 g).

C. (R)-4-[[3-(Dimethylamino)propyl]sulfonyl]-2,3,4,5-tetrahydro-1-(1H-imidazol-4-ylmethyl)-7-phenyl-3-(phenylmethyl)-1H-1,4-benzodiazepine, dihydrochloride A solution of Compound B (7 g) and dimethylamine (2.0 M in THF, 75 mL, 150 mmol) in DMF (150 mL) was warmed to 80° C. (sealed tube) for 30 hr. The DMF was removed. The residue was passed through a short silica gel colum (5% MeOH, 0.5% NH4OH in $CH_2Cl_2$). The eluant was evaporated and the residue was purified by reverse phase preparative HPLC (gradient of aqueous methanol with 0.1% TFA) and converted to the HCl salt to provide Compound C as an off white solid (5.0 g, 60% from Compound D of Example 226) MS: $(M+H)^+$ 544

$^1$H-NMR ($CD_3OD$, 300 Mhz) d: 1.80 (m, 2H), 2.8 (m, 2H), 3.0 (m, 4H), 3.20 (m, 2H), 3.60 (m, 2H), 4.30 (m, 1H), 4.6 (m, 2H), 6.8 (d, 7Hz, 1H), 7.1 to 7.6 (m, 13H), 8.92 (s, 1H).

EXAMPLE 391

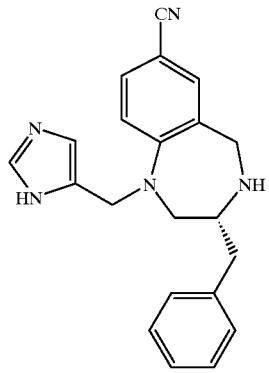

(R)-7-Cyano-2,3,4,5-tetrahydro-1-(1H-imidazol-4-ylmethyl)-3-(phenylmethyl)-1H-1,4-benzodiazepine, trihydrochloride Example 391 is Compound C of Example 280. MS$(M+H)^+$ 244.

EXAMPLE 392

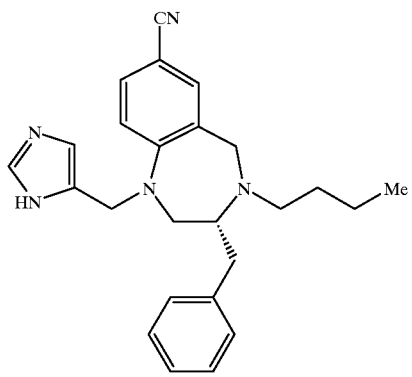

4-Butyl-2,3,4,5-tetrahydro-1-(1H-imidazol-4-ylmethyl)-3-(phenylmethyl)-1H-1,4-benzodiazepine, trihydrochloride A solution of Example 391 (0.23 g, 0.7 mmol) and butyraldehyde (1 g, 14 mmol) in 1:4 AcOH/CH$_2$Cl$_2$ (25 mL) was stirred at rt for 1 hr. NaBH(OAc)$_3$ (3.0 g, 14 mmol) was added and stirring was continued for 14 hrs. The reaction was quenched with conc. NH$_4$OH and diluted with 10% iPrOH in CH$_2$Cl$_2$ (50 mL). The organic phase was washed with 1 N NaOH (2×20 mL), dried over Na$_2$SO$_4$ and evaporated to give a yellow solid (0.4 g) which was purified by reverse phase preparative HPLC (gradient of aqueous methanol with 0.1% TFA) and converted to the HCl salt by lyophilizing with 1 N HCl to give Example 392 as a yellow solid (45 mg, 12%). MS (M+H)$^+$ 400.

EXAMPLE 393

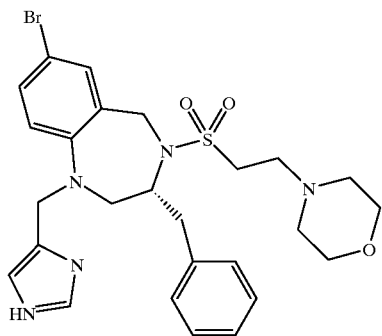

(R)-7-Bromo-2,3,4,5-tetrahydro-1-(1H-imidazol-4-ylmethyl)-4-[[2-(4-morpholinyl)ethyl]sulfonyl]-3-(phenylmethyl)-1H-1,4-benzodiazepine, dihydrochloride A. (R)-7-Bromo-2,3,4,5-tetrahydro-4-[[2-(4-morpholinyl)ethyl]sulfonyl]-3-(phenylmethyl)-1H-1,4-benzodiazepine To a solution of Compound A of Exmaple 386 (0.23 g, 0.34 mmol, 61% pure) in THF (1.5 mL) at rt was added morpholine (0.2 mL). The mixture was stirred 16 hr, diluted with ethyl acetate (15 mL), washed with water and brine (15 mL each), dried and concentrated in vacuo. The residue was purified with flash silica gel column chromatography eluting with 20% acetone in chloroform to afford Compound A as a white solid (130 mg, 77%).

B. (R)-7-Bromo-2,3,4,5-tetrahydro-1-(1H-imidazol-4-ylmethyl)-4-[[2-(4-morpholinyl)ethyl]sulfonyl]-3-(phenylmethyl)-1H-1,4-benzodiazepine, dihydrochloride A mixture of Compound A (0.060 g, 0.12 mmol), 4-formylimidazole (0.011 g, 0.12 mmol), 3A sieves and AcOH (0.2 mL) in dichloroethane (0.3 mL) was stirred at rt, under argon. After 2 hr, sodium triacetoxyborohydride (0.025 g, 0.12 mmol) was added. After stirring for 16 hr, the mixture was diluted with CHCl$_3$ (10 mL), NH$_4$OH (5 mL) and NaHCO$_3$ (5 mL), and stirred for 30 min. The layers were separated and the aqueous layer was extracted with CHCl$_3$ (2×20 mL). The combined organic extracts were washed with NaHCO$_3$, water, brine (3×10 mL each), dried over MgSO$_4$, filtered and concentrated. The residue was purified by reverse phase preparative HPLC (gradient of aqueous methanol with 0.1% TFA). The appropriate fractions were concentrated under vacuum. The residue was evaporated from MeOH (1 mL) and 1 N HCl (1 mL) 3 times. The residue was dissolved in water and lyophilized to afford Compound B as a light yellow solid (0.019 g, 28%). MS (M+H)$^+$ 574.

EXAMPLE 394

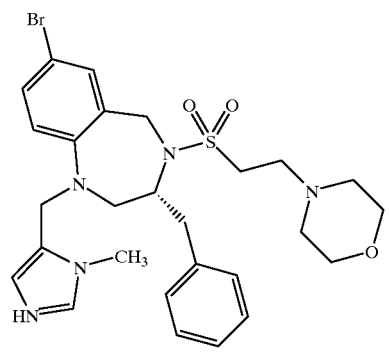

(R)-7-Bromo-2,3,4,5-tetrahydro-1-[(1-methyl-1H-imidazol-5-yl)methyl]-4-[[2-(4-morpholinyl)ethyl]sulfonyl]-3-(phenylmethyl)-1H-1,4-benzodiazepine, dihydrochloride Example 394 was prepared as a light yellow solid in 23% yield from Compound A of Example 393 and N-methyl-5-formylimidazole as described for Compound B of Example 393, with stirring under reflux for 7 hours before addition of hydride, cooling to rt, adding hydride, and stirring 16 hours after addition of hydride. MS (M+H)$^+$ 588.

EXAMPLE 395

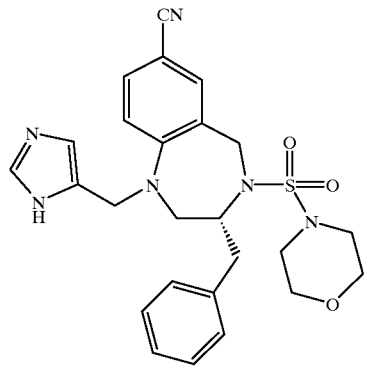

(R)-7-Cyano-1-(1H-imidazol-4-ylmethyl)-4-(4-morpholinylsulfonyl)-3-(phenylmethyl)-1H-1,4-benzodiazepine, monohydrochloride A. (R)-7-Cyano-4-(4-morpholinylsulfonyl)-3-(phenylmethyl)-1H-1,4-benzodiazepine To a solution of Compound C of Example 248 (263 mg, 1 mmol) in acetonitrile (2 mL) at rt under argon were added morpholinesulfamoyl chloride (371 mg, 2 mmol) and DIEA (0.35 mL, 2 mmol). The resulting brown mixture was stirred for 65 hr and concentrated, and the residue was partitioned between 1 N HCl and chloroform (10 mL each). The organic layer was separated, washed with saturated $NaHCO_3$, dried ($MgSO_4$) and concentrated. The residue was purified by flash silica gel column eluting with a step gradient of 40% and 50% EtOAc in hexanes to afford Compound A (95 mg, 71%) as a pale yellow solid. MS $(M+H)^+=413$.

B. (R)-7-Cyano-1-(1H-imidazol-4-ylmethyl)-4-(4-morpholinylsulfonyl)-3-(phenylmethyl)-1H-1,4-benzodiazepine, monohydrochloride To a solution of Compound A (206 mg, 0.5 mmol) in 1,2-dichloroethane (2 mL) at RT under argon were added 4-formylimidazole (380 mg, 4 mmol), HOAc (0.5 mL) and 3A sieves. The mixture was warmed to 50° C. and sodium triacetoxyborohydride (330 mg, 1.5 mmol) was added. After 18 hr, more hydride (212 mg, 1 mmol) was added. After 5 more hrs, the mixture was cooled to RT, filtered through celite and carefully treated with 30% $NH_4OH$ (10 mL) and chloroform (10 mL). The mixture was vigorously stirred for 1 hr, the organic layer was separated and washed with 15% ammonia solution (15 mL), dried ($K_2CO_3$) and concentrated. The brown oil obtained was purified by silica gel column chromatography eluting wih 5% MeOH in chloroform to afford the free base of Compound B (150 mg, 61%) as a white solid. 26 mg of this solid was treated with 1 N HCl in ether followed by concentration in vacuo to afford Compound B (28 mg). MS $(M+H)^+=493$; $(M-H)^-=491$.

EXAMPLE 396

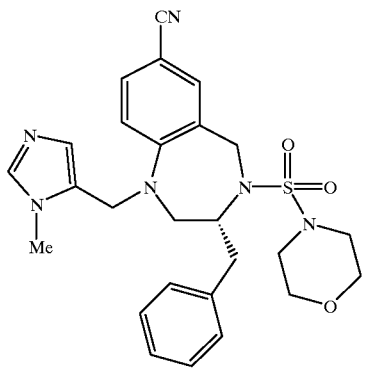

(R)-7-Cyano-1-[(1-methyl-1H-imidazol-5-yl)methyl]-4-[(4-morpholinyl)sulfonyl]-3-(phenylmethyl)-1H-1,4-benzodiazepine, monohydrochloride A. (R)-7-Cyano-1-[(1-triphenylmethyl-1H-imidazol-4-yl)methyl]-4-[(4-morpholinyl)sulfonyl]-3-(phenylmethyl)-1H-1,4-benzodiazepine To a solution of the free base of Example 395 (120 mg, 0.24 mmol) in acetonitrile (2 mL) at RT under argon were added trityl chloride (83 mg, 0.3 mmol) and DIEA (0.053 mL, 0.3 mmol). The mixture was refluxed for 4 hr, cooled to RT and concentrated. The residue was dissolved in chloroform (15 mL) and washed with water and saturated $NaHCO_3$ (15 mL each). The organic layer was dried ($MgSO_4$), and concentrated. The residue was washed with warm hexanes (2×5 mL) to afford Compound A (178 mg, 100%) as a pale yellow solid.

B. (R)-7-Cyano-1-[(1-methyl-1H-imidazol-5-yl)methyl]-4-[(4-morpholinyl)sulfonyl]-3-(phenylmethyl)-1H -1,4-benzodiazepine, monohydrochloride To a solution of Compound A (170 mg, 0.23 mmol) in dichloromethane (2 mL) at −78° C. under argon was added methyl triflate (0.027 mL, 0.24 mmol). After 1 hr, the cold bath was removed and replaced with ice bath (0° C.). After 2 hr, 50% aqueous acetic acid (2 mL) was added and the mixture was refluxed 40 min. Chloroform and saturated $NaHCO_3$ (10 mL each) were added and the mixture was stirred carefully until effervescence subsided. Solid $K_2CO_3$ was added carefully until pH 11 of the aqueous layer was achieved. The organic layer was separated, dried ($K_2CO_3$) and concentrated in vacuo. The solid residue was washed with warm hexanes and ether (2×10 mL each). The solid was dissolved in EtOAc (5 mL) and 1 N HCl in ether (2 mL) was added. The precipitate was collected and washed with EtOAc (3×5 mL). The solid was dried in vacuo at 40° C. to afford Compound B as a pale yellow solid (110 mg, 84%). MS: $(M+H)^+=507$.

Analysis calculated for $C_{26}H_{30}N_6O_3S.1.7$ HCl. Calc'd: C, 54.75; H, 5.61; N, 14.73. Found: C, 55.15; H, 5.68; N, 14.29.

EXAMPLE 397

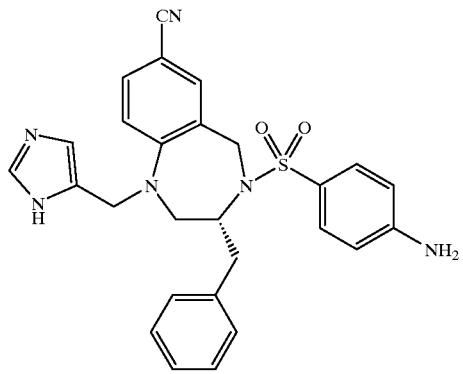

(R)-7-Cyano-2,3,4,5-tetrahydro-1-(1H-imidazol-4-ylmethyl)-4-[(4-aminophenyl)sulfonyl]-3-(phenylmethyl)-1H-1,4-benzodiazepine, hydrochloride To a stirred solution of the free base of Example 383 (5 mg) in ethyl acetate was added SnCl2. The solution was stirred at room temperature for 18 h. NH4OH was added, followed by MgSO4. The suspension was filtered, and the filtrate was concentrated in vacuo. The residue was dissoved in methanol, 1 N HCl in ether was added. The solvent was removed to give 2.0 mg Example 397 (40%) as a yellow solid.

EXAMPLE 398

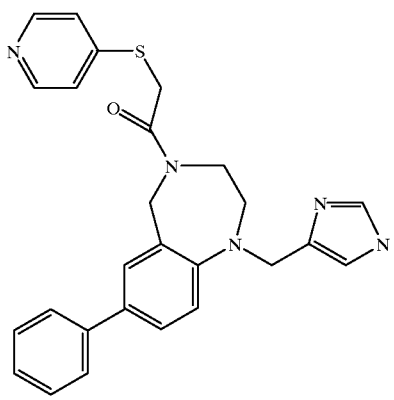

2,3,4,5-Tetrahydro-1-(1H-imidazol-4-ylmethyl)-4-[(4-pyridylthio)acetyl]-7-phenyl-1H-1,4-benzodiazepine, dihydrochloride Example 398 was prepared from Compound B of Example 33 as described for Examples 101–201. MS (M+H)+ 456.

EXAMPLE 399

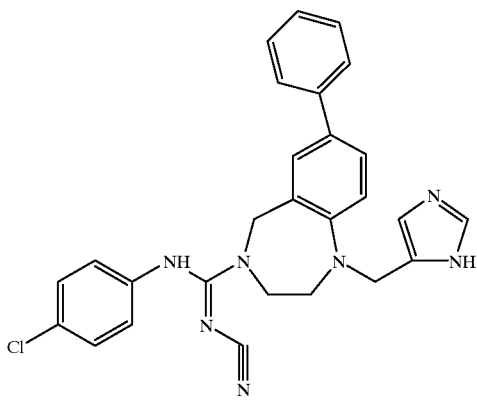

N-(4-Chlorophenyl)-N'-cyano-1,2,3,5-tetrahydro-1-(1H-imidazol-4-ylmethyl)-7-phenyl-4H-1,4-benzodiazepine-4-imidamide, monohydrochloride A. N-(4-Chlorophenyl)-N'-cyano-1,2,3,5-tetrahydro-7-phenyl-4H-1,4-benzodiazepine-4-imidamide To a stirred solution of Compound B of Example 12 (110 mg, 0.5 mmol) in DMF was added sequentially N-(4-chlorophenyl)-N'-cyanothiourea (130 mg, 0.62 mmol), and EDC (120 mg, 0.61 mmol). The solution was stirred at room temperature for 18 h and partititoned between ethyl acetate and sat'd NH4Cl solution. The organic layer was separated, washed with saturated NaHCO3 solution and brine, dried, and concentrated. The residue was crystalized from MeOH to give Compound A as a solid (150 mg, 75%). MS: 402 (M+H).

B. N-(4-Chlorophenyl)-N'-cyano-1,2,3,5-tetrahydro-1-(1H-imidazol-4-ylmethyl)-7-phenyl-4H-1,4-benzodiazepine-4-imidamide, monohydrochloride Compound B was prepared as a solid in 78% yield from Compound A as described for Compound D of Example 1. MS: 482 (M+H)

Analysis calculated for C27H23N7Cl.2.2HCl.2H2O. Calc'd: C, 54.30; H, 4.93; N, 16.42; Cl, 18.99. Found: C, 54.57; H, 4.90; N, 16.76; Cl, 18.90.

EXAMPLE 400

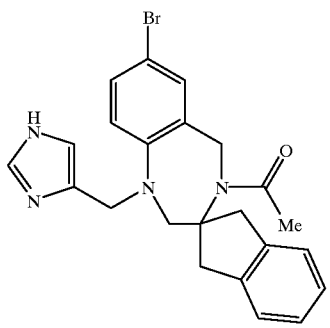

4-Acetyl-7-bromo-1,2,4,5,1',3'-hexahydro-1-(1H-imidazol-4-ylmethyl)spiro[3H-1,4-benzodiazepine-3,2'-[2H]indene], dihydrochloride A. N-[(2-Amino-5-bromophenyl)carbonyl]-2-amino-2-indanecarboxylic acid A solution of 2-amino-2-indanecarboxylic acid (680 mg, 4.15 mmol), bromoisatoic anhydride (1.0 g, 4.15 mmol) and pyridine•HCl (2.0 g, 1.72 mmol) in pyridine (30 mL) was refluxed for 4 h, cooled and concentrated. The residue was partitioned between water (200 mL) and ethyl acetate (200 mL). The organic layer was washed with water (3×100 mL), brine (50 mL), dried (MgSO4) and concentrated to yield compound Compound A as a yellowish glass (350 mg, 22%). MS (M+H)+ 375.

B. 7-Bromo-1,2,4,5,1',3'-hexahydro-spiro[3H-1,4-benzodiazepin-2,5-dione-3,2'-[2H]indene]

A solution of Compound A (350 mg, 0.93 mmol),EDC (203 mg, 1.02 mmol), DIEA (0.35 mL, 2.00 mmol) and HOBt (135 mg, 1.00 mmol) in DMF (10 mL) was stirred for 16 h and poured into water (100 mL). The mixture was extracted with ethyl acetate (2×50 mL). The combined ethyl acetate layers were washed with water (3×100 mL), brine (100 mL), dried (MgSO4) and concentrated to yield compound Compound B as a brown glass (150 mg, 45%). MS (M+H)+ 358.

C. 7-Bromo-1,2,4,5,1',3'-hexahydro-spiro[3H-1,4-benzodiazepine-3,2'-[2H]indene]

To a solution of Compound B (150 mg, 0.42 mmol) in THF (10 mL) was added borane (1 M in THF, 3 mL, 3 mmol). The solution was refluxed for 3 h and cooled to room temperature. Methanol (5 mL) was added and the solution was concentrated. 5 N HCl (10 mL) was added and the mixture was refluxed for 4 h, cooled to room temperature, neutralized to pH 6 with 50% NaOH and extracted with methylene chloride (3×50 mL). The combined organic layers were washed with brine (30 mL), dried (MgSO4) and concentrated to yield compound C as a slightly yellow glass (70 mg, 50%). MS (M+H)+ 330.

D. 4-Acetyl-7-bromo-1,2,4,5,1',3'-hexahydro-spiro[3H-1,4-benzodiazepine-3,2'-[2H]indene]

Compound C (70 mg, 0.21 mmol) was dissolved in THF (5 mL) and DIEA (37 µL, 0.21 mmol) was added followed by acetyl chloride (15 µL, 0.21 mmol). The solution was stirred for 30 min, concentrated, dissolved in ethyl acetate (50 mL) and washed with water (3×20 mL). The organic layer was dried (MgSO4) and concentrated to yield Compound D as a light brown glass.

E. 4-Acetyl-7-bromo-1,2,4,5,1',3'-hexahydro-1-(1H-imidazol-4-ylmethyl)spiro[3H-1,4-benzodiazepine-3,2'-[2H]indene], dihydrochloride Compound D and 4-formylimidazole were dissolved in 1,2-DCE (5 mL) and acetic acid (0.5 mL) was added followed by sodium triacetoxyborohydride. The mixture was stirred at 50° C. for 2 h and saturated NaHCO3 (5 mL) was added. The mixture was concentrated and the residue was partitioned between water (20 mL) and ethyl acetate (20 mL). The organic layer was washed with water (10 mL), brine (10 mL), dried (MgSO4), concentrated and purified by RP preparative HPLC (gradient of aqueous methanol with 0.1% TFA). Fractions containing the desired product were combined, concentrated and lyophilized. This lyophilate was dissolved in methanol (0.5 mL) and 1 N HCl (5 mL). This mixture was concentrated and lyophilized. This procedure was repeated to provide Compound E as a white solid (12 mg, 13%) MS (M+H)+ 451.

EXAMPLE 401

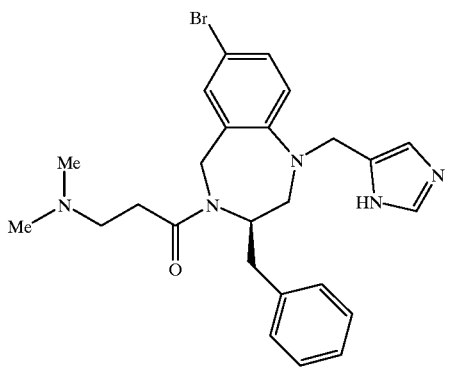

7-Bromo-4-[3-(dimethylamino)-1-oxopropyl]-2,3,4,5-tetrahydro-1-(1H-imidazol-4-ylmethyl)-3-(phenylmethyl)-1H-1,4-benzodiazepine, trifluoroacetate (1:1)

Example 401 was prepared as a white solid in 6% overall yield from Compound B of Example 224 by the following sequence: EDC/HOBt mediated coupling of acrylic acid in DMF, with purification by flash chromatography; Compound D of Example 232; Compound D of Example 224. MS: (M +H)+ 466.

EXAMPLE 402

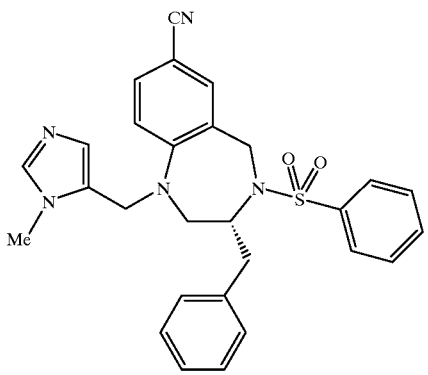

(R)-2,3,4,5-Tetrahydro-1-(1-methyl-1H-imidazol-5-ylmethyl)-4-(phenylsulfonyl)-3-(phenylmethyl)-1H-1,4-benzodiazepine-7-carbonitrile, monohydrochloride A solution of (R)-7-cyano-2,3,4,5-tetrahydro-1-[(((1,1-dimethylethoxy)-carbonyl)-1H-imidazol-4-yl)methyl]-4-(phenylsulfonyl)-3-(phenylmethyl)-1H-1,4-benzodiazepine (0.23 g, 0.4 mmol, prepared from Example 312 as described for Compound A of Example 234) in $CH_2Cl_2$ (3 ml) was added to a cooled solution of methyl triflate (2 mL, 17.6 mmol) in $CH_2Cl_2$ (10 mL) at −78° C. over 30 min. The solution was slowly warmed to 0° C. in 4 hrs. PBS Buffer (10 mL) was added and stirred for 20 min. The organic phase was separated. The aqueous layer was extracted with $CH_2Cl_2$ (2×10 mL). The combined organic layers were dried over $Na_2SO_4$ and evaporated to give an oil which was purified by RP preparative HPLC (gradient of aqueous methanol with 0.1% TFA) and converted to the HCl salt to afford Example 402 as a yellow solid. (60 mg, 289%) MS (M+H)+ 498

EXAMPLE 403

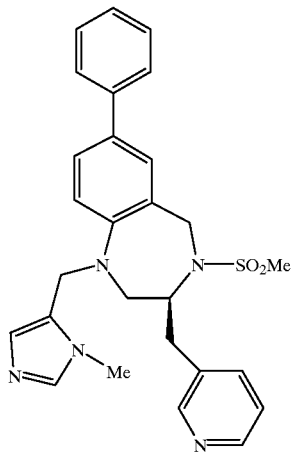

2,3,4,5-Tetrahydro-1-[(1-methyl-1H-imidazol-5-yl)-methyl]-4-(methylsulfonyl)-7-phenyl-3-(pyridin-3-yl-methyl)-1H-1,4-benzodiazepine, hydrochloride (1:1.5), trifluoroacetate (1:0.75) salt 1-Methyl-5-formylimidazole (0.060 g, 0.54 mmol) was added to a solution of 2,3,4,5-tetrahydro-4-(methylsulfonyl)-7-phenyl-3-(pyridin-3-yl-methyl)-1H-1,4-benzodiazepine (0.11 g, 0.27 mmol, prepared as described in Example 328) with 3A molecular sieves (50 mg) in 1/1 DCE: acetic acid (1.8 ml) and the mixture was stirred at 70° C. for 1 h. Sodium triacetoxyborohydride (0.057 g, 0.27 mmol) was added and the mixture was stirred at 700 for 30 minutes. 1-Methyl-5-formylimidazole (0.060 g, 0.54 mmol) was added to the mixture and it was stirred at 70° C. for 1 h. Sodium triacetoxyborohydride (0.057 g, 0.27 mmol) was added and the mixture was stirred at 70° C. for 30 minutes. The latter procedure was repeated. The mixture was cooled to room temperature, diluted with methylene chloride (10 ml), filtered and the filtrate concentrated under vacuum. The residue was diluted with 1 N NaOH (10 ml) and was stirred at room temperature for 10 minutes. The solution was extracted with $CH_2Cl_2$ (3×50 ml), the combined organic extracts were dried ($Na_2SO_4$), filtered and concentrated under vacuum. The residue was purified by preparative HPLC (gradient of aq MeOH with 0.1% TFA) and the appropriate fractions were isolated and concentrated under vacuum. The residue was evaporated from $CH_3CN$ (5 ml) and 1 N HCl (1 ml) 3 times. The residue was dissolved in $CH_3CN$ (1 ml) and 1 N HCl (2 ml) and lyophilized to afford Example 403 (0.025 g, 19%) as a white solid. MS: (M+H)+ 488

Analysis calculated for $C_{27}H_{29}N_5O_2S.1.5$ HCl.2.02 $H_2O.0.75$ TFA. Calc'd: C, 51.54; H, 5.36; N, 10.54. Found: C,51.27; H, 5.72; N, 10.95.

EXAMPLE 404

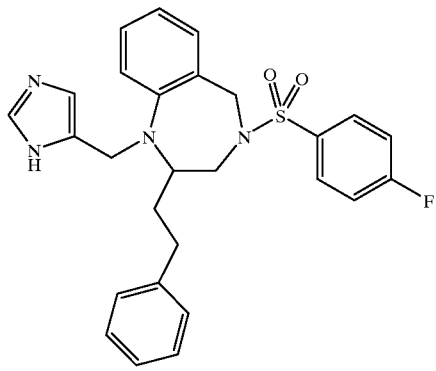

4-[4-(Fluorophenyl)sulfonyl]-2,3,4,5.tetrahydro-1-(1H-imidazol-4-ylmethyl)-2-(2-phenylethyl)-1H-1,4-benzodiazepine, monohydrochloride Example 404 was prepared as a solid in 41% yield from Compound A of Example 364 and 4-fluorobenzenesulfonyl chloride as described for Compound B of Example 364. MS: (M+H)+ 491

EXAMPLE 405

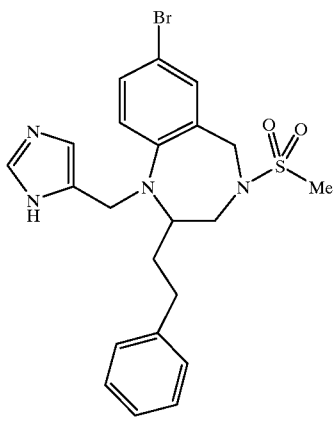

7-Bromo-2,3,4,5-tetrahydro-1-(1H-imidazol-4-yl-methyl)-4-(methyl-sulfonyl)-2-(2-phenylethyl)-1H-1,4-benzodiazepine, monohydrochloride A. 2,3,4,5-Tetrahydro-2-(2-phenylethyl)-1H-1,4-benzodiazepine To a stirred solution of Compound A of Example 363 (140 mg, 0.52 mmol) in anhydrous THF at rt was added LAH (110 mg). The resultant suspension was stirred at rt for 18 h, quenched by addition of ethyl acetate followed by 0.5 mL of concentrated NH4OH solution and filtered. The filtrate was concentrated in vacuo to give Compound A as an oil (110 mg, 84%).

B. 2,3,4,5-Tetrahydro-4-(methylsulfonyl)-2-(2-phenylethyl)-1H-1,4-benzodiazepine Compound B was prepared as an oil in 61% yield from Compound A as described for Compound C of Example 224.

C. 7-Bromo-2,3,4,5-tetrahydro-4-(methylsulfonyl)-2-(2-phenylethyl)-1H-1,4-benzodiazepine To a stirred solution of Compound C (80 mg, 0.24 mmol) in CHCl3 was added tetrabutylammonium perbromide (120 mg, 0.24 mmol) in one portion. The mixture was stirred at room temperature for 30 min and evaporated. The residue was partitioned between water and 50% ethyl acetate and hexanes. The organic layer was separated, washed with water, sat'd NH4Cl solution, dried, and concentrated to give Compound C as an oil (100 mg, 100%).

D. 7-Bromo-2,3,4,5-tetrahydro-1-(1H-imidazol-4-yl-methyl)-4-(methyl-sulfonyl)-2-(2-phenylethyl)-1H-1,4-benzodiazepine, monohydrochloride Compound D was prepared as a solid in 92% yield from Compound C as described for Compound D of Example 224. MS: (M+H)+ 489

EXAMPLE 406

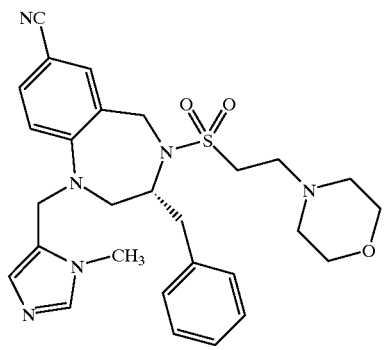

(R)-7-Cyano-2,3,4,5-tetrahydro-1-(1-methyl-1H-imidazol-5-ylmethyl)-4-[[2-(1-morpholinyl)ethyl]sulfonyl]-3-(phenylmethyl)-1H-1,4-benzodiazepine, dihydrochloride A. (R)-7-Cyano-2,3,4,5-tetrahydro-4-[ethenylsulfonyl]-3-(phenyl-methyl)-1H-1,4-benzodiazepine 2-Chloroethanesulfonyl chloride (1.85 g, 11.4 mmol) was added to a solution of Compound C of Example 248 (1.0 g, 3.79 mmol) and DIEA (2.6 mL, 15.16 mmol) in dichloromethane (16 mL) at 0° C. under argon. After stirring for 16 hr, the reaction was diluted with chloroform (20 mL) and NaHCO3 (5 mL). The layers were separated, the aqueous layer was extracted with chloroform (2×50 mL). The combined organic extracts were washed with NaHCO3 (2×20 mL) and brine (2×50 mL), dried over MgSO4, filtered and concentrated, to afford Compound A (1.55 g, 116.5%).

B. (R)-7-Cyano-2,3,4,5-tetrahydro-1-(1-methyl-1H-imidazol-5-ylmethyl)-4-[[2-(1-morpholinyl)ethyl]sulfonyl]-3-(phenylmethyl)-1H-1,4-benzodiazepine, dihydrochloride Compound B was prepared as a light yellow solid in 12% overall yield by the following sequence: Compound B of Example 353, with chromatography with 1:1 ethyl acetate-:hexanes; Compound C of Example 353, with reaction at room temperature, stirring for 2 days and purification by RP preparative HPLC (gradient of aqueous methanol with 0.1% TFA). MS: (M+H)+ 535

EXAMPLE 407

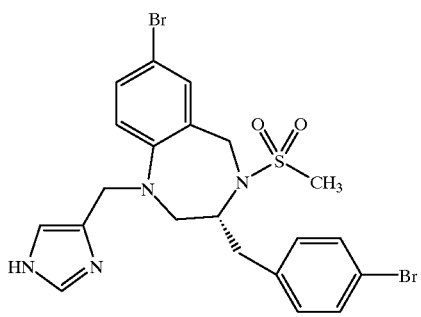

(R)-7-Bromo-2,3,4,5-tetrahydro-1-(1H-imidazol-4-ylmethyl)-4-(methyl-sulfonyl)-3-(4-bromophenylmethyl)-1H-1,4-benzodiazepine, hydrochloride Example 407 was prepared from D-4-bromophenylalanine as described for Example 224; the crude product was purified by RP preparative HPLC (gradient of aqueous methanol with 0.1% TFA). Fractions containing the desired product were combined, neutralized with saturated Na2CO3 aqueous solution and extracted with CH2Cl2. The combined extracts were dried (Na2SO4) and evaporated under reduced pressure. The residue was dissolved in ethyl acetate (10 mL) and 1 N HCl solution in ether (10 mL) was added. The solvent was removed in vacuo to give Example 407 as a yellow solid. MS (M+H)+ 555

EXAMPLE 408

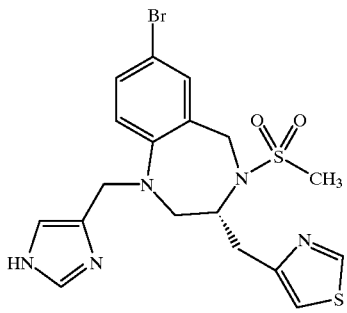

(R)-7-Bromo-2,3,4,5-tetrahydro-1-(1H-imidazol-4-ylmethyl)-4-(methyl-sulfonyl)-3-(thiazol-4-ylmethyl)-1H-1,4-benzodiazepine, hydrochloride Example 408 was prepared as a yellow solid from D-(thiazol-4-yl)alanine methyl ester as described for Example 407. MS (M+H)+ 484

EXAMPLE 409

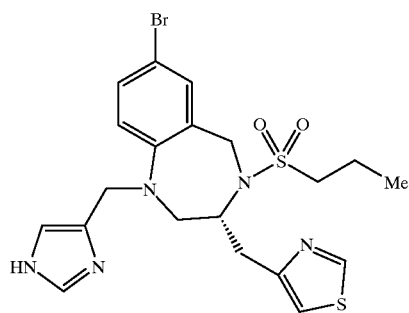

(R)-7-Bromo-2,3,4,5-tetrahydro-1-(1H-imidazol-4-ylmethyl)-4-(propyl-sulfonyl)-3-(thiazol-4-ylmethyl)-1H-1,4-benzodiazepine, hydrochloride Example 409 was prepared as described for Example 408, except that propanesulfonyl chloride was used in place of methanesulfonyl chloride. MS (M+H)+ 510.

EXAMPLE 410

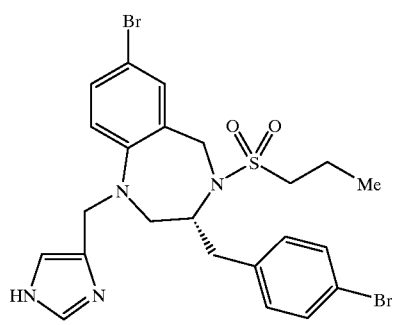

(R)-7-Bromo-2,3,4,5-tetrahydro-1-(1H-imidazol-4-ylmethyl)-4-(propylsulfonyl)-3-(4-bromophenylmethyl)-1H-1,4-benzodiazepine, hydrochloride Example 410 was prepared as described for Example 407, except that propanesulfonyl chloride was used in place of methanesulfonyl chloride. MS (M+H)+ 583

EXAMPLE 411

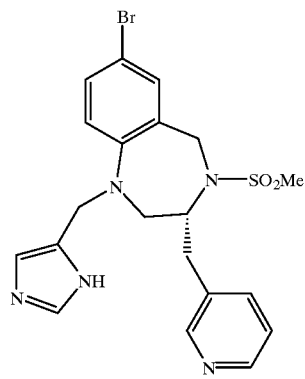

(R)-7-Bromo-2,3,4,5-tetrahydro-1-(1H-imidazol-4-ylmethyl)-3-(pyridin-3-ylmethyl)-4-(methylsulfonyl)-1H-1,4-benzodiazepine, trihydrochloride Example 411 was prepared as a pale yellow solid in 16% yield from Compound A of Example 350 by the following sequence: Compound C of Example 350, with the addition done at 0° C. and chromatography with ethyl acetate; Compound D of Example 350, with heating at 60° C. (M+H)+ 476.

Analysis calculated for $C_{20}H_{22}N_5BrO_2S \cdot 3.00HCl \cdot 0.17H_2O$. Calc'd: C, 40.80; H, 4.34; N, 11.89. Found: C, 40.79; H, 4.36; N, 11.79.

EXAMPLE 412

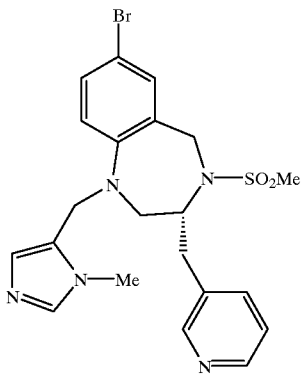

(R)-7-Bromo-2,3,4,5-tetrahydro-1-(1H-1-methyl-imidazol-5-ylmethyl)-3-(pyridin-3-ylmethyl)-4-(methylsulfonyl)-1H-1,4-benzodiazepine, dihydrochloride Example 412 was prepared as a pale yellow solid in 31% yield from (R)-7-bromo-2,3,4,5-tetrahydro-3-(pyridin-3-ylmethyl)-4-(methylsulfonyl)-1H-1,4-benzodiazepine (prepared as described in Example 411) and 1-methyl-5-formylimidazole as described for Compound D of Example 350, with heating at 60° C. (M+H)+ 490.

Analysis calculated for $C_{21}H_{24}N_5BrO_2S \cdot 2.25HCl \cdot 1.38H_2O$. Calc'd: C, 42.23; H, 4.90; N, 11.72. Found: C, 42.23; H, 4.90; N, 11.66.

EXAMPLE 413

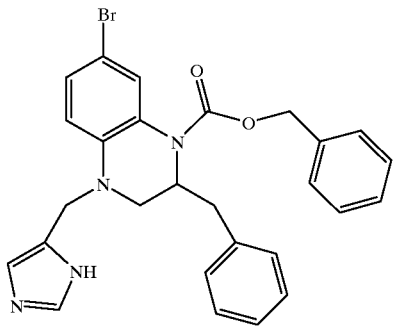

1,2,3,4-Tetrahydro-7-bromo-4-[(1H-imidazol-4-yl)methyl]-2-phenyl-methyl-1-(phenylmethyloxycarbonyl)quinoxaline, hydrochloride A. N-(2-Nitrophenyl)-phenylalanine To a suspension of DL-phenylalanine (490 mg, 3 mmol) in water at rt was added sodium bicarbonate (0.84 g, 10 mmol) and 2-fluoronitrobenzene (0.63 mL, 6 mmol). The mixture was heated to 80° C. After 16 hr, ethanol (95%, 3 mL) was added. After 6 hr, the mixture was partially concentrated to remove ethanol and the resulting solution was washed with ethyl acetate and chloroform (10 mL each). The aqueous layer was acidified to pH 1 and extracted with chloroform (2×10 mL). The chloroform extracts were combined, dried (MgSO4), and concentrated in vacuo to afford Compound A as a solid (0.81 g, 94%). MS (M+H)+ 287

B. N-(2-Nitrophenyl)-phenylalanine, methyl ester

To a solution of Compound A (780 mg, 2.7 mmol) in MeOH (15 mL) at rt was added HCl in dioxane (3 mL, 4 M). After 18 hr, the mixture was concentrated. The residue was dissolved in chloroform (15 mL) and washed with saturated NaHCO3 (10 mL) and brine (15 mL). The organic layer was dried (MgSO4) and concentrated in vacuo. The yellow oil was chromatographed (silica, flash, 20% EtOAc/hexanes) to afford Compound B (740 mg, 91%) as a yellow solid. MS (M+H)+ 301

C. 1,2,3,4-Tetrahydro-3-oxo-2-phenylmethyl-quinoxaline

To a solution of Compound B (720 mg, 2.34 mmol) in ethyl acetate (5 mL) at rt was added 20% Pd(OH)2/C (40 mg). The flask was filled with hydrogen gas via a balloon. After 5 hr, the mixture was filtered through celite, and the filtrate was concentrated in vacuo. The colorless solid was chromatographed (silica, flash, 30% EtOAc/hexanes) to afford Compund C (550 mg, 98%) as a solid. MS (M+H)+ 239.

D. 1,2,3,4-Tetrahydro-3-oxo-2-phenylmethyl-1-(phenylmethyloxy-carbonyl)quinoxaline To a solution of Compound C (525 mg, 2.2 mmol) in dichloromethane (6 mL) at 0° C. were added DIEA (0.52 mL, 3 mmol) and benzylchloroformate. The mixture was allowed to warm to rt over 3 hr. DMAP (10 mg) and pyridine (1 mL) were added and the mixture was stirred overnight (16 hr). The mixture was concentrated in vacuo and the residue was partitioned between ethyl acetate (20 mL) and 1 N HCl (15 mL). The organic layer was separated, washed with 1 N HCl (15 mL), dried (MgSO4), and concentrated in vacuo. The residue was chromatographed (silica, flash, 10% EtOAc/chloroform) to afford Compound D as a solid (440 mg, 54%). MS (M+H)+ 373.1.

E. 1,2,3,4-Tetrahydro-2-phenylmethyl-1-(phenylmethyloxycarbonyl)quinoxaline

A mixture of Compound D (380 mg, 1.02 mmol) and borane in THF (1 M, 3 mL) was stirred at rt under argon. After 24 hr, MeOH (10 mL) was added carefully followed by 1 N HCl (1 M in ether, 5 mL). After 1 hr, the mixture was concentrated in vacuo. The above procedure was repeated once more to afford a white solid which was then treated with chloroform and 10% ammonium hydroxide (20 mL each) and stirred vigorously. After 1 hr, the organic layer was separated, dried (MgSO4), and concentrated in vacuo to afford Compound E as a solid (366 mg, 100%). MS (M+H)+ 359.1.

F. 1,2,3,4-Tetrahydro-7-bromo-2-phenylmethyl-1-(phenyl-methyl-oxycarbonyl)quinoxaline To a stirred solution of Compound E (340 mg, 0.95 mmol) in chloroform (3 mL) at rt was added a solution of tetrabutylammonium tribromide (457 mg, 0.95 mmol) in chloroform (2 mL) over 2 min. After 10 min, an aqueous solution of sodium bisulfite (10 mL) was added and the mixture was extracted with chloroform (10 mL). The organic layer was separated, dried (MgSO4), and concentrated in vacuo. The residue waschromatographed (silica, flash, 15% EtOAc/hexanes) to afford Compound F (355 mg, 86%) as a thick oil. MS (M+H)+ 437, 439.

G. 1,2,3,4-Tetrahydro-7-bromo-4-[(1H-imidazol-4-yl)methyl]-2-phenylmethyl-1-(phenylmethyloxycarbonyl)quinoxaline, hydrochloride To a solution of Compound F (345 mg, 0.79 mmol) in dichloromethane (3 mL) at rt were added 4-formylimidazole (0.3 g, 3.1 mmol), acetic acid (1 mL), 3A sieves and sodium triacetoxyborohydride (212 mg, 1 mmol). After 5 hr, sodium borohydride (212 mg, 1 mmol) was added. After 15 hr, the mixture was filtered and the filtrate concentrated in vacuo. The residue was dissolved in chloroform (15 mL) and stirred vigorously with aqueous ammonia (15 mL). After 1 hr, the organic layer was separated, dried (MgSO$_4$) and concentrated in vacuo. Chromatography (silica, flash, 10% i-PrOH in chloroform) afforded the free base (280 mg, 69%). 1 N HCl in ether (2 mL) was added to this solid (25 mg) and the mixture was dried in vacuo to afford Compound G (28 mg). MS (M+H)$^+$= 517, 519.

EXAMPLE 414

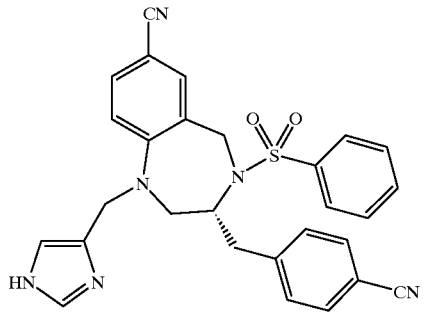

(R)-7-Cyano-2,3,4,5-tetrahydro-1-(1H-imidazol-4-ylmethyl)-4-(phenyl-sulfonyl)-3-(4-cyanophenylmethyl)-1H-1,4-benzodiazepine, hydrochloride Example 414 was prepared as a solid in 12% yield from (R)-7-bromo-2,3,4,5-tetrahydro-3-(4-bromophenylmethyl)-1H-1,4-benzodiazepine (prepared as described in Example 407) by the following sequence: Compound C of Example 248; Compound C of Example 224, using benzenesulfonyl chloride; Compound D of Example 224, with purification by reverse phase preparative HPLC (gradient of aq methanol with 0.1% TFA). MS (M+H)$^+$ 509, $^{13}$C NMR (CD3OD, 100 MHz) 39.60, 47.69, 50.29, 55.65, 60.46, 102.42, 111.55, 116.13, 118.47, 119.87, 125.00, 128.22, 129.73, 132.14, 133.34, 133.48, 133.62, 135.32, 136.22, 141.24, 144.60, 152.53 ppm.

EXAMPLE 415

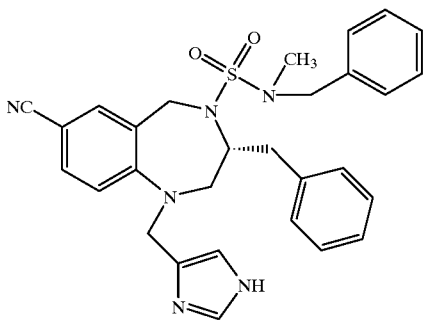

(R)-7-Cyano-4-[(N-methyl-N-phenylmethyl)aminosulfonyl]-1-[(1H-imidazol-4-yl)methyl]-3-(phenylmethyl)-1H-1,4-benzodiazepine, monohydrochloride Example 415 was prepared as a fluffy solid in 8% yield from N-methyl-N-phenylmethyl-sulfamoyl chloride and Compound C of Example 248 by the following sequence: Compound A of Example 355, with reaction at 0° C. to room temperature and chromatography with 20% ethyl acetate/hexanes; Compound C of Example 353, with reaction at reflux in the presence of 3A sieves. MS: [M+H]$^+$=527.

EXAMPLE 416

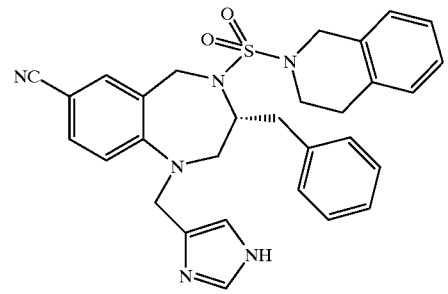

(R)-7-Cyano-4-[N-(tetrahydroisoquinolinyl)sulfonyl]-1-[(1H-imidazol-4-yl)methyl]-3-(phenylmethyl)-1H-1,4-benzodiazepine, monohydrochloride Example 416 was prepared as a white solid in 11% yield from tetrahydroisoquinolinylsulfamoyl chloride and Compound C of Example 248 as described for Example 415. MS: [M+H]$^+$=539.

EXAMPLE 417

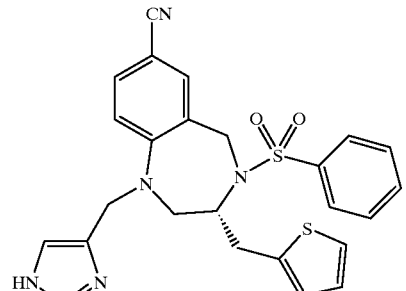

(R)-7-Cyano-2,3,4,5-tetrahydro-1-(1H-imidazol-4-ylmethyl)-4-(phenylsulfonyl)-3-(2-thienylmethyl)-1H-1,4-benzodiazepine, hydrochloride Example 417 was prepared as a yellow solid from 2-(thienyl)alanine and bromoisatoic anhydride as described for Example 407, using benzenesulfonyl chloride in place of methanesulfonyl chloride. MS (M+H)$^+$ 490.

EXAMPLE 418

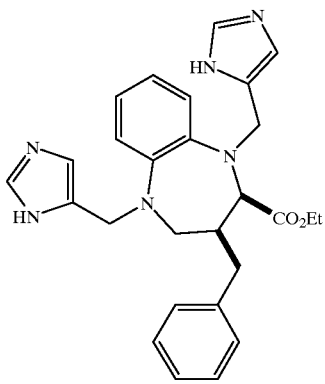

cis-2,3,4,5-Tetrahydro-1,5-bis(1H-imidazol-4-ylmethyl)-3-(phenyl-methyl)-1H-1,5-benzodiazepine-2-carboxylic acid ethyl ester, trifluoroacetate (1:2)

A. 2-Oxo-3-phenylmethyl-but-3-enoic acid, ethyl ester

A solution of ethyl-2-oxo-4-phenylbutyrate (31.8 mmol, 6.0 mL), N,N,N',N'-tetramethyldiaminomethane (6.6 mL, 54 mmol) and acetic anhydride (10 mL, 106 mmol) in DMF (100 mL) was stirred at room temperature for 16 hours and evaporated. The residue was chromatographed (flash silica, 20% EtOAc/Hexanes) to afford Compound A as a clear oil (6.46 g, 93%). MS (M+NH$_4$)+ 236.

B. 2,3-Dihydro-3-(phenylmethyl)-1H-1,5-benzodiazepine-2-carboxylic acid ethyl ester A mixture of Compound A (6.46 g, 29.6 mmol), phenylenediamine (3.5 g, 32.6 mmol) and hydroquinone (300 mg, 2.72 mmol) in toluene (250 mL) was heated to reflux under Dean-Stark conditions for 6 hours. The mixture was concentrated and the residue was purified by flash chromatography (20% EtOAc/Hexanes) affording compound B as viscous yellow oil (3.3 g, 36%). MS (M+H)+ 309.

C. cis-2,3,4,5-Tetrahydro-1,5-bis(1H-imidazol-4-ylmethyl)-3-(phenyl-methyl)-1H-1,5-benzodiazepine-2-carboxylic acid ethyl ester, trifluoroacetate (1:2)

Compound B (165 mg, 0.76 mmol) was dissolved in 2 mL AcOH and 2 mL CH$_2$Cl$_2$ and treated with 4-formylimidazole (183 mg, 1.9 mmol) and NaBH(OAc)$_3$ (645 mg, 3.0 mmol). The mixture was stirred at room temperature for 16 hours, concentrated and partitioned between saturated NaHCO$_3$ (50 mL) and 10% isopropanol-CH$_2$Cl$_2$. The organic phase was washed with saturated NaHCO$_3$ (50 mL), dried over Na$_2$SO$_4$, dissolved in MeOH (2 mL) and purified by reverse phase preparative HPLC (gradient of aqueous methanol with 0.1% TFA) to afford a yellow oil (120 mg, 23%), which was lyophilized from water to yield Compound C as an off-white fluffy solid. MS (M+H)+ 471.

EXAMPLE 419

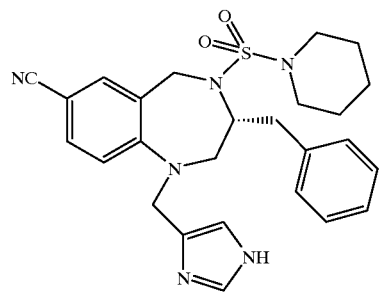

(R)-7-Cyano-4-[(N-piperidinyl)sulfonyl]-1-[(1H-imidazol-4-yl)methyl]-3-(phenylmethyl)-1H-1,4-benzodiazepine, monohydrochloride Example 419 was prepared as a fluffy white solid in 26% yield from N-piperidinylsulfamoyl chloride and Compound C of Example 248 as described for Example 415, with the final chromatography using 5% methanol/chloroform. MS (M+H)$^+$=491.

EXAMPLE 420

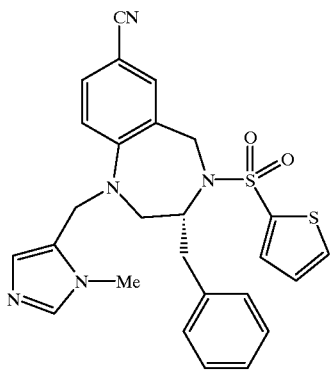

(R)-7-Cyano-2,3,4,5-tetrahydro-1-(1H-1-methyl-imidazol-5-ylmethyl)-3-(phenylmethyl)-4-(2-thienylsulfonyl)-1H-1,4-benzodiazepine, hydrochloride A mixture of Compound A of Example 284 (150 mg, 0.366 mmol), 1-methyl-5-formylimidazole (121 mg, 1.10 mmol) and 200 mg of 3A molecular sieves in 2 mL of 3:1 DCE/AcOH was heated at 60° C. At 1 hr, 4 hr, 7 hr and 10 hr, aliquots of sodium triacetoxyborohydride (116 mg, 0.549 mmol) were added. At 3 hr, 6 hr and 9 hr, aliquots of aldehyde (91 mg, 0.946 mmol) were added. Acetic acid (1 mL) was also added at 9 hr. Following the last addition of hydride, the mixture was stirred at 60° C. for 2 hr diluted with 5 mL of methanol, filtered, and concentrated in vacuo. The residue was diluted with 100 mL of EtOAc and washed with 1 N NaOH (3×50 mL), and brine. The organic layer was dried over Na$_2$SO$_4$, filtered and concentrated in vacuo. The residue was purified by reverse phase preparative HPLC (gradient of aqueous methanol with 0.1% TFA) and the appropriate fractions were concentrated. The residue was dissolved in 1 M HCl (3×5 mL) and concentrated in vacuo. The residue was dissolved in minimal acetonitrile, diluted with water and freeze-dried to provide 60 mg (29%) of Example 420 as a white solid. (M+H)$^+$ 504.

Analysis calculated for C$_{26}$H$_{25}$N$_5$O$_2$S$_2$.1.50 HCl.0.66 H$_2$O. Calc'd: C, 54.77; H, 4.92; N, 12.28. Found: C, 54.77; H, 4.92; N, 12.25.

EXAMPLE 421

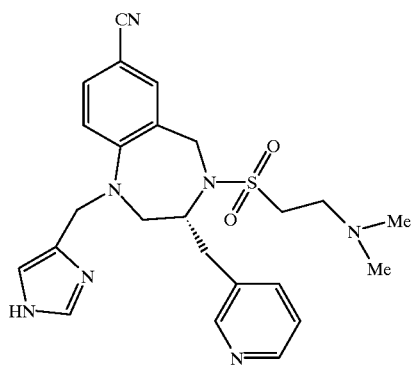

(R)-7-Cyano-2,3,4,5-tetrahydro-1-(1H-imidazol-4-ylmethyl)-3-(pyridin-3-ylmethyl)-4-[[2-(dimethylamino)ethyl]sulfonyl]-1H-1,4-benzodiazepine, trihydrochloride A. (R)-7-Cyano-2,3,4,5-tetrahydro-3-(pyridin-3-ylmethyl)-4-[[2-(dimethylamino)ethyl]sulfonyl]-1H-1,4-benzodiazepine 2-Chloroethane sulfonyl chloride (0.79 ml, 7.6 mmol) was added to a solution of Compound B of Example 350 (1.0 g, 3.8 mmol) and DIEA (0.66 ml, 3.8 mmol) in CH$_2$Cl$_2$ at −78° C. The mixture was stirred at −78° C. for 15 minutes. DIEA (0.66 ml, 3.8 mmol) was added and the mixture was stirred at −78° C. for 1 h. DIEA (2.6 ml, 15.2 mmol) was again added to the reaction mixture at −78° C. The mixture was allowed to warm to room temperature and stirring was continued for 16 h. The solution was concentrated under vacuum. The residue was dissolved in 3/1 THF/CH$_2$Cl$_2$ (4 ml). The mixture was saturated with dimethylamine, condensed using a dry-ice cold finger at room temperature. The mixture was stirred at room temperature for 2 h. The resulting solution was diluted with 10% NaHCO$_3$ (100 ml) and the solution was extracted with 9/1 CH$_2$Cl$_2$/iPrOH (3×150 ml). The combined organic extracts were dried (Na$_2$SO$_4$), filtered and concentrated under vacuum to afford Compound A (1.5 g, 100%). MS: (M+H)$^+$ 400

B. (R)-7-Cyano-2,3,4,5-tetrahydro-1-(1H-imidazol-4-ylmethyl)-3-(pyridin-3-ylmethyl)-4-[[2-(dimethylamino)ethyl]sulfonyl]-1H-1,4-benzo-diazepine, trihydrochloride 4-Formylimidazole (0.14 g, 1.5 mmol) was added to a solution of 1 (0.30 g, 0.75 mmol) and 3A molecular sieves in 1/1 DCE: acetic acid (5 ml) and the mixture was stirred at 70° C. for 0.5 h. Sodium triacetoxyborohydride (0.32 g, 1.5 mmol) was added and the mixture was stirred at 70° C. for 15 minutes. 4-Formylimidazole (0.14 g, 1.5 mmol) was added and the mixture was stirred at 70° C. for 0.5 h. Sodium triacetoxyborohydride (0.32 g, 1.5 mmol) was added and the mixture was stirred at 70° C. for 15 minutes. The latter two steps were repeated four times. The mixture was cooled to room temperature, diluted with methylene chloride (30 ml), filtered and the filtrate concentrated under vacuum. The residue was diluted with 25% NH$_4$OH (50 ml) and the solution was extracted with 9/1 CH$_2$Cl$_2$/iPrOH (4×50 ml). The combined organic extracts were dried (Na$_2$SO$_4$), filtered and concentrated under vacuum. The residue was purified by reverse phase preparative HPLC (gradient of aq MeOH with 0.1% TFA) and the appropriate fractions were isolated and concentrated under vacuum. The residue was evaporated from 1/1 CH$_3$OH/1 N HCl (2 ml) 5×. The residue was dissolved in CH$_3$CN (2 ml) and 1 N HCl (4 ml) and lyophilized to afford Compound B (0.071 g, 16%) as a solid. MS: (M+H)$^+$ 480

Analysis calculated for C$_{24}$H$_{29}$N$_7$O$_2$S.3.3 HCl.0.74 H$_2$O. Calc'd: C,47.01; H, 5.55; N, 15.99; S, 5.23; Cl,19.08. Found: C, 47.00; H, 5.43; N, 15.53; S, 5.00; Cl,18.98.

EXAMPLE 422

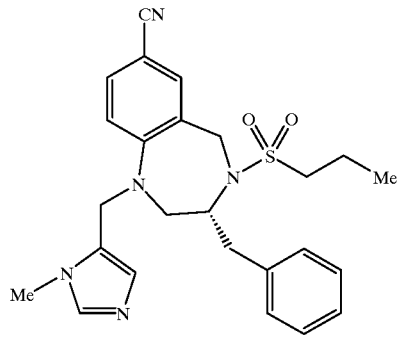

(R)-7-Cyano-2,3,4,5-tetrahydro-1-(1H-1-methyl-imidazol-5-ylmethyl)-3-(phenylmethyl)-4-(propylsulfonyl)-1H-1,4-benzodiazepine, hydrochloride A solution of 320 mg (0.87 mmol) of Compound A of Example 317 in 5 mL of dichloroethane and 500 mL of glacial acetic acid was treated with 478 mg (4.34 mmol) of 1-methyl-imidazole-5-carboxaldehyde and 3A sieves. The mixture was heated to 60° C., stirred for 5 hrs and treated with 763 mg (3.60 mmol) of sodium triacetoxyborohydride. The mixture was allowed to cool to rt, stirred for 18 hrs and filtered. The filtrate was concentrated in vacuo. The residue was partitioned between 150 mL of 1 N sodium hydroxide and 150 mL of ethyl acetate. The organic layer was washed with brine, dried (Na$_2$SO$_4$), filtered and concentrated in vacuo. The brown oil was purified by reverse phase preparative HPLC (gradient of aq methanol with 0.1% TFA). The resulting white foam was evaporated 3× from methanolic hydrogen chloride. The white foam was dissolved in water and lyophilyzed to afford Example 422 (59 mg, 15%) as a white lyophilate. MS: (M+H)$^+$=464$^+$

EXAMPLE 423

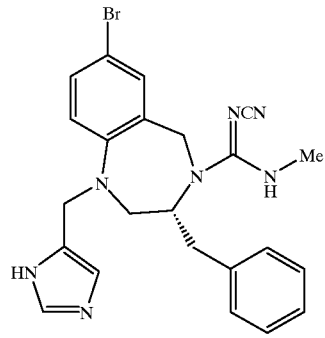

N-(Cyano)-N'-methyl-1,2,3,5-tetrahydro-1-(1H-imidazol-4-ylmethyl)-7-phenyl-4H-1,4-benzodiazepine-4-imidamide, hydrochloride A. N-(Cyano)-O-phenyl-1,2,3,5-tetrahydro-7-phenyl-4H-1,4-benzodiazepine-4-imidate A solution of 500 mg (1.58 mmol) of Compound B of Example 224 in 20 mL of DMF was treated, under argon, with 390 mg (1.64 mmol) of diphenyl cyanocarbonimidate followed by 275 µL (1.58 mmol) of DIEA and 97 mg (0.79 mmol) of DMAP. The mixture was stirred at rt for 15 min, at 80° C. for 3.5 hrs and at rt for 80 hrs. The mixture was partitioned between 250 mL of ethyl acetate and 250 mL of 1 N sodium hydroxide. The aqueous layer was extracted 3x with 100 mL of ethyl acetate. The combined organic layers were washed with brine, dried (Na$_2$SO$_4$), filtered and concentrated in vacuo. The oil was purified by flash chromatography (silica, 40% ethyl acetate/hexane) to give 456 mg (63%) of Compound A as a white solid.

B. N-(Cyano)-N'-methyl-1,2,3,5-tetrahydro-7-phenyl-4H-1,4-benzodiazepine-4-imidamide A solution of 180 mg (0.39 mmol) of Compound A in 1 mL of DMF was treated with 242 μL (1.94 mmol) of a solution of 33% methylamine in ethanol. The mixture was stirred at rt for 1 hr and concentrated. The residue was dissolved in 100 mL of ethyl acetate, washed with brine, dried (Na$_2$SO$_4$) and concentrated in vacuo to give 125 mg (87%) of Compound B as a white solid. MS (M+H)$^+$=400.

C. N-(Cyano)-N'-methyl-1,2,3,5-tetrahydro-1-(1H-imidazol-4-ylmethyl)-7-phenyl-4H-1,4-benzodiazepine-4-imidamide, hydrochloride A solution of 115 mg (0.29 mmol) of Compound B in 2.5 mL of dichloroethane and 2.5 mL of glacial acetic acid was treated with 69 mg (0.71 mmol) of 4-imidazole-carboxaldehyde, 3A sieves and stirred at rt for 18 hrs. The mixture was treated with 122 mg (0.58 mmol) of sodium triacetoxyborohydride in one portion and stirred at rt for 30 min and filtered. The filtrate was partitioned between 100 mL of ethyl acetate and 100 mL of 1 N sodium hydroxide. The organic layer was washed with brine, dried (Na$_2$SO$_4$), and concentrated in vacuo. The oil was purified by reverse phase preparative HPLC (gradient of aq methanol with 0.1% TFA). The yellow foam was evaporated 3x from methanolic hydrogen chloride. The foam was dissolved in water and lyophilyzed to afford 30 mg (22%) of Compound C as a yellow lyophilate. MS: (M+H)$^+$=480.

EXAMPLE 424–430

Examples 424–430 were prepared from Compound C of Example 248 and the appropriate sulfonyl chloride as described by the following sequence: Compound A of Example 299; Compound B of Example 317. Satisfactory C, H and N analyses were obtained for Examples 424–430.

| Example | | | Mass Spectrum |
|---|---|---|---|
| 424 | (R)-7-Cyano-4-[(2-nitrophenyl)-sulfonyl]-2,3,4,5-tetrahydro-1-(1H-imidazol-4-ylmethyl)-3-(phenyl-methyl)-1H-1,4-benzodiazepine, hydrochloride. | | m/z 529 (M + H) |
| 425 | (R)-7-Cyano-4-[(4-methyl-phenyl)sulfonyl]-2,3,4,5-tetrahydro-1-(1H-imidazol-4-ylmethyl)-3-(phenylmethyl)-1H-1,4-benzodiazepine, hydrochloride. | | m/z 498 (M + H) |

-continued

| Example | | | Mass Spectrum |
|---|---|---|---|
| 426 | (R)-7-Cyano-4-(butylsulfonyl)-2,3,4,5-tetrahydro-1-(1H-imidazol-4-ylmethyl)-3-(phenylmethyl)-1H-1,4-benzodiazepine, hydrochloride. | | m/z 464 (M + H) |
| 427 | (R)-7-Cyano-4-[(2-trifluoromethylphenyl)sulfonyl]-2,3,4,5-tetrahydro-1-(1H-imidazol-4-ylmethyl)-3-(phenylmethyl)-1H-1,4-benzodiazepine, hydrochloride. | | m/z 552 (M + H) |
| 428 | (R)-7-Cyano-4-[(2-trifluoromethoxyphenyl)sulfonyl]-2,3,4,5-tetrahydro-1-(1H-imidazol-4-ylmethyl)-3-(phenylmethyl)-1H-1,4-benzodiazepine, hydrochloride. | | m/z 568 (M + H) |
| 429 | (R)-7-Cyano-4-[(2-methoxycarbonylphenyl)sulfonyl]-2,3,4,5-tetrahydro-1-(1H-imidazol-4-ylmethyl)-3-(phenylmethyl)-1H-1,4-benzodiazepine, hydrochloride. | | m/z 568 (M + H) |

| Example | | Mass Spectrum |
|---|---|---|
| 430 | (R)-7-Cyano-4-[(2-methyl-sulfonylphenyl)sulfonyl]-2,3,4,5-tetrahydro-1-(1H-imidazol-4-ylmethyl)-3-(phenylmethyl)-1H-1,4-benzodiazepine, hydrochloride. 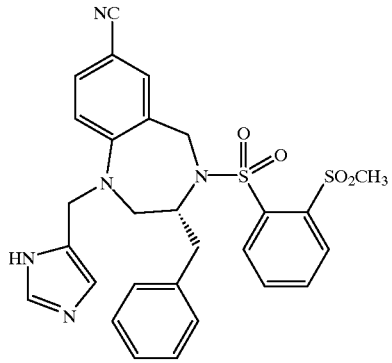 | m/z 562 (M + H) |

EXAMPLE 431

The following examples were prepared using the methods described herein as well as by methods known to those skilled in the art.

| | |
|---|---|
| (R)-7-Cyano-2,3,4,5-tetrahydro-1-(1H-imidazol-4-ylmethyl)-3-(phenylmethyl)4-(((4-methylsulfonyl)-phenyl)-sulfonyl)-1H-1,4-benzodiazepine | m/z 562 (M + H) |
| (R)-7-Cyano-2,3,4,5-tetrahydro-1-(1H-imidazol-4-ylmethyl)-3-(phenylmethyl)-4-(((4-trifluoromethyl)-phenyl)-sulfonyl)-1H-1,4-benzodiazepine | m/z 552 (M + H) |
| (R)-7-Cyano-2,3,4,5-tetrahydro-1-(1H-imidazol-4-ylmethyl)-3-(phenylmethyl)-4-((3-methoxypropyl)-sulfonyl)-1H-1,4-benzodiazepine | m/z 480 (M + H) |
| (R)-7-Cyano-2,3,4,5-tetrahydro-1-(1H-imidazol-4-ylmethyl)-3-(phenylmethyl)-4-((3,4-dimethoxyphenyl)-sulfonyl)-1H-1,4-benzodiazepine | m/z 544 (M + H) |
| (R)-7-Cyano-2,3,4,5-tetrahydro-1-(1H-imidazol-4-ylmethyl)-3-((4-fluorophenyl)methyl)-4-(phenylsulfonyl)-1H-1,4-benzodiazepine | m/z 502 (M + H) |
| (R)-7-Cyano-4-[(N-cyclopropylmethyl-N-propyl)-aminosulfonyl]-1-[(1H-imidazol-4-yl)methyl]-3-(phenylmethyl)-1H-1,4-benzodiazepine | m/z 519 (M + H) |
| (R)-7-Cyano-4-[(N,N-(dibutylamino))-sulfonyl]-1-[(1H-imidazol-4-yl)methyl]-3-(phenylmethyl)-1H-1,4-benzodiazepine | m/z 535 (M + H) |
| (R)-7-Chloro-4-(methanesulfonyl)-2,3,4,5-tetrahydro-1-(1H-imidazol-4-ylmethyl)-3-(phenylmethyl)-1H-pyrido[3,4-e]-1,4-diazepine | m/z 432 (M + H) |
| 1,2,3,4-Tetrahydro-7-bromo-4-[(1H-imidazol-4-yl)methyl]-2-phenylmethyl-1-(methylsulfonyl)quinoxaline | m/z 460 (M + H) |
| (R)-7-Cyano-2,3,4,5-tetrahydro-1-(1H-imidazol-4-ylmethyl)-3-(phenylmethyl)-4-((imidazol-4-yl)methylsulfonyl)-1H-1,4-benzodiazepine | m/z 424 (M + H) |

Following the above procedures, the following compounds may be made:

(R)-7-Cyano-2,3,4,5-tetrahydro-1-(1H-imidazol-4-ylmethyl)-3-((2-thienyl)methyl)-4-(propylsulfonyl)-1H-1,4-benzodiazepine (R)-7-Cyano-2,3,4,5-tetrahydro-1-(1H-imidazol-4-ylmethyl)-3-((2-thienyl)methyl)-4-((2-thienyl)-sulfonyl)-1H-1,4-benzodiazepine (R)-7-Cyano-2,3,4,5-tetrahydro-1-(1H-imidazol-4-ylmethyl)-3-(phenylmethyl)-4-((3-methylthiopropyl)-sulfonyl)-1H-1,4-benzodiazepine (R)-7-Cyano-2,3,4,5-tetrahydro-1-(1H-imidazol-4-ylmethyl)-3-(phenylmethyl)-4-(((3-methylthioxo)-propyl)-sulfonyl)-1H-1,4-benzodiazepine (R)-7-Cyano-2,3,4,5-tetrahydro-1-(1H-imidazol-4-ylmethyl)-3-(phenylmethyl)-4-(((3-methylsulfonyl)-propyl)-sulfonyl)-1H-1,4-benzodiazepine (R)-7-Cyano-2,3,4,5-tetrahydro-1-(1H-imidazol-4-ylmethyl)-3-(phenylmethyl)-4-((2-methylpropyl)-sulfonyl)-1H-1,4-benzodiazepine (R)-7-Cyano-2,3,4,5-tetrahydro-1-(1H-imidazol-4-ylmethyl)-3-(phenylmethyl)-4-(cyclopentylsulfonyl)-1H-1,4-benzodiazepine (R)-7-Cyano-2,3,4,5-tetrahydro-1-(1H-imidazol-4-ylmethyl)-3-(phenylmethyl)-4-((4,4,4-trifluorobutyl)-sulfonyl)-1H-1,4-benzodiazepine (R)-7-Cyano-2,3,4,5-tetrahydro-1-(1H-imidazol-4-ylmethyl)-3-(phenylmethyl)-4-((phenylmethyl)-sulfonyl)-1H-1,4-benzodiazepine (R)-7-Cyano-2,3,4,5-tetrahydro-1-(1H-imidazol-4-ylmethyl)-3-(phenylmethyl)-4-[[2-(5-(N-benzoyl)-aminomethyl)-thienyl]-sulfonyl]-1H-1,4-benzodiazepine (R)-7-Cyano-2,3,4,5-tetrahydro-1-(1H-imidazol-4-ylmethyl)-3-(phenylmethyl)-4-[[2-(1-(3-chloro-5- methyl-pyridin-2-yl))-pyrrolyl]-sulfonyl]-1H-1,4-benzodiazepine
(R)-7-Cyano-2,3,4,5-tetrahydro-1-(1H-imidazol-4-ylmethyl)-3-(phenylmethyl)-4-((4-carboxyphenyl)-sulfonyl)-1H-1,4-benzodiazepine
(R)-7-Cyano-2,3,4,5-tetrahydro-1-(1H-imidazol-4-ylmethyl)-3-(phenylmethyl)-4-[((3-methyl-1,2,4-oxadiazol-5-yl)-phenyl)-sulfonyl]-1H-1,4-benzodiazepine
(R)-7-Cyano-2,3,4,5-tetrahydro-1-(1H-imidazol-4-ylmethyl)-3-(phenylmethyl)-4-((2,5-dimethoxyphenyl)-sulfonyl)-1H-1,4-benzodiazepine
(R)-7-Cyano-4-[(N-tetrahydroquinolinyl)sulfonyl]-1-[(1H-imidazol-4-yl)methyl]-3-(phenylmethyl)-1H-1,4-benzodiazepine
(R)-7-Cyano-4-[(N,N-bis-[1-(2-methylpropyl)amino]-sulfonyl]-1-[(1H-imidazol-4-yl)methyl]-3-(phenylmethyl)-1H-1,4-benzodiazepine
(R)-7-Cyano-4-[(N-methyl-N-phenyl)aminosulfonyl]-1-[(1H-imidazol-4-yl)methyl]-3-(phenylmethyl)-1H-1,4-benzodiazepine
(R)-7-Cyano-2,3,4,5-tetrahydro-1-(1H-imidazol-4-ylmethyl)-3-(2-(2,6-dimethylphenyl)-ethyl)-4-(methylsulfonyl)-1H-1,4-benzodiazepine
(R)-7-Cyano-2,3,4,5-tetrahydro-1-(1-(N-phthalimidoethyl)-imidazol-5-ylmethyl)-3-(phenylmethyl)-4-(methylsulfonyl)-1H-1,4-benzodiazepine
(R)-7-Cyano-2,3,4,5-tetrahydro-1-[2-(N,N-dimethylamino)-ethyl)-imidazol-5-ylmethyl]-3-(phenylmethyl)-4-(methylsulfonyl)-1H-1,4-benzodiazepine
(R)-7-Cyano-2,3,4,5-tetrahydro-1-[(2-aminoethyl)-imidazol-5-ylmethyl]-3-(phenylmethyl)-4-(methylsulfonyl)-1H-1,4-benzodiazepine
(R)-7-Bromo-4-(methanesulfonyl)-2,3,4,5-tetrahydro-1-[(1H-imidazol-4-ylmethyl)-3-(phenylmethyl)-1H-thieno[2,3-e]-1,4-diazepine
(R)-7-Bromo-4-(methanesulfonyl)-2,3,4,5-tetrahydro-1-[(1H-imidazol-4-ylmethyl)-3-(phenylmethyl)-1H-thieno[3,2-e]-1,4-diazepine (R)-4-(methanesulfonyl)-2,3,4,5-tetrahydro-1-[(1H-imidazol-4-ylmethyl)-3-(phenylmethyl)-1H-8-oxo-pyrimidino[4,5-e]-1,4-diazepine
(R)-7-Cyano-2,3,4,5-tetrahydro-1-(1H-imidazol-4-ylmethyl)-3-((4-(2-methoxyethoxy)-phenyl)methyl)-4-(phenylsulfonyl)-1H-1,4-benzodiazepine
(R)-7-Cyano-2,3,4,5-tetrahydro-1-(1H-imidazol-4-ylmethyl)-3-((4-(2-(dimethylamino)-ethoxy)-phenyl)methyl)-4-(phenylsulfonyl)-1H-1,4-benzodiazepine
(R)-7-Cyano-2,3,4,5-tetrahydro-1-(1H-imidazol-4-ylsulfonyl)-3-(phenylmethyl)-4-(methylsulfonyl)-1H-1,4-benzodiazepine
(R)-7-Cyano-2,3,4,5-tetrahydro-1-(1H-imidazol-4-ylsulfonyl)-3-(phenylmethyl)-4-(propylsulfonyl)-1H-1,4-benzodiazepine
(R)-7-Cyano-2,3,4,5-tetrahydro-1-(1H-imidazol-4-ylsulfonyl)-3-(phenylmethyl)-4-(phenylsulfonyl)-1H-1,4-benzodiazepine
(R)-7-Cyano-2,3,4,5-tetrahydro-1-(1H-imidazol-4-ylsulfonyl)-3-(phenylmethyl)-4-(2-thienylsulfonyl)-1H-1,4-benzodiazepine
7-Cyano-2,3,4,5-tetrahydro-1-(1H-imidazol-4-ylmethyl)-3-(R)-[(R)-1-phenyl-ethyl]-4-(methylsulfonyl)-1H-1,4-benzodiazepine
7-Cyano-2,3,4,5-tetrahydro-1-(1H-imidazol-4-ylmethyl)-3-(R)-[(R)-1-phenyl-ethyl]-4-(propylsulfonyl)-1H-1,4-benzodiazepine
7-Cyano-2,3,4,5-tetrahydro-1-(1H-imidazol-4-ylmethyl)-3-(R)-[(R)-1-phenyl-ethyl]-4-(phenylsulfonyl)-1H-1,4-benzodiazepine
7-Cyano-2,3,4,5-tetrahydro-1-(1H-imidazol-4-ylmethyl)-3-(R)-[(R)-1-phenyl-ethyl]-4-((2-thienyl)-sulfonyl)-1H-1,4-benzodiazepine
7-Cyano-2,3,4,5-tetrahydro-1-(1H-imidazol-4-ylmethyl)-3-(S)-[(R)-1-phenyl-ethyl]-4-(methylsulfonyl)-1H-1,4-benzodiazepine
7-Cyano-2,3,4,5-tetrahydro-1-(1H-imidazol-4-ylmethyl)-3-(S)-[(R)-1-phenyl-ethyl]-4-(propylsulfonyl)-1H-1,4-benzodiazepine
7-Cyano-2,3,4,5-tetrahydro-1-(1H-imidazol-4-ylmethyl)-3-(S)-[(R)-1-phenyl-ethyl]-4-(phenylsulfonyl)-1H-1,4-benzodiazepine
7-Cyano-2,3,4,5-tetrahydro-1-(1H-imidazol-4-ylmethyl)-3-(S)-[(R)-1-phenyl-ethyl]-4-((2-thienyl)-sulfonyl)-1H-1,4-benzodiazepine
7-Cyano-2,3,4,5-tetrahydro-1-(1H-imidazol-4-ylmethyl)-3-(R)-[(S)-1-phenyl-ethyl]-4-(methylsulfonyl)-1H-1,4-benzodiazepine
7-Cyano-2,3,4,5-tetrahydro-1-(1H-imidazol-4-ylmethyl)-3-(R)-[(S)-1-phenyl-ethyl]-4-(propylsulfonyl)-1H-1,4-benzodiazepine
7-Cyano-2,3,4,5-tetrahydro-1-(1H-imidazol-4-ylmethyl)-3-(R)-[(S)-1-phenyl-ethyl]-4-(phenylsulfonyl)-1H-1,4-benzodiazepine
7-Cyano-2,3,4,5-tetrahydro-1-(1H-imidazol-4-ylmethyl)-3-(R)-[(S)-1-phenyl-ethyl]-4-((2-thienyl)-sulfonyl)-1H-1,4-benzodiazepine
7-Cyano-2,3,4,5-tetrahydro-1-(1H-imidazol-4-ylmethyl)-3-(S)-[(S)-1-phenyl-ethyl]-4-(methylsulfonyl)-1H-1,4-benzodiazepine
7-Cyano-2,3,4,5-tetrahydro-1-(1H-imidazol-4-ylmethyl)-3-(S)-[(S)-1-phenyl-ethyl]-4-(propylsulfonyl)-1H-1,4-benzodiazepine
7-Cyano-2,3,4,5-tetrahydro-1-(1H-imidazol-4-ylmethyl)-3-(S)-[(S)-1-phenyl-ethyl]-4-(phenylsulfonyl)-1H-1,4-benzodiazepine
7-Cyano-2,3,4,5-tetrahydro-1-(1H-imidazol-4-ylmethyl)-3-(S)-[(S)-1-phenyl-ethyl]-4-((2-thienyl)-sulfonyl)-1H-1,4-benzodiazepine
7-Cyano-2,3,4,5-tetrahydro-1-(1H-imidazol-4-ylmethyl)-3-(R)-[(R)-phenylcyclopropyl)-4-(methylsulfonyl)-1H-1,4-benzodiazepine
7-Cyano-2,3,4,5-tetrahydro-1-(1H-imidazol-4-ylmethyl)-3-(R)-[(R)-phenylcyclopropyl)-4-(propylsulfonyl)-1H-1,4-benzodiazepine
7-Cyano-2,3,4,5-tetrahydro-1-(1H-imidazol-4-ylmethyl)-3-(R)-[(R)-phenylcyclopropyl)-4-(phenylsulfonyl)-1H-1,4-benzodiazepine
7-Cyano-2,3,4,5-tetrahydro-1-(1H-imidazol-4-ylmethyl)-3-(R)-[(R)-phenylcyclopropyl)-4-((2-thienyl)-sulfonyl)-1H-1,4-benzodiazepine
7-Cyano-2,3,4,5-tetrahydro-1-(1H-imidazol-4-ylmethyl)-3-(R)-[(S)-phenylcyclopropyl)-4-(methylsulfonyl)-1H-1,4-benzodiazepine
7-Cyano-2,3,4,5-tetrahydro-1-(1H-imidazol-4-ylmethyl)-3-(R)-[(S)-phenylcyclopropyl)-4-(propylsulfonyl)-1H-1,4-benzodiazepine
7-Cyano-2,3,4,5-tetrahydro-1-(1H-imidazol-4-ylmethyl)-3-(R)-[(S)-phenylcyclopropyl)-4-(phenylsulfonyl)-1H-1,4-benzodiazepine
7-Cyano-2,3,4,5-tetrahydro-1-(1H-imidazol-4-ylmethyl)-3-(R)-[(S)-phenylcyclopropyl)4-((2-thienyl)-sulfonyl)-1H-1,4-benzodiazepine
7-Cyano-2,3,4,5-tetrahydro-1-(1H-imidazol-4-ylmethyl)-3-(S)-[(R)-phenylcyclopropyl)-4-(methylsulfonyl)-1H-1,4-benzodiazepine 7-Cyano-2,3,4,5-tetrahydro-1-(1H-imidazol-4-ylmethyl)-3-(S)-[(R)-phenylcyclopropyl)-4-(propylsulfonyl)-1H-1,4-benzodiazepine 7-Cyano-2,3,4,5-tetrahydro-1-(1H-imidazol-4-ylmethyl)-3-(S)-[(R)-phenylcyclopropyl)-4-(phenylsulfonyl)-1H-1,4-benzodiazepine 7-Cyano-2,3,4,5-tetrahydro-1-(1H-imidazol-4-ylmethyl)-3-(S)-[(R)-phenylcyclopropyl)-4-((2-thienyl)-sulfonyl)-1H-1,4-benzodiazepine 7-Cyano-2,3,4,5-tetrahydro-1-(1H-imidazol-4-ylmethyl)-3-(S)-[(S)-phenylcyclopropyl)-4-(methylsulfonyl)-1H-1,4-benzodiazepine 7-Cyano-2,3,4,5-tetrahydro-1-(1H-imidazol-4-ylmethyl)-3-(S)-[(S)-phenylcyclopropyl)-4-(propylsulfonyl)-1H-1,4-benzodiazepine 7-Cyano-2,3,4,5-tetrahydro-1-(1H-imidazol-4-ylmethyl)-3-(S)-[(S)-phenylcyclopropyl)-4-(phenylsulfonyl)-1H-1,4-benzodiazepine 7-Cyano-2,3,4,5-tetrahydro-1-(1H-imidazol-4-ylmethyl)-3-(S)-[(S)-phenylcyclopropyl)-4-((2-thienyl)-sulfonyl)-1H-1,4-benzodiazepine (R)-7-Cyano-2,3,4,5-tetrahydro-1-(1H-imidazol-4-ylmethyl)-3-(phenylmethyl)-4-[(2-(5-(pyridin-2-yl))-thienyl)-sulfonyl])-1H-1,4-benzodiazepine (R)-7-Cyano-2,3,4,5-tetrahydro-1-(1H-imidazol-4-ylmethyl)-3-(phenylmethyl)-4-[(2-(5-(1,2-isoxazol-3-yl))-thienyl)-sulfonyl])-1H-1,4-benzodiazepine (R)-7-Cyano-2,3,4,5-tetrahydro-1-(3-(1H-imidazol-2-yl)-propyl)-3-(phenylmethyl)-4-(phenylsulfonyl)-1H-1,4-benzodiazepine (R)-7-Cyano-2,3,4,5-tetrahydro-1-(3-(1H-imidazol-2-yl)-propyl)-3-(phenylmethyl)-4-(methylsulfonyl)-1H-1,4-benzodiazepine (R)-7-Cyano-2,3,4,5-tetrahydro-1-(3-(1H-imidazol-2-yl)-propyl)-3-(phenylmethyl)-4-(propylsulfonyl)-1H-1,4-benzodiazepine (R)-7-Cyano-2,3,4,5-tetrahydro-1-(3-(1H-imidazol-2-yl)-propyl)-3-(phenylmethyl)-4-((2-thienyl)-sulfonyl)-1H-1,4-benzodiazepine (R)-7-Cyano-2,3,4,5-tetrahydro-1-(2-(1H-imidazol-2-yl)-ethylsulfonyl)-3-(phenylmethyl)-4-(phenylsulfonyl)-1H-1,4-benzodiazepine (R)-7-Cyano-2,3,4,5-tetrahydro-1-(2-(1H-imidazol-2-yl)-ethylsulfonyl)-3-(phenylmethyl)-4-(methylsulfonyl)-1H-1,4-benzodiazepine (R)-7-Cyano-2,3,4,5-tetrahydro-1-(2-(1H-imidazol-2-yl)-ethylsulfonyl)-3-(phenylmethyl)-4-(propylsulfonyl)-1H-1,4-benzodiazepine (R)-7-Cyano-2,3,4,5-tetrahydro-1-(2-(1H-imidazol-2-yl)-ethylsulfonyl)-3-(phenylmethyl)-4-((2-thienyl)-sulfonyl)-1H-1,4-benzodiazepine (R)-7-Cyano-2,3,4,5-tetrahydro-1-(1H-imidazol-4-ylmethyl)-3-(phenylmethyl)-4-((1-oxoethyl)-amino)-1H-1,4-benzodiazepine (R)-7-Cyano-2,3,4,5-tetrahydro-1-(1H-imidazol-4-ylmethyl)-3-(phenylmethyl)-4-(methanesulfonylamino)-1H-1,4-benzodiazepine (R)-7-Cyano-2,3,4,5-tetrahydro-1-(1H-imidazol-4-ylmethyl)-3-(phenylmethyl)-4-(phenylsulfonylamino)-1H-1,4-benzodiazepine

What is claimed:

1. A compound of the formula,

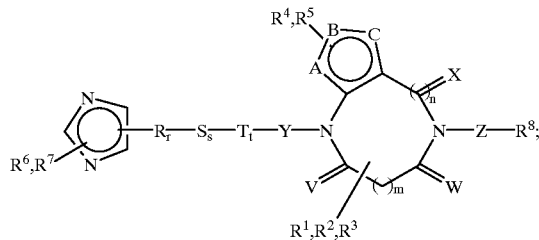

II

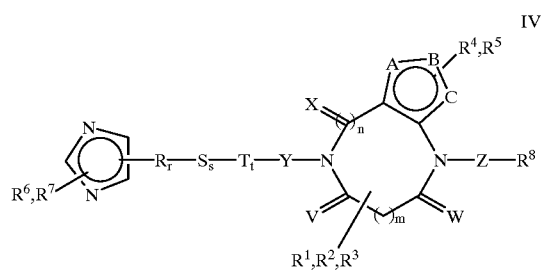

IV their enantiomers, diastereomers, and pharmaceutically acceptable salts, and solvates thereof wherein m is 0; n is 1 and r, s and t are 0 or 1;

p is 0, 1 or 2;

V, W and X are selected from the group consisting of oxygen, $R^1$, $R^2$ and $R^3$ Z and Y are selected from the group consisting of $CHR^9$, $SO_2$, $SO_3$, $CO$, $CO_2$, $O$, $NR^{10}$, $SO_2NR^{11}$, $CONR^{12}$,

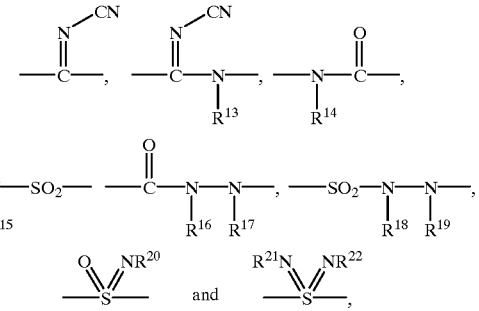

or Z may be absent;

$R^6$, $R^7$, $R^9$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$ and $R^{38}$ are selected from the group consisting of hydrogen, lower alkyl, substituted alkyl, aryl, or substituted aryl;

$R^4$ and $R^5$, are selected from the group consisting of hydrogen, halo, nitro, cyano and $U-R^{23}$;

U is selected from the group consisting of sulfur, oxygen, $NR^{24}$, $CO$, $SO$, $SO_2$, $CO_2$, $NR^{25}CO_2$, $NR^{26}CONR^{27}$, $NR^{28}SO_2$, $NR^{29}SO_2NR^{30}$, $SO_2NR^{31}$, $NR^{32}CO$, $CONR_{33}$, $PO_2R^{34}$, and $PO_3R^{35}$ or U is absent;

$R^1$, $R^2$, and $R^3$ are selected from the group consisting of hydrogen, alkyl, alkoxycarbonyl, substituted alkyl, alkenyl, substituted alkenyl, alkynyl, substituted alkynyl, aralkyl, cycloalkyl, aryl, substituted aryl, hetercyclo, substituted heterocyclo, cyano, carboxy, carboxy, carbamyl or substituted carbamyl;

$R^8$ and $R^{23}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo and substituted heterocyclo;

any two of $R^1$, $R^2$, and $R^3$ may be joined to form a cycloalkyl group;

R, S, and T are selected from the group consisting of $CH_2$, CO and $CH(CH_2)pQ$ wherein Q is $NR^{36}R^{37}$, $OR^{38}$, or CN; and A, B, C and D are carbon, with the provisos that 1. When m is zero then V and W are not both oxygen or
2. W and X together may be oxygen only if Z is either absent, O, $NR^{10}$,

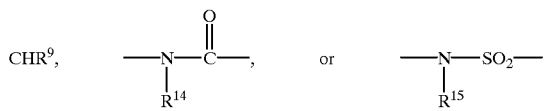

in formula I–II and V and X together may be oxygen only if Y is O, $NR^{10}$,

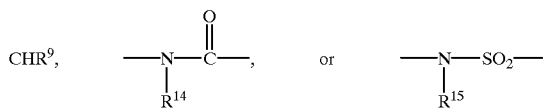

in formula III–IV or

3. $R^{23}$ may be hydrogen except when U is SO, $SO_2$, $NR^{25}CO_2$ or $NR^{28}SO_2$,
4. R8 may be hydrogen except when Z is $SO_2$, $CO_2$, or

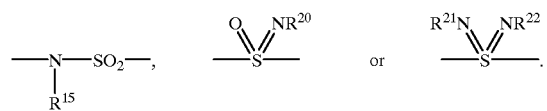

2. The compound of claim 1 wherein the compound is of the formula

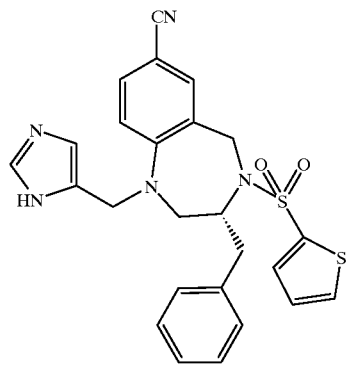

3. A compound of claim 1 selected from the group consisting of:

2,3,4,5-Tetrahydro-1-(1H-imidazol-4-ylmethyl)-4-(1-naphthalenylcarbonyl)-1H-1,4-benzodiazepine, hydrochloride;

8-Chloro-2,3,4,5-tetrahydro-1-(1H-imidazol-4-ylmethyl)-4-(1-naphthalenylcarbonyl)-1H-1,4-benzodiazepine, hydrochloride;

2,3,4,5-Tetrahydro-4-(1H-imidazol-4-yl-methyl)-1-(1-1-naphthalenylcarbonyl)-1H-1,4-benzodiazepine, dihydrochloride;

2,3,4,5-Tetrahydro-1-(1H-imidazol-4-yl-methyl)-2-methyl-4-(1-naphthalenylcarbonyl)-1-H-1,4-benzodiazepine, hydrochloride;

2,3,4,5-Tetrahydro-4-(1-naphthalenylcarbonyl)-1-[[1-(phenylmethyl)-1H-imidazol-5-yl]methyl]-1H-1,4-benzodiazepine, hydrochloride;

2,3,4,5-Tetrahydro-(1H-imidazol-4-yl-methyl)-4-(1-naphthalenylsulfonyl)-1H-1,4-benzodiazepine, hydrochloride;

(S)-2,3,4,5-Tetrahydro-1-(1H-imidazol-4-ylmethyl)-3-[2-(methylthio)ethyl]-4-(1-naphthalenylcarbonyl)-1H-1,4-benzodiazepine, hydrochloride;

2,3,4,5-Tetrahydro-1-(1H-imidazol-4-yl-methyl)-N-methyl-N-phenyl-4H-1,4-benzodiazepine-4-carboxamide, hydrochloride;

2-[2,3,4,5-Tetrahydro-1-(1H-imidazol-4-yl-methyl)-1H-1,4-benzodiazepin-4-yl]sulfonyl]benzoic acid, methyl ester, hydrochloride;

7-Bromo-2,3,4,5-tetrahydro-1-(1H-imidazol-4-ylmethyl)-4-(1-naphthalenylcarbonyl)-1H-1,4-benzodiazepine, hydrochloride;

2,3,4,5-Tetrahydro-1-(1H-imidazol-4-ylmethyl)-4-(1-naphthalenenylcarbonyl)-7-phenyl-1H-1,4-benzodiazepine, hydrochloride;

2,3,4,5-Tetrahydro-1-(1H-imidazol-2-ylmethyl)-4-(1-naphthalenylcarbonyl)-1H-1,4-benzodiazepine, dihydrochloride;

2,3,4,5-Tetrahydro-1-[3-(1H-imidazol-2-yl)propyl]-4-(1-naphthalenylcarbonyl)-1H-1,4-benzodiazepine, dihydrochloride;

1-[3-Amino-3-(1H-imidazol-2-yl)propyl]-2,3,4,5-tetrahydro-4-(1-naphthalenylcarbonyl)-1H-1,4-benzodiazepine, trihydrochloride;

2,3,4,5-Tetrahydro-1-(1H-imidazol-4-ylmethyl)-3-methyl-4-(1-napthalenylcarbonyl)-1H-1,4-benzodiazepine, hydrochloride;

(S)-2,3,4,5-Tetrahydro-1-(1H-imidazol-4-ylmethyl)-3-[2-(methylthio)ethyl]-4-(1-naphthalenylmethyl)-1H-1,4-benzodiazepine, hydrochloride;

2,3,4,5-Tetrahydro-1-(1H-imidazol-4-ylmethyl)-9-methyl-4-(1-naphthalenylcarbonyl)-1H-1,4-benzodiazepine, dihydrochloride;

2,3,4,5-Tetrahydro-4-(1H-imidazol-4-ylmethyl)-9-methyl-1-(1-naphthalenylcarbonyl)-1H-1,4-benzodiazepine, dihyrdochloride;

1-[[2-(2-Aminoethyl)-1H-imidazol-4-yl]methyl]-2,3,4,5-tetrahydro-4-(1-naphthalenylcarbonyl)-1H-1,4-benzodiazepine, trihydrochloride;

1-[[2-Aminomethyl)-1H-imidazol-4-yl]methyl]-2,3,4,5-tetrahydro-4-(1-naphthalenylcarbonyl)-1H-1,4-benzodiazepine, trihydrochloride;

N-[2,3,4,5-Tetrahydro-1-(1H-imidazol-4-ylmethyl)-4-(1-naphthalenylcarbonyl)-1H-1,4-benzodiazepin-8-yl] acetamide, dihydrochloride;

2,3,4,5-Tetrahydro-1-(1H-imidazol-4-ylmethyl)-4-(1-naphthalenylcarbonyl)-8-nitro-1H-1,4-benzodiazepine, dihydrochloride;

2,3,4,5-Tetrahydro-1-(1H-imidazol-4-ylmethyl)-4-(1-naphthalenylcarbonyl)-8-amino-1H-1,4-benzodiazepine, dihydrochloride;

N-[2,3,4,5-Tetrahydro-1-(1H-imidazol-4-ylmethyl)-4-(1-naphthalenylcarbonyl)-1H-1,4-benzodiazepin-8-yl] benzamide, dihydrochloride;

N-[2,3,4,5-Tetrahydro-1-(1H-imidazol-4-ylmethyl)-4-(1-naphthalenylcarbonyl)-1H-1,4-benzodiazepin-8-yl] cyclohexanamide, dihydrochloride;

2,3,4,5-Tetrahydro-1-[2-(1H-imidazol-4-yl)ethyl]-4-(1-naphthalenylcarbonyl)-1H-1,4-benzodiazepine, dihydrochloride;

2,3,4,5-Tetrahydro-1-[2-(1H-imidazol-4-yl)ethyl]-4-(1-naphthalenylcarbonyl)-7-phenyl-1H-1,4-benzodiazepine, dihydrochloride;

7-Bromo-2,3,4,5-tetrahydro-1-[2-(1H-imidazol-4-yl)ethyl]-4-(1-naphthalenylcarbonyl)-1H-1,4-benzodiazepine, dihydrochloride;

1-[[1-(2-Aminoethyl)-1H-imidazol-5-yl]methyl]-2,3,4,5-tetrahydro-4-(1-naphthalenylcarbonyl)-7-phenyl-1H-1,4-benzodiazepine, trihydrochloride;

2,3,4,5-Tetrahydro-1-(1H-imidazol-4-ylmethyl)-7-phenyl-1H-1,4-benzodiazepine-4-carboxylic acid, phenylmethyl ester;

2,3,4,5-Tetrahydro-1-(1H-imidazol-4-ylmethyl)-7-phenyl-4-[2-(trifluoromethoxy)benzoyl]-1H-1,4-benzodiazepine;

1,2,3,5-Tetrahydro-1-(1H-imidazol-4-ylmethyl)-N-methyl-N,7-diphenyl-4H-1,4-benzodiazepine-4-carboxamide, dihydrochloride;

2,3,4,5,-Tetrahydro-1-(1H-imidazol-4-ylmethyl)-4-(1-naphthaleneylcarbonyl)-7-(1-piperidinylsulfonyl)-1H-1,4-benzodiazepine, monohydrochloride;

2,3,4,5-Tetrahydro-1-(1H-imidazol-4-ylmethyl)-4-(1-naphthalenylcarbonyl)-7-pyridin-2-yl-1H-1,4-benzodiazepine, trihydrochloride;

7-(2-Furanyl)-2,3,4,5-tetrahydro-1-(1H-imidazol-4-ylmethyl)-4-(1-naphthalenylcarbonyl)-1H-1,4-benzodiazepine, dihydrochloride;

2,3,4,5-Tetrahydro-1-(1H-imidazol-4-ylmethyl)-4-(1-naphthalenylcarbonyl)-7-(2-thienyl)-1H-1,4-benzodiazepine, dihydrochloride;

2,3,4,5-Tetrahydro-1-(1H-imidazol-4-ylmethyl)-4-(1-naphthalenylcarbonyl)-7-(4-pyridinyl)-1H-1,4-benzodiazepine, trihydrochloride;

2,3,4,5-Tetrahydro-1-[3-(1H-imidazol-2-yl)propyl]-4-(1-naphthalenylcarbonyl)-7-phenyl-1H-1,4-benzodiazepine, dihydrochloride;

7-Bromo-2,3,4,5-tetrahydro-4-(1H-imidazol-4-ylmethyl)-1-(1-naphthalenylcarbonyl)-1H-1,4-benzodiazepine, dihydrochloride;

8-Chloro-2,3,4,5-tetrahydro-4-(1H-imidazol-4-ylmethyl)-1-(1-naphthalenylcarbonyl)-1H-1,4-benzodiazepine, dihydrochloride;

2,3,4,5-Tetrahydro-4-(1H-imidazol-4-ylmethyl)-1-(1-naphthalenylcarbonyl)-7-phenyl-1H-1,4-benzodiazepine, hydrochloride;

5 2,3,4,5-Tetrahydro-1,4-bis(1H-imidazol-4-ylmethyl)-7-phenyl-1H-1,4-benzodiazepine, dihydrochloride;

2,3,4,5-Tetrahydro-1-(1H-imidazol-4-ylmethyl)-4-(1-naphthalenylmethyl)-7-phenyl-1H-1,4-benzodiazepine, trifluoroacetate;

2,3,4,5-Tetrahydro-1-(1H-imidazol-4-ylmethyl)-7-methoxy-4-(1-naphthalenylcarbonyl)-1H-1,4-benzodiazepine, dihydrochloride;

2,3,4,5-Tetrahydro-1-(1H-imidazol-4-ylmethyl)-4-(1-naphthalenylcarbonyl)-1H-1,4-benzodiazepine-7-carboxylic acid, dihydrochloride;

2,3,4,5-Tetrahydro-1-(1H-imidazol-5-ylmethyl)-4-(1-naphthalenylcarbonyl)-7-cyclohexyl-1H-1,4-benzodiazepine, 2.5 hydrochloride;

7-Butyl-2,3,4,5-tetrahydro-1-(1H-imidazol-4-ylmethyl)-4-(1-naphthalenylcarbonyl)-1H-1,4-benzodiazepine, dihydrochloride;

1-[[2-(2-Aminoethyl)-1H-imidazol-4-yl]methyl]-2,3,4,5-tetrahydro-4-(1-naphthalenylcarbonyl)-7-phenyl-1H-1,4-benzodiazepine, trihydrochloride;

1-[[2-(Aminomethyl)-1H-imidazol-4-yl]methyl]-2,3,4,5-tetrahydro-4-(1-naphthalenylcarbonyl)-7-phenyl-1H-1,4-benzodiazepine, trihydrochloride;

2,3,4,5-Tetrahydro-1-(1H-imidazol-4-ylmethyl)-4-(1-naphthalenylcarbonyl)-8-[N,N-bis(phenyl-methyl)amino]-1H-1,4-benzodiazepine, trihydrochloride;

N-[2,3,4,5-Tetrahydro-1-(1H-imidazol-4-yl-methyl)-4-(1-naphthalenylcarbonyl)-1H-1,4-benzodiazepin-8-yl]phenylsulfonamide, dihydrochloride;

N-Phenyl-2,3,4,5-tetrahydro-1-(1H-imidazol-4-yl-methyl)-4-(1-naphthalenylcarbonyl)-1H-1,4-benzo-diazepine-7-carboxamide, dihydrochloride;

N-[2,3,4,5-Tetrahydro-1-(1H-imidazol-4-ylmethyl)-4-(1-naphthalenylcarbonyl)-1H-1,4-benzodiazepin-8-yl]-3-methylbenzamide, dihydrochloride;

N-[2,3,4,5-Tetrahydro-1-(1H-imidazol-4-ylmethyl)-4-(1-naphthalenylcarbonyl)-1H-1,4-benzodiazepin-8-yl]-4-methylbenzamide, dihydrochloride;

3-Chloro-N-[2,3,4,5-tetrahydro-1-(1H-imidazol-4-yl-methyl)-4-(1-naphthalenylcarbonyl)-1H-1,4-benzo-diazepin-8-yl]benzamide, dihydrochloride;

7-Bromo-2,3,4,5,-tetrahydro-1-[[2-[(dimethylamino)-methyl]-1H-imidazol-4-yl]methyl]-4-(1-naphthalenylcarbonyl)-1H-1,4-benzodiazepine, dihydrochloride;

7-(4-Chlorophenyl)-2,3,4,5-tetrahydro-1-(1H-imidazol-4-ylmethyl)-4-(1-naphthalenylcarbonyl)-1H-1,4-benzodiazepine, dihydrochloride;

7-(3-Aminophenyl)-2,3,4,5-tetrahydro-1-(1H-imidazol-4-ylmethyl)-4-(1-naphthalenylcarbonyl)-1H-1,4-benzodiazepine, trihydrochloride;

1-Methyl-N-[2,3,4,5-tetrahydro-1-(1H-imidazol-4-ylmethyl)-4-(1-naphthalenylcarbonyl)-1H-1,4-benzodiazepin-8-yl]-1H-pyrrole-2-carboxamide, trihydrochloride;

N-[2,3,4,5-Tetrahydro-1-(1H-imidazol-4-ylmethyl)-4-(1-naphthalenylcarbonyl)-1H-1,4-benzodiazepin-8-yl]-3-furancarboxamide, dihydrochloride;

7-(3-Chlorophenyl)-2,3,4,5-tetrahydro-1-(1H-imidazol-4-ylmethyl)-4-(1-naphthalenylcarbonyl)-1H-1,4-benzodiazepine, dihydrochloride;

2-Methyl-N-[2,3,4,5-tetrahydro-1-(1H-imidazol-4-ylmethyl)-4-(1-naphthalenylcarbonyl)-1H-1,4-benzodiazepin-8-yl]benzamide, dihydrochloride;

N-Phenyl-N'-[2,3,4,5-tetrahydro-1-(1H-imidazol-4-ylmethyl)-4-(1-naphthalenylcarbonyl)-1H-1,4-benzodiazepin-8-yl]urea, dihydrochloride;

2,3,4,5-Tetrahydro-1-(1H-imidazol-4-ylmethyl)-4-(1-naphthalenylcarbonyl)-7-(3-pyridinyl)-1H-1,4-benzodiazepine, trihydrochloride;

2,3,4,5-Tetrahydro-1-(1H-imidazol-4-ylmethyl)-9-methoxy-4-(1-naphthalenylcarbonyl)-1H-1,4-diazepine, dihydrochloride;

(R)-2,3,4,5-Tetrahydro-1-(1H-imidazol-4-ylmethyl)-3-[2-(methylthio)ethyl]-4-(1-naphthalenylcarbonyl)-1H-1,4-benzodiazepine, hydrochloride;

2,3,4,5-Tetrahydro-1-(1H-imidazol-4-ylmethyl)-4-(1-naphthalenylcarbonyl)-3-(phenylmethyl)-1H-1,4-benzodiazepine, hydrochloride;

2,3,4,5-Tetrahydro-3-(2-hydroxyethyl)-1-(1H-imidazol-4-ylmethyl)-4-(1-naphthalenylcarbonyl)-1H-1,4-benzodiazepine, trifluoroacetate;

2,3,4,5-Tetrahydro-4-(1H-imidazol-4-ylmethyl)-3-[2-(methylthio)ethyl]-4-(1-naphthalenylcarbonyl)-1H-1,4-benzodiazepine, trifluoroacetate;

(S)-2,3,4,5-Tetrahydro-1-(1H-imidazol-4-ylmethyl)-4-(1-naphthalenylcarbonyl)-3-(phenylmethyl)-1H-1,4-benzodiazepine, trifluoroacetate;

4-Acetyl-7-bromo-2,3,4,5-tetrahydro-1-(1H-imidazol-4-ylmethyl)-3-(phenylmethyl)-1H-1,4-benzodiazepine, hydrochloride;

2,3,4,5-Tetrahydro-4-(1H-imidazol-4-ylmethyl)-1-(1-naphthalenylcarbonyl)-3-(phenylmethyl)-1H-1,4-benzodiazepine, 1.5 hydrochloride;

7-Bromo-1,2,3,5-tetrahydro-1-(1H-imidazol-4-ylmethyl)-3-(phenylmethyl)-4H-1,4-benzodiazepine-4-carboxamide, trifluoroacetate;

7-Bromo-2,3,4,5-tetrahydro-1-(1H-imidazol-4-ylmethyl)-4-(methylsulfonyl)-3-(phenylmethyl)-1H-1,4-benzodiazepine, hydrochloride;

4-Acetyl-2,3,4,5-tetrahydro-1-(1H-imidazol-4-ylmethyl)-7-phenyl-3-(phenylmethyl)-1H-1,4-benzodiazepine, trifluoroacetate;

4-Acetyl-7-bromo-3-[(4-chlorophenyl)methyl]-2,3,4,5-tetrahydro-1-(1H-imidazol-4-ylmethyl)-1H-1,4-benzodiazepine, dihydrochloride;

N-Cyclohexyl-N'-[2,3,4,5-tetrahydro-1-(1H-imidazol-4-ylmethyl)-4-(1-naphthalenylcarbonyl)-1H-1,4-benzodiazepin-8-yl]urea, dihydrochloride;

2,2-Dimethyl-N-[2,3,4,5-tetrahydro-1-(1H-imidazol-4-ylmethyl)-4-(1-naphthalenylcarbonyl)-1H-1,4-benzodiazepin-8-yl]propanamide, dihydrochloride;

2,3,4,5-Tetrahydro-1-(1H-imidazol-4-ylmethyl)-4-(1-naphthalenylsulfonyl)-7-phenyl-1H-1,4-benzodiazepine, monohydrochloride;

4-Acetyl-7-bromo-2,3,4,5-tetrahydro-1-(1H-imidazol-4-ylmethyl)-3-(2-naphthalenylmethyl)-1H-1,4-benzodiazepine, dihydrochloride;

4-Acetyl-7-bromo-2,3,4,5-tetrahydro-1-(1H-imidazol-4-ylmethyl)-3-(1-naphthalenylmethyl)-1H-1,4-benzodiazepine, dihydrochloride;

7-(2-Chlorophenyl)-2,3,4,5-tetrahydro-1-(1H-imidazol-4-ylmethyl)-4-(1-naphthalenylcarbonyl)-1H-1,4-benzodiazepine, dihydrochloride;

2,3,4,5-Tetrahydro-1-(1H-imidazol-4-ylmethyl)-7-phenyl-1H-1,4-benzodiazepine, monohydrochloride;

1-Methyl-N-[2,3,4,5-tetrahydro-1-(1H-imidazol-4-ylmethyl)-4-(1-naphthalenylcarbonyl)-1H-1,4-benzodiazepin-8-yl]-2-piperidinecarboxamide, trihydrochloride;

N-[2,3,4,5-tetrahydro-1-(1H-imidazol-4-ylmethyl)-4-(1-naphthalenylcarbonyl)-1H-1,4-benzodiazepin-8-yl]-4-morpholinecarboxamide, dihydrochloride;

N-[2,3,4,5-Tetrahydro-1-(1H-imidazol-4-ylmethyl)-4-(1-naphthalenylcarbonyl)-1H-1,4-benzodiazepin-8-yl]-3-methylbutanamide, dihydrochloride;

1,2,3,5-Tetrahydro-1-(1H-imidazol-4-ylmethyl)-N,N,7-triphenyl-4H-1,4-2 5 benzodiazepine-4-carboxamide, dihydrochloride;

2,3,4,5-Tetrahydro-1-(1H-imidazol-4-ylmethyl)-7-phenyl-4-[(4-phenyl-1,2,3-thiadiazol-5-yl)carbonyl]-1H-1,4-benzodiazepine, trifluoroacetate;

8-[[(Cyclohexylamino)carbonyl]amino]-2,3,4,5-tetrahydro-1-(1H-imidazol-4-ylmethyl)-3-(phenylmethyl)-1H-1,4-benzodiazepine-4-carboxylic acid, 1,1-dimethylethyl ester;

2,3,4,5-Tetrahydro-1-(1H-imidazol-4-ylmethyl)-8-[[(4-methylphenyl)sulfonyl]amino]-3-(phenylmethyl)-1H-1,4-benzodiazepine-4-carboxylic acid, 1,1-dimethylethylester;

7-Bromo-1,2,3,4-tetrahydro-1-(1H-imidazol-4-ylmethyl)-3-(phenylmethyl)-5H-1,4-benzodiazepin-5-one, dihydrochloride;

2,3,4,5-Tetrahydro-1-(1H-imidazol-4-ylmethyl)-4-[1-oxo-3-(1-piperidinyl)propyl]-7-phenyl-1H-1,4-benzodiazepine, trihydrochloride;

2,3,4,5-Tetrahydro-1-(1H-imidazol-4-ylmethyl)-7-phenyl-4-(4-quinolinylcarbonyl)-1H-1,4-benzodiazepine, trihydrochloride;

4-[(5-Bromo-3-pyridinyl)carbonyl]-2,3,4,5-tetrahydro-1-(1H-imidazol-4-ylmethyl)-7-phenyl-1H-1,4-benzodiazepine, trihydrochloride;

(S)-4-[2-(Dimethylamino)-1-oxo-3-phenylpropyl]-2,3,4,5-tetrahydro-1-(1H-imidazol-4-ylmethyl)-7-phenyl-1H-1,4-benzodiazepine, trihydrochloride;

2,3,4,5-Tetrahydro-4-[4-hydroxy-3-(4-morpholinyl-methyl)benzoyl]-1-(1H-imidazol-4-ylmethyl)-7-phenyl-1H-1,4-benzodiazepine, trihydrochloride;

(S)-2,3,4,5-Tetrahydro-1-(1H-imidazol-4-ylmethyl)-4-[(1-methyl-2-pyrrolidinyl)carbonyl]-7-phenyl-1H-1,4-benzodiazepine, trihydrochloride;

2,3,4,5-Tetrahydro-1-(1H-imidazol-4-ylmethyl)-7-phenyl-4-[[2-(propylthio)-3-pyridinyl]carbonyl]-1H-1,4-benzodiazepine, trihydrochloride;

4-[(2-Chloro-6-methyl-4-pyridinyl)carbonyl]-2,3,4,5-tetrahydro-1-(1H-imidazol-4-ylmethyl)-7-phenyl-1H-1,4-benzodiazepine, trihydrochloride;

2,3,4,5-Tetrahydro-1-(1H-imidazol-4-ylmethyl)-7-phenyl-4-[[2-(phenylthio)-3-pyridinyl]carbonyl]-1H-1,4-benzodiazepine, trihydrochloride;

2,3,4,5-Tetrahydro-1-(1H-imidazol-4-ylmethyl)-4-[[2-(4-methylphenoxy)-3-pyridinyl]carbonyl]-7-phenyl-1H-1,4-benzodiazepine, trihydrochloride;

2,3,4,5-Tetrahydro-1-(1H-imidazol-4-ylmethyl)-4-[(2-methoxy-3-pyridinyl)carbonyl]-7-phenyl-1H-1,4-benzodiazepine, trihydrochloride;

2,3,4,5-Tetrahydro-1-(1H-imidazol-4-ylmethyl)-7-phenyl-4-[(5-phenyl-4-oxazolyl)carbonyl]-1H-1,4-benzodiazepine, dihydrochloride;

4-Acetyl-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-7-phenyl-4-[(tetrahydro-3-furanyl)carbonyl]-1H-1,4-benzodiazepine, dihydrochloride;

2,3,4,5-Tetrahydro-1-(1H-imidazol-4-ylmethyl)-4-[(2-methoxyethoxy)acetyl]-7-phenyl-1H-1,4-benzodiazepine, dihydrochloride;

2,3,4,5-Tetrahydro-1-(1H-imidazol-4-ylmethyl)-4-[4-(4-morpholinylmethyl)benzoyl]-7-phenyl-1H-1,4-benzodiazepine, dihydrochloride;

2,3,4,5-Tetrahydro-1-(1H-imidazol-4-ylmethyl)-4-[4-(methylsulfonyl)benzoyl]-7-phenyl-1H-1,4-benzodiazepine, dihydrochloride;

2,3,4,5-Tetrahydro-1-(1H-imidazol-4-ylmethyl)-4-[1-oxo-3-(phenylsulfonyl)propyl]-7-phenyl-1H-1,4-benzodiazepine, dihydrochloride;

2,3,4,5-Tetrahydro-1-(1H-imidazol-4-ylmethyl)-7-phenyl-4-(3-pyridinylacetyl)-1H-1,4-benzodiazepine, trihydrochloride;

2,3,4,5-Tetrahydro-1-(1H-imidazol-4-ylmethyl)-7-phenyl-4-(2-quinoxalinylcarbonyl)-1H-1,4-benzodiazepine, tetrahydrochloride;

2,3,4,5-Tetrahydro-1-(1H-imidazol-4-ylmethyl)-4-(4-isoquinolinylcarbonyl)-7-phenyl-H-1,4-benzodiazepine, trihydrochloride;

4-[(2-Chloro-3-pyridinyl)carbonyl]-2,3,4,5-tetrahydro-1-(1H-imidazol-4-ylmethyl)-7-phenyl-1H-1,4-benzodiazepine, trihydrochloride;

2,3,4,5-Tetrahydro-1-(1H-imidazol-4-ylmethyl)-7-phenyl-4-(3-pyridinylcarbonyl)-1H-1,4-benzodiazepine, trihydrochloride;

4-[(2,6-Dimethoxy-3-pyridinyl)carbonyl]-2,3,4,5-tetrahydro-1-(1H-imidazol-4-ylmethyl)-7-phenyl-1H-1,4-benzodiazepine, trihydrochloride;

2,3,4,5-Tetrahydro-1-(1H-imidazol-4-ylmethyl)-7-phenyl-4-(2-pyrazinylcarbonyl)-1H-1,4-benzodiazepine, tetrahydrochloride;

4-(2-Ethoxybenzoyl)-2,3,4,5-tetrahydro-1-(1H-imidazol-4-ylmethyl)-7-phenyl-1H-1,4-benzodiazepine, dihydrochloride;

4-[3-(Dimethylamino)benzoyl]-2,3,4,5-tetrahydro-1-(1H-imidazol-4-ylmethyl)-7-phenyl-1H-1,4-benzodiazepine, trihydrochloride;

2,3,4,5-Tetrahydro-1-(1H-imidazol-4-ylmethyl)-7-phenyl-4-[(1-phenylcyclopropyl)carbonyl]-1H-1,4-benzodiazepine, dihydrochloride;

4-[(Bicyclo[4.2.0]octa-1,3,5-trien-7-yl)carbonyl]-2,3,4,5-tetrahydro-1-(1H-imidazol-4-ylmethyl)-7-phenyl-1H-1,4-benzodiazepine, dihydrochloride;

4-Benzoyl-2,3,4,5-tetrahydro-1-(1H-imidazol-4-ylmethyl)-7-phenyl-1H-1,4-benzodiazepine, dihydrochloride;

4-(2-Chlorobenzoyl)-2,3,4,5-tetrahydro-1-(1H-imidazol-4-ylmethyl)-7-phenyl-1H-1,4-benzodiazepine, dihydrochloride;

4-(2,3-Dichlorobenzoyl)-2,3,4,5-tetrahydro-1-(1H-imidazol-4-ylmethyl)-7-phenyl-1H-1,4-benzodiazepine, dihydrochloride;

N-[2-[[2,3,4,5-Tetrahydro-1-(1H-imidazol-4-ylmethyl)-7-phenyl-1H-1,4-benzodiazepin-4-yl]carbonyl]phenyl]-acetamide, dihydrochloride;

2,3,4,5-Tetrahydro-1-(1H-imidazol-4-ylmethyl)-4-(2-phenoxybenzoyl)-7-phenyl-1H-1,4-benzodiazepine, dihydrochloride;

2,3,4,5-Tetrahydro-1-(1H-imidazol-4-ylmethyl)-4-(2-methoxybenzoyl)-7-phenyl-1H-1,4-benzodiazepine, dihydrochloride;

4-(2,3-Dimethoxybenzoyl)-2,3,4,5-tetrahydro-1-(1H-imidazol-4-ylmethyl)-7-phenyl-1H-1,4-benzodiazepine, dihydrochloride;

4-(2,4-Dimethoxybenzoyl)-2,3,4,5-tetrahydro-1-(1H-imidazol-4-ylmethyl)-7-phenyl-1H-1,4-benzodiazepine, dihydrochloride;

4-(2,5-Dimethoxybenzoyl)-2,3,4,5-tetrahydro-1-(1H-imidazol-4-ylmethyl)-7-phenyl-1H-1,4-benzodiazepine, dihydrochloride;

4-(2,6-Dimethoxybenzoyl)-2,3,4,5-tetrahydro-1-(1H-imidazol-4-ylmethyl)-7-phenyl-1H-1,4-benzodiazepine, dihydrochloride;

4-(2,3-Dihydroxybenzoyl)-2,3,4,5-tetrahydro-1-(1H-imidazol-4-ylmethyl)-7-phenyl-1H-1,4-benzodiazepine, dihydrochloride;

4-([1,1'-Biphenyl]-2-ylcarbonyl)-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-(2-methylbenzoyl)-7-phenyl-1H-1,4-benzodiazepine, dihydrochloride;

4-(2,3-Dimethylbenzoyl)-2,3,4,5-tetrahydro-1-(1H-imidazol-4-ylmethyl)-7-phenyl-1H-1,4-benzodiazepine, dihydrochloride;

4-(3-Cyanobenzoyl)-2,3,4,5-tetrahydro-1-(1H-imidazol-4-ylmethyl)-7-phenyl-1H-1,4-benzodiazepine, dihydrochloride;

4-(3-Chlorobenzoyl)-2,3,4,5-tetrahydro-1-(1H-imidazol-4-ylmethyl)-7-phenyl-1H-1,4-benzodiazepine, dihydrochloride;

5  2,3,4,5-Tetrahydro-1-(1H-imidazol-4-ylmethyl)-4-(3-phenoxybenzoyl)-7-phenyl-1H-1,4-benzodiazepine, dihydrochloride;

2,3,4,5-Tetrahydro-1-(1H-imidazol-4-ylmethyl)-4-(3-methoxybenzoyl)-7-phenyl-1H-1,4-benzodiazepine, dihydrochloride;

4-(3,4-Dimethoxybenzoyl)-2,3,4,5-tetrahydro-1-(1H-imidazol-4-ylmethyl)-7-phenyl-1H-1,4-benzodiazepine, dihydrochloride;

4-(3,5-Dimethoxybenzoyl)-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-(3-methylbenzoyl)-7-phenyl-1H-1,4-benzodiazepine, dihydrochloride;

4-(1,2-Dioxo-2-phenylethyl)-2,3,4,5-tetrahydro-1-(1H-imidazol-4-ylmethyl)-7-phenyl-1H-1,4-benzodiazepine, dihydrochloride;

4-[(2-Ethoxy-1-naphthalenyl)carbonyl]-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-(2-naphthalenylcarbonyl)-7-phenyl-1H-1,4-benzodiazepine, dihydrochloride;

4-(Fluorophenylacetyl)-2,3,4,5-tetrahydro-1-(1H-imidazol-4-ylmethyl)-7-phenyl-1H-1,4-benzodiazepine, dihydrochloride;

4-(Diphenylacetyl)-2,3,4,5-tetrahydro-1-(1H-imidazol-4-ylmethyl)-7-phenyl-1H-1,4-benzodiazepine, dihydrochloride;

2,3,4,5-Tetrahydro-4-(2-hydroxy-1-oxo-2-phenylpropyl)-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-(1H-indol-2-ylcarbonyl)-7-phenyl-1H-1,4-benzodiazepine, dihydrochloride;

2,3,4,5-Tetrahydro-1-(1H-imidazol-4-ylmethyl)-4-(1H-indol-3-ylcarbonyl)-7-phenyl-1H-1,4-benzodiazepine, dihydrochloride;

2,3,4,5-Tetrahydro-1-(1H-imidazol-4-ylmethyl)-4-(1H-indol-5-ylcarbonyl)-7-phenyl-1H-1,4-benzodiazepine, dihydrochloride;

2,3,4,5-Tetrahydro-1-(1H-imidazol-4-ylmethyl)-4-[(1-methyl-1H-indol-2-yl)carbonyl]-7-phenyl-1H-1,4-benzodiazepine, dihydrochloride;

4-(2-Benzofuranylcarbonyl)-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-7-phenyl-4-(3-pyridinylcarbonyl)-1H-1,4-benzodiazepine, N-oxide, dihydrochloride;

2,3,4,5-Tetrahydro-1-(1H-imidazol-4-ylmethyl)-7-phenyl-4-(2-pyridinylcarbonyl)-1H-1,4-benzodiazepine, trihydrochloride;

2,3,4,5-Tetrahydro-1-(1H-imidazol-4-ylmethyl)-7-phenyl-4-(2-quinolinylcarbonyl)-1H-1,4-benzodiazepine, trihydrochloride;

2,3,4,5-Tetrahydro-1-(1H-imidazol-4-ylmethyl)-7-phenyl-4-(1-isoquinolinylcarbonyl)-1H-1,4-benzodiazepine, trihydrochloride;

4-(3-Chloro-2-nitrobenzoyl)-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-(2-nitrobenzoyl)-7-phenyl-1H-1,4-benzodiazepine, dihydrochloride;

2,3,4,5-Tetrahydro-1-(1H-imidazol-4-ylmethyl)-4-(3-methoxy-2-nitrobenzoyl)-7-phenyl-1H-1,4-benzodiazepine, dihydrochloride;

2,3,4,5-Tetrahydro-1-(1H-imidazol-4-ylmethyl)-4-(1H-indol-4-ylcarbonyl)-7-phenyl-1H-1,4-benzodiazepine, dihydrochloride;

4-[(2,6-Dihydroxy-3-naphthalenyl)carbonyl]-2,3,4,5-tetrahydro-1-(1H-imidazol-4-ylmethyl)-7-phenyl-1H-1,4-benzodiazepine, dihydrochloride;

4-(1H-Benzimidazol-5-ylcarbonyl)-2,3,4,5-tetrahydro-1-(1H-imidazol-4-ylmethyl)-7-phenyl-1H-1,4-benzodiazepine, trihydrochloride;

4-(1H-Benzotriazol-5-ylcarbonyl)-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-[(4-methoxy-2-quinolinyl)carbonyl]-7-phenyl-1H-1,4-benzodiazepine, trihydrochloride;

N-[3-[[2,3,4,5-Tetrahydro-1-(1H-imidazol-4-ylmethyl)-7-phenyl-1H-1,4-benzodiazepin-4-yl]carbonyl]phenyl]-acetamide, dihydrochloride;

2,3,4,5-Tetrahydro-1-(1H-imidazol-4-ylmethyl)-4-(2-methyl-1-oxo-2-phenylpropyl)-7-phenyl-1H-1,4-benzodiazepine, dihydrochloride;

4-[2-(Dimethylamino)benzoyl]-2,3,4,5-tetrahydro-1-(1H-imidazol-4-ylmethyl)-7-phenyl-1H-1,4-benzodiazepine, trihydrochloride;

4-(3-Ethoxybenzoyl)-2,3,4,5-tetrahydro-1-(1H-imidazol-4-ylmethyl)-7-phenyl-1H-1,4-benzodiazepine, dihydrochloride;

2,3,4,5-Tetrahydro-4-(2-hydroxy[1,1'-biphenyl]-3-ylcarbonyl)-1-(1H-imidazol-4-ylmethyl)-7-phenyl-1H-1,4-benzodiazepine, dihydrochloride;

2,3,4,5-Tetrahydro-4-[2-[(2-hydroxyethyl)thio]benzoyl]-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-[(2-methoxy-1-naphthalenyl)carbonyl]-7-phenyl-1H-1,4-benzodiazepine, dihydrochloride;

2,3,4,5-Tetrahydro-4-[(2-hydroxy-4-quinolinyl)-carbonyl]-1-(1H-imidazol-4-ylmethyl)-7-phenyl-1H-1,4-benzodiazepine, dihydrochloride;

2-[[2,3,4,5-Tetrahydro-1-(1H-imidazol-4-ylmethyl)-7-phenyl-1H-1,4-benzodiazepin-4-yl]carbonyl]benzamide, dihydrochloride;

N-(1,1-Dimethylethyl)-2-[[2,3,4,5-tetrahydro-1-(1H-imidazol-4-ylmethyl)-7-phenyl-1H-1,4-benzodiazepin-4-yl]carbonyl]benzamide, dihydrochloride;

N-(4-Fluorophenyl)-N'-[3-[[2,3,4,5-tetrahydro-1-(1H-imidazol-4-ylmethyl)-7-phenyl-1H-1,4-benzodiazepin-4-yl]carbonyl]phenyl]urea, dihydrochloride;

2,3,4,5-Tetrahydro-1-(1H-imidazol-4-ylmethyl)-4-[(3-methyl-4-oxo-2-phenyl-4H-benzopyran-8-yl)carbonyl]-7-phenyl-1H-1,4-benzodiazepine, dihydrochloride;

2,3,4,5-Tetrahydro-1-(1H-imidazol-4-ylmethyl)-7-phenyl-4-[3-(trifluoromethoxy)benzoyl]-1H-1,4-benzodiazepine, dihydrochloride;

4-(2-Cyanobenzoyl)-2,3,4,5-tetrahydro-1-(1H-imidazol-4-ylmethyl)-7-phenyl-1H-1,4-benzodiazepine, dihydrochloride;

2,3,4,5-Tetrahydro-1-(1H-imidazol-4-ylmethyl)-4-[2-[[(4-methylphenyl)sulfonyl]amino]benzoyl]-7-phenyl-1H-1,4-benzodiazepine, dihydrochloride;

2,3,4,5-Tetrahydro-1-(1H-imidazol-4-ylmethyl)-7-phenyl-4-(6-quinolinylcarbonyl)-1H-1,4-benzodiazepine, trihydrochloride;

2,3,4,5-Tetrahydro-1-(1H-imidazol-4-ylmethyl)-7-phenyl-4-(8-quinolinylcarbonyl)-1H-1,4-benzodiazepine, trihydrochloride;

4-(Benzo[b]thiophen-2-ylcarbonyl)-2,3,4,5-tetrahydro-1-(1H-imidazol-4-ylmethyl)-7-phenyl-1H-1,4-benzodiazepine, dihydrochloride;

4-[[4-(Dimethylamino)-1-naphthalenyl]carbonyl]-2,3,4,5-tetrahydro-1-(1H-imidazol-4-ylmethyl)-7-phenyl-1H-1,4-benzodiazepine, trihydrochloride;

2,3,4,5-Tetrahydro-1-(1H-imidazol-4-ylmethyl)-7-phenyl-4-(1H-purin-6-ylcarbonyl)-1H-1,4-benzodiazepine, trihydrochloride;

2,3,4,5-Tetrahydro-1-(1H-imidazol-4-ylmethyl)-4-(methoxyphenylacetyl)-7-phenyl-1H-1,4-benzodiazepine, dihydrochloride;

2,3,4,5-Tetrahydro-1-(1H-imidazol-4-ylmethyl)-4-[(5-methyl-1-phenyl-1H-pyrazol-4-yl)carbonyl]-7-phenyl-1H-1,4-benzodiazepine, trihydrochloride;

2,3,4,5-Tetrahydro-1-(1H-imidazol-4-ylmethyl)-4-[2-(2-methylphenyl)-1-oxopropyl]-7-phenyl-1H-1,4-benzodiazepine, dihydrochloride;

2,3,4,5-Tetrahydro-1-(1H-imidazol-4-ylmethyl)-7-phenyl-4-[(tetrahydro-4-phenyl-2H-pyran-4-yl)carbonyl]-1H-1,4-benzodiazepine, dihydrochloride;

2,3,4,5-Tetrahydro-1-(1H-imidazol-4-ylmethyl)-4-[2-(methylphenylamino)benzoyl]-7-phenyl-1H-1,4-benzodiazepine, trihydrochloride;

2,3,4,5-Tetrahydro-1-(1H-imidazol-4-ylmethyl)-7-phenyl-4-(4-quinolinylcarbonyl)-1H-1,4-benzodiazepine, N-oxide, dihydrochloride;

N-Methyl-N-(2-pyridinylmethyl)-2-[[2,3,4,5-tetrahydro-1-(1H-imidazol-4-ylmethyl)-7-phenyl-1H-1,4-benzodiazepin-4-yl]carbonyl]benzamide, trihydrochloride;

2,3,4,5-Tetrahydro-1-(1H-imidazol-4-ylmethyl)-4-(3-isoquinolinylcarbonyl)-7-phenyl-1H-1,4-benzodiazepine, trihydrochloride;

2,3,4,5-Tetrahydro-1-(1H-imidazol-4-ylmethyl)-4-[(2-naphthalenylthio)acetyl]-1H-1,4-benzodiazepine, trifluoroacetate (1:2);

4-[3-(3,4-Dimethoxyphenyl)-1-oxopropyl]-2,3,4,5-tetrahydro-1-(1H-imidazol-4-ylmethyl)-1H-1,4-benzodiazepine, trifluoroacetate (1:2);

4-([1,1'-Biphenyl]-4-ylacetyl)-2,3,4,5-tetrahydro-1-(1H-imidazol-4-ylmethyl)-1H-1,4-benzodiazepine, trifluoroacetate (1:2);

2,3,4,5-Tetrahydro-1-(1H-imidazol-4-ylmethyl)-4-(2-naphthalenylacetyl)-1H-1,4-benzodiazepine, trifluoroacetate (1:2);

4-([1,1'-Biphenyl]-2-ylcarbonyl)-2,3,4,5-tetrahydro-1-(1H-imidazol-4-ylmethyl)-1H-1,4-benzodiazepine, trifluoroacetate (1:2);

2,3,4,5-Tetrahydro-1-(1H-imidazol-4-ylmethyl)-4-[(2-phenyl4-quinolinyl)carbonyl]-1H-1,4-benzodiazepine, trifluoroacetate (1:3);

2,3,4,5-Tetrahydro-1-(1H-imidazol-4-ylmethyl)-4-(3-pyridinylacetyl)-1H-1,4-benzodiazepine, trifluoroacetate (1:3);

4-(9H-Fluoren-9-ylacetyl)-2,3,4,5-tetrahydro-1-(1H-imidazol-4-ylmethyl)-1H-1,4-benzodiazepine, trifluoroacetate (1:2);

(S)-4-[2-(Dimethylamino)-1-oxo-3-phenylpropyl]-2,3,4,5-tetrahydro-1-(1H-imidazol-4-ylmethyl)-1H-1,4-benzodiazepine, trifluoroacetate (1:3);

(S)-2,3,4,5-Tetrahydro-1-(1H-imidazol-4-ylmethyl)-4-[(2-oxo-4-phenyl-3-oxazolidinyl)acetyl]-1H-1,4-benzodiazepine, trifluoroacetate (1:2);

4-(9-Acridinylcarbonyl)-2,3,4,5-tetrahydro-1-(1H-imidazol-4-ylmethyl)-1H-1,4-benzodiazepine, trifluoroacetate (1:3);

2,3,4,5-Tetrahydro-1-(1H-imidazol-4-ylmethyl)-4-(3-phenoxybenzoyl)-1H-1,4-benzodiazepine, trifluoroacetate (1:2);

2,3,4,5-Tetrahydro-1-(1H-imidazol-4-ylmethyl)-4-[[4'-(trifluoromethyl)[1,1'-biphenyl]-2-yl]carbonyl]-1H-1,4-benzodiazepine, trifluoroacetate (1:2);

2,3,4,5-Tetrahydro-1-(1H-imidazol-4-ylmethyl)-4-(4-phenoxybenzoyl)-1H-1,4-benzodiazepine, trifluoroacetate (1:2);

2,3,4,5-Tetrahydro-1-(1H-imidazol-4-ylmethyl)-4-(2-naphthalenylcarbonyl)-1H-1,4-benzodiazepine, trifluoroacetate (1:2);

2,3,4,5-Tetrahydro-1-(1H-imidazol-4-ylmethyl)-4-(1-oxo-4-phenylbutyl)-1H-1,4-benzodiazepine, trifluoroacetate (1:2);

2,3,4,5-Tetrahydro-1-(1H-imidazol-4-ylmethyl)-4-[(2-phenoxyphenyl)acetyl]-1H-1,4-benzodiazepine, trifluoroacetate (1:2);

2,3,4,5-Tetrahydro-1-(1H-imidazol-4-ylmethyl)-4-[2-[(4-methylphenyl)sulfinyl]benzoyl]-1H-1,4-benzodiazepine, trifluoroacetate (1:2);

2,3,4,5-Tetrahydro-1-(1H-imidazol-4-ylmethyl)-4-[2-[(phenylmethyl)amino]benzoyl]-1H-1,4-benzodiazepine, trifluoroacetate (1:3);

1,2,3,5-Tetrahydro-1-(1H-imidazol-4-yl-methyl)-N,N-diphenyl-4H-1,4-benzodiazepine-4-carboxamide, hydrochloride;

1,2,3,5-Tetrahydro-1-(1H-imidazol-4-yl-methyl)-a,7-diphenyl-4H-1,4-benzodiazepine-4-acetic acid, methyl ester, hydrochloride;

4-Acetyl-2,3,4,5-tetrahydro-1-(1H-imidazol-4-ylmethyl)-3-(phenylmethyl)-1H-1,4-benzodiazepine, hydrochloride;

(R)-7-Bromo-2,3,4,5-tetrahydro-1-(1H-imidazol-4-ylmethyl)-4-(methylsulfonyl)-3-(phenylmethyl)-1H-1,4-benzodiazepine, hydrochloride;

(R)-2,3,4,5-Tetrahydro-1-(1H-imidazol-4-ylmethyl)-4-(methylsulfonyl)-3-(phenylmethyl)-1H-1,4-benzodiazepine-7-carbonitrile, monohydrochloride;

(R)-4-Acetyl-2,3,4,5-tetrahydro-1-(1H-imidazol-4-ylmethyl)-7-phenyl-3-(phenylmethyl)-1H-1,4-benzodiazepine, monohydrochloride;

7-Bromo-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, trifluoroacetate (1:2);

2,3,4,5-Tetrahydro-1-(1H-imidazol-4-ylmethyl)-7-phenyl-4-[(1,2,3,4-tetrahydro-1-quinolinyl)carbonyl]-1H-1,4-benzodiazepine, monohydrochloride;

N-Ethyl-1,2,3,5-tetrahydro-1-(1H-imidazol-4-ylmethyl)-N,7-diphenyl-4H-1,4-benzodiazepine-4-carboxamide, monohydrochloride;

4-[(2,3-Dihydro-1H-indol-1-yl)carbonyl]-2,3,4,5-tetrahydro-1-(1H-imidazol-4-ylmethyl)-7-phenyl-1H-1,4-benzodiazepine, monohydrochloride;

2,3,4,5-Tetrahydro-1-(1H-imidazol-4-ylmethyl)-4-(methylsulfonyl)-3-(phenylmethyl)-7-(4-pyridinyl)-1H-1,4-benzodiazepine, trihydrochloride;

(R)-4-[[2-(Dimethylamino)ethyl]sulfonyl]-2,3,4,5-tetrahydro-1-(1H-imidazol-4-ylmethyl)-7-phenyl-3-(phenylmethyl)-1H-1,4-benzodiazepine, trifluoroacetate (1:1);

[2,3,4,5-Tetrahydro-1-(1H-imidazol-4-ylmethyl)-4-(1-naphthalenylcarbonyl)-1H-1,4-benzodiazepin-8-yl] carbamic acid, cyclohexyl ester, dihydrochloride;

(R)-7-Bromo-2,3,4,5-tetrahydro-1-(1-methyl-1H-imidazol-5-yl)methyl)-4-(methylsulfonyl)-3-(phenylmethyl)-1H-1,4-benzodiazepine, hydrochloride;

(R)-7-Cyano-2,3,4,5-tetrahydro-1-[(1-methyl-1H-imidazol-5-yl)methyl]-4-(methylsulfonyl)-3-(phenylmethyl)-1H-1,4-benzodiazepine, monohydrochloride;

4-[2-(4-Chlorophenyl)-1,2-dioxoethyl]-2,3,4,5-tetrahydro-1-(1H-imidazol-4-ylmethyl)-7-phenyl-1H-1,4-benzodiazepine, hydrochloride;

4-(1,2-Dioxopropyl)-2,3,4,5-tetrahydro-1-(1H-imidazol-4-ylmethyl)-7-phenyl-1H-1,4-benzodiazepine, hydrochloride;

2,3,4,5-Tetrahydro-1-(1H-imidazol-4-ylmethyl)-4-[2-(4-nitrophenyl)-1,2-dioxoethyl]-7-phenyl-1H-1,4-benzodiazepine, hydrochloride;

2,3,4,5-Tetrahydro-1-(1H-imidazol-4-ylmethyl)-4-[2-(4-methoxyphenyl)-1,2-dioxoethyl]-7-phenyl-1H-1,4-benzodiazepine, hydrochloride;

2,3,4,5-Tetrahydro-1-(1H-imidazol-4-ylmethyl)-7-phenyl-4-(3,3,3-trifluoro-1,2-dioxopropyl)-1H-1,4-benzodiazepine, trifluoroacetate (1:2);

(R)-7-Bromo-2,3,4,5-tetrahydro-1-(1H-imidazol-4-ylacetyl)-4-(methylsulfonyl)-3-(phenylmethyl)-1H-1,4-benzodiazepine, monohydrochloride;

(R)-7-Bromo-2,3,4,5-tetrahydro-1-(2-1H-imidazol-4-ylethyl)-4-(methylsulfonyl)-3-(phenylmethyl)-1H-1,4-benzodiazepine, monohydrochloride;

8-[(Cyclohexylcarbonyl)amino]-1,2,3,5-tetrahydro-1-(1H-imidazol-4-ylmethyl)-3-(phenylmethyl)-4H-1,4-benzodiazepine-4-carboxylic acid, methyl ester, dihydrochloride;

N-[2,3,4,5-Tetrahydro-1-(1H-imidazol-4-ylmethyl)-4-(1-naphthalenylcarbonyl)-1H-1,4-benzodiazepin-8-yl-1-piperidinecarboxamide, dihydrochloride;

(R)-7-Cyano-1,2,3,5-tetrahydro-1-(1H-imidazol-4-ylmethyl)-3-(phenylmethyl)-4H-1,4-benzodiazepine-4-carboxylic acid, ethyl ester, hydrochloride;

N-[2,3,4,5-Tetrahydro-1-(1H-imidazol-4-ylmethyl)-4-(methylsulfonyl)-3-(phenylmethyl)-1H-1,4-benzodiazepin-8-yl]cyclohexanecarboxamide, dihydrochloride;

(R)-7-Cyano-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, dihydrochloride;

(R)-7-Cyano-2,3,4,5-tetrahydro-1-(1H-imidazol-4-ylmethyl)-4-[[2-(4-morpholinyl)ethyl]sulfonyl]-3-(phenylmethyl)-4H-1,4-benzodiazepine, dihydrochloride;

N-[2,3,4,5-Tetrahydro-1-(1H-imidazol-4-ylmethyl)-4-(2-methoxy-3-methylbenzoyl)-1H-1,4-benzodiazepin-8-yl] cyclohexanecarboxamide, dihydrochloride, 8-[(Cyclohexylcarbonyl)amino]-2,3,4,5-tetrahydro-1-(1H-imidazol-4-ylmethyl)-N-phenyl-1H-1,4-benzodiazepine-4-carboxamide, dihydrochloride;

N-[2,3,4,5-Tetrahydro-1-(1H-imidazol-4-ylmethyl)-4-[(2-methylphenyl)sulfonyl]-1H-1,4-benzodiazepin-8-yl] cyclohexanamide, dihydrochloride;

N-[2,3,4,5-Tetrahydro-1-(1H-imidazol-4-ylmethyl)-4-[(2-methoxyphenyl)carbonyl]-1H-1,4-benzodiazepin-8-yl] cyclohexanamide, dihydrochloride;

(R)-7-Cyano-1,2,3,5-tetrahydro-1-(1H-imidazol-4-ylmethyl)-3-(phenylmethyl)-4H-1,4-benzodiazepine-4-sulfonic acid, ethyl ester, hydrochloride;

(3R)-7-Bromo-1-[cyano(1H-imidazol-4-yl)methyl]-2,3,4,5-tetrahydro-4-(methylsulfonyl)-3-(phenylmethyl)-1H-1,4-benzodiazepine, monohydrochloride;

(3R)-1-[2-Amino-1-(1H-imidazol-4-yl)ethyl]-2,3,4,5-tetrahydro-4-(methylsulfonyl)-3-(phenylmethyl)-1H-1,4-benzodiazepine, dihydrochloride;

(3R)-1-[2-(Dimethylamino)-1-(1H-imidazol-4-yl)ethyl]-2,3,4,5-tetrahydro-4-(methylsulfonyl)-3-(phenylmethyl)-1H-1,4-benzodiazepine, dihydrochloride;

(3R)-1-[2-Amino-1-(1H-imidazol-4-yl)ethyl]-7-bromo-2,3,4,5-tetrahydro-4-(methylsulfonyl)-3-(phenylmethyl)-1H-1,4-benzodiazepine, dihydrochloride;

(3R)-1-[2-(Dimethylamino)-1-(1H-imidazol-4-yl)ethyl]-7-bromo-2,3,4,5-tetrahydro-4-(methylsulfonyl)-3-(phenylmethyl)-1H-1,4-benzodiazepine, dihydrochloride;

7-Cyano-1,3,4,5-tetrahydro-1-(1-methyl-1H-imidazol-5-ylmethyl)-3-(phenylmethyl)-4-(phenylsulfonyl)-2H-1,4-benzodiazepin-2-one, monohydrochloride;

7-Cyano-1,3,4,5-tetrahydro-1-(1H-imidazol-4-ylmethyl)-3-(phenylmethyl)-4-(phenylsulfonyl)-2H-1,4-benzodiazepin-2-one, monohydrochloride;

7-Bromo-2,3,4,5-tetrahydro-1-(1H-imidazol-4-ylmethyl)-4-(methylsulfonyl)-3-(2-phenylethyl)-1H-1,4-benzodiazepine, dihydrochloride;

7-Bromo-3-[(3-chlorophenyl)methyl]-2,3,4,5-tetrahydro-1-(1H-imidazol-4-ylmethyl)-4-(methylsulfonyl)-1H-1,4-benzodiazepine, dihydrochloride;

(R)-7-Bromo-3-(cyclohexylmethyl)-2,3,4,5-tetrahydro-1-(1H-imidazol-4-ylmethyl)-4-(methylsulfonyl)-1H-1,4-benzodiazepine, dihydrochloride;

7-Bromo-3-[(2-chlorophenyl)methyl]-2,3,4,5-tetrahydro-1-(1H-imidazol-4-ylmethyl)-4-(methylsulfonyl)-1H-1,4-benzodiazepine, dihydrochloride;

(S)-7-Bromo-3-(cyclohexylmethyl)-2,3,4,5-tetrahydro-1-(1H-imidazol-4-ylmethyl)-4-(methylsulfonyl)-1H-1,4-benzodiazepine, dihydrochloride;

7-Bromo-2,3,4,5-tetrahydro-1-(1H-imidazol-4-ylmethyl)-3-[(4-methoxyphenyl)methyl]-4-(methylsulfonyl)-1H-1,4-benzodiazepine, dihydrochloride;

4-Acetyl-7-bromo-3-[(2-chlorophenyl)methyl]-2,3,4,5-tetrahydro-1-(1H-imidazol-4-ylmethyl)-1H-1,4-benzodiazepine, dihydrochloride;

4-Acetyl-7-bromo-3-[(3-chlorophenyl)methyl]-2,3,4,5-tetrahydro-1-(1H-imidazol-4-ylmethyl)-1H-1,4-benzodiazepine, dihydrochloride;

7-Bromo-2,3,4,5-tetrahydro-1-(1H-imidazol-4-ylmethyl)-3-[(4-hydroxyphenyl)methyl]-4-(methylsulfonyl)-1H-1,4-benzodiazepine, dihydrochloride;

(R)-2,3,4,5-Tetrahydro-1-(1H-imidazol-4-ylmethyl)-4-(methylsulfonyl)-7-phenyl-3-(3-pyridinylmethyl)-1H-1,4-benzodiazepine, dihydrochloride;

2,3,4,5-Tetrahydro-8-(hydroxymethyl)-1-(1H-imidazol-4-ylmethyl)-4-(1-naphthalenylcarbonyl)-1H-1,4-benzodiazepine, dihydrochloride;

2,3,4,5-Tetrahydro-1-(1H-imidazol-4-ylmethyl)-4-(1-naphthalenylcarbonyl)-8-(phenoxymethyl)-1H-1,4-benzodiazepine, dihydrochloride;

N-Cyclohexyl-2,3,4,5-tetrahydro-1-(1H-imidazol-4-ylmethyl)-4-(1-naphthalenylcarbonyl)-1H-1,4-benzodiazepine-8-carboxamide, dihydrochloride;

N-(Cyclohexylmethyl)-2,3,4,5-tetrahydro-1-(1H-imidazol-4-ylmethyl)-4-(1-naphthalenylcarbonyl)-1H-1,4-benzodiazepine-8-carboxamide, dihydrochloride;

2,3,4,5-Tetrahydro-1-(1H-imidazol-4-ylmethyl)-4-(1-naphthalenylcarbonyl)-N-(phenylmethyl)-1H-1,4-benzodiazepine-8-carboxamide, dihydrochloride;

(R)-4-Acetyl-7-[2-[(dimethylamino)methyl]phenyl]-2,3,4,5-tetrahydro-1-(1H-imidazol-4-ylmethyl)-3-(phenylmethyl)-1H-1,4-benzodiazepine, dihydrochloride;

(R)-4-Acetyl-7-cyano-2,3,4,5-tetrahydro-1-(1H-imidazol-4-ylmethyl)-3-(phenylmethyl)-1H-1,4-benzodiazepine, monohydrochloride;

(R)-7-Cyano-2,3,4,5-tetrahydro-1-(1H-imidazol-4-ylmethyl)-4-(1-oxobutyl)-3-(phenylmethyl)-1H-1,4-benzodiazepine, monohydrochloride;

(R)-7-Cyano-2,3,4,5-tetrahydro-1-(1H-imidazol-4-ylmethyl)-4-(2-methyl-1-oxopropyl)-3-(phenylmethyl)-1H-1,4-benzodiazepine, monohydrochloride;

(R)-7-Cyano-2,3,4,5-tetrahydro-1-(1H-imidazol-4-ylmethyl)-3-(phenylmethyl)-4-(2-pyridinylacetyl)-1H-1,4-benzodiazepine, dihydrochloride;

(R)-7-Cyano-2,3,4,5-tetrahydro-1-(1H-imidazol-4-ylmethyl)-3-(phenylmethyl)-4-(2-thienylsulfonyl)-1H-1,4-benzodiazepine, monohydrochloride;

(R)-7-Cyano-2,3,4,5-tetrahydro-1-(1H-imidazol-4-ylmethyl)-4-[(1-methylethyl)sulfonyl]-3-(phenylmethyl)-1H-1,4-benzodiazepine, monohydrochloride;

(R)-7-Cyano-2,3,4,5-tetrahydro-1-(1H-imidazol-4-ylmethyl)-3-(phenylmethyl)-4-[(trifluoromethyl)sulfonyl]-1H-1,4-benzodiazepine, monohydrochloride;

(R)-7-Bromo-2,3,4,5-tetrahydro-1-(1H-imidazol-4-ylmethyl)-3-(phenylmethyl)-4-(propylsulfonyl)-1H-1,4-benzodiazepine, monohydrochloride;

(R)-7-Bromo-2,3,4,5-tetrahydro-1-(1H-imidazol-4-ylmethyl)-3-(phenylmethyl)-4-(phenylsulfonyl)-1H-1,4-benzodiazepine, monohydrochloride;

(R)-2,3,4,5-Tetrahydro-1-(1H-imidazol-4-ylmethyl)-7-phenyl-3-(phenylmethyl)-4-(phenylsulfonyl)-1H-1,4-benzodiazepine, monohydrochloride;

(R)-2,3,4,5-Tetrahydro-1-(1H-imidazol-4-ylmethyl)-7-phenyl-3-(phenylmethyl)-4-(propylsulfonyl)-1H-1,4-benzodiazepine, monohydrochloride;

(R)-7-Cyano-4-[(4-fluorophenyl)sulfonyl]-2,3,4,5-tetrahydro-1-(1H-imidazol-4-ylmethyl)-3-(phenylmethyl)-1H-1,4-benzodiazepine, monohydrochloride;

(R)-7-Cyano-4-[(3-cyanophenyl)sulfonyl]-2,3,4,5-tetrahydro-1-(1H-imidazol-4-ylmethyl)-3-(phenylmethyl)-1H-1,4-benzodiazepine, monohydrochloride;

(R)-7-Cyano-2,3,4,5-tetrahydro-1-(1H-imidazol-4-ylmethyl)-4-[(1-methyl-1H-imidazol-2-yl)sulfonyl]-3-(phenylmethyl)-1H-1,4-benzodiazepine, dihydrochloride;

(R)-4-[(3-Bromophenyl)sulfonyl]-7-cyano-2,3,4,5-tetrahydro-1-(1H-imidazol-4-ylmethyl)-3-(phenylmethyl)-1H-1,4-benzodiazepine, monohydrochloride;

(R)-N-[5-[[7-cyano-2,3,4,5-tetrahydro-1-(1H-imidazol-4-ylmethyl)-3-(phenylmethyl)-1H-1,4-benzodiazepin-4-yl]sulfonyl]-4-methyl-2-thiazolyl]acetamide, dihydrochloride;

4-Acetyl-2,3,4,5-tetrahydro-1-(1H-imidazol-4-ylmethyl)-3-(phenylmethyl)-7-(4-pyridinyl)-1H-1,4-benzodiazepine, trihydrochloride;

2,3,4,5-Tetrahydro-1-(1H-imidazol-4-ylmethyl)-4-(2-phenyl-1,2-dioxoethyl)-7-(4-pyridinyl)-1H-1,4-benzodiazepine, trihydrochloride;

2,3,4,5-Tetrahydro-1-(1H-imidazol-4-ylmethyl)-7-(4-pyridinyl)-4-[2-(trifluoromethoxy)benzolyl]-1H-1,4-benzodiazepine, trihydrochloride;

(R)-2,3,4,5-Tetrahydro-1-[(1-methyl-1H-imidazol-5-yl)methyl]-4-(methylsulfonyl)-7-phenyl-3-(phenylmethyl)-1H-1,4-benzodiazepine;

(R)-7-Cyano-2,3,4,5-tetrahydro-1-(1H-imidazol-4-ylmethyl)-4-(phenylacetyl)-3-(phenylmethyl)-1H-1,4-benzodiazepine, monohydrochloride;

4-(2-Benzothiazolyl)-2,3,4,5-tetrahydro-1-(1H-imidazol-4-ylmethyl)-7-phenyl-1H-1,4-benzazepine, trihydrochloride;

2,3,4,5-Tetrahydro-1-(1H-imidazol-4-ylmethyl)-3-(phenylmethyl)-7-(3-pyridinyl)-4-(trifluoroacetyl)-1H-1,4-benzodiazepine, trihydrochloride;

2,3,4,5-Tetrahydro-1-(1H-imidazol-4-ylmethyl)-4-(methylsulfonyl)-3-(phenylmethyl)-7-(3-pyridinyl)-1H-1,4-benzodiazepine, trihydrochloride;

7-Bromo-3-[(1,1-dimethylethoxy)methyl]-1,2,3,4-tetrahydro-1-(1H-imidazol-4-ylmethyl)-5H-1,4-benzodiazepin-5-one;

7-Bromo-2,3,4,5-tetrahydro-1-(1H-imidazol-4-ylmethyl)-4-(methylsulfonyl)-3-(phenoxymethyl)-1H-1,4-benzodiazepine, dihydrochloride;

7-Bromo-2,3,4,5-tetrahydro-3-(hydroxymethyl)-1-(1H-imidazol-4-ylmethyl)-4-(methylsulfonyl)-1H-1,4-benzodiazepine, monohydrochloride;

7-Bromo-3-[(1,1-dimethylethoxy)methyl]-2,3,4,5-tetrahydro-1-(1H-imidazol-4-ylmethyl)-4-(methylsulfonyl)-1H-1,4-benzodiazepine;

[7-Bromo-2,3,4,5-tetrahydro-1-(1H-imidazol-4-ylmethyl)-3-(phenylmethyl)-1H-1,4-benzodiazepin-8-yl]carbamic acid, 2-methylpropyl ester, trihydrochloride;

[4-Acetyl-7-bromo-2,3,4,5-tetrahydro-1-(1H-imidazol-4-ylmethyl)-3-(phenylmethyl)-1H-1,4-benzodiazepin-8-yl]carbamic acid, 2-methylpropyl ester;

N-[4-Acetyl-2,3,4,5-tetrahydro-1-(1H-imidazol-4-ylmethyl)-3-(phenylmethyl)-1H-1,4-benzodiazepin-8-yl]cyclohexanecarboxamide, dihydrochloride;

[7-Bromo-2,3,4,5-tetrahydro-1-(1H-imidazol-4-ylmethyl)-4-(methylsulfonyl)-3-(phenylmethyl)-1H-1,4-benzodiazepin-8-yl]carbamic acid, 2-methylpropyl ester;

(R)-2,3,4,5-Tetrahydro-1-(1H-imidazol-4-ylmethyl)-4-(phenylsulfonyl)-3-(phenylmethyl)-1H-1,4-benzodiazepine-7-carbonitrile, monohydrochloride;

7-Bromo-1,2,3,5-tetrahydro-1-(1H-imidazol-4-ylmethyl)-3-(phenylmethyl)-4H-1,4-benzodiazepine-4-acetamide;

7-Bromo-4-[(dimethylamino)acetyl]-2,3,4,5-tetrahydro-1-(1H-imidazol-4-ylmethyl)-3-(phenylmethyl)-1H-1,4-benzodiazepine;

(R)-7-Bromo-4-(1,2-dioxopropyl)-2,3,4,5-tetrahydro-1-(1H-imidazol-4-ylmethyl)-3-(phenylmethyl)-1H-1,4-benzodiazepine, trifluoroacetate;

(R)-7-Bromo-4-(cyclopropylcarboonyl)-2,3,4,5-tetrahydro-1-(1H-imidazol-4-ylmethyl)-3-(phenylmethyl)-1H-1,4-benzodiazepine, trifluoroacetate;

(R)-7-Cyano-2,3,4,5-tetrahydro-1-(1H-imidazol-4-ylmethyl)-3-(phenylmethyl)-4-(propylsulfonyl)-1H-1,4-benzodiazepine, monohydrochloride;

7-Bromo-2,3,4,5-tetrahydro-1,4-bis(1H-imidazol-4-ylmethyl)-3-(phenylmethyl)-1H-1,4-benzodiazepine, dihydrochloride;

7-Bromo-1,2,3,5-tetrahydro-1-(1H-imidazol-4-ylmethyl)-N,N-dimethyl-3-(phenylmethyl)-4H-1,4-benzodiazepine-4-sulfonamide, monohydrochloride;

2,3,4,5-Tetrahydro-1-(1H-imidazol-4-ylmethyl)-4-(methylsulfonyl)-3-(phenylmethyl)-1H-1,4-benzodiazepine-7-carbonitrile, monohydrochloride;

(R)-7-Cyano-1,2,3,5-tetrahydro-1-(1H-imidazol-4-ylmethyl)-N,N-dimethyl-3-(phenylmethyl)-4H-1,4-benzodiazepine-4-carboxamide, monohydrochloride;

N,N-Diethyl-2,3,4,5-tetrahydro-1-(1H-imidazol-4-ylmethyl)-4-(methylsulfonyl)-3-(phenylmethyl)-1H-1,4-benzodiazepine-7-carboxamide, monohydrochloride;

2,3,4,5-Tetrahydro-1-(1H-imidazol-4-ylmethyl)-7-phenyl-4-(1-phenyl-1H-tetrazol-5-yl)-1H-1,4-benzodiazepine, monohydrochloride;

(R)-7-Cyano-2,3,4,5-tetrahydro-1-(1H-imidazol-4-ylmethyl)-3-(phenylmethyl)-4-(2-pyrazinylcarbonyl)-4H-1,4-benzodiazepine, monohydrochloride;

(R)-4-[7-Bromo-2,3,4,5-tetrahydro-1-(1H-imidazol-4-ylmethyl)-3-(phenylmethyl)-4H-1,4-benzodiazepin-4-yl]-4-oxobutanoic acid, methyl ester, monohydrochloride;

(R)-7-Cyano-2,3,4,5-tetrahydro-1-(1H-imidazol-4-ylmethyl)-4-(4-morpholinylcarbonyl)-3-(phenylmethyl)-1H-1,4-benzodiazepine, monohydrochloride;

(R)-7-Cyano-2,3,4,5-tetrahydro-1-(1H-imidazol-4-ylmethyl)-3-(phenylmethyl)-4-[[2-(1-pyrrolidinyl)ethyl]sulfonyl]-1H-1,4-benzodiazepine, dihydrochloride;

(S)-2,3,4,5-Tetrahydro-1-(1H-imidazol-4-ylmethyl)-4-(methylsulfonyl)-7-phenyl-3-(3-pyridinylmethyl)-1H-1,4-benzodiazepine, dihydrochloride;

(R)-2,3,4,5-Tetrahydro-1-(1H-imidazol-4-ylmethyl)-7-phenyl-3-(3-pyridinylmethyl)-4-(2-thienylsulfonyl)-1H-1,4-benzodiazepine, dihydrochloride;

(R)-2,3,4,5-Tetrahydro-1-(1H-imidazol-4-ylmethyl)-7-phenyl-4-(propylsulfonyl)-3-(3-pyridinylmethyl)-1H-1,4-benzodiazepine, monohydrochloride;

(R)-7-Bromo-2,3,4,5-tetrahydro-1-(1H-imidazol-4-ylmethyl)-4-(methylsulfonyl)-3-(2-pyridinylmethyl)-1H-1,4-benzodiazepine, monohydrochloride;

2,3,4,5-Tetrahydro-1-(1H-imidazol-4-ylmethyl)-4-(methylsulfonyl)-3-(phenylmethyl)-7-(2-pyrimidinyl)-1H-1,4-benzodiazepine, dihydrochloride;

(R)-7-Bromo-2,3,4,5-tetrahydro-1-(1H-imidazol-4-ylmethyl)-3-(phenylmethyl)-4-[(trifluoromethyl)sulfonyl]-1H-1,4-benzodiazepine, monohydrochloride;

(R)-2,3,4,5-Tetrahydro-1-(1H-imidazol-4-ylmethyl)-7-phenyl-3-(phenylmethyl)-4-(trifluoroacetyl)-1H-1,4-benzodiazepine, monohydrochloride;

(R)-2,3,4,5-Tetrahydro-1-(1H-imidazol-4-ylmethyl)-4-(methylsulfonyl)-3-(phenylmethyl)-7-(4-pyridinyl)-1H-1,4-benzodiazepine, dihydrochloride;

(R)-2,3,4,5-Tetrahydro-1-(1H-imidazol-4-ylmethyl)-3-(phenylmethyl)-7-(4-pyridinyl)-4-(2-thienylsulfonyl)-1H-1,4-benzodiazepine, dihydrochloride;

(R)-2,3,4,5-Tetrahydro-1-(1H-imidazol-4-ylmethyl)-3-(phenylmethyl)-4-(phenylsulfonyl)-7-(4-pyridinyl)-1H-1,4-benzodiazepine, dihydrochloride;

(R)-2,3,4,5-Tetrahydro-1-(1H-imidazol-4-ylmethyl)-3-(phenylmethyl)-4-(propylsulfonyl)-7-(4-pyridinyl)-1H-1,4-benzodiazepine, dihydrochloride;

(R)-7-Cyano-2,3,4,5-tetrahydro-1-(1H-imidazol-4-ylmethyl)-3-(phenylmethyl)-4-[(3,5-dimethyl-isoxazol-4-yl)sulfonyl]-1H-1,4-benzodiazepine, dihydrochloride;

(R)-7-Cyano-4-[(4-cyanophenyl)sulfonyl]-2,3,4,5-tetrahydro-1-(1H-imidazol-4-ylmethyl)-3-(phenylmethyl)-1H-1,4-benzodiazepine, dihydrochloride;

(R)-7-Cyano-2,3,4,5-tetrahydro-1-(1H-imidazol-4-ylmethyl)-3-(phenylmethyl)-4-[(2,2,2-trifluoroethyl)sulfonyl]-1H-1,4-benzodiazepine, dihydrochloride;

(R)-[(5-Bromo-2-thienyl)sulfonyl]-7-cyano-2,3,4,5-tetrahydro-1-(1H-imidazol-4-ylmethyl)-3-(phenylmethyl)-1H-1,4-benzodiazepine, dihydrochloride;

(R)-7-Cyano-2,3,4,5-tetrahydro-1-(1H-imidazol-4-ylmethyl)-4-[(4-methoxyphenyl)sulfonyl]-3-(phenylmethyl)-1H-1,4-benzodiazepine, dihydrochloride;

N-[[7-Bromo-2,3,4,5-tetrahydro-1-(1H-imidazol-4-ylmethyl)-4-(methylsulfonyl)-1H-1,4-benzodiazepin-3-yl]methyl]benzamide, dihydrochloride;

(R)-7-Cyano-1,2,3,5-tetrahydro-1-(1H-imidazol-4-ylmethyl)-N,N-dimethyl-3-(phenylmethyl)-4H-1,4-benzodiazepine-4-sulfonamide, hydrochloride;

(R)-7-Cyano-1,2,3,5-tetrahydro-N,N-dimethyl-1-[(1-methyl-1H-imidazol-5-yl)methyl]-3-(phenylmethyl)-4H-1,4-benzodiazepine-4-sulfonamide, hydrochloride;

(R)-7-Chloro-2,3,4,5-tetrahydro-1-[(1-methyl-1H-imidazol-5-yl)methyl]-4-(methylsulfonyl)-3-(phenylmethyl)-1H-1,4-benzodiazepine, monohydrochloride;

(R)-7-Chloro-2,3,4,5-tetrahydro-1-(1H-imidazol-4-ylmethyl)-4-(methylsulfonyl)-3-(phenylmethyl)-1H-1,4-benzodiazepine, monohydrochloride;

(R)-7-Chloro-2,3,4,5-tetrahydro-1-[(1-methyl-1H-imidazol-5-yl)methyl]-4-(phenylsulfonyl)-3-(phenylmethyl)-1H-1,4-benzodiazepine, monohydrochloride;

(R)-7-Cyano-2,3,4,5-tetrahydro-1-(1H-imidazol-4-ylmethyl)-3-(pyridin-3-ylmethyl)-4-(methylsulfonyl)-1H-1,4-benzodiazepine, tetrahydrochloride;

(R)-7-Bromo-2,3,4,5-tetrahydro-1-(1H-imidazol-2-ylmethyl)-4-(methylsulfonyl)-3-(phenylmethyl)-1H-1,4-benzodiazepine, dihydrochloride;

(R)-7-Bromo-2,3,4,5-tetrahydro-1-(1H-imidazol-4-ylmethyl)-4-[(1-methyl-1H-imidazol-4-yl)sulfonyl]-3-(phenylmethyl)-1H-1,4-benzodiazepine, trihydrochloride;

(R)-7-Chloro-2,3,4,5-tetrahydro-1-(1-methyl-imidazol-5-ylmethyl)-4-[(2-morpholin-4-yl-ethyl)sulfonyl]-3-(phenylmethyl)-1H-1,4-benzodiazepine, dihydrochloride;

(R)-7-Chloro-2,3,4,5-tetrahydro-1-(1H-imidazol-4-ylmethyl)-4-[(2-morpholin-4-yl-ethyl)sulfonyl]-3-(phenylmethyl)-1H-1,4-benzodiazepine, dihydrochloride;

(R)-7-Chloro-4-[(dimethylamino)sulfonyl]-1-[(1-methyl-1H-imidazol-5-yl)methyl]-3-(phenylmethyl)-1H-1,4-benzodiazepine, monohydrochloride;

(R)-7-Chloro-2,3,4,5-tetrahydro-1-(1-methyl-imidazol-5-ylmethyl)-4-[(4-methyl-piperidin-4-yl-ethyl)sulfonyl]-3-(phenylmethyl)-1H-1,4-benzodiazepine, dihydrochloride;

(R)-7-Bromo-2,3,4,5-tetrahydro-1-(1-methyl-imidazol-5-ylmethyl)-4-[(4-methyl-piperidin-4-yl-ethyl)sulfonyl]-3-(phenylmethyl)-1H-1,4-benzodiazepine, dihydrochloride;

(R)-7-Cyano-1,2,3,5-tetrahydro-1-(1H-imidazol-4-ylmethyl)-3-(phenylmethyl)-4H-1,4-benzodiazepine-4-carboxylic acid, isopropyl ester, hydrochloride;

(R)-7-Bromo-2,3,4,5-tetrahydro-4-[[2-(1H-imidazol-1-yl)ethyl]sulfonyl]-1-(1H-imidazol-4-ylmethyl)-3-(phenylmethyl)-1H-1,4-benzodiazepine, dihydrochloride;

(R)-7-Cyano-2,3,4,5-tetrahydro-1-(1H-imidazol-4-ylmethyl)-4-(propylsulfonyl)-3-(3-pyridinylmethyl)-1H-1,4-benzodiazepine, hydrochloride;

7-Bromo-2,3,4,5-tetrahydro-1-(1H-imidazol-4-ylmethyl)-3-(phenylmethyl)-1H-1,4-benzodiazepin-5-one, hydrochloride;

(R)-7-Bromo-2,3,4,5-tetrahydro-1-(1H-imidazol-1-ylacetyl)-4-(methylsulfonyl)-3-(phenylmethyl)-1H-1,4-benzodiazepine, trifluoroacetate;

1,2,4,5-Tetrahydro-1-(1H-imidazol-4-ylmethyl)-2-(2-phenylethyl)-3H-1,4-benzodiazepin-3-one;

2,3,4,5-Tetrahydro-1-(1H-imidazol-4-ylmethyl)-4-(methylsulfonyl)-2-(2-phenylethyl)-1H-1,4-benzodiazepine, monohydrochloride;

(R)-2,3,4,5-Tetrahydro-1-(1H-imidazol-4-ylmethyl)-4-(methylsulfonyl)-7-phenyl-3-(4-pyridinylmethyl)-1H-1,4-benzodiazepine, dihydrochloride;

(R)-2,3,4,5-Tetrahydro-1-(1H-imidazol-2-ylmethyl)-4-(phenylsulfonyl)-3-(phenylmethyl)-1H-1,4-benzodiazepine-7-carbonitrile, hydrochloride;

(R)-7-Cyano-1,2,3,5-tetrahydro-1-(1H-imidazol-4-ylmethyl)-N,N-dimethyl-3-(3-pyridinylmethyl)-4H-1,4-benzodiazepine-4-carboxamide, dihydrochloride;

(R)-7-Cyano-1,2,3,5-tetrahydro-1-(1H-imidazol-4-ylmethyl)-N,N-dimethyl-3-(3-pyridinylmethyl)-4H-1,4-benzodiazepine-4-sulfonamide, dihydrochloride;

(R)-2,3,4,5-Tetrahydro-1-(1-(4-cyanophenylmethyl)-imidazol-5-ylmethyl)-4-(methylsulfonyl)-3-(phenylmethyl)-1H-1,4-benzodiazepine-7-carbonitrile, hydrochloride;

(R)-2,3,4,5-Tetrahydro-1-(1-(4-cyanophenylmethyl)-imidazol-4-ylmethyl)-4-(methylsulfonyl)-3-(phenylmethyl)-1H-1,4-benzodiazepine-7-carbonitrile, hydrochloride;

(R)-4-Benzoyl-7-cyano-2,3,4,5-tetrahydro-1-(1H-imidazol-4-ylmethyl)-3-(phenylmethyl)-1H-1,4-benzodiazepine, monohydrochloride;

(R)-7-Cyano-2,3,4,5-tetrahydro-1-[(1-methyl-1H-imidazol-5-yl)methyl]-3-(pyridin-3-ylmethyl)-4-(methylsulfonyl)-1H-1,4-benzodiazepine, dihydrochloride;

(R)-7-Cyano-2,3,4,5-tetrahydro-1-[(1-methyl-1H-imidazol-5-yl)methyl]-3-(pyridin-3-ylmethyl)-4-(propylsulfonyl)-1H-1,4-benzodiazepine, trihydrochloride;

(R)-7-Cyano-2,3,4,5-tetrahydro-1-[(1H-imidazol-4-yl)methyl]-3-(pyridin-3-ylmethyl)-4-(phenylsulfonyl)-1H-1,4-benzodiazepine, dihydrochloride;

2,3,4,5-Tetrahydro-1-(1H-imidazol-4-ylmethyl)-4-(methylsulfonyl)-7-phenyl-3-(phenylmethyl)-1H-1,4-benzodiazepine;

1,2,3,5-Tetrahydro-1-(1H-imidazol-4-ylmethyl)-N-(1-naphthalenyl)-7-phenyl-4H-1,4-benzodiazepine-4-carboxamide, monohydrochloride;

(S)-7-Bromo-2,3,4,5-tetrahydro-1-(1H-imidazol-4-ylmethyl)-4-(methylsulfonyl)-3-(phenylmethyl)-1H-1,4-benzodiazepine, hydrochloride;

N-[2,3,4,5-Tetrahydro-1-(1H-imidazol-4-ylmethyl)-4-(2,3-dimethylbenzoyl)-1H-1,4-benzodiazepin-8-yl]cyclohexanecarboxamide, dihydrochloride;

(R)-7-Cyano-N-[2-(dimethylamino)ethyl]-2,3,4,5-tetrahydro-1-(1H-imidazol-4-ylmethyl)-N-methyl-3-(phenylmethyl)-1H-1,4-benzodiazepine-4-carboxamide, trifluoroacetate (1:2);

7-Bromo-2,3,4,5-tetrahydro-1-(1H-imidazol-4-ylmethyl)-4-(methylsulfonyl)-2-oxo-3-(phenylmethyl)-1H-1,4-benzodiazepine, trifluoroacetate;

(R)-7-Cyano-4-(2-furanylcarbonyl)-2,3,4,5-tetrahydro-1-(1H-imidazol-4-ylmethyl)-3-(phenylmethyl)-1H-1,4-benzodiazepine, trifluoroacetate (1:1);

(R)-7-Cyano-2,3,4,5-tetrahydro-1-(1H-imidazol-4-ylmethyl)-4-[(4-nitrophenyl)sulfonyl]-3-(phenylmethyl)-1H-1,4-benzodiazepine, trifluroracetate;

(R)-7-Cyano-2,3,4,5-tetrahydro-1-(1H-imidazol-4-ylmethyl)-4-[[4-(4-methyl-1-piperazinyl)phenyl]sulfonyl]-3-(phenylmethyl)-1H-1,4-benzodiazepine, trifluoroacetate;

(R)-7-Cyano-2,3,4,5-tetrahydro-1-(1H-imidazol-4-ylmethyl)-4-[[(4-dimethylamino)phenyl]sulfonyl]-3-(phenylmethyl)-1H-1,4-benzodiazepine, trifluoroacetate;

(R)-7-Bromo-4-[[2-(dimethylamino)ethyl]sulfonyl]-2,3,4,5-tetrahydro-1-(1H-imidazol-4-ylmethyl)-3-(phenylmethyl)-4H-1,4-benzodiazepine, dihydrochloride;

(R)-7-Cyano-2,3,4,5-tetrahydro-1-(1H-imidazol-4-ylmethyl)-3-(phenylmethyl)-4-(3-pyridinylsulfonyl)-1H-1,4-benzodiazepine, trihydrochloride;

2,3,4,5-Tetrahydro-1-(1H-imidazol-4-ylmethyl)-4-(methylsulfonyl)-3-(phenylmethyl)-1H-1,4-benzodiazepine, dihydrochloride;

(R)-7-Bromo-2,3,4,5-tetrahydro-1-[(1-methyl-1H-imidazol-4-yl)methyl]-4-(methylsulfonyl)-3-(phenylmethyl)-1H-1,4-benzodiazepine, dihydrochloride;

(R)-4-[[3-(Dimethylamino)propyl]sulfonyl]-2,3,4,5-tetrahydro-1-(1H-imidazol-4-ylmethyl)-7-phenyl-3-(phenylmethyl)-1H-1,4-benzodiazepine, dihydrochloride;

(R)-7-Cyano-2,3,4,5-tetrahydro-1-(1H-imidazol-4-ylmethyl)-3-(phenylmethyl)-1H-1,4-benzodiazepine, trihydrochloride;

4-Butyl-2,3,4,5-tetrahydro-1-(1H-imidazol-4-ylmethyl)-3-(phenylmethyl)-1H-1,4-benzodiazepine, trihydrochloride;

(R)-7-Bromo-2,3,4,5-tetrahydro-1-(1H-imidazol-4-ylmethyl)-4-[[2-(4-morpholinyl)ethyl]sulfonyl]-3-(phenylmethyl)-1H-1,4-benzodiazepine, dihydrochloride;

(R)-7-Bromo-2,3,4,5-tetrahydro-1-[(1-methyl-1H-imidazol-5-yl)methyl]-4-[[2-(4-morpholinyl)ethyl]sulfonyl]-3-(phenylmethyl)-1H-1,4-benzodiazepine, dihydrochloride;

(R)-7-Cyano-1-(1H-imidazol-4-ylmethyl)-4-(4-morpholinylsulfonyl)-3-(phenylmethyl)-1H-1,4-benzodiazepine, monohydrochloride;

(R)-7-Cyano-1-[(1-methyl-1H-imidazol-5-yl)methyl]-4-[(4-morpholinyl)sulfonyl]-3-(phenylmethyl)-1H-1,4-benzodiazepine, monohydrochloride;

(R)-7-Cyano-2,3,4,5-tetrahydro-1-(1H-imidazol-4-ylmethyl)-4-[(4-aminophenyl)sulfonyl]-3-(phenylmethyl)-1H-1,4-benzodiazepine, hydrochloride;

2,3,4,5-Tetrahydro-1-(1H-imidazol-4-ylmethyl)-4-[(4-pyridylthio)acetyl]-7-phenyl-1H-1,4-benzodiazepine, dihydrochloride;

N-(4-Chlorophenyl)-N'-cyano-1,2,3,5-tetrahydro-1-(1H-imidazol-4-ylmethyl)-7-phenyl-4H-1,4-benzodiazepine-4-imidamide, monohydrochloride;

4-Acetyl-7-bromo-1,2,4,5, 1',3'-hexahydro-1-(1H-imidazol-4-ylmethyl)spiro[3H-1,4-benzodiazepine-3,2'-[2H]indene], dihydrochloride;

7-Bromo-4-[3-(dimethylamino)-1-oxopropyl]-2,3,4,5-tetrahydro-1-(1H-imidazol-4-ylmethyl)-3-(phenylmethyl)-1H-1,4-benzodiazepine, trifluoroacetate (1:1);

(R)-2,3,4,5-Tetrahydro-1-(1-methyl-1H-imidazol-5-ylmethyl)-4-(phenylsulfonyl)-3-(phenylmethyl)-1H-1,4-benzodiazepine-7-carbonitrile, monohydrochloride;

2,3,4,5-Tetrahydro-1-[(1-methyl-1H-imidazol-5-yl)methyl]-4-(methyl-sulfonyl)-7-phenyl-3-(pyridin-3-ylmethyl)-1H-1,4-benzodiazepine, hydrochloride (1:1.5), trifluoroacetate (1:0.75) salt;

4-[4-(Fluorophenyl)sulfonyl]-2,3,4,5-tetrahydro-1-(1H-imidazol-4-ylmethyl)-2-(2-phenylethyl)-1H-1,4-benzodiazepine, monohydrochloride;

7-Bromo-2,3,4,5-tetrahydro-1-(1H-imidazol-4-yl-methyl)-4-(methyl-sulfonyl)-2-(2-phenylethyl)-1H-1,4-benzodiazepine, monohydrochloride;

(R)-7-Cyano-2,3,4,5-tetrahydro-1-(1-methyl-1H-imidazol-5-ylmethyl)-4-[[2-(1-morpholinyl)ethyl]sulfonyl]-3-(phenylmethyl)-1H-1,4-benzodiazepine, dihydrochloride;

(R)-7-Bromo-2,3,4,5-tetrahydro-1-(1H-imidazol-4-ylmethyl)-4-(methyl-sulfonyl)-3-(4-bromophenylmethyl)-1H-1,4-benzodiazepine, hydrochloride;

(R)-7-Bromo-2,3,4,5-tetrahydro-1-(1H-imidazol-4-ylmethyl)-4-(methyl-sulfonyl)-3-(thiazol-4-ylmethyl)-1H-1,4-benzodiazepine, hydrochloride;

(R)-7-Bromo-2,3,4,5-tetrahydro-1-(1H-imidazol-4-ylmethyl)-4-(propyl-sulfonyl)-3-(thiazol-4-ylmethyl)-1H-1,4-benzodiazepine, hydrochloride;

(R)-7-Bromo-2,3,4,5-tetrahydro-1-(1H-imidazol-4-ylmethyl)-4-(propylsulfonyl)-3-(4-bromophenylmethyl)-1H-1,4-benzodiazepine, hydrochloride;

(R)-7-Bromo-2,3,4,5-tetrahydro-1-(1H-imidazol-4-ylmethyl)-3-(pyridin-3-ylmethyl)-4-(methylsulfonyl)-1H-1,4-benzodiazepine, trihydrochloride;

(R)-7-Bromo-2,3,4,5-tetrahydro-1-(1H-1-methyl-imidazol-5-ylmethyl)-3-(pyridin-3-ylmethyl)-4-(methylsulfonyl)-1H-1,4-benzodiazepine, dihydrochloride;

(R)-7-Cyano-2,3,4,5-tetrahydro-1-(1H-imidazol-4-ylmethyl)-4-(phenyl-sulfonyl)-3-(4-cyanophenylmethyl)-1H-1,4-benzodiazepine, hydrochloride;

(R)-7-Cyano-4-[(N-methyl-N-phenylmethyl)aminosulfonyl]-1-[(1H-imidazol-4-yl)methyl]-3-(phenylmethyl)-1H-1,4-benzodiazepine, monohydrochloride;

(R)-7-Cyano-4-[N-(tetrahydroisoquinolinyl)sulfonyl]-1-[(1H-imidazol-4-yl)methyl]-3-(phenylmethyl)-1H-1,4-benzodiazepine, monohydrochloride;

(R)-7-Cyano-2,3,4,5-tetrahydro-1-(1H-imidazol-4-ylmethyl)-4-(phenylsulfonyl)-3-(2-thienylmethyl)-1H-1,4-benzodiazepine, hydrochloride;

cis-2,3,4,5-Tetrahydro-1,5-bis(1H-imidazol-4-ylmethyl)-3-(phenylmethyl)-1H-1,5-benzodiazepine-2-carboxylic acid ethyl ester, trifluoroacetate (1:2);

(R)-7-Cyano-4-[(N-piperidinyl)sulfonyl]-1-[(1H-imidazol-4-yl)methyl]-3-(phenylmethyl)-1H-1,4-benzodiazepine, monohydrochloride;

(R)-7-Cyano-2,3,4,5-tetrahydro-1-(1H-1-methyl-imidazol-5-ylmethyl)-3-(phenylmethyl)-4-(2-thienylsulfonyl)-1H-1,4-benzodiazepine, hydrochloride;

(R)-7-Cyano-2,3,4,5-tetrahydro-1-(1H-imidazol-4-ylmethyl)-3-(pyridin-3-ylmethyl)-4-[[2-(dimethylamino)ethyl]sulfonyl]-1H-1,4-benzodiazepine, trihydrochloride;

(R)-7-Cyano-2,3,4,5-tetrahydro-1-(1H-1-methyl-imidazol-5-ylmethyl)-3-(phenylmethyl)-4-(propylsulfonyl)-1H-1,4-benzodiazepine, hydrochloride;

N-(Cyano)-N'-methyl-1,2,3,5-tetrahydro-1-(1H-imidazol-4-ylmethyl)-7-phenyl-4H-1,4-benzodiazepine-4-imidamide, hydrochloride;

(R)-7-Cyano-4-[(2-nitrophenyl)-sulfonyl]-2,3,4,5-tetrahydro-1-(1H-imidazol-4-ylmethyl)-3-(phenylmethyl)-1H-1,4-benzodiazepine, hydrochloride;

R)-7-Cyano-4-[(4-methyl-phenyl)sulfonyl]-2,3,4,5-tetrahydro-1-(1H-imidazol-4-ylmethyl)-3-(phenylmethyl)-1H-1,4-benzodiazepine, hydrochloride;

(R)-7-Cyano-4-(butylsulfonyl)-2,3,4,5-tetrahydro-1-(1H-imidazol-4-ylmethyl)-3-(phenylmethyl)-1H-1,4-benzodiazepine, hydrochloride;

(R)-7-Cyano-4-[(2-trifluoro-methylphenyl)sulfonyl]-2,3,4,5-tetrahydro-1-(1H-imidazol-4-ylmethyl)-3-(phenylmethyl)-1H-1,4-benzodiazepine, hydrochloride;

(R)-7-Cyano-4-[(2-trifluoromethoxyphenyl)sulfonyl]-2,3,4,5-tetrahydro-1-(1H-imidazol-4-ylmethyl)-3-(phenylmethyl)-1H-1,4-benzodiazepine, hydrochloride;

(R)-7-Cyano-4-[(2-methoxy-carbonylphenyl)sulfonyl]-2,3,4,5-tetrahydro-1-(1H-imidazol-4-ylmethyl)-3-(phenylmethyl)-1H-1,4-benzodiazepine, hydrochloride;

(R)-7-Cyano-4-[(2-methyl-sulfonylphenyl)sulfonyl]-2,3,4,5-tetrahydro-1-(1H-imidazol-4-ylmethyl)-3-(phenylmethyl)-1H-1,4-benzodiazepine, hydrochloride;

(R)-7-Cyano-2,3,4,5-tetrahydro-1-(1H-imidazol-4-ylmethyl)-3-(phenylmethyl)-4-(((4-methylsulfonyl)phenyl)-sulfonyl)-1H-1,4-benzodiazepine;

(R)-7-Cyano-2,3,4,5-tetrahydro-1-(1H-imidazol-4-ylmethyl)-3-(phenylmethyl)-4-(((4-trifluoromethyl)phenyl)-sulfonyl)-1H-1,4-benzodiazepine;

(R)-7-Cyano-2,3,4,5-tetrahydro-1-(1H-imidazol-4-ylmethyl)-3-(phenylmethyl)-4-((3-methoxypropyl)sulfonyl)-1H-1,4-benzodiazepine;

(R)-7-Cyano-2,3,4,5-tetrahydro-1-(1H-imidazol-4-ylmethyl)-3-(phenylmethyl)-4-((3,4-dimethoxyphenyl)-sulfonyl)-1H-1,4-benzodiazepine;

(R)-7-Cyano-2,3,4,5-tetrahydro-1-(1H-imidazol-4-ylmethyl)-3-((4-fluorophenyl)methyl)-4-(phenylsulfonyl)-1H-1,4-benzodiazepine;

(R)-7-Cyano-4-[(N-cyclopropylmethyl-N-propyl)-aminosulfonyl]-1-[(1H-imidazol-4-yl)methyl]-3-(phenylmethyl)-1H-1,4-benzodiazepine;

(R)-7-Cyano-4-[(N,N-(dibutylamino))-sulfonyl]-1-[(1H-imidazol-4-yl)methyl]-3-(phenylmethyl)-1H-1,4-benzodiazepine;

1,2,3,4-Tetrahydro-7-bromo-4-[(1H-imidazol-4-yl)methyl]-2-phenylmethyl-1-(methylsulfonyl)quinoxaline;

(R)-7-Cyano-2,3,4,5-tetrahydro-1-(1H-imidazol-4-ylmethyl)-3-(phenylmethyl)-4-((imidazol-4-yl)methylsulfonyl)-1H-1,4-benzodiazepine;

(R)-7-Cyano-2,3,4,5-tetrahydro-1-(1H-imidazol-4-ylmethyl)-3-((2-thienyl)methyl)-4-(propylsulfonyl)-1H-1,4-benzodiazepine;

(R)-7-Cyano-2,3,4,5-tetrahydro-1-(1H-imidazol-4-ylmethyl)-3-((2-thienyl)methyl)-4-((2-thienyl)-sulfonyl)-1H-1,4-benzodiazepine;

(R)-7-Cyano-2,3,4,5-tetrahydro-1-(1H-imidazol-4-ylmethyl)-3-(phenylmethyl)-4-((3-methylthiopropyl)sulfonyl)-1H-1,4-benzodiazepine;

(R)-7-Cyano-2,3,4,5-tetrahydro-1-(1H-imidazol-4-ylmethyl)-3-(phenylmethyl)-4-(((3-methylthioxo)-propyl)-sulfonyl)-1H-1,4-benzodiazepine;

(R)-7-Cyano-2,3,4,5-tetrahydro-1-(1H-imidazol-4-ylmethyl)-3-(phenylmethyl)-4-(((3-methylsulfonyl)-propyl)-sulfonyl)-1H-1,4-benzodiazepine;

(R)-7-Cyano-2,3,4,5-tetrahydro-1-(1H-imidazol-4-ylmethyl)-3-(phenylmethyl)-4-((2-methylpropyl)-sulfonyl)-1H-1,4-benzodiazepine;

(R)-7-Cyano-2,3,4,5-tetrahydro-1-(1H-imidazol-4-ylmethyl)-3-(phenylmethyl)-4-30 (cyclopentylsulfonyl)-1H-1,4-benzodiazepine;

(R)-7-Cyano-2,3,4,5-tetrahydro-1-(1H-imidazol-4-ylmethyl)-3-(phenylmethyl)-4-((4,4,4-trifluorobutyl)-sulfonyl)-1H-1,4-benzodiazepine;

(R)-7-Cyano-2,3,4,5-tetrahydro-1-(1H-imidazol-4-ylmethyl)-3-(phenylmethyl)-4-((phenylmethyl)-sulfonyl)-1H-1,4-benzodiazepine;

(R)-7-Cyano-2,3,4,5-tetrahydro-1-(1H-imidazol-4-ylmethyl)-3-(phenylmethyl)-4-[[2-(5-(N-benzoyl)-aminomethyl)-thienyl]-sulfonyl]-1H-1,4-benzodiazepine (R)-7-Cyano-2,3,4,5-tetrahydro-1-(1H-imidazol-4-ylmethyl)-3-(phenylmethyl)-4-[[2-(1-(3-chloro-5-methyl-pyridin-2-yl))-pyrrolyl]-sulfonyl]-1H-1,4-benzodiazepine;

(R)-7-Cyano-2,3,4,5-tetrahydro-1-(1H-imidazol-4-ylmethyl)-3-(phenylmethyl)-4-((4-carboxyphenyl)-sulfonyl)-1H-1,4-benzodiazepine;

(R)-7-Cyano-2,3,4,5-tetrahydro-1-(1H-imidazol-4-ylmethyl)-3-(phenylmethyl)-4-[((3-methyl-1,2,4-oxadiazol-5-yl)-phenyl)-sulfonyl]-1H-1,4-benzodiazepine;

(R)-7-Cyano-2,3,4,5-tetrahydro-1-(1H-imidazol-4-ylmethyl)-3-(phenylmethyl)-4-((2,5-dimethoxyphenyl)-sulfonyl)-1H-1,4-benzodiazepine;

(R)-7-Cyano-4-[(N-tetrahydroquinolinyl)sulfonyl]-1-[(1H-imidazol-4-yl)methyl]-3-(phenylmethyl)-1H-1,4-benzodiazepine;

(R)-7-Cyano-4-[(N,N-bis-[1-(2-methylpropyl)amino]-sulfonyl]-1-[(1H-imidazol-4-yl)methyl]-3-(phenylmethyl)-1H-1,4-benzodiazepine;

(R)-7-Cyano-4-[(N-methyl-N-phenyl)aminosulfonyl]-1-[(1H-imidazol-4-yl)methyl]-3-(phenylmethyl)-1H-1,4-benzodiazepine;

(R)-7-Cyano-2,3,4,5-tetrahydro-1-(1H-imidazol-4-ylmethyl)-3-(2-(2,6-dimethylphenyl)-ethyl)-4-(methylsulfonyl)-1H-1,4-benzodiazepine;

(R)-7-Cyano-2,3,4,5-tetrahydro-1-(1-(N-phthalimidoethyl)-imidazol-5-ylmethyl)-3-(phenylmethyl)-4-(methylsulfonyl)-1H-1,4-benzodiazepine;

(R)-7-Cyano-2,3,4,5-tetrahydro-1-[(2-(N,N-dimethylamino)-ethyl)-imidazol-5-ylmethyl]-3-(phenylmethyl)-4-(methylsulfonyl)-1H-1,4-benzodiazepine;

(R)-7-Cyano-2,3,4,5-tetrahydro-1-[(2-aminoethyl)-imidazol-5-ylmethyl]-3-(phenylmethyl)-4-(methylsulfonyl)-1H-1,4-benzodiazepine;

(R)-4-(methanesulfonyl)-2,3,4,5-tetrahydro-1-[(1H-imidazol-4-ylmethyl)-3-(phenylmethyl)-1H-8-oxo-pyrimidino[4,5-e]-1,4-diazepine;

(R)-7-Cyano-2,3,4,5-tetrahydro-1-(1H-imidazol-4-ylmethyl)-3-((4-(2-methoxyethoxy)-phenyl)methyl)-4-(phenylsulfonyl)-1H-1,4-benzodiazepine;

(R)-7-Cyano-2,3,4,5-tetrahydro-1-(1H-imidazol-4-ylmethyl)-3-((4-(2-(dimethylamino)-ethoxy)-phenyl)methyl)-4-(phenylsulfonyl)-1H-1,4-benzodiazepine;

(R)-7-Cyano-2,3,4,5-tetrahydro-1-(1H-imidazol-4-ylsulfonyl)-3-(phenylmethyl)-4-(methylsulfonyl)-1H-1,4-benzodiazepine;

(R)-7-Cyano-2,3,4,5-tetrahydro-1-(1H-imidazol-4-ylsulfonyl)-3-(phenylmethyl)-4-(propylsulfonyl)-1H-1,4-benzodiazepine;

(R)-7-Cyano-2,3,4,5-tetrahydro-1-(1H-imidazol-4-ylsulfonyl)-3-(phenylmethyl)-4-(phenylsulfonyl)-1H-1,4-benzodiazepine;

(R)-7-Cyano-2,3,4,5-tetrahydro-1-(1H-imidazol-4-ylsulfonyl)-3-(phenylmethyl)-4-(2-thienylsulfonyl)-1H-1,4-benzodiazepine;

7-Cyano-2,3,4,5-tetrahydro-1-(1H-imidazol-4-ylmethyl)-3-(R)-[(R)-1-phenyl-ethyl]-4-(methylsulfonyl)-1H-1,4-benzodiazepine;

7-Cyano-2,3,4,5-tetrahydro-1-(1H-imidazol-4-ylmethyl)-3-(R)-[(R)-1-phenyl-ethyl]-4-(propylsulfonyl)-1H-1,4-benzodiazepine;

7-Cyano-2,3,4,5-tetrahydro-1-(1H-imidazol-4-ylmethyl)-3-(R)-[(R)-1-phenyl-ethyl]-4-(phenylsulfonyl)-1H-1,4-benzodiazepine;

7-Cyano-2,3,4,5-tetrahydro-1-(1H-imidazol-4-ylmethyl)-3-(R)-[(R)-1-phenyl-ethyl]-4-((2-thienyl)-sulfonyl)-1H-1,4-benzodiazepine;

7-Cyano-2,3,4,5-tetrahydro-1-(1H-imidazol-4-ylmethyl)-3-(S)-[(R)-1-phenyl-ethyl]-4-(methylsulfonyl)-1H-1,4-benzodiazepine;

7-Cyano-2,3,4,5-tetrahydro-1-(1H-imidazol-4-ylmethyl)-3-(S)-[(R)-1-phenyl-ethyl]-4-(propylsulfonyl)-1H-1,4-benzodiazepine;

7-Cyano-2,3,4,5-tetrahydro-1-(1H-imidazol-4-ylmethyl)-3-(S)-[(R)-1-phenyl-ethyl]-4-(phenylsulfonyl)-1H-1,4-benzodiazepine;

7-Cyano-2,3,4,5-tetrahydro-1-(1H-imidazol-4-ylmethyl)-3-(S)-[(R)-1-phenyl-ethyl]-4-((2-thienyl)-sulfonyl)-1H-1,4-benzodiazepine;

7-Cyano-2,3,4,5-tetrahydro-1-(1H-imidazol-4-ylmethyl)-3-(R)-[(S)-1-phenyl-ethyl]-4-(methylsulfonyl)-1H-1,4-benzodiazepine;

7-Cyano-2,3,4,5-tetrahydro-1-(1H-imidazol-4-ylmethyl)-3-(R)-[(S)-1-phenyl-ethyl]-4-(propylsulfonyl)-1H-1,4-benzodiazepine;

7-Cyano-2,3,4,5-tetrahydro-1-(1H-imidazol-4-ylmethyl)-3-(R)-[(S)-i-phenyl-ethyl]-4-(phenylsulfonyl)-1H-1,4-benzodiazepine;

7-Cyano-2,3,4,5-tetrahydro-1-(1H-imidazol-4-ylmethyl)-3-(R)-[(S)-1-phenyl-ethyl]-4-((2-thienyl)-sulfonyl)-1H-1,4-benzodiazepine;

7-Cyano-2,3,4,5-tetrahydro-1-(1H-imidazol-4-ylmethyl)-3-(S)-[(S)-1-phenyl-ethyl]-4-(methylsulfonyl)-1H-1,4-benzodiazepine;

7-Cyano-2,3,4,5-tetrahydro-1-(1H-imidazol-4-ylmethyl)-3-(S)-[(S)-1-phenyl-ethyl]-4-(propylsulfonyl)-1H-1,4-benzodiazepine;

7-Cyano-2,3,4,5-tetrahydro-1-(1H-imidazol-4-ylmethyl)-3-(S)-[(S)-1-phenyl-ethyl]-4-(phenylsulfonyl)-1H-1,4-benzodiazepine;

7-Cyano-2,3,4,5-tetrahydro-1-(1H-imidazol-4-ylmethyl)-3-(S)-[(S)-1-phenyl-ethyl]-4-((2-thienyl)-sulfonyl)-1H-1,4-benzodiazepine;

7-Cyano-2,3,4,5-tetrahydro-1-(1H-imidazol-4-ylmethyl)-3-(R)-[(R)-phenylcyclopropyl)-4-(methylsulfonyl)-1H-1,4-benzodiazepine;

7-Cyano-2,3,4,5-tetrahydro-1-(1H-imidazol-4-ylmethyl)-3-(R)-[(R)-phenylcyclopropyl)-4-(propylsulfonyl)-1H-1,4-benzodiazepine;

7-Cyano-2,3,4,5-tetrahydro-1-(1H-imidazol-4-ylmethyl)-3-(R)-[(R)-phenylcyclopropyl)-4-(phenylsulfonyl)-1H-1,4-benzodiazepine;

7-Cyano-2,3,4,5-tetrahydro-1-(1H-imidazol-4-ylmethyl)-3-(R)-[(R)-phenylcyclopropyl)-4-((2-thienyl)-sulfonyl)-1H-1,4-benzodiazepine;

7-Cyano-2,3,4,5-tetrahydro-1-(1H-imidazol-4-ylmethyl)-3-(R)-[(S)-phenylcyclopropyl)-4-(methylsulfonyl)-1H-1,4-benzodiazepine;

7-Cyano-2,3,4,5-tetrahydro-1-(1H-imidazol-4-ylmethyl)-3-(R)-[(S)-phenylcyclopropyl)-4-(propylsulfonyl)-1H-1,4-benzodiazepine;

7-Cyano-2,3,4,5-tetrahydro-1-(1H-imidazol-4-ylmethyl)-3-(R)-[(S)-phenylcyclopropyl)-4-(phenylsulfonyl)-1H-1,4-benzodiazepine;

7-Cyano-2,3,4,5-tetrahydro-1-(1H-imidazol-4-ylmethyl)-3-(R)-[(S)-phenylcyclopropyl)-4-((2-thienyl)-sulfonyl)-1H-1,4-benzodiazepine;

7-Cyano-2,3,4,5-tetrahydro-1-(1H-imidazol-4-ylmethyl)-3-(S)-[(R)-phenylcyclopropyl)-4-(methylsulfonyl)-1H-1,4-benzodiazepine;

7-Cyano-2,3,4,5-tetrahydro-1-(1H-imidazol-4-ylmethyl)-3-(S)-[(R)-phenylcyclopropyl)-4-(propylsulfonyl)-1H-1,4-benzodiazepine;

7-Cyano-2,3,4,5-tetrahydro-1-(1H-imidazol-4-ylmethyl)-3-(S)-[(R)-phenylcyclopropyl)-4-(phenylsulfonyl)-1H-1,4-benzodiazepine;

7-Cyano-2,3,4,5-tetrahydro-1-(1H-imidazol-4-ylmethyl)-3-(S)-[(R)-phenylcyclopropyl)-4-((2-thienyl)-sulfonyl)-1H-1,4-benzodiazepine;

7-Cyano-2,3,4,5-tetrahydro-1-(1H-imidazol-4-ylmethyl)-3-(S)-[(S)-phenylcyclopropyl)-4-(methylsulfonyl)-1H-1,4-benzodiazepine;

7-Cyano-2,3,4,5-tetrahydro-1-(1H-imidazol-4-ylmethyl)-3-(S)-[(S)-phenylcyclopropyl)-4-(propylsulfonyl)-1H-1,4-benzodiazepine;

7-Cyano-2,3,4,5-tetrahydro-1-(1H-imidazol-4-ylmethyl)-3-(S)-[(S)-phenylcyclopropyl)-4-(phenylsulfonyl)-1H-1,4-benzodiazepine;

7-Cyano-2,3,4,5-tetrahydro-1-(1H-imidazol-4-ylmethyl)-3-(S)-[(S)-phenylcyclopropyl)-4-((2-thienyl)-sulfonyl)-1H-1,4-benzodiazepine;

(R)-7-Cyano-2,3,4,5-tetrahydro-1-(1H-imidazol-4-ylmethyl)-3-(phenylmethyl)-4-[(2-(5-(pyridin-2-yl))-thienyl)-sulfonyl])-1H-1,4-benzodiazepine;

(R)-7-Cyano-2,3,4,5-tetrahydro-1-(1H-imidazol-4-ylmethyl)-3-(phenylmethyl)-4-[(2-(5-(1,2-isoxazol-3-yl))-thienyl)-sulfonyl])-1H-1,4-benzodiazepine;

(R)-7-Cyano-2,3,4,5-tetrahydro-1-(3-(1H-imidazol-2-yl)-propyl)-3-(phenylmethyl)-4-(phenylsulfonyl)-1H-1,4-benzodiazepine;

(R)-7-Cyano-2,3,4,5-tetrahydro-1-(3-(1H-imidazol-2-yl)-propyl)-3-(phenylmethyl)-4-(methylsulfonyl)-1H-1,4-benzodiazepine;

(R)-7-Cyano-2,3,4,5-tetrahydro-1-(3-(1H-imidazol-2-yl)-propyl)-3-(phenylmethyl)-4-(propylsulfonyl)-1H-1,4-benzodiazepine;

(R)-7-Cyano-2,3,4,5-tetrahydro-1-(3-(1H-imidazol-2-yl)-propyl)-3-(phenylmethyl)-4-((2-thienyl)-sulfonyl)-1H-1,4-benzodiazepine;

(R)-7-Cyano-2,3,4,5-tetrahydro-1-(2-(1H-imidazol-2-yl)-ethylsulfonyl)-3-(phenylmethyl)-4-(phenylsulfonyl)-1H-1,4-benzodiazepine;

(R)-7-Cyano-2,3,4,5-tetrahydro-1-(2-(1H-imidazol-2-yl)-ethylsulfonyl)-3-(phenylmethyl)-4-(methylsulfonyl)-1H-1,4-benzodiazepine;

(R)-7-Cyano-2,3,4,5-tetrahydro-1-(2-(1H-imidazol-2-yl)-ethylsulfonyl)-3-(phenylmethyl)-4-(propylsulfonyl)-1H-1,4-benzodiazepine;

(R)-7-Cyano-2,3,4,5-tetrahydro-1-(2-(1H-imidazol-2-yl)-ethylsulfonyl)-3-(phenylmethyl)-4-((2-thienyl)-sulfonyl)-1H-1,4-benzodiazepine;

(R)-7-Cyano-2,3,4,5-tetrahydro-1-(1H-imidazol-4-ylmethyl)-3-(phenylmethyl)-4-((1-oxoethyl)-amino)-1H-1,4-benzodiazepine;

(R)-7-Cyano-2,3,4,5-tetrahydro-1-(1H-imidazol-4-ylmethyl)-3-(phenylmethyl)-4-(methanesulfonylamino)-1H-1,4-benzodiazepine;

(R)-7-Cyano-2,3,4,5-tetrahydro-1-(1H-imidazol-4-ylmethyl)-3-(phenylmethyl)-4-(phenylsulfonylamino)-1H-1,4-benzodiazepine.

4. A compound of the formula

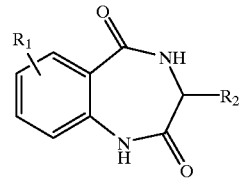

wherein $R_1$ is selected from Cl, Br, phenyl, pyridyl or cyano and $R_2$ is selected from substituted aralkyl or substituted heterocycloalkyl.

5. A compound of the formula

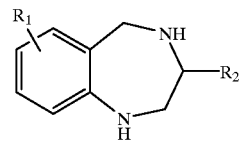

wherein $R_1$ is selected from Cl, Br, phenyl, pyridyl or cyano and $R_2$ is selected from substituted aralkyl or substituted heterocycloalkyl.

6. A compound of the formula

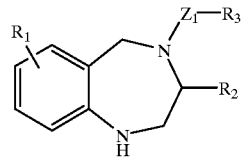

wherein $R_1$ is selected from Cl, Br, phenyl, pyridyl or cyano; $R_2$ is selected from substituted aralkyl or substituted heterocycloalkyl; $R_3$ is selected from substituted alkyl, substituted aryl or substituted heterocyclo; $Z_1$ is selected from CO, $SO_2$, $CO_2$, $CONHR_5$, $SO_3$, $SO_2NR_5$, or $C(NCN)NR_5$; $R_5$ is selected from hydrogen, lower alkyl, substituted alkyl, aryl or substituted aryl.

7. A compound of the formula

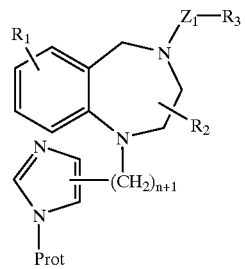

wherein $R_1$ is selected from Cl, Br, phenyl, pyridyl or cyano; $R_2$ is selected from substituted aralkyl or substituted heterocycloalkyl; $R_3$ is selected from substituted alkyl, substituted aryl or substituted heterocyclo; $Z_1$ is selected from CO, $SO_2$, $CO_2$, $CONHR_5$, $SO_3$, $SO_2NR_5$, or $C(NCN)NR_5$, Prot is triphenylmethyl or Boc, $R_5$ is selected from hydrogen, lower alkyl, substituted alkyl, aryl or substituted aryl.

* * * * *

UNITED STATES PATENT AND TRADEMARK OFFICE
CERTIFICATE OF CORRECTION

PATENT NO.    : 6,011,029
DATED         : January 4, 2000
INVENTOR(S)   : Ding et al.

Page 1 of 1

It is certified that error appears in the above-identified patent and that said Letters Patent is hereby corrected as shown below:

Column 316, claim 1,
Delete the compounds II and IV and substitute therefor compounds I and III as follows:

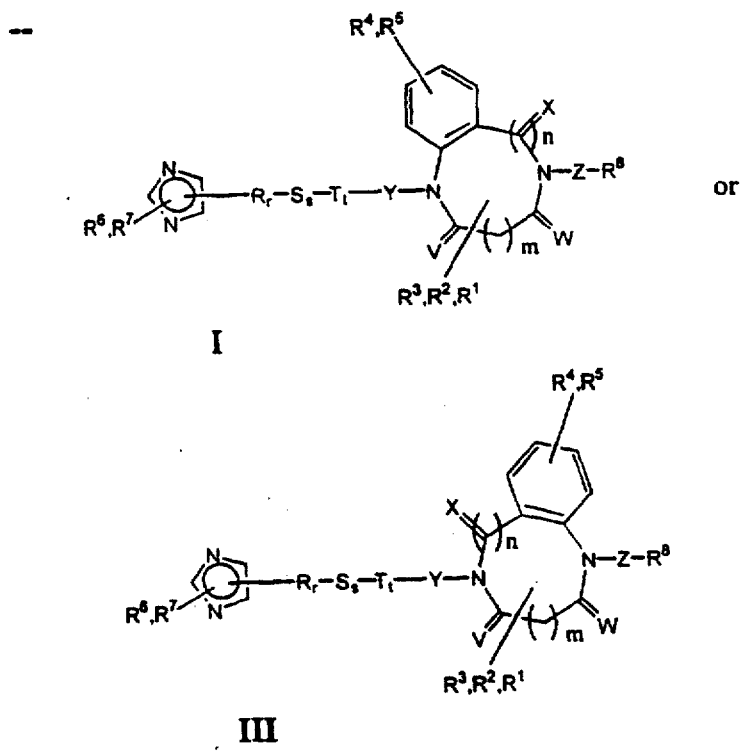

Signed and Sealed this

Eleventh Day of December, 2001

Attest:

NICHOLAS P. GODICI
Attesting Officer    Acting Director of the United States Patent and Trademark Office